US012414987B2

(12) United States Patent
Kong et al.

(10) Patent No.: US 12,414,987 B2
(45) Date of Patent: Sep. 16, 2025

(54) PHOSPHORYLATED POLYPEPTIDE ANTIGEN VACCINE, PREPARATION METHOD THEREFOR AND APPLICATION THEREOF

(71) Applicants: CHANGCHUN BCHT BIOTECHNOLOGY CO., Changchun (CN); JILIN UNIVERSITY, Changchun (CN)

(72) Inventors: Wei Kong, Changchun (CN); Hui Wu, Changchun (CN); Yao Sun, Changchun (CN); Yongqing Guo, Changchun (CN)

(73) Assignees: CHANGCHUN BCHT BIOTECHNOLOGY CO., Changchun (CN); JILIN UNIVERSITY, Changchun (CN)

( * ) Notice: Subject to any disclaimer, the term of this patent is extended or adjusted under 35 U.S.C. 154(b) by 259 days.

(21) Appl. No.: 17/059,665

(22) PCT Filed: Mar. 26, 2019

(86) PCT No.: PCT/CN2019/079708
§ 371 (c)(1),
(2) Date: Nov. 30, 2020

(87) PCT Pub. No.: WO2019/228032
PCT Pub. Date: Dec. 5, 2019

(65) Prior Publication Data

US 2024/0252606 A1 Aug. 1, 2024

(30) Foreign Application Priority Data

May 31, 2018 (CN) ........................ 201810551372.1

(51) Int. Cl.

| | |
|---|---|
| ***C07K 16/18*** | (2006.01) |
| ***A61K 39/00*** | (2006.01) |
| ***A61P 25/28*** | (2006.01) |
| ***A61P 37/04*** | (2006.01) |
| ***C07K 14/47*** | (2006.01) |
| ***C07K 16/44*** | (2006.01) |

(52) U.S. Cl.
CPC .......... *A61K 39/0007* (2013.01); *A61P 25/28* (2018.01); *A61P 37/04* (2018.01); *A61K 2039/55561* (2013.01); *A61K 2039/55566* (2013.01); *A61K 2039/6031* (2013.01); *A61K 2039/6037* (2013.01); *A61K 2039/6068* (2013.01); *A61K 2039/6075* (2013.01); *A61K 2039/6081* (2013.01); *A61K 2039/627* (2013.01)

(58) Field of Classification Search
CPC .......... A61P 25/28; A61P 25/00; C07K 16/18; C07K 14/4711; A61K 39/0007
See application file for complete search history.

(56) References Cited

U.S. PATENT DOCUMENTS

| | | | |
|---|---|---|---|
| 2011/0177109 | A1 | 7/2011 | Smith et al. |
| 2012/0244174 | A1 | 9/2012 | Chain |
| 2016/0122422 | A1 | 5/2016 | Chain |
| 2016/0347804 | A1 | 12/2016 | Griswold-Prenner et al. |
| 2017/0183400 | A1 | 6/2017 | Sigurdsson |

FOREIGN PATENT DOCUMENTS

| | | | |
|---|---|---|---|
| CN | 102596221 | | 7/2012 |
| CN | 102596236 | A1 | 7/2012 |
| CN | 105939722 | A | 9/2016 |
| CN | 105968213 | | 9/2016 |
| CN | 106390107 | | 2/2017 |
| CN | 107034198 | | 8/2017 |
| CN | 110548135 | | 12/2019 |
| WO | 2010/144711 | | 12/2010 |
| WO | 2012/106363 | | 8/2012 |
| WO | WO 2015017280 | A1 | 2/2015 |

OTHER PUBLICATIONS

Search Report and Written Opinion, dated Jul. 8, 2019, corresponding to International Patent Application No. PCT/CN2019/079708, 12 pages.
Asuni et al. (2007) "Immunotherapy Targeting Pathological Tau Conformers in a Tangle Mouse Model Reduces Brain Pathology with Associated Functional Improvements," The Journal of Neuroscience 27(34): 9115-9129.
Fu et al. (2015) "Norovirus P particle: an excellent vaccine platform for antibody production against Alzheimer's disease." Immunology Letters (Accepted Manuscript), 26 pp.
European Search Report in corresponding European Patent Application No. 19812111.3, Mailed May 30, 2022.

(Continued)

*Primary Examiner* — Barry A Chestnut
(74) *Attorney, Agent, or Firm* — LEYDIG, VOIT & MAYER, LTD.

(57) ABSTRACT

The present invention discloses a phosphorylated polypeptide antigen vaccine, comprising at least two polypeptide fragments or conservatively modified variants thereof from human full-length Tau protein, wherein the polypeptide fragments or conservatively modified variants thereof contain phosphorylation sites. The present invention also discloses a complex vaccine formed by coupling a phosphorylated polypeptide antigen vaccine with a carrier. The polypeptide antigen vaccine and the complex vaccine can be used for preventing and/or treating tauopathy comprising Alzheimer's disease (AD).

34 Claims, 45 Drawing Sheets

Specification includes a Sequence Listing.

(56) References Cited

OTHER PUBLICATIONS

First Office Action issued on May 7, 2022, by the State Intellectual Property Office of People's Republic of China in corresponding Chinese Patent Application No. 201810551372.1.
Richter et al. (2014) "Doubly Phosphorylated Peptide Vaccines to Protect Transgenic P301S Mice against Alzheimer's Disease Like Tau Aggregation", Vaccines 2, 601-623.
Search Report issued on May 7, 2022, by the State Intellectual Property Office of People's Republic of China in corresponding Chinese Patent Application No. 201810551372.1.
Sun et al. (2012) "Construction of a prokaryotic expression vector of human tau multi-epitope peptide and immunogenicity of the expressed product", J South Med Univ 32(2), 185-188.

PHOSPHORYLATED POLYPEPTIDE ANTIGEN VACCINE, PREPARATION METHOD THEREFOR AND APPLICATION THEREOF

CROSS-REFERENCE TO RELATED APPLICATIONS

This application is a U.S. National Stage Application filed under 35 U.S.C. § 371 of International Application No. PCT/CN2019/079708, filed Mar. 26, 2019, which claims the benefit of Chinese Application No. 201810551372.1, filed May 31, 2018. Both of these applications are hereby incorporated by reference in their entireties.

REFERENCE TO A SEQUENCE LISTING

A sequence listing containing SEQ ID Nos. 1-1366, created on Nov. 29, 2020, having a size of 398 kb, and entitled "108-20_sequence_listing_filed", is provided herewith in a computer-readable nucleotide/amino acid.txt file and is specifically incorporated by reference.

TECHNICAL FIELD

The present invention relates to the field of molecular biology. In particular, the present invention relates to splicing of truncated Tau proteins to form a phosphorylated polypeptide antigen vaccine. Preferably, this polypeptide antigen vaccine is connected with a suitable carrier to prepare a complex vaccine. The polypeptide antigen vaccine and the complex vaccine can be used for preventing and/or treating tauopathy comprising Alzheimer's disease (AD).

BACKGROUND ART

Alzheimer's disease (AD) is a progressive neurodegenerative disease which causes deficits in cognitive function and declines in learning, memory, language, and motor functions in AD patients. With the progression of the disease, AD patients show concomitant behavioral, emotional, interpersonal, and social deterioration. Late-stage AD patients are unable to speak, understand language, and take care of themselves. Several drugs currently approved can control or relieve complications and side effects from AD and improve AD patients' life quality. Nevertheless, there is still an unmet need for treatments that directly target the disease process and have improved therapeutic effects.

AD is histologically characterized by the deposition of extraneuronal plaques, intracellular and extracellular neurofibrillary tangles and loss of neurons in the brain. The results of numerous studies demonstrate that Tau proteins play an important role in AD pathology and are also the most downstream change in the pathological changes of AD. Studies show that Aβ neurotoxicity in cultured neurons appears to depend on Tau proteins; and a reduction in the amount of Tau proteins in a model of tauopathy can restore memory function thereof. In addition, a reduction in endogenous Tau proteins inhibits behavioral deficits in transgenic mice that express the human amyloid precursor, without altering their Aβ levels. Thus, therapies targeting Tau proteins can become an effective strategy for treating tauopathy comprising AD.

Tau proteins are microtubule-associated proteins. Tau proteins mediate the assembly of tubulin monomers into microtubules (MT) that constitute the neuronal microtubules network; Tau proteins carry nutrients and transmitters on microtubules through phosphorylation and dephosphorylation, which is significant for the proper formation and executive function of neuronal circuits. The binding of Tau to MT is controlled by dynamic phosphorylation and dephosphorylation, as demonstrated by experiments in vitro and in non-neuronal cells. When being hyperphosphorylated, Tau proteins will aggregate with each other and detach from the MT, and the MT will lose their stability so as to disintegrate themselves, thereby causing formation of neurofibrillary tangles (NFT) and neuronal loss.

Notwithstanding AD's prevalence in human beings, its pathogenesis has not been fully elucidated so far, and the current research and treatment methods have not yet met the needs. As demonstrated by experiments conducted in a tauopathy mouse model by Asuni et al., mice vaccinated with Tau protein derived phospho-peptide showed a reduction in neurofibrillary tangles and functional improvements. Although small molecules of short peptides can often interact with immune response products, they usually cannot elicit a response alone. These peptide immunogens are also called "haptens", which cannot, on their own, produce immunogenicity or cause the production of antibodies in the body, and can only be prepared into an immunogenic composition by coupling them with a suitable carrier. On the other hand, full-length recombinant Tau proteins expressed in a prokaryotic system do not seem to be suitable as a vaccine.

In view of the foregoing, there is a need in the art for the development of a method of effectively preventing and/or treating tauopathy.

SUMMARY OF THE INVENTION

With resepct to the aforementioned drawbacks, the present invention, based on human full-length Tau protein, designs phosphorylated polypeptide antigen vaccines, and complex vaccines which are formed by coupling the phosphorylated polypeptide antigen vaccines with suitable carriers for preventing and/or treating tauopathy comprising Alzheimer's disease (AD). The vaccine of the present invention has good safety and high immunogenicity, and can induce the production of high-titer antibodies.

In particular, the first aspect of the present invention provides a phosphorylated polypeptide antigen vaccine, which comprises at least two polypeptide fragments or conservative modified variants thereof from human full-length Tau protein, wherein the polypeptide fragments or conservative modified variants thereof contain phosphorylation sites. In some embodiments, the phosphorylated polypeptide antigen vaccine contains an additional cysteine residue at its C'-terminal.

In the context of the present invention, the term "phosphorylated polypeptide antigen vaccine" means a phosphorylated polypeptide, and can be used interchangeably with the term "phosphorylated polypeptide".

In some embodiments, the polypeptide fragments are derived from a phosphorylation modification site-rich region of human full-length Tau protein. In some preferred embodiments, the polypeptide fragments are derived from the following regions of human full-length Tau protein: amino acids at positions 14 to 22 of human full-length Tau protein, amino acids at positions 194 to 266 of human full-length Tau protein, and/or amino acids at positions 392 to 408 of human full-length Tau protein.

In some embodiments, the polypeptide fragments are connected directly by peptide bonds or connected by amino acid linkers. In preferred embodiments, the polypeptide fragments are connected directly by peptide bonds.

In some specific embodiments, the phosphorylation sites include two or more, preferably all phosphorylated amino acid sites corresponding to positions 18, 202, 205, 212, 214, 231, 235, 238, 262, 396 and 404 of the amino acid sequence of human full-length Tau protein, namely, 18(P-$Tyr_{18}$), 202(P-$Ser_{202}$), 205(P-$Thr_{205}$), 212(P-$Thr_{212}$), 214(P-$Ser_{214}$), 231(P-$Thr_{231}$), 235(P-$Ser_{235}$), 238(P-$Ser_{238}$), 262 (P-$Ser_{262}$), 396(P-$Ser_{396}$) and 404(P-$Ser_{404}$). In some preferred embodiments, 1 to 4, preferably 1 to 3, more preferably 1 to 2, and most preferably 1 Ser site of the phosphorylation sites are substituted by an aspartic acid and/or 1 to 4, preferably 1 to 3, more preferably 1 to 2, and most preferably 1 Thr site of the phosphorylation sites are substituted by a glutamic acid; the overall net charge of the polypeptide fragments or conservatively modified variants thereof thus obtained and the charge distribution on the molecules thereof remain substantially the same as those before the substitution. The simulation of phosphorylation by replacing phosphorylation sites with aspartic acids and/or glutamic acids is well known in the art.

In some embodiments, the conservatively modified variant of the polypeptide fragment contained in the phosphorylated polypeptide antigen vaccine of the present invention is a variant obtained by conservatively substitution of one or more amino acids, preferably 1 to 10 amino acids, more preferably 1 to 6 amino acids, more preferably 1 to 4 amino acids, more preferably 1 to 3 amino acids and most preferably 1 amino acid of the polypeptide fragment with functionally similar amino acids. The conservatively substitution is well known in the art and includes the following 6 groups of amino acids:

1) alanine (A), serine (S) and threonine (T);
2) aspartic acid (D) and glutamic acid (E);
3) asparagine (N) and glutamine (Q);
4) arginine (R) and lysine (K);
5) isoleucine (I), leucine (L), methionine (M) and valine (V); and
6) phenylalanine (F), tyrosine (Y) and tryptophan (W).

The overall net charge of the variant of the polypeptide fragment thus obtained and the charge distribution on the molecules thereof remain substantially the same as those before the substitution.

In some preferred embodiments, the phosphorylated polypeptide antigen vaccine has an amino acid sequence as represented by any one of SEQ ID NOs: 1-1331, and the amino acid sequence contains two or more phosphorylation sites selected from 18(P-$Tyr_{18}$), 202(P-$Ser_{202}$), 205(P-$Thr_{205}$), 212(P-$Thr_{212}$), 214(P-$Ser_{214}$), 231(P-$Thr_{231}$), 235 (P-$Ser_{235}$), 238(P-$Ser_{238}$), 262(P-$Ser_{262}$), 396(P-$Ser_{396}$) and 404(P-$Ser_{404}$). In some embodiments, the phosphorylated polypeptide antigen vaccine has an amino acid sequence which has at least 80%, at least 85%, at least 90%, at least 95%, preferably at least 98%, more preferably at least 99% sequence identity to any one of SEQ ID NOs: 1-1331, and the phosphorylated polypeptide antigen vaccine has basically the same immunogenic activity as the original phosphorylated polypeptide antigen vaccine, and the amino acid sequence contains two or more phosphorylation sites selected from 18(P-$Tyr_{18}$), 202(P-$Ser_{202}$), 205(P-$Thr_{205}$), 212(P-$Thr_{212}$), 214(P-$Ser_{214}$), 231(P-$Thr_{231}$), 235(P-$Ser_{235}$), 238(P-$Ser_{238}$), 262(P-$Ser_{262}$), 396(P-$Ser_{396}$) and 404(P-$Ser_{404}$).

In a more preferred embodiment, the phosphorylated polypeptide antigen vaccine has an amino acid sequence as represented by any one of SEQ ID NO: 201, SEQ ID NO: 225, SEQ ID NO: 306, SEQ ID NO: 387, SEQ ID NO: 468, SEQ ID NO: 558, SEQ ID NO: 567, SEQ ID NO: 769, SEQ ID NO: 784, SEQ ID NO: 875, SEQ ID NO: 1020, SEQ ID NO: 1101, SEQ ID NO: 1182, SEQ ID NO: 1272, SEQ ID NO: 1313 and SEQ ID NO: 1330, and the amino acid sequence contains two or more phosphorylation sites selected from 18(P-$Tyr_{18}$), 202(P-$Ser_{202}$), 205(P-$Thr_{205}$), 212(P-$Thr_{212}$), 214(P-$Ser_{214}$), 231(P-$Thr_{231}$), 235(P-$Ser_{235}$), 238(P-$Ser_{238}$), 262(P-$Ser_{262}$), 396(P-$Ser_{396}$) and 404(P-$Ser_{404}$). In some embodiments, the phosphorylated polypeptide antigen vaccine has an amino acid sequence which has at least 80%, at least 85%, at least 90%, at least 95%, preferably at least 98%, and more preferably at least 99% sequence identity to any one of the above sequences, and the phosphorylated polypeptide antigen vaccine has basically the same immunogenic activity as the original phosphorylated polypeptide antigen vaccine, and the amino acid sequence contains two or more phosphorylation sites selected from 18(P-$Tyr_{18}$), 202(P-$Ser_{202}$), 205(P-$Thr_{205}$), 212(P-$Thr_{212}$), 214(P-$Ser_{214}$), 231(P-$Thr_{231}$), 235(P-$Ser_{235}$), 238(P-$Ser_{238}$), 262(P-$Ser_{262}$), 396(P-$Ser_{396}$) and 404(P-$Ser_{404}$).

In a particularly specific embodiment, the phosphorylated polypeptide antigen vaccine has an amino acid sequence as represented by any one of SEQ ID NO: 201, SEQ ID NO: 225, SEQ ID NO: 306, SEQ ID NO: 387, SEQ ID NO: 468, SEQ ID NO: 558, SEQ ID NO: 567, SEQ ID NO: 769, SEQ ID NO: 784, SEQ ID NO: 875, SEQ ID NO: 1020, SEQ ID NO: 1101, SEQ ID NO: 1182, SEQ ID NO: 1272, SEQ ID NO: 1313 and SEQ ID NO: 1330, and the amino acid sequence respectively contains the following phosphorylation sites: 18(P-$Tyr_{18}$), 202(P-$Ser_{202}$), 205(P-$Thr_{205}$); 18(P-$Tyr_{18}$), 202(P-$Ser_{202}$), 205(P-$Thr_{205}$); 18(P-$Tyr_{18}$), 212 (P-$Thr_{212}$), 214(P-$Ser_{214}$); 18(P-$Tyr_{18}$), 231(P-$Thr_{231}$), 235 (P-$Ser_{235}$); 18(P-$Tyr_{18}$), 238(P-$Ser_{238}$), 262(P-$Ser_{262}$); 18(P-$Tyr_{18}$), 396(P-$Ser_{396}$), 404(P-$Ser_{404}$); 202(P-$Ser_{202}$), 205(P-$Thr_{205}$), 231(P-$Thr_{231}$), 235(P-$Ser_{235}$); 202(P-$Ser_{202}$), 205 (P-$Thr_{205}$), 231(P-$Thr_{231}$), 235(P-$Ser_{235}$); 202(P-$Ser_{202}$), 205(P-$Thr_{205}$), 238(P-$Ser_{238}$), 262(P-$Ser_{262}$); 202(P-$Ser_{202}$), 205(P-$Thr_{205}$), 396(P-$Ser_{396}$), 404(P-$Ser_{404}$); 202(P-$Ser_{202}$), 205(P-$Thr_{205}$), 396(P-$Ser_{396}$), 404(P-$Ser_{404}$); 212(P-$Thr_{212}$), 214(P-$Ser_{214}$), 231(P-$Thr_{231}$), 235(P-$Ser_{235}$); 212 (P-$Thr_{212}$), 214(P-$Ser_{214}$), 238(P-$Ser_{238}$), 262(P-$Ser_{262}$); 212(P-$Thr_{212}$), 214(P-$Ser_{214}$), 396(P-$Ser_{396}$), 404(P-$Ser_{404}$); 238(P-$Ser_{238}$), 262(P-$Ser_{262}$), 396(P-$Ser_{396}$), 404(P-$Ser_{404}$); 238(P-$Ser_{238}$), 262(P-$Ser_{262}$), 396(P-$Ser_{396}$) and 404(P-$Ser_{404}$).

The second aspect of the present invention provides a complex vaccine formed by coupling the phosphorylated polypeptide antigen vaccine of the first aspect of the present invention with a carrier.

In some embodiments, the carrier is selected from the group comprising human serum albumin, keyhole limpet hemocyanin, bacterium-like particles (BLP), immunoglobulin molecules, thyroglobulin, ovalbumin, bovine serum albumin component V, influenza hemagglutinin, PAN-DR binding peptide (PADRE polypeptide), malaria circumsporozoite (CS) protein, hepatitis B surface antigen ($HB_sAg_{19-28}$), Heat Shock Protein (HSP) 65, Bacille Calmette-Guérin (BCG), cholera toxin, attenuated cholera toxin variants, diphtheria toxin, norovirus capsid P protein, recombinant *Streptococcus* C5a peptidase, *Streptococcus pyogenes* ORF1224, *Streptococcus pyogenes* ORF1664, *Streptococcus pyogenes* ORF2452, pneumolysin, attenuated pneumolysin toxicity variants, *Chlamydia pneumoniae* ORFT367, *Chlamydia pneumoniae* ORFT858, Tetanus toxoid, HIV gp120T1, microbial surface components recognizing adhesive matrix molecules (MSCRAMMS), growth factor/hormone and chemokines, etc. Complex vaccines formed by coupling or mixing with carriers can, to the greatest extent, stimulate the body to produce a specific immune response against phosphorylated polypeptides.

In some preferred embodiments, the carrier is norovirus capsid P protein.

The term "norovirus capsid P protein", herein also referred to as P protein, refers to the P protein in the norovirus capsid proteins, which can self-assemble in vitro into a P particle. When used herein, P protein used at the gene level means a gene fragment, nucleotide sequence, plasmid, etc. encoding a P protein; P protein used at the protein level means a P protein monomer or polymer.

The term P particle (abbreviated as PP) refers to a protein particle formed by the in vitro self-assembly of P protein in norovirus. The most common form of P particle is a tetracosamer. When used herein, P particle (PP) is only used at the protein level and means the form of polymer (such as a tetracosamer), including various proteins used for property detection and immunization.

In some specific embodiments, one amino acid in each of the three loops in loop domain of the norovirus capsid P protein is mutated to a cysteine to facilitate chemical connection with the phosphorylated polypeptide vaccine. The norovirus capsid P protein modified with this mutation was named PP-3C (whose sequence is represented by SEQ ID NO: 1357), wherein the mutation would not result in a frameshift mutation of the norovirus P protein.

In other specific embodiments, a lysine is inserted into each of the three loops in loop domain of the norovirus P protein to facilitate chemical coupling with spliced phosphorylated polypeptide. The norovirus capsid P protein modified with this mutation was named PP-3K (whose sequence is represented by SEQ ID NO: 1359), wherein the mutation would not result in a frameshift mutation of the norovirus P protein.

In other preferred embodiments, the carrier is bacterium-like particles (BLP).

In some specific embodiments, the BLP is coupled with a phosphorylated polypeptide antigen vaccine by means of a protein adaptor (PA); specifically, the BLP is connected with a PA (a GGGGSCGGGGS sequence is added to the N-terminal of the PA) (i.e., C-PA) through covalent binding to obtain C-PA-BLP, and then C-PA-BLP is coupled with a phosphorylated polypeptide antigen vaccine which contains a cysteine at the C-terminal.

The term "bacterium-like particles (BLP)" refers to a new mucosal adjuvant which is obtained by hot acid treatment of *Lactococcus lactis*, and is an inanimate spherical particle with a *Lactococcus lactis* peptidoglycan shell as its main component. BLP particles, as a carrier for vaccine antigen components, can be effectively bound to the antigen and display the antigen on its surface. The peptidoglycan shell of BLP itself activates the innate immune system by interacting with Toll-like receptors to function as an adjuvant. BLP can be obtained by methods known in the art.

The term "protein adaptor (PA)" refers to PA protein, which is a full-length or truncated sequence in the *Lactococcus lactis* cell wall hydrolase ACMA cell wall binding region. The PA protein used in the present invention is a product (i.e., a C-PA protein) obtained by adding a GGGGSCGGGGS sequence to the N-terminal of the amino acid sequence from positions 219 to 437 of the *Lactococcus lactis* cell wall hydrolase ACMA (GenBank: U17696.1), and has a sequence as represented by SEQ ID NO: 1364.

The third aspect of the present invention provides a method for preparing the complex vaccine of the second aspect of the present invention, the method comprising the following steps:

1) artificially synthesizing the phosphorylated polypeptide antigen vaccine of the first aspect of the present invention;
2) preparing a carrier to be coupled with the phosphorylated polypeptide antigen vaccine;
3) mixing the phosphorylated polypeptide antigen vaccine with the carrier to preform coupling reaction; and
4) separating and purifying the conjugate obtained in 3), thereby obtaining a complex vaccine.

In some embodiments, the carrier in step 2) of the method is a norovirus capsid P protein, preferably PP-3C or PP-3K, and step 2) specifically includes i) obtaining an expression vector comprising a nucleic acid encoding a PP-3C or PP-3K protein;
ii) transferring the expression vector into a recipient cell;
iii) expressing the PP-3C or PP-3K protein, and allowing it to self-assemble into a recombinant P particle in the recipient cell;

preferably, step 2) also comprises isolation and purification steps. In some specific embodiments, ion exchange chromatography and/or hydrophobic chromatography can be used for purification.

In some embodiments, in step 3) of the method, PP-3C is used as a vaccine carrier for coupling, a preferred buffer system is an ammonium bicarbonate buffer system, and a preferred pH ranges from 7.5 to 8.8; preferably, the phosphorylated polypeptide antigen vaccine and the carrier are mixed in a ratio of 10:1 to 100:1, and a preferred reaction temperature ranges from 2° C. to 10° C.

In some embodiments, in step 3) of the method, PP-3K is used as a vaccine carrier for coupling, a preferred buffer system is a phosphate buffer system, and a preferred pH ranges from 7.0 to 8.5; preferably, the phosphorylated polypeptide antigen vaccine and the carrier are mixed in a ratio of 10:1 to 100:1, and a preferred reaction temperature ranges from 2° C. to 25° C.

In other embodiments, the carrier in step 2) of the method is bacterium-like particles (BLP). In some embodiments, step 3) of the method specifically comprises i) obtaining a purified protein adaptor—C-PA protein (whose sequence is represented by SEQ ID NO: 1364); ii) connecting the carrier—bacterium-like particles (BLP)—obtained in step 2) with the C-PA protein to obtain C-PA-BLP; and iii) preforming coupling reaction of C-PA-BLP with the phosphorylated polypeptide antigen vaccine; wherein a Tris buffer system is used as a buffer system, and a preferred pH ranges from 7.2 to 8.8; a preferred C-PA protein concentration is 0.1 mg/mL to 1.5 mg/mL, and a preferred reaction temperature ranges from 2° C. to 30° C. In some embodiments, the buffer system used in step 3) of the method is an ammonium bicarbonate buffer system, and a preferred pH ranges from 7.5 to 8.8; preferably, the phosphorylated polypeptide antigen vaccine and the C-PA-BLP are mixed in a ratio of 10:1 to 100:1, and a preferred reaction temperature ranges from 2° C. to 10° C.

In some embodiments, step 4) of the method comprises removing carriers and polypeptide antigens which are not successfully connected by methods including centrifugation, dialysis, and ultrafiltration.

The fourth aspect of the present invention provides a vaccine composition comprising the phosphorylated polypeptide antigen vaccine of the first aspect of the present invention or the complex vaccine of the second aspect of the present invention. Preferably, the vaccine composition further comprises pharmaceutically acceptable adjuvants.

In some embodiments, the pharmaceutically acceptable adjuvants are selected from one or more of CpG, MF59, AS02, AS03, Freund's complete adjuvant and Freund's incomplete adjuvant.

The fifth aspect of the present invention provides use of the phosphorylated polypeptide antigen vaccine of the first aspect of the present invention or the complex vaccine of the second aspect of the present invention or the vaccine composition of the fourth aspect of the present invention for preparing a medicament for prevention and/or treatment of neurodegenerative disorders.

In the present inventimon, the "neurodegenerative disorders" include, but not limited to, AD, Creutzfeldt-Jacob Syndrome, Dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis/parkinsonism syndrome-dementia syndrome, argyrophilic grain dementia, corticobasal degeneration, diffuse neurofibrillary tangles with calcification, frontotemporal dementia with parkinsonism syndrome linked to chromosome 17, Hallevorden-Spatz disease, multiple system atrophy, Niemann-Pick disease type C, Pick's disease, progressive subcortical gliosis and progressive supranuclear panencephalitis; preferably the "neurodegenerative disorder" is AD.

In some embodiments, the vaccine or vaccine composition is preferably immunized subcutaneously, intraperitoneally or intramuscularly, and more preferably immunized intramuscularly.

The sixth aspect of the present invention provides use of the phosphorylated polypeptide antigen vaccine of the first aspect of the present invention or the complex vaccine of the second aspect of the present invention or the vaccine composition of the fourth aspect of the present invention for preparing a medicament for maintaining or improving, preferably recovering, and more preferably completely recovering the cognitive memory of mammals, especially human beings.

The seventh aspect of the present invention provides a method for treating or preventing neurodegenerative disorders, comprising administering to a subject the phosphorylated polypeptide antigen vaccine of the first aspect of the present invention or the complex vaccine of the second aspect of the present invention or the vaccine composition of the fourth aspect of the present invention.

In some embodiments, the subject is a mammal, preferably a human.

In some embodiments, the vaccine or vaccine composition is preferably administered subcutaneously, intraperitoneally or intramuscularly, and more preferably administered intramuscularly.

The eighth aspect of the present invention provides a method for maintaining or improving, preferably recovering, and more preferably completely recovering the cognitive memory of a subject, the method comprising administering to the subject the phosphorylated polypeptide antigen vaccine of the first aspect of the present invention or the complex vaccine of the second aspect of the present invention or the vaccine composition of the fourth aspect of the present invention.

The ninth aspect of the present invention provides a norovirus capsid P protein to be coupled with the phosphorylated polypeptide antigen vaccine of the first aspect of the present invention, wherein one amino acid in each of the three loops in loop domain of the norovirus capsid P protein is mutated to a cysteine—the P protein thus obtained is called PP-3C (with a sequence as represented by SEQ ID NO: 1357), or a lysine is inserted into each of the three loops in loop domain of the norovirus capsid P protein—the P protein thus obtained is called PP-3K (with a sequence as represented by SEQ ID NO: 1359).

The tenth aspect of the present invention provides a method for preparing the norovirus capsid P protein of the ninth aspect of the present invention, comprising the following steps:

i) obtaining an expression vector comprising a nucleic acid encoding a PP-3C or PP-3K protein;
ii) transferring the expression vector into a recipient cell;
iii) expressing the PP-3C or PP-3K protein, and allowing it to self-assemble into a recombinant P particle in the recipient cell;

preferably, the method also comprises isolation and purification steps. In some specific embodiments, ion exchange chromatography and/or hydrophobic chromatography can be used for purification.

The eleventh aspect of the present invention provides a protein adaptor with a GGGGSCGGGGS sequence inserted at its N-terminal—the protein adaptor thus obtained is C-PA (whose sequence is represented by SEQ ID NO: 1364).

The twelfth aspect of the present invention provides a method for preparing the protein adaptor of the eleventh aspect of the present invention, comprising the following steps:

i) obtaining an expression vector comprising a nucleic acid encoding a C-PA protein;
ii) transferring the expression vector into a host cell; and
iii) expressing the C-PA protein, and obtaining the C-PA protein by isolating and purifying.

BRIEF DESCRIPTION OF DRAWINGS

FIG. 1A is a schematic diagram of pET26b-PP plasmid that has been constructed; FIG. 1B is a schematic diagram of pET26b-PP-3C plasmid that has been constructed; FIG. 1C is a schematic diagram of pET28a-PP plasmid that has been constructed; FIG. 1D is a schematic diagram of pET28a-PP-3K plasmid that has been constructed; FIG. 1E is a schematic diagram of pColdIV-PP-3C plasmid that has been constructed.

FIG. 2A is a schematic diagram of a PP-3C particle. FIG. 2B is a schematic diagram of identification of pET26b—PP-3C plasmid that has been constructed by double-enzyme digestion; as shown in FIG. 2B, the target band is at 1,000 bp. FIG. 2C is a diagram of native gel electrophoresis of PP-3C and PP-3K protein samples; as shown in FIG. 2C, both of the protein bands appeared above 250 kDa, and it is determined from analysis that they are in the form of a dodecamer and a tetracosamer.

FIG. 3A is a schematic diagram of a PP-3K particle. FIG. 3B is a schematic diagram of identification of pET28a-PP-3K plasmid that has been constructed by double-enzyme digestion; as shown in FIG. 3B, the target band is at 1,000 bp. FIG. 3C is a SDS-PAGE graph of the target protein elution peak protein sample; as shown in FIG. 3C, the target proteins were enriched at 35 kDa.

FIG. 6A shows the levels of anti-Tau14-22 (pY18) IgG antibodies produced in WT mice immunized with the vaccines A1 to A16; each group contained 6 mice; each group of mice was immunized four times at two-week intervals using complete Freund's adjuvant for the first immunization and incomplete Freund's adjuvant for the second, third and fourth immunization; two weeks after the fourth immunization, the mice were subjected to blood sampling to obtain mouse serum for ELISA experiment; the results were expressed as the mean O.D.+SD values obtained by each group of mice. FIG. 6B shows the levels of anti-Tau198-209 (pS202/pT205) IgG antibodies produced in WT mice immunized with the vaccines A1 to A16; each group contained 6 mice; each group of mice was immunized four times at two-week intervals using complete Freund's adjuvant for the first immunization and incomplete Freund's adjuvant for the second, third and fourth immunization; two weeks after the fourth immunization, the mice were subjected to blood sampling to obtain mouse serum for ELISA experiment; the results were expressed as the mean O.D.+SD values obtained by each group of mice. FIG. 6C shows the levels of anti-Tau208-218 (pT212/pS214) IgG antibodies produced in WT mice immunized with the vaccines A1 to A16; each group contained 6 mice; each group of mice was immunized four times at two-week intervals using complete Freund's adjuvant for the first immunization and incomplete Freund's adjuvant for the second, third and fourth immunization; two weeks after the fourth immunization, the mice were subjected to blood sampling to obtain mouse serum for ELISA experiment; the results were expressed as the mean O.D.+SD values obtained by each group of mice. FIG. 6D shows the levels of anti-Tau227-239 (pS231/pS235) IgG antibodies produced in WT mice immunized with the vaccines A1 to A16; each group contained 6 mice; each group of mice was immunized four times at two-week intervals using complete Freund's adjuvant for the first immunization and incomplete Freund's adjuvant for the second, third and fourth immunization; two weeks after the fourth immunization, the mice were subjected to blood sampling to obtain mouse serum for ELISA experiment; the results were expressed as the mean O.D.+SD values obtained by each group of mice. FIG. 6E shows the levels of anti-Tau234-242 (pS238) IgG antibodies produced in WT mice immunized with the vaccines A1 to A16; each group contained 6 mice; each group of mice was immunized four times at two-week intervals using complete Freund's adjuvant for the first immunization and incomplete Freund's adjuvant for the second, third and fourth immunization; two weeks after the fourth immunization, the mice were subjected to blood sampling to obtain mouse serum for ELISA experiment; the results were expressed as the mean O.D.+SD values obtained by each group of mice. FIG. 6F shows the levels of anti-Tau258-266 (pS262) IgG antibodies produced in WT mice immunized with the vaccines A1 to A16; each group contained 6 mice; each group of mice was immunized four times at two-week intervals using complete Freund's adjuvant for the first immunization and incomplete Freund's adjuvant for the second, third and fourth immunization; two weeks after the fourth immunization, the mice were subjected to blood sampling to obtain mouse serum for ELISA experiment; the results were expressed as the mean O.D.+SD values obtained by each group of mice. FIG. 6G shows the levels of anti-Tau392-400 (pS396) IgG antibodies produced in WT mice immunized with the vaccines A1 to A16; each group contained 6 mice; each group of mice was immunized four times at two-week intervals using complete Freund's adjuvant for the first immunization and incomplete Freund's adjuvant for the second, third and fourth immunization; two weeks after the fourth immunization, the mice were subjected to blood sampling to obtain mouse serum for ELISA experiment; the results were expressed as the mean O.D.+SD values obtained by each group of mice. FIG. 6H shows the levels of anti-Tau401-408 (pS404) IgG antibodies produced in WT mice immunized with the vaccines A1 to A16; each group contained 6 mice; each group of mice was immunized four times at two-week intervals using complete Freund's adjuvant for the first immunization and incomplete Freund's adjuvant for the second, third and fourth immunization; two weeks after the fourth immunization, the mice were subjected to blood sampling to obtain mouse serum for ELISA experiment; the results were expressed as the mean O.D.+SD values obtained by each group of mice.

FIG. 7A shows the results of intramuscular immunization of WT mice with A1 coupled with a norovirus P protein; the contents of anti-Tau14-22 (pY18) IgG antibodies and anti-Tau198-209 (pS202/pT205) IgG antibodies in the mouse serum were detected by ELISA method; the results were expressed as the mean O.D.+SD values obtained at a dilution of 1/200 of the mouse serum.

IgG antibodies in the mouse serum were detected by ELISA method; the results were expressed as the mean O.D.+SD values obtained at a dilution of 1/200 of the mouse serum. FIG. 7S shows the results of subcutaneous immunization of WT mice with A16 coupled with a norovirus P protein; the contents of anti-Tau234-242 (pS238) IgG antibodies, anti-Tau258-266 (pS262) IgG antibodies, anti-Tau392-400 (pS396) IgG antibodies and anti-Tau401-408 (pS404) IgG antibodies in the mouse serum were detected by ELISA method; the results were expressed as the mean O.D.+SD values obtained at a dilution of 1/200 of the mouse serum.

FIG. 9A shows the results of immunization of WT mice with phosphorylated polypeptide antigen A5 coupled with PP-3K and combined with AS02+CpG adjuvant; the content of antibodies in the mouse serum against the phosphorylated polypeptide with a sequence of SEQ ID NO: 1355 was detected. The results were expressed as the mean O.D.+SD value obtained at different dilutions of the mouse serum. FIG. 9B shows the results of immunization of P301S mice with phosphorylated polypeptide antigen A5 coupled with PP-3K and combined with AS02+CpG adjuvant; the content of antibodies in the mouse serum against the phosphorylated polypeptide with a sequence of SEQ ID NO: 1355 was detected. The results were expressed as the mean O.D.+SD value obtained at different dilutions of the mouse serum. FIG. 9C shows the results of immunization of P301S mice with phosphorylated polypeptide antigen A11 coupled with PP-3C and combined with AS02+CpG adjuvant; the content of antibodies in the mouse serum against the phosphorylated polypeptide with a sequence of SEQ ID NO: 1354 was detected. The results were expressed as the mean O.D.+SD value obtained at different dilutions of the mouse serum. FIG. 9D shows the results of immunization of P301S mice with phosphorylated polypeptide antigen A11 coupled with PP-3K and combined with AS02+CpG adjuvant; the content of antibodies in the mouse serum against the phosphorylated polypeptide with a sequence of SEQ ID NO: 1354 was detected. The results were expressed as the mean O.D.+SD value obtained at different dilutions of the mouse serum. FIG. 9E shows the results of immunization of WT mice with phosphorylated polypeptide antigen A12 coupled with PP-3K and combined with AS02+CpG adjuvant; the content of antibodies in the mouse serum against the phosphorylated polypeptide with a sequence of SEQ ID NO: 1356 was detected. The results were expressed as the mean O.D.+SD value obtained at different dilutions of the mouse serum. FIG. 9F shows the results of immunization of P301S mice with phosphorylated polypeptide antigen A12 coupled with PP-3K and combined with AS02+CpG adjuvant; the content of antibodies in the mouse serum against the phosphorylated polypeptide with a sequence of SEQ ID NO: 1356 was detected. The results were expressed as the mean O.D.+SD value obtained at different dilutions of the mouse serum.

FIG. 10A shows the ELISPOT results for PP-3K-A5 complex vaccine in P301S transgenic mice; the results were expressed as the number of IFN-γ spots generated per $10^6$ cells when the animal spleen cells in different immune groups were stimulated by a prokaryotically expressed full-length Tau protein stimulus. FIG. 10B shows the ELISPOT results for PP-3K-A5 complex vaccine in P301S transgenic mice; the results were expressed as the number of IFN-γ spots generated per $10^6$ cells when the animal spleen cells in different immune groups were stimulated by a nonphosphorylated A5 polypeptide stimulus. FIG. 10C shows the ELISPOT results for PP-3K-A11 complex vaccine in P301S transgenic mice; the results were expressed as the number of IFN-γ spots generated per $10^6$ cells when the animal spleen cells in different immune groups were stimulated by a prokaryotically expressed full-length Tau protein stimulus. FIG. 10D shows the ELISPOT results for PP-3K-A11 complex vaccine in P301S transgenic mice; the results were expressed as the number of IFN-γ spots generated per $10^6$ cells when the animal spleen cells in different immune groups were stimulated by a nonphosphorylated A11 polypeptide stimulus. FIG. 10E shows the ELISPOT results for PP-3C-A11 complex vaccine in P301S transgenic mice; the results were expressed as the number of IFN-γ spots generated per $10^6$ cells when the animal spleen cells in different immune groups were stimulated by a prokaryotically expressed full-length Tau protein stimulus. FIG. 10F shows the ELISPOT results for PP-3C-A11 complex vaccine in P301S transgenic mice; the results were expressed as the number of IFN-γ spots generated per $10^6$ cells when the animal spleen cells in different immune groups were stimulated by a nonphosphorylated A11 polypeptide stimulus. FIG. 10G shows the ELISPOT results for PP-3K-A12 complex vaccine in P301S transgenic mice; the results were expressed as the number of IFN-γ spots generated per $10^6$ cells when the animal spleen cells in different immune groups were stimulated by a prokaryotically expressed full-length Tau protein stimulus. FIG. 10H shows the ELISPOT results for PP-3K-A12 complex vaccine in P301S transgenic mice; the results were expressed as the number of IFN-γ spots generated per $10^6$ cells when the animal spleen cells in different immune groups were stimulated by a nonphosphorylated A12 polypeptide stimulus.

FIG. 11A shows the results of the rota-rod experiment for PP-3K-A5 complex vaccine in P301S transgenic mice; the results are expressed as curves of the average time until mice fell from the rota-rod within 300 s versus the detection time points for animals in different immune groups. FIG. 11B shows the results of the rota-rod experiment for PP-3C-A11 complex vaccine in P301S transgenic mice; the results are expressed as curves of the average time until mice fell from the rota-rod within 300 s versus the detection time points for animals in different immune groups. FIG. 11C shows the results of the rota-rod experiment for PP-3K-A11 complex vaccine in P301S transgenic mice; the results are expressed as curves of the average time until mice fell from the rota-rod within 300 s versus the detection time points for animals in different immune groups. FIG. 11D shows the results of the rota-rod experiment for PP-3K-A12 complex vaccine in P301S transgenic mice; the results are expressed as curves of the average time until mice fell from the rota-rod within 300 s versus the detection time points for animals in different immune groups.

FIG. 12A shows the results of the nesting test for PP-3K-A5 complex vaccine in P301S transgenic mice; the results are expressed as the average of the scores given by three persons for each mouse in the nesting test. The results show that the mice in the immune group are statistically significantly different from the PBS group. FIG. 12B shows the results of the nesting test for PP-3C-A11 complex vaccine in P301S transgenic mice; the results are expressed as the average of the scores given by three persons for each mouse in the nesting test. The results show that the mice in the immune group are statistically significantly different from the PBS group. FIG. 12C shows the results of the nesting test for PP-3K-A11 complex vaccine in P301S transgenic mice; the results are expressed as the average of the scores given by three persons for each mouse in the nesting test. The results show that the mice in the immune group are statistically significantly different from the PBS group. FIG. 12D shows the results of the nesting test for PP-3K-A12 complex vaccine in P301S transgenic mice; the results are expressed as the average of the scores given by three persons for each mouse in the nesting test. The results show that the mice in the immune group are statistically significantly different from the PBS group.

FIG. 13A shows the HPLC diagram when the concentration of the standard was 0.03125 mg/mL; the peak labelled in the figure is the peak position of the standard. FIG. 13B exemplarily shows the HPLC diagram of the phosphorylated polypeptide dissociated from the phosphorylated polypeptide sample coupled with PP-3C prepared in Example 4-2; the peak labelled in the figure is the peak position of the sample. FIG. 13C exemplarily shows the HPLC diagram of the phosphorylated polypeptide dissociated from the phosphorylated polypeptide sample coupled with C-PA-BLP prepared in Example 33; the peak labelled in the figure is the peak position of the sample. FIG. 13D shows a graph of a standard curve of the concentration of the standard versus the peak area.

FIG. 15A is a schematic diagram of identification of pET28a-C-PA plasmid that has been constructed by double-enzyme digestion; as shown in FIG. 15A, the target band is at 700 bp. FIG. 15B is a SDS-PAGE graph of a C-PA protein sample; as shown in FIG. 15B, the protein band appeared around 24 kDa.

DETAILED DESCRIPTION OF THE INVENTION

Figure 1A:
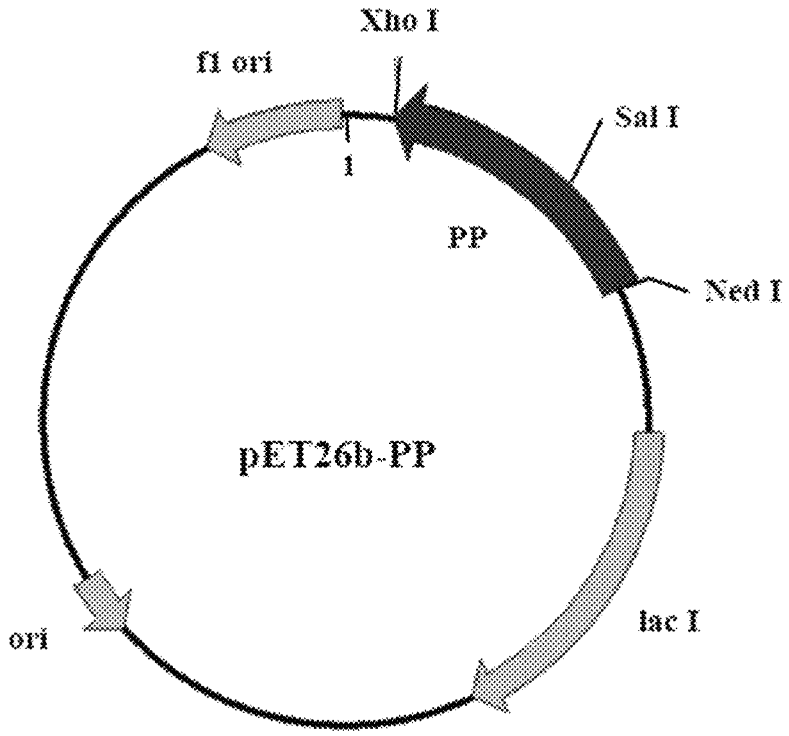
FIGS. 1A to 1E show the maps of the various recombinant plasmid constructs.

The content of the present invention is illustrated below through specific embodiments. It should be understood that the specific embodiments are for illustrative purposes only, and do not mean that the content of the present invention is limited to the specific embodiments.

Example 1: Preparation of Phosphorylated Polypeptide Antigen Vaccines

In this example, based on human full-length Tau protein (SEQ ID NO: 1332), the inventor designed the following 15 phosphorylated polypeptide antigen vaccines comprising two polypeptide fragments from the human full-length Tau protein; the specific sequence information of the 15 phosphorylated polypeptide antigen vaccines is shown in Table 1 below:

TABLE 1

Sequence information of the 15 phosphorylated polypeptide antigen vaccines

| Sequence No. | Vaccine No. | Sequences | The corresponding full-length Tau protein fragmets and phosphorylation sites |
|---|---|---|---|
| SEQ ID NO: 201 | A1 | HAGTYGLGDSSPGSP GTPGSRC | Tau14-22[pY18], Tau198-209[pS202, pT205] |
| SEQ ID NO: 225 | A2 | HAGTYGLGDRSGYSS PGSPGTPGSRSRTPC | Tau14-22[pY18], Tau194-213[pS202, pT205] |
| SEQ ID NO: 306 | A3 | HAGTYGLGDSRSRTP SLPTPC | Tau14-22[pY18], Tau208-218[pT212, pS214] |
| SEQ ID NO: 387 | A4 | HAGTYGLGDAVVRTPP KSPSSAC | Tau14-22[pY18], Tau227-239[pT231, pS235] |
| SEQ ID NO: 468 | A5 | HAGTYGLGDKSPSSA KSRSKIGSTENLC | Tau14-22[pY18], Tau234-242[pS238], Tau258-266[pS262] |
| SEQ ID NO: 558 | A6 | HAGTYGLGDIVYKSPV VSGDTSPRHLC | Tau14-22[pY18], Tau392-408[pS396, pS404] |
| SEQ ID NO: 567 | A7 | SSPGSPGTPGSRAVV RTPPKSPSSAC | Tau198-209[pS202, pT205], Tau227-239[pT231, pS235] |
| SEQ ID NO: 769 | A8 | SGYSSPGSPGTPGSR SRTPVVRTPPKSPSSAC | Tau195-213[pS202, pT205], Tau228-239[pT231, pS235] |
| SEQ ID NO: 784 | A9 | SSPGSPGTPGSRKSP SSAKSRSKIGSTENLC | Tau198-209[pS202, pT205], Tau234-242[pS238], Tau258-266[pS262] |
| SEQ ID NO: 875 | A10 | SSPGSPGTPGSRIVYK SPVVSGDTSPRHLC | Tau198-209[pS202, pT205], Tau395-406[pS396, pS404] |
| SEQ ID NO: 1020 | A11 | SGYSSPGSPGTPGSR SRTPKSPVVSGDTSPRC | Tau195-213[pS202, pT205], Tau395-406[PS396, pS404] |
| SEQ ID NO: 1101 | A12 | SRSRTPSLPTPAVVRT PPKSPSSAC | Tau208-218[pT212, pS214], Tau227-239[pT231, pS235] |
| SEQ ID NO: 1182 | A13 | SRSRTPSLPTPKSPSS AKSRSKIGSTENLC | Tau208-218[pT212, pS214], Tau234-242[pS238], Tau258-266[pS262] |
| SEQ ID NO: 1272 | A14 | SRSRTPSLPTPIVYKSP VVSGDTSPRHLC | Tau208-218[pT212, pS214], Tau392-408[pS396, pS404] |

TABLE 1-continued

Sequence information of the 15 phosphorylated polypeptide antigen vaccines

| Sequence No. | Vaccine No. | Sequences | The corresponding full-length Tau protein fragmets and phosphorylation sites |
|---|---|---|---|
| SEQ ID NO: 1313 | A15 | SPSSAKSRSKIGSTEN VYKSPVVSGDTSPRH C | Tau235-242[pS238], Tau258-265[pS262], Tau393-407[pS396, pS404] |
| SEQ ID NO: 1330 | A16 | KSPSSAKSRSKIGSTE NLKSPVVSGDTSPRC | Tau234-242[pS238], Tau258-266[pS262], Tau395-406[pS396, pS404] |

The aforementioned 15 phosphorylated polypeptide antigen vaccines were synthesized and prepared by GL biochem (Shanghai) Ltd., and are presented in lyophilized form.

Example 2: Preparation of a Cysteine-Modified Norovirus P Protein (PP-3C)

The preparation of norovirus P protein plasmid using pET26b(+) as a vector has been described in Chinese invention patent application 2015104155561. In this example, three point mutations were performed using this plasmid as a template, one amino acid in each of the three loop structures of the norovirus P particle was mutated to a cysteine, and the protein was expressed and purified.

2.1 Construction of PP-3C Plasmid

Three rounds of site-directed mutagenesis were performed by site-directed mutation method using the pET26b-P protein plasmid which has already been constructed in Chinese invention patent application 2015104155561. Respectively, 5'ATCGCTGGAACACAA3" in loop1 was mutated to 5'ATCGCTTGCACACAA3'. The specific method was as follows:

```
SEQ ID NO: 1334 (forward):
CTGTGAACATCGCTACTTTCCGCGGCGACGTCACACACATCGCTTGCAC

ACAAAACTAC,
and

SEQ ID NO: 1335 (reverse):
GTAGTTTTGTGTGCAAGCGATGTGTGTGACGTCGCCGCGGAAAGTAGCG

ATGTTCACAG;
```

the entire plasmid was subjected to PCR reaction, wherein the PCR reaction system was a KOD-Plus DNA polymerase system (purchased from TOYOBO Corporation), and the total volume of the reaction system was 50 μL (5 μL buffer, 0.2 mM dNTP, 1 mM magnesium sulfate, 0.3 μM upstream primer and 0.3 μM downstream primer, 50 ng template DNA, 1 μL KOD enzyme, and water which was added to a final volume of 50 μL). PCR was carried out in accordance with the reaction system instructions to obtain 20 μL of PCR products. 1 μL of DpnI enzyme (purchased from NEB Corporation) was added to the PCR products. Digestion was carried out at 37° C. for 1 h. 10 μL of the digested products were added to Tran1-Blue competent cells (purchased from Beijing TransGen Biotech, Ltd.), and placed on ice for 30 min. After that, the cells were subjected to heat shock at 42° C. for 45 s, placed on ice for 2 min and then were added to 600 μL of fluid LB medium without resistance, and recovered at 200 rpm at 37° C. for 1 h. The culture broth was plated on a LB solid culture plate containing kanamycin (15 μg/mL), and were placed upside down at 37° C. overnight. The mutant plasmid clones were obtained, and the sequence was verified by sequencing.

The plasmid obtained by the first round of point mutation was subjected to a second round of point mutation. 5'ACCTCAAACGAT3' in loop2 was mutated to 5'ACCTGCAACGA3'. The specific method was as follows:

```
SEQ ID NO: 1336 (forward):
GCAATTCAGCACAGACACCTGCAACGATTTCGAGACTGGCC,
and

SEQ ID NO: 1337 (reverse):
GGCCAGTCTCGAAATCGTTGCAGGTGTCTGTGCTGAATTGC;
```

the entire plasmid was subjected to PCR reaction, wherein the PCR reaction system was a KOD-Plus DNA polymerase system (purchased from TOYOBO Corporation), and the total volume of the reaction system was 50 μL (5 μL buffer, 0.2 mM dNTP, 1 mM magnesium sulfate, 0.3 μM upstream primer and 0.3 μM downstream primer, 50 ng template DNA, 1 μL KOD enzyme, and water which was added to a final volume of 50 μL). PCR was carried out in accordance with the reaction system instructions to obtain 20 μL of PCR products. 1 μL of DpnI enzyme (purchased from NEB Corporation) was added to the PCR products. Digestion was carried out at 37° C. for 1 h. 10 μL of the digested products were added to Tran1-Blue competent cells (purchased from Beijing TransGen Biotech, Ltd.), and placed on ice for 30 min. After that, the cells were subjected to heat shock at 42° C. for 45 s, placed on ice for 2 min. and then were added to 600 μL of fluid LB medium without resistance, and recovered at 200 rpm at 37° C. for 1 h. The culture broth was plated on a LB solid culture plate containing kanamycin (15 μg/mL), and were placed upside down at 37° C. overnight. The mutant plasmid clones were obtained, and the sequence was verified by sequencing.

The plasmid obtained by the second round of point mutation was subjected to a third round of point mutation. 5'GACGGCAGCACC3' in loop3 was mutated to 5'GACTGCAGCACC3'. The specific method was as follows:

```
SEQ ID NO: 1338 (forward):
CCGTGGGTGTCGTTCAAGACTGCAGCACCACTCACCAGAACG,
and

Figure 1B:
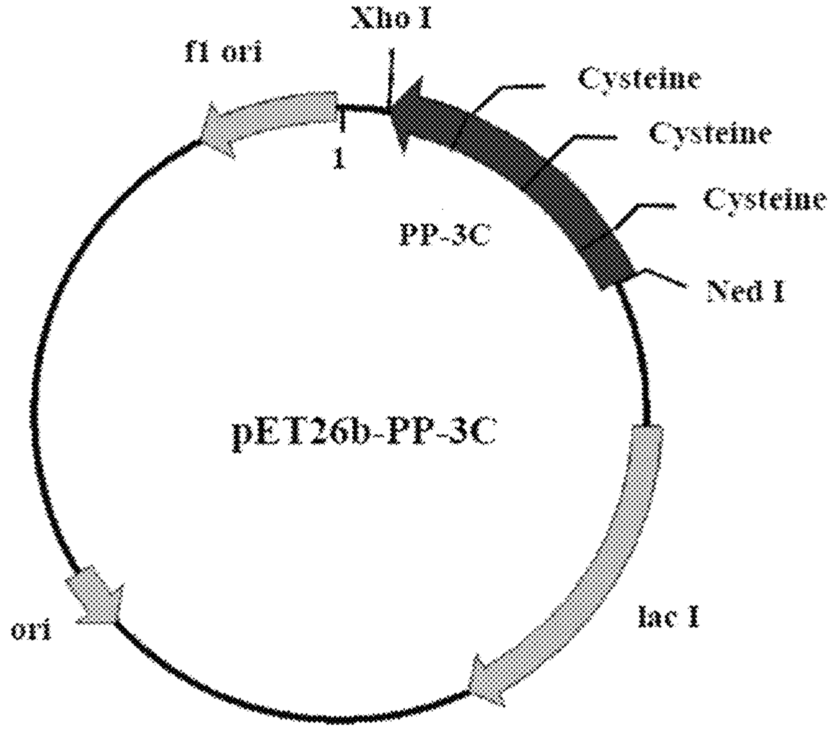

SEQ ID NO: 1339 (reverse):
CGTTCTGGTGAGTGGTGCTGCAGTCTTGAACGACACCCACGG;
``` the entire plasmid was subjected to PCR reaction, wherein the PCR reaction system was a KOD-Plus DNA polymerase system (purchased from TOYOBO Corporation), and the total volume of the reaction system was 50 μL (5 μL buffer, 0.2 mM dNTP, 1 mM magnesium sulfate, 0.3 UM upstream primer and 0.3 μM downstream primer, 50 ng template DNA, 1 μL KOD enzyme, and water which was added to a final volume of 50 μL). PCR was carried out in accordance with the reaction system instructions to obtain 20 μL of PCR products. 1 μL of DpnI enzyme (purchased from NEB Corporation) was added to the PCR products. Digestion was carried out at 37° C. for 1 h. 10 μL of the digested products were added to Tran1-Blue competent cells (purchased from Beijing TransGen Biotech, Ltd.), and placed on ice for 30 min. After that, the cells were subjected to heat shock at 42° C. for 45 s, placed on ice for 2 min. and then were added to 600 μL of fluid LB medium without resistance, and recovered at 200 rpm at 37° C. for 1 h. The culture broth was plated on a LB solid culture plate containing kanamycin (15 μg/mL), and were placed upside down at 37° C. overnight. The mutant plasmid clones were obtained, and the sequence was verified by sequencing. The resulting plasmid of pET26b-PP-3C is shown in FIG. 1B.

2.2 Construction of the P Protein that has been Successfully Mutated, Namely the PP-3C Gene, on a pCold IV Carrier An EcoR I restriction site was introduced at the 5' end of the PP-3C gene (whose sequence is represented by SEQ ID NO: 1358) by PCR method, and a Hind Ill restriction site was introduced at the 3' end. The specific method was as follows:

```
SEQ ID NO: 1340 (forward):
GGGAATTCCATATGAAGCCCTTCTCGGTCCCTATCCTGACAG,
and

SEQ ID NO: 1341 (reverse):
CCCAAGCTTTTACAAGGCTCTGCGACGACCGGCTC;
```

the pET26b-PP-3C plasmid obtained above was subjected to PCR reaction, wherein the PCR reaction system was a KOD-Plus DNA polymerase system (purchased from TOYOBO Corporation), and the total volume of the reaction system was 50 μL (5 μL buffer, 0.2 mM dNTP, 1 mM magnesium sulfate, 0.3 UM upstream primer and 0.3 μM downstream primer, 50 ng template DNA, 1 μL KOD enzyme, and water which was added to a final volume of 50 μL). PCR was carried out in accordance with the reaction system instructions to obtain 50 μL of PCR products. The products were subjected to agarose gel electrophoresis, and the fragments of interest were recovered using gel recovery kit (purchased from Tiangen Biotech Co., Ltd.) to obtain a PP-3C gene fragment with an EcoRI restriction site at the 5' end and a Hind III restriction site at the 3' end.

1 μL of Hind III enzyme and 1 μL of EcoR I enzyme (purchased from Takara Corporation) and 5 μL of enzyme digestion buffer (purchased from Takara Corporation) were added respectively to 2 μg of the aforementioned recovered fragment, and finally sterile water was added to the system to reach a final volume of 50 μL. Digestion was carried out at 37° C. for 2 hours. The products were purified using common DNA product purification kit (purchased from Tiangen Biotech Co., Ltd.) to obtain the fragment of interest having sticky ends.

Figure 1C:
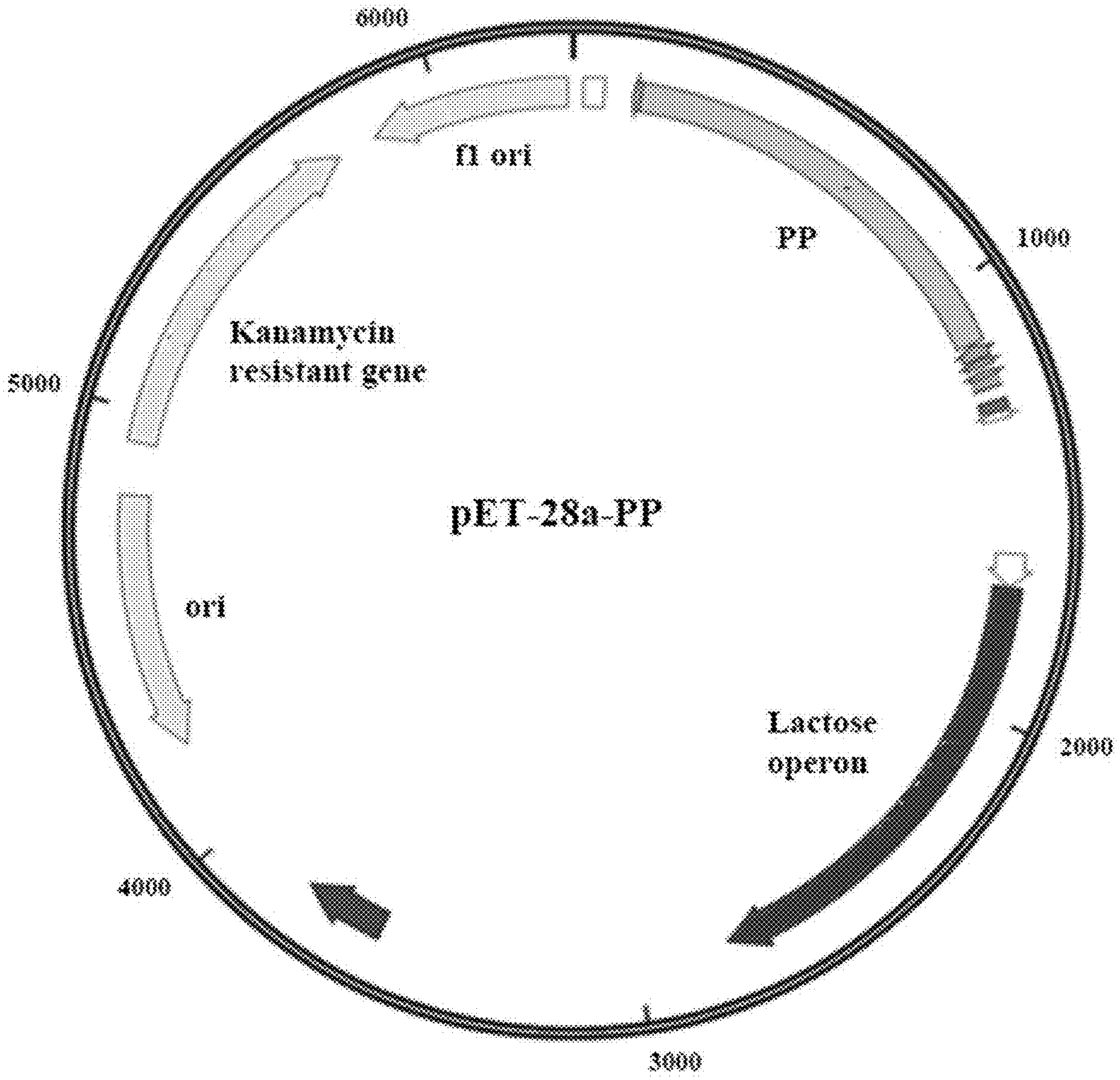
Figure 1D:
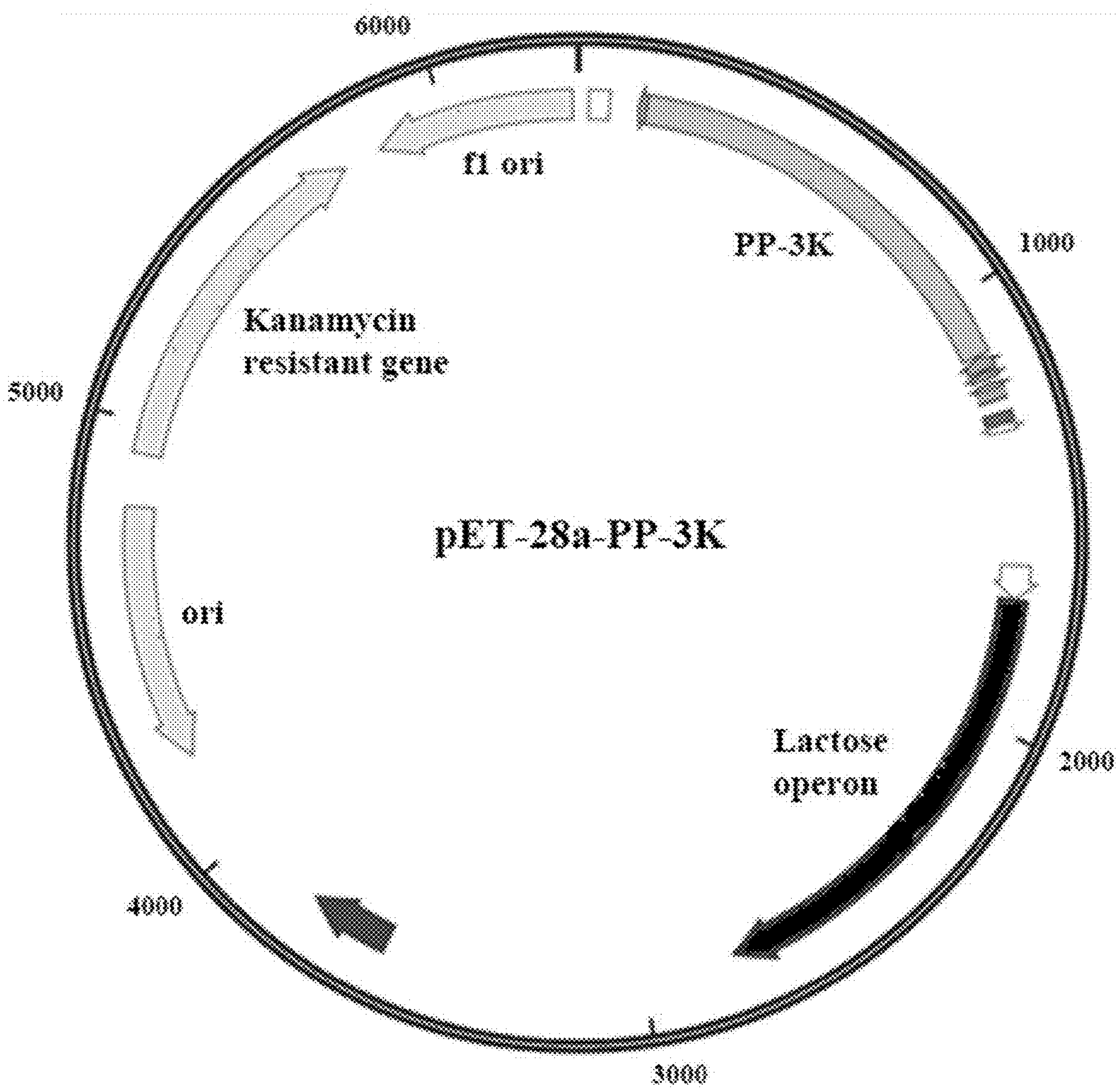
Figure 1E:
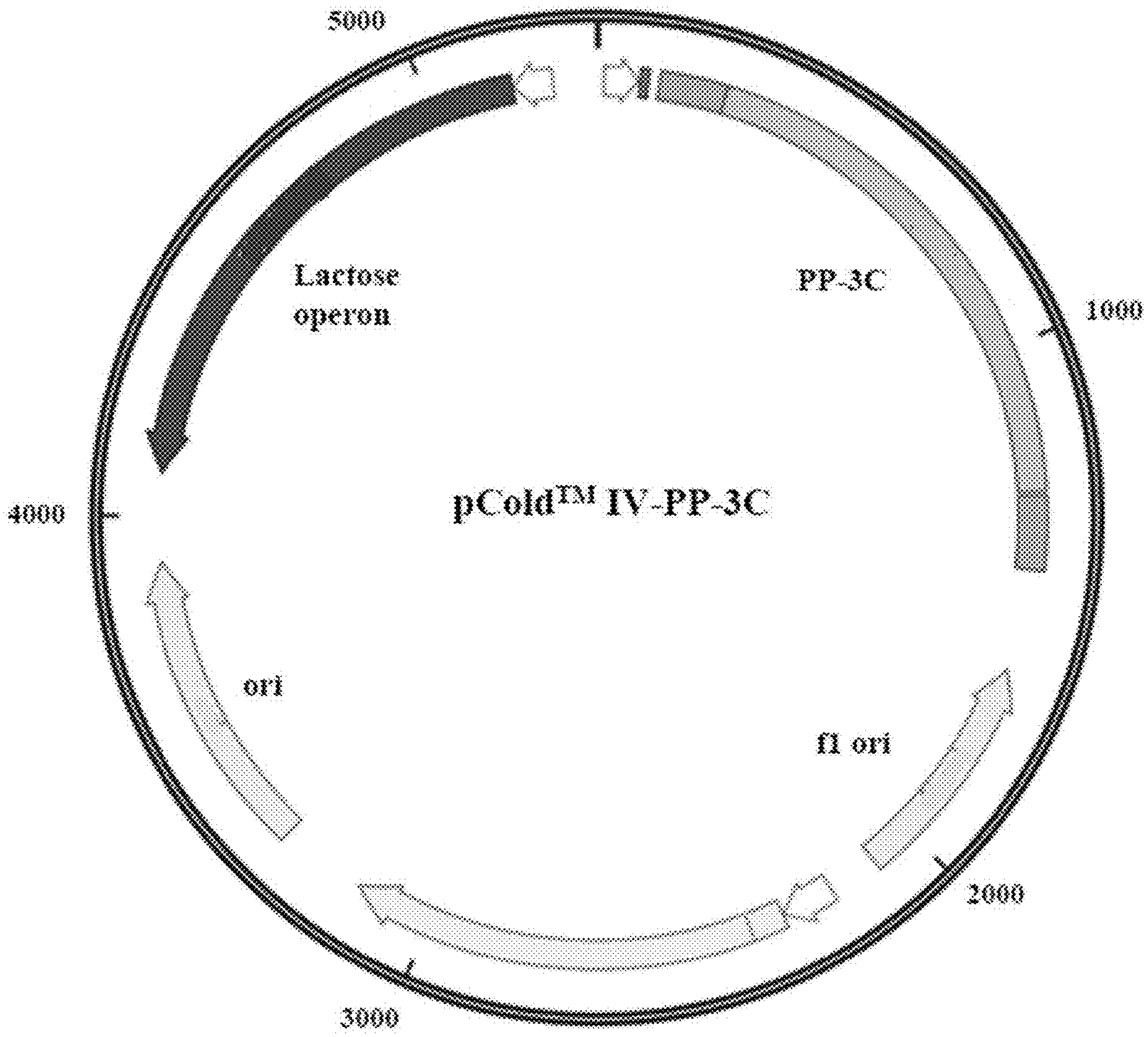

1 μL of Hind III enzyme and 1 μL of EcoR I enzyme (purchased from Takara Corporation) and 5 μL of enzyme digestion buffer (purchased from Takara Corporation) were added respectively to 2 μg of pCold IV vector plasmid (purchased from Novagen Corporation), and finally sterile water was added to the system to reach a final volume of 50 μL. Digestion was carried out at 37° C. for 2 hours. The products were subjected to agarose gel electrophoresis, and the vector fragments were recovered using gel recovery kit (purchased from Tiangen Biotech Co., Ltd.) to obtain a plasmid vector having double enzyme-digested sticky ends The above double enzyme-digested vector fragment and fragment of interest (with a molar ratio of 1:3, and a total volume of 15 μL) were mixed, and 0.75 μL of T4 ligase (purchased from Takara Corporation) and 1.5 μL of ligase buffer (purchased from Takara Corporation) were added. The ligation was carried out at 16° C. overnight. 10 μL of the ligated products were added to Tran1-Blue competent cells (purchased from Beijing TransGen Biotech, Ltd.), and placed on ice for 30 min. After that, the cells were subjected to heat shock at 42° C. for 45 s, placed on ice for 2 min, and then were added to 600 μL of fluid LB medium without resistance, and recovered at 200 rpm at 37° C. for 1 h. The culture broth was plated on a LB solid culture plate containing ampicillin (15 μg/mL), and were placed upside down at 37° C. overnight. The recombinant clones were obtained, and the sequence was verified by sequencing. A pColdIV-PP-3C plasmid that can express PP-3C protein was obtained, as shown in FIG. 1E.

2.3 Expression of the Cysteine-Modified Norovirus P Protein

1 μL of the recombinant plasmids prepared in the above examples were respectively added to 100 μL of *E. coli* BL21 competent cells (purchased from TransGen Corporation), ice-bathed for 30 min, heat shocked for 90 s in a water-bath at 42° C., and then ice-bathed for 2 min. 600 UL of LB medium was added to the mixture, and cultured at 180 rpm/min at 37° C. for 1 h. The mixture was coated evenly on a LB solid medium containing kanamycin (15 μg/mL) resistance and cultured at 37° C. for 24 h to obtain strains that can stably express recombinant proteins. A growing colony was picked and inoculated into 20 mL of LB medium. The mixture was cultured at 220 rpm at 37° C. When the OD value of the culture mixture reached 1.0, induction by Isopropyl β-D-Thiogalactoside (IPTG at a final concentration of 0.5 mmol/L) was carried out at 220 rpm at 16° C. overnight. After the induction, the culture broth was centrifuged at 4,000 rpm for 20 min. The supernatant was discarded, and the bacterial precipitates were resuspended with PBS. Centrifugation was conducted again at 4,000 rpm for 20 min and the supernatant was discarded to obtain the bacterial precipitates containing proteins of interest.

2.4 Purification of the Cysteine-Modified Norovirus P Protein

The bacterial precipitates obtained in 2.3 were resuspended by adding 20 mL of protein buffer (pH8.0, containing 50 mM Tris and 300 mM KCl). The bacteria were lysed by sonication on ice for 30 min. The mixture was centrifuged at 12,000 rpm at 4° C. for 30 min. Subsequently, the supernatant was taken and allowed to pass through 0.45 μm filter membrane to obtain crude extracts of proteins.

Figure 2A:
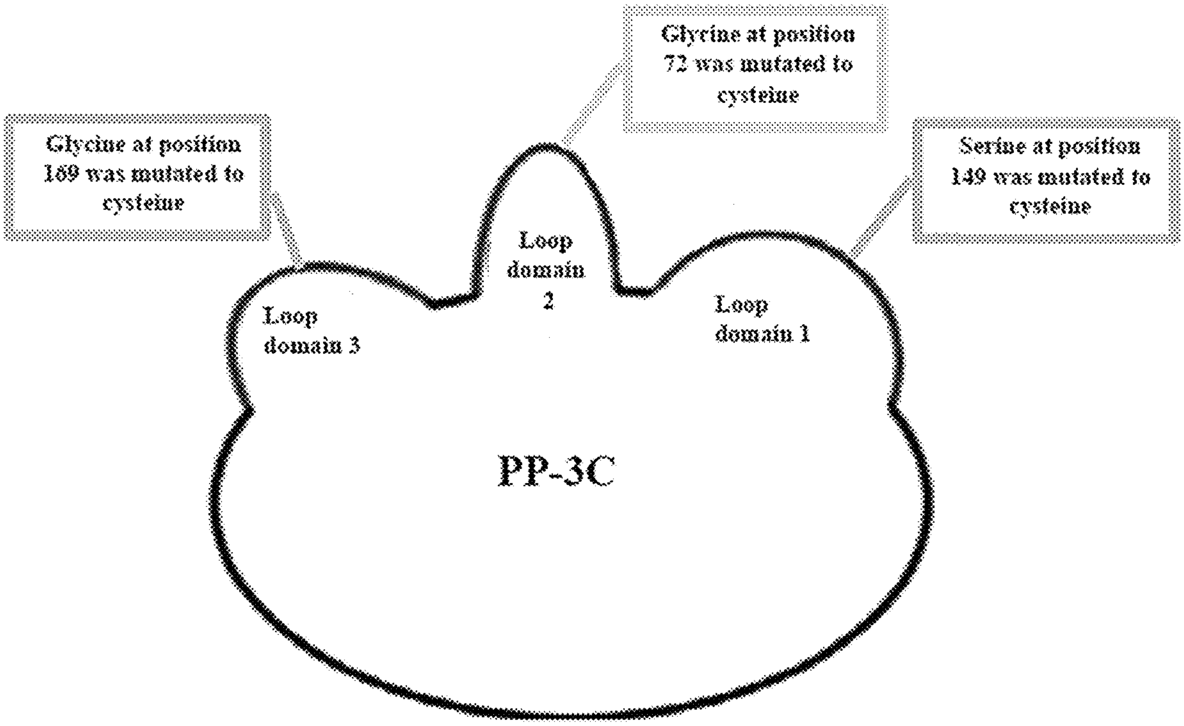
FIGS. 2A to 2C show the recombinant pET26b plasmid construct and the results of purification and expression.
Figure 2B:
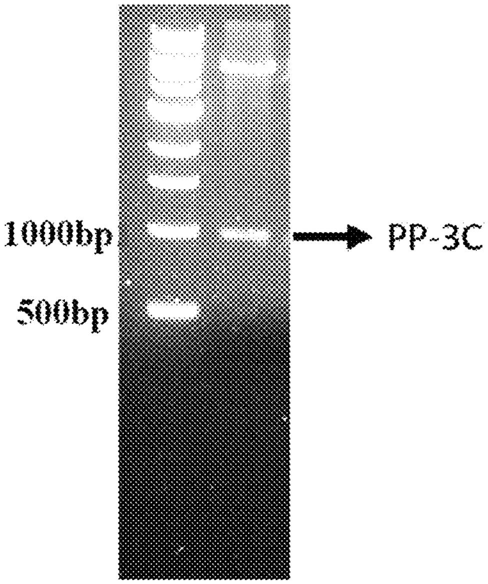

The structure of the recombinant PP-3C particle protein is shown in FIG. 2A.

The crude extracts of proteins were purified using an anion exchange column (purchased from GE Corporation). The specific scheme was as follows: First, the exchange column was rinsed with ultrapure water in a volume of about 100 mL, followed by equilibration with PB solution (pH 5.0) at a flow rate of 2 mL/min. Then 20 mL of the crude extracts of proteins were added to the exchange column at a flow rate of 1 ml/min. After the sample was completely loaded onto the column, the exchange column was rinsed with PB solution (pH 7.0) to remove hybrid protein, and then eluted with PB solution containing 0.5 mol/L NaCl. The proteins at peak value were collected to obtain the proteins of interest.

The proteins were further purified by a hydrophobic chromatography column (purchased from GE Corporation). The specific scheme was as follows: First, the column was rinsed with ultrapure water, and then the hydrophobic column was rinsed with PB solution (pH 7.0) at a flow rate of 2 mL/min. After the column was equilibrated well, the protein sample was loaded onto it. After the sample was completely loaded onto the column, the column was eluted by gradient with PB (pH 7.0) and 1 mol/L NaCl solution for 2 hours. The concentration of NaCl decreases from 1 mol/L to 0.1 mol/L. The proteins were collected at peak value.

The sizes of the resulting P particle protein monomers were identified by reductive SDS-PAGE.

Figure 2C:
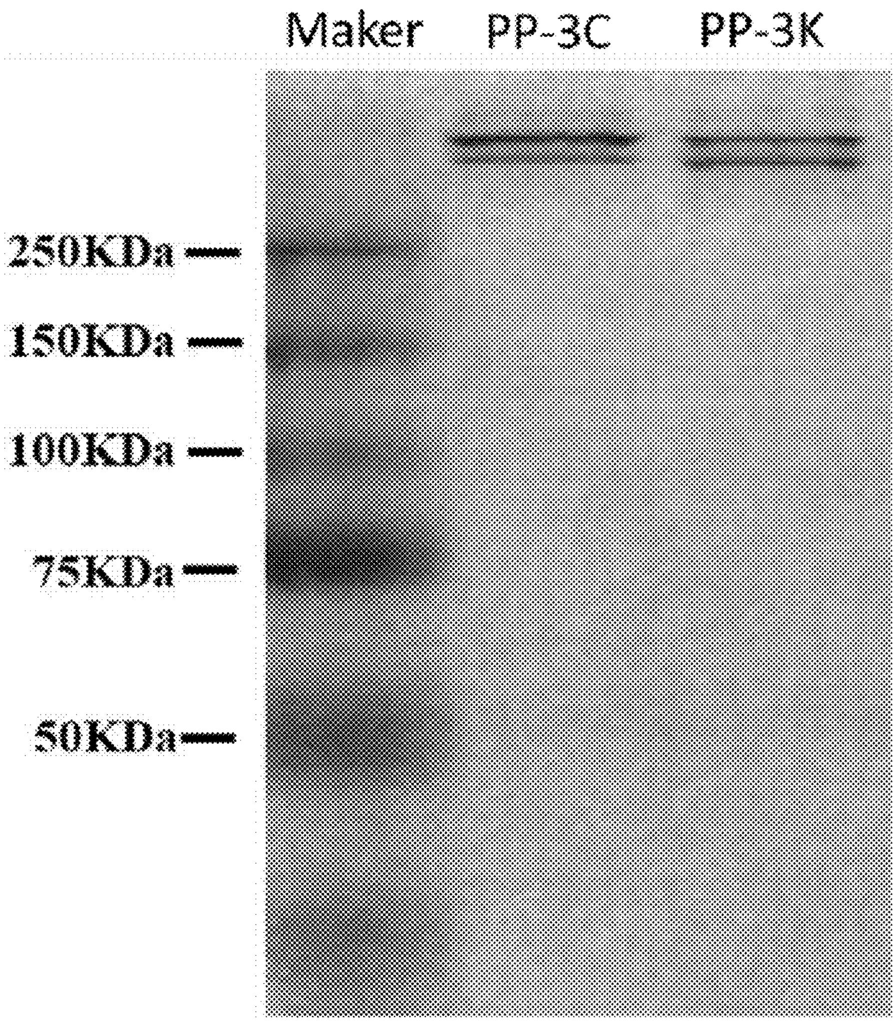
Figure 4:
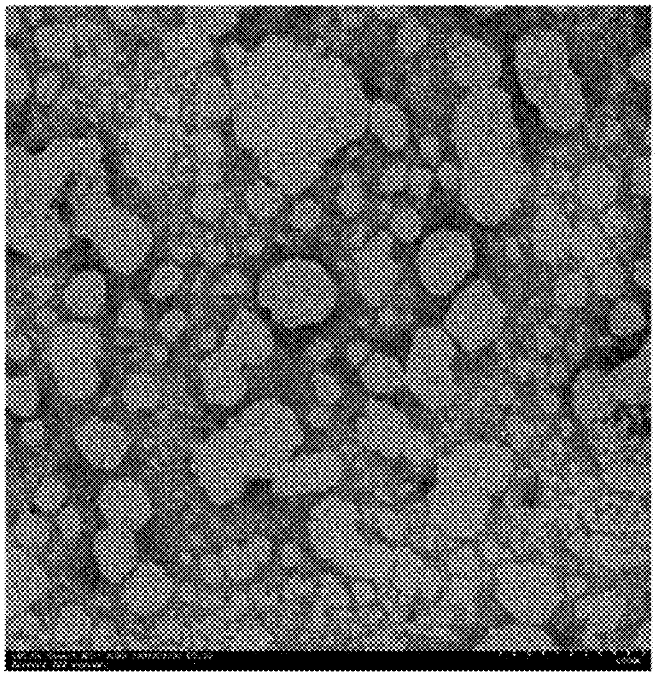
FIG. 4 shows an electron microscope image of recombinant pET28a-PP-3K protein particles.

Then the tetracosamers of P protein particles were further isolated and purified using a Superdex 200 molecular sieve (purchased from GE Corporation). The procedures were as follows: The column was rinsed with ultrapure water at a flow rate of 1 mL/min for one volume of the column, and then again with about 120 mL of PB buffer (pH=5). After that, 2 mL of protein extraction solution was added to the column and washed with PB buffer at a flow rate of 1 mL/min. The proteins at peak value were collected to obtain the tetracosamers of P particle proteins. Three proteins were tested for their polymer structures by native polyacrylamide gel electrophoresis. As shown in FIG. 2C, the protein bands are above 250 KDa, which indicates that recombinant P proteins can self-assemble into dodecamers and tetracosamers of P protein particles in vitro and maintain equilibrium; and the proteins can remain their polymer form after being purified. Electron microscopy analysis of purified PP-3C protein particles showed that PP-3C mostly formed large particle aggregates (as shown in FIG. 4).

Example 3: Preparation of a Lysine-Modified Norovirus P Protein (PP-3K)

In this example, three point mutations were performed using the norovirus P protein plasmid (which was obtained by constructing the PP gene in the pET26b-PP plasmid provided in the Chinese patent application for invention 2015104155561 into pET28a by homologous recombination method) as a template, a lysine is inserted into each of the three loops loop structure of the norovirus P particle, and the protein was expressed and purified.

3.1 Construction of pET28a-PP Plasmid

The PP genes in pET 26b-PP plasmid were enriched by PCR method. The specific method was as follows:

```
SEQ ID NO: 1361 (forward):
AACTTTAAGAAGGAGATATACCATGGGCAAGCCCTTCTCGGTCCCTA,
and

SEQ ID NO: 1362 (reverse):
CGGATCTCAGTGGTGGTGGTGGTGGTGCTCGAGTTACAAGGCTCTGCG

ACGACCGGC;
```

the pET26b-P protein plasmid was subjected to PCR reaction, wherein the PCR reaction system was a KOD-Plus DNA polymerase system (purchased from TOYOBO Corporation), and the total volume of the reaction system was 50 μL (5 μL buffer, 0.2 mM dNTP, 1 mM magnesium sulfate, 0.3 μM upstream primer and 0.3 μM downstream primer, 50 ng template DNA, 1 μL KOD enzyme, and water which was added to a final volume of 50 μL). PCR was carried out in accordance with the reaction system instructions to obtain 50 μL of PCR products. The products were subjected to agarose gel electrophoresis, and the fragments of interest were recovered using gel recovery kit (purchased from Tiangen Biotech Co., Ltd.).

1 μL of BamHI enzyme and 1 μL of XhoI enzyme (purchased from Takara Corporation) and 5 μL of enzyme digestion buffer (purchased from Takara Corporation) were added respectively to 2 μg of pET28a vector plasmid (purchased from Novagen Corporation), and finally sterile water was added to the system to reach a final volume of 50 μL. Digestion was carried out at 37° C. for 2 hours. The products were subjected to agarose gel electrophoresis, and the vector fragments were recovered using gel recovery kit (purchased from Tiangen Biotech Co., Ltd.) to obtain a linear plasmid vector.

The above double enzyme-digested vector fragment and fragment of interest (with a molar ratio of 1:3, and a total volume of 5 μL) were mixed, and 5 μL of homologous recombination mix (purchased from Taihe Corporation) was added. The ligation was carried out at 25° C. for 15 min. 10 μL of the ligated products were added to DH10B competent cells (purchased from Taihe Corporation), and placed on ice for 30 min. After that, the cells were subjected to heat shock at 42° C. for 30 s, placed on ice for 2 min. and then were added to 600 μL of fluid LB medium without resistance, and recovered at 200 rpm at 37° C. for 1 h. The culture broth was plated on a LB solid culture plate containing kanamycin (15 μg/mL), and were placed upside down at 37° C. overnight. The recombinant clones were obtained, and the sequence was verified by sequencing. A pET28a-PP plasmid that can express PP protein was obtained, as shown in FIG. 1C.

3.2 Construction of PP-3K Plasmid

Three rounds of site-directed mutagenesis were performed by site-directed mutation method using the pET28a-PP plasmid which has already been constructed. Respectively, 5' CGCTGGAACACAAA3' in loop1 was mutated to 5' CGCTGGAAAGACACAAA3'. The specific method was as follows:

```
SEQ ID NO: 1340 (forward):
GACGTCACACACATCGCTGGAAAGACACAAAACTACACCATGAAC,
and

SEQ ID NO: 1341 (reverse):
GTTCATGGTGTAGTTTTGTGTCTTTCCAGCGATGTGTGTGACGTC;
```

the entire plasmid was subjected to PCR reaction, wherein the PCR reaction system was a KOD-Plus DNA polymerase system (purchased from TOYOBO Corporation), and the total volume of the reaction system was 50 μL (5 μL buffer, 0.2 mM dNTP, 1 mM magnesium sulfate, 0.3 μM upstream primer and 0.3 μM downstream primer, 50 ng template DNA, 1 μL KOD enzyme, and water which was added to a final volume of 50 μL). PCR was carried out in accordance with the reaction system instructions to obtain 20 μL of PCR products. 1 μL of DpnI enzyme (purchased from NEB Corporation) was added to the PCR products. Digestion was carried out at 37° C. for 1 h. 10 μL of the digested products were added to Tran1-Blue competent cells (purchased from Beijing TransGen Biotech, Ltd.), and placed on ice for 30 min. After that, the cells were subjected to heat shock at 42° C. for 45 s, placed on ice for 2 min, and then were added to 600 μL of fluid LB medium without resistance, and recovered at 200 rpm at 37° C. for 1 h. The culture broth was plated on a LB solid culture plate containing kanamycin (15

μg/mL), and were placed upside down at 37° C. overnight. The mutant plasmid clones were obtained, and the sequence was verified by sequencing.

The PCR product obtained by the first round of site-directed mutation was subjected to a second round of site-directed mutation. 5' ACCTCAAACGAT 3' in loop2 was mutated to 5' ACCTCAAAGAACGAT3'. The specific method was as follows:

```
SEQ ID NO: 1342 (forward):
CAATTCAGCACAGACACCTCAAAGAACGATTTCGAGACTGGCCAG,
and

SEQ ID NO: 1343 (reverse):
CTGGCCAGTCTCGAAATCGTTCTTTGAGGTGTCTGTGCTGAATTG;
```

the entire plasmid was subjected to PCR reaction, wherein the PCR reaction system was a KOD-Plus DNA polymerase system (purchased from TOYOBO Corporation), and the total volume of the reaction system was 50 μL (5 μL buffer, 0.2 mM dNTP, 1 mM magnesium sulfate, 0.3 μM upstream primer and 0.3 μM downstream primer, 50 ng template DNA, 1 μL KOD enzyme, and water which was added to a final volume of 50 μL). PCR was carried out in accordance with the reaction system instructions to obtain 20 μL of PCR products. 1 μL of DpnI enzyme (purchased from NEB Corporation) was added to the PCR products. Digestion was carried out at 37° C. for 1 h. 10 μL of the digested products were added to Tran1-Blue competent cells (purchased from Beijing TransGen Biotech, Ltd.), and placed on ice for 30 min. After that, the cells were subjected to heat shock at 42° C. for 45 s, placed on ice for 2 min, and then were added to 600 μL of fluid LB medium without resistance, and recovered at 200 rpm at 37° C. for 1 h. The culture broth was plated on a LB solid culture plate containing kanamycin (15 μg/mL), and were placed upside down at 37° C. overnight. The mutant plasmid clones were obtained, and the sequence was verified by sequencing.

The PCR product obtained by the second round of site-directed mutation was subjected to a third round of site-directed mutation. 5' GACGGCAGCACC 3' in loop3 was mutated to 5' GACGGCAGCACC3'. The specific method was as follows:

```
SEQ ID NO: 1344 (forward):
GTGGGTGTCGTTCAAGACGGCAAGAGCACCACTCACCAGAACGAA,
and

SEQ ID NO: 1345 (reverse):
TTCGTTCTGGTGAGTGGTGCTCTTGCCGTCTTGAACGACACCCAC;
```

the entire plasmid was subjected to PCR reaction, wherein the PCR reaction system was a KOD-Plus DNA polymerase system (purchased from TOYOBO Corporation), and the total volume of the reaction system was 50 μL (5 μL buffer, 0.2 mM dNTP, 1 mM magnesium sulfate, 0.3 μM upstream primer and 0.3 μM downstream primer, 50 ng template DNA, 1 μL KOD enzyme, and water which was added to a final volume of 50 μL). PCR was carried out in accordance with the reaction system instructions to obtain 20 μL of PCR products. 1 μL of DpnI enzyme (purchased from NEB Corporation) was added to the PCR products. Digestion was carried out at 37° C. for 1 h. 10 μL of the digested products were added to Tran1-Blue competent cells (purchased from Beijing TransGen Biotech, Ltd.), and placed on ice for 30 min. After that, the cells were subjected to heat shock at 42° C. for 45 s, placed on ice for 2 min. and then were added to 600 μL of fluid LB medium without resistance, and recovered at 200 rpm at 37° C. for 1 h. The culture broth was plated on a LB solid culture plate containing kanamycin (15 μg/mL), and were placed upside down at 37° C. overnight. The mutant plasmid clones were obtained, and the sequence was verified by sequencing (the sequence of the PP-3K gene is represented by SEQ ID NO: 1360). The pET28a-P protein-3K plasmid is shown as FIG. 1D.

3.3 Expression of the Lysine-Modified Norovirus P Protein

1 μL of the recombinant plasmids prepared in the above examples were respectively added to 100 μL of *E. coli* BL21 competent cells (purchased from TransGen Corporation), ice-bathed for 30 min, heat shocked for 90 s in a water-bath at 42° C., and then ice-bathed for 2 min. 600 UL of LB medium was added to the mixture, and cultured at 180 rpm/min at 37° C. for 1 h. The mixture was coated evenly on a LB solid medium containing kanamycin (15 μg/mL) resistance and cultured at 37° C. for 24 h to obtain strains that can stably express recombinant proteins. A growing colony was picked and inoculated into 20 mL of LB medium. The mixture was cultured at 220 rpm at 37° C. When the OD value of the culture mixture reached 1.0, induction by Isopropyl β-D-Thiogalactoside (IPTG at a final concentration of 0.5 mmol/L) was carried out at 220 rpm at 16° C. overnight. After the induction, the culture broth was centrifuged at 4,000 rpm for 20 min. The supernatant was discarded, and the bacterial precipitates were resuspended with PBS. Centrifugation was conducted again at 4,000 rpm for 20 min and the supernatant was discarded to obtain the bacterial precipitates containing proteins of interest.

3.4 Purification of the Lysine-Modified Norovirus P Protein

The bacterial precipitates obtained in 3.3 were resuspended by adding 20 ml of protein buffer (pH8.0, containing 50 mM Tris and 300 mM KCl). The bacteria were lysed by sonication on ice for 30 min. The mixture was centrifuged at 12,000 rpm at 4° C. for 30 min. Subsequently, the supernatant was taken and allowed to pass through 0.45 μm filter membrane to obtain crude extracts of proteins.

Figure 3A:
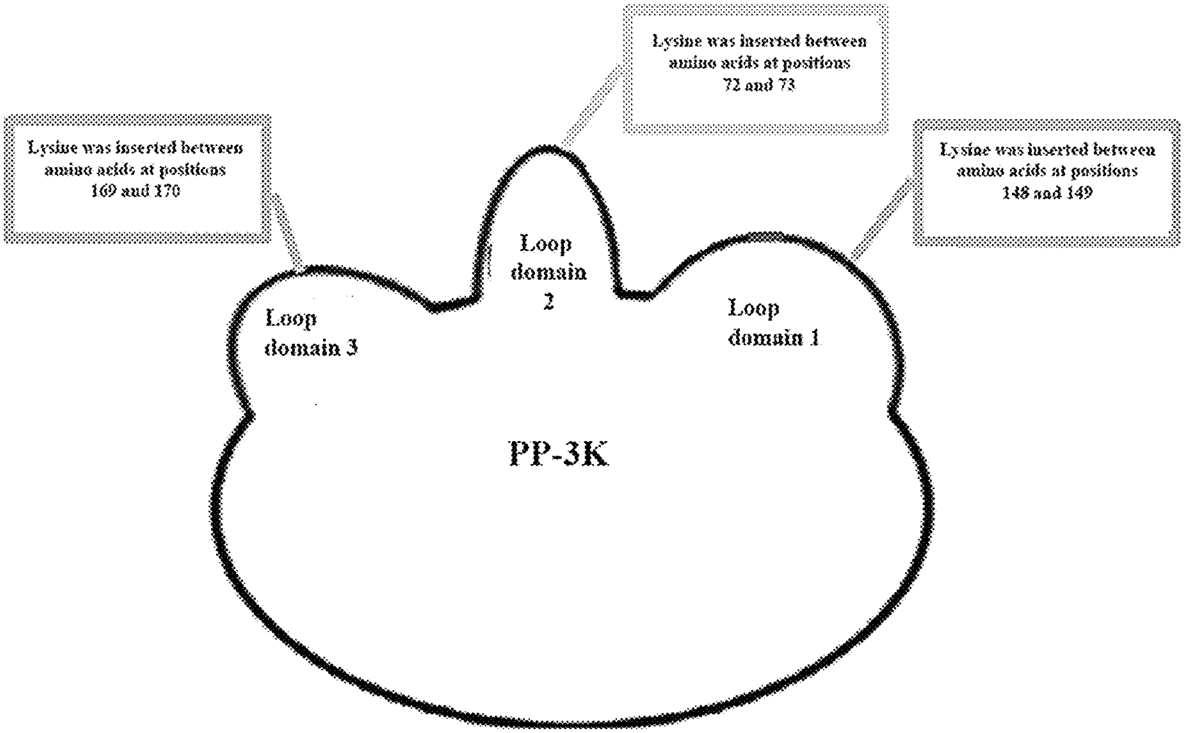
FIGS. 3A to 3C show the recombinant pET28a plasmid construct and the results of purification and expression.
Figure 3B:
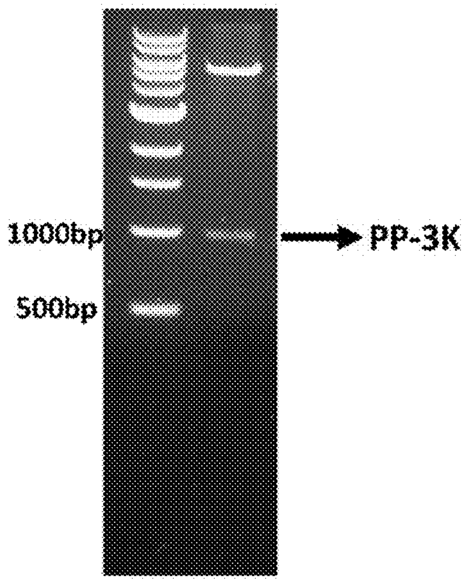
Figure 3C:
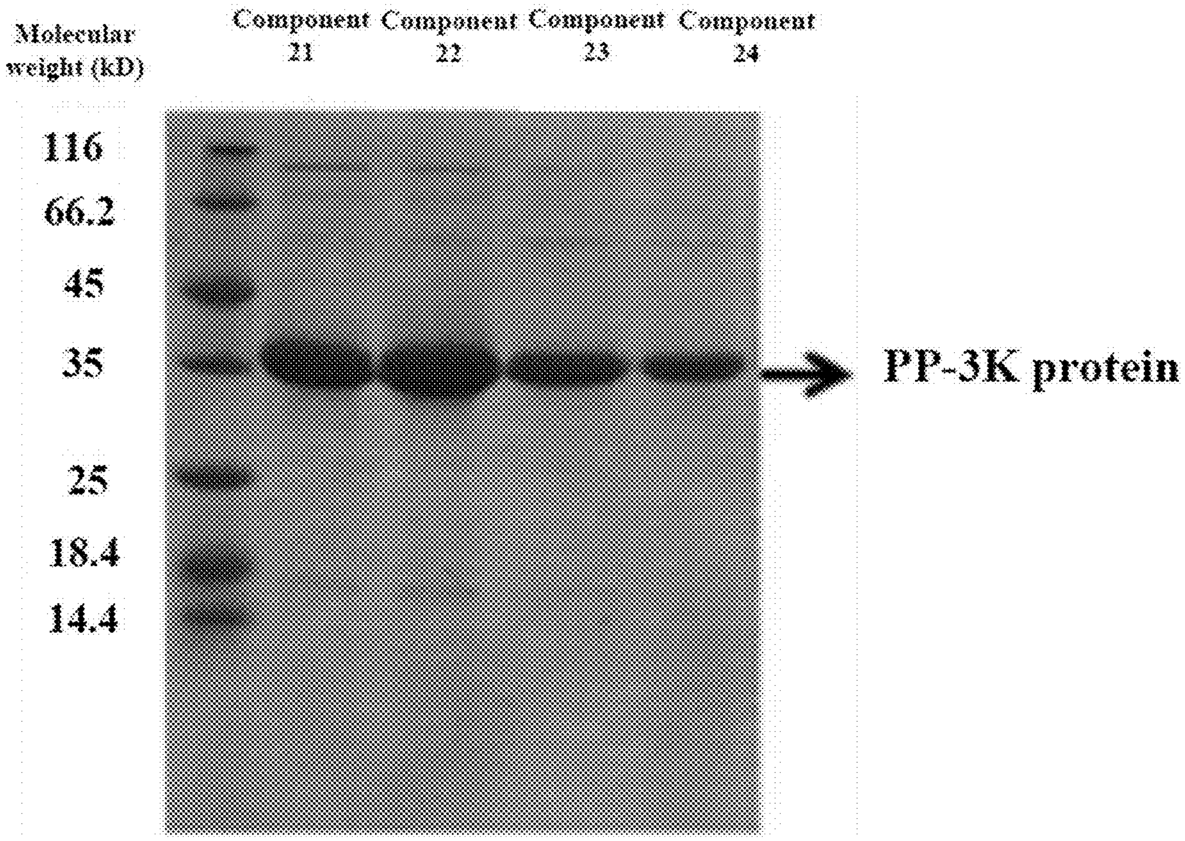

The structure of the recombinant PP-3K particle is shown as FIG. 3A.

The crude extracts of proteins were purified using an anion exchange column (purchased from GE Corporation). The specific scheme was as follows: First, the exchange column was rinsed with ultrapure water in a volume of about 100 mL, followed by equilibration with PB solution (pH 5.0) at a flow rate of 2 mL/min. Then 20 mL of the crude extracts of proteins were added to the exchange column at a flow rate of 1 ml/min. After the sample was completely loaded onto the column, the exchange column was rinsed with PB solution (pH 7.0) to remove hybrid protein, and then eluted with PB solution containing 0.5 mol/L NaCl. The proteins at peak value were collected to obtain the proteins of interest.

The proteins were further purified by a hydrophobic chromatography column (purchased from GE Corporation). The specific scheme was as follows: First, the column was rinsed with ultrapure water, and then the hydrophobic column was rinsed with PB solution (pH 7.0) at a flow rate of 2 mL/min. After the column was equilibrated well, the protein sample was loaded onto it. After the sample was completely loaded onto the column, the column was eluted by gradient with PB (pH 7.0) and 1 mol/L NaCl solution for 2 hours. The concentration of NaCl decreases from 1 mol/L to 0.1 mol/L. The proteins were collected at peak value.

Figure 5:
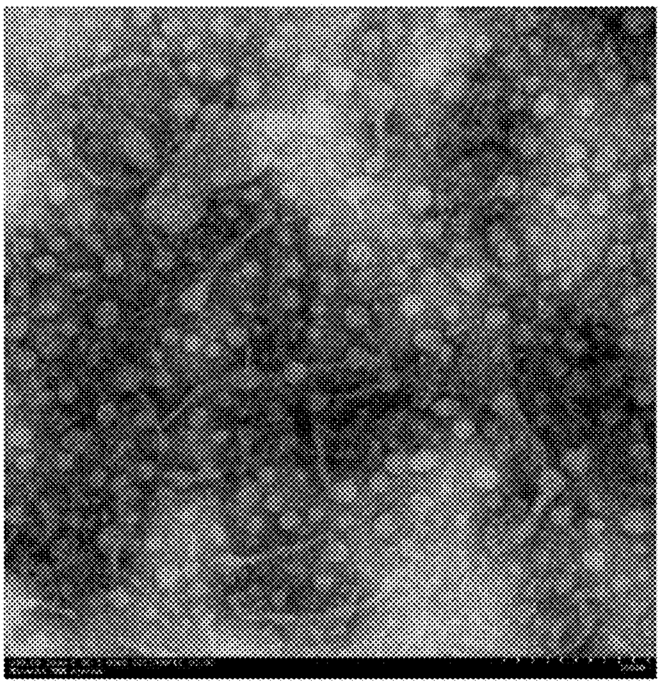
FIG. 5 shows an electron microscope image of recombinant pET26b-PP-3C protein particles.

The sizes of P particle protein monomers were identified by reductive SDS-PAGE. Then the tetracosamers of P protein particles were further isolated and purified using a Superdex 200 molecular sieve (purchased from GE Corporation). The procedures were as follows: The column was rinsed with ultrapure water at a flow rate of 1 mL/min for one volume of the column, and then again with about 120 mL of PB buffer (pH=5). After that, 2 mL of protein extraction solution was added to the column and washed with PB buffer at a flow rate of 1 mL/min. The proteins at peak value were collected to obtain the tetracosamers of P particle proteins. Three proteins were tested for their polymer structures by native polyacrylamide gel electrophoresis, as shown in FIG. 2C. Protein bands are above 250 KDa, which indicates that recombinant P proteins can self-assemble into dodecamers and tetracosamers of P protein particles in vitro and maintain equilibrium; and the proteins can remain their polymer form after being purified. Electron microscopy analysis of purified PP-3K protein particles showed that PP-3K mostly formed large particle aggregates (as shown in FIG. 5).

Example 4: Coupling Reaction of PP-3C with a Phosphorylated Polypeptide Antigen Vaccine Example 4-1: The purified PP-3C was subjected to a buffer-exchange treatment with a desalting column from GE Corporation to change the buffer system of the protein to a 0.1 M ammonium bicarbonate solution (pH=7.5). The PP-3C after the buffer-exchange treatment was quantified, and was diluted to a concentration of 0.3 mg/mL. In the ratio of the molar amount of protein to the molar amount of polypeptide of 1:30, each of the phosphorylated polypeptide antigen vaccines in lyophilized form prepared in Example 1 was added and mixed slowly. The mixed system was incubated at 2° C. to 8° C. with slow shaking for 48 hours. The resulting product was concentrated by ultrafiltration to remove unbound polypeptides, and the buffer system was changed to a PBS buffer system.

Example 4-2: The purified PP-3C was subjected to a buffer-exchange treatment with a desalting column from GE Corporation to change the buffer system of the protein to a 1 M ammonium bicarbonate solution (pH=8.0). The PP-3C after the buffer-exchange treatment was quantified, and was diluted to a concentration of 0.5 mg/mL. In the ratio of the molar amount of protein to the molar amount of polypeptide of 1:50, each of the phosphorylated polypeptide antigen vaccines in lyophilized form prepared in Example 1 was added and mixed slowly. The mixed system was incubated at 2° C. to 8° C. with slow shaking for 48 hours. The resulting product was concentrated by ultrafiltration to remove unbound polypeptides, and the buffer system was changed to a PBS buffer system.

Example 4-3: The purified PP-3C was subjected to a buffer-exchange treatment with a desalting column from GE Corporation to change the buffer system of the protein to a 0.1 M ammonium bicarbonate solution (pH=7.8). The PP-3C after the buffer-exchange treatment was quantified, and was diluted to a concentration of 0.3 mg/mL. In the ratio of the molar amount of protein to the molar amount of polypeptide of 1:100, each of the phosphorylated polypeptide antigen vaccines in lyophilized form prepared in Example 1 was added and mixed slowly. The mixed system was incubated at 2° C. to 8° C. with slow shaking for 48 hours. The resulting product was concentrated by ultrafiltration to remove unbound polypeptides, and the buffer system was changed to a PBS buffer system.

Example 4-4: The purified PP-3C was subjected to a buffer-exchange treatment with a desalting column from GE Corporation to change the buffer system of the protein to a 0.1 M ammonium bicarbonate solution (pH=8.8). The PP-3C after the buffer-exchange treatment was quantified, and was diluted to a concentration of 0.3 mg/mL. In the ratio of the molar amount of protein to the molar amount of polypeptide of 1:30, each of the phosphorylated polypeptide antigen vaccines in lyophilized form prepared in Example 1 was added and mixed slowly. The mixed system was incubated at 2° C. to 8° C. with slow shaking for 72 hours. The resulting product was concentrated by ultrafiltration to remove unbound polypeptides, and the buffer system was changed to a PBS buffer system.

Example 5: Coupling Reaction of PP-3K with a Phosphorylated Polypeptide Antigen Vaccine Example 5-1: The purified PP-3K solution was quantified by BCA and the pH was adjusted to 7.2. This protein solution was mixed with a 1 mg/mL sulfo-maleimide (sulfo-SMCC) solution in the ratio of the molar amount of SMCC to the molar amount of PP-3K of 5:1, and the mixture was reacted in a water bath at 25° C. for 30 min. The mixture was subjected to a desalting treatment with a desalting column from GE Corporation, the system was changed to a PBS solution (pH=7.2-7.4), and unbound sulfo-SMCC was removed. The reaction product was taken and each of the lyophilized products of the phosphorylated polypeptide antigen vaccines prepared in Example 1 was added to the system in the ratio of the molar amount of PP-3K to the molar amount of phosphorylated polypeptide of 1:5, and mixed slowly. Then, the reaction system was reacted in a water bath at 25° C. for 30 min. The reaction product was collected, and the mixture was subjected to a desalting treatment with a desalting column from GE Corporation, the system was changed to a PBS solution (pH=7.2-7.4), and unbound phosphorylated polypeptides were removed.

Example 5-2: The purified PP-3K solution was quantified by BCA. This protein solution was mixed with a 1 mg/mL sulfo-maleimide (sulfo-SMCC) solution in the ratio of the molar amount of SMCC to the molar amount of PP-3K of 20:1, and the mixture was reacted in a water bath at 25° C. for 30 min. The mixture was subjected to a desalting treatment with a desalting column from GE Corporation, the system was changed to a PB solution (pH=8.5), and unbound sulfo-SMCC was removed. The reaction product was taken and each of the lyophilized products of the phosphorylated polypeptide antigen vaccines prepared in Example 1 was added to the system in the ratio of the molar amount of PP-3K to the molar amount of phosphorylated polypeptides of 1:30, and mixed slowly. Then, the reaction system was reacted in a water bath at 25° C. for 30 min. The reaction product was collected, and the mixture was subjected to a desalting treatment with a desalting column from GE Corporation, the system was changed to a PB solution (pH=8.5), and unbound phosphorylated polypeptides were removed.

Example 5-3: The purified PP-3K solution was quantified by BCA. This protein solution was mixed with a 1 mg/mL sulfo-maleimide (sulfo-SMCC) solution in the ratio of the molar amount of SMCC to the molar amount of PP-3K of 20:1, and the mixture was reacted in a water bath at 25° C. for 30 min. The mixture was subjected to a desalting treatment with a dialysis bag having a molecular weight cut-off of 20 kd (the dialysis volume ratio is 1,000:1), and was dialyzed overnight at 2° C. to 8° C., the system was changed to a PB solution (pH=7.0), and unbound sulfo-SMCC was removed. The reaction product was taken and each of the lyophilized products of the phosphorylated polypeptide antigen vaccines prepared in Example 1 was added to the system in the ratio of the molar amount of PP-3K to the molar amount of phosphorylated polypeptides of 1:50, and mixed slowly. Then, the reaction system was reacted in a water bath at 25° C. for 30 min. The mixture was subjected to a desalting treatment with a dialysis bag having a molecular weight cut-off of 20 kDa (the dialysis volume ratio is 1,000:1), and was dialyzed overnight at 2° C. to 8° C., the system was changed to a PB solution (pH=7.0), and unbound phosphorylated polypeptides were removed.

Example 5-4: The purified PP-3K solution was quantified by BCA. This protein solution was mixed with a 1 mg/mL sulfo-maleimide (sulfo-SMCC) solution in the ratio of the molar amount of SMCC to the molar amount of PP-3K of 20:1, and the mixture was reacted with slow shaking overnight at 2° C. to 8° C. The mixture was subjected to a desalting treatment with a dialysis bag having a molecular weight cut-off of 20 kd (the dialysis volume ratio is 1,000:1), and was dialyzed overnight at 2° C. to 8° C., the system was changed to a PBS solution (pH=7.2-7.4), and unbound sulfo-SMCC was removed. The reaction product was taken and each of the lyophilized products of the phosphorylated polypeptide antigen vaccines prepared in Example 1 was added to the system in the ratio of the molar amount of PP-3K to the molar amount of phosphorylated polypeptides of 1:50, and mixed slowly. Then, the reaction system was reacted with slow shaking overnight at 2° C. to 8° C. The mixture was subjected to a desalting treatment with a dialysis bag having a molecular weight cut-off of 20 kd (the dialysis volume ratio is 1,000:1), and was dialyzed overnight at 2° C. to 8° C., the system was changed to a PBS solution (pH=7.2-7.4), and unbound phosphorylated polypeptides were removed.

Example 5-5: The purified PP-3K solution was quantified by BCA. This protein solution was mixed with a 20 mg/ml dimethylformamide (DMF) solution of maleimide (SMCC) in the ratio of the molar amount of SMCC to the molar amount of PP-3K of 10:1, and the mixture was reacted in a water bath at 25° C. for 30 min. The mixture was subjected to a desalting treatment with a desalting column from GE Corporation, the system was changed to a PBS solution (pH=7.2-7.4), and unbound SMCC was removed. The reaction product was taken and each of the lyophilized products of the phosphorylated polypeptide antigen vaccines prepared in Example 1 was added to the system in a ratio of the molar amount of PP-3K to the molar amount of phosphorylated polypeptides of 1:30, and mixed slowly. Then, the reaction system was reacted in a water bath at 25° C. for 30 min. The reaction product was collected, and the mixture was subjected to a desalting treatment with a desalting column from GE Corporation, the system was changed to a PBS solution (pH=7.2), and unbound phosphorylated polypeptides were removed.

Example 5-6: The purified PP-3K solution was quantified by BCA. This protein solution was mixed with a 20 mg/ml dimethylformamide (DMF) solution of maleimide (SMCC) in the ratio of the molar amount of SMCC to the molar amount of PP-3K of 30:1, and the mixture was reacted with slow shaking overnight at 2° C. to 8° C. The mixture was subjected to a desalting treatment with a desalting column from GE Corporation, the system was changed to a PBS solution (pH=7.2-7.4), and unbound SMCC was removed. The reaction product was taken and each of the lyophilized products of the phosphorylated polypeptide antigen vaccines prepared in Example 1 was added to the system in the ratio of the molar amount of PP-3K to the molar amount of phosphorylated polypeptides of 1:50, and mixed slowly. The mixture was reacted with slow shaking overnight at 2° C. to 8° C. The reaction product was collected, and the mixture was subjected to a desalting treatment with a desalting column from GE Corporation, the system was changed to a PBS solution (pH=7.2), and unbound phosphorylated polypeptides were removed.

Example 5-7: The purified PP-3K solution was quantified by BCA. This protein solution was mixed with a 20 mg/ml dimethylformamide (DMF) solution of maleimide (SMCC) in the ratio of the molar amount of SMCC to the molar amount of PP-3K of 5:1, and the mixture was reacted in a water bath at 25° C. for 30 min. The mixture was subjected to a desalting treatment with a dialysis bag having a molecular weight cut-off of 20 kDa (the dialysis volume ratio is 1,000:1), and was dialyzed overnight at 2° C. to 8° C., the system was changed to a PBS solution (pH=7.2-7.4), and unbound SMCC was removed. The reaction product was taken and each of the lyophilized products of the phosphorylated polypeptide antigen vaccines prepared in Example 1 was added to the system in the ratio of the molar amount of PP-3K to the molar amount of phosphorylated polypeptides of 1:100, and mixed slowly. The mixture was reacted with slow shaking overnight at 2° C. to 8° C. The reaction product was collected, and the mixture was subjected to a desalting treatment with a dialysis bag having a molecular weight cut-off of 20 kDa (the dialysis volume ratio is 1,000:1), and was dialyzed overnight at 2° C. to 8° C., the system was changed to a PBS solution (pH=7.2), and unbound phosphorylated polypeptides were removed.

Figure 13A:
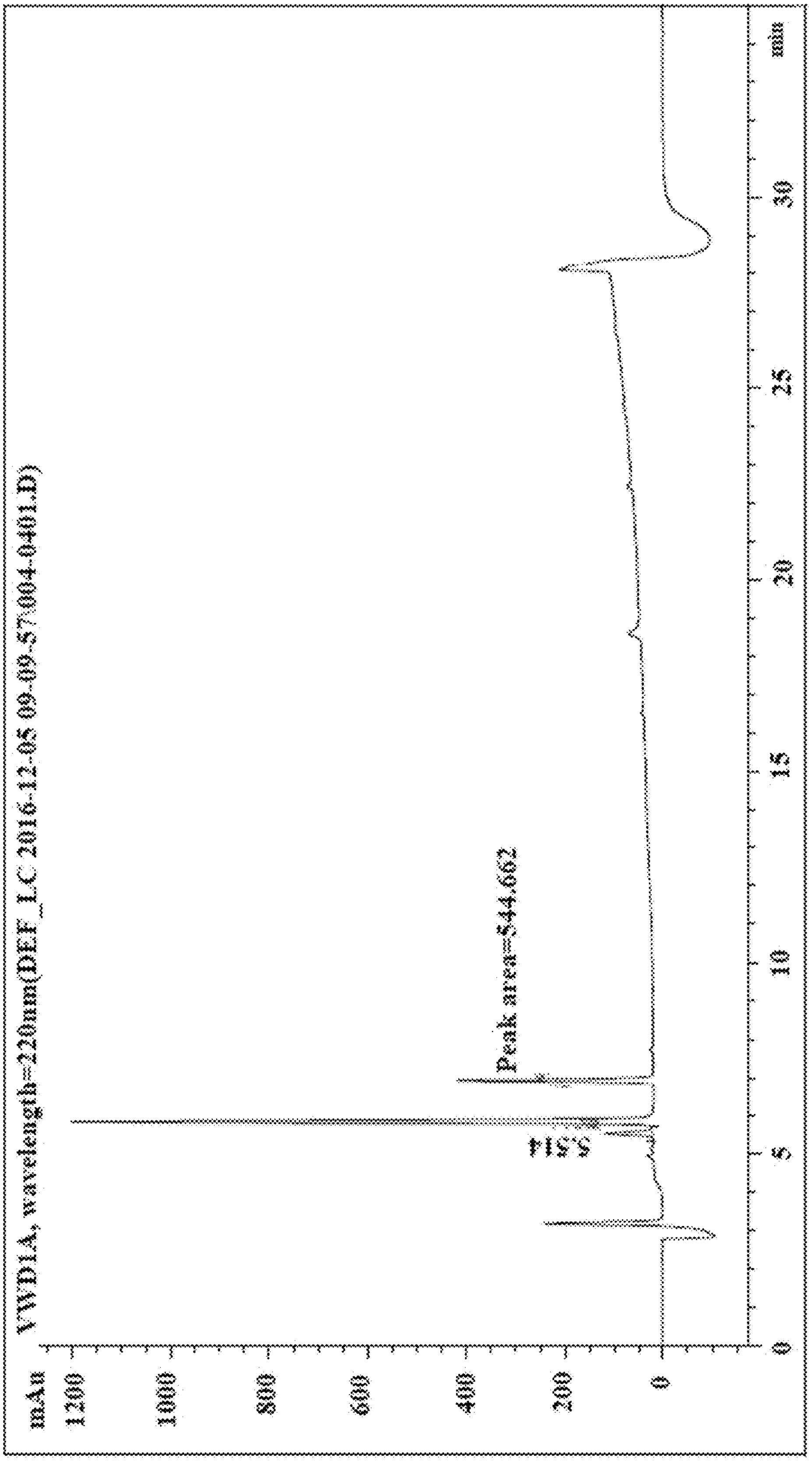
FIGS. 13A to 13D show schematic diagrams of the results of HPLC quantification of the phosphorylated polypeptides coupled with PP-3C/C-PA-BLP.
Figure 13B:
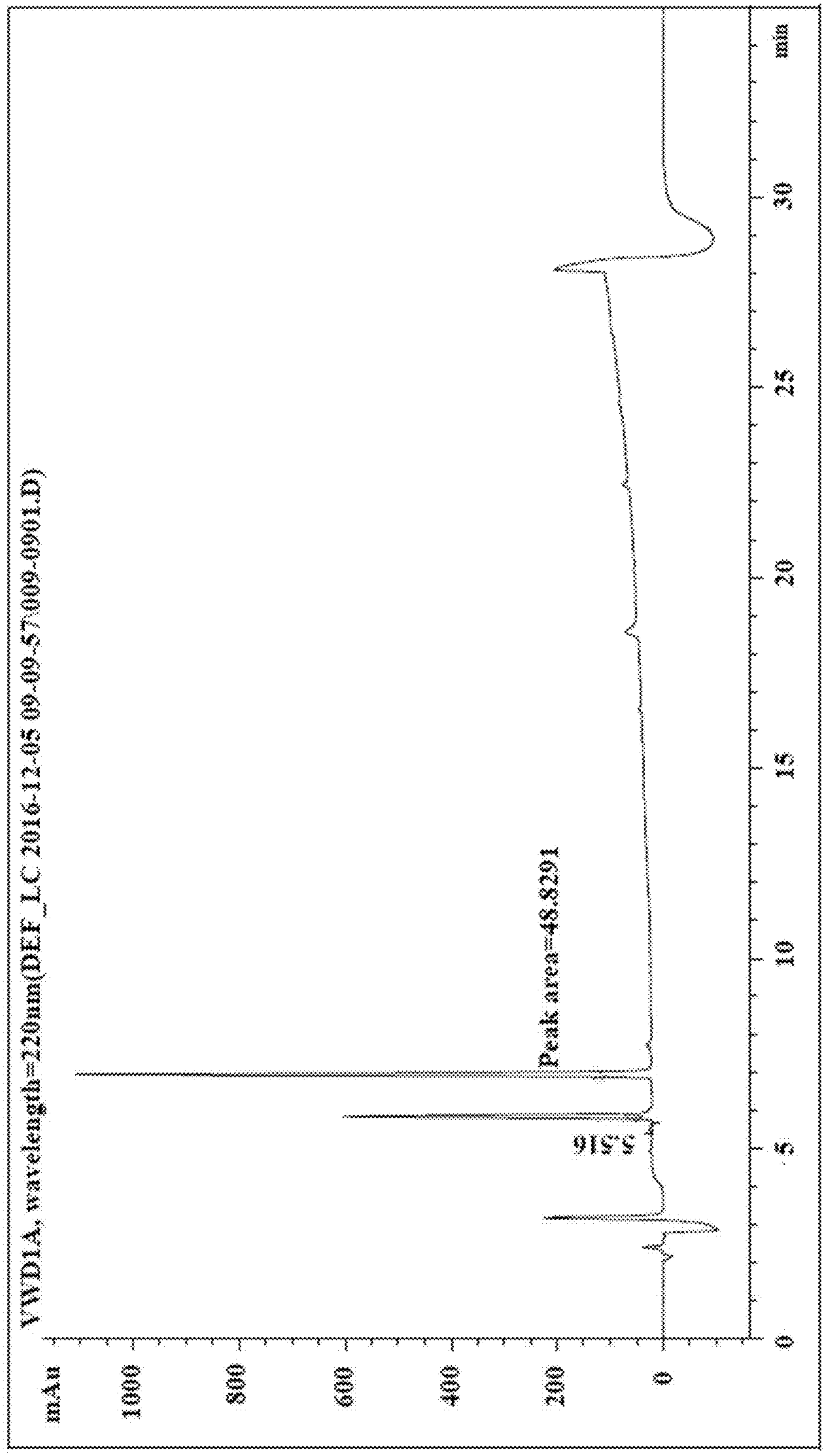
Figure 13C:
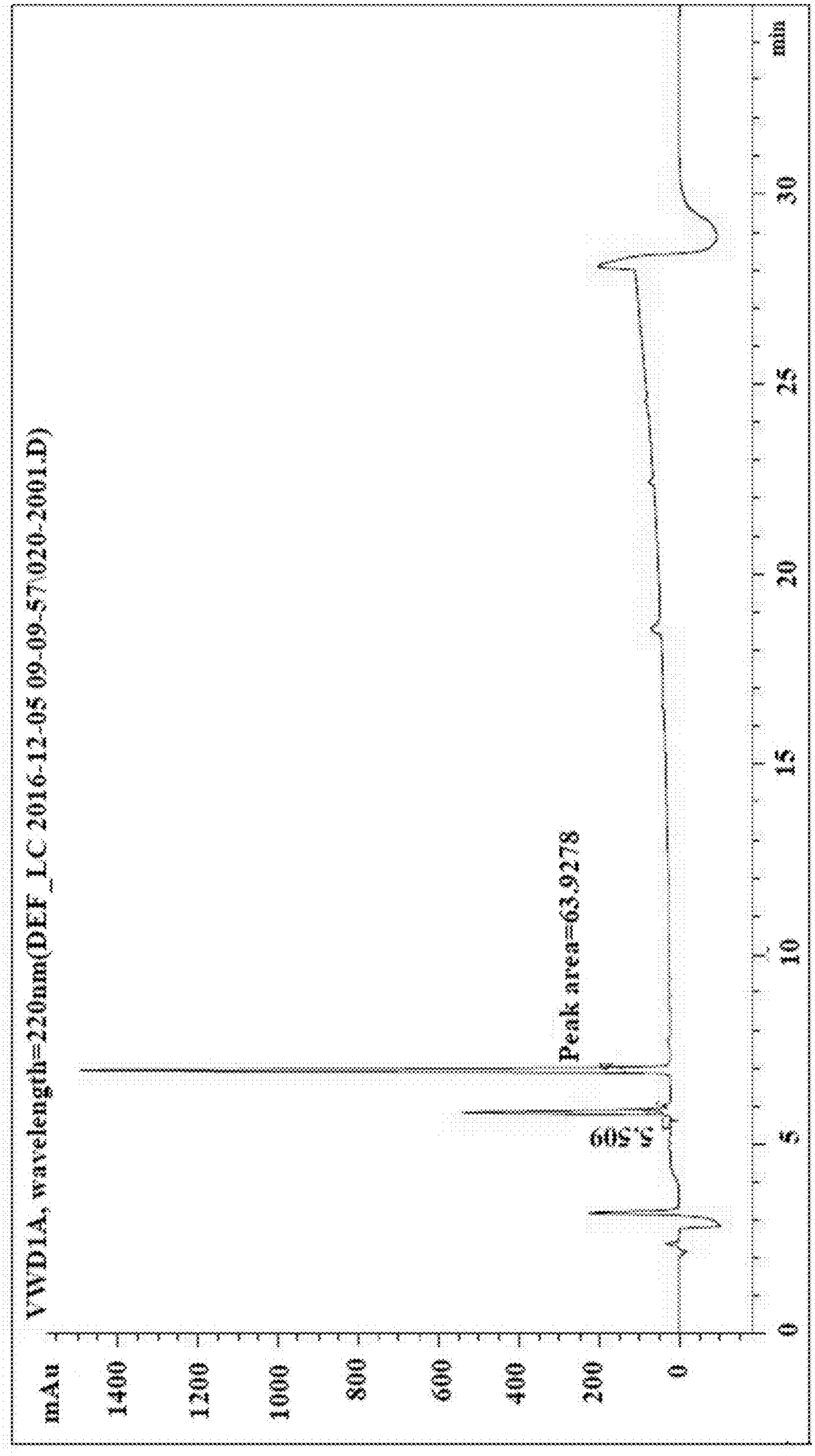
Figure 13D:
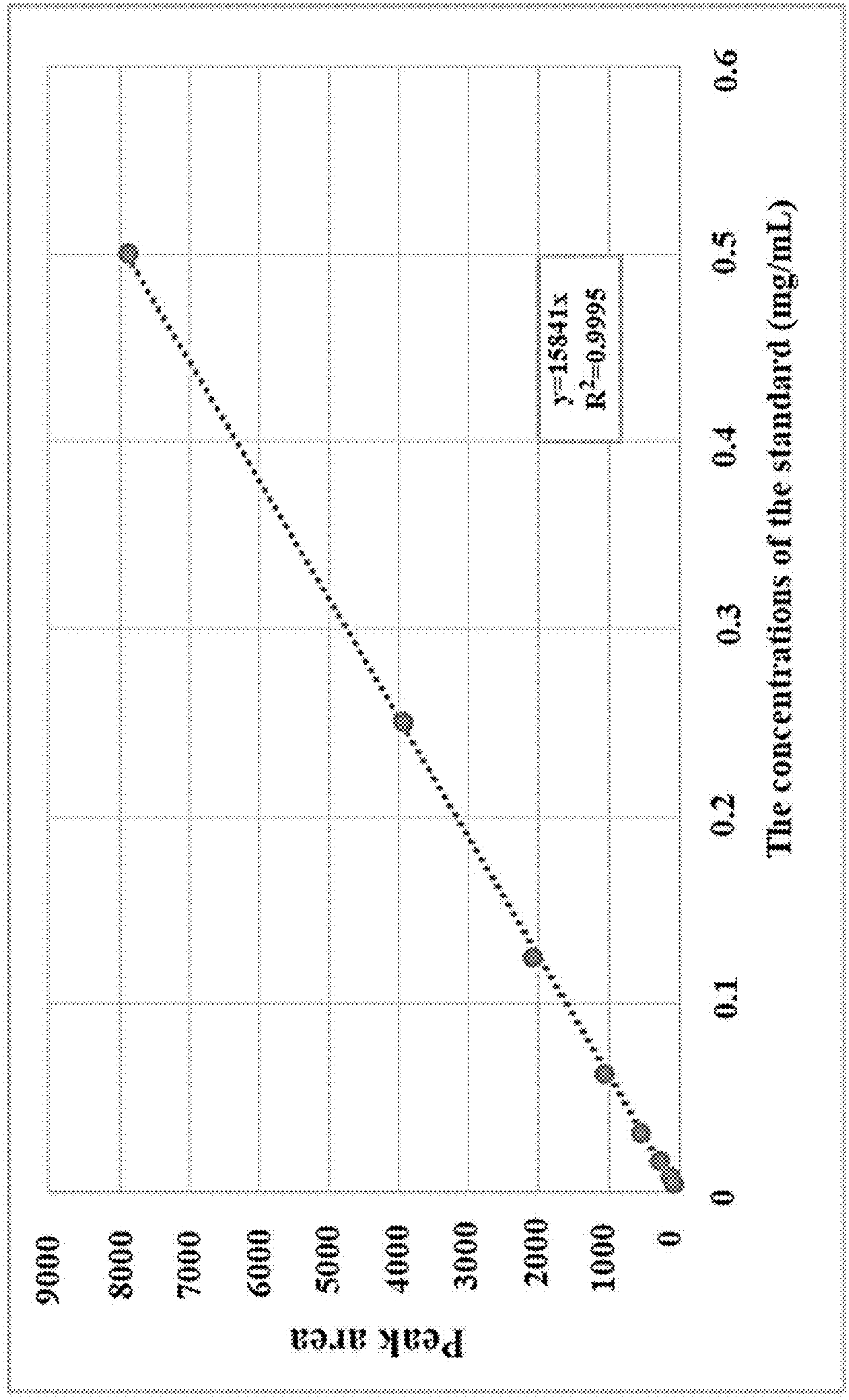
Figure 14:
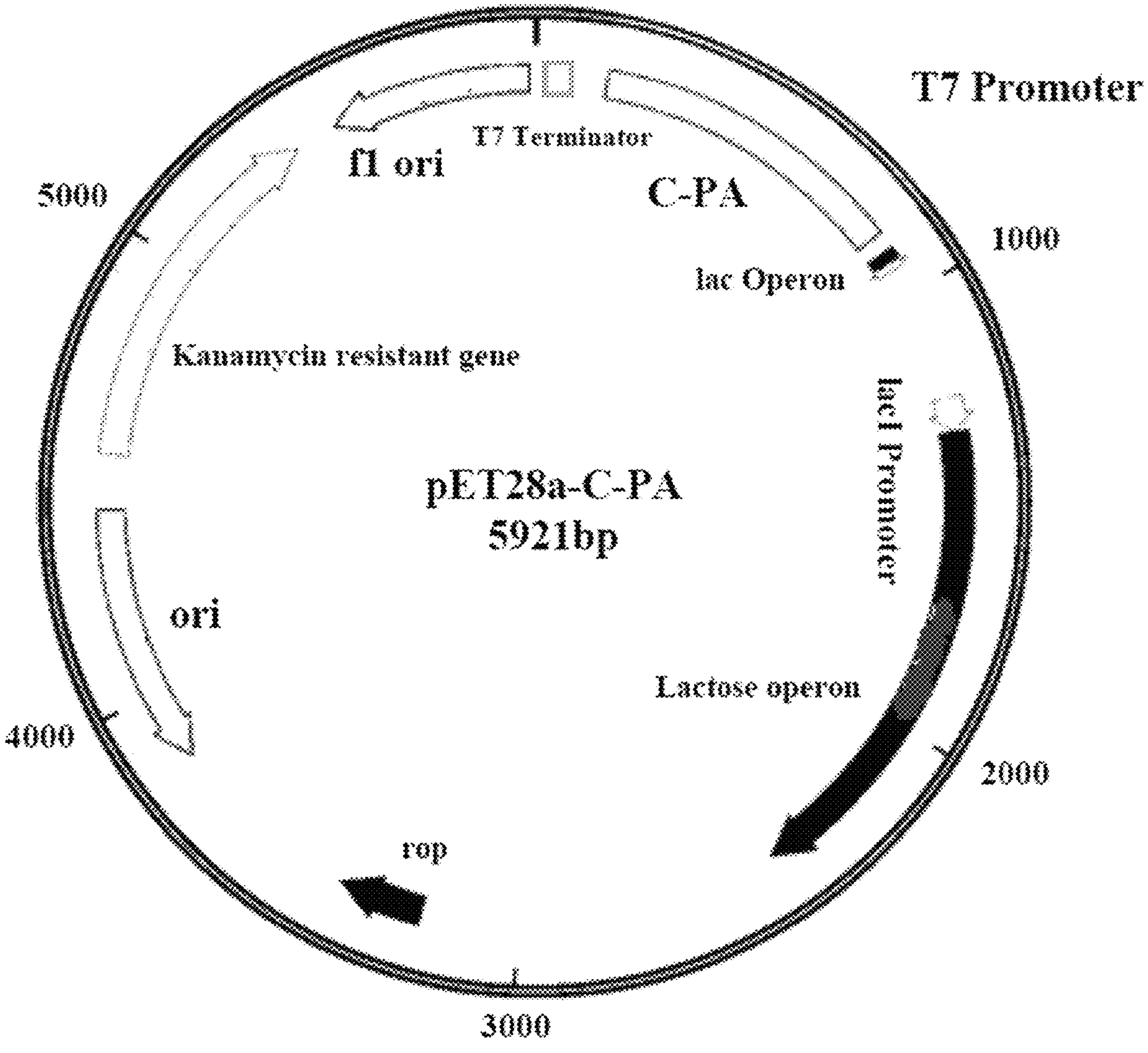
FIG. 14 show is a schematic diagram of pET28a-C-PA plasmid that has been constructed.

Example 6: Determination of the Ligation Efficiency of the Phosphorylated Polypeptide Antigen Product Coupled with PP-3C A10 mM dithiothreitol solution was added to the phosphorylated polypeptide antigen product coupled with PP-3C at a volume ratio of 1:1, and mixed homogeneously, and the mixture was left to stand at room temperature and react for 16 hours. The reaction product was centrifuged at 16,000 g at 4° C. for 15 min. The supernatants were taken for HPLC determination. Using 0.5 mg/mL, 0.25 mg/mL, 0.125 mg/mL, 0.0625 mg/mL, 0.03125 mg/mL, 0.03125 mg/mL, and 0.015625 mg/mL phosphorylated polypeptide dissolved in 10 mM of a dithiothreitol solution as standard, a standard curve of the concentration of the standard versus the peak area of the phosphorylated polypeptide was plotted for quantitatively analyzing the concentration of the test sample (the results are shown in FIGS. 13A, 13B and 13D).

Example 7: Determination of the Ligation Efficiency of the Phosphorylated Polypeptide Antigen Product Coupled with PP-3K The phosphorylated polypeptide antigen product coupled with PP-3K was subjected to a mass spectrometric analysis, and the concentration of the test sample was quantitatively analyzed using the phosphorylated polypeptide dissolved in PBS as standard (the results are not shown).

Example 8: Analysis of the Immunogenicity of Phosphorylated Polypeptide Antigen Vaccines in Wild Mice The phosphorylated polypeptide antigens with sequences as represented by SEQ ID NO: 201, SEQ ID NO: 225, SEQ ID NO: 306, SEQ ID NO: 387, SEQ ID NO: 468, SEQ ID NO: 558, SEQ ID NO: 567, SEQ ID NO: 769, SEQ ID NO: 784, SEQ ID NO: 875, SEQ ID NO: 1020, SEQ ID NO: 1101, SEQ ID NO: 1182, SEQ ID NO: 1272, SEQ ID NO:

1313 and SEQ ID NO: 1330 were dissolved to 1 mg/mL, and mixed with a complete Freund's adjuvant or an incomplete Freund's adjuvant at a volume ratio of 1:1 to form a water-in-oil emulsion so as to prepare vaccines A1 to A16. Each wild mouse was injected intramuscularly with 50 μL. Each wild mouse was vaccinated four times at two-week intervals using complete Freund's adjuvant for the first immunization and incomplete Freund's adjuvant for the second, third and fourth immunizations. Two weeks after the fourth injection, the mice were subjected to blood sampling to obtain mouse serum for ELISA analysis.

The polypeptide (whose sequence is represented by SEQ ID NO: 1346) which was coupled with BSA and phosphorylated at a position corresponding to amino acid 18 of full-length Tau protein was used as the coating antigen to detect the antiserum titer against a phosphorylation Y18 site; the phosphorylatd polypeptide (whose sequence is represented by SEQ ID NO: 1347) which was coupled with BSA and phosphorylated at positions corresponding to amino acids 202 and 205 of full-length Tau protein was used as the coating antigen to detect the antiserum titer against phosphorylation S202 and T205 sites; the phosphorylatd polypeptide (whose sequence is represented by SEQ ID NO: 1348) which was coupled with BSA and phosphorylated at a position corresponding to amino acid 212/214 of full-length Tau protein was used as the coating antigen to detect the antiserum titer against phosphorylation T212 and S214 sites; the phosphorylatd polypeptide (whose sequence is represented by SEQ ID NO: 1349) which was coupled with BSA and phosphorylated at a position corresponding to amino acid 231/235 of full-length Tau protein was used as the coating antigen to detect the antiserum titer against phosphorylation T231 and S235 sites; the phosphorylatd polypeptide (whose sequence is represented by SEQ ID NO: 1350) which was coupled with BSA and phosphorylated at a position corresponded to amino acid 238 of full-length Tau protein was used as the coating antigen to detect the antiserum titer against a phosphorylation S238 site; the phosphorylatd polypeptide (whose sequence is represented by SEQ ID NO: 1351) which was coupled with BSA and phosphorylated at a position corresponding to amino acid 262 of full-length Tau protein was used as the coating antigen to detect the antiserum titer against a phosphorylation S262 site; the phosphorylatd polypeptide (whose sequence is represented by SEQ ID NO: 1352) which was coupled with BSA and phosphorylated at a position corresponding to amino acid 396 of full-length Tau protein was used as the coating antigen to detect the antiserum titer against a phosphorylation S396 site; the phosphorylatd polypeptide (whose sequence is represented by SEQ ID NO: 1353) which was coupled with BSA and phosphorylated at a position corresponding to amino acid 404 of full-length Tau protein was used as the coating antigen to detect the antiserum titer against a phosphorylated S404 site.

Figure 6A:
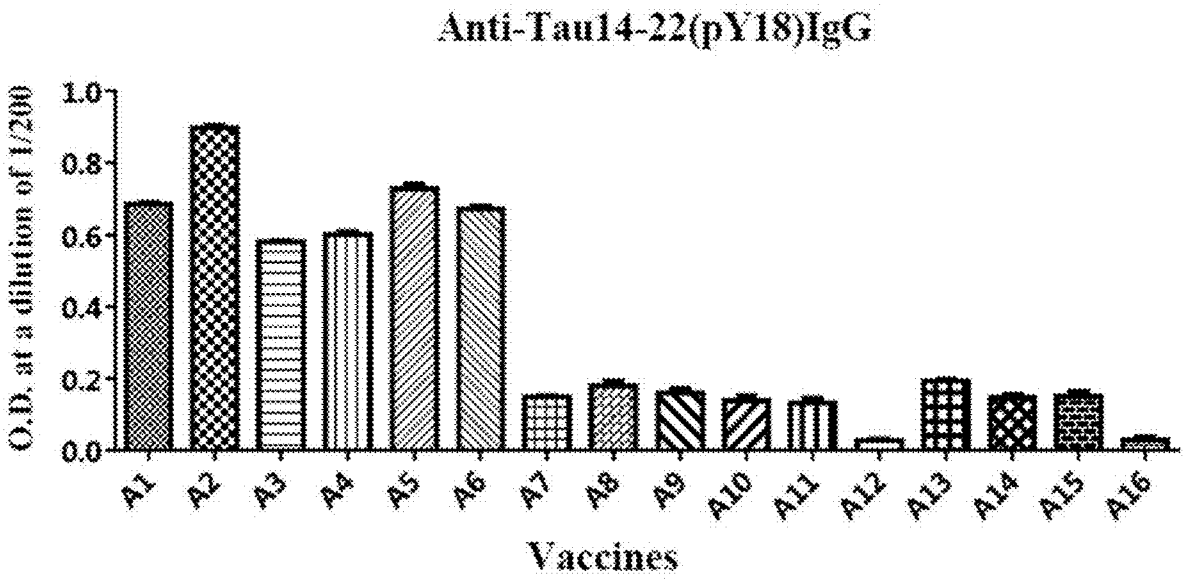
FIGS. 6A to 6H show the levels of IgG antibodies against different antigens produced in mice immunized with phosphorylated polypeptide antigen vaccines in combination with Freund's adjuvant.
Figure 6B:
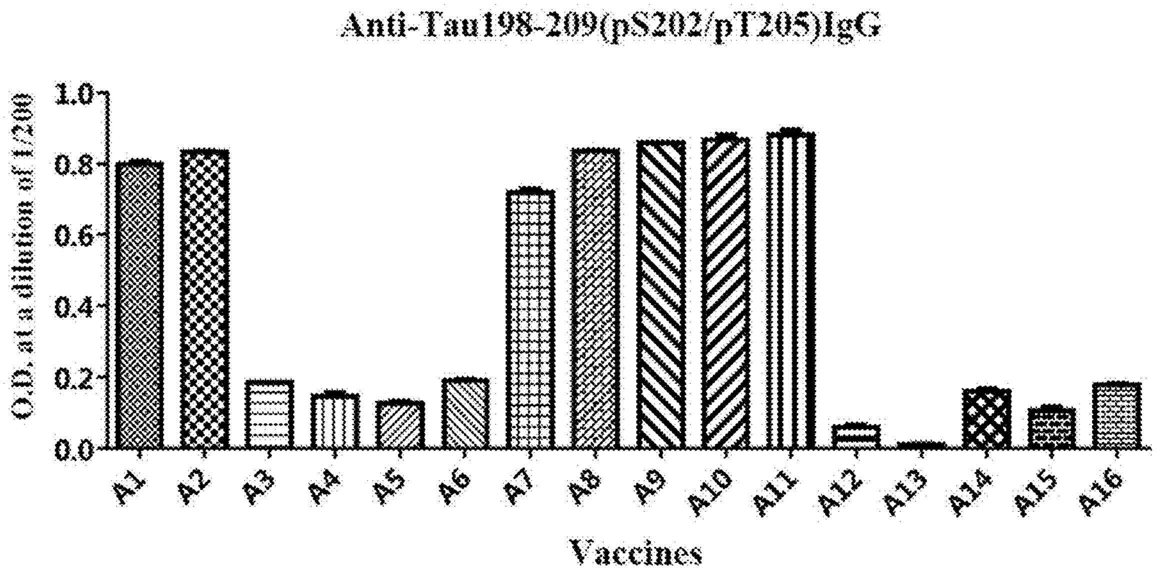
Figure 6C:
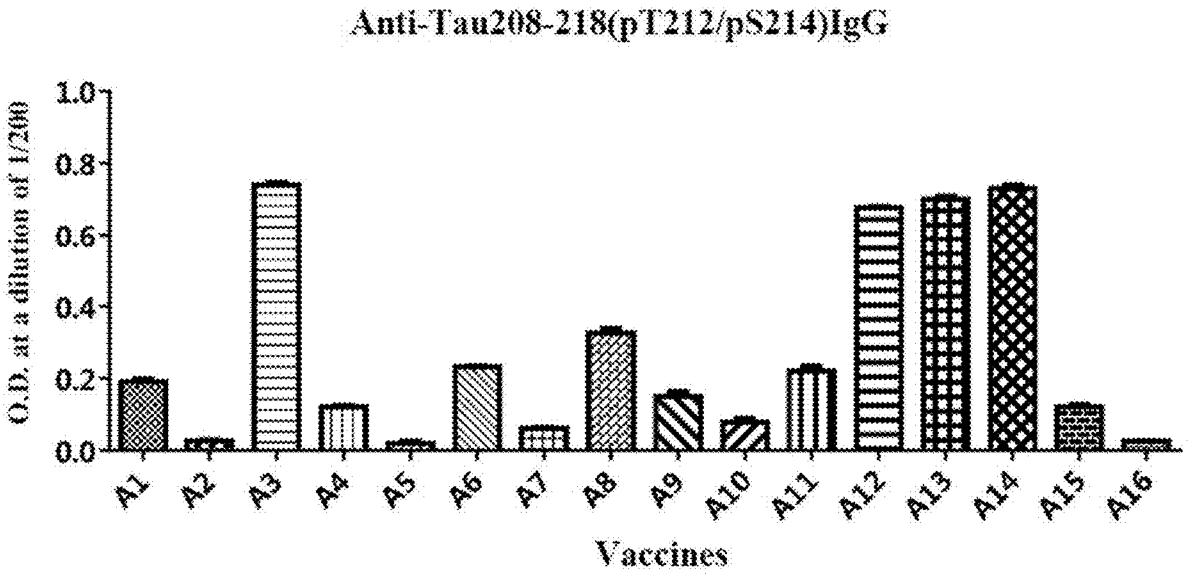
Figure 6D:
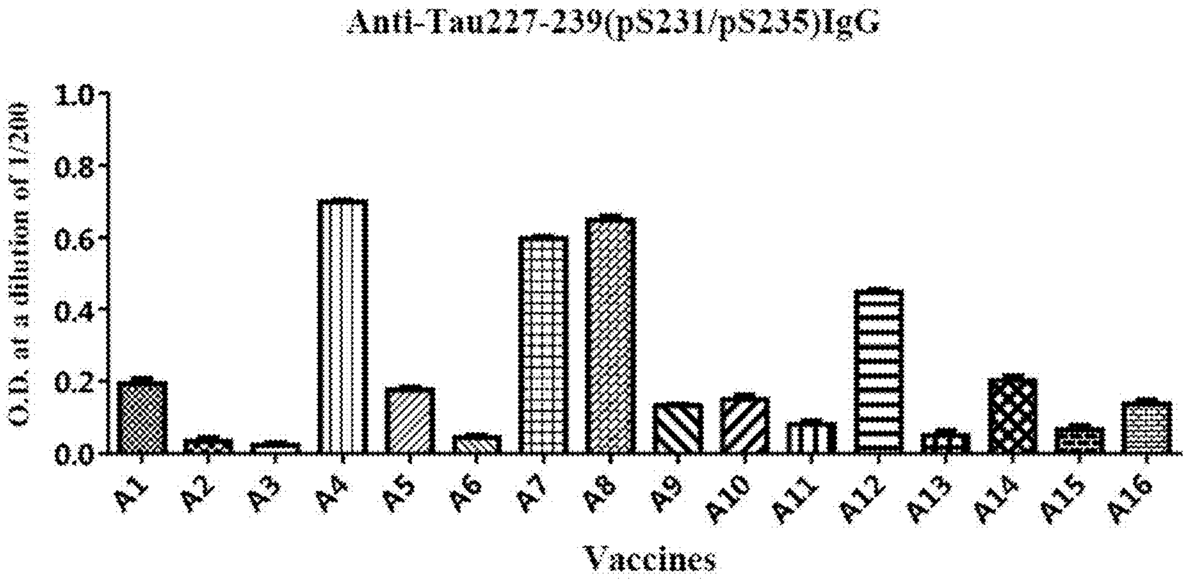
Figure 6E:
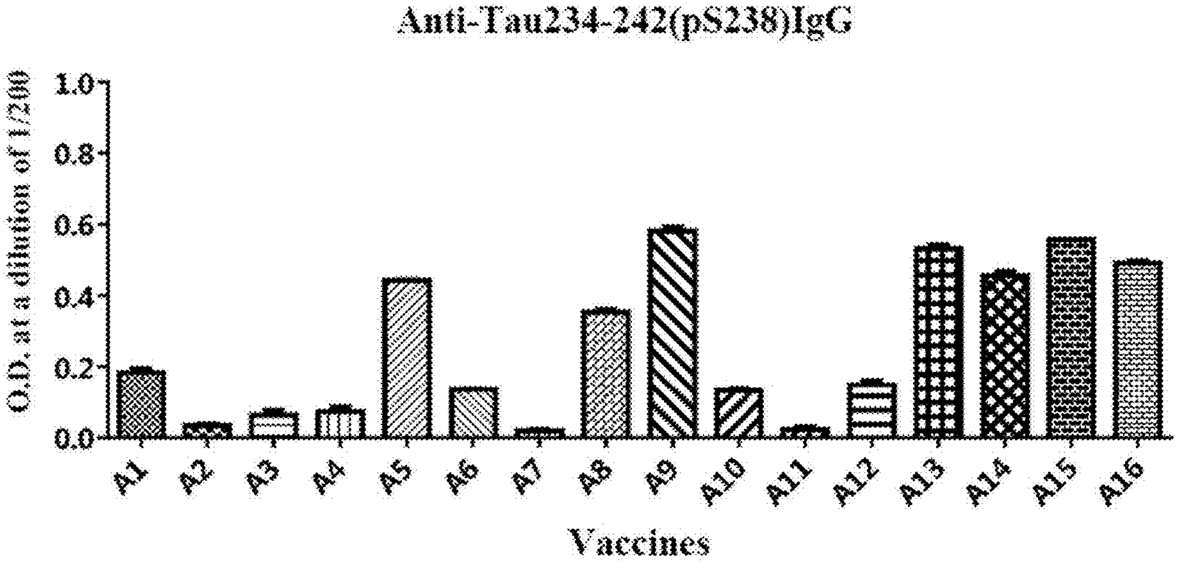
Figure 6F:
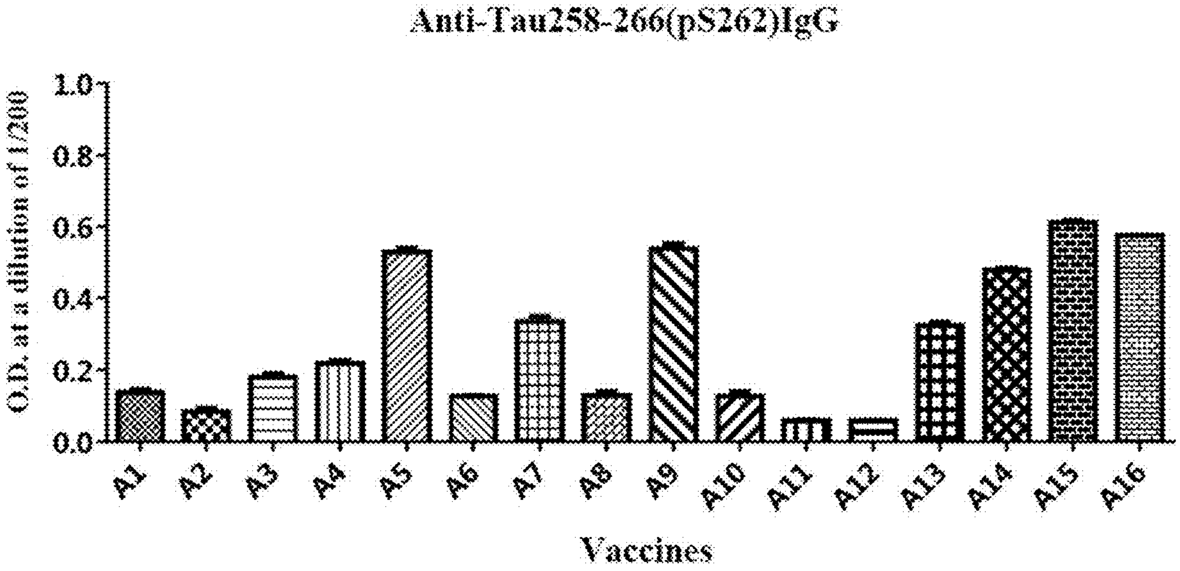
Figure 6G:
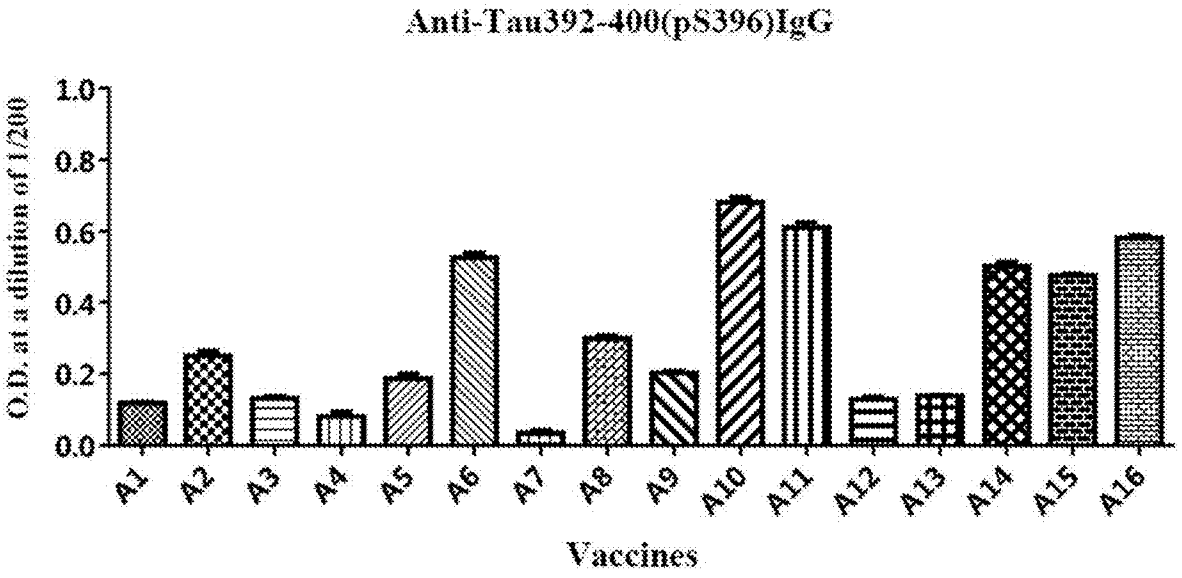
Figure 6H:
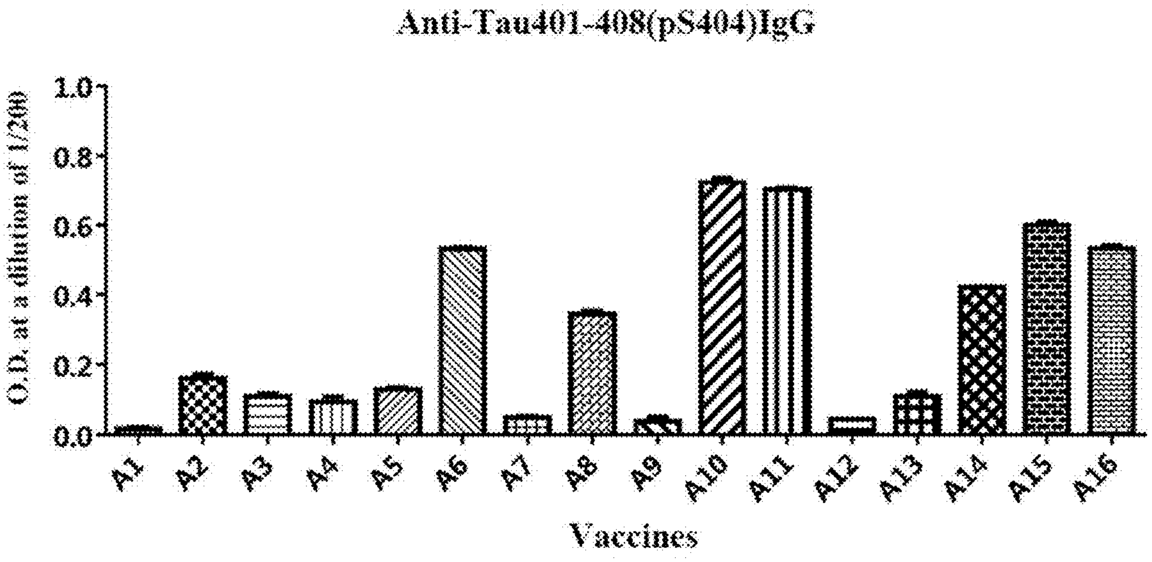

The above antigens were respectively dissolved in carbonate buffer with pH=9.5, diluted to 1 μg/mL, and added to an ELISA plate (100 μL/well) at 4° C. overnight. The liquid in the plate was discarded, and after the 96-well plate was washed three times with PBST (300 μL/well), the liquid in the plate was discarded. A3% BSA (PBS) solution was added (200 μL/well), and incubation was carried out at 37° C. for 1 hour. The liquid in the plate was discarded, and after the 96-well plate was washed three times with PBST (300 μL/well), the liquid in the plate was discarded. Mouse serum diluted by gradient with a 1% BSA (PBS) solution was added (100 μL/well), and incubation was carried out at 37° C. for 2 hour. The liquid in the plate was discarded, and after the 96-well plate was washed three times with PBST (300 L/well), the liquid in the plate was discarded. A goat-anti-mouse HRP labled antibody solution diluted with a 1% BSA (PBS) solution was added (100 μL/well), and incubation was carried out at 37° C. for 1 hour. The liquid in the plate was discarded, and after the 96-well plate was washed three times with PBST (300 μL/well), the liquid in the plate was discarded. TMB was added (300 μL/well) and incubation was carried out in the dark at room temperature for 25 min. 1M sulfuric acid aqueous solution was added to terminate the reaction. Absorbance was detected at 450 nm using a microplate reader The levels of the antibodies against different antigens in the serum after the fourth immunization by vaccines A1 to A16 are shown in FIG. 6. The results show that all mice in groups of vaccines A1 to A6 can successfully produce antibodies against the pY18 site after immunization, wherein vaccines A2 and A5 can produce high concentrations of antibodies; and vaccines A7 to A16 can hardly produce antibodies against the pY18 site (FIG. 6A). All the groups of mice immunized with vaccines A1 to A2 and A7 to A11 can successfully produce antibodies against the pS202/pT205 site after immunization, wherein vaccines A8 to A11 can produce high concentrations of antibodies; and vaccines A3 to A6 and A12 to A16 can hardly produce antibodies against the pS202/pT205 site (FIG. 6B). All the groups of mice immunized with vaccines A3 and A12 to A14 can successfully produce high concentrations of antibodies against the pT212/pS214 site after immunization, vaccines A6, A8 and A11 can produce low concentrations of antibodies; and vaccines A1, A2, A4, A5, A7, A9 to A11, A15 and A16 can hardly produce antibodies against the pT212/pS214 site (FIG. 6C). All the groups of mice immunized with vaccines A4, A7 to A8 and A12 can successfully produce high concentrations of antibodies against the pS231/pS235 site after immunization, vaccines A1, A5 and A14 can produce low concentrations of antibodies; and vaccines A2, A3, A6, A9 to A11, A13, A15 and A16 can hardly produce antibodies against the pS231/pS235 site (FIG. 6D). All the groups of mice immunized with vaccines A5, A9, A13 and A15 to A16 can successfully produce high concentrations of antibodies against the pS238 site after immunization, vaccines A8 and A14 can also produce relatively high concentrations of antibodies; and vaccines A1 to A4, A6, A7 and A10 to A12 can hardly procude antibodies against the pS238 site (FIG. 6E). All the groups of mice immunized with vaccines A5, A9, A13 and A16 can successfully produce high concentrations of antibodies against the pS262 site after immunization, vaccines A7 and A14 can also produce relatively high concentrations of antibodies; and vaccines A1 to A4, A6, A8 and A10 to A12 can hardly produce antibodies against the pS238 site (FIG. 6F). All the groups of mice immunized with vaccines A6, A10, A11 and A14 to A16 can successfully produce high concentrations of antibodies against the pS396 site after immunization, vaccine A8 can produce low concentrations of antibodies; and vaccines A1 to A5, A7, A9 and A12 to A13 can hardly produce antibodies against the pS396 site (FIG. 6G). All the groups of mice immunized with vaccine A6, A10, A11 and A14 to A16 can successfully produce high concentrations of antibodies against the pS404 site after immunization, vaccine A8 can produce low concentrations of antibodies; and vaccine A1 to A5, A7, A9 and A12 to A13 can hardly produce antibodies against the pS396 site (FIG. 6H). In conclusion, after used for immunizing animals, all the phosphorylated polypeptide vaccines designed in Example 1 can produce antibodies against the corresponding phosphorylation sites and have immunogenicity, and vaccine A8 and vaccine A14 can produce cross-protection responses against other phosphorylation sites; meanwhile, it was found that immunization with relatively long phosphorylated peptides can lead to relatively high concentrations of antibodies.

Figure 7A:
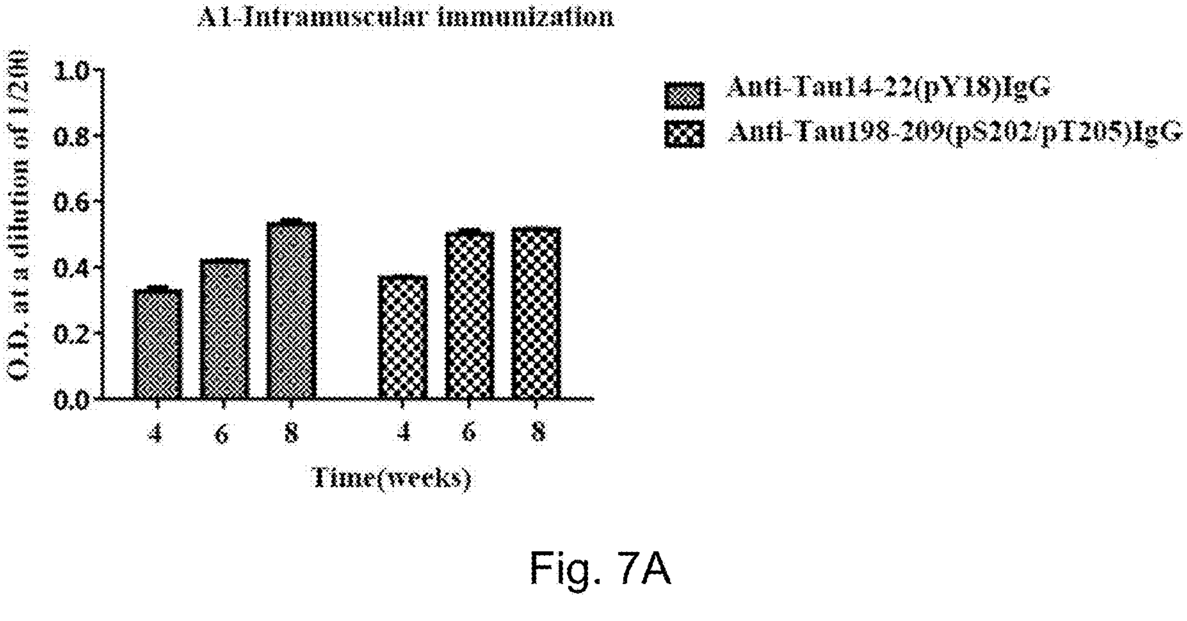
FIGS. 7A to 7S show the results of immunization of mice with phosphorylated polypeptide antigens coupled with a norovirus P protein through different immunization routes. Each group contained 6 mice. Each group of mice was immunized four times at two-week intervals. In the fourth week, sixth week and eighth week after the first immunization, the mice were subjected to blood sampling to obtain serum for ELISA experiment.
Figure 7B:
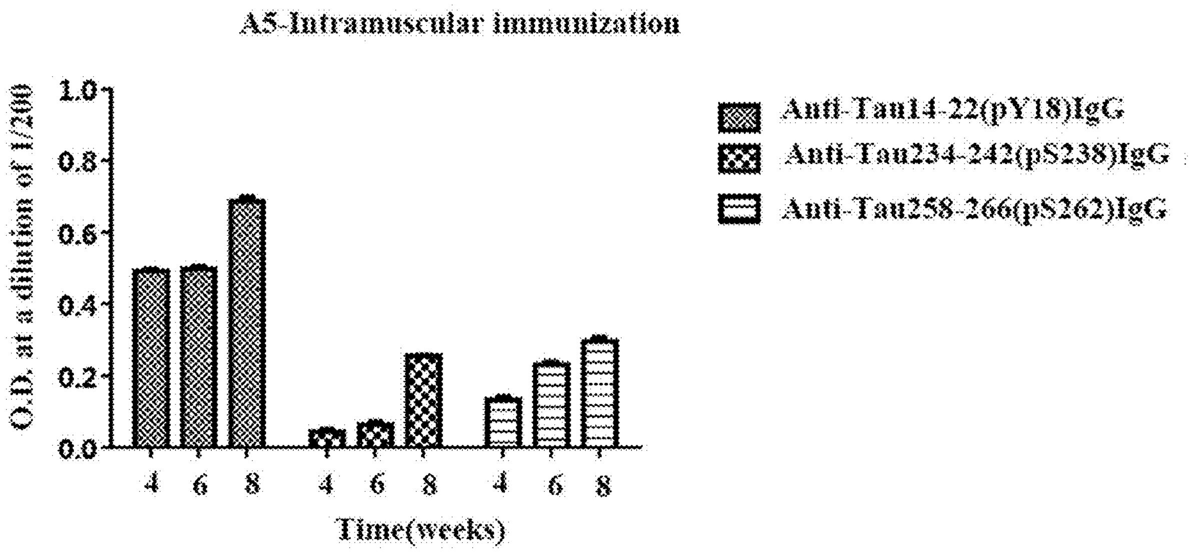
FIG. 7B shows the results of intramuscular immunization of WT mice with A5 coupled with a norovirus P protein; the contents of anti-Tau14-22 (pY18) IgG antibodies, anti-Tau234-242 (pS238) IgG antibodies and anti-Tau258-266 (pS262) IgG antibodies in the mouse serum were detected by ELISA method; the results were expressed as the mean O.D.+SD values obtained at a dilution of 1/200 of the mouse serum.
Figure 7C:
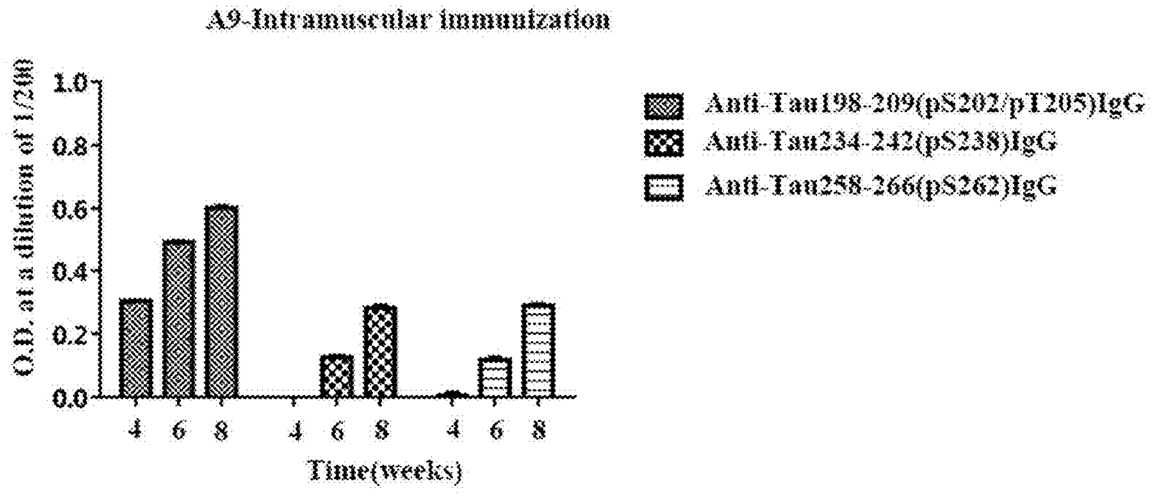
FIG. 7C shows the results of intramuscular immunization of WT mice with A9 coupled with a norovirus P protein; the contents of anti-Tau198-209 (pS202/pT205) IgG antibodies, anti-Tau234-242 (pS238) IgG antibodies and anti-Tau258-266 (pS262) IgG antibodies in the mouse serum were detected by ELISA method; the results were expressed as the mean O.D.+SD values obtained at a dilution of 1/200 of the mouse serum.
Figure 7D:
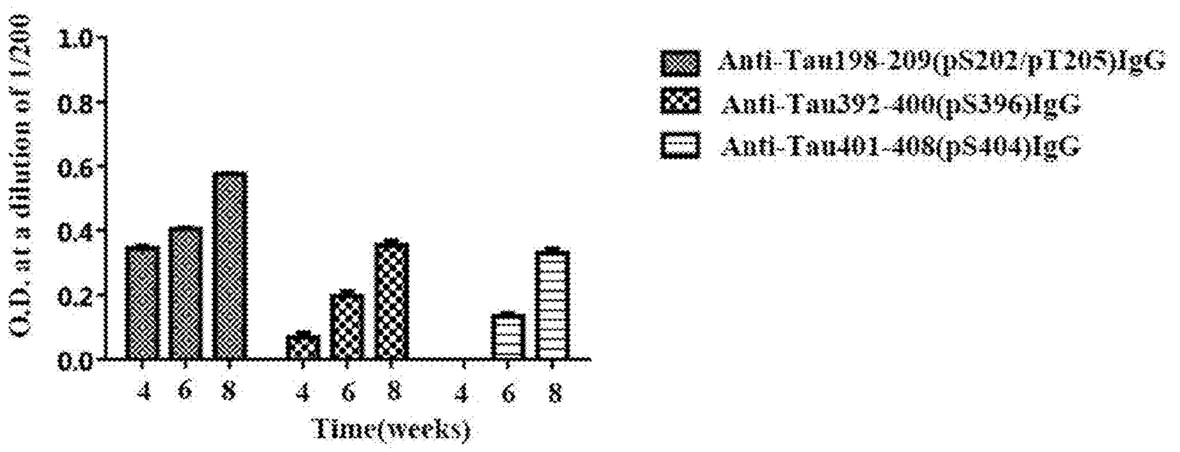
FIG. 7D shows the results of intramuscular immunization of WT mice with A10 coupled with a norovirus P protein; the contents of anti-Tau198-209 (pS202/pT205) IgG antibodies, anti-Tau392-400 (pS396) IgG antibodies and anti-Tau401-408 (pS404) IgG antibodies in the mouse serum were detected by ELISA method; the results were expressed as the mean O.D.+SD values obtained at a dilution of 1/200 of the mouse serum.
Figure 7E:
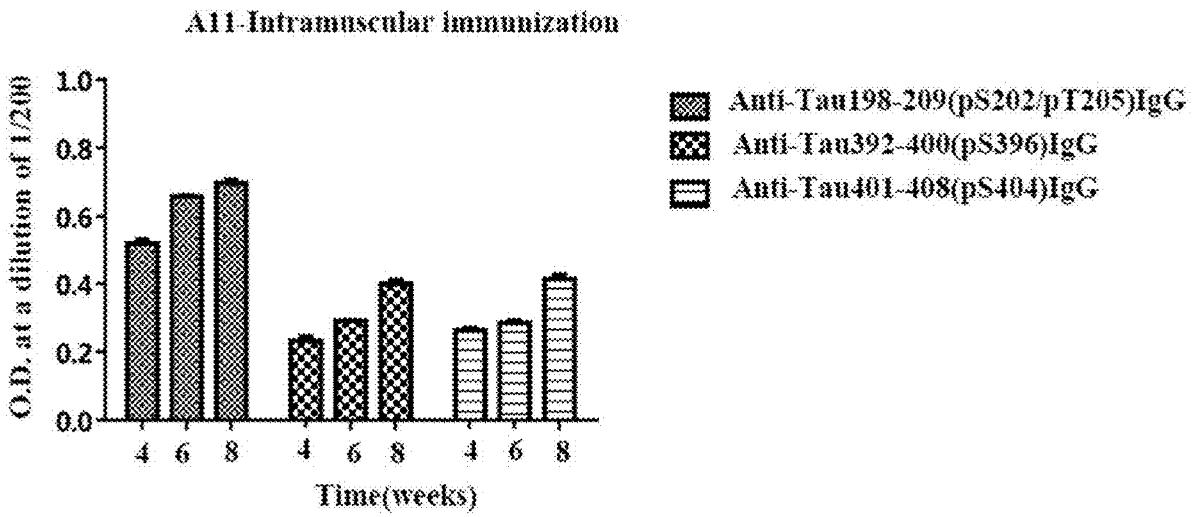
FIG. 7E shows the results of intramuscular immunization of WT mice with A11 coupled with a norovirus P protein; the contents of anti-Tau198-209 (pS202/pT205) IgG antibodies, anti-Tau392-400 (pS396) IgG antibodies and anti-Tau401-408 (pS404) IgG antibodies in the mouse serum were detected by ELISA method; the results were expressed as the mean O.D.+SD values obtained at a dilution of 1/200 of the mouse serum.
Figure 7F:
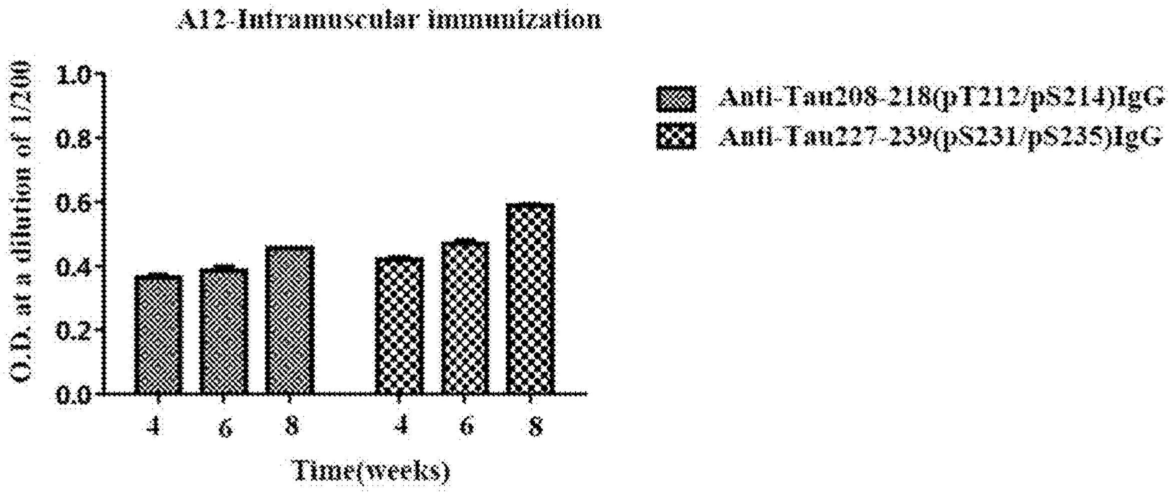
FIG. 7F shows the results of intramuscular immunization of WT mice with A12 coupled with a norovirus P protein; the contents of anti-Tau208-218 (pT212/pS214) IgG antibodies and anti-Tau227-239 (pS231/pS235)
Figure 7G:
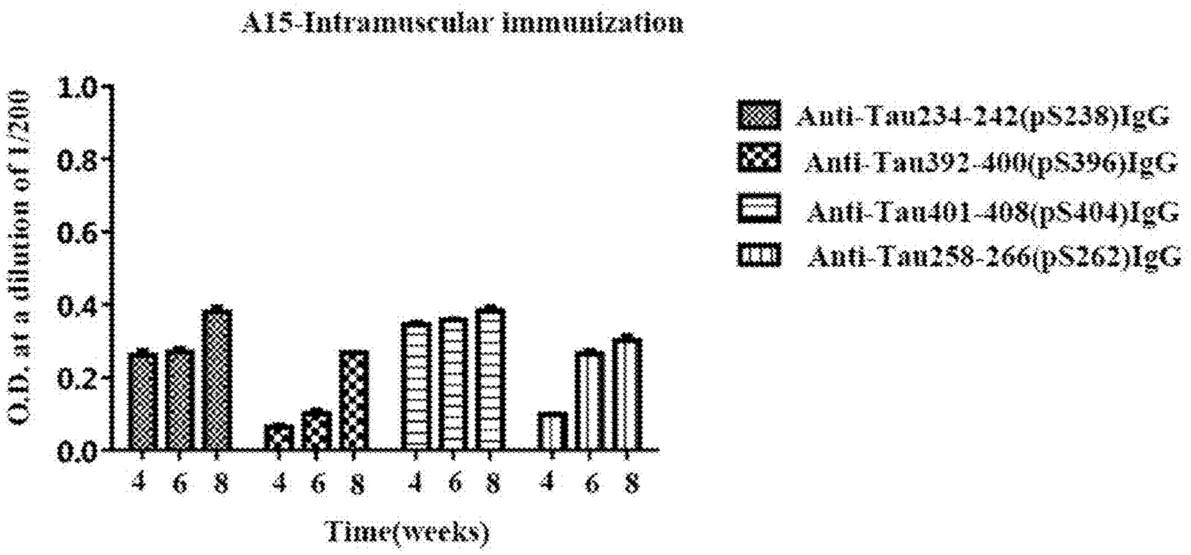
FIG. 7G shows the results of intramuscular immunization of WT mice with A15 coupled with a norovirus P protein; the contents of anti-Tau234-242 (pS238) IgG antibodies, anti-Tau258-266 (pS262) IgG antibodies, anti-Tau392-400 (pS396) IgG antibodies and anti-Tau401-408 (pS404) IgG antibodies in the mouse serum were detected by ELISA method; the results were expressed as the mean O.D.+SD values obtained at a dilution of 1/200 of the mouse serum.

Example 9: Evaluation of the Immunogenicity of Phosphorylated Polypeptide Antigens Coupled with the Norovirus P Protein PP-3C in Wild Mice Immunized with the Same by Intramuscular Injection The PP-3C protein was coupled with A1, A5, A9, A10, A11, A12 and A15 respectively to prepare complex vaccines, and wild mice were immunized with the complex vaccines by intramuscular injection. Each group contained 6 mice. The immune dosage of the protein was 25 μg/animal. The immunization was carried out at week 0, week 2, week 4 and week 6. Blood was taken two weeks after every immunization to obtain serum for ELISA assessment. The assessment was performed by the same method as in Example 8. The results are shown in FIGS. 7A-7G. As apparent from the figures, mice immunized with complex vaccine A1 can produce specific antibodies against pY18 and pS202/pT205 (FIG. 7A); mice immunized with complex vaccine A5 can produce specific antibodies against pY18, pS238 and pS262 (FIG. 7B); mice immunized with complex vaccine A9 can produce specific antibodies against pS202/pT205, pS238 and pS262 (FIG. 7C); mice immunized with complex vaccine A9 can produce specific antibodies against pS202/pT205, pS396 and pS404 (FIG. 7D); mice immunized with complex vaccine A11 can produce specific antibodies against pS202/pT205, pS396 and pS404 (FIG. 7E); mice immunized with complex vaccine A12 can produce specific antibodies against pT212/pS214 and pS231/pS235 (FIG. 7F); and mice immunized with complex vaccine A15 can produce specific antibodies against pS238, pS262, pS396 and pS404 (FIG. 7G). Thus, it can be seen that the concentration of the specific antibodies in the serum increased with each intramuscular immunization with the complex vaccine in each group, and after the fourth immunization high concentrations of antibodies were produced, wherein pY18 and pS202/pT205 epitopes are prone to leading to high concentrations of specific antibodies. Compared with other immunization routes, intramuscular immunization generally can lead to higher concentrations of antibodies.

Figure 7H:
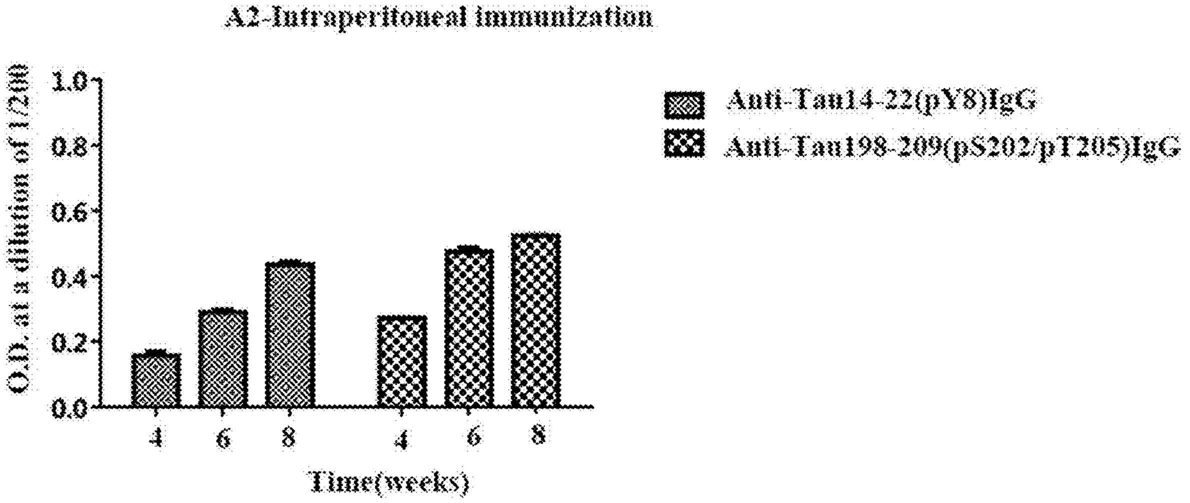
FIG. 7H shows the results of intraperitoneal immunization of WT mice with A2 coupled with a norovirus P protein; the contents of anti-Tau14-22 (pY18) IgG antibodies and anti-Tau198-209 (pS202/pT205) IgG antibodies in the mouse serum were detected by ELISA method; the results were expressed as the mean O.D.+SD values obtained at a dilution of 1/200 of the mouse serum.
Figure 7J:
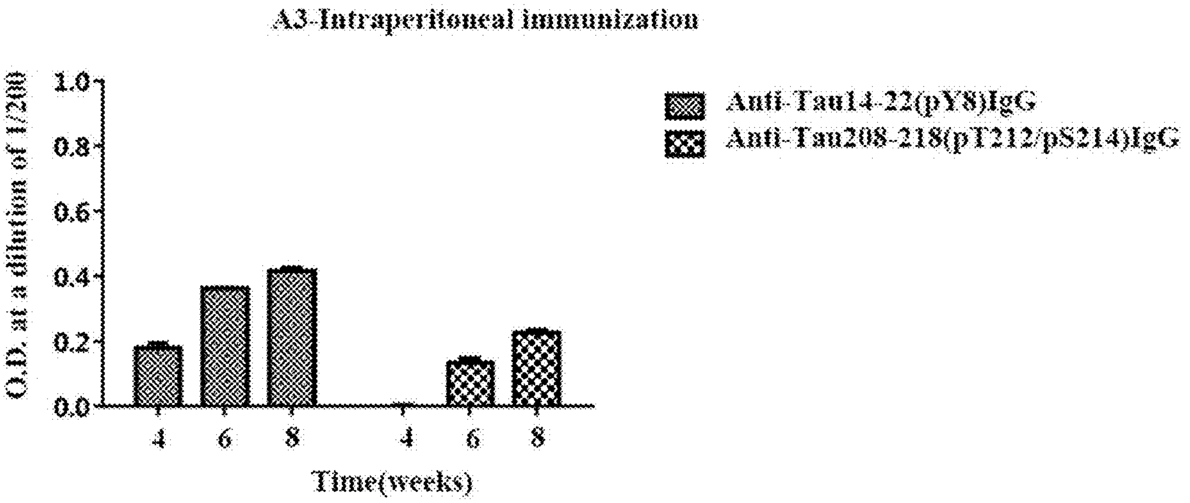
FIG. 7J shows the results of intraperitoneal immunization of WT mice with A3 coupled with a norovirus P protein; the contents of anti-Tau14-22 (pY18) IgG antibodies and anti-Tau208-218 (pT212/pS214) IgG antibodies in the mouse serum were detected by ELISA method; the results were expressed as the mean O.D.+SD values obtained at a dilution of 1/200 of the mouse serum.
Figure 7K:
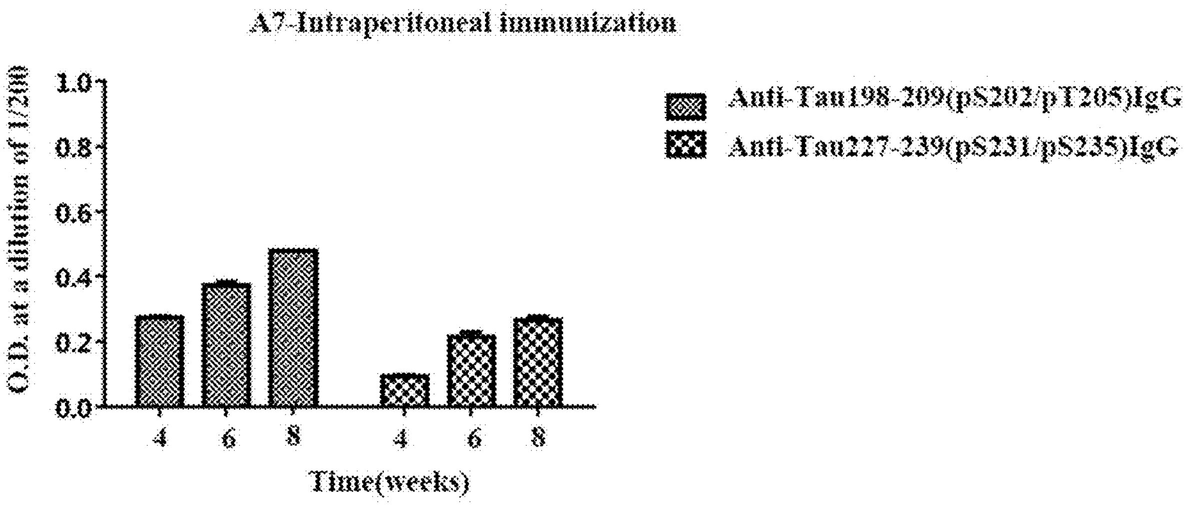
FIG. 7K shows the results of intraperitoneal immunization of WT mice with A7 coupled with a norovirus P protein; the contents of anti-Tau198-209 (pS202/pT205) IgG antibodies and anti-Tau227-239 (pS231/pS235) IgG antibodies in the mouse serum were detected by ELISA method; the results were expressed as the mean O.D.+SD values obtained at a dilution of 1/200 of the mouse serum.
Figure 7L:
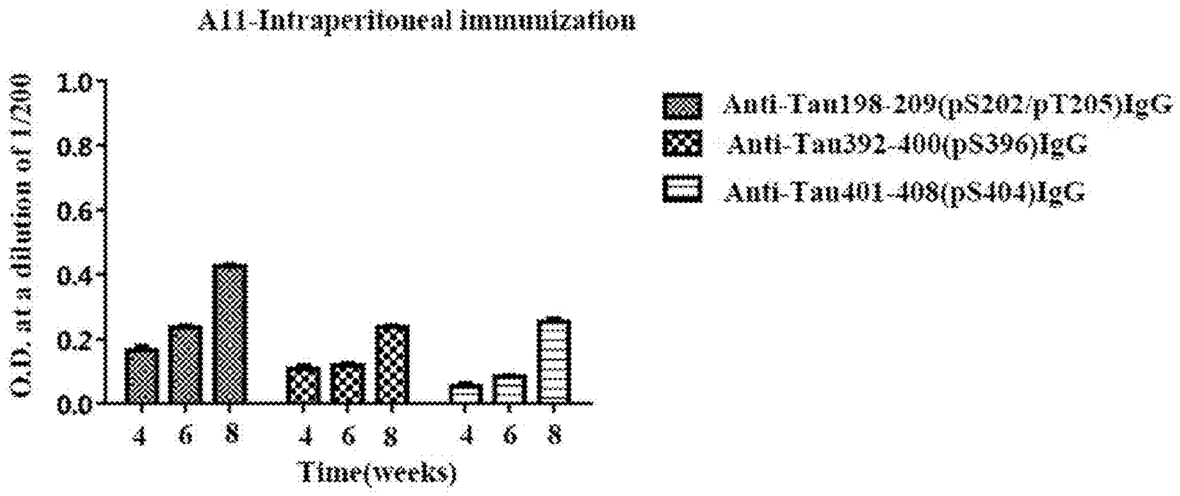
FIG. 7L shows the results of intraperitoneal immunization of WT mice with A11 coupled with a norovirus P protein; the contents of anti-Tau198-209 (pS202/pT205) IgG antibodies, anti-Tau392-400 (pS396) IgG antibodies and anti-Tau401-408 (pS404) IgG antibodies in the mouse serum were detected by ELISA method; the results were expressed as the mean O.D.+SD values obtained at a dilution of 1/200 of the mouse serum.
Figure 7M:
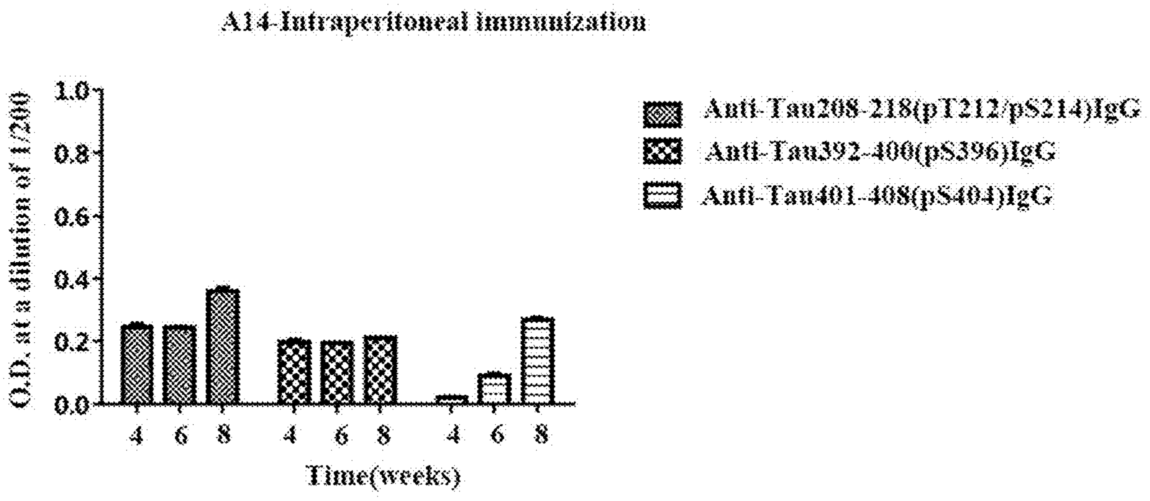
FIG. 7M shows the results of intraperitoneal immunization of WT mice with A14 coupled with a norovirus P protein; the contents of anti-Tau208-218 (pT212/pS214) IgG antibodies, anti-Tau392-400 (pS396) IgG antibodies and anti-Tau401-408 (pS404) IgG antibodies in the mouse serum were detected by ELISA method; the results were expressed as the mean O.D.+SD values obtained at a dilution of 1/200 of the mouse serum.

Example 10: Evaluation of the Immunogenicity of Phosphorylated Polypeptide Antigens Coupled with the Norovirus P Protein PP-3C in Wild Mice Immunized with the Same by Intraperitoneal Injection The PP-3C protein was coupled with A2, A3, A7, A11 and A14 respectively to prepare complex vaccines, and wild mice were immunized with the complex vaccines by intraperitoneal injection. Each group contained 6 mice. The immune dosage of the protein was 25 μg/animal. The immunization was carried out at week 0, week 2, week 4 and week 6. Blood was taken two weeks after every immunization to obtain serum for ELISA assessment. The assessment was performed by the same method as in Example 10. The results were shown in FIGS. 7H-7M. As apparent from the figures, mice immunized with complex vaccine A2 can produce specific antibodies against pY18 and pS202/pT205 (FIG. 7H); mice immunized with complex vaccine A3 can produce specific antibodies against pY18 and pT212/pS214 (FIG. 7J); mice immunized with complex vaccine A7 can produce specific antibodies against pS202/pT205 and pS231/pS235 (FIG. 7K); mice immunized with complex vaccine A11 can produce specific antibodies against pS202/pT205, pS396 and pS404 (FIG. 7L); mice immunized with complex vaccine A14 can produce specific antibodies against pT212/pS214, pS396 and pS404 (FIG. 7M). Thus, it can be seen that the concentration of the specific antibodies in the serum increased with each intraperitoneal immunization with the complex vaccine in each group, and after the fourth immunization high concentrations of antibodies were produced.

Figure 7N:
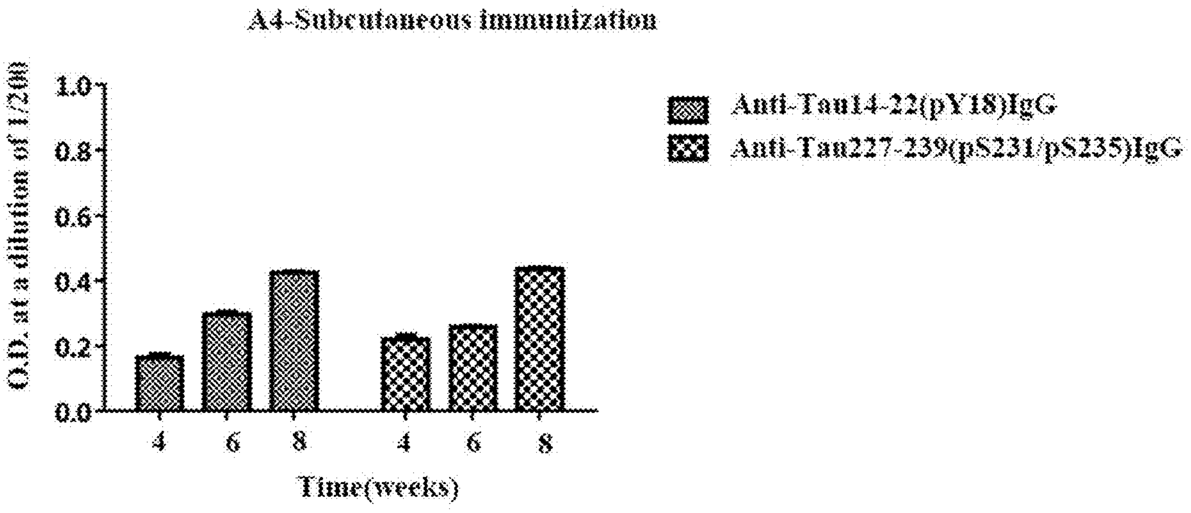
FIG. 7N shows the results of subcutaneous immunization of WT mice with A4 coupled with a norovirus P protein; the contents of anti-Tau14-22 (pY18) IgG antibodies and anti-Tau227-239 (pS231/pS235) IgG antibodies in the mouse serum were detected by ELISA method; the results were expressed as the mean O.D.+SD values obtained at a dilution of 1/200 of the mouse serum.
Figure 7O:
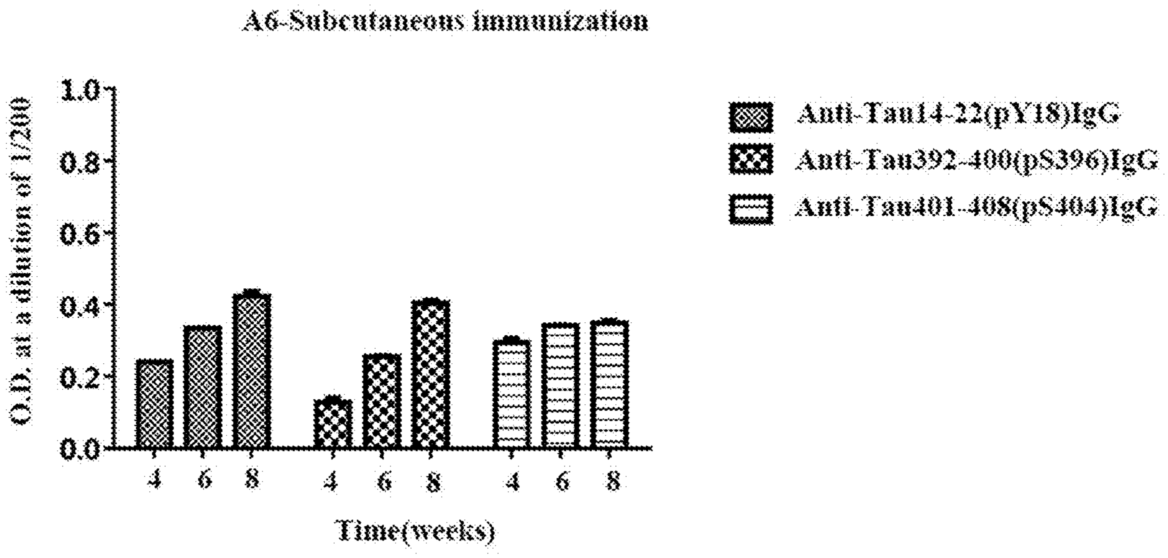
FIG. 7O shows the results of subcutaneous immunization of WT mice with A6 coupled with a norovirus P protein; the contents of anti-Tau14-22 (pY18) IgG antibodies, anti-Tau392-400 (pS396) IgG antibodies and anti-Tau401-408 (pS404) IgG antibodies in the mouse serum were detected by ELISA method; the results were expressed as the mean O.D.+SD values obtained at a dilution of 1/200 of the mouse serum.
Figure 7P:
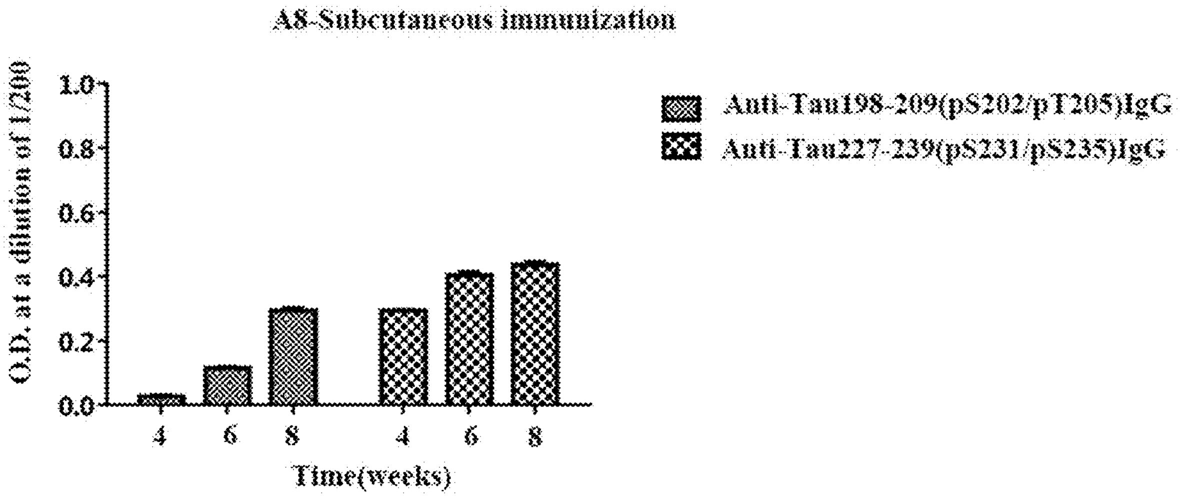
FIG. 7P shows the results of subcutaneous immunization of WT mice with A8 coupled with a norovirus P protein; the contents of anti-Tau198-209 (pS202/pT205) IgG antibodies and anti-Tau227-239 (pS231/pS235) IgG antibodies in the mouse serum were detected by ELISA method; the results were expressed as the mean O.D.+SD values obtained at a dilution of 1/200 of the mouse serum.
Figure 7Q:
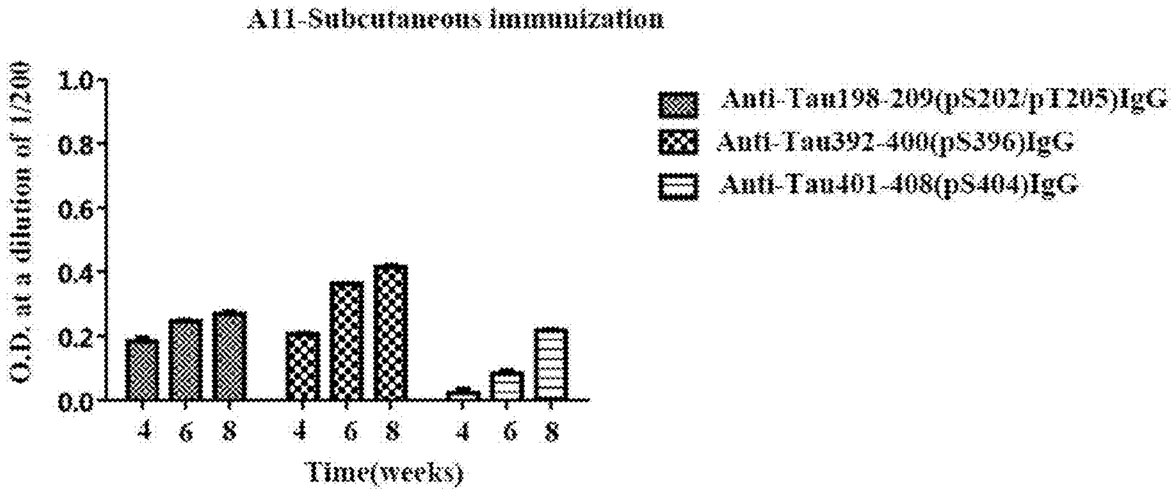
FIG. 7Q shows the results of subcutaneous immunization of WT mice with A11 coupled with a norovirus P protein; the contents of anti-Tau198-209 (pS202/pT205) IgG antibodies, anti-Tau392-400 (pS396) IgG antibodies and anti-Tau401-408 (pS404) IgG antibodies in the mouse serum were detected by ELISA method; the results were expressed as the mean O.D.+SD values obtained at a dilution of 1/200 of the mouse serum.
Figure 7R:
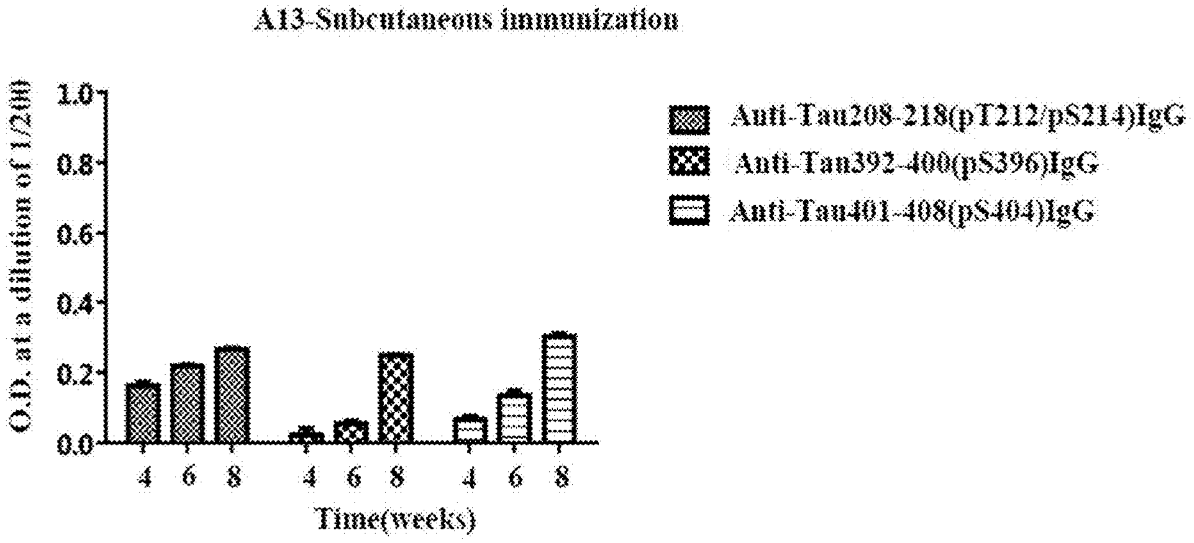
FIG. 7R shows the results of subcutaneous immunization of WT mice with A13 coupled with a norovirus P protein; the contents of anti-Tau208-218 (pT212/pS214) IgG antibodies, anti-Tau392-400 (pS396) IgG antibodies and anti-Tau401-408 (pS404) IgG antibodies in the mouse serum were detected by ELISA method; the results were expressed as the mean O.D.+SD values obtained at a dilution of 1/200 of the mouse serum.
Figure 7S:
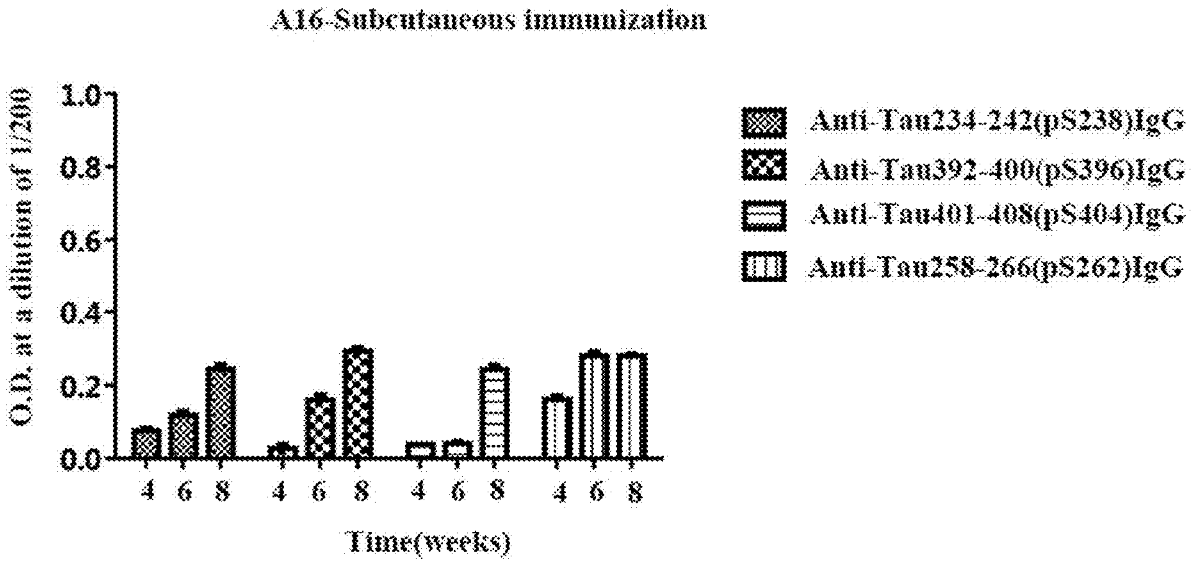

Example 11: Evaluation of the Immunogenicity of Phosphorylated Polypeptide Antigens Coupled with the Norovirus P Protein PP-3C in Wild Mice Immunized with the Same by Subcutaneous Injection The PP-3C protein was coupled with A4, A6, A8, A11, A13 and A16 respectively to prepare complex vaccines, and wild mice were immunized with the complex vaccines by subcutaneous injection. Each group contained 6 mice. The immune dosage of the protein was 25 μg/animal. The immunization was carried out at week 0, week 2, week 4 and week 6. Blood was taken two weeks after every immunization to obtain serum for ELISA assessment. The assessment was performed by the same method as in Example 10. The results were shown in FIGS. 7N-7S. As apparent from the figures, mice immunized with complex vaccine A4 can produce specific antibodies against pY18 and pS231/pS235 (FIG. 7N); mice immunized with complex vaccine A6 can produce specific antibodies against pY18, pS396 and pS404 (FIG. 7O); mice immunized with complex vaccine A8 can produce specific antibodies against pS202/pT205 and pS231/pS235 (FIG. 7P); mice immunized with complex vaccine A11 can produce specific antibodies against pS202/pT205, pS396 and pS404 (FIG. 7Q); mice immunized with complex vaccine A13 can produce specific antibodies against pT212/pS214, pS396 and pS404 (FIG. 7R); and mice immunized with complex vaccine A16 can produce specific antibodies against pS238, pS262, pS396 and pS404 (FIG. 7S). Thus, it can be seen that the concentration of the specific antibodies in the serum increased with each subcutaneous immunization with the complex vaccine in each group, and after the fourth immunization high concentrations of antibodies were produced.

Figure 8:
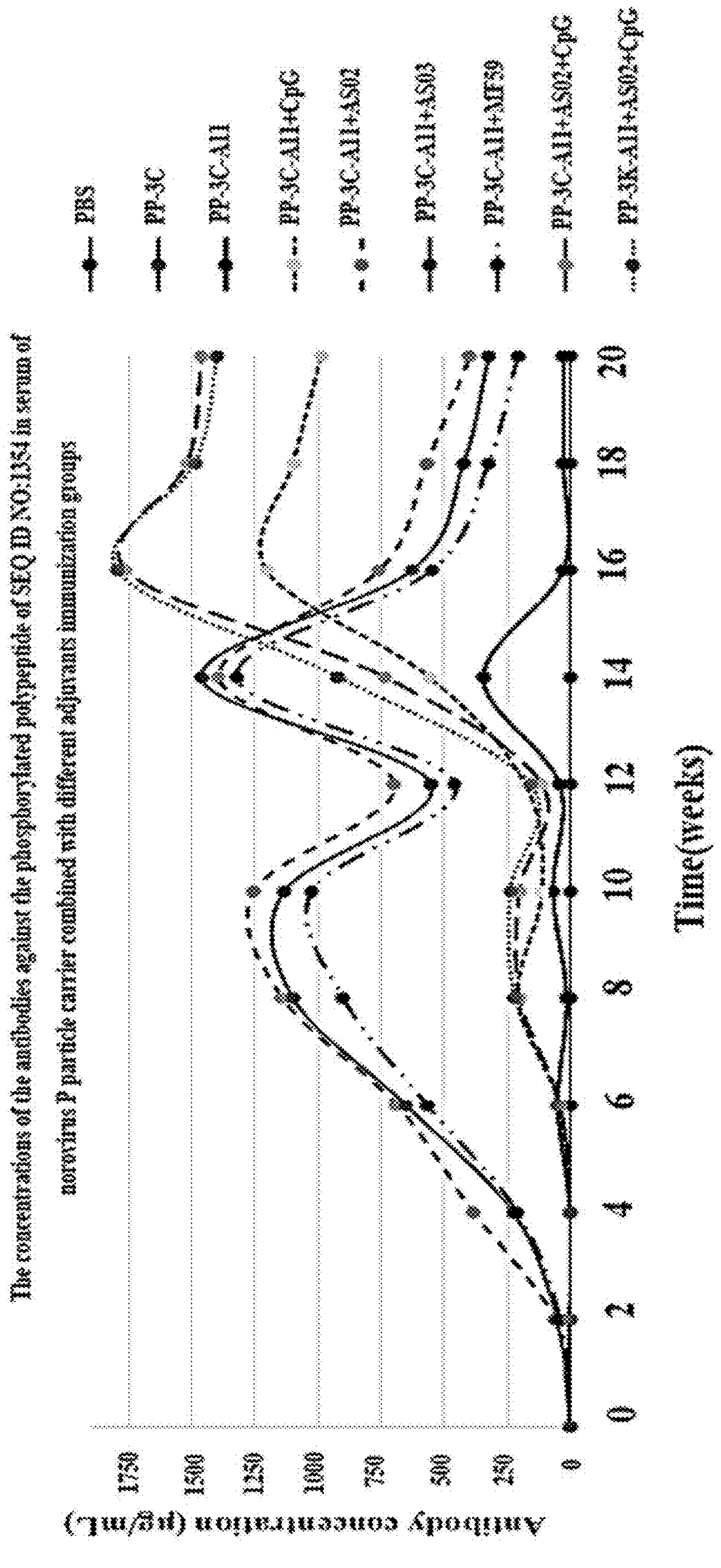
FIG. 8 show that a phosphorylated polypeptide antigen coupled with PP-3C was combined respectively with CpG, AS02, AS03, MF59 and AS02+CpG adjuvant and a phosphorylated polypeptide antigen coupled with PP-3K was combined with AS02+CpG adjuvant to form different combinations; wild mice were intramuscularly immunized respectively with the above different combinations at week 0, week 2, week 4, week 6 and week 12; blood was taken two weeks after every immunization to obtain serum. The phosphorylated polypeptide of SEQ ID NO: 1354 corresponding to phosphorylated amino acids at sites 202, 205, 396, and 404 of full-length Tau protein, was used as the coating antigen for ELISA experiment. The results were expressed as the concentrations (standardized by AT8 antibodies) of the antibodies of anti-phosphorylated polypeptide obtained in each group of mice.

Example 12: Evaluation of the Immunogenicity of Phosphorylated Polypeptide Antigens Coupled with a Norovirus P Protein in Wild Mice Take vaccine A11 as an example. Wild mice were intramuscularly immunized with A11 coupled with PP-3C or PP-3K and combined with CpG, AS02, AS03, MF59 and AS02+CpG adjuvants respectively. Each group contained 6 mice. The immune dosage of the protein was 25 μg/animal. The immunization was carried out at week 0, week 2, week 4, week 6 and week 12. Blood was taken two weeks after every immunization to obtain serum for ELISA assessment. In the ELISA experiments, the phosphorylated polypeptide (whose sequence is SEQ ID NO: 1354) coupled with BSA was used as the coating antigen, and was phosphorylated at sites corresponding to amino acids 202, 205, 396 and 404 of full-length Tau protein. A standard curve was plotted with the concentration of the AT8 antibody (Thermo scientific MN1020) diluted by gradient versus the O.D. value to calibrate the concentration of the antibodies in the mouse serum. The change in antibody concentration in each group is shown in FIG. 8. As can be seen from FIG. 8, vaccine A11 coupled with a norovirus P protein and combined with different adjuvants could elicit relatively high immune responses in wild mice, wherein the vaccine in combination with AS02, AS03 and MF59 enabled gradual production of relatively high concentrations of antibodies through four consecutive immunizations, and failed to stimulate and elicit a relatively high immune response in one immunization after an interval of 6 weeks; the vaccine combined with CpG adjuvant and AS02+CpG adjuvant enabled gradual production of relatively low concentrations of antibodies through four consecutive immunizations, and stimulated the production of a relatively high concentration of antibodies in one immunization after an interval of 6 weeks, and the antibody content could maintain a high level for a long time. The production of antibodies in mice immunized with vaccine A11 coupled with PP-3C was basically the same with that in mice immunized with vaccine A11 coupled with PP-3K. Immunization of wild mice with the other phosphorylated polypeptide vaccines produced similar effects (the results are not shown).

Figure 9A:
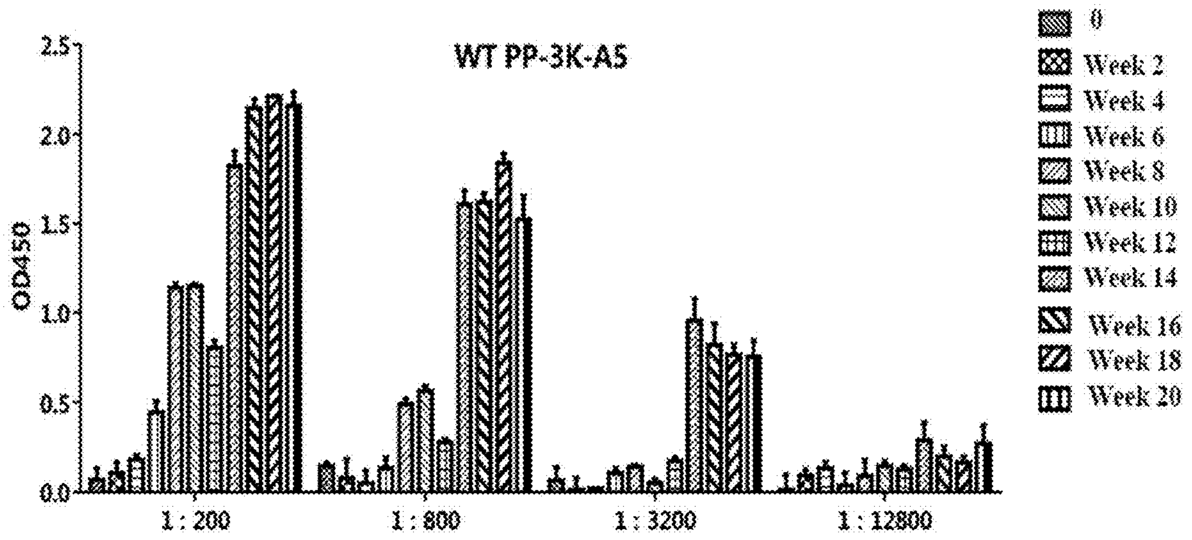
FIG. 9A to 9F show the analysis of immunogenicity of phosphorylated polypeptide antigen A5 coupled with PP-3K and combined with AS02+CpG adjuvant in mice.

Example 13: Evaluation of the Immunogenicity of Phosphorylated Polypeptide Antigen A5 Coupled with a Norovirus P Protein in Wild Mice Wild mice were intramuscularly immunized with the vaccine prepared by combining phosphorylated polypeptide antigen A5 coupled with PP-3K with AS02+CpG adjuvant. Each group contained 6 mice. The immune dosage of the protein was 25 μg/animal. The immunization was carried out at week 0, week 2, week 4, week 6 and week 12. Blood was taken two weeks after every immunization to obtain serum for ELISA assessment. In the ELISA experiments, the phosphorylated polypeptide (whose sequence is SEQ ID NO: 1355) coupled with BSA was used as the coating antigen, and was phosphorylated at sites corresponding to amino acids 18, 238 and 262 of full-length Tau protein. The change in the concentration of antibodies in the mouse serum is shown in FIG. 9A. The results showed that intramuscular immunization with the PP-3K-A5 complex vaccine in combiantion with AS02+CpG adjuvant led to an increase in antibodies with each immunization, the vaccine had good immunogenicity, and high antibody concentrations could be maintained for at least 6 weeks after the last immunization, with antibody titer ≥12,800.

Figure 9B:
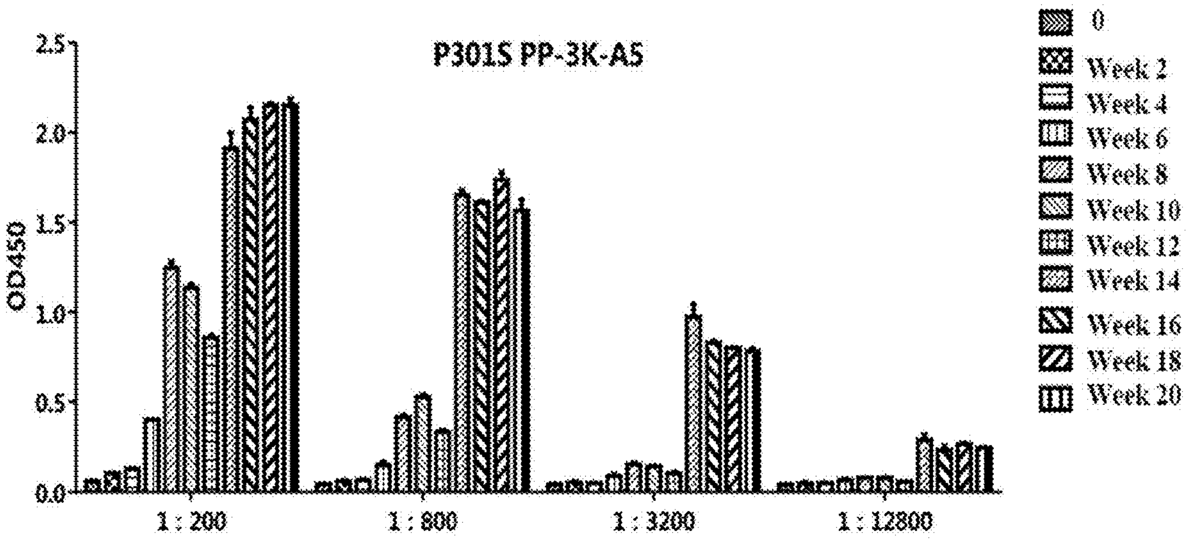

Example 14: Evaluation of the Immunogenicity of Phosphorylated Polypeptide Antigen A5 Coupled with a Norovirus P Protein in P301S Transgenic Mice P301S transgenic mice were intramuscularly immunized with the vaccine prepared by combining phosphorylated polypeptide antigen A5 coupled with PP-3K with AS02+CpG adjuvant. Each group contained 8 mice. The immune dosage of the protein was 25 μg/animal. The immunization was carried out at week 0, week 2, week 4, week 6 and week 12. Blood was taken two weeks after every immunization to obtain serum for ELISA assessment. In the ELISA experiments, the phosphorylated polypeptide (whose sequence is SEQ ID NO: 1355) coupled with BSA was used as the coating antigen, and was phosphorylated at sites corresponding to amino acids 18, 238 and 262 of full-length Tau protein. The change in the concentration of antibodies in the mouse serum is shown in FIG. 9B. The results showed that intramuscular immunization with the PP-3K-A5 complex vaccine in combination with AS02+CpG adjuvant led to an increase in antibodies with each immunization, the vaccine had good immunogenicity, and high antibody concentrations could be maintained for at least 6 weeks after the last immunization, with antibody titer ≥12,800.

Figure 9C:
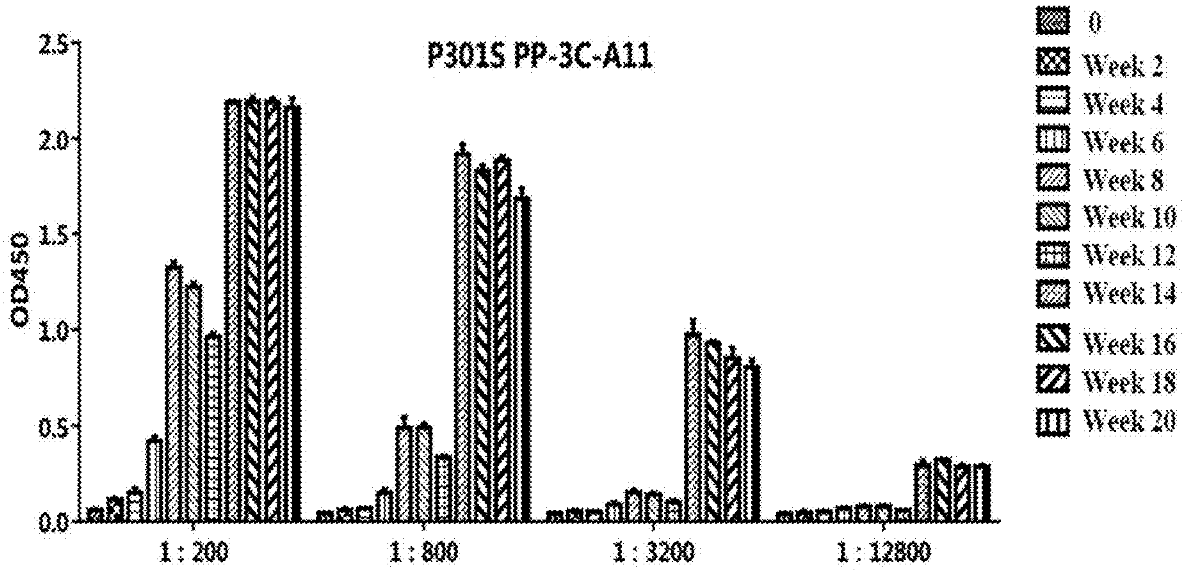

Example 15: Evaluation of the Immunogenicity of Phosphorylated Polypeptide Antigen A11 Coupled with a Norovirus P Protein in P301S Transgenic Mice P301S transgenic mice were intramuscularly immunized with the vaccine prepared by combining phosphorylated polypeptide antigen A11 coupled with PP-3C with AS02+CpG adjuvant. Each group contained 12 mice. The immune dosage of the protein was 25 μg/animal. The immunization was carried out at week 0, week 2, week 4, week 6 and week 12. Blood was taken two weeks after every immunization to obtain serum for ELISA assessment. In the ELISA experiments, the phosphorylated polypeptide (whose sequence is SEQ ID NO: 1354) coupled with BSA was used as the coating antigen, and was phosphorylated at sites corresponding to amino acids 202, 205, 396 and 404 of full-length Tau protein. The change in the concentration of antibodies in the mouse serum is shown in FIG. 9C. The results showed that intramuscular immunization with the PP-3K-A11 complex vaccine in combination with AS02+CpG adjuvant led to an increase in antibodies with each immunization, the vaccine had good immunogenicity, and high antibody concentrations could be maintained for at least 6 weeks after the last immunization, with antibody titer ≥12,800.

Figure 9D:
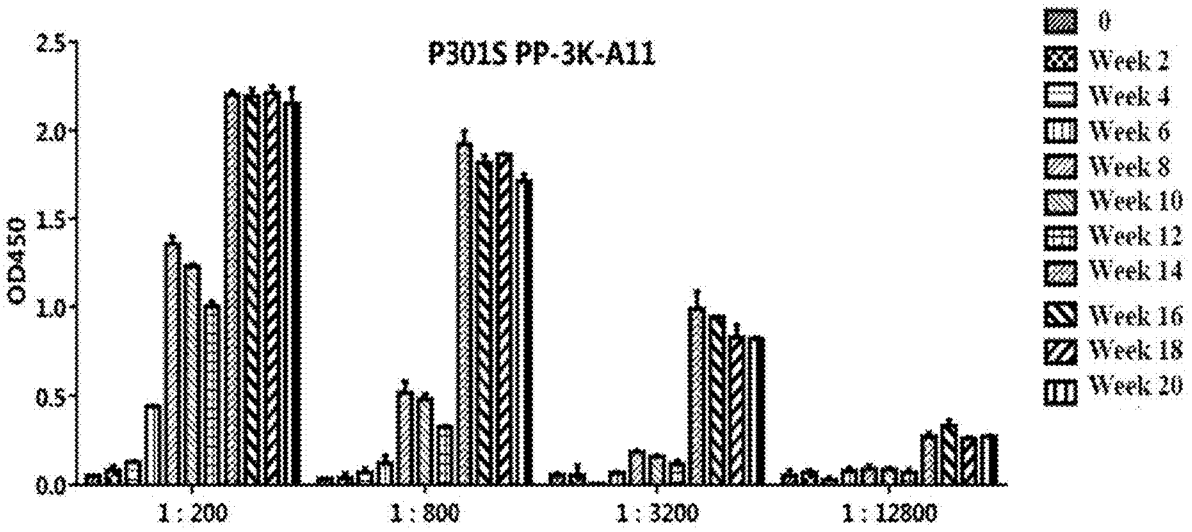

Example 16: Evaluation of the Immunogenicity of Phosphorylated Polypeptide Antigen A11 Coupled with a Norovirus P Protein in P301S Transgenic Mice P301S transgenic mice were intramuscularly immunized with the vaccine prepared by combining phosphorylated polypeptide antigen A11 coupled with PP-3K with AS02+CpG adjuvant. Each group contained 12 mice. The immune dosage of the protein was 25 μg/animal. The immunization was carried out at week 0, week 2, week 4, week 6 and week 12. Blood was taken two weeks after every immunization to obtain serum for ELISA assessment. In the ELISA experiments, the phosphorylated polypeptide (whose sequence is SEQ ID NO: 1354) coupled with BSA was used as the coating antigen, and was phosphorylated at sites corresponding to amino acids 202, 205, 396 and 404 of full-length Tau protein. The change in the concentration of antibodies in the mouse serum is shown in FIG. 9D. The results showed that intramuscular immunization with the PP-3K-A5 complex vaccine in combination with AS02+CpG adjuvant led to an increase in antibodies with each immunization, the vaccine had good immunogenicity, and high antibody concentrations could be maintained for at least 6 weeks after the last immunization, with antibody titer ≥12,800.

Figure 9E:
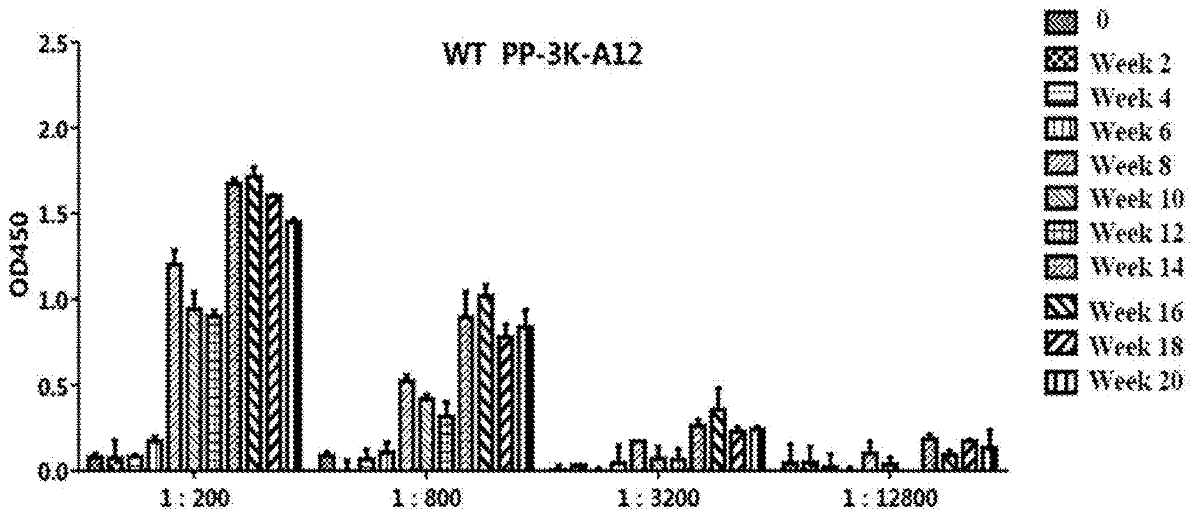

Example 17: Evaluation of the Immunogenicity of Phosphorylated Polypeptide Antigen A12 Coupled with a Norovirus P Protein in Wild Mice Wild mice were intramuscularly immunized with the vaccine prepared by combining phosphorylated polypeptide antigen A12 coupled with PP-3K with AS02+CpG adjuvant. Each group contained 6 mice. The immune dosage of the protein was 25 μg/animal. The immunization was carried out at week 0, week 2, week 4, week 6 and week 12. Blood was taken two weeks after every immunization to obtain serum for ELISA assessment. In the ELISA experiments, the phosphorylated polypeptide (whose sequence is SEQ ID NO: 1356) coupled with BSA was used as the coating antigen, and was phosphorylated at sites corresponding to amino acids 212, 214, 231 and 235 of full-length Tau protein. The change in the concentration of antibodies in the mouse serum is shown in FIG. 9E. The results showed that intramuscular immunization with the PP-3K-A12 complex vaccine in combination with AS02+CpG adjuvant led to an increase in antibodies with each immunization, the vaccine had good immunogenicity, and high antibody concentrations could be maintained for at least 6 weeks after the last immunization, with antibody titer ≥12,800.

Figure 9F:
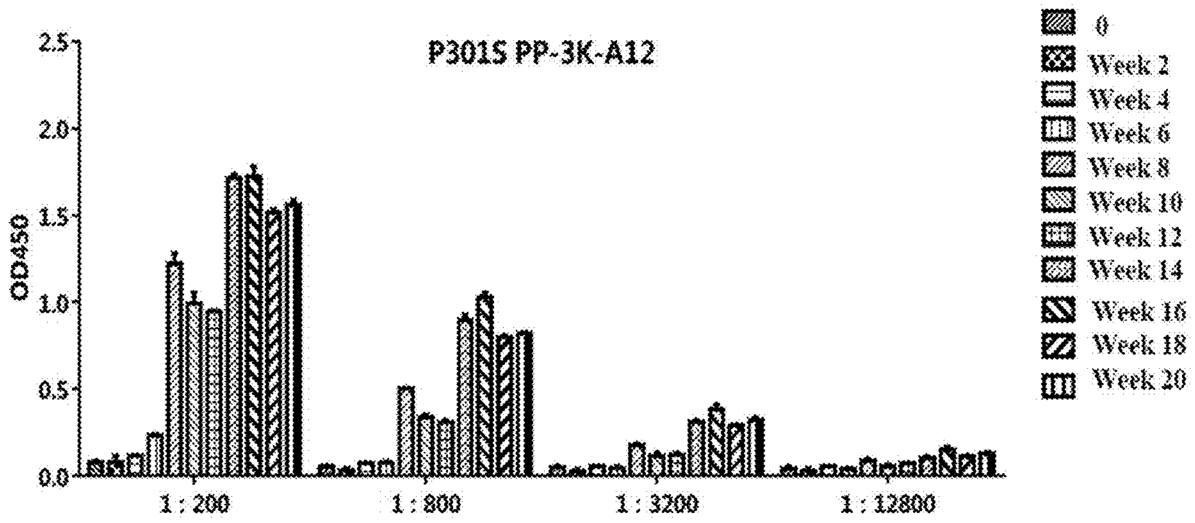

Example 18: Evaluation of the Immunogenicity of Phosphorylated Polypeptide Antigen A12 Coupled with a Norovirus P Protein in P301S Transgenic Mice P301S transgenic mice were intramuscularly immunized with the vaccine prepared by combining phosphorylated polypeptide antigen A12 coupled with PP-3K with AS02+ CpG adjuvant. Each group contained 12 mice. The immune dosage of the protein was 25 μg/animal. The immunization was carried out at week 0, week 2, week 4, week 6 and week 12. Blood was taken two weeks after every immunization to obtain serum for ELISA assessment. In the ELISA experiments, the phosphorylated polypeptide (whose sequence is SEQ ID NO: 1356) coupled with BSA was used as the coating antigen, and was phosphorylated at sites corresponding to amino acids 212, 214, 231 and 235 of full-length Tau protein. The change in the concentration of antibodies in the mouse serum is shown in FIG. 9F. The results showed that intramuscular immunization with the PP-3K-A12 complex vaccine combined with AS02+CpG adjuvant led to an increase in antibodies with each immunization, the vaccine had good immunogenicity, and high antibody concentrations could be maintained for at least 6 weeks after the last immunization, with antibody titer ≥12,800.

Example 19: Evaluation of the Cellular Immunity of Phosphorylated Polypeptide Antigen A5 Coupled with a Norovirus P Protein in P301S Transgenic Mice—ELISPOT Detection A96-well plate was coated with the monoclonal antibody against cytokine interferon γ (from elispot kit purchased from BD Corporation) in a concentration of 5 μg/mL (50 μL/well), and covered at 4° C. overnight. After discarding the coating antibody and washing once with a complete medium containing 10% fetal bovine serum, 200 μL of this complete medium was added to each well. Blocking was carried out at 37° C. for 1 hour, and then the medium was discarded. Mice used in the experiment were sacrificed by neck-pulling. Spleen cells of the mice were taken out and formulated into a cell suspension in a cell concentration of 107/mL. The cell suspension was added to the coated 96-well plate (100 μL/well). 100 μL of 1 μg/mL prokaryotically expressed full-length Tau protein and nonphosphorylated A5 polypeptide antigen were added to each well. The plate was then cultured at 37° C. in an incubator containing 5% $CO_2$ for 24 h to stimulate and activate the cells. 24 h later, the plate was washed two times with sterile water, and six times with sterile PBST (pH7.4, 0.01 mol/L PBS, containing 0.05% Tween-20) buffer to wash the cells away. 50 μL of 2 μg/mL antibody against interferon γ (from elispot kit purchased from BD Corporation) was added to each well and incubated at room temperature for 2 hours. The 96-well plate was washed, and horse radish peroxidase labeled biotin secondary antibody (from elispot kit purchased from BD Corporation) was added (50 μL/well). The plate was cultured at room temperature for 2 h, and washed four times with PBST, and two times with PBS. 50 μL of Elispot color developing solution (AEC substrate) was added to each well and reacted in the dark at room temperature for 5-60 min. The staining solution was discarded, and the plate was washed with distilled water. After being dried overnight, the sample was calculated for the number of activated cells using a microscope.

Figure 10A:
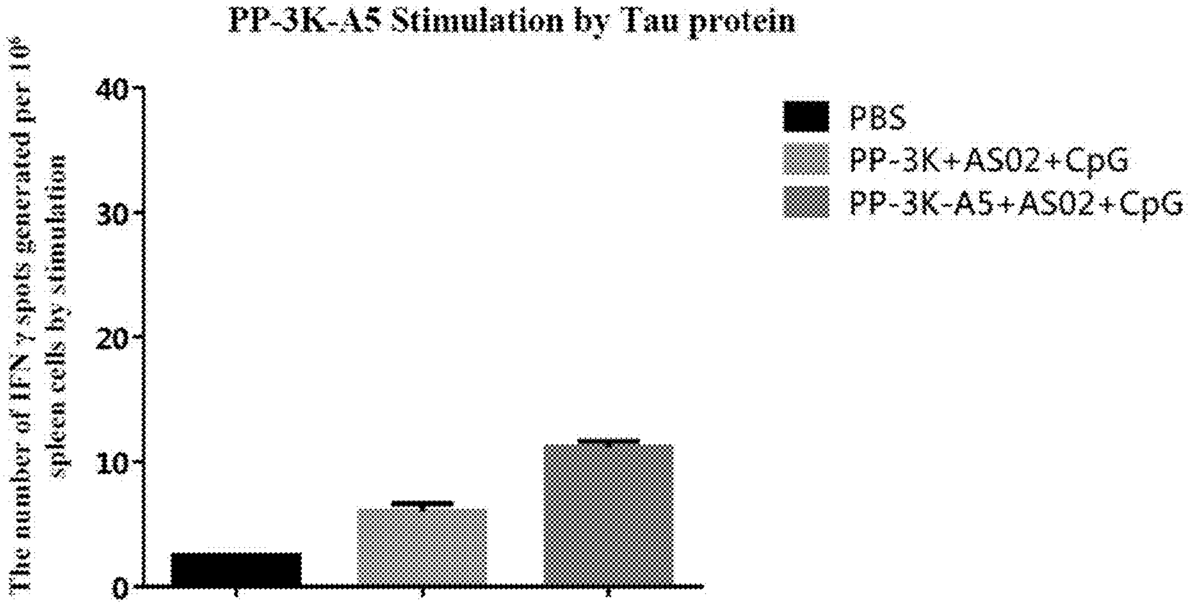
FIGS. 10A to 10H show the cellular immunity of the vaccines in P301S transgenic mice.
Figure 10B:
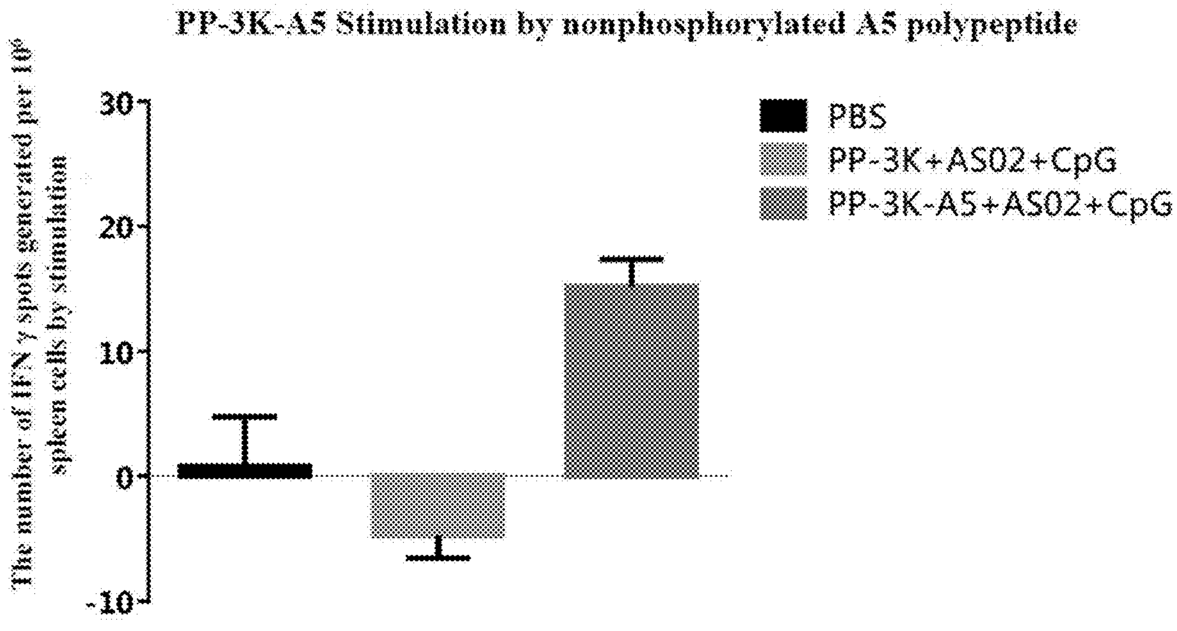

The experimental results are shown in FIGS. 10A and 10B. The PP-3K-A5 complex vaccine combined with AS02+CpG adjuvant could stimulate spleen cells to produce fewer spots after five immunizations, which demonstrates no evident T cell response occurring in the body, and as described in Example 14, this immunization strategy can stimulate the mice to produce the highest titer of specific antibodies against phosphorylated A5 polypeptide. Considering the safety of vaccines, this immunization strategy can be selected as a preferred immunization strategy.

Example 20: Evaluation of the Cellular Immunity of Phosphorylated Polypeptide Antigen A11 Coupled with a Norovirus P Protein in P301S Transgenic Mice—ELISPOT Detection The experiment was performed by the same method as in Example 19. The stimulus was 100 μL of 1 μg/mL prokaryotically expressed full-length Tau protein and nonphosphorylated A11 polypeptide antigen.

Figure 10C:
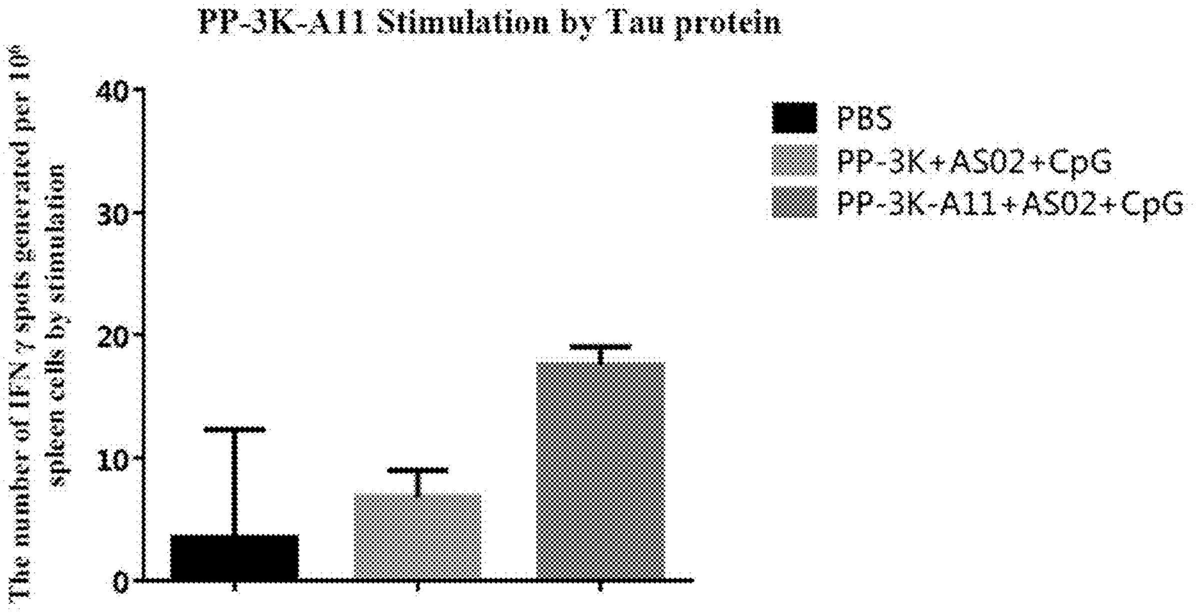
Figure 10D:
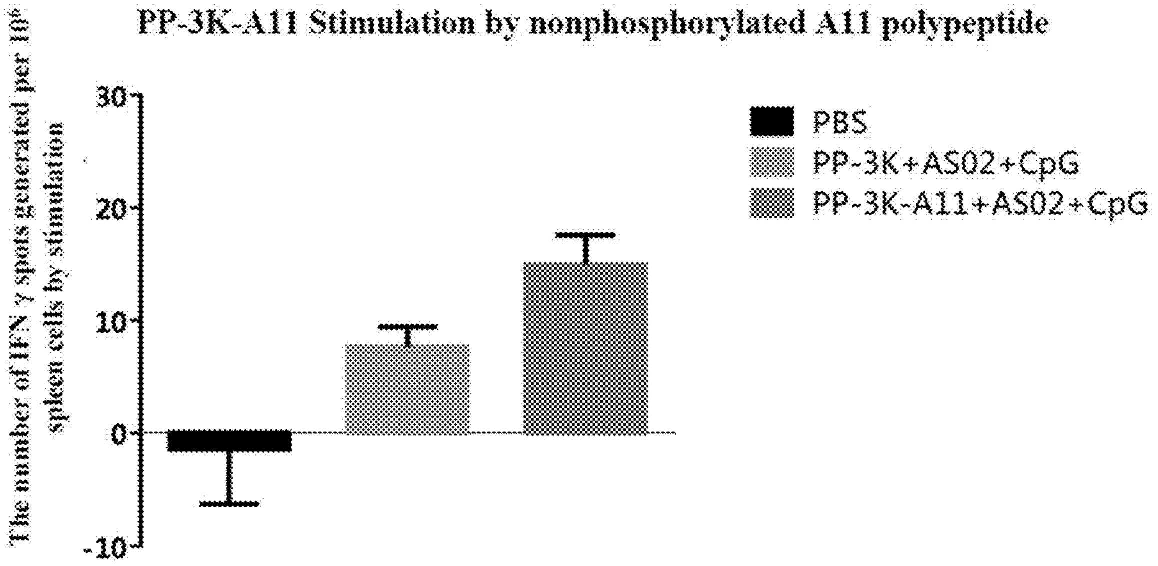

The experimental results are shown in FIGS. 10C and 10D. The PP-3K-A11 complex vaccine combined with AS02+CpG adjuvant could stimulate spleen cells to produce fewer spots after five immunizations, which demonstrates no evident T cell response occurring in the body, and as described in Example 15, this immunization strategy can stimulate the mice to produce the highest titer of specific antibodies against phosphorylated A11 polypeptide. Considering the safety of vaccines, this immunization strategy can be selected as a preferred immunization strategy.

Example 21: Evaluation of the Cellular Immunity of Phosphorylated Polypeptide Antigen A11 Coupled with a Norovirus P Protein in P301S Transgenic Mice—ELISPOT Detection The experiment was performed by the same method as in Example 19. The stimulus was 100 μL of 1 μg/mL prokaryotically expressed full-length Tau protein and nonphosphorylated A11 polypeptide antigen.

Figure 10E:
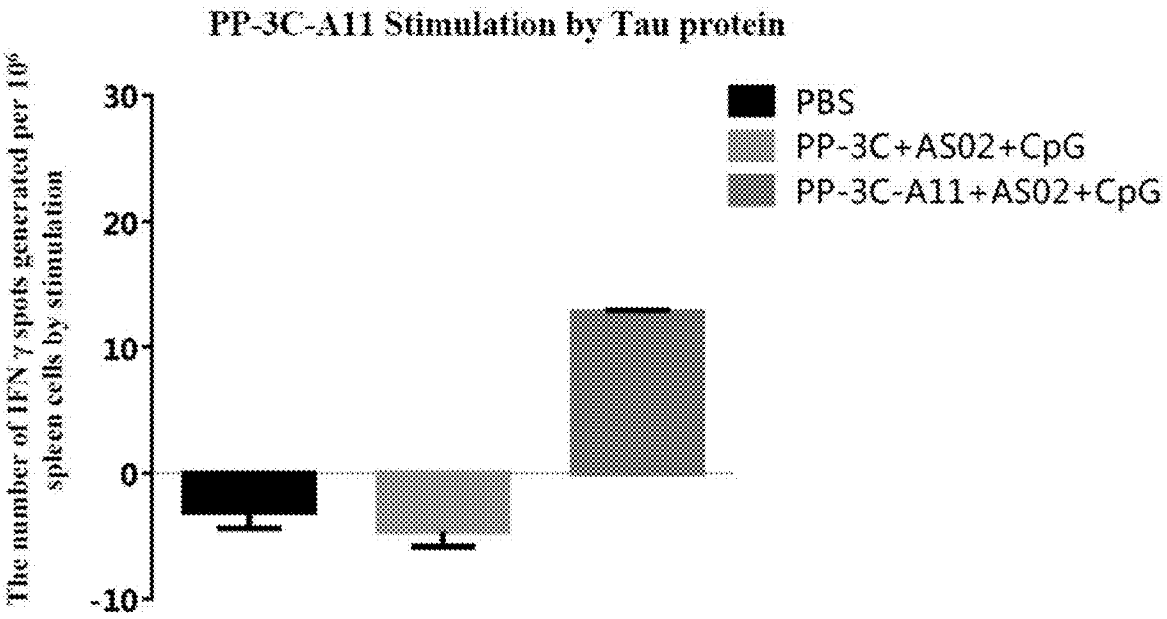
Figure 10F:
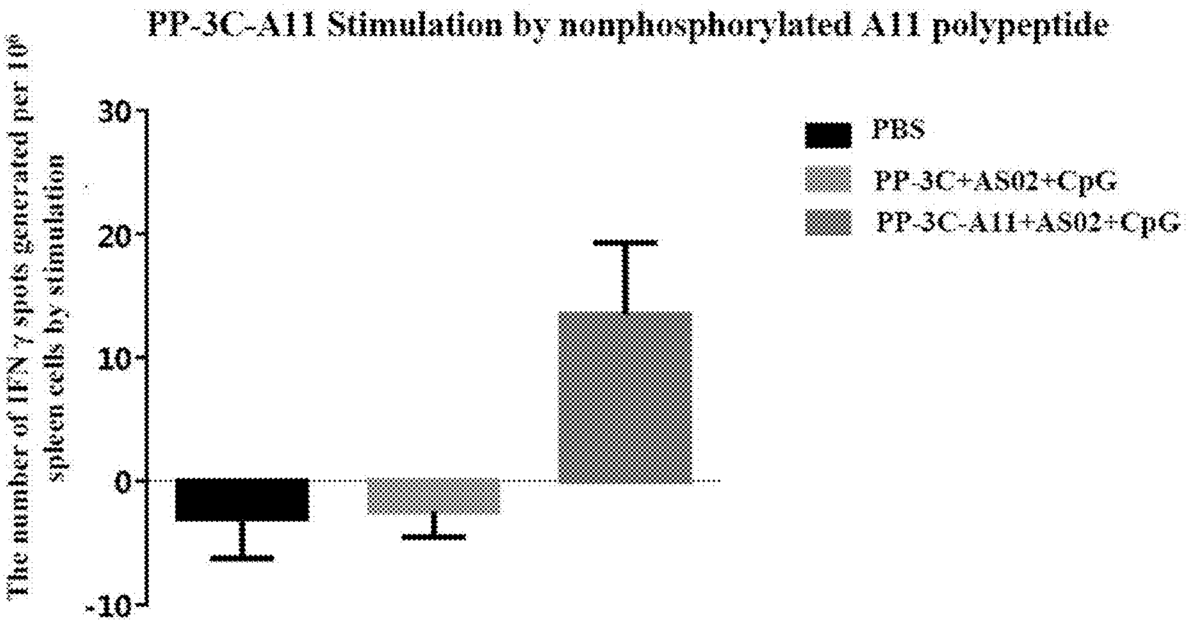

The experimental results are shown in FIGS. 10E and 10F. The PP-3K-A11 complex vaccine combined with AS02+ CpG adjuvant could stimulate spleen cells to produce fewer spots after five immunizations, which demonstrates no evident T cell response occurring in the body, and as described in Example 15, this immunization strategy can stimulate the mice to produce the highest titer of specific antibodies against phosphorylated A11 polypeptide. Considering the safety of vaccines, this immunization strategy can be selected as a preferred immunization strategy.

Example 22: Evaluation of the Cellular Immunity of Phosphorylated Polypeptide Antigen A12 Coupled with a Norovirus P Protein in P301S Transgenic Mice—ELISPOT Detection The experiment was performed by the same method as in Example 19. The stimulus was 100 μL of 1 μg/mL prokaryotically expressed full-length Tau protein and nonphosphorylated A12 polypeptide antigen.

Figure 10G:
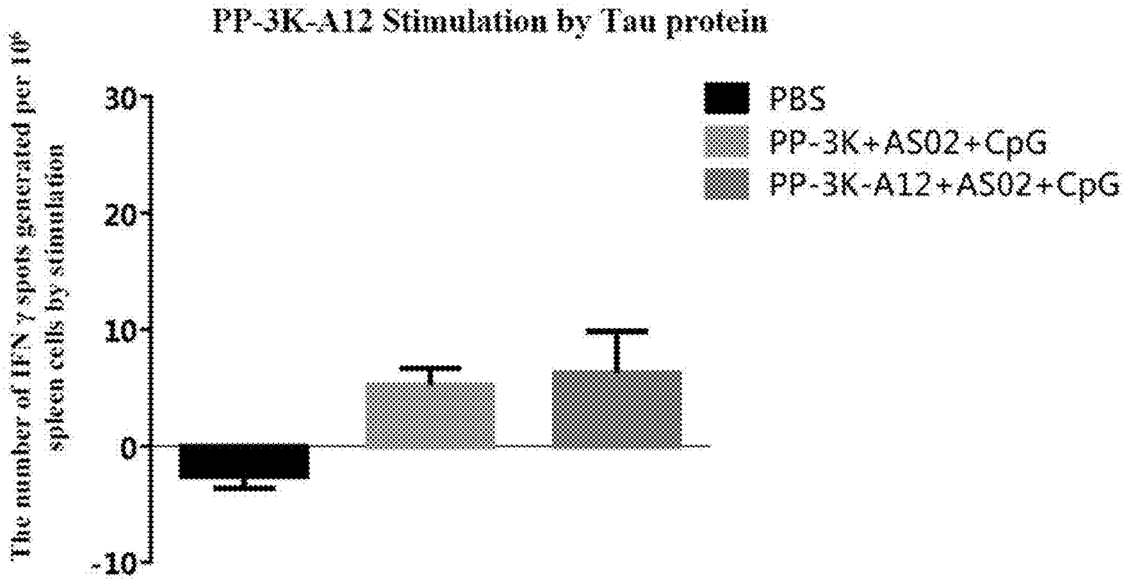
Figure 10H:
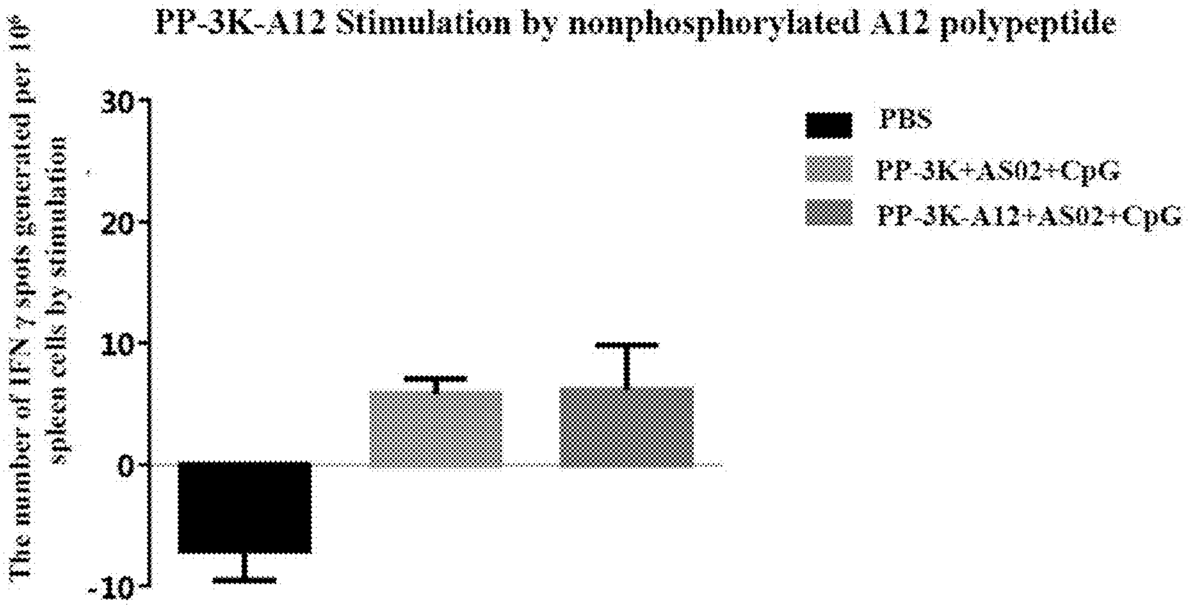

The experimental results are shown in FIGS. 10G and 10H. The PP-3K-A12 complex vaccine combined with AS02+CpG adjuvant could stimulate spleen cells to produce fewer spots after five immunizations, which demonstrates no evident T cell response occurring in the body, and as described in Example 15, this immunization strategy can stimulate the mice to produce the highest titer of specific antibodies against phosphorylated A12 polypeptide. Considering the safety of vaccines, this immunization strategy can be selected as a preferred immunization strategy.

Figure 11A:
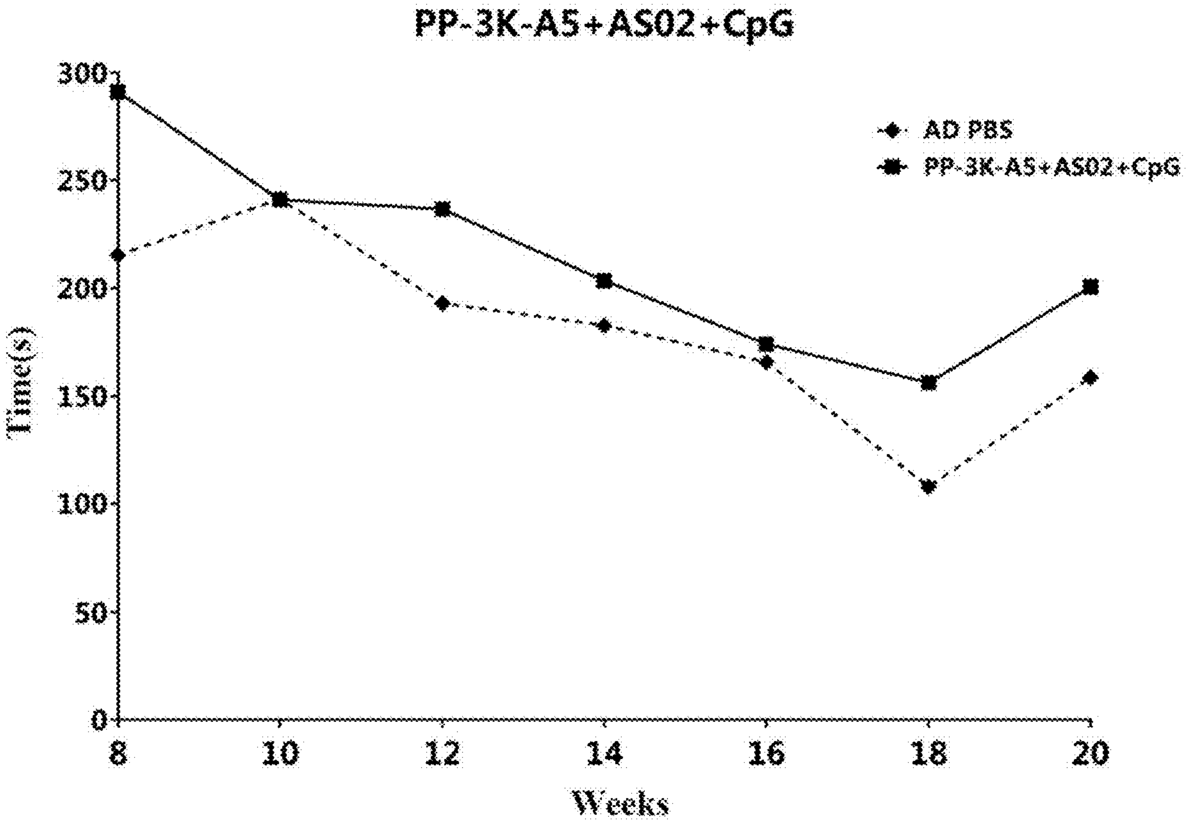
FIGS. 11A to 11D show the rota-rod behavior of the vaccines in P301S transgenic mice.

Example 23: Evaluation of the Behavior of P301S Transgenic Mice Immunized with Phosphorylated Polypeptide Antigen A5 Coupled with a Norovirus P Protein P301S transgenic mice were immunized with phosphorylated polypeptide antigen A5 which was coupled with PP-3K and combined with AS02+CpG adjuvant. Eight weeks after the start of the experiment, mice in the immune group were subjected to a rota-rod endurance test every two weeks. The mice were placed on the mouse rota-rod apparatus, and after the rota-rod apparatus was turned on, its rotation speed rose from 5 rpm to 40 rpm within 1.5 minutes and remained constant. The time until the mice fell from the rota-rod within 300 s was recorded. The experiment showed that the immunized mice had stronger endurance in the rota-rod experiment than the PBS group (the results are shown in FIG. 11A).

Figure 11B:
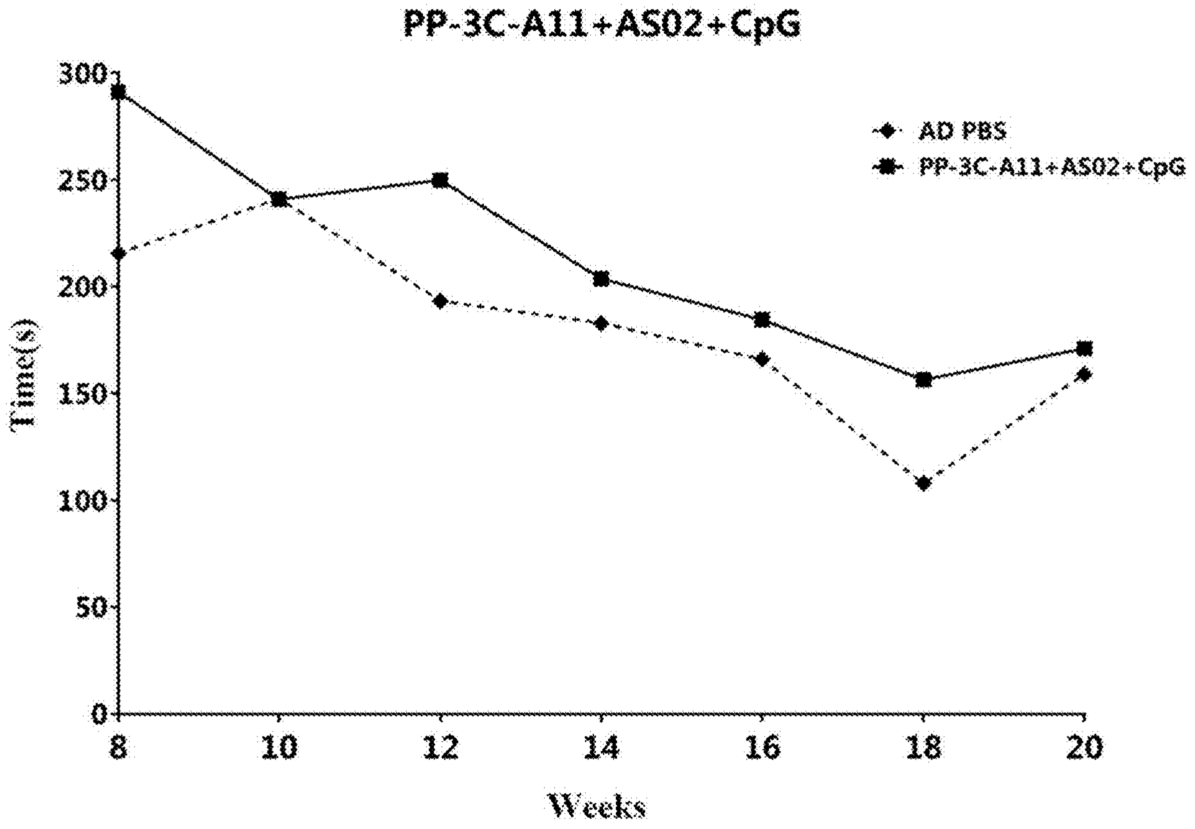

Example 24: Evaluation of the Behavior of P301S Transgenic Mice Immunized with Phosphorylated Polypeptide Antigen A11 Coupled with a Norovirus P Protein P301S transgenic mice were immunized with phosphorylated polypeptide antigen A11 which was coupled with PP-3C and combined with AS02+CpG adjuvant. Eight weeks after the start of the experiment, mice in the immune group were subjected to a rota-rod endurance test every two weeks. The mice were placed on the mouse rota-rod apparatus, and after the rota-rod apparatus was turned on, its rotation speed rose from 5 rpm to 40 rpm within 1.5 minutes and remained constant. The time until the mice fell from the rota-rod within 300 s was recorded. The experiment showed that the immunized mice had stronger endurance in the rota-rod experiment than the PBS group (the results are shown in FIG. 11B).

Figure 11C:
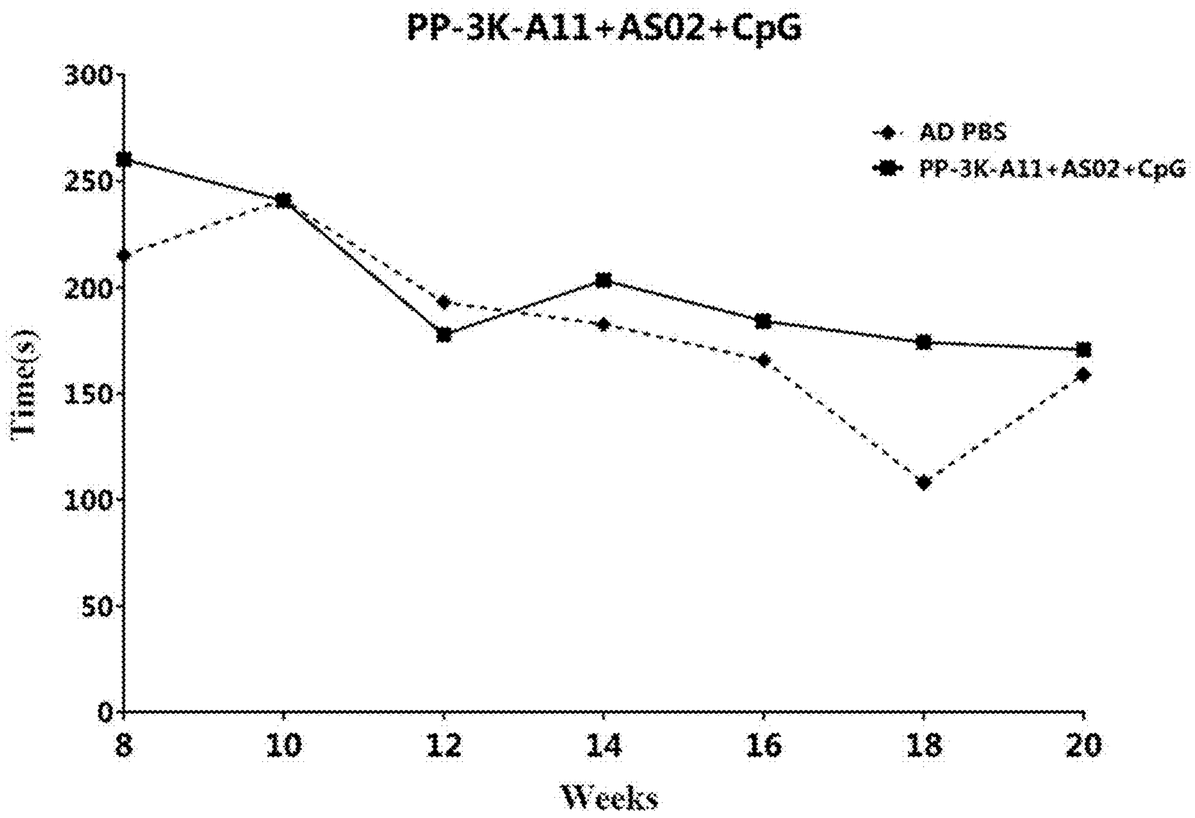

Example 25: Evaluation of the Behavior of P301S Transgenic Mice Immunized with Phosphorylated Polypeptide Antigen A11 Coupled with a Norovirus P Protein P301S transgenic mice were immunized with phosphorylated polypeptide antigen A11 which was coupled with PP-3K and combined with AS02+CpG adjuvant. Eight weeks after the start of the experiment, mice in the immune group were subjected to a rota-rod endurance test every two weeks. The mice were placed on the mouse rota-rod apparatus, and after the rota-rod apparatus was turned on, its rotation speed rose from 5 rpm to 40 rpm within 1.5 minutes and remained constant. The time until the mice fell from the rota-rod within 300 s was recorded. The experiment showed that the immunized mice had stronger endurance in the rota-rod experiment than the PBS group (the results are shown in FIG. 11C).

Figure 11D:
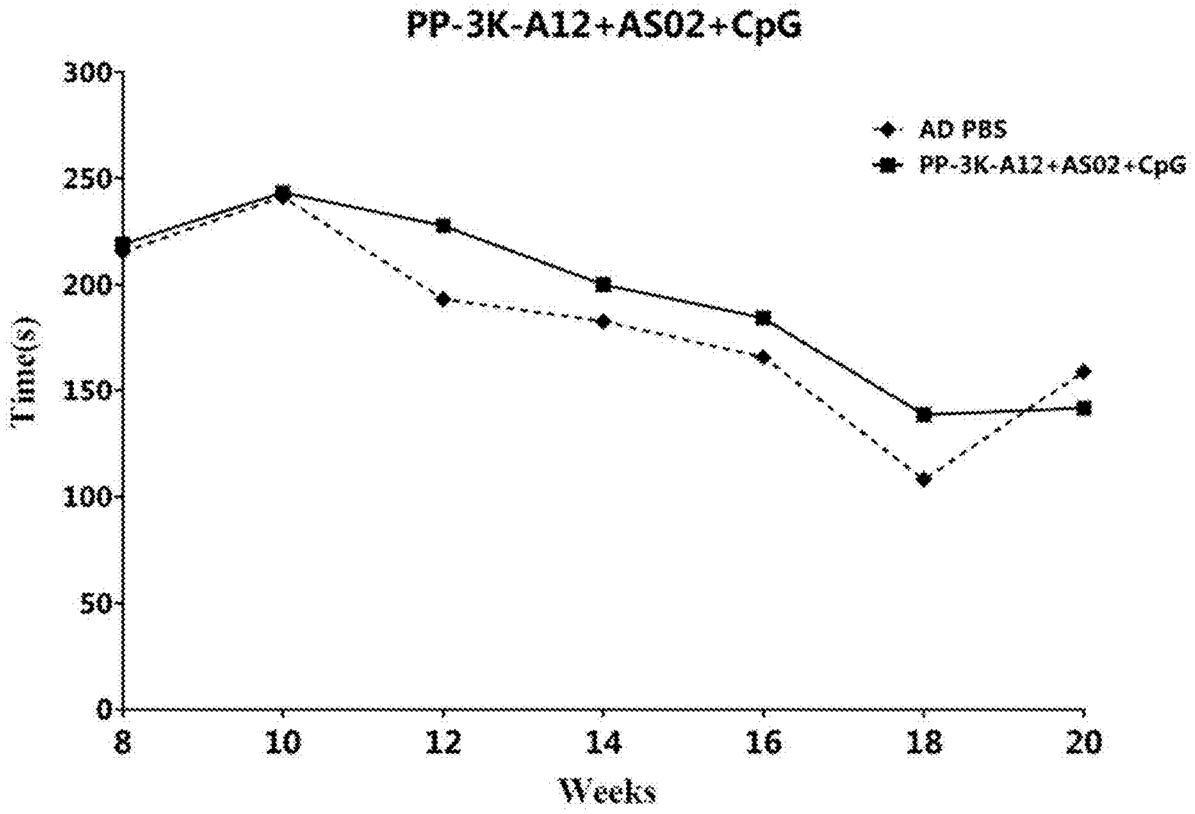

Example 26: Evaluation of the Behavior of P301S Transgenic Mice Immunized with Phosphorylated Polypeptide Antigen A12 Coupled with a Norovirus P Protein P301S transgenic mice were immunized with phosphorylated polypeptide antigen A12 which was coupled with PP-3K and combined with AS02+CpG adjuvant. Eight weeks after the start of the experiment, mice in the immune group were subjected to a rota-rod endurance test every two weeks. The mice were placed on the mouse rota-rod apparatus, and after the rota-rod apparatus was turned on, its rotation speed rose from 5 rpm to 40 rpm within 1.5 minutes and remained constant. The time until the mice fell from the rota-rod within 300 s was recorded. The experiment showed that the immunized mice had stronger endurance in the rota-rod experiment than the PBS group (the results are shown in FIG. 11D).

Example 27: Evaluation of the Behavior of P301S Transgenic Mice Immunized with Phosphorylated Polypeptide Antigen A5 Coupled with a Norovirus P Protein P301S transgenic mice were immunized with phosphorylated polypeptide antigen A5 couplded to PP-3K and combined with AS02+CpG adjuvant. Ten weeks after the start of the experiment, a nesting test was performed. All mice were transferred to new sterile mouse boxes. New sterile bedding was spread evenly to a thickness of 0.8 cm/box. Two 5 cm×5 cm cotton pieces were placed in the center of the right side of each mouse box, the total weight of the cotton being 1.2 g to 1.3 g. The mice were transferred to the mouse boxes at 16:00 and the indoor lighting was turned off. The lighting was turned on at 7:00 the next day and the nesting effect of mice was scored at 8:00. The labels with mouse numbers were hidden and three trained operators performed the scoring independently of each other. The average of the three scores represents the score of one mouse in the nesting test.

The scoring criteria were as follows: 1: the cotton was not completely torn; 2: the cotton was completely torn for nest building, the nest being shallow and flat; 3: the cotton was completely torn for nest building, but the nest had other notches besides those for exposing drinking water and the like, or the upper edge of the nest entrance was lower than the mouse's head; 4: the cotton was completely torn for nest building, and the nest entrance was higher than the mouse's head, or the nest was three-dimensional and had no notch.

Figure 12A:
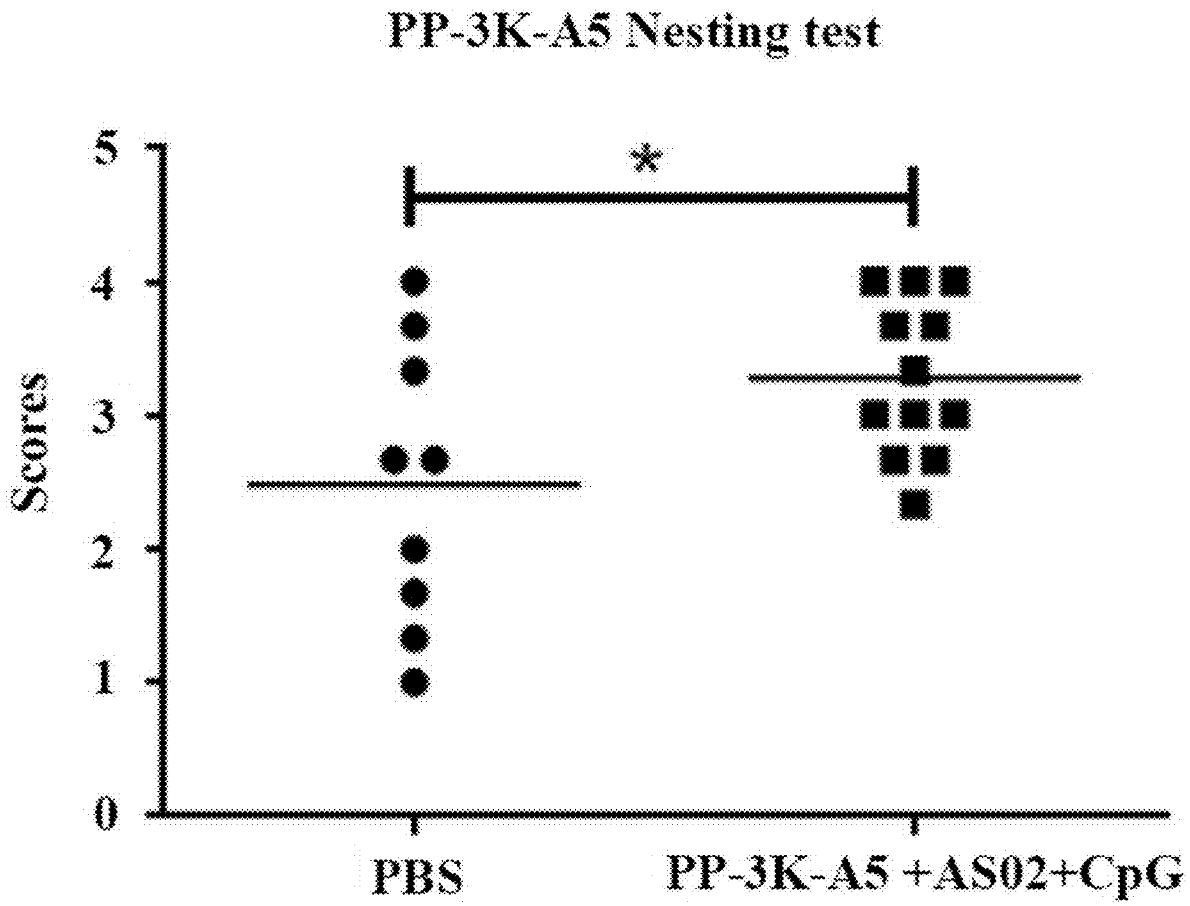
FIGS. 12A to 12D show the nesting behavior of the vaccines in P301S transgenic mice.

The nesting test can reflect the integrity of the consciousness of mice. The experiment showed that the immunized mice performed significantly better than the PBS group in the nesting test (the results are shown in FIG. 12A).

Figure 12B:
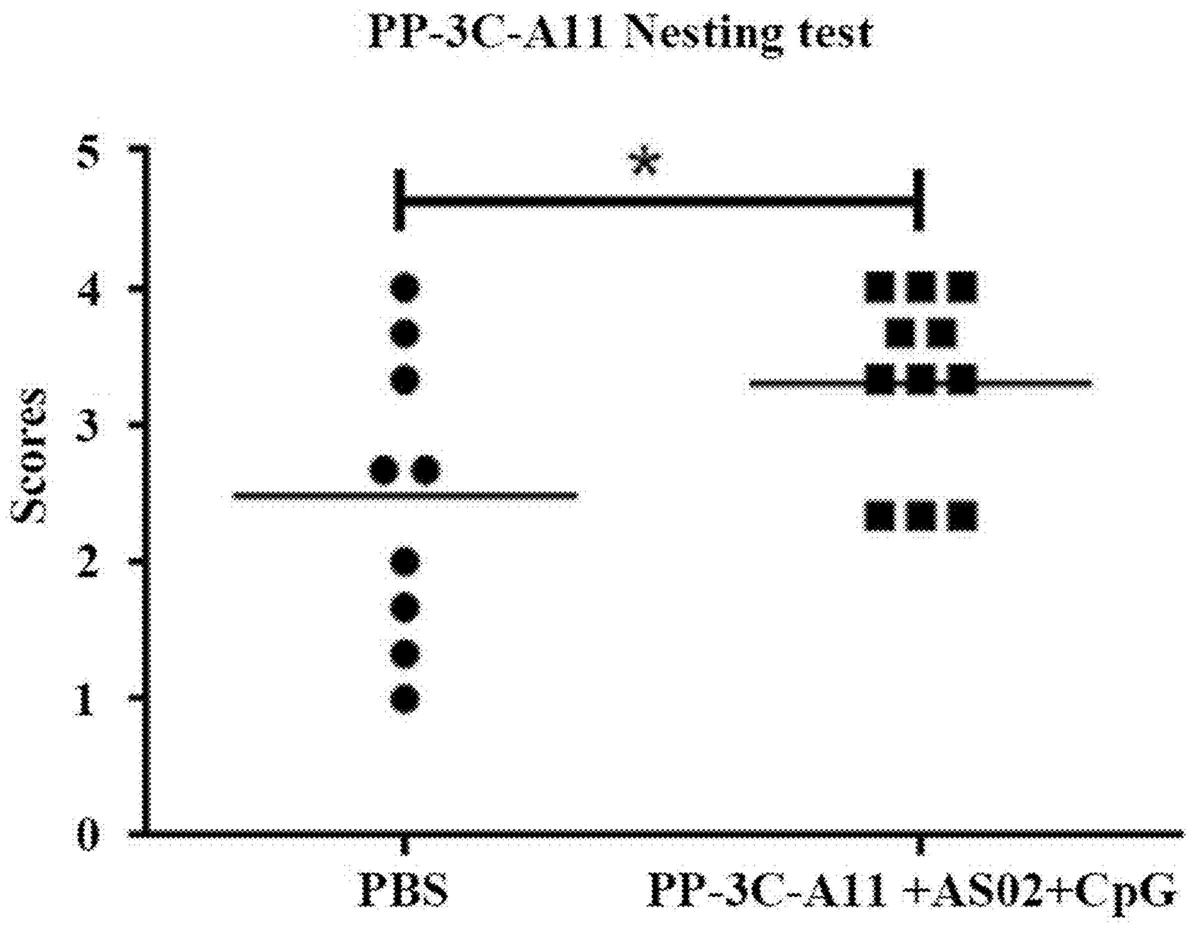

Example 28: Evaluation of the Behavior of P301S Transgenic Mice Immunized with Phosphorylated Polypeptide Antigen A11 Coupled with a Norovirus P Protein P301S transgenic mice were immunized with phosphorylated polypeptide antigen A11 coupled with PP-3C and combined with AS02+CpG adjuvant. Ten weeks after the start of the experiment, a nesting test was performed by the same method as in Example 27. The experiment showed that the immunized mice performed significantly better than the PBS group in the nesting test (the results are shown in FIG. 12B).

Figure 12C:
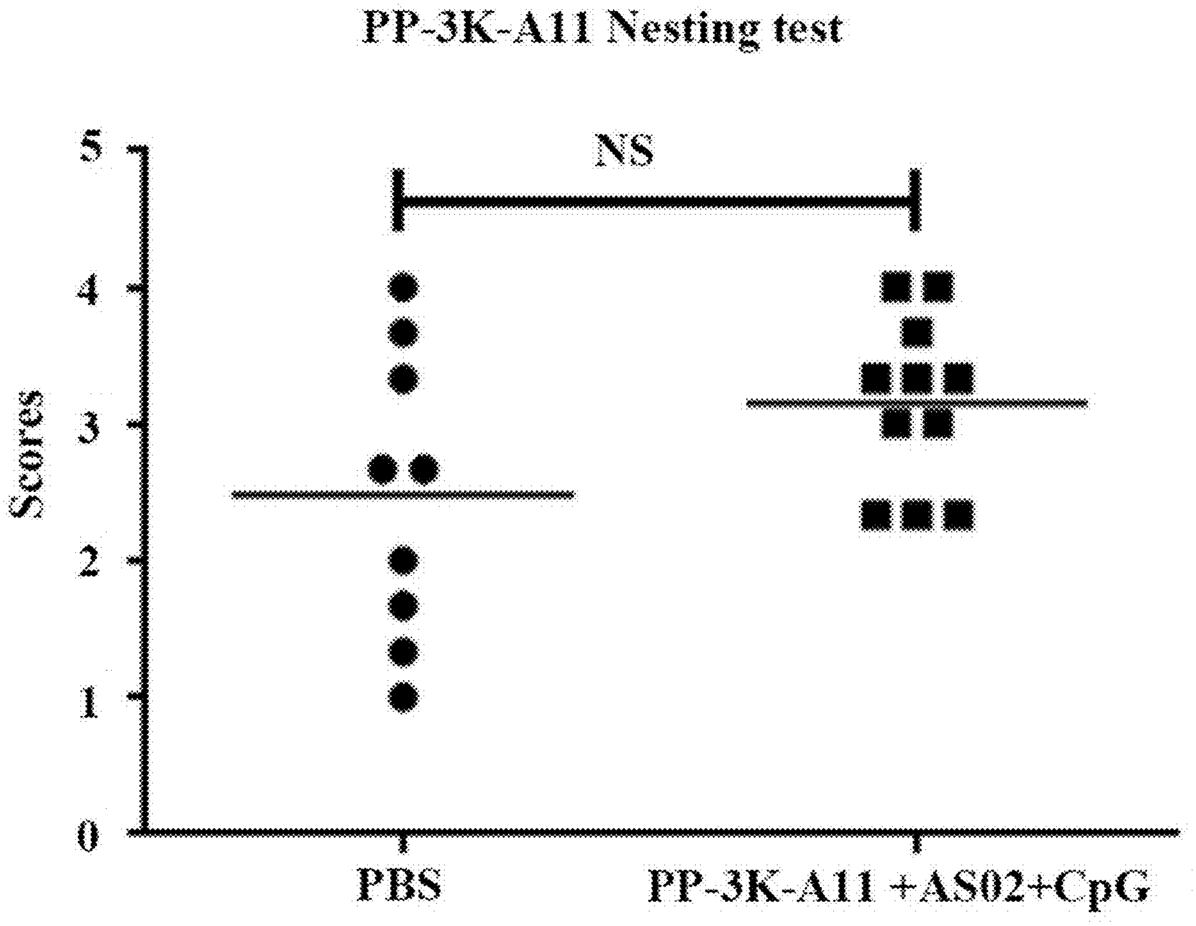

Example 29: Evaluation of the Behavior of P301S Transgenic Mice Immunized with Phosphorylated Polypeptide Antigen A11 Coupled with a Norovirus P Protein P301S transgenic mice were immunized with phosphorylated polypeptide antigen A11 coupled with PP-3K and combined with AS02+CpG adjuvant. Ten weeks after the start of the experiment, a nesting test was performed by the same method as in Example 27. The experiment showed that the immunized mice performed significantly better than the PBS group in the nesting test (the results are shown in FIG. 12C).

Figure 12D:
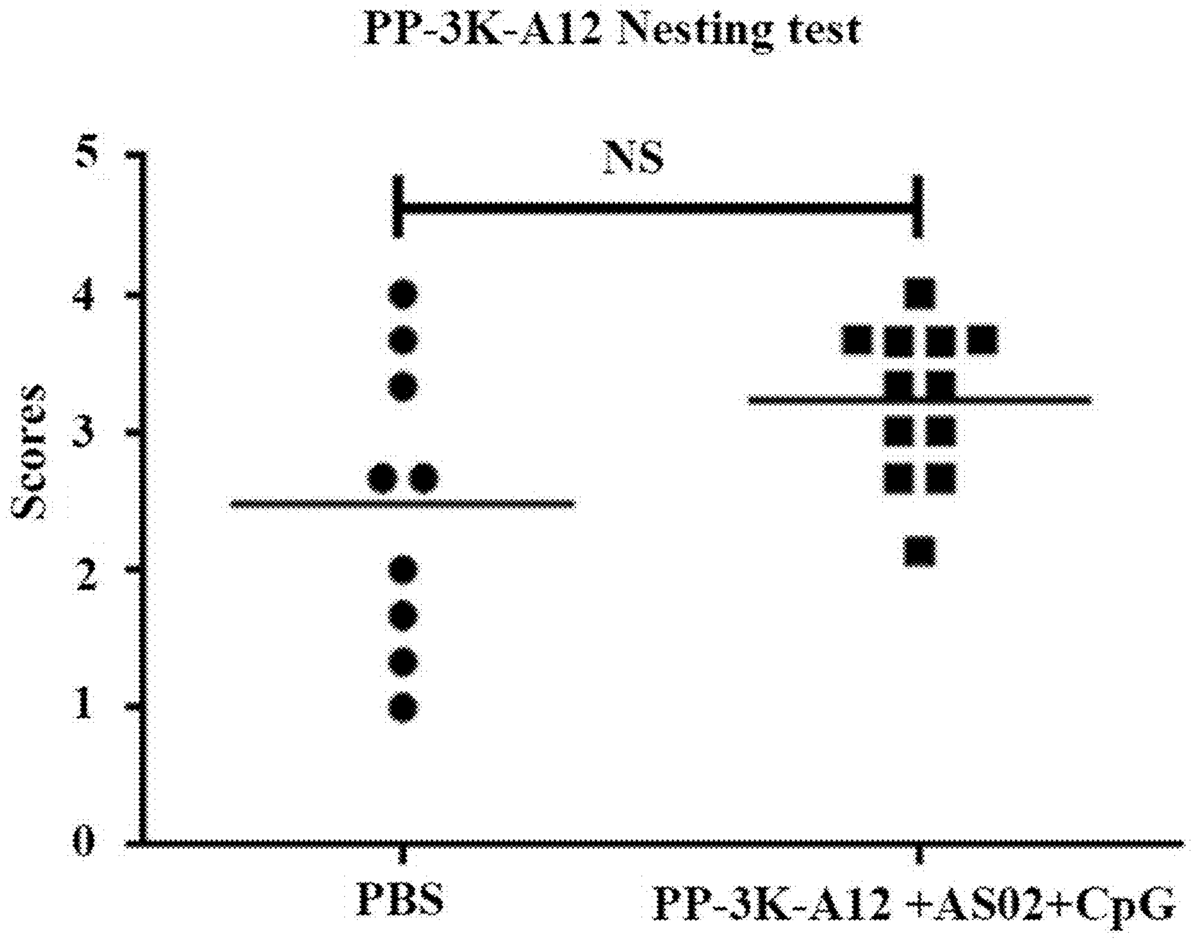

Example 30: Evaluation of the Behavior of P301S Transgenic Mice Immunized with Phosphorylated Polypeptide Antigen A12 Coupled with a Norovirus P Protein P301S transgenic mice were immunized with phosphorylated polypeptide antigen A12 coupled with PP-3K and combined with AS02+CpG adjuvant. Ten weeks after the start of the experiment, a nesting test was performed by the same method as in Example 27. The experiment showed that the immunized mice performed significantly better than the PBS group in the nesting test (the results are shown in FIG. 12D).

Example 31: Construction of pET28a-C-PA Plasmid

The plasmid containing C-PA was obtained through sequence optimization and gene synthesis (GL Bio).

The C-PA genes were enriched by PCR method and the sequence of the genes was represented by SEQ ID NO: 1363. The specific method was as follows:

```
SEQ ID NO: 1365 (forward):
TTTAACTTTAAGAAGGAGATATACATATGGGTGGTGGTGGTTCTTGCGG

CGGCG,
and

SEQ ID NO: 1366 (reverse):
GTGGTGGTGGTGGTGGTGCTCGAGTTATTTAATACGCAGATACTGGCCA

ATCA;
```

The plasmid containing C-PA was subjected to PCR reaction, wherein the PCR reaction system was a KOD-Plus DNA polymerase system (purchased from TOYOBO Corporation), and the total volume of the reaction system was 50 μL (5 μL buffer, 0.2 mM dNTP, 1 mM magnesium sulfate, 0.3 μM upstream primer and 0.3 μM downstream primer, 50 ng template DNA, 1 μL KOD enzyme, and water which was added to a final volume of 50 μL). PCR was carried out in accordance with the reaction system instructions to obtain 50 μL of PCR products. The products were subjected to agarose gel electrophoresis, and the fragments of interest were recovered using gel recovery kit (purchased from Tiangen Biotech Co., Ltd.)

1 μL of BamHI enzyme and 1 μL of XhoI enzyme (purchased from Takara Corporation) and 5 μL of enzyme digestion buffer (purchased from Takara Corporation) were added respectively to 2 μg of pET28a vector plasmid (purchased from Novagen Corporation), and finally sterile water was added to the system to reach a final volume of 50 μL. Digestion was carried out at 37° C. for 2 hours. The products were subjected to agarose gel electrophoresis, and the vector fragments were recovered using gel recovery kit (purchased from Tiangen Biotech Co., Ltd.) to obtain a linear plasmid vector.

Figure 15A:
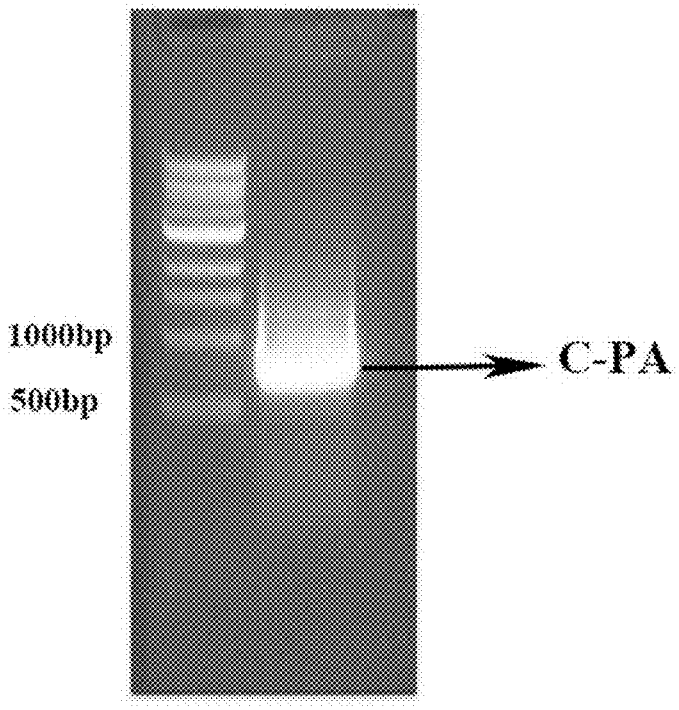
FIGS. 15A to 15B show the recombinant pET28a-C-PA plasmid construct and the results of purification and expression.

The above double enzyme-digested vector fragment and fragment of interest (with a molar ratio of 1:3, and a total volume of 5 μL) were mixed, and 5 μL of homologous recombination mix (purchased from Taihe Corporation) was added. The ligation was carried out at 25° C. for 15 min. 10 μL of the ligated products were added to DH10B competent cells (purchased from Taihe Corporation), and placed on ice for 30 min. After that, the cells were subjected to heat shock at 42° C. for 30 s, placed on ice for 2 min, and then were added to 600 L of fluid LB medium without resistance, and recovered at 200 rpm at 37° C. for 1 h. The culture broth was plated on a LB solid culture plate containing kanamycin (15 μg/mL), and were placed upside down at 37° C. overnight. The recombinant clones were obtained, and the sequence was verified by sequencing, which was represented by SEQ ID NO: 1363. A pET28a-C-PA plasmid that can express C-PA protein was obtained, as shown in FIG. 15A.

Example 32: Expression and Purification of a C-PA Protein 32.1 Expression of a C-PA Protein 1 μL of the recombinant plasmids prepared in the above examples were respectively added to 100 μL of *E. coli* BL21 competent cells (purchased from TransGen Corporation), ice-bathed for 30 min, heat shocked for 90 s in a water-bath at 42° C., and then ice-bathed for 2 min. 600 μL of LB medium was added to the mixture, and cultured at 180 rpm/min at 37° C. for 1 h. The mixture was coated evenly on a LB solid medium containing kanamycin (15 μg/mL) resistance and cultured at 37° C. for 24 h to obtain strains that can stably express recombinant proteins. A growing colony was picked and inoculated into 20 mL of LB medium. The mixture was cultured at 220 rpm at 37° C. When the OD value of the culture mixture reached 2.0, induction by Isopropyl β-D-Thiogalactoside (IPTG at a final concentration of 1.0 mmol/L) was carried out at 220 rpm at 37° C. for six hours. After the induction, the culture broth was centrifuged at 4,000 rpm for 20 min. The supernatant was discarded, and the bacterial precipitates were resuspended with PBS. Centrifugation was conducted again at 4,000 rpm for 20 min and the supernatant was discarded to obtain the bacterial precipitates containing proteins of interest.

32.2 Purification of a C-PA Protein

Figure 15B:
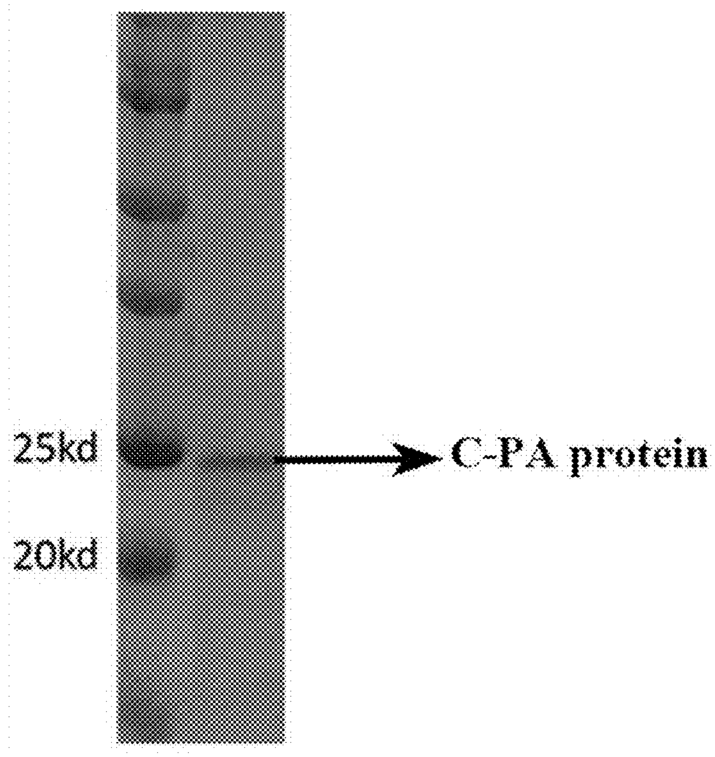

The bacterial precipitates obtained in 32.1 were resuspended by adding 20 mL of protein buffer (pH=7.0, containing 50 mM Tris and 300 mM KCl). The bacteria were lysed by sonication on ice for 30 min. The mixture was centrifuged at 12,000 rpm at 4° C. for 30 min and the supernatant was discarded. The collected precipitates were resuspended in 8M urea buffer (pH=7.0, containing 50 mM Tris, 300 mM KCl and 8M urea) and stirred overnight at 4° C. The collected solution was centrifuged at 16,000 rpm at 4° C. for 30 min. The supernatant was collected and transferred to a dialysis bag with a cut-off size of 10 kd. Dialysis was performed in the ratio of the volume of glycine dialysate to the volume of protein solution of 10:1, and the fluid was changed every 4 hours. The dialysis was performed 6 times to slowly renature the protein. The collected protein solution was concentrated by ultrafiltration to a protein concentration of 1.0 mg/mL to 2.0 mg/mL. The results of SDS-PAGE of the protein are shown in FIG. 15B, and the molecular weight of the protein is about 24 kd.

Example 33: Coupling Reaction of Phosphorylated Polypeptide Antigen Vaccines with BLP

Example 33.1: Ligation Reaction of C-PA with BLP

The method for preparing BLP was described in the Chinese Patent Application CN 105968213. 1 mL of 15 mg/mL BLP solution was centrifuged at 5,000 g at 4° C. for 30 min, and the supernatant was discarded. BLP was resuspended with 5 mL of C-PA solution and slowly shaked at 25° C. for 30 min to prepare C-PA-BLP. Centrifuge was performed at 5,000 g for 30 min at 4° C., the supernatant was discarded, and resuspension was performed with 10 mL sterile PBS (pH=7.2). This operation was repeated 4 times. The washed precipitates were resuspended with 1 mL PBS, OD600 was detected, and the concentration of C-PA-BLP was calibrated with a BLP standard.

Example 33.2: Ligation Reaction of C-PA with BLP

The method for preparing BLP was described in the Chinese Patent Application CN 105968213. 1 mL of 15 mg/mL BLP solution was centrifuged at 5,000 g at 4° C. for 30 min, and the supernatant was discarded. BLP was resuspended with 3 mL of C-PA solution and slowly shaked at 4° C. for 6 h to prepare C-PA-BLP. Centrifuge was performed at 5,000 g for 30 min at 4° C., the supernatant was discarded, and resuspension was performed with 10 mL sterile PBS (pH=7.2). This operation was repeated 4 times. The washed precipitates were resuspended with 1 mL PBS, OD600 was detected, and the concentration of C-PA-BLP was calibrated with a BLP standard.

Example 33.3: Coupling Reaction of the Phosphorylated Polypeptide Antigen Vaccines with C-PA-BLP The phosphorylated polypeptide in each of the phosphorylated polypeptide antigen vaccines in lyophilized form prepared in Example 1 was diluted with a 0.1 M ammonium bicarbonate solution (pH=7.5) to a concentration of 1 mg/mL and was quantified. In the ratio of the molar amount of the C-PA protein to the molar amount of the polypeptide of 1:30, the polypeptide solution was slowly added to the precipitates obtained after centrifugation of C-PA-BLP, and mixed slowly. The mixed system was incubated at 2° C. to 8° C. with slow shaking for 48 hours. The obtained product was centrifuged and resuspended with PBS to remove unbound polypeptide.

Example 33.4: Coupling Reaction of the Phosphorylated Polypeptide Antigen Vaccines with C-PA-BLP The phosphorylated polypeptide in each of the phosphorylated polypeptide antigen vaccines in lyophilized form prepared in Example 1 was diluted with a 0.1 M ammonium bicarbonate solution (pH=8.0) to a concentration of 2 mg/mL and was quantified. In the ratio of the molar amount of the C-PA protein to the molar amount of the polypeptide of 1:100, the polypeptide solution was slowly added to the precipitates obtained after centrifugation of C-PA-BLP, and mixed slowly. The mixed system was incubated at 2° C. to 8° C. with slow shaking for 48 hours. The obtained product was centrifuged and resuspended with PBS to remove unbound polypeptide.

Example 33.5: Coupling Reaction of the Phosphorylated Polypeptide Antigen Vaccines with C-PA-BLP The phosphorylated polypeptide in each of the phosphorylated polypeptide antigen vaccines in lyophilized form prepared in Example 1 was diluted with a 0.1 M ammonium bicarbonate solution (pH=8.0) to a concentration of 2 mg/mL and was quantified. In the ratio of the molar amount of the C-PA protein to the molar amount of the polypeptide of 1:100, the polypeptide solution was slowly added to the precipitates obtained after centrifugation of C-PA-BLP, and mixed slowly. The mixed system was incubated at 2° C. to 8° C. with slow shaking for 48 hours. The obtained product was centrifuged and resuspended with PBS to remove unbound polypeptide.

Example 34: Determination of the Ligation Efficiency of the Phosphorylated Polypeptide Antigen Product Coupled with BLP A10 mM dithiothreitol solution was added to the phosphorylated polypeptide antigen product coupled with C-PA-BLP at a volume ratio of 1:1, and mixed homogeneously, and the mixture was left to stand at room temperature to react for 16 hours. The reaction product was centrifuged at 16,000 g at 4° C. for 15 min. The supernatants were taken for HPLC determination. Using 0.5 mg/mL, 0.25 mg/ml, 0.125 mg/ml, 0.0625 mg/ml, 0.03125 mg/mL, 0.03125 mg/mL, and 0.015625 mg/mL phosphorylated polypeptide dissolved in 10 mM of a dithiothreitol solution as standard, a standard curve was plotted with the concentration of the standard versus the peak area of the phosphorylated peptide to quantitatively analyze the concentration of the test sample (the results are shown in FIGS. 13A, 13C and 13D).

It should be understood that specific embodiments described herein are only used for explaining the present invention, instead of limiting the present invention. The protection scope of the present invention is subject to the protection scope defined in claims. For those of ordinary skill in the art, a variety of changes and modifications can be made without departing from the spirit and scope of the present invention, and these changes and modifications should be considered to belong to the protection scope of the present invention.

The invention claimed is:

1. A phosphorylated polypeptide antigen vaccine, which comprises at least two polypeptide fragments or conservatively modified variants thereof from human full-length Tau protein, wherein the polypeptide fragments or conservatively modified variants thereof contain phosphorylation sites, wherein the polypeptide fragments are connected directly by peptide bonds or connected by amino acid linkers.

2. The phosphorylated polypeptide antigen vaccine of claim 1, wherein the polypeptide fragments are connected directly by peptide bonds.

3. The phosphorylated polypeptide antigen vaccine of claim 1, wherein the polypeptide fragments are derived from phosphorylation modification site-rich regions of human full-length Tau protein.

4. The phosphorylated polypeptide antigen vaccine of claim 3, wherein the phosphorylation sites include two or more of phosphorylated amino acid sites corresponding to positions 18, 202, 205, 212, 214, 231, 235, 238, 262, 396 and 404 of the amino acid sequence of human full-length Tau protein, namely, 18(P-$Tyr_{18}$), 202(P-$Ser_{202}$), 205(P-$Thr_{205}$), 212(P-$Thr_{212}$), 214(P-$Ser_{214}$), 231(P-$Thr_{231}$), 235(P-$Ser_{235}$), 238(P-$Ser_{238}$), 262(P-$Ser_{262}$), 396(P-$Ser_{396}$) and 404(P-$Ser_{404}$).

5. The phosphorylated polypeptide antigen vaccine of claim 1, wherein the conservatively modified variant of the polypeptide fragment is a variant obtained by conservatively substitution of one or more amino acids of the polypeptide fragment with functionally similar amino acids.

6. The phosphorylated polypeptide antigen vaccine of claim 1, which has an amino acid sequence as represented by any one of SEQ ID NOs: 1-1331 and the amino acid sequence contains two or more phosphorylation sites selected from 18(P-$Tyr_{18}$), 202(P-$Ser_{202}$), 205(P-$Thr_{205}$), 212(P-$Thr_{212}$), 214(P-$Ser_{214}$), 231(P-$Thr_{231}$), 235(P-$Ser_{235}$), 238(P-$Ser_{238}$), 262(P-$Ser_{262}$), 396(P-$Ser_{396}$) and 404(P-$Ser_{404}$).

7. A complex vaccine formed by coupling the phosphorylated polypeptide antigen vaccine of claim 1 with a carrier.

8. The complex vaccine of claim 7, wherein the carrier is selected from the group consisting of human serum albumin, keyhole limpet hemocyanin, bacterium-like particles (BLP), immunoglobulin molecules, thyroglobulin, ovalbumin, bovine serum albumin component V, influenza hemagglutinin, PAN-DR binding peptide (PADRE polypeptide), malaria circumsporozoite (CS) protein, hepatitis B surface antigen ($HB_SAg_{19-28}$), Heat Shock Protein (HSP) 65, Bacille Calmette-Guérin (BCG), cholera toxin, attenuated cholera toxin variants, diphtheria toxin, norovirus capsid P protein, recombinant *Streptococcus* C5a peptidase, *Streptococcus pyogenes* ORF1224, *Streptococcus pyogenes* ORF1664, *Streptococcus pyogenes* ORF2452, pneumolysin, attenuated pneumolysin toxicity variants, *Chlamydia pneumoniae* ORFT367, *Chlamydia pneumoniae* ORFT858, Tetanus toxoid, HIV gp120T1, microbial surface components recognizing adhesive matrix molecules (MSCRAMMS), growth factor/hormone and/or chemokines.

9. A method for preparing the complex vaccine of claim 7, comprising the following steps:

1) artificially synthesizing the phosphorylated polypeptide antigen vaccine of claim 1;
2) preparing a carrier to be coupled to the phosphorylated polypeptide antigen vaccine;
3) mixing the phosphorylated polypeptide antigen vaccine with the carrier to perform coupling reaction; and
4) separating and purifying the conjugate obtained in 3), thereby obtaining a complex vaccine.

10. The method of claim 9, wherein the carrier in step 2) is a norovirus capsid P protein, preferably PP-3C or PP-3K, and step 2) specifically comprises:

i) obtaining an expression vector comprising a nucleic acid encoding a PP-3C or PP-3K protein;
ii) transferring the expression vector into a receptor cell;
iii) expressing the PP-3C or PP-3K protein, and allowing it to self-assemble into a recombinant P particle in the receptor cell;

preferably, step 2) also comprises isolation and purification steps; and more preferably, ion exchange chromatography and/or hydrophobic chromatography are used for purification.

11. The method of claim 9, wherein in step 3), PP-3C is used as a vaccine carrier for coupling, a preferred buffer system is an ammonium bicarbonate buffer system, and a preferred pH ranges from 7.5 to 8.8; preferably, the phosphorylated polypeptide antigen vaccine and the carrier are mixed in a ratio of 10:1 to 100:1, and a preferred reaction temperature ranges from 2° C. to 10° C.; or in step 3), PP-3K is used as a vaccine carrier for coupling, and a preferred buffer system is a phosphate buffer system, and a preferred pH ranges from 7.0 to 8.5; preferably, the phosphorylated polypeptide antigen vaccine and the carrier are mixed in a ratio of 10:1 to 100:1, and a preferred reaction temperature ranges from 2° C. to 25° C.

12. The method of claim 9, wherein the carrier in step 2) is bacterium-like particles (BLP), and step 3) specifically comprises:

i) obtaining a purified protein adaptor—C-PA protein with a sequence as represented by SEQ ID NO: 1364; and
ii) connecting the carrier—bacterium-like particles (BLP)—obtained in step 2) with the C-PA protein to obtain C-PA-BLP; and iii) preforming coupling reaction of C-PA-BLP with the phosphorylated polypeptide antigen vaccine;

wherein a Tris buffer system is used as a buffer system and a preferred pH ranges from 7.2 to 8.8; a preferred C-PA protein concentration is 0.1 mg/mL to 1.5 mg/mL, and a preferred reaction temperature ranges from 2° C. to 30° C.; or an ammonium bicarbonate buffer system is used as a buffer system, and a preferred pH ranges from 7.5 to 8.8; preferably, the phosphorylated polypeptide antigen vaccine and the C-PA-BLP are mixed in a ratio of 10:1 to 100:1, and a preferred reaction temperature ranges from 2° C. to 10° C.

13. The method of claim 9, wherein step 4) comprises removing coupling agent and polypeptide antigens which are not successfully connected by methods including desalting chromatography, dialysis and ultrafiltration.

14. A vaccine composition, wherein the vaccine composition comprises the phosphorylated polypeptide antigen vaccine of claim 1 or a complex vaccine; preferably, the vaccine composition further comprises a pharmaceutically acceptable adjuvant; more preferably, the pharmaceutically acceptable adjuvant is selected from one or more of CpG, MF59, AS02, AS03, Freund's complete adjuvant and Freund's incomplete adjuvant;

wherein the complex vaccine is formed by coupling the phosphorylated polypeptide antigen vaccine of claim 1 with a carrier.

15. Use of the phosphorylated polypeptide antigen vaccine of claim 1 or a complex vaccine or a vaccine composition for preparing a medicament for prevention and/or treatment of neurodegenerative disorders; and/or for preparing a medicament for maintaining or improving, preferably recovering, and more preferably completely recovering the cognitive memory of mammals, especially human beings;

wherein the complex vaccine is formed by coupling the phosphorylated polypeptide antigen vaccine of claim 1 with a carrier;

wherein the vaccine composition comprises the phosphorylated polypeptide antigen vaccine of claim 1 or the complex vaccine; preferably, the vaccine composition further comprises a pharmaceutically acceptable adjuvant; more preferably, the pharmaceutically acceptable adjuvant is selected from one or more of CpG, MF59, AS02, AS03, Freund's complete adjuvant and Freund's incomplete adjuvant.

16. Use of claim 15, wherein the neurodegenerative disorders are selected from one or more of AD, Creutzfeldt-Jacob Syndrome, Dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis/parkinsonism syndrome-dementia syndrome, argyrophilic grain dementia, corticobasal degeneration, diffuse neurofibrillary tangles with calcification, frontotemporal dementia with parkinsonism syndrome linked to chromosome 17, Hallevorden-Spatz disease, multiple system atrophy, Niemann-Pick disease type C, Pick's disease, progressive subcortical gliosis and progressive supranuclear panencephalitis; preferably the neurodegenerative disorder is AD; preferably, the vaccine or vaccine composition is preferably immunized subcutaneously, intraperitoneally or intramuscularly, and more preferably immunized intramuscularly.

17. The phosphorylated polypeptide antigen vaccine of claim 1, wherein the phosphorylated polypeptide antigen vaccine contains an additional cysteine residue at its C'-terminal.

18. The phosphorylated polypeptide antigen vaccine of claim 3, wherein the polypeptide fragments are derived from regions of human full-length Tau protein as follows: amino acids at positions 14 to 22 of human full-length Tau protein, amino acids at positions 194 to 266 of human full-length Tau protein, and/or amino acids at positions 392 to 408 of human full-length Tau protein.

19. The phosphorylated polypeptide antigen vaccine of claim 4, wherein the phosphorylation sites include all phosphorylated amino acid sites corresponding to positions 18, 202, 205, 212, 214, 231, 235, 238, 262, 396 and 404 of the amino acid sequence of human full-length Tau protein, namely, 18(P-$Tyr_{18}$), 202(P-$Ser_{202}$), 205(P-$Thr_{205}$), 212(P-$Thr_{212}$), 214(P-$Ser_{214}$), 231(P-$Thr_{231}$), 235(P-$Ser_{235}$), 238 (P-$Ser_{238}$), 262(P-$Ser_{262}$), 396(P-$Ser_{396}$) and 404(P-$Ser_{404}$).

20. The phosphorylated polypeptide antigen vaccine of claim 5, wherein the conservatively modified variant of the polypeptide fragment is a variant obtained by conservatively substitution of 1 to 10 amino acids of the polypeptide fragment with functionally similar amino acids.

21. The phosphorylated polypeptide antigen vaccine of claim 20, wherein the conservatively modified variant of the polypeptide fragment is a variant obtained by conservatively substitution of 1 to 6 amino acids of the polypeptide fragment with functionally similar amino acids.

22. The phosphorylated polypeptide antigen vaccine of claim 21, wherein the conservatively modified variant of the polypeptide fragment is a variant obtained by conservatively substitution of 1 to 4 amino acids of the polypeptide fragment with functionally similar amino acids.

23. The phosphorylated polypeptide antigen vaccine of claim 22, wherein the conservatively modified variant of the polypeptide fragment is a variant obtained by conservatively substitution of 1 to 3 amino acids of the polypeptide fragment with functionally similar amino acids.

24. The phosphorylated polypeptide antigen vaccine of claim 23, wherein the conservatively modified variant of the polypeptide fragment is a variant obtained by conservatively substitution of 1 amino acid of the polypeptide fragment with functionally similar amino acids.

25. The phosphorylated polypeptide antigen vaccine of claim 6, wherein the phosphorylated polypeptide antigen vaccine has an amino acid sequence which has at least 80%, at least 85%, at least 90%, at least 95% sequence identity to any one of SEQ ID NOs: 1-1331.

26. The phosphorylated polypeptide antigen vaccine of claim 25, wherein the phosphorylated polypeptide antigen vaccine has an amino acid sequence which has at least 98% sequence identity to any one of SEQ ID NOs: 1-1331.

27. The phosphorylated polypeptide antigen vaccine of claim 26, wherein the phosphorylated polypeptide antigen vaccine has an amino acid sequence which has at least 99% sequence identity to any one of SEQ ID NOs: 1-1331.

28. The phosphorylated polypeptide antigen vaccine of claim 25, wherein the phosphorylated polypeptide antigen vaccine has an amino acid sequence as represented by any one of SEQ ID NO: 201, SEQ ID NO: 225, SEQ ID NO: 306, SEQ ID NO: 387, SEQ ID NO: 468, SEQ ID NO: 558, SEQ ID NO: 567, SEQ ID NO: 769, SEQ ID NO: 784, SEQ ID NO: 875, SEQ ID NO: 1020, SEQ ID NO: 1101, SEQ ID NO: 1182, SEQ ID NO: 1272, SEQ ID NO: 1313 and SEQ ID NO: 1330, and the amino acid sequence contains two or more phosphorylation sites selected from 18(P-$Tyr_{18}$), 202 (P-$Ser_{202}$), 205(P-$Thr_{205}$), 212(P-$Thr_{212}$), 214(P-$Ser_{214}$), 231(P-$Thr_{231}$), 235(P-$Ser_{235}$), 238(P-$Ser_{238}$), 262(P-$Ser_{262}$), 396(P-$Ser_{396}$) and 404(P-$Ser_{404}$).

29. The phosphorylated polypeptide antigen vaccine of claim 28, wherein the phosphorylated polypeptide antigen vaccine has an amino acid sequence as represented by any one of SEQ ID NO: 201, SEQ ID NO: 225, SEQ ID NO:

306, SEQ ID NO: 387, SEQ ID NO: 468, SEQ ID NO: 558, SEQ ID NO: 567, SEQ ID NO: 769, SEQ ID NO: 784, SEQ ID NO: 875, SEQ ID NO: 1020, SEQ ID NO: 1101, SEQ ID NO: 1182, SEQ ID NO: 1272, SEQ ID NO: 1313 and SEQ ID NO: 1330, and the amino acid sequence respectively contain phosphorylation sites as follows: 18(P-$Tyr_{18}$), 202 (P-$Ser_{202}$), 205(P-$Thr_{205}$); 18(P-$Tyr_{18}$), 202(P-$Ser_{202}$), 205 (P-$Thr_{205}$); 18(P-$Tyr_{18}$), 212(P-$Thr_{212}$), 214(P-$Ser_{214}$); 18(P-$Tyr_{18}$), 231(P-$Thr_{231}$), 235(P-$Ser_{235}$); 18(P-$Tyr_{18}$), 238 (P-$Ser_{238}$), 262(P-$Ser_{262}$); 18(P-$Tyr_{18}$), 396(P-$Ser_{396}$), 404 (P-$Ser_{404}$); 202(P-$Ser_{202}$), 205(P-$Thr_{205}$), 231(P-$Thr_{231}$), 235(P-$Ser_{235}$); 202(P-$Ser_{202}$), 205(P-$Thr_{205}$), 231(P-$Thr_{231}$), 235(P-$Ser_{235}$); 202(P-$Ser_{202}$), 205(P-$Thr_{205}$), 238 (P-$Ser_{238}$), 262(P-$Ser_{262}$); 202(P-$Ser_{202}$), 205(P-$Thr_{205}$), 396(P-$Ser_{396}$), 404(P-$Ser_{404}$); 202(P-$Ser_{202}$), 205(P-$Thr_{205}$), 396(P-$Ser_{396}$), 404(P-$Ser_{404}$); 212(P-$Thr_{212}$), 214(P-$Ser_{214}$), 231(P-$Thr_{231}$), 235(P-$Ser_{235}$); 212(P-$Thr_{212}$), 214(P-$Ser_{214}$), 238(P-$Ser_{238}$), 262(P-$Ser_{262}$); 212(P-$Thr_{212}$), 214 (P-$Ser_{214}$), 396(P-$Ser_{396}$), 404(P-$Ser_{404}$); 238(P-$Ser_{238}$), 262(P-$Ser_{262}$), 396(P-$Ser_{396}$), 404(P-$Ser_{404}$); 238(P-$Ser_{238}$), 262(P-$Ser_{262}$), 396(P-$Ser_{396}$) and 404(P-$Ser_{404}$).

30. The complex vaccine of claim 8, wherein the carrier is bacterium-like particles (BLP).

31. The complex vaccine of claim 30, wherein the BLP is coupled with a phosphorylated polypeptide antigen vaccine by means of a protein adaptor.

32. The complex vaccine of claim 31, wherein the protein adaptor has a sequence as represented by SEQ ID NO: 1364.

33. The complex vaccine of claim 8, wherein the carrier is norovirus capsid P protein.

34. The complex vaccine of claim 33, wherein the norovirus capsid P protein is PP-3C with a sequence as represented by SEQ ID NO: 1357 or PP-3K with a sequence as represented by SEQ ID NO: 1359.

* * * * *

SEQUENCE LISTING

<160> NUMBER OF SEQ ID NOS: 1366

<210> SEQ ID NO 1
<211> LENGTH: 18
<212> TYPE: PRT
<213> ORGANISM: Artificial Sequence
<220> FEATURE:
<223> OTHER INFORMATION: Synthetic construct

<400> SEQUENCE: 1

```
Gly Thr Tyr Gly Leu Ser Ser Pro Gly Ser Pro Gly Thr Pro Gly Ser
1               5                   10                  15

Arg Cys
```

<210> SEQ ID NO 2
<211> LENGTH: 19
<212> TYPE: PRT
<213> ORGANISM: Artificial Sequence
<220> FEATURE:
<223> OTHER INFORMATION: Synthetic construct

<400> SEQUENCE: 2

```
Gly Thr Tyr Gly Leu Tyr Ser Ser Pro Gly Ser Pro Gly Thr Pro Gly
1               5                   10                  15

Ser Arg Cys
```

<210> SEQ ID NO 3
<211> LENGTH: 19
<212> TYPE: PRT
<213> ORGANISM: Artificial Sequence
<220> FEATURE:
<223> OTHER INFORMATION: Synthetic construct

<400> SEQUENCE: 3

```
Gly Thr Tyr Gly Leu Ser Ser Pro Gly Ser Pro Gly Thr Pro Gly Ser
1               5                   10                  15

Arg Ser Cys
```

<210> SEQ ID NO 4
<211> LENGTH: 20
<212> TYPE: PRT
<213> ORGANISM: Artificial Sequence
<220> FEATURE:
<223> OTHER INFORMATION: Synthetic construct

<400> SEQUENCE: 4

```
Gly Thr Tyr Gly Leu Gly Tyr Ser Ser Pro Gly Ser Pro Gly Thr Pro
1               5                   10                  15

Gly Ser Arg Cys
            20
```

<210> SEQ ID NO 5
<211> LENGTH: 20
<212> TYPE: PRT
<213> ORGANISM: Artificial Sequence
<220> FEATURE:
<223> OTHER INFORMATION: Synthetic construct

<400> SEQUENCE: 5

```
Gly Thr Tyr Gly Leu Tyr Ser Ser Pro Gly Ser Pro Gly Thr Pro Gly
1               5                   10                  15

Ser Arg Ser Cys
            20
```

<210> SEQ ID NO 6
<211> LENGTH: 20
<212> TYPE: PRT
<213> ORGANISM: Artificial Sequence
<220> FEATURE:
<223> OTHER INFORMATION: Synthetic construct

<400> SEQUENCE: 6

```
Gly Thr Tyr Gly Leu Ser Ser Pro Gly Ser Pro Gly Thr Pro Gly Ser
1               5                   10                  15

Arg Ser Arg Cys
            20
```

<210> SEQ ID NO 7
<211> LENGTH: 21
<212> TYPE: PRT
<213> ORGANISM: Artificial Sequence
<220> FEATURE:
<223> OTHER INFORMATION: Synthetic construct

<400> SEQUENCE: 7

```
Gly Thr Tyr Gly Leu Ser Gly Tyr Ser Ser Pro Gly Ser Pro Gly Thr
1               5                   10                  15

Pro Gly Ser Arg Cys
            20
```

<210> SEQ ID NO 8
<211> LENGTH: 21
<212> TYPE: PRT
<213> ORGANISM: Artificial Sequence
<220> FEATURE:
<223> OTHER INFORMATION: Synthetic construct

<400> SEQUENCE: 8

```
Gly Thr Tyr Gly Leu Gly Tyr Ser Ser Pro Gly Ser Pro Gly Thr Pro
1               5                   10                  15

Gly Ser Arg Ser Cys
            20
```

<210> SEQ ID NO 9
<211> LENGTH: 21
<212> TYPE: PRT
<213> ORGANISM: Artificial Sequence
<220> FEATURE:
<223> OTHER INFORMATION: Synthetic construct

<400> SEQUENCE: 9

```
Gly Thr Tyr Gly Leu Tyr Ser Ser Pro Gly Ser Pro Gly Thr Pro Gly
1               5                   10                  15

Ser Arg Ser Arg Cys
            20
```

<210> SEQ ID NO 10
<211> LENGTH: 21
<212> TYPE: PRT
<213> ORGANISM: Artificial Sequence
<220> FEATURE:
<223> OTHER INFORMATION: Synthetic construct

<400> SEQUENCE: 10

```
Gly Thr Tyr Gly Leu Ser Ser Pro Gly Ser Pro Gly Thr Pro Gly Ser
1               5                   10                  15

Arg Ser Arg Thr Cys
            20
```

-continued

<210> SEQ ID NO 11
<211> LENGTH: 22
<212> TYPE: PRT
<213> ORGANISM: Artificial Sequence
<220> FEATURE:
<223> OTHER INFORMATION: Synthetic construct

<400> SEQUENCE: 11

Gly Thr Tyr Gly Leu Arg Ser Gly Tyr Ser Ser Pro Gly Ser Pro Gly
1 5 10 15

Thr Pro Gly Ser Arg Cys
20

<210> SEQ ID NO 12
<211> LENGTH: 22
<212> TYPE: PRT
<213> ORGANISM: Artificial Sequence
<220> FEATURE:
<223> OTHER INFORMATION: Synthetic construct

<400> SEQUENCE: 12

Gly Thr Tyr Gly Leu Ser Gly Tyr Ser Ser Pro Gly Ser Pro Gly Thr
1 5 10 15

Pro Gly Ser Arg Ser Cys
20

<210> SEQ ID NO 13
<211> LENGTH: 22
<212> TYPE: PRT
<213> ORGANISM: Artificial Sequence
<220> FEATURE:
<223> OTHER INFORMATION: Synthetic construct

<400> SEQUENCE: 13

Gly Thr Tyr Gly Leu Gly Tyr Ser Ser Pro Gly Ser Pro Gly Thr Pro
1 5 10 15

Gly Ser Arg Ser Arg Cys
20

<210> SEQ ID NO 14
<211> LENGTH: 22
<212> TYPE: PRT
<213> ORGANISM: Artificial Sequence
<220> FEATURE:
<223> OTHER INFORMATION: Synthetic construct

<400> SEQUENCE: 14

Gly Thr Tyr Gly Leu Tyr Ser Ser Pro Gly Ser Pro Gly Thr Pro Gly
1 5 10 15

Ser Arg Ser Arg Thr Cys
20

<210> SEQ ID NO 15
<211> LENGTH: 22
<212> TYPE: PRT
<213> ORGANISM: Artificial Sequence
<220> FEATURE:
<223> OTHER INFORMATION: Synthetic construct

<400> SEQUENCE: 15

Gly Thr Tyr Gly Leu Ser Ser Pro Gly Ser Pro Gly Thr Pro Gly Ser
1 5 10 15

Arg Ser Arg Thr Pro Cys

```
            20


<210> SEQ ID NO 16
<211> LENGTH: 23
<212> TYPE: PRT
<213> ORGANISM: Artificial Sequence
<220> FEATURE:
<223> OTHER INFORMATION: Synthetic construct

<400> SEQUENCE: 16

Gly Thr Tyr Gly Leu Arg Ser Gly Tyr Ser Ser Pro Gly Ser Pro Gly
1               5                   10                  15

Thr Pro Gly Ser Arg Ser Cys
            20


<210> SEQ ID NO 17
<211> LENGTH: 23
<212> TYPE: PRT
<213> ORGANISM: Artificial Sequence
<220> FEATURE:
<223> OTHER INFORMATION: Synthetic construct

<400> SEQUENCE: 17

Gly Thr Tyr Gly Leu Ser Gly Tyr Ser Ser Pro Gly Ser Pro Gly Thr
1               5                   10                  15

Pro Gly Ser Arg Ser Arg Cys
            20


<210> SEQ ID NO 18
<211> LENGTH: 23
<212> TYPE: PRT
<213> ORGANISM: Artificial Sequence
<220> FEATURE:
<223> OTHER INFORMATION: Synthetic construct

<400> SEQUENCE: 18

Gly Thr Tyr Gly Leu Gly Tyr Ser Ser Pro Gly Ser Pro Gly Thr Pro
1               5                   10                  15

Gly Ser Arg Ser Arg Thr Cys
            20


<210> SEQ ID NO 19
<211> LENGTH: 23
<212> TYPE: PRT
<213> ORGANISM: Artificial Sequence
<220> FEATURE:
<223> OTHER INFORMATION: Synthetic construct

<400> SEQUENCE: 19

Gly Thr Tyr Gly Leu Tyr Ser Ser Pro Gly Ser Pro Gly Thr Pro Gly
1               5                   10                  15

Ser Arg Ser Arg Thr Pro Cys
            20


<210> SEQ ID NO 20
<211> LENGTH: 24
<212> TYPE: PRT
<213> ORGANISM: Artificial Sequence
<220> FEATURE:
<223> OTHER INFORMATION: Synthetic construct

<400> SEQUENCE: 20

Gly Thr Tyr Gly Leu Arg Ser Gly Tyr Ser Ser Pro Gly Ser Pro Gly
1               5                   10                  15
```

Thr Pro Gly Ser Arg Ser Arg Cys
20

<210> SEQ ID NO 21
<211> LENGTH: 24
<212> TYPE: PRT
<213> ORGANISM: Artificial Sequence
<220> FEATURE:
<223> OTHER INFORMATION: Synthetic construct

<400> SEQUENCE: 21

Gly Thr Tyr Gly Leu Ser Gly Tyr Ser Ser Pro Gly Ser Pro Gly Thr
1 5 10 15

Pro Gly Ser Arg Ser Arg Thr Cys
20

<210> SEQ ID NO 22
<211> LENGTH: 24
<212> TYPE: PRT
<213> ORGANISM: Artificial Sequence
<220> FEATURE:
<223> OTHER INFORMATION: Synthetic construct

<400> SEQUENCE: 22

Gly Thr Tyr Gly Leu Gly Tyr Ser Ser Pro Gly Ser Pro Gly Thr Pro
1 5 10 15

Gly Ser Arg Ser Arg Thr Pro Cys
20

<210> SEQ ID NO 23
<211> LENGTH: 25
<212> TYPE: PRT
<213> ORGANISM: Artificial Sequence
<220> FEATURE:
<223> OTHER INFORMATION: Synthetic construct

<400> SEQUENCE: 23

Gly Thr Tyr Gly Leu Arg Ser Gly Tyr Ser Ser Pro Gly Ser Pro Gly
1 5 10 15

Thr Pro Gly Ser Arg Ser Arg Thr Cys
20 25

<210> SEQ ID NO 24
<211> LENGTH: 25
<212> TYPE: PRT
<213> ORGANISM: Artificial Sequence
<220> FEATURE:
<223> OTHER INFORMATION: Synthetic construct

<400> SEQUENCE: 24

Gly Thr Tyr Gly Leu Ser Gly Tyr Ser Ser Pro Gly Ser Pro Gly Thr
1 5 10 15

Pro Gly Ser Arg Ser Arg Thr Pro Cys
20 25

<210> SEQ ID NO 25
<211> LENGTH: 26
<212> TYPE: PRT
<213> ORGANISM: Artificial Sequence
<220> FEATURE:
<223> OTHER INFORMATION: Synthetic construct

<400> SEQUENCE: 25

Gly Thr Tyr Gly Leu Arg Ser Gly Tyr Ser Ser Pro Gly Ser Pro Gly
1 5 10 15

```
Thr Pro Gly Ser Arg Ser Arg Thr Pro Cys
            20                  25


<210> SEQ ID NO 26
<211> LENGTH: 19
<212> TYPE: PRT
<213> ORGANISM: Artificial Sequence
<220> FEATURE:
<223> OTHER INFORMATION: Synthetic construct

<400> SEQUENCE: 26

Ala Gly Thr Tyr Gly Leu Ser Ser Pro Gly Ser Pro Gly Thr Pro Gly
1               5                   10                  15

Ser Arg Cys


<210> SEQ ID NO 27
<211> LENGTH: 20
<212> TYPE: PRT
<213> ORGANISM: Artificial Sequence
<220> FEATURE:
<223> OTHER INFORMATION: Synthetic construct

<400> SEQUENCE: 27

Ala Gly Thr Tyr Gly Leu Tyr Ser Ser Pro Gly Ser Pro Gly Thr Pro
1               5                   10                  15

Gly Ser Arg Cys
            20


<210> SEQ ID NO 28
<211> LENGTH: 20
<212> TYPE: PRT
<213> ORGANISM: Artificial Sequence
<220> FEATURE:
<223> OTHER INFORMATION: Synthetic construct

<400> SEQUENCE: 28

Ala Gly Thr Tyr Gly Leu Ser Ser Pro Gly Ser Pro Gly Thr Pro Gly
1               5                   10                  15

Ser Arg Ser Cys
            20


<210> SEQ ID NO 29
<211> LENGTH: 21
<212> TYPE: PRT
<213> ORGANISM: Artificial Sequence
<220> FEATURE:
<223> OTHER INFORMATION: Synthetic construct

<400> SEQUENCE: 29

Ala Gly Thr Tyr Gly Leu Gly Tyr Ser Ser Pro Gly Ser Pro Gly Thr
1               5                   10                  15

Pro Gly Ser Arg Cys
            20


<210> SEQ ID NO 30
<211> LENGTH: 21
<212> TYPE: PRT
<213> ORGANISM: Artificial Sequence
<220> FEATURE:
<223> OTHER INFORMATION: Synthetic construct

<400> SEQUENCE: 30

Ala Gly Thr Tyr Gly Leu Tyr Ser Ser Pro Gly Ser Pro Gly Thr Pro
1               5                   10                  15
```

Gly Ser Arg Ser Cys
20

<210> SEQ ID NO 31
<211> LENGTH: 21
<212> TYPE: PRT
<213> ORGANISM: Artificial Sequence
<220> FEATURE:
<223> OTHER INFORMATION: Synthetic construct

<400> SEQUENCE: 31

Ala Gly Thr Tyr Gly Leu Ser Ser Pro Gly Ser Pro Gly Thr Pro Gly
1 5 10 15

Ser Arg Ser Arg Cys
20

<210> SEQ ID NO 32
<211> LENGTH: 22
<212> TYPE: PRT
<213> ORGANISM: Artificial Sequence
<220> FEATURE:
<223> OTHER INFORMATION: Synthetic construct

<400> SEQUENCE: 32

Ala Gly Thr Tyr Gly Leu Ser Gly Tyr Ser Ser Pro Gly Ser Pro Gly
1 5 10 15

Thr Pro Gly Ser Arg Cys
20

<210> SEQ ID NO 33
<211> LENGTH: 22
<212> TYPE: PRT
<213> ORGANISM: Artificial Sequence
<220> FEATURE:
<223> OTHER INFORMATION: Synthetic construct

<400> SEQUENCE: 33

Ala Gly Thr Tyr Gly Leu Gly Tyr Ser Ser Pro Gly Ser Pro Gly Thr
1 5 10 15

Pro Gly Ser Arg Ser Cys
20

<210> SEQ ID NO 34
<211> LENGTH: 22
<212> TYPE: PRT
<213> ORGANISM: Artificial Sequence
<220> FEATURE:
<223> OTHER INFORMATION: Synthetic construct

<400> SEQUENCE: 34

Ala Gly Thr Tyr Gly Leu Tyr Ser Ser Pro Gly Ser Pro Gly Thr Pro
1 5 10 15

Gly Ser Arg Ser Arg Cys
20

<210> SEQ ID NO 35
<211> LENGTH: 22
<212> TYPE: PRT
<213> ORGANISM: Artificial Sequence
<220> FEATURE:
<223> OTHER INFORMATION: Synthetic construct

<400> SEQUENCE: 35

Ala Gly Thr Tyr Gly Leu Ser Ser Pro Gly Ser Pro Gly Thr Pro Gly

-continued

```
1               5                   10                  15

Ser Arg Ser Arg Thr Cys
            20


<210> SEQ ID NO 36
<211> LENGTH: 23
<212> TYPE: PRT
<213> ORGANISM: Artificial Sequence
<220> FEATURE:
<223> OTHER INFORMATION: Synthetic construct

<400> SEQUENCE: 36

Ala Gly Thr Tyr Gly Leu Arg Ser Gly Tyr Ser Ser Pro Gly Ser Pro
1               5                   10                  15

Gly Thr Pro Gly Ser Arg Cys
            20


<210> SEQ ID NO 37
<211> LENGTH: 23
<212> TYPE: PRT
<213> ORGANISM: Artificial Sequence
<220> FEATURE:
<223> OTHER INFORMATION: Synthetic construct

<400> SEQUENCE: 37

Ala Gly Thr Tyr Gly Leu Ser Gly Tyr Ser Ser Pro Gly Ser Pro Gly
1               5                   10                  15

Thr Pro Gly Ser Arg Ser Cys
            20


<210> SEQ ID NO 38
<211> LENGTH: 23
<212> TYPE: PRT
<213> ORGANISM: Artificial Sequence
<220> FEATURE:
<223> OTHER INFORMATION: Synthetic construct

<400> SEQUENCE: 38

Ala Gly Thr Tyr Gly Leu Gly Tyr Ser Ser Pro Gly Ser Pro Gly Thr
1               5                   10                  15

Pro Gly Ser Arg Ser Arg Cys
            20


<210> SEQ ID NO 39
<211> LENGTH: 23
<212> TYPE: PRT
<213> ORGANISM: Artificial Sequence
<220> FEATURE:
<223> OTHER INFORMATION: Synthetic construct

<400> SEQUENCE: 39

Ala Gly Thr Tyr Gly Leu Tyr Ser Ser Pro Gly Ser Pro Gly Thr Pro
1               5                   10                  15

Gly Ser Arg Ser Arg Thr Cys
            20


<210> SEQ ID NO 40
<211> LENGTH: 23
<212> TYPE: PRT
<213> ORGANISM: Artificial Sequence
<220> FEATURE:
<223> OTHER INFORMATION: Synthetic construct

<400> SEQUENCE: 40
```

Ala Gly Thr Tyr Gly Leu Ser Ser Pro Gly Ser Pro Gly Thr Pro Gly
1 5 10 15

Ser Arg Ser Arg Thr Pro Cys
20

<210> SEQ ID NO 41
<211> LENGTH: 24
<212> TYPE: PRT
<213> ORGANISM: Artificial Sequence
<220> FEATURE:
<223> OTHER INFORMATION: Synthetic construct

<400> SEQUENCE: 41

Ala Gly Thr Tyr Gly Leu Arg Ser Gly Tyr Ser Ser Pro Gly Ser Pro
1 5 10 15

Gly Thr Pro Gly Ser Arg Ser Cys
20

<210> SEQ ID NO 42
<211> LENGTH: 24
<212> TYPE: PRT
<213> ORGANISM: Artificial Sequence
<220> FEATURE:
<223> OTHER INFORMATION: Synthetic construct

<400> SEQUENCE: 42

Ala Gly Thr Tyr Gly Leu Ser Gly Tyr Ser Ser Pro Gly Ser Pro Gly
1 5 10 15

Thr Pro Gly Ser Arg Ser Arg Cys
20

<210> SEQ ID NO 43
<211> LENGTH: 24
<212> TYPE: PRT
<213> ORGANISM: Artificial Sequence
<220> FEATURE:
<223> OTHER INFORMATION: Synthetic construct

<400> SEQUENCE: 43

Ala Gly Thr Tyr Gly Leu Gly Tyr Ser Ser Pro Gly Ser Pro Gly Thr
1 5 10 15

Pro Gly Ser Arg Ser Arg Thr Cys
20

<210> SEQ ID NO 44
<211> LENGTH: 24
<212> TYPE: PRT
<213> ORGANISM: Artificial Sequence
<220> FEATURE:
<223> OTHER INFORMATION: Synthetic construct

<400> SEQUENCE: 44

Ala Gly Thr Tyr Gly Leu Tyr Ser Ser Pro Gly Ser Pro Gly Thr Pro
1 5 10 15

Gly Ser Arg Ser Arg Thr Pro Cys
20

<210> SEQ ID NO 45
<211> LENGTH: 25
<212> TYPE: PRT
<213> ORGANISM: Artificial Sequence
<220> FEATURE:
<223> OTHER INFORMATION: Synthetic construct

<400> SEQUENCE: 45

```
Ala Gly Thr Tyr Gly Leu Arg Ser Gly Tyr Ser Ser Pro Gly Ser Pro
1               5                   10                  15

Gly Thr Pro Gly Ser Arg Ser Arg Cys
            20                  25


<210> SEQ ID NO 46
<211> LENGTH: 25
<212> TYPE: PRT
<213> ORGANISM: Artificial Sequence
<220> FEATURE:
<223> OTHER INFORMATION: Synthetic construct

<400> SEQUENCE: 46

Ala Gly Thr Tyr Gly Leu Ser Gly Tyr Ser Ser Pro Gly Ser Pro Gly
1               5                   10                  15

Thr Pro Gly Ser Arg Ser Arg Thr Cys
            20                  25


<210> SEQ ID NO 47
<211> LENGTH: 25
<212> TYPE: PRT
<213> ORGANISM: Artificial Sequence
<220> FEATURE:
<223> OTHER INFORMATION: Synthetic construct

<400> SEQUENCE: 47

Ala Gly Thr Tyr Gly Leu Gly Tyr Ser Ser Pro Gly Ser Pro Gly Thr
1               5                   10                  15

Pro Gly Ser Arg Ser Arg Thr Pro Cys
            20                  25


<210> SEQ ID NO 48
<211> LENGTH: 26
<212> TYPE: PRT
<213> ORGANISM: Artificial Sequence
<220> FEATURE:
<223> OTHER INFORMATION: Synthetic construct

<400> SEQUENCE: 48

Ala Gly Thr Tyr Gly Leu Arg Ser Gly Tyr Ser Ser Pro Gly Ser Pro
1               5                   10                  15

Gly Thr Pro Gly Ser Arg Ser Arg Thr Cys
            20                  25


<210> SEQ ID NO 49
<211> LENGTH: 26
<212> TYPE: PRT
<213> ORGANISM: Artificial Sequence
<220> FEATURE:
<223> OTHER INFORMATION: Synthetic construct

<400> SEQUENCE: 49

Ala Gly Thr Tyr Gly Leu Ser Gly Tyr Ser Ser Pro Gly Ser Pro Gly
1               5                   10                  15

Thr Pro Gly Ser Arg Ser Arg Thr Pro Cys
            20                  25


<210> SEQ ID NO 50
<211> LENGTH: 27
<212> TYPE: PRT
<213> ORGANISM: Artificial Sequence
<220> FEATURE:
<223> OTHER INFORMATION: Synthetic construct
```

<400> SEQUENCE: 50

Ala Gly Thr Tyr Gly Leu Arg Ser Gly Tyr Ser Ser Pro Gly Ser Pro
1               5                   10                  15

Gly Thr Pro Gly Ser Arg Ser Arg Thr Pro Cys
            20                  25

<210> SEQ ID NO 51
<211> LENGTH: 19
<212> TYPE: PRT
<213> ORGANISM: Artificial Sequence
<220> FEATURE:
<223> OTHER INFORMATION: Synthetic construct

<400> SEQUENCE: 51

Gly Thr Tyr Gly Leu Gly Ser Ser Pro Gly Ser Pro Gly Thr Pro Gly
1               5                   10                  15

Ser Arg Cys

<210> SEQ ID NO 52
<211> LENGTH: 20
<212> TYPE: PRT
<213> ORGANISM: Artificial Sequence
<220> FEATURE:
<223> OTHER INFORMATION: Synthetic construct

<400> SEQUENCE: 52

Gly Thr Tyr Gly Leu Gly Tyr Ser Ser Pro Gly Ser Pro Gly Thr Pro
1               5                   10                  15

Gly Ser Arg Cys
            20

<210> SEQ ID NO 53
<211> LENGTH: 20
<212> TYPE: PRT
<213> ORGANISM: Artificial Sequence
<220> FEATURE:
<223> OTHER INFORMATION: Synthetic construct

<400> SEQUENCE: 53

Gly Thr Tyr Gly Leu Gly Ser Ser Pro Gly Ser Pro Gly Thr Pro Gly
1               5                   10                  15

Ser Arg Ser Cys
            20

<210> SEQ ID NO 54
<211> LENGTH: 21
<212> TYPE: PRT
<213> ORGANISM: Artificial Sequence
<220> FEATURE:
<223> OTHER INFORMATION: Synthetic construct

<400> SEQUENCE: 54

Gly Thr Tyr Gly Leu Gly Gly Tyr Ser Ser Pro Gly Ser Pro Gly Thr
1               5                   10                  15

Pro Gly Ser Arg Cys
            20

<210> SEQ ID NO 55
<211> LENGTH: 21
<212> TYPE: PRT
<213> ORGANISM: Artificial Sequence
<220> FEATURE:
<223> OTHER INFORMATION: Synthetic construct

<400> SEQUENCE: 55

Gly Thr Tyr Gly Leu Gly Tyr Ser Ser Pro Gly Ser Pro Gly Thr Pro
1               5                   10                  15

Gly Ser Arg Ser Cys
            20

<210> SEQ ID NO 56
<211> LENGTH: 21
<212> TYPE: PRT
<213> ORGANISM: Artificial Sequence
<220> FEATURE:
<223> OTHER INFORMATION: Synthetic construct

<400> SEQUENCE: 56

Gly Thr Tyr Gly Leu Gly Ser Ser Pro Gly Ser Pro Gly Thr Pro Gly
1               5                   10                  15

Ser Arg Ser Arg Cys
            20

<210> SEQ ID NO 57
<211> LENGTH: 22
<212> TYPE: PRT
<213> ORGANISM: Artificial Sequence
<220> FEATURE:
<223> OTHER INFORMATION: Synthetic construct

<400> SEQUENCE: 57

Gly Thr Tyr Gly Leu Gly Ser Gly Tyr Ser Ser Pro Gly Ser Pro Gly
1               5                   10                  15

Thr Pro Gly Ser Arg Cys
            20

<210> SEQ ID NO 58
<211> LENGTH: 22
<212> TYPE: PRT
<213> ORGANISM: Artificial Sequence
<220> FEATURE:
<223> OTHER INFORMATION: Synthetic construct

<400> SEQUENCE: 58

Gly Thr Tyr Gly Leu Gly Gly Tyr Ser Ser Pro Gly Ser Pro Gly Thr
1               5                   10                  15

Pro Gly Ser Arg Ser Cys
            20

<210> SEQ ID NO 59
<211> LENGTH: 22
<212> TYPE: PRT
<213> ORGANISM: Artificial Sequence
<220> FEATURE:
<223> OTHER INFORMATION: Synthetic construct

<400> SEQUENCE: 59

Gly Thr Tyr Gly Leu Gly Tyr Ser Ser Pro Gly Ser Pro Gly Thr Pro
1               5                   10                  15

Gly Ser Arg Ser Arg Cys
            20

<210> SEQ ID NO 60
<211> LENGTH: 22
<212> TYPE: PRT
<213> ORGANISM: Artificial Sequence
<220> FEATURE:
<223> OTHER INFORMATION: Synthetic construct

<400> SEQUENCE: 60

Gly Thr Tyr Gly Leu Gly Ser Ser Pro Gly Ser Pro Gly Thr Pro Gly
1 5 10 15

Ser Arg Ser Arg Thr Cys
20

<210> SEQ ID NO 61
<211> LENGTH: 23
<212> TYPE: PRT
<213> ORGANISM: Artificial Sequence
<220> FEATURE:
<223> OTHER INFORMATION: Synthetic construct

<400> SEQUENCE: 61

Gly Thr Tyr Gly Leu Gly Arg Ser Gly Tyr Ser Ser Pro Gly Ser Pro
1 5 10 15

Gly Thr Pro Gly Ser Arg Cys
20

<210> SEQ ID NO 62
<211> LENGTH: 23
<212> TYPE: PRT
<213> ORGANISM: Artificial Sequence
<220> FEATURE:
<223> OTHER INFORMATION: Synthetic construct

<400> SEQUENCE: 62

Gly Thr Tyr Gly Leu Gly Ser Gly Tyr Ser Ser Pro Gly Ser Pro Gly
1 5 10 15

Thr Pro Gly Ser Arg Ser Cys
20

<210> SEQ ID NO 63
<211> LENGTH: 23
<212> TYPE: PRT
<213> ORGANISM: Artificial Sequence
<220> FEATURE:
<223> OTHER INFORMATION: Synthetic construct

<400> SEQUENCE: 63

Gly Thr Tyr Gly Leu Gly Gly Tyr Ser Ser Pro Gly Ser Pro Gly Thr
1 5 10 15

Pro Gly Ser Arg Ser Arg Cys
20

<210> SEQ ID NO 64
<211> LENGTH: 23
<212> TYPE: PRT
<213> ORGANISM: Artificial Sequence
<220> FEATURE:
<223> OTHER INFORMATION: Synthetic construct

<400> SEQUENCE: 64

Gly Thr Tyr Gly Leu Gly Tyr Ser Ser Pro Gly Ser Pro Gly Thr Pro
1 5 10 15

Gly Ser Arg Ser Arg Thr Cys
20

<210> SEQ ID NO 65
<211> LENGTH: 23
<212> TYPE: PRT
<213> ORGANISM: Artificial Sequence
<220> FEATURE:

-continued

<223> OTHER INFORMATION: Synthetic construct

<400> SEQUENCE: 65

```
Gly Thr Tyr Gly Leu Gly Ser Ser Pro Gly Ser Pro Gly Thr Pro Gly
1               5                   10                  15

Ser Arg Ser Arg Thr Pro Cys
            20
```

<210> SEQ ID NO 66
<211> LENGTH: 24
<212> TYPE: PRT
<213> ORGANISM: Artificial Sequence
<220> FEATURE:
<223> OTHER INFORMATION: Synthetic construct

<400> SEQUENCE: 66

```
Gly Thr Tyr Gly Leu Gly Arg Ser Gly Tyr Ser Ser Pro Gly Ser Pro
1               5                   10                  15

Gly Thr Pro Gly Ser Arg Ser Cys
            20
```

<210> SEQ ID NO 67
<211> LENGTH: 24
<212> TYPE: PRT
<213> ORGANISM: Artificial Sequence
<220> FEATURE:
<223> OTHER INFORMATION: Synthetic construct

<400> SEQUENCE: 67

```
Gly Thr Tyr Gly Leu Gly Ser Gly Tyr Ser Ser Pro Gly Ser Pro Gly
1               5                   10                  15

Thr Pro Gly Ser Arg Ser Arg Cys
            20
```

<210> SEQ ID NO 68
<211> LENGTH: 24
<212> TYPE: PRT
<213> ORGANISM: Artificial Sequence
<220> FEATURE:
<223> OTHER INFORMATION: Synthetic construct

<400> SEQUENCE: 68

```
Gly Thr Tyr Gly Leu Gly Gly Tyr Ser Ser Pro Gly Ser Pro Gly Thr
1               5                   10                  15

Pro Gly Ser Arg Ser Arg Thr Cys
            20
```

<210> SEQ ID NO 69
<211> LENGTH: 24
<212> TYPE: PRT
<213> ORGANISM: Artificial Sequence
<220> FEATURE:
<223> OTHER INFORMATION: Synthetic construct

<400> SEQUENCE: 69

```
Gly Thr Tyr Gly Leu Gly Tyr Ser Ser Pro Gly Ser Pro Gly Thr Pro
1               5                   10                  15

Gly Ser Arg Ser Arg Thr Pro Cys
            20
```

<210> SEQ ID NO 70
<211> LENGTH: 25
<212> TYPE: PRT
<213> ORGANISM: Artificial Sequence
<220> FEATURE:
<223> OTHER INFORMATION: Synthetic construct

<400> SEQUENCE: 70

Gly Thr Tyr Gly Leu Gly Arg Ser Gly Tyr Ser Ser Pro Gly Ser Pro
1 5 10 15

Gly Thr Pro Gly Ser Arg Ser Arg Cys
20 25

<210> SEQ ID NO 71
<211> LENGTH: 25
<212> TYPE: PRT
<213> ORGANISM: Artificial Sequence
<220> FEATURE:
<223> OTHER INFORMATION: Synthetic construct

<400> SEQUENCE: 71

Gly Thr Tyr Gly Leu Gly Ser Gly Tyr Ser Ser Pro Gly Ser Pro Gly
1 5 10 15

Thr Pro Gly Ser Arg Ser Arg Thr Cys
20 25

<210> SEQ ID NO 72
<211> LENGTH: 25
<212> TYPE: PRT
<213> ORGANISM: Artificial Sequence
<220> FEATURE:
<223> OTHER INFORMATION: Synthetic construct

<400> SEQUENCE: 72

Gly Thr Tyr Gly Leu Gly Gly Tyr Ser Ser Pro Gly Ser Pro Gly Thr
1 5 10 15

Pro Gly Ser Arg Ser Arg Thr Pro Cys
20 25

<210> SEQ ID NO 73
<211> LENGTH: 26
<212> TYPE: PRT
<213> ORGANISM: Artificial Sequence
<220> FEATURE:
<223> OTHER INFORMATION: Synthetic construct

<400> SEQUENCE: 73

Gly Thr Tyr Gly Leu Gly Arg Ser Gly Tyr Ser Ser Pro Gly Ser Pro
1 5 10 15

Gly Thr Pro Gly Ser Arg Ser Arg Thr Cys
20 25

<210> SEQ ID NO 74
<211> LENGTH: 26
<212> TYPE: PRT
<213> ORGANISM: Artificial Sequence
<220> FEATURE:
<223> OTHER INFORMATION: Synthetic construct

<400> SEQUENCE: 74

Gly Thr Tyr Gly Leu Gly Ser Gly Tyr Ser Ser Pro Gly Ser Pro Gly
1 5 10 15

Thr Pro Gly Ser Arg Ser Arg Thr Pro Cys
20 25

<210> SEQ ID NO 75
<211> LENGTH: 27
<212> TYPE: PRT

<213> ORGANISM: Artificial Sequence
<220> FEATURE:
<223> OTHER INFORMATION: Synthetic construct

<400> SEQUENCE: 75

```
Gly Thr Tyr Gly Leu Gly Arg Ser Gly Tyr Ser Ser Pro Gly Ser Pro
1               5                   10                  15

Gly Thr Pro Gly Ser Arg Ser Arg Thr Pro Cys
            20                  25
```

<210> SEQ ID NO 76
<211> LENGTH: 20
<212> TYPE: PRT
<213> ORGANISM: Artificial Sequence
<220> FEATURE:
<223> OTHER INFORMATION: Synthetic construct

<400> SEQUENCE: 76

```
His Ala Gly Thr Tyr Gly Leu Ser Ser Pro Gly Ser Pro Gly Thr Pro
1               5                   10                  15

Gly Ser Arg Cys
            20
```

<210> SEQ ID NO 77
<211> LENGTH: 21
<212> TYPE: PRT
<213> ORGANISM: Artificial Sequence
<220> FEATURE:
<223> OTHER INFORMATION: Synthetic construct

<400> SEQUENCE: 77

```
His Ala Gly Thr Tyr Gly Leu Tyr Ser Ser Pro Gly Ser Pro Gly Thr
1               5                   10                  15

Pro Gly Ser Arg Cys
            20
```

<210> SEQ ID NO 78
<211> LENGTH: 21
<212> TYPE: PRT
<213> ORGANISM: Artificial Sequence
<220> FEATURE:
<223> OTHER INFORMATION: Synthetic construct

<400> SEQUENCE: 78

```
His Ala Gly Thr Tyr Gly Leu Ser Ser Pro Gly Ser Pro Gly Thr Pro
1               5                   10                  15

Gly Ser Arg Ser Cys
            20
```

<210> SEQ ID NO 79
<211> LENGTH: 22
<212> TYPE: PRT
<213> ORGANISM: Artificial Sequence
<220> FEATURE:
<223> OTHER INFORMATION: Synthetic construct

<400> SEQUENCE: 79

```
His Ala Gly Thr Tyr Gly Leu Gly Tyr Ser Ser Pro Gly Ser Pro Gly
1               5                   10                  15

Thr Pro Gly Ser Arg Cys
            20
```

<210> SEQ ID NO 80
<211> LENGTH: 22

<212> TYPE: PRT
<213> ORGANISM: Artificial Sequence
<220> FEATURE:
<223> OTHER INFORMATION: Synthetic construct

<400> SEQUENCE: 80

His Ala Gly Thr Tyr Gly Leu Tyr Ser Ser Pro Gly Ser Pro Gly Thr
1               5                   10                  15

Pro Gly Ser Arg Ser Cys
            20

<210> SEQ ID NO 81
<211> LENGTH: 22
<212> TYPE: PRT
<213> ORGANISM: Artificial Sequence
<220> FEATURE:
<223> OTHER INFORMATION: Synthetic construct

<400> SEQUENCE: 81

His Ala Gly Thr Tyr Gly Leu Ser Ser Pro Gly Ser Pro Gly Thr Pro
1               5                   10                  15

Gly Ser Arg Ser Arg Cys
            20

<210> SEQ ID NO 82
<211> LENGTH: 23
<212> TYPE: PRT
<213> ORGANISM: Artificial Sequence
<220> FEATURE:
<223> OTHER INFORMATION: Synthetic construct

<400> SEQUENCE: 82

His Ala Gly Thr Tyr Gly Leu Ser Gly Tyr Ser Ser Pro Gly Ser Pro
1               5                   10                  15

Gly Thr Pro Gly Ser Arg Cys
            20

<210> SEQ ID NO 83
<211> LENGTH: 23
<212> TYPE: PRT
<213> ORGANISM: Artificial Sequence
<220> FEATURE:
<223> OTHER INFORMATION: Synthetic construct

<400> SEQUENCE: 83

His Ala Gly Thr Tyr Gly Leu Gly Tyr Ser Ser Pro Gly Ser Pro Gly
1               5                   10                  15

Thr Pro Gly Ser Arg Ser Cys
            20

<210> SEQ ID NO 84
<211> LENGTH: 23
<212> TYPE: PRT
<213> ORGANISM: Artificial Sequence
<220> FEATURE:
<223> OTHER INFORMATION: Synthetic construct

<400> SEQUENCE: 84

His Ala Gly Thr Tyr Gly Leu Tyr Ser Ser Pro Gly Ser Pro Gly Thr
1               5                   10                  15

Pro Gly Ser Arg Ser Arg Cys
            20

<210> SEQ ID NO 85

<211> LENGTH: 23
<212> TYPE: PRT
<213> ORGANISM: Artificial Sequence
<220> FEATURE:
<223> OTHER INFORMATION: Synthetic construct

<400> SEQUENCE: 85

His Ala Gly Thr Tyr Gly Leu Ser Ser Pro Gly Ser Pro Gly Thr Pro
1 5 10 15

Gly Ser Arg Ser Arg Thr Cys
20

<210> SEQ ID NO 86
<211> LENGTH: 24
<212> TYPE: PRT
<213> ORGANISM: Artificial Sequence
<220> FEATURE:
<223> OTHER INFORMATION: Synthetic construct

<400> SEQUENCE: 86

His Ala Gly Thr Tyr Gly Leu Arg Ser Gly Tyr Ser Ser Pro Gly Ser
1 5 10 15

Pro Gly Thr Pro Gly Ser Arg Cys
20

<210> SEQ ID NO 87
<211> LENGTH: 24
<212> TYPE: PRT
<213> ORGANISM: Artificial Sequence
<220> FEATURE:
<223> OTHER INFORMATION: Synthetic construct

<400> SEQUENCE: 87

His Ala Gly Thr Tyr Gly Leu Ser Gly Tyr Ser Ser Pro Gly Ser Pro
1 5 10 15

Gly Thr Pro Gly Ser Arg Ser Cys
20

<210> SEQ ID NO 88
<211> LENGTH: 24
<212> TYPE: PRT
<213> ORGANISM: Artificial Sequence
<220> FEATURE:
<223> OTHER INFORMATION: Synthetic construct

<400> SEQUENCE: 88

His Ala Gly Thr Tyr Gly Leu Gly Tyr Ser Ser Pro Gly Ser Pro Gly
1 5 10 15

Thr Pro Gly Ser Arg Ser Arg Cys
20

<210> SEQ ID NO 89
<211> LENGTH: 24
<212> TYPE: PRT
<213> ORGANISM: Artificial Sequence
<220> FEATURE:
<223> OTHER INFORMATION: Synthetic construct

<400> SEQUENCE: 89

His Ala Gly Thr Tyr Gly Leu Tyr Ser Ser Pro Gly Ser Pro Gly Thr
1 5 10 15

Pro Gly Ser Arg Ser Arg Thr Cys
20

<210> SEQ ID NO 90
<211> LENGTH: 24
<212> TYPE: PRT
<213> ORGANISM: Artificial Sequence
<220> FEATURE:
<223> OTHER INFORMATION: Synthetic construct

<400> SEQUENCE: 90

His Ala Gly Thr Tyr Gly Leu Ser Ser Pro Gly Ser Pro Gly Thr Pro
1 5 10 15

Gly Ser Arg Ser Arg Thr Pro Cys
20

<210> SEQ ID NO 91
<211> LENGTH: 25
<212> TYPE: PRT
<213> ORGANISM: Artificial Sequence
<220> FEATURE:
<223> OTHER INFORMATION: Synthetic construct

<400> SEQUENCE: 91

His Ala Gly Thr Tyr Gly Leu Arg Ser Gly Tyr Ser Ser Pro Gly Ser
1 5 10 15

Pro Gly Thr Pro Gly Ser Arg Ser Cys
20 25

<210> SEQ ID NO 92
<211> LENGTH: 25
<212> TYPE: PRT
<213> ORGANISM: Artificial Sequence
<220> FEATURE:
<223> OTHER INFORMATION: Synthetic construct

<400> SEQUENCE: 92

His Ala Gly Thr Tyr Gly Leu Ser Gly Tyr Ser Ser Pro Gly Ser Pro
1 5 10 15

Gly Thr Pro Gly Ser Arg Ser Arg Cys
20 25

<210> SEQ ID NO 93
<211> LENGTH: 25
<212> TYPE: PRT
<213> ORGANISM: Artificial Sequence
<220> FEATURE:
<223> OTHER INFORMATION: Synthetic construct

<400> SEQUENCE: 93

His Ala Gly Thr Tyr Gly Leu Gly Tyr Ser Ser Pro Gly Ser Pro Gly
1 5 10 15

Thr Pro Gly Ser Arg Ser Arg Thr Cys
20 25

<210> SEQ ID NO 94
<211> LENGTH: 25
<212> TYPE: PRT
<213> ORGANISM: Artificial Sequence
<220> FEATURE:
<223> OTHER INFORMATION: Synthetic construct

<400> SEQUENCE: 94

His Ala Gly Thr Tyr Gly Leu Tyr Ser Ser Pro Gly Ser Pro Gly Thr
1 5 10 15

Pro Gly Ser Arg Ser Arg Thr Pro Cys
20 25

<210> SEQ ID NO 95
<211> LENGTH: 26
<212> TYPE: PRT
<213> ORGANISM: Artificial Sequence
<220> FEATURE:
<223> OTHER INFORMATION: Synthetic construct

<400> SEQUENCE: 95

```
His Ala Gly Thr Tyr Gly Leu Arg Ser Gly Tyr Ser Ser Pro Gly Ser
1               5                   10                  15

Pro Gly Thr Pro Gly Ser Arg Ser Arg Cys
            20                  25
```

<210> SEQ ID NO 96
<211> LENGTH: 26
<212> TYPE: PRT
<213> ORGANISM: Artificial Sequence
<220> FEATURE:
<223> OTHER INFORMATION: Synthetic construct

<400> SEQUENCE: 96

```
His Ala Gly Thr Tyr Gly Leu Ser Gly Tyr Ser Ser Pro Gly Ser Pro
1               5                   10                  15

Gly Thr Pro Gly Ser Arg Ser Arg Thr Cys
            20                  25
```

<210> SEQ ID NO 97
<211> LENGTH: 26
<212> TYPE: PRT
<213> ORGANISM: Artificial Sequence
<220> FEATURE:
<223> OTHER INFORMATION: Synthetic construct

<400> SEQUENCE: 97

```
His Ala Gly Thr Tyr Gly Leu Gly Tyr Ser Ser Pro Gly Ser Pro Gly
1               5                   10                  15

Thr Pro Gly Ser Arg Ser Arg Thr Pro Cys
            20                  25
```

<210> SEQ ID NO 98
<211> LENGTH: 27
<212> TYPE: PRT
<213> ORGANISM: Artificial Sequence
<220> FEATURE:
<223> OTHER INFORMATION: Synthetic construct

<400> SEQUENCE: 98

```
His Ala Gly Thr Tyr Gly Leu Arg Ser Gly Tyr Ser Ser Pro Gly Ser
1               5                   10                  15

Pro Gly Thr Pro Gly Ser Arg Ser Arg Thr Cys
            20                  25
```

<210> SEQ ID NO 99
<211> LENGTH: 27
<212> TYPE: PRT
<213> ORGANISM: Artificial Sequence
<220> FEATURE:
<223> OTHER INFORMATION: Synthetic construct

<400> SEQUENCE: 99

```
His Ala Gly Thr Tyr Gly Leu Ser Gly Tyr Ser Ser Pro Gly Ser Pro
1               5                   10                  15

Gly Thr Pro Gly Ser Arg Ser Arg Thr Pro Cys
            20                  25
```

<210> SEQ ID NO 100
<211> LENGTH: 28
<212> TYPE: PRT
<213> ORGANISM: Artificial Sequence
<220> FEATURE:
<223> OTHER INFORMATION: Synthetic construct

<400> SEQUENCE: 100

His Ala Gly Thr Tyr Gly Leu Arg Ser Gly Tyr Ser Ser Pro Gly Ser
1 5 10 15

Pro Gly Thr Pro Gly Ser Arg Ser Arg Thr Pro Cys
20 25

<210> SEQ ID NO 101
<211> LENGTH: 20
<212> TYPE: PRT
<213> ORGANISM: Artificial Sequence
<220> FEATURE:
<223> OTHER INFORMATION: Synthetic construct

<400> SEQUENCE: 101

Ala Gly Thr Tyr Gly Leu Gly Ser Ser Pro Gly Ser Pro Gly Thr Pro
1 5 10 15

Gly Ser Arg Cys
20

<210> SEQ ID NO 102
<211> LENGTH: 21
<212> TYPE: PRT
<213> ORGANISM: Artificial Sequence
<220> FEATURE:
<223> OTHER INFORMATION: Synthetic construct

<400> SEQUENCE: 102

Ala Gly Thr Tyr Gly Leu Gly Tyr Ser Ser Pro Gly Ser Pro Gly Thr
1 5 10 15

Pro Gly Ser Arg Cys
20

<210> SEQ ID NO 103
<211> LENGTH: 21
<212> TYPE: PRT
<213> ORGANISM: Artificial Sequence
<220> FEATURE:
<223> OTHER INFORMATION: Synthetic construct

<400> SEQUENCE: 103

Ala Gly Thr Tyr Gly Leu Gly Ser Ser Pro Gly Ser Pro Gly Thr Pro
1 5 10 15

Gly Ser Arg Ser Cys
20

<210> SEQ ID NO 104
<211> LENGTH: 22
<212> TYPE: PRT
<213> ORGANISM: Artificial Sequence
<220> FEATURE:
<223> OTHER INFORMATION: Synthetic construct

<400> SEQUENCE: 104

Ala Gly Thr Tyr Gly Leu Gly Gly Tyr Ser Ser Pro Gly Ser Pro Gly
1 5 10 15

Thr Pro Gly Ser Arg Cys

20

<210> SEQ ID NO 105
<211> LENGTH: 22
<212> TYPE: PRT
<213> ORGANISM: Artificial Sequence
<220> FEATURE:
<223> OTHER INFORMATION: Synthetic construct

<400> SEQUENCE: 105

Ala Gly Thr Tyr Gly Leu Gly Tyr Ser Ser Pro Gly Ser Pro Gly Thr
1 5 10 15

Pro Gly Ser Arg Ser Cys
20

<210> SEQ ID NO 106
<211> LENGTH: 22
<212> TYPE: PRT
<213> ORGANISM: Artificial Sequence
<220> FEATURE:
<223> OTHER INFORMATION: Synthetic construct

<400> SEQUENCE: 106

Ala Gly Thr Tyr Gly Leu Gly Ser Ser Pro Gly Ser Pro Gly Thr Pro
1 5 10 15

Gly Ser Arg Ser Arg Cys
20

<210> SEQ ID NO 107
<211> LENGTH: 23
<212> TYPE: PRT
<213> ORGANISM: Artificial Sequence
<220> FEATURE:
<223> OTHER INFORMATION: Synthetic construct

<400> SEQUENCE: 107

Ala Gly Thr Tyr Gly Leu Gly Ser Gly Tyr Ser Ser Pro Gly Ser Pro
1 5 10 15

Gly Thr Pro Gly Ser Arg Cys
20

<210> SEQ ID NO 108
<211> LENGTH: 23
<212> TYPE: PRT
<213> ORGANISM: Artificial Sequence
<220> FEATURE:
<223> OTHER INFORMATION: Synthetic construct

<400> SEQUENCE: 108

Ala Gly Thr Tyr Gly Leu Gly Gly Tyr Ser Ser Pro Gly Ser Pro Gly
1 5 10 15

Thr Pro Gly Ser Arg Ser Cys
20

<210> SEQ ID NO 109
<211> LENGTH: 23
<212> TYPE: PRT
<213> ORGANISM: Artificial Sequence
<220> FEATURE:
<223> OTHER INFORMATION: Synthetic construct

<400> SEQUENCE: 109

Ala Gly Thr Tyr Gly Leu Gly Tyr Ser Ser Pro Gly Ser Pro Gly Thr
1 5 10 15

Pro Gly Ser Arg Ser Arg Cys
20

<210> SEQ ID NO 110
<211> LENGTH: 23
<212> TYPE: PRT
<213> ORGANISM: Artificial Sequence
<220> FEATURE:
<223> OTHER INFORMATION: Synthetic construct

<400> SEQUENCE: 110

Ala Gly Thr Tyr Gly Leu Gly Ser Ser Pro Gly Ser Pro Gly Thr Pro
1 5 10 15

Gly Ser Arg Ser Arg Thr Cys
20

<210> SEQ ID NO 111
<211> LENGTH: 24
<212> TYPE: PRT
<213> ORGANISM: Artificial Sequence
<220> FEATURE:
<223> OTHER INFORMATION: Synthetic construct

<400> SEQUENCE: 111

Ala Gly Thr Tyr Gly Leu Gly Arg Ser Gly Tyr Ser Ser Pro Gly Ser
1 5 10 15

Pro Gly Thr Pro Gly Ser Arg Cys
20

<210> SEQ ID NO 112
<211> LENGTH: 24
<212> TYPE: PRT
<213> ORGANISM: Artificial Sequence
<220> FEATURE:
<223> OTHER INFORMATION: Synthetic construct

<400> SEQUENCE: 112

Ala Gly Thr Tyr Gly Leu Gly Ser Gly Tyr Ser Ser Pro Gly Ser Pro
1 5 10 15

Gly Thr Pro Gly Ser Arg Ser Cys
20

<210> SEQ ID NO 113
<211> LENGTH: 24
<212> TYPE: PRT
<213> ORGANISM: Artificial Sequence
<220> FEATURE:
<223> OTHER INFORMATION: Synthetic construct

<400> SEQUENCE: 113

Ala Gly Thr Tyr Gly Leu Gly Gly Tyr Ser Ser Pro Gly Ser Pro Gly
1 5 10 15

Thr Pro Gly Ser Arg Ser Arg Cys
20

<210> SEQ ID NO 114
<211> LENGTH: 24
<212> TYPE: PRT
<213> ORGANISM: Artificial Sequence
<220> FEATURE:
<223> OTHER INFORMATION: Synthetic construct

<400> SEQUENCE: 114

Ala Gly Thr Tyr Gly Leu Gly Tyr Ser Ser Pro Gly Ser Pro Gly Thr
1 5 10 15

Pro Gly Ser Arg Ser Arg Thr Cys
20

<210> SEQ ID NO 115
<211> LENGTH: 24
<212> TYPE: PRT
<213> ORGANISM: Artificial Sequence
<220> FEATURE:
<223> OTHER INFORMATION: Synthetic construct

<400> SEQUENCE: 115

Ala Gly Thr Tyr Gly Leu Gly Ser Ser Pro Gly Ser Pro Gly Thr Pro
1 5 10 15

Gly Ser Arg Ser Arg Thr Pro Cys
20

<210> SEQ ID NO 116
<211> LENGTH: 25
<212> TYPE: PRT
<213> ORGANISM: Artificial Sequence
<220> FEATURE:
<223> OTHER INFORMATION: Synthetic construct

<400> SEQUENCE: 116

Ala Gly Thr Tyr Gly Leu Gly Arg Ser Gly Tyr Ser Ser Pro Gly Ser
1 5 10 15

Pro Gly Thr Pro Gly Ser Arg Ser Cys
20 25

<210> SEQ ID NO 117
<211> LENGTH: 25
<212> TYPE: PRT
<213> ORGANISM: Artificial Sequence
<220> FEATURE:
<223> OTHER INFORMATION: Synthetic construct

<400> SEQUENCE: 117

Ala Gly Thr Tyr Gly Leu Gly Ser Gly Tyr Ser Ser Pro Gly Ser Pro
1 5 10 15

Gly Thr Pro Gly Ser Arg Ser Arg Cys
20 25

<210> SEQ ID NO 118
<211> LENGTH: 25
<212> TYPE: PRT
<213> ORGANISM: Artificial Sequence
<220> FEATURE:
<223> OTHER INFORMATION: Synthetic construct

<400> SEQUENCE: 118

Ala Gly Thr Tyr Gly Leu Gly Gly Tyr Ser Ser Pro Gly Ser Pro Gly
1 5 10 15

Thr Pro Gly Ser Arg Ser Arg Thr Cys
20 25

<210> SEQ ID NO 119
<211> LENGTH: 25
<212> TYPE: PRT
<213> ORGANISM: Artificial Sequence
<220> FEATURE:
<223> OTHER INFORMATION: Synthetic construct

<400> SEQUENCE: 119

Ala Gly Thr Tyr Gly Leu Gly Tyr Ser Ser Pro Gly Ser Pro Gly Thr 1 5 10 15

Pro Gly Ser Arg Ser Arg Thr Pro Cys
20 25

<210> SEQ ID NO 120
<211> LENGTH: 26
<212> TYPE: PRT
<213> ORGANISM: Artificial Sequence
<220> FEATURE:
<223> OTHER INFORMATION: Synthetic construct

<400> SEQUENCE: 120

Ala Gly Thr Tyr Gly Leu Gly Arg Ser Gly Tyr Ser Ser Pro Gly Ser
1 5 10 15

Pro Gly Thr Pro Gly Ser Arg Ser Arg Cys
20 25

<210> SEQ ID NO 121
<211> LENGTH: 26
<212> TYPE: PRT
<213> ORGANISM: Artificial Sequence
<220> FEATURE:
<223> OTHER INFORMATION: Synthetic construct

<400> SEQUENCE: 121

Ala Gly Thr Tyr Gly Leu Gly Ser Gly Tyr Ser Ser Pro Gly Ser Pro
1 5 10 15

Gly Thr Pro Gly Ser Arg Ser Arg Thr Cys
20 25

<210> SEQ ID NO 122
<211> LENGTH: 26
<212> TYPE: PRT
<213> ORGANISM: Artificial Sequence
<220> FEATURE:
<223> OTHER INFORMATION: Synthetic construct

<400> SEQUENCE: 122

Ala Gly Thr Tyr Gly Leu Gly Gly Tyr Ser Ser Pro Gly Ser Pro Gly
1 5 10 15

Thr Pro Gly Ser Arg Ser Arg Thr Pro Cys
20 25

<210> SEQ ID NO 123
<211> LENGTH: 27
<212> TYPE: PRT
<213> ORGANISM: Artificial Sequence
<220> FEATURE:
<223> OTHER INFORMATION: Synthetic construct

<400> SEQUENCE: 123

Ala Gly Thr Tyr Gly Leu Gly Arg Ser Gly Tyr Ser Ser Pro Gly Ser
1 5 10 15

Pro Gly Thr Pro Gly Ser Arg Ser Arg Thr Cys
20 25

<210> SEQ ID NO 124
<211> LENGTH: 27
<212> TYPE: PRT
<213> ORGANISM: Artificial Sequence
<220> FEATURE:
<223> OTHER INFORMATION: Synthetic construct

<400> SEQUENCE: 124

-continued

```
Ala Gly Thr Tyr Gly Leu Gly Ser Gly Tyr Ser Ser Pro Gly Ser Pro
1               5                   10                  15

Gly Thr Pro Gly Ser Arg Ser Arg Thr Pro Cys
            20                  25


<210> SEQ ID NO 125
<211> LENGTH: 28
<212> TYPE: PRT
<213> ORGANISM: Artificial Sequence
<220> FEATURE:
<223> OTHER INFORMATION: Synthetic construct

<400> SEQUENCE: 125

Ala Gly Thr Tyr Gly Leu Gly Arg Ser Gly Tyr Ser Ser Pro Gly Ser
1               5                   10                  15

Pro Gly Thr Pro Gly Ser Arg Ser Arg Thr Pro Cys
            20                  25


<210> SEQ ID NO 126
<211> LENGTH: 20
<212> TYPE: PRT
<213> ORGANISM: Artificial Sequence
<220> FEATURE:
<223> OTHER INFORMATION: Synthetic construct

<400> SEQUENCE: 126

Gly Thr Tyr Gly Leu Gly Asp Ser Ser Pro Gly Ser Pro Gly Thr Pro
1               5                   10                  15

Gly Ser Arg Cys
            20


<210> SEQ ID NO 127
<211> LENGTH: 21
<212> TYPE: PRT
<213> ORGANISM: Artificial Sequence
<220> FEATURE:
<223> OTHER INFORMATION: Synthetic construct

<400> SEQUENCE: 127

Gly Thr Tyr Gly Leu Gly Asp Tyr Ser Ser Pro Gly Ser Pro Gly Thr
1               5                   10                  15

Pro Gly Ser Arg Cys
            20


<210> SEQ ID NO 128
<211> LENGTH: 21
<212> TYPE: PRT
<213> ORGANISM: Artificial Sequence
<220> FEATURE:
<223> OTHER INFORMATION: Synthetic construct

<400> SEQUENCE: 128

Gly Thr Tyr Gly Leu Gly Asp Ser Ser Pro Gly Ser Pro Gly Thr Pro
1               5                   10                  15

Gly Ser Arg Ser Cys
            20


<210> SEQ ID NO 129
<211> LENGTH: 22
<212> TYPE: PRT
<213> ORGANISM: Artificial Sequence
<220> FEATURE:
<223> OTHER INFORMATION: Synthetic construct

<400> SEQUENCE: 129
```

Gly Thr Tyr Gly Leu Gly Asp Gly Tyr Ser Ser Pro Gly Ser Pro Gly
1 5 10 15

Thr Pro Gly Ser Arg Cys
20

<210> SEQ ID NO 130
<211> LENGTH: 22
<212> TYPE: PRT
<213> ORGANISM: Artificial Sequence
<220> FEATURE:
<223> OTHER INFORMATION: Synthetic construct

<400> SEQUENCE: 130

Gly Thr Tyr Gly Leu Gly Asp Tyr Ser Ser Pro Gly Ser Pro Gly Thr
1 5 10 15

Pro Gly Ser Arg Ser Cys
20

<210> SEQ ID NO 131
<211> LENGTH: 22
<212> TYPE: PRT
<213> ORGANISM: Artificial Sequence
<220> FEATURE:
<223> OTHER INFORMATION: Synthetic construct

<400> SEQUENCE: 131

Gly Thr Tyr Gly Leu Gly Asp Ser Ser Pro Gly Ser Pro Gly Thr Pro
1 5 10 15

Gly Ser Arg Ser Arg Cys
20

<210> SEQ ID NO 132
<211> LENGTH: 23
<212> TYPE: PRT
<213> ORGANISM: Artificial Sequence
<220> FEATURE:
<223> OTHER INFORMATION: Synthetic construct

<400> SEQUENCE: 132

Gly Thr Tyr Gly Leu Gly Asp Ser Gly Tyr Ser Ser Pro Gly Ser Pro
1 5 10 15

Gly Thr Pro Gly Ser Arg Cys
20

<210> SEQ ID NO 133
<211> LENGTH: 23
<212> TYPE: PRT
<213> ORGANISM: Artificial Sequence
<220> FEATURE:
<223> OTHER INFORMATION: Synthetic construct

<400> SEQUENCE: 133

Gly Thr Tyr Gly Leu Gly Asp Gly Tyr Ser Ser Pro Gly Ser Pro Gly
1 5 10 15

Thr Pro Gly Ser Arg Ser Cys
20

<210> SEQ ID NO 134
<211> LENGTH: 23
<212> TYPE: PRT
<213> ORGANISM: Artificial Sequence
<220> FEATURE:
<223> OTHER INFORMATION: Synthetic construct

<400> SEQUENCE: 134

Gly Thr Tyr Gly Leu Gly Asp Tyr Ser Ser Pro Gly Ser Pro Gly Thr
1 5 10 15

Pro Gly Ser Arg Ser Arg Cys
20

<210> SEQ ID NO 135
<211> LENGTH: 23
<212> TYPE: PRT
<213> ORGANISM: Artificial Sequence
<220> FEATURE:
<223> OTHER INFORMATION: Synthetic construct

<400> SEQUENCE: 135

Gly Thr Tyr Gly Leu Gly Asp Ser Ser Pro Gly Ser Pro Gly Thr Pro
1 5 10 15

Gly Ser Arg Ser Arg Thr Cys
20

<210> SEQ ID NO 136
<211> LENGTH: 24
<212> TYPE: PRT
<213> ORGANISM: Artificial Sequence
<220> FEATURE:
<223> OTHER INFORMATION: Synthetic construct

<400> SEQUENCE: 136

Gly Thr Tyr Gly Leu Gly Asp Arg Ser Gly Tyr Ser Ser Pro Gly Ser
1 5 10 15

Pro Gly Thr Pro Gly Ser Arg Cys
20

<210> SEQ ID NO 137
<211> LENGTH: 24
<212> TYPE: PRT
<213> ORGANISM: Artificial Sequence
<220> FEATURE:
<223> OTHER INFORMATION: Synthetic construct

<400> SEQUENCE: 137

Gly Thr Tyr Gly Leu Gly Asp Ser Gly Tyr Ser Ser Pro Gly Ser Pro
1 5 10 15

Gly Thr Pro Gly Ser Arg Ser Cys
20

<210> SEQ ID NO 138
<211> LENGTH: 24
<212> TYPE: PRT
<213> ORGANISM: Artificial Sequence
<220> FEATURE:
<223> OTHER INFORMATION: Synthetic construct

<400> SEQUENCE: 138

Gly Thr Tyr Gly Leu Gly Asp Gly Tyr Ser Ser Pro Gly Ser Pro Gly
1 5 10 15

Thr Pro Gly Ser Arg Ser Arg Cys
20

<210> SEQ ID NO 139
<211> LENGTH: 24
<212> TYPE: PRT
<213> ORGANISM: Artificial Sequence
<220> FEATURE:
<223> OTHER INFORMATION: Synthetic construct

<400> SEQUENCE: 139

Gly Thr Tyr Gly Leu Gly Asp Tyr Ser Ser Pro Gly Ser Pro Gly Thr
1 5 10 15

Pro Gly Ser Arg Ser Arg Thr Cys
20

<210> SEQ ID NO 140
<211> LENGTH: 24
<212> TYPE: PRT
<213> ORGANISM: Artificial Sequence
<220> FEATURE:
<223> OTHER INFORMATION: Synthetic construct

<400> SEQUENCE: 140

Gly Thr Tyr Gly Leu Gly Asp Ser Ser Pro Gly Ser Pro Gly Thr Pro
1 5 10 15

Gly Ser Arg Ser Arg Thr Pro Cys
20

<210> SEQ ID NO 141
<211> LENGTH: 25
<212> TYPE: PRT
<213> ORGANISM: Artificial Sequence
<220> FEATURE:
<223> OTHER INFORMATION: Synthetic construct

<400> SEQUENCE: 141

Gly Thr Tyr Gly Leu Gly Asp Arg Ser Gly Tyr Ser Ser Pro Gly Ser
1 5 10 15

Pro Gly Thr Pro Gly Ser Arg Ser Cys
20 25

<210> SEQ ID NO 142
<211> LENGTH: 25
<212> TYPE: PRT
<213> ORGANISM: Artificial Sequence
<220> FEATURE:
<223> OTHER INFORMATION: Synthetic construct

<400> SEQUENCE: 142

Gly Thr Tyr Gly Leu Gly Asp Ser Gly Tyr Ser Ser Pro Gly Ser Pro
1 5 10 15

Gly Thr Pro Gly Ser Arg Ser Arg Cys
20 25

<210> SEQ ID NO 143
<211> LENGTH: 25
<212> TYPE: PRT
<213> ORGANISM: Artificial Sequence
<220> FEATURE:
<223> OTHER INFORMATION: Synthetic construct

<400> SEQUENCE: 143

Gly Thr Tyr Gly Leu Gly Asp Gly Tyr Ser Ser Pro Gly Ser Pro Gly
1 5 10 15

Thr Pro Gly Ser Arg Ser Arg Thr Cys
20 25

<210> SEQ ID NO 144
<211> LENGTH: 25
<212> TYPE: PRT
<213> ORGANISM: Artificial Sequence
<220> FEATURE:

-continued

```
<223> OTHER INFORMATION: Synthetic construct

<400> SEQUENCE: 144

Gly Thr Tyr Gly Leu Gly Asp Tyr Ser Ser Pro Gly Ser Pro Gly Thr
1               5                   10                  15

Pro Gly Ser Arg Ser Arg Thr Pro Cys
            20                  25


<210> SEQ ID NO 145
<211> LENGTH: 26
<212> TYPE: PRT
<213> ORGANISM: Artificial Sequence
<220> FEATURE:
<223> OTHER INFORMATION: Synthetic construct

<400> SEQUENCE: 145

Gly Thr Tyr Gly Leu Gly Asp Arg Ser Gly Tyr Ser Ser Pro Gly Ser
1               5                   10                  15

Pro Gly Thr Pro Gly Ser Arg Ser Arg Cys
            20                  25


<210> SEQ ID NO 146
<211> LENGTH: 26
<212> TYPE: PRT
<213> ORGANISM: Artificial Sequence
<220> FEATURE:
<223> OTHER INFORMATION: Synthetic construct

<400> SEQUENCE: 146

Gly Thr Tyr Gly Leu Gly Asp Ser Gly Tyr Ser Ser Pro Gly Ser Pro
1               5                   10                  15

Gly Thr Pro Gly Ser Arg Ser Arg Thr Cys
            20                  25


<210> SEQ ID NO 147
<211> LENGTH: 26
<212> TYPE: PRT
<213> ORGANISM: Artificial Sequence
<220> FEATURE:
<223> OTHER INFORMATION: Synthetic construct

<400> SEQUENCE: 147

Gly Thr Tyr Gly Leu Gly Asp Gly Tyr Ser Ser Pro Gly Ser Pro Gly
1               5                   10                  15

Thr Pro Gly Ser Arg Ser Arg Thr Pro Cys
            20                  25


<210> SEQ ID NO 148
<211> LENGTH: 27
<212> TYPE: PRT
<213> ORGANISM: Artificial Sequence
<220> FEATURE:
<223> OTHER INFORMATION: Synthetic construct

<400> SEQUENCE: 148

Gly Thr Tyr Gly Leu Gly Asp Arg Ser Gly Tyr Ser Ser Pro Gly Ser
1               5                   10                  15

Pro Gly Thr Pro Gly Ser Arg Ser Arg Thr Cys
            20                  25


<210> SEQ ID NO 149
<211> LENGTH: 27
<212> TYPE: PRT
<213> ORGANISM: Artificial Sequence
```

<220> FEATURE:
<223> OTHER INFORMATION: Synthetic construct

<400> SEQUENCE: 149

Gly Thr Tyr Gly Leu Gly Asp Ser Gly Tyr Ser Ser Pro Gly Ser Pro
1 5 10 15

Gly Thr Pro Gly Ser Arg Ser Arg Thr Pro Cys
20 25

<210> SEQ ID NO 150
<211> LENGTH: 28
<212> TYPE: PRT
<213> ORGANISM: Artificial Sequence
<220> FEATURE:
<223> OTHER INFORMATION: Synthetic construct

<400> SEQUENCE: 150

Gly Thr Tyr Gly Leu Gly Asp Arg Ser Gly Tyr Ser Ser Pro Gly Ser
1 5 10 15

Pro Gly Thr Pro Gly Ser Arg Ser Arg Thr Pro Cys
20 25

<210> SEQ ID NO 151
<211> LENGTH: 21
<212> TYPE: PRT
<213> ORGANISM: Artificial Sequence
<220> FEATURE:
<223> OTHER INFORMATION: Synthetic construct

<400> SEQUENCE: 151

His Ala Gly Thr Tyr Gly Leu Gly Ser Ser Pro Gly Ser Pro Gly Thr
1 5 10 15

Pro Gly Ser Arg Cys
20

<210> SEQ ID NO 152
<211> LENGTH: 22
<212> TYPE: PRT
<213> ORGANISM: Artificial Sequence
<220> FEATURE:
<223> OTHER INFORMATION: Synthetic construct

<400> SEQUENCE: 152

His Ala Gly Thr Tyr Gly Leu Gly Tyr Ser Ser Pro Gly Ser Pro Gly
1 5 10 15

Thr Pro Gly Ser Arg Cys
20

<210> SEQ ID NO 153
<211> LENGTH: 22
<212> TYPE: PRT
<213> ORGANISM: Artificial Sequence
<220> FEATURE:
<223> OTHER INFORMATION: Synthetic construct

<400> SEQUENCE: 153

His Ala Gly Thr Tyr Gly Leu Gly Ser Ser Pro Gly Ser Pro Gly Thr
1 5 10 15

Pro Gly Ser Arg Ser Cys
20

<210> SEQ ID NO 154
<211> LENGTH: 23
<212> TYPE: PRT

```
<213> ORGANISM: Artificial Sequence
<220> FEATURE:
<223> OTHER INFORMATION: Synthetic construct

<400> SEQUENCE: 154

His Ala Gly Thr Tyr Gly Leu Gly Gly Tyr Ser Ser Pro Gly Ser Pro
1               5                   10                  15

Gly Thr Pro Gly Ser Arg Cys
            20


<210> SEQ ID NO 155
<211> LENGTH: 23
<212> TYPE: PRT
<213> ORGANISM: Artificial Sequence
<220> FEATURE:
<223> OTHER INFORMATION: Synthetic construct

<400> SEQUENCE: 155

His Ala Gly Thr Tyr Gly Leu Gly Tyr Ser Ser Pro Gly Ser Pro Gly
1               5                   10                  15

Thr Pro Gly Ser Arg Ser Cys
            20


<210> SEQ ID NO 156
<211> LENGTH: 23
<212> TYPE: PRT
<213> ORGANISM: Artificial Sequence
<220> FEATURE:
<223> OTHER INFORMATION: Synthetic construct

<400> SEQUENCE: 156

His Ala Gly Thr Tyr Gly Leu Gly Ser Ser Pro Gly Ser Pro Gly Thr
1               5                   10                  15

Pro Gly Ser Arg Ser Arg Cys
            20


<210> SEQ ID NO 157
<211> LENGTH: 24
<212> TYPE: PRT
<213> ORGANISM: Artificial Sequence
<220> FEATURE:
<223> OTHER INFORMATION: Synthetic construct

<400> SEQUENCE: 157

His Ala Gly Thr Tyr Gly Leu Gly Ser Gly Tyr Ser Ser Pro Gly Ser
1               5                   10                  15

Pro Gly Thr Pro Gly Ser Arg Cys
            20


<210> SEQ ID NO 158
<211> LENGTH: 24
<212> TYPE: PRT
<213> ORGANISM: Artificial Sequence
<220> FEATURE:
<223> OTHER INFORMATION: Synthetic construct

<400> SEQUENCE: 158

His Ala Gly Thr Tyr Gly Leu Gly Gly Tyr Ser Ser Pro Gly Ser Pro
1               5                   10                  15

Gly Thr Pro Gly Ser Arg Ser Cys
            20


<210> SEQ ID NO 159
<211> LENGTH: 24
```

<212> TYPE: PRT
<213> ORGANISM: Artificial Sequence
<220> FEATURE:
<223> OTHER INFORMATION: Synthetic construct

<400> SEQUENCE: 159

His Ala Gly Thr Tyr Gly Leu Gly Tyr Ser Ser Pro Gly Ser Pro Gly
1               5                   10                  15

Thr Pro Gly Ser Arg Ser Arg Cys
            20

<210> SEQ ID NO 160
<211> LENGTH: 24
<212> TYPE: PRT
<213> ORGANISM: Artificial Sequence
<220> FEATURE:
<223> OTHER INFORMATION: Synthetic construct

<400> SEQUENCE: 160

His Ala Gly Thr Tyr Gly Leu Gly Ser Ser Pro Gly Ser Pro Gly Thr
1               5                   10                  15

Pro Gly Ser Arg Ser Arg Thr Cys
            20

<210> SEQ ID NO 161
<211> LENGTH: 25
<212> TYPE: PRT
<213> ORGANISM: Artificial Sequence
<220> FEATURE:
<223> OTHER INFORMATION: Synthetic construct

<400> SEQUENCE: 161

His Ala Gly Thr Tyr Gly Leu Gly Arg Ser Gly Tyr Ser Ser Pro Gly
1               5                   10                  15

Ser Pro Gly Thr Pro Gly Ser Arg Cys
            20                  25

<210> SEQ ID NO 162
<211> LENGTH: 25
<212> TYPE: PRT
<213> ORGANISM: Artificial Sequence
<220> FEATURE:
<223> OTHER INFORMATION: Synthetic construct

<400> SEQUENCE: 162

His Ala Gly Thr Tyr Gly Leu Gly Ser Gly Tyr Ser Ser Pro Gly Ser
1               5                   10                  15

Pro Gly Thr Pro Gly Ser Arg Ser Cys
            20                  25

<210> SEQ ID NO 163
<211> LENGTH: 25
<212> TYPE: PRT
<213> ORGANISM: Artificial Sequence
<220> FEATURE:
<223> OTHER INFORMATION: Synthetic construct

<400> SEQUENCE: 163

His Ala Gly Thr Tyr Gly Leu Gly Gly Tyr Ser Ser Pro Gly Ser Pro
1               5                   10                  15

Gly Thr Pro Gly Ser Arg Ser Arg Cys
            20                  25

<210> SEQ ID NO 164

<211> LENGTH: 25
<212> TYPE: PRT
<213> ORGANISM: Artificial Sequence
<220> FEATURE:
<223> OTHER INFORMATION: Synthetic construct

<400> SEQUENCE: 164

His Ala Gly Thr Tyr Gly Leu Gly Tyr Ser Ser Pro Gly Ser Pro Gly
1 5 10 15

Thr Pro Gly Ser Arg Ser Arg Thr Cys
20 25

<210> SEQ ID NO 165
<211> LENGTH: 25
<212> TYPE: PRT
<213> ORGANISM: Artificial Sequence
<220> FEATURE:
<223> OTHER INFORMATION: Synthetic construct

<400> SEQUENCE: 165

His Ala Gly Thr Tyr Gly Leu Gly Ser Ser Pro Gly Ser Pro Gly Thr
1 5 10 15

Pro Gly Ser Arg Ser Arg Thr Pro Cys
20 25

<210> SEQ ID NO 166
<211> LENGTH: 26
<212> TYPE: PRT
<213> ORGANISM: Artificial Sequence
<220> FEATURE:
<223> OTHER INFORMATION: Synthetic construct

<400> SEQUENCE: 166

His Ala Gly Thr Tyr Gly Leu Gly Arg Ser Gly Tyr Ser Ser Pro Gly
1 5 10 15

Ser Pro Gly Thr Pro Gly Ser Arg Ser Cys
20 25

<210> SEQ ID NO 167
<211> LENGTH: 26
<212> TYPE: PRT
<213> ORGANISM: Artificial Sequence
<220> FEATURE:
<223> OTHER INFORMATION: Synthetic construct

<400> SEQUENCE: 167

His Ala Gly Thr Tyr Gly Leu Gly Ser Gly Tyr Ser Ser Pro Gly Ser
1 5 10 15

Pro Gly Thr Pro Gly Ser Arg Ser Arg Cys
20 25

<210> SEQ ID NO 168
<211> LENGTH: 26
<212> TYPE: PRT
<213> ORGANISM: Artificial Sequence
<220> FEATURE:
<223> OTHER INFORMATION: Synthetic construct

<400> SEQUENCE: 168

His Ala Gly Thr Tyr Gly Leu Gly Gly Tyr Ser Ser Pro Gly Ser Pro
1 5 10 15

Gly Thr Pro Gly Ser Arg Ser Arg Thr Cys
20 25

<210> SEQ ID NO 169
<211> LENGTH: 26
<212> TYPE: PRT
<213> ORGANISM: Artificial Sequence
<220> FEATURE:
<223> OTHER INFORMATION: Synthetic construct

<400> SEQUENCE: 169

His Ala Gly Thr Tyr Gly Leu Gly Tyr Ser Ser Pro Gly Ser Pro Gly
1 5 10 15

Thr Pro Gly Ser Arg Ser Arg Thr Pro Cys
20 25

<210> SEQ ID NO 170
<211> LENGTH: 27
<212> TYPE: PRT
<213> ORGANISM: Artificial Sequence
<220> FEATURE:
<223> OTHER INFORMATION: Synthetic construct

<400> SEQUENCE: 170

His Ala Gly Thr Tyr Gly Leu Gly Arg Ser Gly Tyr Ser Ser Pro Gly
1 5 10 15

Ser Pro Gly Thr Pro Gly Ser Arg Ser Arg Cys
20 25

<210> SEQ ID NO 171
<211> LENGTH: 27
<212> TYPE: PRT
<213> ORGANISM: Artificial Sequence
<220> FEATURE:
<223> OTHER INFORMATION: Synthetic construct

<400> SEQUENCE: 171

His Ala Gly Thr Tyr Gly Leu Gly Ser Gly Tyr Ser Ser Pro Gly Ser
1 5 10 15

Pro Gly Thr Pro Gly Ser Arg Ser Arg Thr Cys
20 25

<210> SEQ ID NO 172
<211> LENGTH: 27
<212> TYPE: PRT
<213> ORGANISM: Artificial Sequence
<220> FEATURE:
<223> OTHER INFORMATION: Synthetic construct

<400> SEQUENCE: 172

His Ala Gly Thr Tyr Gly Leu Gly Gly Tyr Ser Ser Pro Gly Ser Pro
1 5 10 15

Gly Thr Pro Gly Ser Arg Ser Arg Thr Pro Cys
20 25

<210> SEQ ID NO 173
<211> LENGTH: 28
<212> TYPE: PRT
<213> ORGANISM: Artificial Sequence
<220> FEATURE:
<223> OTHER INFORMATION: Synthetic construct

<400> SEQUENCE: 173

His Ala Gly Thr Tyr Gly Leu Gly Arg Ser Gly Tyr Ser Ser Pro Gly
1 5 10 15

Ser Pro Gly Thr Pro Gly Ser Arg Ser Arg Thr Cys
20 25

<210> SEQ ID NO 174
<211> LENGTH: 28
<212> TYPE: PRT
<213> ORGANISM: Artificial Sequence
<220> FEATURE:
<223> OTHER INFORMATION: Synthetic construct

<400> SEQUENCE: 174

His Ala Gly Thr Tyr Gly Leu Gly Ser Gly Tyr Ser Ser Pro Gly Ser
1 5 10 15

Pro Gly Thr Pro Gly Ser Arg Ser Arg Thr Pro Cys
20 25

<210> SEQ ID NO 175
<211> LENGTH: 29
<212> TYPE: PRT
<213> ORGANISM: Artificial Sequence
<220> FEATURE:
<223> OTHER INFORMATION: Synthetic construct

<400> SEQUENCE: 175

His Ala Gly Thr Tyr Gly Leu Gly Arg Ser Gly Tyr Ser Ser Pro Gly
1 5 10 15

Ser Pro Gly Thr Pro Gly Ser Arg Ser Arg Thr Pro Cys
20 25

<210> SEQ ID NO 176
<211> LENGTH: 21
<212> TYPE: PRT
<213> ORGANISM: Artificial Sequence
<220> FEATURE:
<223> OTHER INFORMATION: Synthetic construct

<400> SEQUENCE: 176

Ala Gly Thr Tyr Gly Leu Gly Asp Ser Ser Pro Gly Ser Pro Gly Thr
1 5 10 15

Pro Gly Ser Arg Cys
20

<210> SEQ ID NO 177
<211> LENGTH: 22
<212> TYPE: PRT
<213> ORGANISM: Artificial Sequence
<220> FEATURE:
<223> OTHER INFORMATION: Synthetic construct

<400> SEQUENCE: 177

Ala Gly Thr Tyr Gly Leu Gly Asp Tyr Ser Ser Pro Gly Ser Pro Gly
1 5 10 15

Thr Pro Gly Ser Arg Cys
20

<210> SEQ ID NO 178
<211> LENGTH: 22
<212> TYPE: PRT
<213> ORGANISM: Artificial Sequence
<220> FEATURE:
<223> OTHER INFORMATION: Synthetic construct

<400> SEQUENCE: 178

Ala Gly Thr Tyr Gly Leu Gly Asp Ser Ser Pro Gly Ser Pro Gly Thr
1 5 10 15

Pro Gly Ser Arg Ser Cys
20

<210> SEQ ID NO 179
<211> LENGTH: 23
<212> TYPE: PRT
<213> ORGANISM: Artificial Sequence
<220> FEATURE:
<223> OTHER INFORMATION: Synthetic construct

<400> SEQUENCE: 179

```
Ala Gly Thr Tyr Gly Leu Gly Asp Gly Tyr Ser Ser Pro Gly Ser Pro
1               5                   10                  15

Gly Thr Pro Gly Ser Arg Cys
            20
```

<210> SEQ ID NO 180
<211> LENGTH: 23
<212> TYPE: PRT
<213> ORGANISM: Artificial Sequence
<220> FEATURE:
<223> OTHER INFORMATION: Synthetic construct

<400> SEQUENCE: 180

```
Ala Gly Thr Tyr Gly Leu Gly Asp Tyr Ser Ser Pro Gly Ser Pro Gly
1               5                   10                  15

Thr Pro Gly Ser Arg Ser Cys
            20
```

<210> SEQ ID NO 181
<211> LENGTH: 23
<212> TYPE: PRT
<213> ORGANISM: Artificial Sequence
<220> FEATURE:
<223> OTHER INFORMATION: Synthetic construct

<400> SEQUENCE: 181

```
Ala Gly Thr Tyr Gly Leu Gly Asp Ser Ser Pro Gly Ser Pro Gly Thr
1               5                   10                  15

Pro Gly Ser Arg Ser Arg Cys
            20
```

<210> SEQ ID NO 182
<211> LENGTH: 24
<212> TYPE: PRT
<213> ORGANISM: Artificial Sequence
<220> FEATURE:
<223> OTHER INFORMATION: Synthetic construct

<400> SEQUENCE: 182

```
Ala Gly Thr Tyr Gly Leu Gly Asp Ser Gly Tyr Ser Ser Pro Gly Ser
1               5                   10                  15

Pro Gly Thr Pro Gly Ser Arg Cys
            20
```

<210> SEQ ID NO 183
<211> LENGTH: 24
<212> TYPE: PRT
<213> ORGANISM: Artificial Sequence
<220> FEATURE:
<223> OTHER INFORMATION: Synthetic construct

<400> SEQUENCE: 183

```
Ala Gly Thr Tyr Gly Leu Gly Asp Gly Tyr Ser Ser Pro Gly Ser Pro
1               5                   10                  15

Gly Thr Pro Gly Ser Arg Ser Cys
```

20

<210> SEQ ID NO 184
<211> LENGTH: 24
<212> TYPE: PRT
<213> ORGANISM: Artificial Sequence
<220> FEATURE:
<223> OTHER INFORMATION: Synthetic construct

<400> SEQUENCE: 184

Ala Gly Thr Tyr Gly Leu Gly Asp Tyr Ser Ser Pro Gly Ser Pro Gly
1 5 10 15

Thr Pro Gly Ser Arg Ser Arg Cys
20

<210> SEQ ID NO 185
<211> LENGTH: 24
<212> TYPE: PRT
<213> ORGANISM: Artificial Sequence
<220> FEATURE:
<223> OTHER INFORMATION: Synthetic construct

<400> SEQUENCE: 185

Ala Gly Thr Tyr Gly Leu Gly Asp Ser Ser Pro Gly Ser Pro Gly Thr
1 5 10 15

Pro Gly Ser Arg Ser Arg Thr Cys
20

<210> SEQ ID NO 186
<211> LENGTH: 25
<212> TYPE: PRT
<213> ORGANISM: Artificial Sequence
<220> FEATURE:
<223> OTHER INFORMATION: Synthetic construct

<400> SEQUENCE: 186

Ala Gly Thr Tyr Gly Leu Gly Asp Arg Ser Gly Tyr Ser Ser Pro Gly
1 5 10 15

Ser Pro Gly Thr Pro Gly Ser Arg Cys
20 25

<210> SEQ ID NO 187
<211> LENGTH: 25
<212> TYPE: PRT
<213> ORGANISM: Artificial Sequence
<220> FEATURE:
<223> OTHER INFORMATION: Synthetic construct

<400> SEQUENCE: 187

Ala Gly Thr Tyr Gly Leu Gly Asp Ser Gly Tyr Ser Ser Pro Gly Ser
1 5 10 15

Pro Gly Thr Pro Gly Ser Arg Ser Cys
20 25

<210> SEQ ID NO 188
<211> LENGTH: 25
<212> TYPE: PRT
<213> ORGANISM: Artificial Sequence
<220> FEATURE:
<223> OTHER INFORMATION: Synthetic construct

<400> SEQUENCE: 188

Ala Gly Thr Tyr Gly Leu Gly Asp Gly Tyr Ser Ser Pro Gly Ser Pro
1 5 10 15

Gly Thr Pro Gly Ser Arg Ser Arg Cys
20 25

<210> SEQ ID NO 189
<211> LENGTH: 25
<212> TYPE: PRT
<213> ORGANISM: Artificial Sequence
<220> FEATURE:
<223> OTHER INFORMATION: Synthetic construct

<400> SEQUENCE: 189

Ala Gly Thr Tyr Gly Leu Gly Asp Tyr Ser Ser Pro Gly Ser Pro Gly
1 5 10 15

Thr Pro Gly Ser Arg Ser Arg Thr Cys
20 25

<210> SEQ ID NO 190
<211> LENGTH: 25
<212> TYPE: PRT
<213> ORGANISM: Artificial Sequence
<220> FEATURE:
<223> OTHER INFORMATION: Synthetic construct

<400> SEQUENCE: 190

Ala Gly Thr Tyr Gly Leu Gly Asp Ser Ser Pro Gly Ser Pro Gly Thr
1 5 10 15

Pro Gly Ser Arg Ser Arg Thr Pro Cys
20 25

<210> SEQ ID NO 191
<211> LENGTH: 26
<212> TYPE: PRT
<213> ORGANISM: Artificial Sequence
<220> FEATURE:
<223> OTHER INFORMATION: Synthetic construct

<400> SEQUENCE: 191

Ala Gly Thr Tyr Gly Leu Gly Asp Arg Ser Gly Tyr Ser Ser Pro Gly
1 5 10 15

Ser Pro Gly Thr Pro Gly Ser Arg Ser Cys
20 25

<210> SEQ ID NO 192
<211> LENGTH: 26
<212> TYPE: PRT
<213> ORGANISM: Artificial Sequence
<220> FEATURE:
<223> OTHER INFORMATION: Synthetic construct

<400> SEQUENCE: 192

Ala Gly Thr Tyr Gly Leu Gly Asp Ser Gly Tyr Ser Ser Pro Gly Ser
1 5 10 15

Pro Gly Thr Pro Gly Ser Arg Ser Arg Cys
20 25

<210> SEQ ID NO 193
<211> LENGTH: 26
<212> TYPE: PRT
<213> ORGANISM: Artificial Sequence
<220> FEATURE:
<223> OTHER INFORMATION: Synthetic construct

<400> SEQUENCE: 193

Ala Gly Thr Tyr Gly Leu Gly Asp Gly Tyr Ser Ser Pro Gly Ser Pro
1 5 10 15

Gly Thr Pro Gly Ser Arg Ser Arg Thr Cys
20 25

<210> SEQ ID NO 194
<211> LENGTH: 26
<212> TYPE: PRT
<213> ORGANISM: Artificial Sequence
<220> FEATURE:
<223> OTHER INFORMATION: Synthetic construct

<400> SEQUENCE: 194

Ala Gly Thr Tyr Gly Leu Gly Asp Tyr Ser Ser Pro Gly Ser Pro Gly
1 5 10 15

Thr Pro Gly Ser Arg Ser Arg Thr Pro Cys
20 25

<210> SEQ ID NO 195
<211> LENGTH: 27
<212> TYPE: PRT
<213> ORGANISM: Artificial Sequence
<220> FEATURE:
<223> OTHER INFORMATION: Synthetic construct

<400> SEQUENCE: 195

Ala Gly Thr Tyr Gly Leu Gly Asp Arg Ser Gly Tyr Ser Ser Pro Gly
1 5 10 15

Ser Pro Gly Thr Pro Gly Ser Arg Ser Arg Cys
20 25

<210> SEQ ID NO 196
<211> LENGTH: 27
<212> TYPE: PRT
<213> ORGANISM: Artificial Sequence
<220> FEATURE:
<223> OTHER INFORMATION: Synthetic construct

<400> SEQUENCE: 196

Ala Gly Thr Tyr Gly Leu Gly Asp Ser Gly Tyr Ser Ser Pro Gly Ser
1 5 10 15

Pro Gly Thr Pro Gly Ser Arg Ser Arg Thr Cys
20 25

<210> SEQ ID NO 197
<211> LENGTH: 27
<212> TYPE: PRT
<213> ORGANISM: Artificial Sequence
<220> FEATURE:
<223> OTHER INFORMATION: Synthetic construct

<400> SEQUENCE: 197

Ala Gly Thr Tyr Gly Leu Gly Asp Gly Tyr Ser Ser Pro Gly Ser Pro
1 5 10 15

Gly Thr Pro Gly Ser Arg Ser Arg Thr Pro Cys
20 25

<210> SEQ ID NO 198
<211> LENGTH: 28
<212> TYPE: PRT
<213> ORGANISM: Artificial Sequence
<220> FEATURE:
<223> OTHER INFORMATION: Synthetic construct

<400> SEQUENCE: 198

Ala Gly Thr Tyr Gly Leu Gly Asp Arg Ser Gly Tyr Ser Ser Pro Gly 1 5 10 15

Ser Pro Gly Thr Pro Gly Ser Arg Ser Arg Thr Cys
20 25

<210> SEQ ID NO 199
<211> LENGTH: 28
<212> TYPE: PRT
<213> ORGANISM: Artificial Sequence
<220> FEATURE:
<223> OTHER INFORMATION: Synthetic construct

<400> SEQUENCE: 199

Ala Gly Thr Tyr Gly Leu Gly Asp Ser Gly Tyr Ser Ser Pro Gly Ser
1 5 10 15

Pro Gly Thr Pro Gly Ser Arg Ser Arg Thr Pro Cys
20 25

<210> SEQ ID NO 200
<211> LENGTH: 29
<212> TYPE: PRT
<213> ORGANISM: Artificial Sequence
<220> FEATURE:
<223> OTHER INFORMATION: Synthetic construct

<400> SEQUENCE: 200

Ala Gly Thr Tyr Gly Leu Gly Asp Arg Ser Gly Tyr Ser Ser Pro Gly
1 5 10 15

Ser Pro Gly Thr Pro Gly Ser Arg Ser Arg Thr Pro Cys
20 25

<210> SEQ ID NO 201
<211> LENGTH: 22
<212> TYPE: PRT
<213> ORGANISM: Artificial Sequence
<220> FEATURE:
<223> OTHER INFORMATION: Synthetic construct

<400> SEQUENCE: 201

His Ala Gly Thr Tyr Gly Leu Gly Asp Ser Ser Pro Gly Ser Pro Gly
1 5 10 15

Thr Pro Gly Ser Arg Cys
20

<210> SEQ ID NO 202
<211> LENGTH: 23
<212> TYPE: PRT
<213> ORGANISM: Artificial Sequence
<220> FEATURE:
<223> OTHER INFORMATION: Synthetic construct

<400> SEQUENCE: 202

His Ala Gly Thr Tyr Gly Leu Gly Asp Tyr Ser Ser Pro Gly Ser Pro
1 5 10 15

Gly Thr Pro Gly Ser Arg Cys
20

<210> SEQ ID NO 203
<211> LENGTH: 23
<212> TYPE: PRT
<213> ORGANISM: Artificial Sequence
<220> FEATURE:
<223> OTHER INFORMATION: Synthetic construct

<400> SEQUENCE: 203

His Ala Gly Thr Tyr Gly Leu Gly Asp Ser Ser Pro Gly Ser Pro Gly
1 5 10 15

Thr Pro Gly Ser Arg Ser Cys
20

<210> SEQ ID NO 204
<211> LENGTH: 24
<212> TYPE: PRT
<213> ORGANISM: Artificial Sequence
<220> FEATURE:
<223> OTHER INFORMATION: Synthetic construct

<400> SEQUENCE: 204

His Ala Gly Thr Tyr Gly Leu Gly Asp Gly Tyr Ser Ser Pro Gly Ser
1 5 10 15

Pro Gly Thr Pro Gly Ser Arg Cys
20

<210> SEQ ID NO 205
<211> LENGTH: 24
<212> TYPE: PRT
<213> ORGANISM: Artificial Sequence
<220> FEATURE:
<223> OTHER INFORMATION: Synthetic construct

<400> SEQUENCE: 205

His Ala Gly Thr Tyr Gly Leu Gly Asp Tyr Ser Ser Pro Gly Ser Pro
1 5 10 15

Gly Thr Pro Gly Ser Arg Ser Cys
20

<210> SEQ ID NO 206
<211> LENGTH: 24
<212> TYPE: PRT
<213> ORGANISM: Artificial Sequence
<220> FEATURE:
<223> OTHER INFORMATION: Synthetic construct

<400> SEQUENCE: 206

His Ala Gly Thr Tyr Gly Leu Gly Asp Ser Ser Pro Gly Ser Pro Gly
1 5 10 15

Thr Pro Gly Ser Arg Ser Arg Cys
20

<210> SEQ ID NO 207
<211> LENGTH: 25
<212> TYPE: PRT
<213> ORGANISM: Artificial Sequence
<220> FEATURE:
<223> OTHER INFORMATION: Synthetic construct

<400> SEQUENCE: 207

His Ala Gly Thr Tyr Gly Leu Gly Asp Ser Gly Tyr Ser Ser Pro Gly
1 5 10 15

Ser Pro Gly Thr Pro Gly Ser Arg Cys
20 25

<210> SEQ ID NO 208
<211> LENGTH: 25
<212> TYPE: PRT
<213> ORGANISM: Artificial Sequence
<220> FEATURE:
<223> OTHER INFORMATION: Synthetic construct

<400> SEQUENCE: 208

```
His Ala Gly Thr Tyr Gly Leu Gly Asp Gly Tyr Ser Ser Pro Gly Ser
1               5                   10                  15

Pro Gly Thr Pro Gly Ser Arg Ser Cys
            20                  25


<210> SEQ ID NO 209
<211> LENGTH: 25
<212> TYPE: PRT
<213> ORGANISM: Artificial Sequence
<220> FEATURE:
<223> OTHER INFORMATION: Synthetic construct

<400> SEQUENCE: 209

His Ala Gly Thr Tyr Gly Leu Gly Asp Tyr Ser Ser Pro Gly Ser Pro
1               5                   10                  15

Gly Thr Pro Gly Ser Arg Ser Arg Cys
            20                  25


<210> SEQ ID NO 210
<211> LENGTH: 25
<212> TYPE: PRT
<213> ORGANISM: Artificial Sequence
<220> FEATURE:
<223> OTHER INFORMATION: Synthetic construct

<400> SEQUENCE: 210

His Ala Gly Thr Tyr Gly Leu Gly Asp Ser Ser Pro Gly Ser Pro Gly
1               5                   10                  15

Thr Pro Gly Ser Arg Ser Arg Thr Cys
            20                  25


<210> SEQ ID NO 211
<211> LENGTH: 26
<212> TYPE: PRT
<213> ORGANISM: Artificial Sequence
<220> FEATURE:
<223> OTHER INFORMATION: Synthetic construct

<400> SEQUENCE: 211

His Ala Gly Thr Tyr Gly Leu Gly Asp Arg Ser Gly Tyr Ser Ser Pro
1               5                   10                  15

Gly Ser Pro Gly Thr Pro Gly Ser Arg Cys
            20                  25


<210> SEQ ID NO 212
<211> LENGTH: 26
<212> TYPE: PRT
<213> ORGANISM: Artificial Sequence
<220> FEATURE:
<223> OTHER INFORMATION: Synthetic construct

<400> SEQUENCE: 212

His Ala Gly Thr Tyr Gly Leu Gly Asp Ser Gly Tyr Ser Ser Pro Gly
1               5                   10                  15

Ser Pro Gly Thr Pro Gly Ser Arg Ser Cys
            20                  25


<210> SEQ ID NO 213
<211> LENGTH: 26
<212> TYPE: PRT
<213> ORGANISM: Artificial Sequence
<220> FEATURE:
<223> OTHER INFORMATION: Synthetic construct
```

<400> SEQUENCE: 213

His Ala Gly Thr Tyr Gly Leu Gly Asp Gly Tyr Ser Ser Pro Gly Ser
1               5                   10                  15

Pro Gly Thr Pro Gly Ser Arg Ser Arg Cys
            20                  25

<210> SEQ ID NO 214
<211> LENGTH: 26
<212> TYPE: PRT
<213> ORGANISM: Artificial Sequence
<220> FEATURE:
<223> OTHER INFORMATION: Synthetic construct

<400> SEQUENCE: 214

His Ala Gly Thr Tyr Gly Leu Gly Asp Tyr Ser Ser Pro Gly Ser Pro
1               5                   10                  15

Gly Thr Pro Gly Ser Arg Ser Arg Thr Cys
            20                  25

<210> SEQ ID NO 215
<211> LENGTH: 26
<212> TYPE: PRT
<213> ORGANISM: Artificial Sequence
<220> FEATURE:
<223> OTHER INFORMATION: Synthetic construct

<400> SEQUENCE: 215

His Ala Gly Thr Tyr Gly Leu Gly Asp Ser Ser Pro Gly Ser Pro Gly
1               5                   10                  15

Thr Pro Gly Ser Arg Ser Arg Thr Pro Cys
            20                  25

<210> SEQ ID NO 216
<211> LENGTH: 27
<212> TYPE: PRT
<213> ORGANISM: Artificial Sequence
<220> FEATURE:
<223> OTHER INFORMATION: Synthetic construct

<400> SEQUENCE: 216

His Ala Gly Thr Tyr Gly Leu Gly Asp Arg Ser Gly Tyr Ser Ser Pro
1               5                   10                  15

Gly Ser Pro Gly Thr Pro Gly Ser Arg Ser Cys
            20                  25

<210> SEQ ID NO 217
<211> LENGTH: 27
<212> TYPE: PRT
<213> ORGANISM: Artificial Sequence
<220> FEATURE:
<223> OTHER INFORMATION: Synthetic construct

<400> SEQUENCE: 217

His Ala Gly Thr Tyr Gly Leu Gly Asp Ser Gly Tyr Ser Ser Pro Gly
1               5                   10                  15

Ser Pro Gly Thr Pro Gly Ser Arg Ser Arg Cys
            20                  25

<210> SEQ ID NO 218
<211> LENGTH: 27
<212> TYPE: PRT
<213> ORGANISM: Artificial Sequence
<220> FEATURE:
<223> OTHER INFORMATION: Synthetic construct

<400> SEQUENCE: 218

His Ala Gly Thr Tyr Gly Leu Gly Asp Gly Tyr Ser Ser Pro Gly Ser
1 5 10 15

Pro Gly Thr Pro Gly Ser Arg Ser Arg Thr Cys
20 25

<210> SEQ ID NO 219
<211> LENGTH: 27
<212> TYPE: PRT
<213> ORGANISM: Artificial Sequence
<220> FEATURE:
<223> OTHER INFORMATION: Synthetic construct

<400> SEQUENCE: 219

His Ala Gly Thr Tyr Gly Leu Gly Asp Tyr Ser Ser Pro Gly Ser Pro
1 5 10 15

Gly Thr Pro Gly Ser Arg Ser Arg Thr Pro Cys
20 25

<210> SEQ ID NO 220
<211> LENGTH: 28
<212> TYPE: PRT
<213> ORGANISM: Artificial Sequence
<220> FEATURE:
<223> OTHER INFORMATION: Synthetic construct

<400> SEQUENCE: 220

His Ala Gly Thr Tyr Gly Leu Gly Asp Arg Ser Gly Tyr Ser Ser Pro
1 5 10 15

Gly Ser Pro Gly Thr Pro Gly Ser Arg Ser Arg Cys
20 25

<210> SEQ ID NO 221
<211> LENGTH: 28
<212> TYPE: PRT
<213> ORGANISM: Artificial Sequence
<220> FEATURE:
<223> OTHER INFORMATION: Synthetic construct

<400> SEQUENCE: 221

His Ala Gly Thr Tyr Gly Leu Gly Asp Ser Gly Tyr Ser Ser Pro Gly
1 5 10 15

Ser Pro Gly Thr Pro Gly Ser Arg Ser Arg Thr Cys
20 25

<210> SEQ ID NO 222
<211> LENGTH: 28
<212> TYPE: PRT
<213> ORGANISM: Artificial Sequence
<220> FEATURE:
<223> OTHER INFORMATION: Synthetic construct

<400> SEQUENCE: 222

His Ala Gly Thr Tyr Gly Leu Gly Asp Gly Tyr Ser Ser Pro Gly Ser
1 5 10 15

Pro Gly Thr Pro Gly Ser Arg Ser Arg Thr Pro Cys
20 25

<210> SEQ ID NO 223
<211> LENGTH: 29
<212> TYPE: PRT
<213> ORGANISM: Artificial Sequence
<220> FEATURE:

<223> OTHER INFORMATION: Synthetic construct

<400> SEQUENCE: 223

His Ala Gly Thr Tyr Gly Leu Gly Asp Arg Ser Gly Tyr Ser Ser Pro
1 5 10 15

Gly Ser Pro Gly Thr Pro Gly Ser Arg Ser Arg Thr Cys
20 25

<210> SEQ ID NO 224
<211> LENGTH: 29
<212> TYPE: PRT
<213> ORGANISM: Artificial Sequence
<220> FEATURE:
<223> OTHER INFORMATION: Synthetic construct

<400> SEQUENCE: 224

His Ala Gly Thr Tyr Gly Leu Gly Asp Ser Gly Tyr Ser Ser Pro Gly
1 5 10 15

Ser Pro Gly Thr Pro Gly Ser Arg Ser Arg Thr Pro Cys
20 25

<210> SEQ ID NO 225
<211> LENGTH: 30
<212> TYPE: PRT
<213> ORGANISM: Artificial Sequence
<220> FEATURE:
<223> OTHER INFORMATION: Synthetic construct

<400> SEQUENCE: 225

His Ala Gly Thr Tyr Gly Leu Gly Asp Arg Ser Gly Tyr Ser Ser Pro
1 5 10 15

Gly Ser Pro Gly Thr Pro Gly Ser Arg Ser Arg Thr Pro Cys
20 25 30

<210> SEQ ID NO 226
<211> LENGTH: 13
<212> TYPE: PRT
<213> ORGANISM: Artificial Sequence
<220> FEATURE:
<223> OTHER INFORMATION: Synthetic construct

<400> SEQUENCE: 226

Gly Thr Tyr Gly Leu Ser Arg Thr Pro Ser Leu Pro Cys
1 5 10

<210> SEQ ID NO 227
<211> LENGTH: 14
<212> TYPE: PRT
<213> ORGANISM: Artificial Sequence
<220> FEATURE:
<223> OTHER INFORMATION: Synthetic construct

<400> SEQUENCE: 227

Gly Thr Tyr Gly Leu Arg Ser Arg Thr Pro Ser Leu Pro Cys
1 5 10

<210> SEQ ID NO 228
<211> LENGTH: 14
<212> TYPE: PRT
<213> ORGANISM: Artificial Sequence
<220> FEATURE:
<223> OTHER INFORMATION: Synthetic construct

<400> SEQUENCE: 228

Gly Thr Tyr Gly Leu Ser Arg Thr Pro Ser Leu Pro Thr Cys

-continued 1 5 10

<210> SEQ ID NO 229
<211> LENGTH: 15
<212> TYPE: PRT
<213> ORGANISM: Artificial Sequence
<220> FEATURE:
<223> OTHER INFORMATION: Synthetic construct

<400> SEQUENCE: 229

Gly Thr Tyr Gly Leu Ser Arg Ser Arg Thr Pro Ser Leu Pro Cys
1 5 10 15

<210> SEQ ID NO 230
<211> LENGTH: 15
<212> TYPE: PRT
<213> ORGANISM: Artificial Sequence
<220> FEATURE:
<223> OTHER INFORMATION: Synthetic construct

<400> SEQUENCE: 230

Gly Thr Tyr Gly Leu Arg Ser Arg Thr Pro Ser Leu Pro Thr Cys
1 5 10 15

<210> SEQ ID NO 231
<211> LENGTH: 15
<212> TYPE: PRT
<213> ORGANISM: Artificial Sequence
<220> FEATURE:
<223> OTHER INFORMATION: Synthetic construct

<400> SEQUENCE: 231

Gly Thr Tyr Gly Leu Ser Arg Thr Pro Ser Leu Pro Thr Pro Cys
1 5 10 15

<210> SEQ ID NO 232
<211> LENGTH: 16
<212> TYPE: PRT
<213> ORGANISM: Artificial Sequence
<220> FEATURE:
<223> OTHER INFORMATION: Synthetic construct

<400> SEQUENCE: 232

Gly Thr Tyr Gly Leu Ser Arg Ser Arg Thr Pro Ser Leu Pro Thr Cys
1 5 10 15

<210> SEQ ID NO 233
<211> LENGTH: 16
<212> TYPE: PRT
<213> ORGANISM: Artificial Sequence
<220> FEATURE:
<223> OTHER INFORMATION: Synthetic construct

<400> SEQUENCE: 233

Gly Thr Tyr Gly Leu Arg Ser Arg Thr Pro Ser Leu Pro Thr Pro Cys
1 5 10 15

<210> SEQ ID NO 234
<211> LENGTH: 17
<212> TYPE: PRT
<213> ORGANISM: Artificial Sequence
<220> FEATURE:
<223> OTHER INFORMATION: Synthetic construct

<400> SEQUENCE: 234

Gly Thr Tyr Gly Leu Ser Arg Ser Arg Thr Pro Ser Leu Pro Thr Pro
1 5 10 15

Cys

<210> SEQ ID NO 235
<211> LENGTH: 14
<212> TYPE: PRT
<213> ORGANISM: Artificial Sequence
<220> FEATURE:
<223> OTHER INFORMATION: Synthetic construct

<400> SEQUENCE: 235

Ala Gly Thr Tyr Gly Leu Ser Arg Thr Pro Ser Leu Pro Cys
1 5 10

<210> SEQ ID NO 236
<211> LENGTH: 15
<212> TYPE: PRT
<213> ORGANISM: Artificial Sequence
<220> FEATURE:
<223> OTHER INFORMATION: Synthetic construct

<400> SEQUENCE: 236

Ala Gly Thr Tyr Gly Leu Arg Ser Arg Thr Pro Ser Leu Pro Cys
1 5 10 15

<210> SEQ ID NO 237
<211> LENGTH: 15
<212> TYPE: PRT
<213> ORGANISM: Artificial Sequence
<220> FEATURE:
<223> OTHER INFORMATION: Synthetic construct

<400> SEQUENCE: 237

Ala Gly Thr Tyr Gly Leu Ser Arg Thr Pro Ser Leu Pro Thr Cys
1 5 10 15

<210> SEQ ID NO 238
<211> LENGTH: 16
<212> TYPE: PRT
<213> ORGANISM: Artificial Sequence
<220> FEATURE:
<223> OTHER INFORMATION: Synthetic construct

<400> SEQUENCE: 238

Ala Gly Thr Tyr Gly Leu Ser Arg Ser Arg Thr Pro Ser Leu Pro Cys
1 5 10 15

<210> SEQ ID NO 239
<211> LENGTH: 16
<212> TYPE: PRT
<213> ORGANISM: Artificial Sequence
<220> FEATURE:
<223> OTHER INFORMATION: Synthetic construct

<400> SEQUENCE: 239

Ala Gly Thr Tyr Gly Leu Arg Ser Arg Thr Pro Ser Leu Pro Thr Cys
1 5 10 15

<210> SEQ ID NO 240
<211> LENGTH: 16
<212> TYPE: PRT
<213> ORGANISM: Artificial Sequence
<220> FEATURE:
<223> OTHER INFORMATION: Synthetic construct

<400> SEQUENCE: 240

Ala Gly Thr Tyr Gly Leu Ser Arg Thr Pro Ser Leu Pro Thr Pro Cys 1 5 10 15

<210> SEQ ID NO 241
<211> LENGTH: 17
<212> TYPE: PRT
<213> ORGANISM: Artificial Sequence
<220> FEATURE:
<223> OTHER INFORMATION: Synthetic construct

<400> SEQUENCE: 241

Ala Gly Thr Tyr Gly Leu Ser Arg Ser Arg Thr Pro Ser Leu Pro Thr
1 5 10 15

Cys

<210> SEQ ID NO 242
<211> LENGTH: 17
<212> TYPE: PRT
<213> ORGANISM: Artificial Sequence
<220> FEATURE:
<223> OTHER INFORMATION: Synthetic construct

<400> SEQUENCE: 242

Ala Gly Thr Tyr Gly Leu Arg Ser Arg Thr Pro Ser Leu Pro Thr Pro
1 5 10 15

Cys

<210> SEQ ID NO 243
<211> LENGTH: 18
<212> TYPE: PRT
<213> ORGANISM: Artificial Sequence
<220> FEATURE:
<223> OTHER INFORMATION: Synthetic construct

<400> SEQUENCE: 243

Ala Gly Thr Tyr Gly Leu Ser Arg Ser Arg Thr Pro Ser Leu Pro Thr
1 5 10 15

Pro Cys

<210> SEQ ID NO 244
<211> LENGTH: 14
<212> TYPE: PRT
<213> ORGANISM: Artificial Sequence
<220> FEATURE:
<223> OTHER INFORMATION: Synthetic construct

<400> SEQUENCE: 244

Gly Thr Tyr Gly Leu Gly Ser Arg Thr Pro Ser Leu Pro Cys
1 5 10

<210> SEQ ID NO 245
<211> LENGTH: 15
<212> TYPE: PRT
<213> ORGANISM: Artificial Sequence
<220> FEATURE:
<223> OTHER INFORMATION: Synthetic construct

<400> SEQUENCE: 245

Gly Thr Tyr Gly Leu Gly Arg Ser Arg Thr Pro Ser Leu Pro Cys
1 5 10 15

<210> SEQ ID NO 246
<211> LENGTH: 15
<212> TYPE: PRT
<213> ORGANISM: Artificial Sequence
<220> FEATURE:

<223> OTHER INFORMATION: Synthetic construct

<400> SEQUENCE: 246

Gly Thr Tyr Gly Leu Gly Ser Arg Thr Pro Ser Leu Pro Thr Cys
1 5 10 15

<210> SEQ ID NO 247
<211> LENGTH: 16
<212> TYPE: PRT
<213> ORGANISM: Artificial Sequence
<220> FEATURE:
<223> OTHER INFORMATION: Synthetic construct

<400> SEQUENCE: 247

Gly Thr Tyr Gly Leu Gly Ser Arg Ser Arg Thr Pro Ser Leu Pro Cys
1 5 10 15

<210> SEQ ID NO 248
<211> LENGTH: 16
<212> TYPE: PRT
<213> ORGANISM: Artificial Sequence
<220> FEATURE:
<223> OTHER INFORMATION: Synthetic construct

<400> SEQUENCE: 248

Gly Thr Tyr Gly Leu Gly Arg Ser Arg Thr Pro Ser Leu Pro Thr Cys
1 5 10 15

<210> SEQ ID NO 249
<211> LENGTH: 16
<212> TYPE: PRT
<213> ORGANISM: Artificial Sequence
<220> FEATURE:
<223> OTHER INFORMATION: Synthetic construct

<400> SEQUENCE: 249

Gly Thr Tyr Gly Leu Gly Ser Arg Thr Pro Ser Leu Pro Thr Pro Cys
1 5 10 15

<210> SEQ ID NO 250
<211> LENGTH: 17
<212> TYPE: PRT
<213> ORGANISM: Artificial Sequence
<220> FEATURE:
<223> OTHER INFORMATION: Synthetic construct

<400> SEQUENCE: 250

Gly Thr Tyr Gly Leu Gly Ser Arg Ser Arg Thr Pro Ser Leu Pro Thr
1 5 10 15

Cys

<210> SEQ ID NO 251
<211> LENGTH: 17
<212> TYPE: PRT
<213> ORGANISM: Artificial Sequence
<220> FEATURE:
<223> OTHER INFORMATION: Synthetic construct

<400> SEQUENCE: 251

Gly Thr Tyr Gly Leu Gly Arg Ser Arg Thr Pro Ser Leu Pro Thr Pro
1 5 10 15

Cys

<210> SEQ ID NO 252
<211> LENGTH: 18

<212> TYPE: PRT
<213> ORGANISM: Artificial Sequence
<220> FEATURE:
<223> OTHER INFORMATION: Synthetic construct

<400> SEQUENCE: 252

Gly Thr Tyr Gly Leu Gly Ser Arg Ser Arg Thr Pro Ser Leu Pro Thr
1               5                   10                  15

Pro Cys

<210> SEQ ID NO 253
<211> LENGTH: 15
<212> TYPE: PRT
<213> ORGANISM: Artificial Sequence
<220> FEATURE:
<223> OTHER INFORMATION: Synthetic construct

<400> SEQUENCE: 253

His Ala Gly Thr Tyr Gly Leu Ser Arg Thr Pro Ser Leu Pro Cys
1               5                   10                  15

<210> SEQ ID NO 254
<211> LENGTH: 16
<212> TYPE: PRT
<213> ORGANISM: Artificial Sequence
<220> FEATURE:
<223> OTHER INFORMATION: Synthetic construct

<400> SEQUENCE: 254

His Ala Gly Thr Tyr Gly Leu Arg Ser Arg Thr Pro Ser Leu Pro Cys
1               5                   10                  15

<210> SEQ ID NO 255
<211> LENGTH: 16
<212> TYPE: PRT
<213> ORGANISM: Artificial Sequence
<220> FEATURE:
<223> OTHER INFORMATION: Synthetic construct

<400> SEQUENCE: 255

His Ala Gly Thr Tyr Gly Leu Ser Arg Thr Pro Ser Leu Pro Thr Cys
1               5                   10                  15

<210> SEQ ID NO 256
<211> LENGTH: 17
<212> TYPE: PRT
<213> ORGANISM: Artificial Sequence
<220> FEATURE:
<223> OTHER INFORMATION: Synthetic construct

<400> SEQUENCE: 256

His Ala Gly Thr Tyr Gly Leu Ser Arg Ser Arg Thr Pro Ser Leu Pro
1               5                   10                  15

Cys

<210> SEQ ID NO 257
<211> LENGTH: 17
<212> TYPE: PRT
<213> ORGANISM: Artificial Sequence
<220> FEATURE:
<223> OTHER INFORMATION: Synthetic construct

<400> SEQUENCE: 257

His Ala Gly Thr Tyr Gly Leu Arg Ser Arg Thr Pro Ser Leu Pro Thr
1               5                   10                  15

Cys

<210> SEQ ID NO 258
<211> LENGTH: 17
<212> TYPE: PRT
<213> ORGANISM: Artificial Sequence
<220> FEATURE:
<223> OTHER INFORMATION: Synthetic construct

<400> SEQUENCE: 258

His Ala Gly Thr Tyr Gly Leu Ser Arg Thr Pro Ser Leu Pro Thr Pro
1               5                   10                  15

Cys

<210> SEQ ID NO 259
<211> LENGTH: 18
<212> TYPE: PRT
<213> ORGANISM: Artificial Sequence
<220> FEATURE:
<223> OTHER INFORMATION: Synthetic construct

<400> SEQUENCE: 259

His Ala Gly Thr Tyr Gly Leu Ser Arg Ser Arg Thr Pro Ser Leu Pro
1               5                   10                  15

Thr Cys

<210> SEQ ID NO 260
<211> LENGTH: 18
<212> TYPE: PRT
<213> ORGANISM: Artificial Sequence
<220> FEATURE:
<223> OTHER INFORMATION: Synthetic construct

<400> SEQUENCE: 260

His Ala Gly Thr Tyr Gly Leu Arg Ser Arg Thr Pro Ser Leu Pro Thr
1               5                   10                  15

Pro Cys

<210> SEQ ID NO 261
<211> LENGTH: 19
<212> TYPE: PRT
<213> ORGANISM: Artificial Sequence
<220> FEATURE:
<223> OTHER INFORMATION: Synthetic construct

<400> SEQUENCE: 261

His Ala Gly Thr Tyr Gly Leu Ser Arg Ser Arg Thr Pro Ser Leu Pro
1               5                   10                  15

Thr Pro Cys

<210> SEQ ID NO 262
<211> LENGTH: 15
<212> TYPE: PRT
<213> ORGANISM: Artificial Sequence
<220> FEATURE:
<223> OTHER INFORMATION: Synthetic construct

<400> SEQUENCE: 262

Ala Gly Thr Tyr Gly Leu Gly Ser Arg Thr Pro Ser Leu Pro Cys
1               5                   10                  15

<210> SEQ ID NO 263
<211> LENGTH: 16
<212> TYPE: PRT

<213> ORGANISM: Artificial Sequence
<220> FEATURE:
<223> OTHER INFORMATION: Synthetic construct

<400> SEQUENCE: 263

Ala Gly Thr Tyr Gly Leu Gly Arg Ser Arg Thr Pro Ser Leu Pro Cys
1 5 10 15

<210> SEQ ID NO 264
<211> LENGTH: 16
<212> TYPE: PRT
<213> ORGANISM: Artificial Sequence
<220> FEATURE:
<223> OTHER INFORMATION: Synthetic construct

<400> SEQUENCE: 264

Ala Gly Thr Tyr Gly Leu Gly Ser Arg Thr Pro Ser Leu Pro Thr Cys
1 5 10 15

<210> SEQ ID NO 265
<211> LENGTH: 17
<212> TYPE: PRT
<213> ORGANISM: Artificial Sequence
<220> FEATURE:
<223> OTHER INFORMATION: Synthetic construct

<400> SEQUENCE: 265

Ala Gly Thr Tyr Gly Leu Gly Ser Arg Ser Arg Thr Pro Ser Leu Pro
1 5 10 15

Cys

<210> SEQ ID NO 266
<211> LENGTH: 17
<212> TYPE: PRT
<213> ORGANISM: Artificial Sequence
<220> FEATURE:
<223> OTHER INFORMATION: Synthetic construct

<400> SEQUENCE: 266

Ala Gly Thr Tyr Gly Leu Gly Arg Ser Arg Thr Pro Ser Leu Pro Thr
1 5 10 15

Cys

<210> SEQ ID NO 267
<211> LENGTH: 17
<212> TYPE: PRT
<213> ORGANISM: Artificial Sequence
<220> FEATURE:
<223> OTHER INFORMATION: Synthetic construct

<400> SEQUENCE: 267

Ala Gly Thr Tyr Gly Leu Gly Ser Arg Thr Pro Ser Leu Pro Thr Pro
1 5 10 15

Cys

<210> SEQ ID NO 268
<211> LENGTH: 18
<212> TYPE: PRT
<213> ORGANISM: Artificial Sequence
<220> FEATURE:
<223> OTHER INFORMATION: Synthetic construct

<400> SEQUENCE: 268

Ala Gly Thr Tyr Gly Leu Gly Ser Arg Ser Arg Thr Pro Ser Leu Pro
1 5 10 15

Thr Cys

<210> SEQ ID NO 269
<211> LENGTH: 18
<212> TYPE: PRT
<213> ORGANISM: Artificial Sequence
<220> FEATURE:
<223> OTHER INFORMATION: Synthetic construct

<400> SEQUENCE: 269

Ala Gly Thr Tyr Gly Leu Gly Arg Ser Arg Thr Pro Ser Leu Pro Thr
1 5 10 15

Pro Cys

<210> SEQ ID NO 270
<211> LENGTH: 19
<212> TYPE: PRT
<213> ORGANISM: Artificial Sequence
<220> FEATURE:
<223> OTHER INFORMATION: Synthetic construct

<400> SEQUENCE: 270

Ala Gly Thr Tyr Gly Leu Gly Ser Arg Ser Arg Thr Pro Ser Leu Pro
1 5 10 15

Thr Pro Cys

<210> SEQ ID NO 271
<211> LENGTH: 15
<212> TYPE: PRT
<213> ORGANISM: Artificial Sequence
<220> FEATURE:
<223> OTHER INFORMATION: Synthetic construct

<400> SEQUENCE: 271

Gly Thr Tyr Gly Leu Gly Asp Ser Arg Thr Pro Ser Leu Pro Cys
1 5 10 15

<210> SEQ ID NO 272
<211> LENGTH: 16
<212> TYPE: PRT
<213> ORGANISM: Artificial Sequence
<220> FEATURE:
<223> OTHER INFORMATION: Synthetic construct

<400> SEQUENCE: 272

Gly Thr Tyr Gly Leu Gly Asp Arg Ser Arg Thr Pro Ser Leu Pro Cys
1 5 10 15

<210> SEQ ID NO 273
<211> LENGTH: 16
<212> TYPE: PRT
<213> ORGANISM: Artificial Sequence
<220> FEATURE:
<223> OTHER INFORMATION: Synthetic construct

<400> SEQUENCE: 273

Gly Thr Tyr Gly Leu Gly Asp Ser Arg Thr Pro Ser Leu Pro Thr Cys
1 5 10 15

<210> SEQ ID NO 274
<211> LENGTH: 17
<212> TYPE: PRT
<213> ORGANISM: Artificial Sequence
<220> FEATURE:
<223> OTHER INFORMATION: Synthetic construct

<400> SEQUENCE: 274

Gly Thr Tyr Gly Leu Gly Asp Ser Arg Ser Arg Thr Pro Ser Leu Pro
1 5 10 15

Cys

<210> SEQ ID NO 275
<211> LENGTH: 17
<212> TYPE: PRT
<213> ORGANISM: Artificial Sequence
<220> FEATURE:
<223> OTHER INFORMATION: Synthetic construct

<400> SEQUENCE: 275

Gly Thr Tyr Gly Leu Gly Asp Arg Ser Arg Thr Pro Ser Leu Pro Thr
1 5 10 15

Cys

<210> SEQ ID NO 276
<211> LENGTH: 17
<212> TYPE: PRT
<213> ORGANISM: Artificial Sequence
<220> FEATURE:
<223> OTHER INFORMATION: Synthetic construct

<400> SEQUENCE: 276

Gly Thr Tyr Gly Leu Gly Asp Ser Arg Thr Pro Ser Leu Pro Thr Pro
1 5 10 15

Cys

<210> SEQ ID NO 277
<211> LENGTH: 18
<212> TYPE: PRT
<213> ORGANISM: Artificial Sequence
<220> FEATURE:
<223> OTHER INFORMATION: Synthetic construct

<400> SEQUENCE: 277

Gly Thr Tyr Gly Leu Gly Asp Ser Arg Ser Arg Thr Pro Ser Leu Pro
1 5 10 15

Thr Cys

<210> SEQ ID NO 278
<211> LENGTH: 18
<212> TYPE: PRT
<213> ORGANISM: Artificial Sequence
<220> FEATURE:
<223> OTHER INFORMATION: Synthetic construct

<400> SEQUENCE: 278

Gly Thr Tyr Gly Leu Gly Asp Arg Ser Arg Thr Pro Ser Leu Pro Thr
1 5 10 15

Pro Cys

<210> SEQ ID NO 279
<211> LENGTH: 19
<212> TYPE: PRT
<213> ORGANISM: Artificial Sequence
<220> FEATURE:
<223> OTHER INFORMATION: Synthetic construct

<400> SEQUENCE: 279

Gly Thr Tyr Gly Leu Gly Asp Ser Arg Ser Arg Thr Pro Ser Leu Pro

-continued

```
1               5                   10                  15

Thr Pro Cys


<210> SEQ ID NO 280
<211> LENGTH: 16
<212> TYPE: PRT
<213> ORGANISM: Artificial Sequence
<220> FEATURE:
<223> OTHER INFORMATION: Synthetic construct

<400> SEQUENCE: 280

His Ala Gly Thr Tyr Gly Leu Gly Ser Arg Thr Pro Ser Leu Pro Cys
1               5                   10                  15


<210> SEQ ID NO 281
<211> LENGTH: 17
<212> TYPE: PRT
<213> ORGANISM: Artificial Sequence
<220> FEATURE:
<223> OTHER INFORMATION: Synthetic construct

<400> SEQUENCE: 281

His Ala Gly Thr Tyr Gly Leu Gly Arg Ser Arg Thr Pro Ser Leu Pro
1               5                   10                  15

Cys


<210> SEQ ID NO 282
<211> LENGTH: 17
<212> TYPE: PRT
<213> ORGANISM: Artificial Sequence
<220> FEATURE:
<223> OTHER INFORMATION: Synthetic construct

<400> SEQUENCE: 282

His Ala Gly Thr Tyr Gly Leu Gly Ser Arg Thr Pro Ser Leu Pro Thr
1               5                   10                  15

Cys


<210> SEQ ID NO 283
<211> LENGTH: 18
<212> TYPE: PRT
<213> ORGANISM: Artificial Sequence
<220> FEATURE:
<223> OTHER INFORMATION: Synthetic construct

<400> SEQUENCE: 283

His Ala Gly Thr Tyr Gly Leu Gly Ser Arg Ser Arg Thr Pro Ser Leu
1               5                   10                  15

Pro Cys


<210> SEQ ID NO 284
<211> LENGTH: 18
<212> TYPE: PRT
<213> ORGANISM: Artificial Sequence
<220> FEATURE:
<223> OTHER INFORMATION: Synthetic construct

<400> SEQUENCE: 284

His Ala Gly Thr Tyr Gly Leu Gly Arg Ser Arg Thr Pro Ser Leu Pro
1               5                   10                  15

Thr Cys


<210> SEQ ID NO 285
```

<211> LENGTH: 18
<212> TYPE: PRT
<213> ORGANISM: Artificial Sequence
<220> FEATURE:
<223> OTHER INFORMATION: Synthetic construct

<400> SEQUENCE: 285

His Ala Gly Thr Tyr Gly Leu Gly Ser Arg Thr Pro Ser Leu Pro Thr
1 5 10 15

Pro Cys

<210> SEQ ID NO 286
<211> LENGTH: 19
<212> TYPE: PRT
<213> ORGANISM: Artificial Sequence
<220> FEATURE:
<223> OTHER INFORMATION: Synthetic construct

<400> SEQUENCE: 286

His Ala Gly Thr Tyr Gly Leu Gly Ser Arg Ser Arg Thr Pro Ser Leu
1 5 10 15

Pro Thr Cys

<210> SEQ ID NO 287
<211> LENGTH: 19
<212> TYPE: PRT
<213> ORGANISM: Artificial Sequence
<220> FEATURE:
<223> OTHER INFORMATION: Synthetic construct

<400> SEQUENCE: 287

His Ala Gly Thr Tyr Gly Leu Gly Arg Ser Arg Thr Pro Ser Leu Pro
1 5 10 15

Thr Pro Cys

<210> SEQ ID NO 288
<211> LENGTH: 20
<212> TYPE: PRT
<213> ORGANISM: Artificial Sequence
<220> FEATURE:
<223> OTHER INFORMATION: Synthetic construct

<400> SEQUENCE: 288

His Ala Gly Thr Tyr Gly Leu Gly Ser Arg Ser Arg Thr Pro Ser Leu
1 5 10 15

Pro Thr Pro Cys
20

<210> SEQ ID NO 289
<211> LENGTH: 16
<212> TYPE: PRT
<213> ORGANISM: Artificial Sequence
<220> FEATURE:
<223> OTHER INFORMATION: Synthetic construct

<400> SEQUENCE: 289

Ala Gly Thr Tyr Gly Leu Gly Asp Ser Arg Thr Pro Ser Leu Pro Cys
1 5 10 15

<210> SEQ ID NO 290
<211> LENGTH: 17
<212> TYPE: PRT
<213> ORGANISM: Artificial Sequence
<220> FEATURE:
<223> OTHER INFORMATION: Synthetic construct

<400> SEQUENCE: 290

Ala Gly Thr Tyr Gly Leu Gly Asp Arg Ser Arg Thr Pro Ser Leu Pro
1 5 10 15

Cys

<210> SEQ ID NO 291
<211> LENGTH: 17
<212> TYPE: PRT
<213> ORGANISM: Artificial Sequence
<220> FEATURE:
<223> OTHER INFORMATION: Synthetic construct

<400> SEQUENCE: 291

Ala Gly Thr Tyr Gly Leu Gly Asp Ser Arg Thr Pro Ser Leu Pro Thr
1 5 10 15

Cys

<210> SEQ ID NO 292
<211> LENGTH: 18
<212> TYPE: PRT
<213> ORGANISM: Artificial Sequence
<220> FEATURE:
<223> OTHER INFORMATION: Synthetic construct

<400> SEQUENCE: 292

Ala Gly Thr Tyr Gly Leu Gly Asp Ser Arg Ser Arg Thr Pro Ser Leu
1 5 10 15

Pro Cys

<210> SEQ ID NO 293
<211> LENGTH: 18
<212> TYPE: PRT
<213> ORGANISM: Artificial Sequence
<220> FEATURE:
<223> OTHER INFORMATION: Synthetic construct

<400> SEQUENCE: 293

Ala Gly Thr Tyr Gly Leu Gly Asp Arg Ser Arg Thr Pro Ser Leu Pro
1 5 10 15

Thr Cys

<210> SEQ ID NO 294
<211> LENGTH: 18
<212> TYPE: PRT
<213> ORGANISM: Artificial Sequence
<220> FEATURE:
<223> OTHER INFORMATION: Synthetic construct

<400> SEQUENCE: 294

Ala Gly Thr Tyr Gly Leu Gly Asp Ser Arg Thr Pro Ser Leu Pro Thr
1 5 10 15

Pro Cys

<210> SEQ ID NO 295
<211> LENGTH: 19
<212> TYPE: PRT
<213> ORGANISM: Artificial Sequence
<220> FEATURE:
<223> OTHER INFORMATION: Synthetic construct

<400> SEQUENCE: 295

Ala Gly Thr Tyr Gly Leu Gly Asp Ser Arg Ser Arg Thr Pro Ser Leu 1 5 10 15

Pro Thr Cys

<210> SEQ ID NO 296
<211> LENGTH: 19
<212> TYPE: PRT
<213> ORGANISM: Artificial Sequence
<220> FEATURE:
<223> OTHER INFORMATION: Synthetic construct

<400> SEQUENCE: 296

Ala Gly Thr Tyr Gly Leu Gly Asp Arg Ser Arg Thr Pro Ser Leu Pro
1 5 10 15

Thr Pro Cys

<210> SEQ ID NO 297
<211> LENGTH: 20
<212> TYPE: PRT
<213> ORGANISM: Artificial Sequence
<220> FEATURE:
<223> OTHER INFORMATION: Synthetic construct

<400> SEQUENCE: 297

Ala Gly Thr Tyr Gly Leu Gly Asp Ser Arg Ser Arg Thr Pro Ser Leu
1 5 10 15

Pro Thr Pro Cys
20

<210> SEQ ID NO 298
<211> LENGTH: 17
<212> TYPE: PRT
<213> ORGANISM: Artificial Sequence
<220> FEATURE:
<223> OTHER INFORMATION: Synthetic construct

<400> SEQUENCE: 298

His Ala Gly Thr Tyr Gly Leu Gly Asp Ser Arg Thr Pro Ser Leu Pro
1 5 10 15

Cys

<210> SEQ ID NO 299
<211> LENGTH: 18
<212> TYPE: PRT
<213> ORGANISM: Artificial Sequence
<220> FEATURE:
<223> OTHER INFORMATION: Synthetic construct

<400> SEQUENCE: 299

His Ala Gly Thr Tyr Gly Leu Gly Asp Arg Ser Arg Thr Pro Ser Leu
1 5 10 15

Pro Cys

<210> SEQ ID NO 300
<211> LENGTH: 18
<212> TYPE: PRT
<213> ORGANISM: Artificial Sequence
<220> FEATURE:
<223> OTHER INFORMATION: Synthetic construct

<400> SEQUENCE: 300

His Ala Gly Thr Tyr Gly Leu Gly Asp Ser Arg Thr Pro Ser Leu Pro
1 5 10 15

Thr Cys

<210> SEQ ID NO 301
<211> LENGTH: 19
<212> TYPE: PRT
<213> ORGANISM: Artificial Sequence
<220> FEATURE:
<223> OTHER INFORMATION: Synthetic construct

<400> SEQUENCE: 301

```
His Ala Gly Thr Tyr Gly Leu Gly Asp Ser Arg Ser Arg Thr Pro Ser
1               5                   10                  15

Leu Pro Cys
```

<210> SEQ ID NO 302
<211> LENGTH: 19
<212> TYPE: PRT
<213> ORGANISM: Artificial Sequence
<220> FEATURE:
<223> OTHER INFORMATION: Synthetic construct

<400> SEQUENCE: 302

```
His Ala Gly Thr Tyr Gly Leu Gly Asp Arg Ser Arg Thr Pro Ser Leu
1               5                   10                  15

Pro Thr Cys
```

<210> SEQ ID NO 303
<211> LENGTH: 19
<212> TYPE: PRT
<213> ORGANISM: Artificial Sequence
<220> FEATURE:
<223> OTHER INFORMATION: Synthetic construct

<400> SEQUENCE: 303

```
His Ala Gly Thr Tyr Gly Leu Gly Asp Ser Arg Thr Pro Ser Leu Pro
1               5                   10                  15

Thr Pro Cys
```

<210> SEQ ID NO 304
<211> LENGTH: 20
<212> TYPE: PRT
<213> ORGANISM: Artificial Sequence
<220> FEATURE:
<223> OTHER INFORMATION: Synthetic construct

<400> SEQUENCE: 304

```
His Ala Gly Thr Tyr Gly Leu Gly Asp Ser Arg Ser Arg Thr Pro Ser
1               5                   10                  15

Leu Pro Thr Cys
            20
```

<210> SEQ ID NO 305
<211> LENGTH: 20
<212> TYPE: PRT
<213> ORGANISM: Artificial Sequence
<220> FEATURE:
<223> OTHER INFORMATION: Synthetic construct

<400> SEQUENCE: 305

```
His Ala Gly Thr Tyr Gly Leu Gly Asp Arg Ser Arg Thr Pro Ser Leu
1               5                   10                  15

Pro Thr Pro Cys
            20
```

<210> SEQ ID NO 306
<211> LENGTH: 21
<212> TYPE: PRT
<213> ORGANISM: Artificial Sequence
<220> FEATURE:
<223> OTHER INFORMATION: Synthetic construct

<400> SEQUENCE: 306

His Ala Gly Thr Tyr Gly Leu Gly Asp Ser Arg Ser Arg Thr Pro Ser
1 5 10 15

Leu Pro Thr Pro Cys
20

<210> SEQ ID NO 307
<211> LENGTH: 15
<212> TYPE: PRT
<213> ORGANISM: Artificial Sequence
<220> FEATURE:
<223> OTHER INFORMATION: Synthetic construct

<400> SEQUENCE: 307

Gly Thr Tyr Gly Leu Val Arg Thr Pro Pro Lys Ser Pro Ser Cys
1 5 10 15

<210> SEQ ID NO 308
<211> LENGTH: 16
<212> TYPE: PRT
<213> ORGANISM: Artificial Sequence
<220> FEATURE:
<223> OTHER INFORMATION: Synthetic construct

<400> SEQUENCE: 308

Gly Thr Tyr Gly Leu Val Val Arg Thr Pro Pro Lys Ser Pro Ser Cys
1 5 10 15

<210> SEQ ID NO 309
<211> LENGTH: 16
<212> TYPE: PRT
<213> ORGANISM: Artificial Sequence
<220> FEATURE:
<223> OTHER INFORMATION: Synthetic construct

<400> SEQUENCE: 309

Gly Thr Tyr Gly Leu Val Arg Thr Pro Pro Lys Ser Pro Ser Ser Cys
1 5 10 15

<210> SEQ ID NO 310
<211> LENGTH: 17
<212> TYPE: PRT
<213> ORGANISM: Artificial Sequence
<220> FEATURE:
<223> OTHER INFORMATION: Synthetic construct

<400> SEQUENCE: 310

Gly Thr Tyr Gly Leu Ala Val Val Arg Thr Pro Pro Lys Ser Pro Ser
1 5 10 15

Cys

<210> SEQ ID NO 311
<211> LENGTH: 17
<212> TYPE: PRT
<213> ORGANISM: Artificial Sequence
<220> FEATURE:
<223> OTHER INFORMATION: Synthetic construct

<400> SEQUENCE: 311

```
Gly Thr Tyr Gly Leu Val Val Arg Thr Pro Pro Lys Ser Pro Ser Ser
1               5                   10                  15

Cys


<210> SEQ ID NO 312
<211> LENGTH: 17
<212> TYPE: PRT
<213> ORGANISM: Artificial Sequence
<220> FEATURE:
<223> OTHER INFORMATION: Synthetic construct

<400> SEQUENCE: 312

Gly Thr Tyr Gly Leu Val Arg Thr Pro Pro Lys Ser Pro Ser Ser Ala
1               5                   10                  15

Cys


<210> SEQ ID NO 313
<211> LENGTH: 18
<212> TYPE: PRT
<213> ORGANISM: Artificial Sequence
<220> FEATURE:
<223> OTHER INFORMATION: Synthetic construct

<400> SEQUENCE: 313

Gly Thr Tyr Gly Leu Ala Val Val Arg Thr Pro Pro Lys Ser Pro Ser
1               5                   10                  15

Ser Cys


<210> SEQ ID NO 314
<211> LENGTH: 18
<212> TYPE: PRT
<213> ORGANISM: Artificial Sequence
<220> FEATURE:
<223> OTHER INFORMATION: Synthetic construct

<400> SEQUENCE: 314

Gly Thr Tyr Gly Leu Val Val Arg Thr Pro Pro Lys Ser Pro Ser Ser
1               5                   10                  15

Ala Cys


<210> SEQ ID NO 315
<211> LENGTH: 19
<212> TYPE: PRT
<213> ORGANISM: Artificial Sequence
<220> FEATURE:
<223> OTHER INFORMATION: Synthetic construct

<400> SEQUENCE: 315

Gly Thr Tyr Gly Leu Ala Val Val Arg Thr Pro Pro Lys Ser Pro Ser
1               5                   10                  15

Ser Ala Cys


<210> SEQ ID NO 316
<211> LENGTH: 16
<212> TYPE: PRT
<213> ORGANISM: Artificial Sequence
<220> FEATURE:
<223> OTHER INFORMATION: Synthetic construct

<400> SEQUENCE: 316

Ala Gly Thr Tyr Gly Leu Val Arg Thr Pro Pro Lys Ser Pro Ser Cys
1               5                   10                  15
```

<210> SEQ ID NO 317
<211> LENGTH: 17
<212> TYPE: PRT
<213> ORGANISM: Artificial Sequence
<220> FEATURE:
<223> OTHER INFORMATION: Synthetic construct

<400> SEQUENCE: 317

Ala Gly Thr Tyr Gly Leu Val Val Arg Thr Pro Pro Lys Ser Pro Ser
1 5 10 15

Cys

<210> SEQ ID NO 318
<211> LENGTH: 17
<212> TYPE: PRT
<213> ORGANISM: Artificial Sequence
<220> FEATURE:
<223> OTHER INFORMATION: Synthetic construct

<400> SEQUENCE: 318

Ala Gly Thr Tyr Gly Leu Val Arg Thr Pro Pro Lys Ser Pro Ser Ser
1 5 10 15

Cys

<210> SEQ ID NO 319
<211> LENGTH: 18
<212> TYPE: PRT
<213> ORGANISM: Artificial Sequence
<220> FEATURE:
<223> OTHER INFORMATION: Synthetic construct

<400> SEQUENCE: 319

Ala Gly Thr Tyr Gly Leu Ala Val Val Arg Thr Pro Pro Lys Ser Pro
1 5 10 15

Ser Cys

<210> SEQ ID NO 320
<211> LENGTH: 18
<212> TYPE: PRT
<213> ORGANISM: Artificial Sequence
<220> FEATURE:
<223> OTHER INFORMATION: Synthetic construct

<400> SEQUENCE: 320

Ala Gly Thr Tyr Gly Leu Val Val Arg Thr Pro Pro Lys Ser Pro Ser
1 5 10 15

Ser Cys

<210> SEQ ID NO 321
<211> LENGTH: 18
<212> TYPE: PRT
<213> ORGANISM: Artificial Sequence
<220> FEATURE:
<223> OTHER INFORMATION: Synthetic construct

<400> SEQUENCE: 321

Ala Gly Thr Tyr Gly Leu Val Arg Thr Pro Pro Lys Ser Pro Ser Ser
1 5 10 15

Ala Cys

<210> SEQ ID NO 322
<211> LENGTH: 19
<212> TYPE: PRT
<213> ORGANISM: Artificial Sequence
<220> FEATURE:
<223> OTHER INFORMATION: Synthetic construct

<400> SEQUENCE: 322

Ala Gly Thr Tyr Gly Leu Ala Val Val Arg Thr Pro Pro Lys Ser Pro
1               5                   10                  15

Ser Ser Cys

<210> SEQ ID NO 323
<211> LENGTH: 19
<212> TYPE: PRT
<213> ORGANISM: Artificial Sequence
<220> FEATURE:
<223> OTHER INFORMATION: Synthetic construct

<400> SEQUENCE: 323

Ala Gly Thr Tyr Gly Leu Val Val Arg Thr Pro Pro Lys Ser Pro Ser
1               5                   10                  15

Ser Ala Cys

<210> SEQ ID NO 324
<211> LENGTH: 20
<212> TYPE: PRT
<213> ORGANISM: Artificial Sequence
<220> FEATURE:
<223> OTHER INFORMATION: Synthetic construct

<400> SEQUENCE: 324

Ala Gly Thr Tyr Gly Leu Ala Val Val Arg Thr Pro Pro Lys Ser Pro
1               5                   10                  15

Ser Ser Ala Cys
            20

<210> SEQ ID NO 325
<211> LENGTH: 16
<212> TYPE: PRT
<213> ORGANISM: Artificial Sequence
<220> FEATURE:
<223> OTHER INFORMATION: Synthetic construct

<400> SEQUENCE: 325

Gly Thr Tyr Gly Leu Gly Val Arg Thr Pro Pro Lys Ser Pro Ser Cys
1               5                   10                  15

<210> SEQ ID NO 326
<211> LENGTH: 17
<212> TYPE: PRT
<213> ORGANISM: Artificial Sequence
<220> FEATURE:
<223> OTHER INFORMATION: Synthetic construct

<400> SEQUENCE: 326

Gly Thr Tyr Gly Leu Gly Val Val Arg Thr Pro Pro Lys Ser Pro Ser
1               5                   10                  15

Cys

<210> SEQ ID NO 327
<211> LENGTH: 17
<212> TYPE: PRT
<213> ORGANISM: Artificial Sequence
<220> FEATURE:
<223> OTHER INFORMATION: Synthetic construct

<400> SEQUENCE: 327

Gly Thr Tyr Gly Leu Gly Val Arg Thr Pro Pro Lys Ser Pro Ser Ser
1 5 10 15

Cys

<210> SEQ ID NO 328
<211> LENGTH: 18
<212> TYPE: PRT
<213> ORGANISM: Artificial Sequence
<220> FEATURE:
<223> OTHER INFORMATION: Synthetic construct

<400> SEQUENCE: 328

Gly Thr Tyr Gly Leu Gly Ala Val Val Arg Thr Pro Pro Lys Ser Pro
1 5 10 15

Ser Cys

<210> SEQ ID NO 329
<211> LENGTH: 18
<212> TYPE: PRT
<213> ORGANISM: Artificial Sequence
<220> FEATURE:
<223> OTHER INFORMATION: Synthetic construct

<400> SEQUENCE: 329

Gly Thr Tyr Gly Leu Gly Val Val Arg Thr Pro Pro Lys Ser Pro Ser
1 5 10 15

Ser Cys

<210> SEQ ID NO 330
<211> LENGTH: 18
<212> TYPE: PRT
<213> ORGANISM: Artificial Sequence
<220> FEATURE:
<223> OTHER INFORMATION: Synthetic construct

<400> SEQUENCE: 330

Gly Thr Tyr Gly Leu Gly Val Arg Thr Pro Pro Lys Ser Pro Ser Ser
1 5 10 15

Ala Cys

<210> SEQ ID NO 331
<211> LENGTH: 19
<212> TYPE: PRT
<213> ORGANISM: Artificial Sequence
<220> FEATURE:
<223> OTHER INFORMATION: Synthetic construct

<400> SEQUENCE: 331

Gly Thr Tyr Gly Leu Gly Ala Val Val Arg Thr Pro Pro Lys Ser Pro
1 5 10 15

Ser Ser Cys

<210> SEQ ID NO 332
<211> LENGTH: 19
<212> TYPE: PRT
<213> ORGANISM: Artificial Sequence
<220> FEATURE:
<223> OTHER INFORMATION: Synthetic construct

<400> SEQUENCE: 332

Gly Thr Tyr Gly Leu Gly Val Val Arg Thr Pro Pro Lys Ser Pro Ser
1 5 10 15

Ser Ala Cys

<210> SEQ ID NO 333
<211> LENGTH: 20
<212> TYPE: PRT
<213> ORGANISM: Artificial Sequence
<220> FEATURE:
<223> OTHER INFORMATION: Synthetic construct

<400> SEQUENCE: 333

```
Gly Thr Tyr Gly Leu Gly Ala Val Val Arg Thr Pro Pro Lys Ser Pro
1               5                   10                  15

Ser Ser Ala Cys
            20
```

<210> SEQ ID NO 334
<211> LENGTH: 17
<212> TYPE: PRT
<213> ORGANISM: Artificial Sequence
<220> FEATURE:
<223> OTHER INFORMATION: Synthetic construct

<400> SEQUENCE: 334

```
His Ala Gly Thr Tyr Gly Leu Val Arg Thr Pro Pro Lys Ser Pro Ser
1               5                   10                  15

Cys
```

<210> SEQ ID NO 335
<211> LENGTH: 18
<212> TYPE: PRT
<213> ORGANISM: Artificial Sequence
<220> FEATURE:
<223> OTHER INFORMATION: Synthetic construct

<400> SEQUENCE: 335

```
His Ala Gly Thr Tyr Gly Leu Val Val Arg Thr Pro Pro Lys Ser Pro
1               5                   10                  15

Ser Cys
```

<210> SEQ ID NO 336
<211> LENGTH: 18
<212> TYPE: PRT
<213> ORGANISM: Artificial Sequence
<220> FEATURE:
<223> OTHER INFORMATION: Synthetic construct

<400> SEQUENCE: 336

```
His Ala Gly Thr Tyr Gly Leu Val Arg Thr Pro Pro Lys Ser Pro Ser
1               5                   10                  15

Ser Cys
```

<210> SEQ ID NO 337
<211> LENGTH: 19
<212> TYPE: PRT
<213> ORGANISM: Artificial Sequence
<220> FEATURE:
<223> OTHER INFORMATION: Synthetic construct

<400> SEQUENCE: 337

```
His Ala Gly Thr Tyr Gly Leu Ala Val Val Arg Thr Pro Pro Lys Ser
1               5                   10                  15

Pro Ser Cys
```

<210> SEQ ID NO 338

<211> LENGTH: 19
<212> TYPE: PRT
<213> ORGANISM: Artificial Sequence
<220> FEATURE:
<223> OTHER INFORMATION: Synthetic construct

<400> SEQUENCE: 338

His Ala Gly Thr Tyr Gly Leu Val Val Arg Thr Pro Pro Lys Ser Pro
1 5 10 15

Ser Ser Cys

<210> SEQ ID NO 339
<211> LENGTH: 19
<212> TYPE: PRT
<213> ORGANISM: Artificial Sequence
<220> FEATURE:
<223> OTHER INFORMATION: Synthetic construct

<400> SEQUENCE: 339

His Ala Gly Thr Tyr Gly Leu Val Arg Thr Pro Pro Lys Ser Pro Ser
1 5 10 15

Ser Ala Cys

<210> SEQ ID NO 340
<211> LENGTH: 20
<212> TYPE: PRT
<213> ORGANISM: Artificial Sequence
<220> FEATURE:
<223> OTHER INFORMATION: Synthetic construct

<400> SEQUENCE: 340

His Ala Gly Thr Tyr Gly Leu Ala Val Val Arg Thr Pro Pro Lys Ser
1 5 10 15

Pro Ser Ser Cys
20

<210> SEQ ID NO 341
<211> LENGTH: 20
<212> TYPE: PRT
<213> ORGANISM: Artificial Sequence
<220> FEATURE:
<223> OTHER INFORMATION: Synthetic construct

<400> SEQUENCE: 341

His Ala Gly Thr Tyr Gly Leu Val Val Arg Thr Pro Pro Lys Ser Pro
1 5 10 15

Ser Ser Ala Cys
20

<210> SEQ ID NO 342
<211> LENGTH: 21
<212> TYPE: PRT
<213> ORGANISM: Artificial Sequence
<220> FEATURE:
<223> OTHER INFORMATION: Synthetic construct

<400> SEQUENCE: 342

His Ala Gly Thr Tyr Gly Leu Ala Val Val Arg Thr Pro Pro Lys Ser
1 5 10 15

Pro Ser Ser Ala Cys
20

<210> SEQ ID NO 343
<211> LENGTH: 17

<212> TYPE: PRT
<213> ORGANISM: Artificial Sequence
<220> FEATURE:
<223> OTHER INFORMATION: Synthetic construct

<400> SEQUENCE: 343

Ala Gly Thr Tyr Gly Leu Gly Val Arg Thr Pro Pro Lys Ser Pro Ser
1 5 10 15

Cys

<210> SEQ ID NO 344
<211> LENGTH: 18
<212> TYPE: PRT
<213> ORGANISM: Artificial Sequence
<220> FEATURE:
<223> OTHER INFORMATION: Synthetic construct

<400> SEQUENCE: 344

Ala Gly Thr Tyr Gly Leu Gly Val Val Arg Thr Pro Pro Lys Ser Pro
1 5 10 15

Ser Cys

<210> SEQ ID NO 345
<211> LENGTH: 18
<212> TYPE: PRT
<213> ORGANISM: Artificial Sequence
<220> FEATURE:
<223> OTHER INFORMATION: Synthetic construct

<400> SEQUENCE: 345

Ala Gly Thr Tyr Gly Leu Gly Val Arg Thr Pro Pro Lys Ser Pro Ser
1 5 10 15

Ser Cys

<210> SEQ ID NO 346
<211> LENGTH: 19
<212> TYPE: PRT
<213> ORGANISM: Artificial Sequence
<220> FEATURE:
<223> OTHER INFORMATION: Synthetic construct

<400> SEQUENCE: 346

Ala Gly Thr Tyr Gly Leu Gly Ala Val Val Arg Thr Pro Pro Lys Ser
1 5 10 15

Pro Ser Cys

<210> SEQ ID NO 347
<211> LENGTH: 19
<212> TYPE: PRT
<213> ORGANISM: Artificial Sequence
<220> FEATURE:
<223> OTHER INFORMATION: Synthetic construct

<400> SEQUENCE: 347

Ala Gly Thr Tyr Gly Leu Gly Val Val Arg Thr Pro Pro Lys Ser Pro
1 5 10 15

Ser Ser Cys

<210> SEQ ID NO 348
<211> LENGTH: 19
<212> TYPE: PRT
<213> ORGANISM: Artificial Sequence
<220> FEATURE:
<223> OTHER INFORMATION: Synthetic construct

<400> SEQUENCE: 348

Ala Gly Thr Tyr Gly Leu Gly Val Arg Thr Pro Pro Lys Ser Pro Ser
1 5 10 15

Ser Ala Cys

<210> SEQ ID NO 349
<211> LENGTH: 20
<212> TYPE: PRT
<213> ORGANISM: Artificial Sequence
<220> FEATURE:
<223> OTHER INFORMATION: Synthetic construct

<400> SEQUENCE: 349

Ala Gly Thr Tyr Gly Leu Gly Ala Val Val Arg Thr Pro Pro Lys Ser
1 5 10 15

Pro Ser Ser Cys
20

<210> SEQ ID NO 350
<211> LENGTH: 20
<212> TYPE: PRT
<213> ORGANISM: Artificial Sequence
<220> FEATURE:
<223> OTHER INFORMATION: Synthetic construct

<400> SEQUENCE: 350

Ala Gly Thr Tyr Gly Leu Gly Val Val Arg Thr Pro Pro Lys Ser Pro
1 5 10 15

Ser Ser Ala Cys
20

<210> SEQ ID NO 351
<211> LENGTH: 21
<212> TYPE: PRT
<213> ORGANISM: Artificial Sequence
<220> FEATURE:
<223> OTHER INFORMATION: Synthetic construct

<400> SEQUENCE: 351

Ala Gly Thr Tyr Gly Leu Gly Ala Val Val Arg Thr Pro Pro Lys Ser
1 5 10 15

Pro Ser Ser Ala Cys
20

<210> SEQ ID NO 352
<211> LENGTH: 17
<212> TYPE: PRT
<213> ORGANISM: Artificial Sequence
<220> FEATURE:
<223> OTHER INFORMATION: Synthetic construct

<400> SEQUENCE: 352

Gly Thr Tyr Gly Leu Gly Asp Val Arg Thr Pro Pro Lys Ser Pro Ser
1 5 10 15

Cys

<210> SEQ ID NO 353
<211> LENGTH: 18
<212> TYPE: PRT
<213> ORGANISM: Artificial Sequence
<220> FEATURE:
<223> OTHER INFORMATION: Synthetic construct

<400> SEQUENCE: 353

Gly Thr Tyr Gly Leu Gly Asp Val Val Arg Thr Pro Pro Lys Ser Pro
1 5 10 15

Ser Cys

<210> SEQ ID NO 354
<211> LENGTH: 18
<212> TYPE: PRT
<213> ORGANISM: Artificial Sequence
<220> FEATURE:
<223> OTHER INFORMATION: Synthetic construct

<400> SEQUENCE: 354

Gly Thr Tyr Gly Leu Gly Asp Val Arg Thr Pro Pro Lys Ser Pro Ser
1 5 10 15

Ser Cys

<210> SEQ ID NO 355
<211> LENGTH: 19
<212> TYPE: PRT
<213> ORGANISM: Artificial Sequence
<220> FEATURE:
<223> OTHER INFORMATION: Synthetic construct

<400> SEQUENCE: 355

Gly Thr Tyr Gly Leu Gly Asp Ala Val Val Arg Thr Pro Pro Lys Ser
1 5 10 15

Pro Ser Cys

<210> SEQ ID NO 356
<211> LENGTH: 19
<212> TYPE: PRT
<213> ORGANISM: Artificial Sequence
<220> FEATURE:
<223> OTHER INFORMATION: Synthetic construct

<400> SEQUENCE: 356

Gly Thr Tyr Gly Leu Gly Asp Val Val Arg Thr Pro Pro Lys Ser Pro
1 5 10 15

Ser Ser Cys

<210> SEQ ID NO 357
<211> LENGTH: 19
<212> TYPE: PRT
<213> ORGANISM: Artificial Sequence
<220> FEATURE:
<223> OTHER INFORMATION: Synthetic construct

<400> SEQUENCE: 357

Gly Thr Tyr Gly Leu Gly Asp Val Arg Thr Pro Pro Lys Ser Pro Ser
1 5 10 15

Ser Ala Cys

<210> SEQ ID NO 358
<211> LENGTH: 20
<212> TYPE: PRT
<213> ORGANISM: Artificial Sequence
<220> FEATURE:
<223> OTHER INFORMATION: Synthetic construct

<400> SEQUENCE: 358

Gly Thr Tyr Gly Leu Gly Asp Ala Val Val Arg Thr Pro Pro Lys Ser
1 5 10 15

Pro Ser Ser Cys
20

<210> SEQ ID NO 359
<211> LENGTH: 20
<212> TYPE: PRT
<213> ORGANISM: Artificial Sequence
<220> FEATURE:
<223> OTHER INFORMATION: Synthetic construct

<400> SEQUENCE: 359

Gly Thr Tyr Gly Leu Gly Asp Val Val Arg Thr Pro Pro Lys Ser Pro
1 5 10 15

Ser Ser Ala Cys
20

<210> SEQ ID NO 360
<211> LENGTH: 21
<212> TYPE: PRT
<213> ORGANISM: Artificial Sequence
<220> FEATURE:
<223> OTHER INFORMATION: Synthetic construct

<400> SEQUENCE: 360

Gly Thr Tyr Gly Leu Gly Asp Ala Val Val Arg Thr Pro Pro Lys Ser
1 5 10 15

Pro Ser Ser Ala Cys
20

<210> SEQ ID NO 361
<211> LENGTH: 18
<212> TYPE: PRT
<213> ORGANISM: Artificial Sequence
<220> FEATURE:
<223> OTHER INFORMATION: Synthetic construct

<400> SEQUENCE: 361

His Ala Gly Thr Tyr Gly Leu Gly Val Arg Thr Pro Pro Lys Ser Pro
1 5 10 15

Ser Cys

<210> SEQ ID NO 362
<211> LENGTH: 19
<212> TYPE: PRT
<213> ORGANISM: Artificial Sequence
<220> FEATURE:
<223> OTHER INFORMATION: Synthetic construct

<400> SEQUENCE: 362

His Ala Gly Thr Tyr Gly Leu Gly Val Val Arg Thr Pro Pro Lys Ser
1 5 10 15

Pro Ser Cys

<210> SEQ ID NO 363
<211> LENGTH: 19
<212> TYPE: PRT
<213> ORGANISM: Artificial Sequence
<220> FEATURE:
<223> OTHER INFORMATION: Synthetic construct

<400> SEQUENCE: 363

His Ala Gly Thr Tyr Gly Leu Gly Val Arg Thr Pro Pro Lys Ser Pro
1 5 10 15

-continued

Ser Ser Cys

<210> SEQ ID NO 364
<211> LENGTH: 20
<212> TYPE: PRT
<213> ORGANISM: Artificial Sequence
<220> FEATURE:
<223> OTHER INFORMATION: Synthetic construct

<400> SEQUENCE: 364

His Ala Gly Thr Tyr Gly Leu Gly Ala Val Val Arg Thr Pro Pro Lys
1 5 10 15

Ser Pro Ser Cys
20

<210> SEQ ID NO 365
<211> LENGTH: 20
<212> TYPE: PRT
<213> ORGANISM: Artificial Sequence
<220> FEATURE:
<223> OTHER INFORMATION: Synthetic construct

<400> SEQUENCE: 365

His Ala Gly Thr Tyr Gly Leu Gly Val Val Arg Thr Pro Pro Lys Ser
1 5 10 15

Pro Ser Ser Cys
20

<210> SEQ ID NO 366
<211> LENGTH: 20
<212> TYPE: PRT
<213> ORGANISM: Artificial Sequence
<220> FEATURE:
<223> OTHER INFORMATION: Synthetic construct

<400> SEQUENCE: 366

His Ala Gly Thr Tyr Gly Leu Gly Val Arg Thr Pro Pro Lys Ser Pro
1 5 10 15

Ser Ser Ala Cys
20

<210> SEQ ID NO 367
<211> LENGTH: 21
<212> TYPE: PRT
<213> ORGANISM: Artificial Sequence
<220> FEATURE:
<223> OTHER INFORMATION: Synthetic construct

<400> SEQUENCE: 367

His Ala Gly Thr Tyr Gly Leu Gly Ala Val Val Arg Thr Pro Pro Lys
1 5 10 15

Ser Pro Ser Ser Cys
20

<210> SEQ ID NO 368
<211> LENGTH: 21
<212> TYPE: PRT
<213> ORGANISM: Artificial Sequence
<220> FEATURE:
<223> OTHER INFORMATION: Synthetic construct

<400> SEQUENCE: 368

His Ala Gly Thr Tyr Gly Leu Gly Val Val Arg Thr Pro Pro Lys Ser
1 5 10 15

Pro Ser Ser Ala Cys
20

<210> SEQ ID NO 369
<211> LENGTH: 22
<212> TYPE: PRT
<213> ORGANISM: Artificial Sequence
<220> FEATURE:
<223> OTHER INFORMATION: Synthetic construct

<400> SEQUENCE: 369

His Ala Gly Thr Tyr Gly Leu Gly Ala Val Val Arg Thr Pro Pro Lys
1 5 10 15

Ser Pro Ser Ser Ala Cys
20

<210> SEQ ID NO 370
<211> LENGTH: 18
<212> TYPE: PRT
<213> ORGANISM: Artificial Sequence
<220> FEATURE:
<223> OTHER INFORMATION: Synthetic construct

<400> SEQUENCE: 370

Ala Gly Thr Tyr Gly Leu Gly Asp Val Arg Thr Pro Pro Lys Ser Pro
1 5 10 15

Ser Cys

<210> SEQ ID NO 371
<211> LENGTH: 19
<212> TYPE: PRT
<213> ORGANISM: Artificial Sequence
<220> FEATURE:
<223> OTHER INFORMATION: Synthetic construct

<400> SEQUENCE: 371

Ala Gly Thr Tyr Gly Leu Gly Asp Val Val Arg Thr Pro Pro Lys Ser
1 5 10 15

Pro Ser Cys

<210> SEQ ID NO 372
<211> LENGTH: 19
<212> TYPE: PRT
<213> ORGANISM: Artificial Sequence
<220> FEATURE:
<223> OTHER INFORMATION: Synthetic construct

<400> SEQUENCE: 372

Ala Gly Thr Tyr Gly Leu Gly Asp Val Arg Thr Pro Pro Lys Ser Pro
1 5 10 15

Ser Ser Cys

<210> SEQ ID NO 373
<211> LENGTH: 20
<212> TYPE: PRT
<213> ORGANISM: Artificial Sequence
<220> FEATURE:
<223> OTHER INFORMATION: Synthetic construct

<400> SEQUENCE: 373

Ala Gly Thr Tyr Gly Leu Gly Asp Ala Val Val Arg Thr Pro Pro Lys
1 5 10 15

Ser Pro Ser Cys
20

<210> SEQ ID NO 374
<211> LENGTH: 20
<212> TYPE: PRT
<213> ORGANISM: Artificial Sequence
<220> FEATURE:
<223> OTHER INFORMATION: Synthetic construct

<400> SEQUENCE: 374

Ala Gly Thr Tyr Gly Leu Gly Asp Val Val Arg Thr Pro Pro Lys Ser
1               5                   10                  15

Pro Ser Ser Cys
            20

<210> SEQ ID NO 375
<211> LENGTH: 20
<212> TYPE: PRT
<213> ORGANISM: Artificial Sequence
<220> FEATURE:
<223> OTHER INFORMATION: Synthetic construct

<400> SEQUENCE: 375

Ala Gly Thr Tyr Gly Leu Gly Asp Val Arg Thr Pro Pro Lys Ser Pro
1               5                   10                  15

Ser Ser Ala Cys
            20

<210> SEQ ID NO 376
<211> LENGTH: 21
<212> TYPE: PRT
<213> ORGANISM: Artificial Sequence
<220> FEATURE:
<223> OTHER INFORMATION: Synthetic construct

<400> SEQUENCE: 376

Ala Gly Thr Tyr Gly Leu Gly Asp Ala Val Val Arg Thr Pro Pro Lys
1               5                   10                  15

Ser Pro Ser Ser Cys
            20

<210> SEQ ID NO 377
<211> LENGTH: 21
<212> TYPE: PRT
<213> ORGANISM: Artificial Sequence
<220> FEATURE:
<223> OTHER INFORMATION: Synthetic construct

<400> SEQUENCE: 377

Ala Gly Thr Tyr Gly Leu Gly Asp Val Val Arg Thr Pro Pro Lys Ser
1               5                   10                  15

Pro Ser Ser Ala Cys
            20

<210> SEQ ID NO 378
<211> LENGTH: 22
<212> TYPE: PRT
<213> ORGANISM: Artificial Sequence
<220> FEATURE:
<223> OTHER INFORMATION: Synthetic construct

<400> SEQUENCE: 378

Ala Gly Thr Tyr Gly Leu Gly Asp Ala Val Val Arg Thr Pro Pro Lys
1               5                   10                  15

Ser Pro Ser Ser Ala Cys

20

<210> SEQ ID NO 379
<211> LENGTH: 19
<212> TYPE: PRT
<213> ORGANISM: Artificial Sequence
<220> FEATURE:
<223> OTHER INFORMATION: Synthetic construct

<400> SEQUENCE: 379

His Ala Gly Thr Tyr Gly Leu Gly Asp Val Arg Thr Pro Pro Lys Ser
1 5 10 15

Pro Ser Cys

<210> SEQ ID NO 380
<211> LENGTH: 20
<212> TYPE: PRT
<213> ORGANISM: Artificial Sequence
<220> FEATURE:
<223> OTHER INFORMATION: Synthetic construct

<400> SEQUENCE: 380

His Ala Gly Thr Tyr Gly Leu Gly Asp Val Val Arg Thr Pro Pro Lys
1 5 10 15

Ser Pro Ser Cys
20

<210> SEQ ID NO 381
<211> LENGTH: 20
<212> TYPE: PRT
<213> ORGANISM: Artificial Sequence
<220> FEATURE:
<223> OTHER INFORMATION: Synthetic construct

<400> SEQUENCE: 381

His Ala Gly Thr Tyr Gly Leu Gly Asp Val Arg Thr Pro Pro Lys Ser
1 5 10 15

Pro Ser Ser Cys
20

<210> SEQ ID NO 382
<211> LENGTH: 21
<212> TYPE: PRT
<213> ORGANISM: Artificial Sequence
<220> FEATURE:
<223> OTHER INFORMATION: Synthetic construct

<400> SEQUENCE: 382

His Ala Gly Thr Tyr Gly Leu Gly Asp Ala Val Val Arg Thr Pro Pro
1 5 10 15

Lys Ser Pro Ser Cys
20

<210> SEQ ID NO 383
<211> LENGTH: 21
<212> TYPE: PRT
<213> ORGANISM: Artificial Sequence
<220> FEATURE:
<223> OTHER INFORMATION: Synthetic construct

<400> SEQUENCE: 383

His Ala Gly Thr Tyr Gly Leu Gly Asp Val Val Arg Thr Pro Pro Lys
1 5 10 15

Ser Pro Ser Ser Cys

20

<210> SEQ ID NO 384
<211> LENGTH: 21
<212> TYPE: PRT
<213> ORGANISM: Artificial Sequence
<220> FEATURE:
<223> OTHER INFORMATION: Synthetic construct

<400> SEQUENCE: 384

His Ala Gly Thr Tyr Gly Leu Gly Asp Val Arg Thr Pro Pro Lys Ser
1 5 10 15

Pro Ser Ser Ala Cys
20

<210> SEQ ID NO 385
<211> LENGTH: 22
<212> TYPE: PRT
<213> ORGANISM: Artificial Sequence
<220> FEATURE:
<223> OTHER INFORMATION: Synthetic construct

<400> SEQUENCE: 385

His Ala Gly Thr Tyr Gly Leu Gly Asp Ala Val Val Arg Thr Pro Pro
1 5 10 15

Lys Ser Pro Ser Ser Cys
20

<210> SEQ ID NO 386
<211> LENGTH: 22
<212> TYPE: PRT
<213> ORGANISM: Artificial Sequence
<220> FEATURE:
<223> OTHER INFORMATION: Synthetic construct

<400> SEQUENCE: 386

His Ala Gly Thr Tyr Gly Leu Gly Asp Val Val Arg Thr Pro Pro Lys
1 5 10 15

Ser Pro Ser Ser Ala Cys
20

<210> SEQ ID NO 387
<211> LENGTH: 23
<212> TYPE: PRT
<213> ORGANISM: Artificial Sequence
<220> FEATURE:
<223> OTHER INFORMATION: Synthetic construct

<400> SEQUENCE: 387

His Ala Gly Thr Tyr Gly Leu Gly Asp Ala Val Val Arg Thr Pro Pro
1 5 10 15

Lys Ser Pro Ser Ser Ala Cys
20

<210> SEQ ID NO 388
<211> LENGTH: 20
<212> TYPE: PRT
<213> ORGANISM: Artificial Sequence
<220> FEATURE:
<223> OTHER INFORMATION: Synthetic construct

<400> SEQUENCE: 388

Gly Thr Tyr Gly Leu Pro Ser Ser Ala Lys Ser Arg Ser Lys Ile Gly
1 5 10 15

Ser Thr Glu Cys
20

<210> SEQ ID NO 389
<211> LENGTH: 21
<212> TYPE: PRT
<213> ORGANISM: Artificial Sequence
<220> FEATURE:
<223> OTHER INFORMATION: Synthetic construct

<400> SEQUENCE: 389

Gly Thr Tyr Gly Leu Ser Pro Ser Ser Ala Lys Ser Arg Ser Lys Ile
1 5 10 15

Gly Ser Thr Glu Cys
20

<210> SEQ ID NO 390
<211> LENGTH: 21
<212> TYPE: PRT
<213> ORGANISM: Artificial Sequence
<220> FEATURE:
<223> OTHER INFORMATION: Synthetic construct

<400> SEQUENCE: 390

Gly Thr Tyr Gly Leu Pro Ser Ser Ala Lys Ser Arg Ser Lys Ile Gly
1 5 10 15

Ser Thr Glu Asn Cys
20

<210> SEQ ID NO 391
<211> LENGTH: 22
<212> TYPE: PRT
<213> ORGANISM: Artificial Sequence
<220> FEATURE:
<223> OTHER INFORMATION: Synthetic construct

<400> SEQUENCE: 391

Gly Thr Tyr Gly Leu Lys Ser Pro Ser Ser Ala Lys Ser Arg Ser Lys
1 5 10 15

Ile Gly Ser Thr Glu Cys
20

<210> SEQ ID NO 392
<211> LENGTH: 22
<212> TYPE: PRT
<213> ORGANISM: Artificial Sequence
<220> FEATURE:
<223> OTHER INFORMATION: Synthetic construct

<400> SEQUENCE: 392

Gly Thr Tyr Gly Leu Ser Pro Ser Ser Ala Lys Ser Arg Ser Lys Ile
1 5 10 15

Gly Ser Thr Glu Asn Cys
20

<210> SEQ ID NO 393
<211> LENGTH: 22
<212> TYPE: PRT
<213> ORGANISM: Artificial Sequence
<220> FEATURE:
<223> OTHER INFORMATION: Synthetic construct

<400> SEQUENCE: 393

Gly Thr Tyr Gly Leu Pro Ser Ser Ala Lys Ser Arg Ser Lys Ile Gly
1 5 10 15

Ser Thr Glu Asn Leu Cys
20

<210> SEQ ID NO 394
<211> LENGTH: 23
<212> TYPE: PRT
<213> ORGANISM: Artificial Sequence
<220> FEATURE:
<223> OTHER INFORMATION: Synthetic construct

<400> SEQUENCE: 394

Gly Thr Tyr Gly Leu Lys Ser Pro Ser Ser Ala Lys Ser Arg Ser Lys
1 5 10 15

Ile Gly Ser Thr Glu Asn Cys
20

<210> SEQ ID NO 395
<211> LENGTH: 23
<212> TYPE: PRT
<213> ORGANISM: Artificial Sequence
<220> FEATURE:
<223> OTHER INFORMATION: Synthetic construct

<400> SEQUENCE: 395

Gly Thr Tyr Gly Leu Ser Pro Ser Ser Ala Lys Ser Arg Ser Lys Ile
1 5 10 15

Gly Ser Thr Glu Asn Leu Cys
20

<210> SEQ ID NO 396
<211> LENGTH: 24
<212> TYPE: PRT
<213> ORGANISM: Artificial Sequence
<220> FEATURE:
<223> OTHER INFORMATION: Synthetic construct

<400> SEQUENCE: 396

Gly Thr Tyr Gly Leu Lys Ser Pro Ser Ser Ala Lys Ser Arg Ser Lys
1 5 10 15

Ile Gly Ser Thr Glu Asn Leu Cys
20

<210> SEQ ID NO 397
<211> LENGTH: 21
<212> TYPE: PRT
<213> ORGANISM: Artificial Sequence
<220> FEATURE:
<223> OTHER INFORMATION: Synthetic construct

<400> SEQUENCE: 397

Ala Gly Thr Tyr Gly Leu Pro Ser Ser Ala Lys Ser Arg Ser Lys Ile
1 5 10 15

Gly Ser Thr Glu Cys
20

<210> SEQ ID NO 398
<211> LENGTH: 22
<212> TYPE: PRT
<213> ORGANISM: Artificial Sequence
<220> FEATURE:
<223> OTHER INFORMATION: Synthetic construct

<400> SEQUENCE: 398

Ala Gly Thr Tyr Gly Leu Ser Pro Ser Ser Ala Lys Ser Arg Ser Lys 1 5 10 15

Ile Gly Ser Thr Glu Cys
20

<210> SEQ ID NO 399
<211> LENGTH: 22
<212> TYPE: PRT
<213> ORGANISM: Artificial Sequence
<220> FEATURE:
<223> OTHER INFORMATION: Synthetic construct

<400> SEQUENCE: 399

Ala Gly Thr Tyr Gly Leu Pro Ser Ser Ala Lys Ser Arg Ser Lys Ile
1 5 10 15

Gly Ser Thr Glu Asn Cys
20

<210> SEQ ID NO 400
<211> LENGTH: 23
<212> TYPE: PRT
<213> ORGANISM: Artificial Sequence
<220> FEATURE:
<223> OTHER INFORMATION: Synthetic construct

<400> SEQUENCE: 400

Ala Gly Thr Tyr Gly Leu Lys Ser Pro Ser Ser Ala Lys Ser Arg Ser
1 5 10 15

Lys Ile Gly Ser Thr Glu Cys
20

<210> SEQ ID NO 401
<211> LENGTH: 23
<212> TYPE: PRT
<213> ORGANISM: Artificial Sequence
<220> FEATURE:
<223> OTHER INFORMATION: Synthetic construct

<400> SEQUENCE: 401

Ala Gly Thr Tyr Gly Leu Ser Pro Ser Ser Ala Lys Ser Arg Ser Lys
1 5 10 15

Ile Gly Ser Thr Glu Asn Cys
20

<210> SEQ ID NO 402
<211> LENGTH: 23
<212> TYPE: PRT
<213> ORGANISM: Artificial Sequence
<220> FEATURE:
<223> OTHER INFORMATION: Synthetic construct

<400> SEQUENCE: 402

Ala Gly Thr Tyr Gly Leu Pro Ser Ser Ala Lys Ser Arg Ser Lys Ile
1 5 10 15

Gly Ser Thr Glu Asn Leu Cys
20

<210> SEQ ID NO 403
<211> LENGTH: 24
<212> TYPE: PRT
<213> ORGANISM: Artificial Sequence
<220> FEATURE:
<223> OTHER INFORMATION: Synthetic construct

<400> SEQUENCE: 403

```
Ala Gly Thr Tyr Gly Leu Lys Ser Pro Ser Ser Ala Lys Ser Arg Ser
1               5                   10                  15

Lys Ile Gly Ser Thr Glu Asn Cys
            20


<210> SEQ ID NO 404
<211> LENGTH: 24
<212> TYPE: PRT
<213> ORGANISM: Artificial Sequence
<220> FEATURE:
<223> OTHER INFORMATION: Synthetic construct

<400> SEQUENCE: 404

Ala Gly Thr Tyr Gly Leu Ser Pro Ser Ser Ala Lys Ser Arg Ser Lys
1               5                   10                  15

Ile Gly Ser Thr Glu Asn Leu Cys
            20


<210> SEQ ID NO 405
<211> LENGTH: 25
<212> TYPE: PRT
<213> ORGANISM: Artificial Sequence
<220> FEATURE:
<223> OTHER INFORMATION: Synthetic construct

<400> SEQUENCE: 405

Ala Gly Thr Tyr Gly Leu Lys Ser Pro Ser Ser Ala Lys Ser Arg Ser
1               5                   10                  15

Lys Ile Gly Ser Thr Glu Asn Leu Cys
            20                  25


<210> SEQ ID NO 406
<211> LENGTH: 21
<212> TYPE: PRT
<213> ORGANISM: Artificial Sequence
<220> FEATURE:
<223> OTHER INFORMATION: Synthetic construct

<400> SEQUENCE: 406

Gly Thr Tyr Gly Leu Gly Pro Ser Ser Ala Lys Ser Arg Ser Lys Ile
1               5                   10                  15

Gly Ser Thr Glu Cys
            20


<210> SEQ ID NO 407
<211> LENGTH: 22
<212> TYPE: PRT
<213> ORGANISM: Artificial Sequence
<220> FEATURE:
<223> OTHER INFORMATION: Synthetic construct

<400> SEQUENCE: 407

Gly Thr Tyr Gly Leu Gly Ser Pro Ser Ser Ala Lys Ser Arg Ser Lys
1               5                   10                  15

Ile Gly Ser Thr Glu Cys
            20


<210> SEQ ID NO 408
<211> LENGTH: 22
<212> TYPE: PRT
<213> ORGANISM: Artificial Sequence
<220> FEATURE:
<223> OTHER INFORMATION: Synthetic construct

<400> SEQUENCE: 408
```

Gly Thr Tyr Gly Leu Gly Pro Ser Ser Ala Lys Ser Arg Ser Lys Ile
1 5 10 15

Gly Ser Thr Glu Asn Cys
20

<210> SEQ ID NO 409
<211> LENGTH: 23
<212> TYPE: PRT
<213> ORGANISM: Artificial Sequence
<220> FEATURE:
<223> OTHER INFORMATION: Synthetic construct

<400> SEQUENCE: 409

Gly Thr Tyr Gly Leu Gly Lys Ser Pro Ser Ser Ala Lys Ser Arg Ser
1 5 10 15

Lys Ile Gly Ser Thr Glu Cys
20

<210> SEQ ID NO 410
<211> LENGTH: 23
<212> TYPE: PRT
<213> ORGANISM: Artificial Sequence
<220> FEATURE:
<223> OTHER INFORMATION: Synthetic construct

<400> SEQUENCE: 410

Gly Thr Tyr Gly Leu Gly Ser Pro Ser Ser Ala Lys Ser Arg Ser Lys
1 5 10 15

Ile Gly Ser Thr Glu Asn Cys
20

<210> SEQ ID NO 411
<211> LENGTH: 23
<212> TYPE: PRT
<213> ORGANISM: Artificial Sequence
<220> FEATURE:
<223> OTHER INFORMATION: Synthetic construct

<400> SEQUENCE: 411

Gly Thr Tyr Gly Leu Gly Pro Ser Ser Ala Lys Ser Arg Ser Lys Ile
1 5 10 15

Gly Ser Thr Glu Asn Leu Cys
20

<210> SEQ ID NO 412
<211> LENGTH: 24
<212> TYPE: PRT
<213> ORGANISM: Artificial Sequence
<220> FEATURE:
<223> OTHER INFORMATION: Synthetic construct

<400> SEQUENCE: 412

Gly Thr Tyr Gly Leu Gly Lys Ser Pro Ser Ser Ala Lys Ser Arg Ser
1 5 10 15

Lys Ile Gly Ser Thr Glu Asn Cys
20

<210> SEQ ID NO 413
<211> LENGTH: 24
<212> TYPE: PRT
<213> ORGANISM: Artificial Sequence
<220> FEATURE:
<223> OTHER INFORMATION: Synthetic construct

<400> SEQUENCE: 413

Gly Thr Tyr Gly Leu Gly Ser Pro Ser Ser Ala Lys Ser Arg Ser Lys
1 5 10 15

Ile Gly Ser Thr Glu Asn Leu Cys
20

<210> SEQ ID NO 414
<211> LENGTH: 25
<212> TYPE: PRT
<213> ORGANISM: Artificial Sequence
<220> FEATURE:
<223> OTHER INFORMATION: Synthetic construct

<400> SEQUENCE: 414

Gly Thr Tyr Gly Leu Gly Lys Ser Pro Ser Ser Ala Lys Ser Arg Ser
1 5 10 15

Lys Ile Gly Ser Thr Glu Asn Leu Cys
20 25

<210> SEQ ID NO 415
<211> LENGTH: 22
<212> TYPE: PRT
<213> ORGANISM: Artificial Sequence
<220> FEATURE:
<223> OTHER INFORMATION: Synthetic construct

<400> SEQUENCE: 415

His Ala Gly Thr Tyr Gly Leu Pro Ser Ser Ala Lys Ser Arg Ser Lys
1 5 10 15

Ile Gly Ser Thr Glu Cys
20

<210> SEQ ID NO 416
<211> LENGTH: 23
<212> TYPE: PRT
<213> ORGANISM: Artificial Sequence
<220> FEATURE:
<223> OTHER INFORMATION: Synthetic construct

<400> SEQUENCE: 416

His Ala Gly Thr Tyr Gly Leu Ser Pro Ser Ser Ala Lys Ser Arg Ser
1 5 10 15

Lys Ile Gly Ser Thr Glu Cys
20

<210> SEQ ID NO 417
<211> LENGTH: 23
<212> TYPE: PRT
<213> ORGANISM: Artificial Sequence
<220> FEATURE:
<223> OTHER INFORMATION: Synthetic construct

<400> SEQUENCE: 417

His Ala Gly Thr Tyr Gly Leu Pro Ser Ser Ala Lys Ser Arg Ser Lys
1 5 10 15

Ile Gly Ser Thr Glu Asn Cys
20

<210> SEQ ID NO 418
<211> LENGTH: 24
<212> TYPE: PRT
<213> ORGANISM: Artificial Sequence
<220> FEATURE:
<223> OTHER INFORMATION: Synthetic construct

<400> SEQUENCE: 418

His Ala Gly Thr Tyr Gly Leu Lys Ser Pro Ser Ser Ala Lys Ser Arg
1 5 10 15

Ser Lys Ile Gly Ser Thr Glu Cys
20

<210> SEQ ID NO 419
<211> LENGTH: 24
<212> TYPE: PRT
<213> ORGANISM: Artificial Sequence
<220> FEATURE:
<223> OTHER INFORMATION: Synthetic construct

<400> SEQUENCE: 419

His Ala Gly Thr Tyr Gly Leu Ser Pro Ser Ser Ala Lys Ser Arg Ser
1 5 10 15

Lys Ile Gly Ser Thr Glu Asn Cys
20

<210> SEQ ID NO 420
<211> LENGTH: 24
<212> TYPE: PRT
<213> ORGANISM: Artificial Sequence
<220> FEATURE:
<223> OTHER INFORMATION: Synthetic construct

<400> SEQUENCE: 420

His Ala Gly Thr Tyr Gly Leu Pro Ser Ser Ala Lys Ser Arg Ser Lys
1 5 10 15

Ile Gly Ser Thr Glu Asn Leu Cys
20

<210> SEQ ID NO 421
<211> LENGTH: 25
<212> TYPE: PRT
<213> ORGANISM: Artificial Sequence
<220> FEATURE:
<223> OTHER INFORMATION: Synthetic construct

<400> SEQUENCE: 421

His Ala Gly Thr Tyr Gly Leu Lys Ser Pro Ser Ser Ala Lys Ser Arg
1 5 10 15

Ser Lys Ile Gly Ser Thr Glu Asn Cys
20 25

<210> SEQ ID NO 422
<211> LENGTH: 25
<212> TYPE: PRT
<213> ORGANISM: Artificial Sequence
<220> FEATURE:
<223> OTHER INFORMATION: Synthetic construct

<400> SEQUENCE: 422

His Ala Gly Thr Tyr Gly Leu Ser Pro Ser Ser Ala Lys Ser Arg Ser
1 5 10 15

Lys Ile Gly Ser Thr Glu Asn Leu Cys
20 25

<210> SEQ ID NO 423
<211> LENGTH: 26
<212> TYPE: PRT
<213> ORGANISM: Artificial Sequence
<220> FEATURE:

<223> OTHER INFORMATION: Synthetic construct

<400> SEQUENCE: 423

His Ala Gly Thr Tyr Gly Leu Lys Ser Pro Ser Ser Ala Lys Ser Arg
1               5                   10                  15

Ser Lys Ile Gly Ser Thr Glu Asn Leu Cys
            20                  25

<210> SEQ ID NO 424
<211> LENGTH: 22
<212> TYPE: PRT
<213> ORGANISM: Artificial Sequence
<220> FEATURE:
<223> OTHER INFORMATION: Synthetic construct

<400> SEQUENCE: 424

Ala Gly Thr Tyr Gly Leu Gly Pro Ser Ser Ala Lys Ser Arg Ser Lys
1               5                   10                  15

Ile Gly Ser Thr Glu Cys
            20

<210> SEQ ID NO 425
<211> LENGTH: 23
<212> TYPE: PRT
<213> ORGANISM: Artificial Sequence
<220> FEATURE:
<223> OTHER INFORMATION: Synthetic construct

<400> SEQUENCE: 425

Ala Gly Thr Tyr Gly Leu Gly Ser Pro Ser Ser Ala Lys Ser Arg Ser
1               5                   10                  15

Lys Ile Gly Ser Thr Glu Cys
            20

<210> SEQ ID NO 426
<211> LENGTH: 23
<212> TYPE: PRT
<213> ORGANISM: Artificial Sequence
<220> FEATURE:
<223> OTHER INFORMATION: Synthetic construct

<400> SEQUENCE: 426

Ala Gly Thr Tyr Gly Leu Gly Pro Ser Ser Ala Lys Ser Arg Ser Lys
1               5                   10                  15

Ile Gly Ser Thr Glu Asn Cys
            20

<210> SEQ ID NO 427
<211> LENGTH: 24
<212> TYPE: PRT
<213> ORGANISM: Artificial Sequence
<220> FEATURE:
<223> OTHER INFORMATION: Synthetic construct

<400> SEQUENCE: 427

Ala Gly Thr Tyr Gly Leu Gly Lys Ser Pro Ser Ser Ala Lys Ser Arg
1               5                   10                  15

Ser Lys Ile Gly Ser Thr Glu Cys
            20

<210> SEQ ID NO 428
<211> LENGTH: 24
<212> TYPE: PRT
<213> ORGANISM: Artificial Sequence
<220> FEATURE:
<223> OTHER INFORMATION: Synthetic construct

<400> SEQUENCE: 428

Ala Gly Thr Tyr Gly Leu Gly Ser Pro Ser Ser Ala Lys Ser Arg Ser
1 5 10 15

Lys Ile Gly Ser Thr Glu Asn Cys
20

<210> SEQ ID NO 429
<211> LENGTH: 24
<212> TYPE: PRT
<213> ORGANISM: Artificial Sequence
<220> FEATURE:
<223> OTHER INFORMATION: Synthetic construct

<400> SEQUENCE: 429

Ala Gly Thr Tyr Gly Leu Gly Pro Ser Ser Ala Lys Ser Arg Ser Lys
1 5 10 15

Ile Gly Ser Thr Glu Asn Leu Cys
20

<210> SEQ ID NO 430
<211> LENGTH: 25
<212> TYPE: PRT
<213> ORGANISM: Artificial Sequence
<220> FEATURE:
<223> OTHER INFORMATION: Synthetic construct

<400> SEQUENCE: 430

Ala Gly Thr Tyr Gly Leu Gly Lys Ser Pro Ser Ser Ala Lys Ser Arg
1 5 10 15

Ser Lys Ile Gly Ser Thr Glu Asn Cys
20 25

<210> SEQ ID NO 431
<211> LENGTH: 25
<212> TYPE: PRT
<213> ORGANISM: Artificial Sequence
<220> FEATURE:
<223> OTHER INFORMATION: Synthetic construct

<400> SEQUENCE: 431

Ala Gly Thr Tyr Gly Leu Gly Ser Pro Ser Ser Ala Lys Ser Arg Ser
1 5 10 15

Lys Ile Gly Ser Thr Glu Asn Leu Cys
20 25

<210> SEQ ID NO 432
<211> LENGTH: 26
<212> TYPE: PRT
<213> ORGANISM: Artificial Sequence
<220> FEATURE:
<223> OTHER INFORMATION: Synthetic construct

<400> SEQUENCE: 432

Ala Gly Thr Tyr Gly Leu Gly Lys Ser Pro Ser Ser Ala Lys Ser Arg
1 5 10 15

Ser Lys Ile Gly Ser Thr Glu Asn Leu Cys
20 25

<210> SEQ ID NO 433
<211> LENGTH: 22
<212> TYPE: PRT

<213> ORGANISM: Artificial Sequence
<220> FEATURE:
<223> OTHER INFORMATION: Synthetic construct

<400> SEQUENCE: 433

Gly Thr Tyr Gly Leu Gly Asp Pro Ser Ser Ala Lys Ser Arg Ser Lys
1 5 10 15

Ile Gly Ser Thr Glu Cys
20

<210> SEQ ID NO 434
<211> LENGTH: 23
<212> TYPE: PRT
<213> ORGANISM: Artificial Sequence
<220> FEATURE:
<223> OTHER INFORMATION: Synthetic construct

<400> SEQUENCE: 434

Gly Thr Tyr Gly Leu Gly Asp Ser Pro Ser Ser Ala Lys Ser Arg Ser
1 5 10 15

Lys Ile Gly Ser Thr Glu Cys
20

<210> SEQ ID NO 435
<211> LENGTH: 23
<212> TYPE: PRT
<213> ORGANISM: Artificial Sequence
<220> FEATURE:
<223> OTHER INFORMATION: Synthetic construct

<400> SEQUENCE: 435

Gly Thr Tyr Gly Leu Gly Asp Pro Ser Ser Ala Lys Ser Arg Ser Lys
1 5 10 15

Ile Gly Ser Thr Glu Asn Cys
20

<210> SEQ ID NO 436
<211> LENGTH: 24
<212> TYPE: PRT
<213> ORGANISM: Artificial Sequence
<220> FEATURE:
<223> OTHER INFORMATION: Synthetic construct

<400> SEQUENCE: 436

Gly Thr Tyr Gly Leu Gly Asp Lys Ser Pro Ser Ser Ala Lys Ser Arg
1 5 10 15

Ser Lys Ile Gly Ser Thr Glu Cys
20

<210> SEQ ID NO 437
<211> LENGTH: 24
<212> TYPE: PRT
<213> ORGANISM: Artificial Sequence
<220> FEATURE:
<223> OTHER INFORMATION: Synthetic construct

<400> SEQUENCE: 437

Gly Thr Tyr Gly Leu Gly Asp Ser Pro Ser Ser Ala Lys Ser Arg Ser
1 5 10 15

Lys Ile Gly Ser Thr Glu Asn Cys
20

<210> SEQ ID NO 438
<211> LENGTH: 24

<212> TYPE: PRT
<213> ORGANISM: Artificial Sequence
<220> FEATURE:
<223> OTHER INFORMATION: Synthetic construct

<400> SEQUENCE: 438

Gly Thr Tyr Gly Leu Gly Asp Pro Ser Ser Ala Lys Ser Arg Ser Lys
1 5 10 15

Ile Gly Ser Thr Glu Asn Leu Cys
20

<210> SEQ ID NO 439
<211> LENGTH: 25
<212> TYPE: PRT
<213> ORGANISM: Artificial Sequence
<220> FEATURE:
<223> OTHER INFORMATION: Synthetic construct

<400> SEQUENCE: 439

Gly Thr Tyr Gly Leu Gly Asp Lys Ser Pro Ser Ser Ala Lys Ser Arg
1 5 10 15

Ser Lys Ile Gly Ser Thr Glu Asn Cys
20 25

<210> SEQ ID NO 440
<211> LENGTH: 25
<212> TYPE: PRT
<213> ORGANISM: Artificial Sequence
<220> FEATURE:
<223> OTHER INFORMATION: Synthetic construct

<400> SEQUENCE: 440

Gly Thr Tyr Gly Leu Gly Asp Ser Pro Ser Ser Ala Lys Ser Arg Ser
1 5 10 15

Lys Ile Gly Ser Thr Glu Asn Leu Cys
20 25

<210> SEQ ID NO 441
<211> LENGTH: 26
<212> TYPE: PRT
<213> ORGANISM: Artificial Sequence
<220> FEATURE:
<223> OTHER INFORMATION: Synthetic construct

<400> SEQUENCE: 441

Gly Thr Tyr Gly Leu Gly Asp Lys Ser Pro Ser Ser Ala Lys Ser Arg
1 5 10 15

Ser Lys Ile Gly Ser Thr Glu Asn Leu Cys
20 25

<210> SEQ ID NO 442
<211> LENGTH: 23
<212> TYPE: PRT
<213> ORGANISM: Artificial Sequence
<220> FEATURE:
<223> OTHER INFORMATION: Synthetic construct

<400> SEQUENCE: 442

His Ala Gly Thr Tyr Gly Leu Gly Pro Ser Ser Ala Lys Ser Arg Ser
1 5 10 15

Lys Ile Gly Ser Thr Glu Cys
20

<210> SEQ ID NO 443

<211> LENGTH: 24
<212> TYPE: PRT
<213> ORGANISM: Artificial Sequence
<220> FEATURE:
<223> OTHER INFORMATION: Synthetic construct

<400> SEQUENCE: 443

His Ala Gly Thr Tyr Gly Leu Gly Ser Pro Ser Ser Ala Lys Ser Arg
1 5 10 15

Ser Lys Ile Gly Ser Thr Glu Cys
20

<210> SEQ ID NO 444
<211> LENGTH: 24
<212> TYPE: PRT
<213> ORGANISM: Artificial Sequence
<220> FEATURE:
<223> OTHER INFORMATION: Synthetic construct

<400> SEQUENCE: 444

His Ala Gly Thr Tyr Gly Leu Gly Pro Ser Ser Ala Lys Ser Arg Ser
1 5 10 15

Lys Ile Gly Ser Thr Glu Asn Cys
20

<210> SEQ ID NO 445
<211> LENGTH: 25
<212> TYPE: PRT
<213> ORGANISM: Artificial Sequence
<220> FEATURE:
<223> OTHER INFORMATION: Synthetic construct

<400> SEQUENCE: 445

His Ala Gly Thr Tyr Gly Leu Gly Lys Ser Pro Ser Ser Ala Lys Ser
1 5 10 15

Arg Ser Lys Ile Gly Ser Thr Glu Cys
20 25

<210> SEQ ID NO 446
<211> LENGTH: 25
<212> TYPE: PRT
<213> ORGANISM: Artificial Sequence
<220> FEATURE:
<223> OTHER INFORMATION: Synthetic construct

<400> SEQUENCE: 446

His Ala Gly Thr Tyr Gly Leu Gly Ser Pro Ser Ser Ala Lys Ser Arg
1 5 10 15

Ser Lys Ile Gly Ser Thr Glu Asn Cys
20 25

<210> SEQ ID NO 447
<211> LENGTH: 25
<212> TYPE: PRT
<213> ORGANISM: Artificial Sequence
<220> FEATURE:
<223> OTHER INFORMATION: Synthetic construct

<400> SEQUENCE: 447

His Ala Gly Thr Tyr Gly Leu Gly Pro Ser Ser Ala Lys Ser Arg Ser
1 5 10 15

Lys Ile Gly Ser Thr Glu Asn Leu Cys
20 25

<210> SEQ ID NO 448
<211> LENGTH: 26
<212> TYPE: PRT
<213> ORGANISM: Artificial Sequence
<220> FEATURE:
<223> OTHER INFORMATION: Synthetic construct

<400> SEQUENCE: 448

His Ala Gly Thr Tyr Gly Leu Gly Lys Ser Pro Ser Ser Ala Lys Ser
1               5                   10                  15

Arg Ser Lys Ile Gly Ser Thr Glu Asn Cys
            20                  25

<210> SEQ ID NO 449
<211> LENGTH: 26
<212> TYPE: PRT
<213> ORGANISM: Artificial Sequence
<220> FEATURE:
<223> OTHER INFORMATION: Synthetic construct

<400> SEQUENCE: 449

His Ala Gly Thr Tyr Gly Leu Gly Ser Pro Ser Ser Ala Lys Ser Arg
1               5                   10                  15

Ser Lys Ile Gly Ser Thr Glu Asn Leu Cys
            20                  25

<210> SEQ ID NO 450
<211> LENGTH: 27
<212> TYPE: PRT
<213> ORGANISM: Artificial Sequence
<220> FEATURE:
<223> OTHER INFORMATION: Synthetic construct

<400> SEQUENCE: 450

His Ala Gly Thr Tyr Gly Leu Gly Lys Ser Pro Ser Ser Ala Lys Ser
1               5                   10                  15

Arg Ser Lys Ile Gly Ser Thr Glu Asn Leu Cys
            20                  25

<210> SEQ ID NO 451
<211> LENGTH: 23
<212> TYPE: PRT
<213> ORGANISM: Artificial Sequence
<220> FEATURE:
<223> OTHER INFORMATION: Synthetic construct

<400> SEQUENCE: 451

Ala Gly Thr Tyr Gly Leu Gly Asp Pro Ser Ser Ala Lys Ser Arg Ser
1               5                   10                  15

Lys Ile Gly Ser Thr Glu Cys
            20

<210> SEQ ID NO 452
<211> LENGTH: 24
<212> TYPE: PRT
<213> ORGANISM: Artificial Sequence
<220> FEATURE:
<223> OTHER INFORMATION: Synthetic construct

<400> SEQUENCE: 452

Ala Gly Thr Tyr Gly Leu Gly Asp Ser Pro Ser Ser Ala Lys Ser Arg
1               5                   10                  15

Ser Lys Ile Gly Ser Thr Glu Cys
            20

```
<210> SEQ ID NO 453
<211> LENGTH: 24
<212> TYPE: PRT
<213> ORGANISM: Artificial Sequence
<220> FEATURE:
<223> OTHER INFORMATION: Synthetic construct

<400> SEQUENCE: 453

Ala Gly Thr Tyr Gly Leu Gly Asp Pro Ser Ser Ala Lys Ser Arg Ser
1               5                   10                  15

Lys Ile Gly Ser Thr Glu Asn Cys
            20


<210> SEQ ID NO 454
<211> LENGTH: 25
<212> TYPE: PRT
<213> ORGANISM: Artificial Sequence
<220> FEATURE:
<223> OTHER INFORMATION: Synthetic construct

<400> SEQUENCE: 454

Ala Gly Thr Tyr Gly Leu Gly Asp Lys Ser Pro Ser Ser Ala Lys Ser
1               5                   10                  15

Arg Ser Lys Ile Gly Ser Thr Glu Cys
            20                  25


<210> SEQ ID NO 455
<211> LENGTH: 25
<212> TYPE: PRT
<213> ORGANISM: Artificial Sequence
<220> FEATURE:
<223> OTHER INFORMATION: Synthetic construct

<400> SEQUENCE: 455

Ala Gly Thr Tyr Gly Leu Gly Asp Ser Pro Ser Ser Ala Lys Ser Arg
1               5                   10                  15

Ser Lys Ile Gly Ser Thr Glu Asn Cys
            20                  25


<210> SEQ ID NO 456
<211> LENGTH: 25
<212> TYPE: PRT
<213> ORGANISM: Artificial Sequence
<220> FEATURE:
<223> OTHER INFORMATION: Synthetic construct

<400> SEQUENCE: 456

Ala Gly Thr Tyr Gly Leu Gly Asp Pro Ser Ser Ala Lys Ser Arg Ser
1               5                   10                  15

Lys Ile Gly Ser Thr Glu Asn Leu Cys
            20                  25


<210> SEQ ID NO 457
<211> LENGTH: 26
<212> TYPE: PRT
<213> ORGANISM: Artificial Sequence
<220> FEATURE:
<223> OTHER INFORMATION: Synthetic construct

<400> SEQUENCE: 457

Ala Gly Thr Tyr Gly Leu Gly Asp Lys Ser Pro Ser Ser Ala Lys Ser
1               5                   10                  15

Arg Ser Lys Ile Gly Ser Thr Glu Asn Cys
            20                  25
```

<210> SEQ ID NO 458
<211> LENGTH: 26
<212> TYPE: PRT
<213> ORGANISM: Artificial Sequence
<220> FEATURE:
<223> OTHER INFORMATION: Synthetic construct

<400> SEQUENCE: 458

Ala Gly Thr Tyr Gly Leu Gly Asp Ser Pro Ser Ser Ala Lys Ser Arg
1 5 10 15

Ser Lys Ile Gly Ser Thr Glu Asn Leu Cys
20 25

<210> SEQ ID NO 459
<211> LENGTH: 27
<212> TYPE: PRT
<213> ORGANISM: Artificial Sequence
<220> FEATURE:
<223> OTHER INFORMATION: Synthetic construct

<400> SEQUENCE: 459

Ala Gly Thr Tyr Gly Leu Gly Asp Lys Ser Pro Ser Ser Ala Lys Ser
1 5 10 15

Arg Ser Lys Ile Gly Ser Thr Glu Asn Leu Cys
20 25

<210> SEQ ID NO 460
<211> LENGTH: 24
<212> TYPE: PRT
<213> ORGANISM: Artificial Sequence
<220> FEATURE:
<223> OTHER INFORMATION: Synthetic construct

<400> SEQUENCE: 460

His Ala Gly Thr Tyr Gly Leu Gly Asp Pro Ser Ser Ala Lys Ser Arg
1 5 10 15

Ser Lys Ile Gly Ser Thr Glu Cys
20

<210> SEQ ID NO 461
<211> LENGTH: 25
<212> TYPE: PRT
<213> ORGANISM: Artificial Sequence
<220> FEATURE:
<223> OTHER INFORMATION: Synthetic construct

<400> SEQUENCE: 461

His Ala Gly Thr Tyr Gly Leu Gly Asp Ser Pro Ser Ser Ala Lys Ser
1 5 10 15

Arg Ser Lys Ile Gly Ser Thr Glu Cys
20 25

<210> SEQ ID NO 462
<211> LENGTH: 25
<212> TYPE: PRT
<213> ORGANISM: Artificial Sequence
<220> FEATURE:
<223> OTHER INFORMATION: Synthetic construct

<400> SEQUENCE: 462

His Ala Gly Thr Tyr Gly Leu Gly Asp Pro Ser Ser Ala Lys Ser Arg
1 5 10 15

Ser Lys Ile Gly Ser Thr Glu Asn Cys 20 25

<210> SEQ ID NO 463
<211> LENGTH: 26
<212> TYPE: PRT
<213> ORGANISM: Artificial Sequence
<220> FEATURE:
<223> OTHER INFORMATION: Synthetic construct

<400> SEQUENCE: 463

His Ala Gly Thr Tyr Gly Leu Gly Asp Lys Ser Pro Ser Ser Ala Lys
1 5 10 15

Ser Arg Ser Lys Ile Gly Ser Thr Glu Cys
20 25

<210> SEQ ID NO 464
<211> LENGTH: 26
<212> TYPE: PRT
<213> ORGANISM: Artificial Sequence
<220> FEATURE:
<223> OTHER INFORMATION: Synthetic construct

<400> SEQUENCE: 464

His Ala Gly Thr Tyr Gly Leu Gly Asp Ser Pro Ser Ser Ala Lys Ser
1 5 10 15

Arg Ser Lys Ile Gly Ser Thr Glu Asn Cys
20 25

<210> SEQ ID NO 465
<211> LENGTH: 26
<212> TYPE: PRT
<213> ORGANISM: Artificial Sequence
<220> FEATURE:
<223> OTHER INFORMATION: Synthetic construct

<400> SEQUENCE: 465

His Ala Gly Thr Tyr Gly Leu Gly Asp Pro Ser Ser Ala Lys Ser Arg
1 5 10 15

Ser Lys Ile Gly Ser Thr Glu Asn Leu Cys
20 25

<210> SEQ ID NO 466
<211> LENGTH: 27
<212> TYPE: PRT
<213> ORGANISM: Artificial Sequence
<220> FEATURE:
<223> OTHER INFORMATION: Synthetic construct

<400> SEQUENCE: 466

His Ala Gly Thr Tyr Gly Leu Gly Asp Lys Ser Pro Ser Ser Ala Lys
1 5 10 15

Ser Arg Ser Lys Ile Gly Ser Thr Glu Asn Cys
20 25

<210> SEQ ID NO 467
<211> LENGTH: 27
<212> TYPE: PRT
<213> ORGANISM: Artificial Sequence
<220> FEATURE:
<223> OTHER INFORMATION: Synthetic construct

<400> SEQUENCE: 467

His Ala Gly Thr Tyr Gly Leu Gly Asp Ser Pro Ser Ser Ala Lys Ser
1 5 10 15

-continued

Arg Ser Lys Ile Gly Ser Thr Glu Asn Leu Cys
20 25

<210> SEQ ID NO 468
<211> LENGTH: 28
<212> TYPE: PRT
<213> ORGANISM: Artificial Sequence
<220> FEATURE:
<223> OTHER INFORMATION: Synthetic construct

<400> SEQUENCE: 468

His Ala Gly Thr Tyr Gly Leu Gly Asp Lys Ser Pro Ser Ser Ala Lys
1 5 10 15

Ser Arg Ser Lys Ile Gly Ser Thr Glu Asn Leu Cys
20 25

<210> SEQ ID NO 469
<211> LENGTH: 18
<212> TYPE: PRT
<213> ORGANISM: Artificial Sequence
<220> FEATURE:
<223> OTHER INFORMATION: Synthetic construct

<400> SEQUENCE: 469

Gly Thr Tyr Gly Leu Lys Ser Pro Val Val Ser Gly Asp Thr Ser Pro
1 5 10 15

Arg Cys

<210> SEQ ID NO 470
<211> LENGTH: 19
<212> TYPE: PRT
<213> ORGANISM: Artificial Sequence
<220> FEATURE:
<223> OTHER INFORMATION: Synthetic construct

<400> SEQUENCE: 470

Gly Thr Tyr Gly Leu Tyr Lys Ser Pro Val Val Ser Gly Asp Thr Ser
1 5 10 15

Pro Arg Cys

<210> SEQ ID NO 471
<211> LENGTH: 20
<212> TYPE: PRT
<213> ORGANISM: Artificial Sequence
<220> FEATURE:
<223> OTHER INFORMATION: Synthetic construct

<400> SEQUENCE: 471

Gly Thr Tyr Gly Leu Val Tyr Lys Ser Pro Val Val Ser Gly Asp Thr
1 5 10 15

Ser Pro Arg Cys
20

<210> SEQ ID NO 472
<211> LENGTH: 20
<212> TYPE: PRT
<213> ORGANISM: Artificial Sequence
<220> FEATURE:
<223> OTHER INFORMATION: Synthetic construct

<400> SEQUENCE: 472

Gly Thr Tyr Gly Leu Tyr Lys Ser Pro Val Val Ser Gly Asp Thr Ser
1 5 10 15

Pro Arg His Cys

20

<210> SEQ ID NO 473
<211> LENGTH: 21
<212> TYPE: PRT
<213> ORGANISM: Artificial Sequence
<220> FEATURE:
<223> OTHER INFORMATION: Synthetic construct

<400> SEQUENCE: 473

Gly Thr Tyr Gly Leu Ile Val Tyr Lys Ser Pro Val Val Ser Gly Asp
1 5 10 15

Thr Ser Pro Arg Cys
20

<210> SEQ ID NO 474
<211> LENGTH: 21
<212> TYPE: PRT
<213> ORGANISM: Artificial Sequence
<220> FEATURE:
<223> OTHER INFORMATION: Synthetic construct

<400> SEQUENCE: 474

Gly Thr Tyr Gly Leu Val Tyr Lys Ser Pro Val Val Ser Gly Asp Thr
1 5 10 15

Ser Pro Arg His Cys
20

<210> SEQ ID NO 475
<211> LENGTH: 21
<212> TYPE: PRT
<213> ORGANISM: Artificial Sequence
<220> FEATURE:
<223> OTHER INFORMATION: Synthetic construct

<400> SEQUENCE: 475

Gly Thr Tyr Gly Leu Tyr Lys Ser Pro Val Val Ser Gly Asp Thr Ser
1 5 10 15

Pro Arg His Leu Cys
20

<210> SEQ ID NO 476
<211> LENGTH: 22
<212> TYPE: PRT
<213> ORGANISM: Artificial Sequence
<220> FEATURE:
<223> OTHER INFORMATION: Synthetic construct

<400> SEQUENCE: 476

Gly Thr Tyr Gly Leu Ile Val Tyr Lys Ser Pro Val Val Ser Gly Asp
1 5 10 15

Thr Ser Pro Arg His Cys
20

<210> SEQ ID NO 477
<211> LENGTH: 22
<212> TYPE: PRT
<213> ORGANISM: Artificial Sequence
<220> FEATURE:
<223> OTHER INFORMATION: Synthetic construct

<400> SEQUENCE: 477

Gly Thr Tyr Gly Leu Val Tyr Lys Ser Pro Val Val Ser Gly Asp Thr
1 5 10 15

Ser Pro Arg His Leu Cys
20

<210> SEQ ID NO 478
<211> LENGTH: 23
<212> TYPE: PRT
<213> ORGANISM: Artificial Sequence
<220> FEATURE:
<223> OTHER INFORMATION: Synthetic construct

<400> SEQUENCE: 478

Gly Thr Tyr Gly Leu Ile Val Tyr Lys Ser Pro Val Val Ser Gly Asp
1 5 10 15

Thr Ser Pro Arg His Leu Cys
20

<210> SEQ ID NO 479
<211> LENGTH: 19
<212> TYPE: PRT
<213> ORGANISM: Artificial Sequence
<220> FEATURE:
<223> OTHER INFORMATION: Synthetic construct

<400> SEQUENCE: 479

Ala Gly Thr Tyr Gly Leu Lys Ser Pro Val Val Ser Gly Asp Thr Ser
1 5 10 15

Pro Arg Cys

<210> SEQ ID NO 480
<211> LENGTH: 20
<212> TYPE: PRT
<213> ORGANISM: Artificial Sequence
<220> FEATURE:
<223> OTHER INFORMATION: Synthetic construct

<400> SEQUENCE: 480

Ala Gly Thr Tyr Gly Leu Tyr Lys Ser Pro Val Val Ser Gly Asp Thr
1 5 10 15

Ser Pro Arg Cys
20

<210> SEQ ID NO 481
<211> LENGTH: 21
<212> TYPE: PRT
<213> ORGANISM: Artificial Sequence
<220> FEATURE:
<223> OTHER INFORMATION: Synthetic construct

<400> SEQUENCE: 481

Ala Gly Thr Tyr Gly Leu Val Tyr Lys Ser Pro Val Val Ser Gly Asp
1 5 10 15

Thr Ser Pro Arg Cys
20

<210> SEQ ID NO 482
<211> LENGTH: 21
<212> TYPE: PRT
<213> ORGANISM: Artificial Sequence
<220> FEATURE:
<223> OTHER INFORMATION: Synthetic construct

<400> SEQUENCE: 482

Ala Gly Thr Tyr Gly Leu Tyr Lys Ser Pro Val Val Ser Gly Asp Thr
1 5 10 15

Ser Pro Arg His Cys
20

<210> SEQ ID NO 483
<211> LENGTH: 22
<212> TYPE: PRT
<213> ORGANISM: Artificial Sequence
<220> FEATURE:
<223> OTHER INFORMATION: Synthetic construct

<400> SEQUENCE: 483

Ala Gly Thr Tyr Gly Leu Ile Val Tyr Lys Ser Pro Val Val Ser Gly
1 5 10 15

Asp Thr Ser Pro Arg Cys
20

<210> SEQ ID NO 484
<211> LENGTH: 22
<212> TYPE: PRT
<213> ORGANISM: Artificial Sequence
<220> FEATURE:
<223> OTHER INFORMATION: Synthetic construct

<400> SEQUENCE: 484

Ala Gly Thr Tyr Gly Leu Val Tyr Lys Ser Pro Val Val Ser Gly Asp
1 5 10 15

Thr Ser Pro Arg His Cys
20

<210> SEQ ID NO 485
<211> LENGTH: 22
<212> TYPE: PRT
<213> ORGANISM: Artificial Sequence
<220> FEATURE:
<223> OTHER INFORMATION: Synthetic construct

<400> SEQUENCE: 485

Ala Gly Thr Tyr Gly Leu Tyr Lys Ser Pro Val Val Ser Gly Asp Thr
1 5 10 15

Ser Pro Arg His Leu Cys
20

<210> SEQ ID NO 486
<211> LENGTH: 23
<212> TYPE: PRT
<213> ORGANISM: Artificial Sequence
<220> FEATURE:
<223> OTHER INFORMATION: Synthetic construct

<400> SEQUENCE: 486

Ala Gly Thr Tyr Gly Leu Ile Val Tyr Lys Ser Pro Val Val Ser Gly
1 5 10 15

Asp Thr Ser Pro Arg His Cys
20

<210> SEQ ID NO 487
<211> LENGTH: 23
<212> TYPE: PRT
<213> ORGANISM: Artificial Sequence
<220> FEATURE:
<223> OTHER INFORMATION: Synthetic construct

<400> SEQUENCE: 487

Ala Gly Thr Tyr Gly Leu Val Tyr Lys Ser Pro Val Val Ser Gly Asp
1 5 10 15

Thr Ser Pro Arg His Leu Cys
20

<210> SEQ ID NO 488
<211> LENGTH: 24
<212> TYPE: PRT
<213> ORGANISM: Artificial Sequence
<220> FEATURE:
<223> OTHER INFORMATION: Synthetic construct

<400> SEQUENCE: 488

Ala Gly Thr Tyr Gly Leu Ile Val Tyr Lys Ser Pro Val Val Ser Gly
1 5 10 15

Asp Thr Ser Pro Arg His Leu Cys
20

<210> SEQ ID NO 489
<211> LENGTH: 19
<212> TYPE: PRT
<213> ORGANISM: Artificial Sequence
<220> FEATURE:
<223> OTHER INFORMATION: Synthetic construct

<400> SEQUENCE: 489

Ala Gly Thr Tyr Gly Leu Lys Ser Pro Val Val Ser Gly Asp Thr Ser
1 5 10 15

Pro Arg Cys

<210> SEQ ID NO 490
<211> LENGTH: 20
<212> TYPE: PRT
<213> ORGANISM: Artificial Sequence
<220> FEATURE:
<223> OTHER INFORMATION: Synthetic construct

<400> SEQUENCE: 490

Gly Thr Tyr Gly Leu Gly Tyr Lys Ser Pro Val Val Ser Gly Asp Thr
1 5 10 15

Ser Pro Arg Cys
20

<210> SEQ ID NO 491
<211> LENGTH: 21
<212> TYPE: PRT
<213> ORGANISM: Artificial Sequence
<220> FEATURE:
<223> OTHER INFORMATION: Synthetic construct

<400> SEQUENCE: 491

Ala Gly Thr Tyr Gly Leu Val Tyr Lys Ser Pro Val Val Ser Gly Asp
1 5 10 15

Thr Ser Pro Arg Cys
20

<210> SEQ ID NO 492
<211> LENGTH: 21
<212> TYPE: PRT
<213> ORGANISM: Artificial Sequence
<220> FEATURE:
<223> OTHER INFORMATION: Synthetic construct

<400> SEQUENCE: 492

Gly Thr Tyr Gly Leu Gly Tyr Lys Ser Pro Val Val Ser Gly Asp Thr
1 5 10 15

Ser Pro Arg His Cys
20

<210> SEQ ID NO 493
<211> LENGTH: 22
<212> TYPE: PRT
<213> ORGANISM: Artificial Sequence
<220> FEATURE:
<223> OTHER INFORMATION: Synthetic construct

<400> SEQUENCE: 493

Gly Thr Tyr Gly Leu Gly Ile Val Tyr Lys Ser Pro Val Val Ser Gly
1 5 10 15

Asp Thr Ser Pro Arg Cys
20

<210> SEQ ID NO 494
<211> LENGTH: 22
<212> TYPE: PRT
<213> ORGANISM: Artificial Sequence
<220> FEATURE:
<223> OTHER INFORMATION: Synthetic construct

<400> SEQUENCE: 494

Gly Thr Tyr Gly Leu Gly Val Tyr Lys Ser Pro Val Val Ser Gly Asp
1 5 10 15

Thr Ser Pro Arg His Cys
20

<210> SEQ ID NO 495
<211> LENGTH: 22
<212> TYPE: PRT
<213> ORGANISM: Artificial Sequence
<220> FEATURE:
<223> OTHER INFORMATION: Synthetic construct

<400> SEQUENCE: 495

Gly Thr Tyr Gly Leu Gly Tyr Lys Ser Pro Val Val Ser Gly Asp Thr
1 5 10 15

Ser Pro Arg His Leu Cys
20

<210> SEQ ID NO 496
<211> LENGTH: 23
<212> TYPE: PRT
<213> ORGANISM: Artificial Sequence
<220> FEATURE:
<223> OTHER INFORMATION: Synthetic construct

<400> SEQUENCE: 496

Gly Thr Tyr Gly Leu Gly Ile Val Tyr Lys Ser Pro Val Val Ser Gly
1 5 10 15

Asp Thr Ser Pro Arg His Cys
20

<210> SEQ ID NO 497
<211> LENGTH: 23
<212> TYPE: PRT
<213> ORGANISM: Artificial Sequence
<220> FEATURE:
<223> OTHER INFORMATION: Synthetic construct

<400> SEQUENCE: 497

Gly Thr Tyr Gly Leu Gly Val Tyr Lys Ser Pro Val Val Ser Gly Asp 1 5 10 15

Thr Ser Pro Arg His Leu Cys
20

<210> SEQ ID NO 498
<211> LENGTH: 24
<212> TYPE: PRT
<213> ORGANISM: Artificial Sequence
<220> FEATURE:
<223> OTHER INFORMATION: Synthetic construct

<400> SEQUENCE: 498

Gly Thr Tyr Gly Leu Gly Ile Val Tyr Lys Ser Pro Val Val Ser Gly
1 5 10 15

Asp Thr Ser Pro Arg His Leu Cys
20

<210> SEQ ID NO 499
<211> LENGTH: 19
<212> TYPE: PRT
<213> ORGANISM: Artificial Sequence
<220> FEATURE:
<223> OTHER INFORMATION: Synthetic construct

<400> SEQUENCE: 499

Ala Gly Thr Tyr Gly Leu Lys Ser Pro Val Val Ser Gly Asp Thr Ser
1 5 10 15

Pro Arg Cys

<210> SEQ ID NO 500
<211> LENGTH: 21
<212> TYPE: PRT
<213> ORGANISM: Artificial Sequence
<220> FEATURE:
<223> OTHER INFORMATION: Synthetic construct

<400> SEQUENCE: 500

His Ala Gly Thr Tyr Gly Leu Tyr Lys Ser Pro Val Val Ser Gly Asp
1 5 10 15

Thr Ser Pro Arg Cys
20

<210> SEQ ID NO 501
<211> LENGTH: 22
<212> TYPE: PRT
<213> ORGANISM: Artificial Sequence
<220> FEATURE:
<223> OTHER INFORMATION: Synthetic construct

<400> SEQUENCE: 501

His Ala Gly Thr Tyr Gly Leu Val Tyr Lys Ser Pro Val Val Ser Gly
1 5 10 15

Asp Thr Ser Pro Arg Cys
20

<210> SEQ ID NO 502
<211> LENGTH: 21
<212> TYPE: PRT
<213> ORGANISM: Artificial Sequence
<220> FEATURE:
<223> OTHER INFORMATION: Synthetic construct

<400> SEQUENCE: 502

Ala Gly Thr Tyr Gly Leu Tyr Lys Ser Pro Val Val Ser Gly Asp Thr 1 5 10 15

Ser Pro Arg His Cys
20

<210> SEQ ID NO 503
<211> LENGTH: 23
<212> TYPE: PRT
<213> ORGANISM: Artificial Sequence
<220> FEATURE:
<223> OTHER INFORMATION: Synthetic construct

<400> SEQUENCE: 503

His Ala Gly Thr Tyr Gly Leu Ile Val Tyr Lys Ser Pro Val Val Ser
1 5 10 15

Gly Asp Thr Ser Pro Arg Cys
20

<210> SEQ ID NO 504
<211> LENGTH: 23
<212> TYPE: PRT
<213> ORGANISM: Artificial Sequence
<220> FEATURE:
<223> OTHER INFORMATION: Synthetic construct

<400> SEQUENCE: 504

His Ala Gly Thr Tyr Gly Leu Val Tyr Lys Ser Pro Val Val Ser Gly
1 5 10 15

Asp Thr Ser Pro Arg His Cys
20

<210> SEQ ID NO 505
<211> LENGTH: 23
<212> TYPE: PRT
<213> ORGANISM: Artificial Sequence
<220> FEATURE:
<223> OTHER INFORMATION: Synthetic construct

<400> SEQUENCE: 505

His Ala Gly Thr Tyr Gly Leu Tyr Lys Ser Pro Val Val Ser Gly Asp
1 5 10 15

Thr Ser Pro Arg His Leu Cys
20

<210> SEQ ID NO 506
<211> LENGTH: 24
<212> TYPE: PRT
<213> ORGANISM: Artificial Sequence
<220> FEATURE:
<223> OTHER INFORMATION: Synthetic construct

<400> SEQUENCE: 506

His Ala Gly Thr Tyr Gly Leu Ile Val Tyr Lys Ser Pro Val Val Ser
1 5 10 15

Gly Asp Thr Ser Pro Arg His Cys
20

<210> SEQ ID NO 507
<211> LENGTH: 24
<212> TYPE: PRT
<213> ORGANISM: Artificial Sequence
<220> FEATURE:
<223> OTHER INFORMATION: Synthetic construct

<400> SEQUENCE: 507

```
His Ala Gly Thr Tyr Gly Leu Val Tyr Lys Ser Pro Val Val Ser Gly
1               5                   10                  15

Asp Thr Ser Pro Arg His Leu Cys
            20


<210> SEQ ID NO 508
<211> LENGTH: 25
<212> TYPE: PRT
<213> ORGANISM: Artificial Sequence
<220> FEATURE:
<223> OTHER INFORMATION: Synthetic construct

<400> SEQUENCE: 508

His Ala Gly Thr Tyr Gly Leu Ile Val Tyr Lys Ser Pro Val Val Ser
1               5                   10                  15

Gly Asp Thr Ser Pro Arg His Leu Cys
            20                  25


<210> SEQ ID NO 509
<211> LENGTH: 19
<212> TYPE: PRT
<213> ORGANISM: Artificial Sequence
<220> FEATURE:
<223> OTHER INFORMATION: Synthetic construct

<400> SEQUENCE: 509

Ala Gly Thr Tyr Gly Leu Lys Ser Pro Val Val Ser Gly Asp Thr Ser
1               5                   10                  15

Pro Arg Cys


<210> SEQ ID NO 510
<211> LENGTH: 21
<212> TYPE: PRT
<213> ORGANISM: Artificial Sequence
<220> FEATURE:
<223> OTHER INFORMATION: Synthetic construct

<400> SEQUENCE: 510

Ala Gly Thr Tyr Gly Leu Gly Tyr Lys Ser Pro Val Val Ser Gly Asp
1               5                   10                  15

Thr Ser Pro Arg Cys
            20


<210> SEQ ID NO 511
<211> LENGTH: 21
<212> TYPE: PRT
<213> ORGANISM: Artificial Sequence
<220> FEATURE:
<223> OTHER INFORMATION: Synthetic construct

<400> SEQUENCE: 511

Ala Gly Thr Tyr Gly Leu Val Tyr Lys Ser Pro Val Val Ser Gly Asp
1               5                   10                  15

Thr Ser Pro Arg Cys
            20


<210> SEQ ID NO 512
<211> LENGTH: 21
<212> TYPE: PRT
<213> ORGANISM: Artificial Sequence
<220> FEATURE:
<223> OTHER INFORMATION: Synthetic construct

<400> SEQUENCE: 512
```

Ala Gly Thr Tyr Gly Leu Tyr Lys Ser Pro Val Val Ser Gly Asp Thr
1 5 10 15

Ser Pro Arg His Cys
20

<210> SEQ ID NO 513
<211> LENGTH: 23
<212> TYPE: PRT
<213> ORGANISM: Artificial Sequence
<220> FEATURE:
<223> OTHER INFORMATION: Synthetic construct

<400> SEQUENCE: 513

Ala Gly Thr Tyr Gly Leu Gly Ile Val Tyr Lys Ser Pro Val Val Ser
1 5 10 15

Gly Asp Thr Ser Pro Arg Cys
20

<210> SEQ ID NO 514
<211> LENGTH: 23
<212> TYPE: PRT
<213> ORGANISM: Artificial Sequence
<220> FEATURE:
<223> OTHER INFORMATION: Synthetic construct

<400> SEQUENCE: 514

Ala Gly Thr Tyr Gly Leu Gly Val Tyr Lys Ser Pro Val Val Ser Gly
1 5 10 15

Asp Thr Ser Pro Arg His Cys
20

<210> SEQ ID NO 515
<211> LENGTH: 23
<212> TYPE: PRT
<213> ORGANISM: Artificial Sequence
<220> FEATURE:
<223> OTHER INFORMATION: Synthetic construct

<400> SEQUENCE: 515

Ala Gly Thr Tyr Gly Leu Gly Tyr Lys Ser Pro Val Val Ser Gly Asp
1 5 10 15

Thr Ser Pro Arg His Leu Cys
20

<210> SEQ ID NO 516
<211> LENGTH: 24
<212> TYPE: PRT
<213> ORGANISM: Artificial Sequence
<220> FEATURE:
<223> OTHER INFORMATION: Synthetic construct

<400> SEQUENCE: 516

Ala Gly Thr Tyr Gly Leu Gly Ile Val Tyr Lys Ser Pro Val Val Ser
1 5 10 15

Gly Asp Thr Ser Pro Arg His Cys
20

<210> SEQ ID NO 517
<211> LENGTH: 24
<212> TYPE: PRT
<213> ORGANISM: Artificial Sequence
<220> FEATURE:
<223> OTHER INFORMATION: Synthetic construct

<400> SEQUENCE: 517

```
Ala Gly Thr Tyr Gly Leu Gly Val Tyr Lys Ser Pro Val Val Ser Gly
1               5                   10                  15

Asp Thr Ser Pro Arg His Leu Cys
            20


<210> SEQ ID NO 518
<211> LENGTH: 25
<212> TYPE: PRT
<213> ORGANISM: Artificial Sequence
<220> FEATURE:
<223> OTHER INFORMATION: Synthetic construct

<400> SEQUENCE: 518

Ala Gly Thr Tyr Gly Leu Gly Ile Val Tyr Lys Ser Pro Val Val Ser
1               5                   10                  15

Gly Asp Thr Ser Pro Arg His Leu Cys
            20                  25


<210> SEQ ID NO 519
<211> LENGTH: 20
<212> TYPE: PRT
<213> ORGANISM: Artificial Sequence
<220> FEATURE:
<223> OTHER INFORMATION: Synthetic construct

<400> SEQUENCE: 519

Gly Thr Tyr Gly Leu Gly Asp Lys Ser Pro Val Val Ser Gly Asp Thr
1               5                   10                  15

Ser Pro Arg Cys
            20


<210> SEQ ID NO 520
<211> LENGTH: 21
<212> TYPE: PRT
<213> ORGANISM: Artificial Sequence
<220> FEATURE:
<223> OTHER INFORMATION: Synthetic construct

<400> SEQUENCE: 520

Gly Thr Tyr Gly Leu Gly Asp Tyr Lys Ser Pro Val Val Ser Gly Asp
1               5                   10                  15

Thr Ser Pro Arg Cys
            20


<210> SEQ ID NO 521
<211> LENGTH: 22
<212> TYPE: PRT
<213> ORGANISM: Artificial Sequence
<220> FEATURE:
<223> OTHER INFORMATION: Synthetic construct

<400> SEQUENCE: 521

Gly Thr Tyr Gly Leu Gly Asp Val Tyr Lys Ser Pro Val Val Ser Gly
1               5                   10                  15

Asp Thr Ser Pro Arg Cys
            20


<210> SEQ ID NO 522
<211> LENGTH: 22
<212> TYPE: PRT
<213> ORGANISM: Artificial Sequence
<220> FEATURE:
<223> OTHER INFORMATION: Synthetic construct
```

<400> SEQUENCE: 522

Gly Thr Tyr Gly Leu Gly Asp Tyr Lys Ser Pro Val Val Ser Gly Asp
1 5 10 15

Thr Ser Pro Arg His Cys
20

<210> SEQ ID NO 523
<211> LENGTH: 23
<212> TYPE: PRT
<213> ORGANISM: Artificial Sequence
<220> FEATURE:
<223> OTHER INFORMATION: Synthetic construct

<400> SEQUENCE: 523

Gly Thr Tyr Gly Leu Gly Asp Ile Val Tyr Lys Ser Pro Val Val Ser
1 5 10 15

Gly Asp Thr Ser Pro Arg Cys
20

<210> SEQ ID NO 524
<211> LENGTH: 23
<212> TYPE: PRT
<213> ORGANISM: Artificial Sequence
<220> FEATURE:
<223> OTHER INFORMATION: Synthetic construct

<400> SEQUENCE: 524

Gly Thr Tyr Gly Leu Gly Asp Val Tyr Lys Ser Pro Val Val Ser Gly
1 5 10 15

Asp Thr Ser Pro Arg His Cys
20

<210> SEQ ID NO 525
<211> LENGTH: 23
<212> TYPE: PRT
<213> ORGANISM: Artificial Sequence
<220> FEATURE:
<223> OTHER INFORMATION: Synthetic construct

<400> SEQUENCE: 525

Gly Thr Tyr Gly Leu Gly Asp Tyr Lys Ser Pro Val Val Ser Gly Asp
1 5 10 15

Thr Ser Pro Arg His Leu Cys
20

<210> SEQ ID NO 526
<211> LENGTH: 24
<212> TYPE: PRT
<213> ORGANISM: Artificial Sequence
<220> FEATURE:
<223> OTHER INFORMATION: Synthetic construct

<400> SEQUENCE: 526

Gly Thr Tyr Gly Leu Gly Asp Ile Val Tyr Lys Ser Pro Val Val Ser
1 5 10 15

Gly Asp Thr Ser Pro Arg His Cys
20

<210> SEQ ID NO 527
<211> LENGTH: 24
<212> TYPE: PRT
<213> ORGANISM: Artificial Sequence
<220> FEATURE:
<223> OTHER INFORMATION: Synthetic construct

<400> SEQUENCE: 527

Gly Thr Tyr Gly Leu Gly Asp Val Tyr Lys Ser Pro Val Val Ser Gly
1               5                   10                  15

Asp Thr Ser Pro Arg His Leu Cys
            20

<210> SEQ ID NO 528
<211> LENGTH: 25
<212> TYPE: PRT
<213> ORGANISM: Artificial Sequence
<220> FEATURE:
<223> OTHER INFORMATION: Synthetic construct

<400> SEQUENCE: 528

Gly Thr Tyr Gly Leu Gly Asp Ile Val Tyr Lys Ser Pro Val Val Ser
1               5                   10                  15

Gly Asp Thr Ser Pro Arg His Leu Cys
            20                  25

<210> SEQ ID NO 529
<211> LENGTH: 21
<212> TYPE: PRT
<213> ORGANISM: Artificial Sequence
<220> FEATURE:
<223> OTHER INFORMATION: Synthetic construct

<400> SEQUENCE: 529

His Ala Gly Thr Tyr Gly Leu Gly Lys Ser Pro Val Val Ser Gly Asp
1               5                   10                  15

Thr Ser Pro Arg Cys
            20

<210> SEQ ID NO 530
<211> LENGTH: 22
<212> TYPE: PRT
<213> ORGANISM: Artificial Sequence
<220> FEATURE:
<223> OTHER INFORMATION: Synthetic construct

<400> SEQUENCE: 530

His Ala Gly Thr Tyr Gly Leu Gly Tyr Lys Ser Pro Val Val Ser Gly
1               5                   10                  15

Asp Thr Ser Pro Arg Cys
            20

<210> SEQ ID NO 531
<211> LENGTH: 23
<212> TYPE: PRT
<213> ORGANISM: Artificial Sequence
<220> FEATURE:
<223> OTHER INFORMATION: Synthetic construct

<400> SEQUENCE: 531

His Ala Gly Thr Tyr Gly Leu Gly Val Tyr Lys Ser Pro Val Val Ser
1               5                   10                  15

Gly Asp Thr Ser Pro Arg Cys
            20

<210> SEQ ID NO 532
<211> LENGTH: 23
<212> TYPE: PRT
<213> ORGANISM: Artificial Sequence
<220> FEATURE:

<223> OTHER INFORMATION: Synthetic construct

<400> SEQUENCE: 532

His Ala Gly Thr Tyr Gly Leu Gly Tyr Lys Ser Pro Val Val Ser Gly
1 5 10 15

Asp Thr Ser Pro Arg His Cys
20

<210> SEQ ID NO 533
<211> LENGTH: 24
<212> TYPE: PRT
<213> ORGANISM: Artificial Sequence
<220> FEATURE:
<223> OTHER INFORMATION: Synthetic construct

<400> SEQUENCE: 533

His Ala Gly Thr Tyr Gly Leu Gly Ile Val Tyr Lys Ser Pro Val Val
1 5 10 15

Ser Gly Asp Thr Ser Pro Arg Cys
20

<210> SEQ ID NO 534
<211> LENGTH: 24
<212> TYPE: PRT
<213> ORGANISM: Artificial Sequence
<220> FEATURE:
<223> OTHER INFORMATION: Synthetic construct

<400> SEQUENCE: 534

His Ala Gly Thr Tyr Gly Leu Gly Val Tyr Lys Ser Pro Val Val Ser
1 5 10 15

Gly Asp Thr Ser Pro Arg His Cys
20

<210> SEQ ID NO 535
<211> LENGTH: 24
<212> TYPE: PRT
<213> ORGANISM: Artificial Sequence
<220> FEATURE:
<223> OTHER INFORMATION: Synthetic construct

<400> SEQUENCE: 535

His Ala Gly Thr Tyr Gly Leu Gly Tyr Lys Ser Pro Val Val Ser Gly
1 5 10 15

Asp Thr Ser Pro Arg His Leu Cys
20

<210> SEQ ID NO 536
<211> LENGTH: 25
<212> TYPE: PRT
<213> ORGANISM: Artificial Sequence
<220> FEATURE:
<223> OTHER INFORMATION: Synthetic construct

<400> SEQUENCE: 536

His Ala Gly Thr Tyr Gly Leu Gly Ile Val Tyr Lys Ser Pro Val Val
1 5 10 15

Ser Gly Asp Thr Ser Pro Arg His Cys
20 25

<210> SEQ ID NO 537
<211> LENGTH: 25
<212> TYPE: PRT
<213> ORGANISM: Artificial Sequence
<220> FEATURE:
<223> OTHER INFORMATION: Synthetic construct

<400> SEQUENCE: 537

His Ala Gly Thr Tyr Gly Leu Gly Val Tyr Lys Ser Pro Val Val Ser
1 5 10 15

Gly Asp Thr Ser Pro Arg His Leu Cys
20 25

<210> SEQ ID NO 538
<211> LENGTH: 26
<212> TYPE: PRT
<213> ORGANISM: Artificial Sequence
<220> FEATURE:
<223> OTHER INFORMATION: Synthetic construct

<400> SEQUENCE: 538

His Ala Gly Thr Tyr Gly Leu Gly Ile Val Tyr Lys Ser Pro Val Val
1 5 10 15

Ser Gly Asp Thr Ser Pro Arg His Leu Cys
20 25

<210> SEQ ID NO 539
<211> LENGTH: 21
<212> TYPE: PRT
<213> ORGANISM: Artificial Sequence
<220> FEATURE:
<223> OTHER INFORMATION: Synthetic construct

<400> SEQUENCE: 539

Ala Gly Thr Tyr Gly Leu Gly Asp Lys Ser Pro Val Val Ser Gly Asp
1 5 10 15

Thr Ser Pro Arg Cys
20

<210> SEQ ID NO 540
<211> LENGTH: 22
<212> TYPE: PRT
<213> ORGANISM: Artificial Sequence
<220> FEATURE:
<223> OTHER INFORMATION: Synthetic construct

<400> SEQUENCE: 540

Ala Gly Thr Tyr Gly Leu Gly Asp Tyr Lys Ser Pro Val Val Ser Gly
1 5 10 15

Asp Thr Ser Pro Arg Cys
20

<210> SEQ ID NO 541
<211> LENGTH: 23
<212> TYPE: PRT
<213> ORGANISM: Artificial Sequence
<220> FEATURE:
<223> OTHER INFORMATION: Synthetic construct

<400> SEQUENCE: 541

Ala Gly Thr Tyr Gly Leu Gly Asp Val Tyr Lys Ser Pro Val Val Ser
1 5 10 15

Gly Asp Thr Ser Pro Arg Cys
20

<210> SEQ ID NO 542
<211> LENGTH: 23
<212> TYPE: PRT

<213> ORGANISM: Artificial Sequence
<220> FEATURE:
<223> OTHER INFORMATION: Synthetic construct

<400> SEQUENCE: 542

Ala Gly Thr Tyr Gly Leu Gly Asp Tyr Lys Ser Pro Val Val Ser Gly
1               5                   10                  15

Asp Thr Ser Pro Arg His Cys
            20

<210> SEQ ID NO 543
<211> LENGTH: 24
<212> TYPE: PRT
<213> ORGANISM: Artificial Sequence
<220> FEATURE:
<223> OTHER INFORMATION: Synthetic construct

<400> SEQUENCE: 543

Ala Gly Thr Tyr Gly Leu Gly Asp Ile Val Tyr Lys Ser Pro Val Val
1               5                   10                  15

Ser Gly Asp Thr Ser Pro Arg Cys
            20

<210> SEQ ID NO 544
<211> LENGTH: 24
<212> TYPE: PRT
<213> ORGANISM: Artificial Sequence
<220> FEATURE:
<223> OTHER INFORMATION: Synthetic construct

<400> SEQUENCE: 544

Ala Gly Thr Tyr Gly Leu Gly Asp Val Tyr Lys Ser Pro Val Val Ser
1               5                   10                  15

Gly Asp Thr Ser Pro Arg His Cys
            20

<210> SEQ ID NO 545
<211> LENGTH: 24
<212> TYPE: PRT
<213> ORGANISM: Artificial Sequence
<220> FEATURE:
<223> OTHER INFORMATION: Synthetic construct

<400> SEQUENCE: 545

Ala Gly Thr Tyr Gly Leu Gly Asp Tyr Lys Ser Pro Val Val Ser Gly
1               5                   10                  15

Asp Thr Ser Pro Arg His Leu Cys
            20

<210> SEQ ID NO 546
<211> LENGTH: 25
<212> TYPE: PRT
<213> ORGANISM: Artificial Sequence
<220> FEATURE:
<223> OTHER INFORMATION: Synthetic construct

<400> SEQUENCE: 546

Ala Gly Thr Tyr Gly Leu Gly Asp Ile Val Tyr Lys Ser Pro Val Val
1               5                   10                  15

Ser Gly Asp Thr Ser Pro Arg His Cys
            20                  25

<210> SEQ ID NO 547
<211> LENGTH: 25

<212> TYPE: PRT
<213> ORGANISM: Artificial Sequence
<220> FEATURE:
<223> OTHER INFORMATION: Synthetic construct

<400> SEQUENCE: 547

Ala Gly Thr Tyr Gly Leu Gly Asp Val Tyr Lys Ser Pro Val Val Ser
1 5 10 15

Gly Asp Thr Ser Pro Arg His Leu Cys
20 25

<210> SEQ ID NO 548
<211> LENGTH: 26
<212> TYPE: PRT
<213> ORGANISM: Artificial Sequence
<220> FEATURE:
<223> OTHER INFORMATION: Synthetic construct

<400> SEQUENCE: 548

Ala Gly Thr Tyr Gly Leu Gly Asp Ile Val Tyr Lys Ser Pro Val Val
1 5 10 15

Ser Gly Asp Thr Ser Pro Arg His Leu Cys
20 25

<210> SEQ ID NO 549
<211> LENGTH: 22
<212> TYPE: PRT
<213> ORGANISM: Artificial Sequence
<220> FEATURE:
<223> OTHER INFORMATION: Synthetic construct

<400> SEQUENCE: 549

His Ala Gly Thr Tyr Gly Leu Gly Asp Lys Ser Pro Val Val Ser Gly
1 5 10 15

Asp Thr Ser Pro Arg Cys
20

<210> SEQ ID NO 550
<211> LENGTH: 23
<212> TYPE: PRT
<213> ORGANISM: Artificial Sequence
<220> FEATURE:
<223> OTHER INFORMATION: Synthetic construct

<400> SEQUENCE: 550

His Ala Gly Thr Tyr Gly Leu Gly Asp Tyr Lys Ser Pro Val Val Ser
1 5 10 15

Gly Asp Thr Ser Pro Arg Cys
20

<210> SEQ ID NO 551
<211> LENGTH: 24
<212> TYPE: PRT
<213> ORGANISM: Artificial Sequence
<220> FEATURE:
<223> OTHER INFORMATION: Synthetic construct

<400> SEQUENCE: 551

His Ala Gly Thr Tyr Gly Leu Gly Asp Val Tyr Lys Ser Pro Val Val
1 5 10 15

Ser Gly Asp Thr Ser Pro Arg Cys
20

<210> SEQ ID NO 552

```
<211> LENGTH: 24
<212> TYPE: PRT
<213> ORGANISM: Artificial Sequence
<220> FEATURE:
<223> OTHER INFORMATION: Synthetic construct

<400> SEQUENCE: 552

His Ala Gly Thr Tyr Gly Leu Gly Asp Tyr Lys Ser Pro Val Val Ser
1               5                   10                  15

Gly Asp Thr Ser Pro Arg His Cys
            20


<210> SEQ ID NO 553
<211> LENGTH: 25
<212> TYPE: PRT
<213> ORGANISM: Artificial Sequence
<220> FEATURE:
<223> OTHER INFORMATION: Synthetic construct

<400> SEQUENCE: 553

His Ala Gly Thr Tyr Gly Leu Gly Asp Ile Val Tyr Lys Ser Pro Val
1               5                   10                  15

Val Ser Gly Asp Thr Ser Pro Arg Cys
            20                  25


<210> SEQ ID NO 554
<211> LENGTH: 25
<212> TYPE: PRT
<213> ORGANISM: Artificial Sequence
<220> FEATURE:
<223> OTHER INFORMATION: Synthetic construct

<400> SEQUENCE: 554

His Ala Gly Thr Tyr Gly Leu Gly Asp Val Tyr Lys Ser Pro Val Val
1               5                   10                  15

Ser Gly Asp Thr Ser Pro Arg His Cys
            20                  25


<210> SEQ ID NO 555
<211> LENGTH: 25
<212> TYPE: PRT
<213> ORGANISM: Artificial Sequence
<220> FEATURE:
<223> OTHER INFORMATION: Synthetic construct

<400> SEQUENCE: 555

His Ala Gly Thr Tyr Gly Leu Gly Asp Tyr Lys Ser Pro Val Val Ser
1               5                   10                  15

Gly Asp Thr Ser Pro Arg His Leu Cys
            20                  25


<210> SEQ ID NO 556
<211> LENGTH: 26
<212> TYPE: PRT
<213> ORGANISM: Artificial Sequence
<220> FEATURE:
<223> OTHER INFORMATION: Synthetic construct

<400> SEQUENCE: 556

His Ala Gly Thr Tyr Gly Leu Gly Asp Ile Val Tyr Lys Ser Pro Val
1               5                   10                  15

Val Ser Gly Asp Thr Ser Pro Arg His Cys
            20                  25
```

<210> SEQ ID NO 557
<211> LENGTH: 26
<212> TYPE: PRT
<213> ORGANISM: Artificial Sequence
<220> FEATURE:
<223> OTHER INFORMATION: Synthetic construct

<400> SEQUENCE: 557

```
His Ala Gly Thr Tyr Gly Leu Gly Asp Val Tyr Lys Ser Pro Val Val
1               5                   10                  15

Ser Gly Asp Thr Ser Pro Arg His Leu Cys
            20                  25
```

<210> SEQ ID NO 558
<211> LENGTH: 27
<212> TYPE: PRT
<213> ORGANISM: Artificial Sequence
<220> FEATURE:
<223> OTHER INFORMATION: Synthetic construct

<400> SEQUENCE: 558

```
His Ala Gly Thr Tyr Gly Leu Gly Asp Ile Val Tyr Lys Ser Pro Val
1               5                   10                  15

Val Ser Gly Asp Thr Ser Pro Arg His Leu Cys
            20                  25
```

<210> SEQ ID NO 559
<211> LENGTH: 22
<212> TYPE: PRT
<213> ORGANISM: Artificial Sequence
<220> FEATURE:
<223> OTHER INFORMATION: Synthetic construct

<400> SEQUENCE: 559

```
Ser Ser Pro Gly Ser Pro Gly Thr Pro Gly Ser Arg Val Arg Thr Pro
1               5                   10                  15

Pro Lys Ser Pro Ser Cys
            20
```

<210> SEQ ID NO 560
<211> LENGTH: 23
<212> TYPE: PRT
<213> ORGANISM: Artificial Sequence
<220> FEATURE:
<223> OTHER INFORMATION: Synthetic construct

<400> SEQUENCE: 560

```
Ser Ser Pro Gly Ser Pro Gly Thr Pro Gly Ser Arg Val Val Arg Thr
1               5                   10                  15

Pro Pro Lys Ser Pro Ser Cys
            20
```

<210> SEQ ID NO 561
<211> LENGTH: 23
<212> TYPE: PRT
<213> ORGANISM: Artificial Sequence
<220> FEATURE:
<223> OTHER INFORMATION: Synthetic construct

<400> SEQUENCE: 561

```
Ser Ser Pro Gly Ser Pro Gly Thr Pro Gly Ser Arg Val Arg Thr Pro
1               5                   10                  15

Pro Lys Ser Pro Ser Ser Cys
            20
```

<210> SEQ ID NO 562
<211> LENGTH: 24
<212> TYPE: PRT
<213> ORGANISM: Artificial Sequence
<220> FEATURE:
<223> OTHER INFORMATION: Synthetic construct

<400> SEQUENCE: 562

Ser Ser Pro Gly Ser Pro Gly Thr Pro Gly Ser Arg Ala Val Val Arg
1 5 10 15

Thr Pro Pro Lys Ser Pro Ser Cys
20

<210> SEQ ID NO 563
<211> LENGTH: 24
<212> TYPE: PRT
<213> ORGANISM: Artificial Sequence
<220> FEATURE:
<223> OTHER INFORMATION: Synthetic construct

<400> SEQUENCE: 563

Ser Ser Pro Gly Ser Pro Gly Thr Pro Gly Ser Arg Val Val Arg Thr
1 5 10 15

Pro Pro Lys Ser Pro Ser Ser Cys
20

<210> SEQ ID NO 564
<211> LENGTH: 24
<212> TYPE: PRT
<213> ORGANISM: Artificial Sequence
<220> FEATURE:
<223> OTHER INFORMATION: Synthetic construct

<400> SEQUENCE: 564

Ser Ser Pro Gly Ser Pro Gly Thr Pro Gly Ser Arg Val Arg Thr Pro
1 5 10 15

Pro Lys Ser Pro Ser Ser Ala Cys
20

<210> SEQ ID NO 565
<211> LENGTH: 25
<212> TYPE: PRT
<213> ORGANISM: Artificial Sequence
<220> FEATURE:
<223> OTHER INFORMATION: Synthetic construct

<400> SEQUENCE: 565

Ser Ser Pro Gly Ser Pro Gly Thr Pro Gly Ser Arg Ala Val Val Arg
1 5 10 15

Thr Pro Pro Lys Ser Pro Ser Ser Cys
20 25

<210> SEQ ID NO 566
<211> LENGTH: 25
<212> TYPE: PRT
<213> ORGANISM: Artificial Sequence
<220> FEATURE:
<223> OTHER INFORMATION: Synthetic construct

<400> SEQUENCE: 566

Ser Ser Pro Gly Ser Pro Gly Thr Pro Gly Ser Arg Val Val Arg Thr
1 5 10 15

Pro Pro Lys Ser Pro Ser Ser Ala Cys
20 25

<210> SEQ ID NO 567
<211> LENGTH: 26
<212> TYPE: PRT
<213> ORGANISM: Artificial Sequence
<220> FEATURE:
<223> OTHER INFORMATION: Synthetic construct

<400> SEQUENCE: 567

```
Ser Ser Pro Gly Ser Pro Gly Thr Pro Gly Ser Arg Ala Val Val Arg
1               5                   10                  15

Thr Pro Pro Lys Ser Pro Ser Ser Ala Cys
            20                  25
```

<210> SEQ ID NO 568
<211> LENGTH: 23
<212> TYPE: PRT
<213> ORGANISM: Artificial Sequence
<220> FEATURE:
<223> OTHER INFORMATION: Synthetic construct

<400> SEQUENCE: 568

```
Tyr Ser Ser Pro Gly Ser Pro Gly Thr Pro Gly Ser Arg Val Arg Thr
1               5                   10                  15

Pro Pro Lys Ser Pro Ser Cys
            20
```

<210> SEQ ID NO 569
<211> LENGTH: 24
<212> TYPE: PRT
<213> ORGANISM: Artificial Sequence
<220> FEATURE:
<223> OTHER INFORMATION: Synthetic construct

<400> SEQUENCE: 569

```
Tyr Ser Ser Pro Gly Ser Pro Gly Thr Pro Gly Ser Arg Val Val Arg
1               5                   10                  15

Thr Pro Pro Lys Ser Pro Ser Cys
            20
```

<210> SEQ ID NO 570
<211> LENGTH: 24
<212> TYPE: PRT
<213> ORGANISM: Artificial Sequence
<220> FEATURE:
<223> OTHER INFORMATION: Synthetic construct

<400> SEQUENCE: 570

```
Tyr Ser Ser Pro Gly Ser Pro Gly Thr Pro Gly Ser Arg Val Arg Thr
1               5                   10                  15

Pro Pro Lys Ser Pro Ser Ser Cys
            20
```

<210> SEQ ID NO 571
<211> LENGTH: 25
<212> TYPE: PRT
<213> ORGANISM: Artificial Sequence
<220> FEATURE:
<223> OTHER INFORMATION: Synthetic construct

<400> SEQUENCE: 571

```
Tyr Ser Ser Pro Gly Ser Pro Gly Thr Pro Gly Ser Arg Ala Val Val
1               5                   10                  15

Arg Thr Pro Pro Lys Ser Pro Ser Cys
```

20 25

<210> SEQ ID NO 572
<211> LENGTH: 25
<212> TYPE: PRT
<213> ORGANISM: Artificial Sequence
<220> FEATURE:
<223> OTHER INFORMATION: Synthetic construct

<400> SEQUENCE: 572

Tyr Ser Ser Pro Gly Ser Pro Gly Thr Pro Gly Ser Arg Val Val Arg
1 5 10 15

Thr Pro Pro Lys Ser Pro Ser Ser Cys
20 25

<210> SEQ ID NO 573
<211> LENGTH: 25
<212> TYPE: PRT
<213> ORGANISM: Artificial Sequence
<220> FEATURE:
<223> OTHER INFORMATION: Synthetic construct

<400> SEQUENCE: 573

Tyr Ser Ser Pro Gly Ser Pro Gly Thr Pro Gly Ser Arg Val Arg Thr
1 5 10 15

Pro Pro Lys Ser Pro Ser Ser Ala Cys
20 25

<210> SEQ ID NO 574
<211> LENGTH: 26
<212> TYPE: PRT
<213> ORGANISM: Artificial Sequence
<220> FEATURE:
<223> OTHER INFORMATION: Synthetic construct

<400> SEQUENCE: 574

Tyr Ser Ser Pro Gly Ser Pro Gly Thr Pro Gly Ser Arg Ala Val Val
1 5 10 15

Arg Thr Pro Pro Lys Ser Pro Ser Ser Cys
20 25

<210> SEQ ID NO 575
<211> LENGTH: 26
<212> TYPE: PRT
<213> ORGANISM: Artificial Sequence
<220> FEATURE:
<223> OTHER INFORMATION: Synthetic construct

<400> SEQUENCE: 575

Tyr Ser Ser Pro Gly Ser Pro Gly Thr Pro Gly Ser Arg Val Val Arg
1 5 10 15

Thr Pro Pro Lys Ser Pro Ser Ser Ala Cys
20 25

<210> SEQ ID NO 576
<211> LENGTH: 27
<212> TYPE: PRT
<213> ORGANISM: Artificial Sequence
<220> FEATURE:
<223> OTHER INFORMATION: Synthetic construct

<400> SEQUENCE: 576

Tyr Ser Ser Pro Gly Ser Pro Gly Thr Pro Gly Ser Arg Ala Val Val
1 5 10 15

```
Arg Thr Pro Pro Lys Ser Pro Ser Ser Ala Cys
            20                  25


<210> SEQ ID NO 577
<211> LENGTH: 23
<212> TYPE: PRT
<213> ORGANISM: Artificial Sequence
<220> FEATURE:
<223> OTHER INFORMATION: Synthetic construct

<400> SEQUENCE: 577

Ser Ser Pro Gly Ser Pro Gly Thr Pro Gly Ser Arg Ser Val Arg Thr
1               5                   10                  15

Pro Pro Lys Ser Pro Ser Cys
            20


<210> SEQ ID NO 578
<211> LENGTH: 24
<212> TYPE: PRT
<213> ORGANISM: Artificial Sequence
<220> FEATURE:
<223> OTHER INFORMATION: Synthetic construct

<400> SEQUENCE: 578

Ser Ser Pro Gly Ser Pro Gly Thr Pro Gly Ser Arg Ser Val Val Arg
1               5                   10                  15

Thr Pro Pro Lys Ser Pro Ser Cys
            20


<210> SEQ ID NO 579
<211> LENGTH: 24
<212> TYPE: PRT
<213> ORGANISM: Artificial Sequence
<220> FEATURE:
<223> OTHER INFORMATION: Synthetic construct

<400> SEQUENCE: 579

Ser Ser Pro Gly Ser Pro Gly Thr Pro Gly Ser Arg Ser Val Arg Thr
1               5                   10                  15

Pro Pro Lys Ser Pro Ser Ser Cys
            20


<210> SEQ ID NO 580
<211> LENGTH: 25
<212> TYPE: PRT
<213> ORGANISM: Artificial Sequence
<220> FEATURE:
<223> OTHER INFORMATION: Synthetic construct

<400> SEQUENCE: 580

Ser Ser Pro Gly Ser Pro Gly Thr Pro Gly Ser Arg Ser Ala Val Val
1               5                   10                  15

Arg Thr Pro Pro Lys Ser Pro Ser Cys
            20                  25


<210> SEQ ID NO 581
<211> LENGTH: 25
<212> TYPE: PRT
<213> ORGANISM: Artificial Sequence
<220> FEATURE:
<223> OTHER INFORMATION: Synthetic construct

<400> SEQUENCE: 581

Ser Ser Pro Gly Ser Pro Gly Thr Pro Gly Ser Arg Ser Val Val Arg
1               5                   10                  15
```

Thr Pro Pro Lys Ser Pro Ser Ser Cys
20 25

<210> SEQ ID NO 582
<211> LENGTH: 25
<212> TYPE: PRT
<213> ORGANISM: Artificial Sequence
<220> FEATURE:
<223> OTHER INFORMATION: Synthetic construct

<400> SEQUENCE: 582

Ser Ser Pro Gly Ser Pro Gly Thr Pro Gly Ser Arg Ser Val Arg Thr
1 5 10 15

Pro Pro Lys Ser Pro Ser Ser Ala Cys
20 25

<210> SEQ ID NO 583
<211> LENGTH: 26
<212> TYPE: PRT
<213> ORGANISM: Artificial Sequence
<220> FEATURE:
<223> OTHER INFORMATION: Synthetic construct

<400> SEQUENCE: 583

Ser Ser Pro Gly Ser Pro Gly Thr Pro Gly Ser Arg Ser Ala Val Val
1 5 10 15

Arg Thr Pro Pro Lys Ser Pro Ser Ser Cys
20 25

<210> SEQ ID NO 584
<211> LENGTH: 26
<212> TYPE: PRT
<213> ORGANISM: Artificial Sequence
<220> FEATURE:
<223> OTHER INFORMATION: Synthetic construct

<400> SEQUENCE: 584

Ser Ser Pro Gly Ser Pro Gly Thr Pro Gly Ser Arg Ser Val Val Arg
1 5 10 15

Thr Pro Pro Lys Ser Pro Ser Ser Ala Cys
20 25

<210> SEQ ID NO 585
<211> LENGTH: 27
<212> TYPE: PRT
<213> ORGANISM: Artificial Sequence
<220> FEATURE:
<223> OTHER INFORMATION: Synthetic construct

<400> SEQUENCE: 585

Ser Ser Pro Gly Ser Pro Gly Thr Pro Gly Ser Arg Ser Ala Val Val
1 5 10 15

Arg Thr Pro Pro Lys Ser Pro Ser Ser Ala Cys
20 25

<210> SEQ ID NO 586
<211> LENGTH: 24
<212> TYPE: PRT
<213> ORGANISM: Artificial Sequence
<220> FEATURE:
<223> OTHER INFORMATION: Synthetic construct

<400> SEQUENCE: 586

Gly Tyr Ser Ser Pro Gly Ser Pro Gly Thr Pro Gly Ser Arg Val Arg

```
1               5                   10                  15

Thr Pro Pro Lys Ser Pro Ser Cys
            20


<210> SEQ ID NO 587
<211> LENGTH: 25
<212> TYPE: PRT
<213> ORGANISM: Artificial Sequence
<220> FEATURE:
<223> OTHER INFORMATION: Synthetic construct

<400> SEQUENCE: 587

Gly Tyr Ser Ser Pro Gly Ser Pro Gly Thr Pro Gly Ser Arg Val Val
1               5                   10                  15

Arg Thr Pro Pro Lys Ser Pro Ser Cys
            20                  25


<210> SEQ ID NO 588
<211> LENGTH: 25
<212> TYPE: PRT
<213> ORGANISM: Artificial Sequence
<220> FEATURE:
<223> OTHER INFORMATION: Synthetic construct

<400> SEQUENCE: 588

Gly Tyr Ser Ser Pro Gly Ser Pro Gly Thr Pro Gly Ser Arg Val Arg
1               5                   10                  15

Thr Pro Pro Lys Ser Pro Ser Ser Cys
            20                  25


<210> SEQ ID NO 589
<211> LENGTH: 26
<212> TYPE: PRT
<213> ORGANISM: Artificial Sequence
<220> FEATURE:
<223> OTHER INFORMATION: Synthetic construct

<400> SEQUENCE: 589

Gly Tyr Ser Ser Pro Gly Ser Pro Gly Thr Pro Gly Ser Arg Ala Val
1               5                   10                  15

Val Arg Thr Pro Pro Lys Ser Pro Ser Cys
            20                  25


<210> SEQ ID NO 590
<211> LENGTH: 26
<212> TYPE: PRT
<213> ORGANISM: Artificial Sequence
<220> FEATURE:
<223> OTHER INFORMATION: Synthetic construct

<400> SEQUENCE: 590

Gly Tyr Ser Ser Pro Gly Ser Pro Gly Thr Pro Gly Ser Arg Val Val
1               5                   10                  15

Arg Thr Pro Pro Lys Ser Pro Ser Ser Cys
            20                  25


<210> SEQ ID NO 591
<211> LENGTH: 26
<212> TYPE: PRT
<213> ORGANISM: Artificial Sequence
<220> FEATURE:
<223> OTHER INFORMATION: Synthetic construct

<400> SEQUENCE: 591
```

Gly Tyr Ser Ser Pro Gly Ser Pro Gly Thr Pro Gly Ser Arg Val Arg
1 5 10 15

Thr Pro Pro Lys Ser Pro Ser Ser Ala Cys
20 25

<210> SEQ ID NO 592
<211> LENGTH: 27
<212> TYPE: PRT
<213> ORGANISM: Artificial Sequence
<220> FEATURE:
<223> OTHER INFORMATION: Synthetic construct

<400> SEQUENCE: 592

Gly Tyr Ser Ser Pro Gly Ser Pro Gly Thr Pro Gly Ser Arg Ala Val
1 5 10 15

Val Arg Thr Pro Pro Lys Ser Pro Ser Ser Cys
20 25

<210> SEQ ID NO 593
<211> LENGTH: 27
<212> TYPE: PRT
<213> ORGANISM: Artificial Sequence
<220> FEATURE:
<223> OTHER INFORMATION: Synthetic construct

<400> SEQUENCE: 593

Gly Tyr Ser Ser Pro Gly Ser Pro Gly Thr Pro Gly Ser Arg Val Val
1 5 10 15

Arg Thr Pro Pro Lys Ser Pro Ser Ser Ala Cys
20 25

<210> SEQ ID NO 594
<211> LENGTH: 28
<212> TYPE: PRT
<213> ORGANISM: Artificial Sequence
<220> FEATURE:
<223> OTHER INFORMATION: Synthetic construct

<400> SEQUENCE: 594

Gly Tyr Ser Ser Pro Gly Ser Pro Gly Thr Pro Gly Ser Arg Ala Val
1 5 10 15

Val Arg Thr Pro Pro Lys Ser Pro Ser Ser Ala Cys
20 25

<210> SEQ ID NO 595
<211> LENGTH: 24
<212> TYPE: PRT
<213> ORGANISM: Artificial Sequence
<220> FEATURE:
<223> OTHER INFORMATION: Synthetic construct

<400> SEQUENCE: 595

Tyr Ser Ser Pro Gly Ser Pro Gly Thr Pro Gly Ser Arg Ser Val Arg
1 5 10 15

Thr Pro Pro Lys Ser Pro Ser Cys
20

<210> SEQ ID NO 596
<211> LENGTH: 25
<212> TYPE: PRT
<213> ORGANISM: Artificial Sequence
<220> FEATURE:
<223> OTHER INFORMATION: Synthetic construct

<400> SEQUENCE: 596

Tyr Ser Ser Pro Gly Ser Pro Gly Thr Pro Gly Ser Arg Ser Val Val
1 5 10 15

Arg Thr Pro Pro Lys Ser Pro Ser Cys
20 25

<210> SEQ ID NO 597
<211> LENGTH: 25
<212> TYPE: PRT
<213> ORGANISM: Artificial Sequence
<220> FEATURE:
<223> OTHER INFORMATION: Synthetic construct

<400> SEQUENCE: 597

Tyr Ser Ser Pro Gly Ser Pro Gly Thr Pro Gly Ser Arg Ser Val Arg
1 5 10 15

Thr Pro Pro Lys Ser Pro Ser Ser Cys
20 25

<210> SEQ ID NO 598
<211> LENGTH: 26
<212> TYPE: PRT
<213> ORGANISM: Artificial Sequence
<220> FEATURE:
<223> OTHER INFORMATION: Synthetic construct

<400> SEQUENCE: 598

Tyr Ser Ser Pro Gly Ser Pro Gly Thr Pro Gly Ser Arg Ser Ala Val
1 5 10 15

Val Arg Thr Pro Pro Lys Ser Pro Ser Cys
20 25

<210> SEQ ID NO 599
<211> LENGTH: 26
<212> TYPE: PRT
<213> ORGANISM: Artificial Sequence
<220> FEATURE:
<223> OTHER INFORMATION: Synthetic construct

<400> SEQUENCE: 599

Tyr Ser Ser Pro Gly Ser Pro Gly Thr Pro Gly Ser Arg Ser Val Val
1 5 10 15

Arg Thr Pro Pro Lys Ser Pro Ser Ser Cys
20 25

<210> SEQ ID NO 600
<211> LENGTH: 26
<212> TYPE: PRT
<213> ORGANISM: Artificial Sequence
<220> FEATURE:
<223> OTHER INFORMATION: Synthetic construct

<400> SEQUENCE: 600

Tyr Ser Ser Pro Gly Ser Pro Gly Thr Pro Gly Ser Arg Ser Val Arg
1 5 10 15

Thr Pro Pro Lys Ser Pro Ser Ser Ala Cys
20 25

<210> SEQ ID NO 601
<211> LENGTH: 27
<212> TYPE: PRT
<213> ORGANISM: Artificial Sequence
<220> FEATURE:
<223> OTHER INFORMATION: Synthetic construct

<400> SEQUENCE: 601

Tyr Ser Ser Pro Gly Ser Pro Gly Thr Pro Gly Ser Arg Ser Ala Val
1               5                   10                  15

Val Arg Thr Pro Pro Lys Ser Pro Ser Ser Cys
            20                  25

<210> SEQ ID NO 602
<211> LENGTH: 27
<212> TYPE: PRT
<213> ORGANISM: Artificial Sequence
<220> FEATURE:
<223> OTHER INFORMATION: Synthetic construct

<400> SEQUENCE: 602

Tyr Ser Ser Pro Gly Ser Pro Gly Thr Pro Gly Ser Arg Ser Val Val
1               5                   10                  15

Arg Thr Pro Pro Lys Ser Pro Ser Ser Ala Cys
            20                  25

<210> SEQ ID NO 603
<211> LENGTH: 28
<212> TYPE: PRT
<213> ORGANISM: Artificial Sequence
<220> FEATURE:
<223> OTHER INFORMATION: Synthetic construct

<400> SEQUENCE: 603

Tyr Ser Ser Pro Gly Ser Pro Gly Thr Pro Gly Ser Arg Ser Ala Val
1               5                   10                  15

Val Arg Thr Pro Pro Lys Ser Pro Ser Ser Ala Cys
            20                  25

<210> SEQ ID NO 604
<211> LENGTH: 24
<212> TYPE: PRT
<213> ORGANISM: Artificial Sequence
<220> FEATURE:
<223> OTHER INFORMATION: Synthetic construct

<400> SEQUENCE: 604

Ser Ser Pro Gly Ser Pro Gly Thr Pro Gly Ser Arg Ser Arg Val Arg
1               5                   10                  15

Thr Pro Pro Lys Ser Pro Ser Cys
            20

<210> SEQ ID NO 605
<211> LENGTH: 25
<212> TYPE: PRT
<213> ORGANISM: Artificial Sequence
<220> FEATURE:
<223> OTHER INFORMATION: Synthetic construct

<400> SEQUENCE: 605

Ser Ser Pro Gly Ser Pro Gly Thr Pro Gly Ser Arg Ser Arg Val Val
1               5                   10                  15

Arg Thr Pro Pro Lys Ser Pro Ser Cys
            20                  25

<210> SEQ ID NO 606
<211> LENGTH: 25
<212> TYPE: PRT
<213> ORGANISM: Artificial Sequence
<220> FEATURE:
<223> OTHER INFORMATION: Synthetic construct

<400> SEQUENCE: 606

Ser Ser Pro Gly Ser Pro Gly Thr Pro Gly Ser Arg Ser Arg Val Arg
1               5                   10                  15

Thr Pro Pro Lys Ser Pro Ser Ser Cys
            20                  25

<210> SEQ ID NO 607
<211> LENGTH: 26
<212> TYPE: PRT
<213> ORGANISM: Artificial Sequence
<220> FEATURE:
<223> OTHER INFORMATION: Synthetic construct

<400> SEQUENCE: 607

Ser Ser Pro Gly Ser Pro Gly Thr Pro Gly Ser Arg Ser Arg Ala Val
1               5                   10                  15

Val Arg Thr Pro Pro Lys Ser Pro Ser Cys
            20                  25

<210> SEQ ID NO 608
<211> LENGTH: 26
<212> TYPE: PRT
<213> ORGANISM: Artificial Sequence
<220> FEATURE:
<223> OTHER INFORMATION: Synthetic construct

<400> SEQUENCE: 608

Ser Ser Pro Gly Ser Pro Gly Thr Pro Gly Ser Arg Ser Arg Val Val
1               5                   10                  15

Arg Thr Pro Pro Lys Ser Pro Ser Ser Cys
            20                  25

<210> SEQ ID NO 609
<211> LENGTH: 26
<212> TYPE: PRT
<213> ORGANISM: Artificial Sequence
<220> FEATURE:
<223> OTHER INFORMATION: Synthetic construct

<400> SEQUENCE: 609

Ser Ser Pro Gly Ser Pro Gly Thr Pro Gly Ser Arg Ser Arg Val Arg
1               5                   10                  15

Thr Pro Pro Lys Ser Pro Ser Ser Ala Cys
            20                  25

<210> SEQ ID NO 610
<211> LENGTH: 27
<212> TYPE: PRT
<213> ORGANISM: Artificial Sequence
<220> FEATURE:
<223> OTHER INFORMATION: Synthetic construct

<400> SEQUENCE: 610

Ser Ser Pro Gly Ser Pro Gly Thr Pro Gly Ser Arg Ser Arg Ala Val
1               5                   10                  15

Val Arg Thr Pro Pro Lys Ser Pro Ser Ser Cys
            20                  25

<210> SEQ ID NO 611
<211> LENGTH: 27
<212> TYPE: PRT
<213> ORGANISM: Artificial Sequence
<220> FEATURE:

<223> OTHER INFORMATION: Synthetic construct

<400> SEQUENCE: 611

Ser Ser Pro Gly Ser Pro Gly Thr Pro Gly Ser Arg Ser Arg Val Val
1 5 10 15

Arg Thr Pro Pro Lys Ser Pro Ser Ser Ala Cys
20 25

<210> SEQ ID NO 612
<211> LENGTH: 28
<212> TYPE: PRT
<213> ORGANISM: Artificial Sequence
<220> FEATURE:
<223> OTHER INFORMATION: Synthetic construct

<400> SEQUENCE: 612

Ser Ser Pro Gly Ser Pro Gly Thr Pro Gly Ser Arg Ser Arg Ala Val
1 5 10 15

Val Arg Thr Pro Pro Lys Ser Pro Ser Ser Ala Cys
20 25

<210> SEQ ID NO 613
<211> LENGTH: 25
<212> TYPE: PRT
<213> ORGANISM: Artificial Sequence
<220> FEATURE:
<223> OTHER INFORMATION: Synthetic construct

<400> SEQUENCE: 613

Ser Gly Tyr Ser Ser Pro Gly Ser Pro Gly Thr Pro Gly Ser Arg Val
1 5 10 15

Arg Thr Pro Pro Lys Ser Pro Ser Cys
20 25

<210> SEQ ID NO 614
<211> LENGTH: 26
<212> TYPE: PRT
<213> ORGANISM: Artificial Sequence
<220> FEATURE:
<223> OTHER INFORMATION: Synthetic construct

<400> SEQUENCE: 614

Ser Gly Tyr Ser Ser Pro Gly Ser Pro Gly Thr Pro Gly Ser Arg Val
1 5 10 15

Val Arg Thr Pro Pro Lys Ser Pro Ser Cys
20 25

<210> SEQ ID NO 615
<211> LENGTH: 26
<212> TYPE: PRT
<213> ORGANISM: Artificial Sequence
<220> FEATURE:
<223> OTHER INFORMATION: Synthetic construct

<400> SEQUENCE: 615

Ser Gly Tyr Ser Ser Pro Gly Ser Pro Gly Thr Pro Gly Ser Arg Val
1 5 10 15

Arg Thr Pro Pro Lys Ser Pro Ser Ser Cys
20 25

<210> SEQ ID NO 616
<211> LENGTH: 27
<212> TYPE: PRT
<213> ORGANISM: Artificial Sequence
<220> FEATURE:
<223> OTHER INFORMATION: Synthetic construct

<400> SEQUENCE: 616

Ser Gly Tyr Ser Ser Pro Gly Ser Pro Gly Thr Pro Gly Ser Arg Ala
1               5                   10                  15

Val Val Arg Thr Pro Pro Lys Ser Pro Ser Cys
            20                  25

<210> SEQ ID NO 617
<211> LENGTH: 27
<212> TYPE: PRT
<213> ORGANISM: Artificial Sequence
<220> FEATURE:
<223> OTHER INFORMATION: Synthetic construct

<400> SEQUENCE: 617

Ser Gly Tyr Ser Ser Pro Gly Ser Pro Gly Thr Pro Gly Ser Arg Val
1               5                   10                  15

Val Arg Thr Pro Pro Lys Ser Pro Ser Ser Cys
            20                  25

<210> SEQ ID NO 618
<211> LENGTH: 27
<212> TYPE: PRT
<213> ORGANISM: Artificial Sequence
<220> FEATURE:
<223> OTHER INFORMATION: Synthetic construct

<400> SEQUENCE: 618

Ser Gly Tyr Ser Ser Pro Gly Ser Pro Gly Thr Pro Gly Ser Arg Val
1               5                   10                  15

Arg Thr Pro Pro Lys Ser Pro Ser Ser Ala Cys
            20                  25

<210> SEQ ID NO 619
<211> LENGTH: 28
<212> TYPE: PRT
<213> ORGANISM: Artificial Sequence
<220> FEATURE:
<223> OTHER INFORMATION: Synthetic construct

<400> SEQUENCE: 619

Ser Gly Tyr Ser Ser Pro Gly Ser Pro Gly Thr Pro Gly Ser Arg Ala
1               5                   10                  15

Val Val Arg Thr Pro Pro Lys Ser Pro Ser Ser Cys
            20                  25

<210> SEQ ID NO 620
<211> LENGTH: 28
<212> TYPE: PRT
<213> ORGANISM: Artificial Sequence
<220> FEATURE:
<223> OTHER INFORMATION: Synthetic construct

<400> SEQUENCE: 620

Ser Gly Tyr Ser Ser Pro Gly Ser Pro Gly Thr Pro Gly Ser Arg Val
1               5                   10                  15

Val Arg Thr Pro Pro Lys Ser Pro Ser Ser Ala Cys
            20                  25

<210> SEQ ID NO 621
<211> LENGTH: 29
<212> TYPE: PRT

<213> ORGANISM: Artificial Sequence
<220> FEATURE:
<223> OTHER INFORMATION: Synthetic construct

<400> SEQUENCE: 621

Ser Gly Tyr Ser Ser Pro Gly Ser Pro Gly Thr Pro Gly Ser Arg Ala
1               5                   10                  15

Val Val Arg Thr Pro Pro Lys Ser Pro Ser Ser Ala Cys
            20                  25

<210> SEQ ID NO 622
<211> LENGTH: 25
<212> TYPE: PRT
<213> ORGANISM: Artificial Sequence
<220> FEATURE:
<223> OTHER INFORMATION: Synthetic construct

<400> SEQUENCE: 622

Gly Tyr Ser Ser Pro Gly Ser Pro Gly Thr Pro Gly Ser Arg Ser Val
1               5                   10                  15

Arg Thr Pro Pro Lys Ser Pro Ser Cys
            20                  25

<210> SEQ ID NO 623
<211> LENGTH: 26
<212> TYPE: PRT
<213> ORGANISM: Artificial Sequence
<220> FEATURE:
<223> OTHER INFORMATION: Synthetic construct

<400> SEQUENCE: 623

Gly Tyr Ser Ser Pro Gly Ser Pro Gly Thr Pro Gly Ser Arg Ser Val
1               5                   10                  15

Val Arg Thr Pro Pro Lys Ser Pro Ser Cys
            20                  25

<210> SEQ ID NO 624
<211> LENGTH: 26
<212> TYPE: PRT
<213> ORGANISM: Artificial Sequence
<220> FEATURE:
<223> OTHER INFORMATION: Synthetic construct

<400> SEQUENCE: 624

Gly Tyr Ser Ser Pro Gly Ser Pro Gly Thr Pro Gly Ser Arg Ser Val
1               5                   10                  15

Arg Thr Pro Pro Lys Ser Pro Ser Ser Cys
            20                  25

<210> SEQ ID NO 625
<211> LENGTH: 27
<212> TYPE: PRT
<213> ORGANISM: Artificial Sequence
<220> FEATURE:
<223> OTHER INFORMATION: Synthetic construct

<400> SEQUENCE: 625

Gly Tyr Ser Ser Pro Gly Ser Pro Gly Thr Pro Gly Ser Arg Ser Ala
1               5                   10                  15

Val Val Arg Thr Pro Pro Lys Ser Pro Ser Cys
            20                  25

<210> SEQ ID NO 626
<211> LENGTH: 27

<212> TYPE: PRT
<213> ORGANISM: Artificial Sequence
<220> FEATURE:
<223> OTHER INFORMATION: Synthetic construct

<400> SEQUENCE: 626

Gly Tyr Ser Ser Pro Gly Ser Pro Gly Thr Pro Gly Ser Arg Ser Val
1 5 10 15

Val Arg Thr Pro Pro Lys Ser Pro Ser Ser Cys
20 25

<210> SEQ ID NO 627
<211> LENGTH: 27
<212> TYPE: PRT
<213> ORGANISM: Artificial Sequence
<220> FEATURE:
<223> OTHER INFORMATION: Synthetic construct

<400> SEQUENCE: 627

Gly Tyr Ser Ser Pro Gly Ser Pro Gly Thr Pro Gly Ser Arg Ser Val
1 5 10 15

Arg Thr Pro Pro Lys Ser Pro Ser Ser Ala Cys
20 25

<210> SEQ ID NO 628
<211> LENGTH: 28
<212> TYPE: PRT
<213> ORGANISM: Artificial Sequence
<220> FEATURE:
<223> OTHER INFORMATION: Synthetic construct

<400> SEQUENCE: 628

Gly Tyr Ser Ser Pro Gly Ser Pro Gly Thr Pro Gly Ser Arg Ser Ala
1 5 10 15

Val Val Arg Thr Pro Pro Lys Ser Pro Ser Ser Cys
20 25

<210> SEQ ID NO 629
<211> LENGTH: 28
<212> TYPE: PRT
<213> ORGANISM: Artificial Sequence
<220> FEATURE:
<223> OTHER INFORMATION: Synthetic construct

<400> SEQUENCE: 629

Gly Tyr Ser Ser Pro Gly Ser Pro Gly Thr Pro Gly Ser Arg Ser Val
1 5 10 15

Val Arg Thr Pro Pro Lys Ser Pro Ser Ser Ala Cys
20 25

<210> SEQ ID NO 630
<211> LENGTH: 29
<212> TYPE: PRT
<213> ORGANISM: Artificial Sequence
<220> FEATURE:
<223> OTHER INFORMATION: Synthetic construct

<400> SEQUENCE: 630

Gly Tyr Ser Ser Pro Gly Ser Pro Gly Thr Pro Gly Ser Arg Ser Ala
1 5 10 15

Val Val Arg Thr Pro Pro Lys Ser Pro Ser Ser Ala Cys
20 25

<210> SEQ ID NO 631

<211> LENGTH: 25
<212> TYPE: PRT
<213> ORGANISM: Artificial Sequence
<220> FEATURE:
<223> OTHER INFORMATION: Synthetic construct

<400> SEQUENCE: 631

Tyr Ser Ser Pro Gly Ser Pro Gly Thr Pro Gly Ser Arg Ser Arg Val
1 5 10 15

Arg Thr Pro Pro Lys Ser Pro Ser Cys
20 25

<210> SEQ ID NO 632
<211> LENGTH: 26
<212> TYPE: PRT
<213> ORGANISM: Artificial Sequence
<220> FEATURE:
<223> OTHER INFORMATION: Synthetic construct

<400> SEQUENCE: 632

Tyr Ser Ser Pro Gly Ser Pro Gly Thr Pro Gly Ser Arg Ser Arg Val
1 5 10 15

Val Arg Thr Pro Pro Lys Ser Pro Ser Cys
20 25

<210> SEQ ID NO 633
<211> LENGTH: 26
<212> TYPE: PRT
<213> ORGANISM: Artificial Sequence
<220> FEATURE:
<223> OTHER INFORMATION: Synthetic construct

<400> SEQUENCE: 633

Tyr Ser Ser Pro Gly Ser Pro Gly Thr Pro Gly Ser Arg Ser Arg Val
1 5 10 15

Arg Thr Pro Pro Lys Ser Pro Ser Ser Cys
20 25

<210> SEQ ID NO 634
<211> LENGTH: 27
<212> TYPE: PRT
<213> ORGANISM: Artificial Sequence
<220> FEATURE:
<223> OTHER INFORMATION: Synthetic construct

<400> SEQUENCE: 634

Tyr Ser Ser Pro Gly Ser Pro Gly Thr Pro Gly Ser Arg Ser Arg Ala
1 5 10 15

Val Val Arg Thr Pro Pro Lys Ser Pro Ser Cys
20 25

<210> SEQ ID NO 635
<211> LENGTH: 27
<212> TYPE: PRT
<213> ORGANISM: Artificial Sequence
<220> FEATURE:
<223> OTHER INFORMATION: Synthetic construct

<400> SEQUENCE: 635

Tyr Ser Ser Pro Gly Ser Pro Gly Thr Pro Gly Ser Arg Ser Arg Val
1 5 10 15

Val Arg Thr Pro Pro Lys Ser Pro Ser Ser Cys
20 25

<210> SEQ ID NO 636
<211> LENGTH: 27
<212> TYPE: PRT
<213> ORGANISM: Artificial Sequence
<220> FEATURE:
<223> OTHER INFORMATION: Synthetic construct

<400> SEQUENCE: 636

```
Tyr Ser Ser Pro Gly Ser Pro Gly Thr Pro Gly Ser Arg Ser Arg Val
1               5                   10                  15

Arg Thr Pro Pro Lys Ser Pro Ser Ser Ala Cys
            20                  25
```

<210> SEQ ID NO 637
<211> LENGTH: 28
<212> TYPE: PRT
<213> ORGANISM: Artificial Sequence
<220> FEATURE:
<223> OTHER INFORMATION: Synthetic construct

<400> SEQUENCE: 637

```
Tyr Ser Ser Pro Gly Ser Pro Gly Thr Pro Gly Ser Arg Ser Arg Ala
1               5                   10                  15

Val Val Arg Thr Pro Pro Lys Ser Pro Ser Ser Cys
            20                  25
```

<210> SEQ ID NO 638
<211> LENGTH: 28
<212> TYPE: PRT
<213> ORGANISM: Artificial Sequence
<220> FEATURE:
<223> OTHER INFORMATION: Synthetic construct

<400> SEQUENCE: 638

```
Tyr Ser Ser Pro Gly Ser Pro Gly Thr Pro Gly Ser Arg Ser Arg Val
1               5                   10                  15

Val Arg Thr Pro Pro Lys Ser Pro Ser Ser Ala Cys
            20                  25
```

<210> SEQ ID NO 639
<211> LENGTH: 29
<212> TYPE: PRT
<213> ORGANISM: Artificial Sequence
<220> FEATURE:
<223> OTHER INFORMATION: Synthetic construct

<400> SEQUENCE: 639

```
Tyr Ser Ser Pro Gly Ser Pro Gly Thr Pro Gly Ser Arg Ser Arg Ala
1               5                   10                  15

Val Val Arg Thr Pro Pro Lys Ser Pro Ser Ser Ala Cys
            20                  25
```

<210> SEQ ID NO 640
<211> LENGTH: 25
<212> TYPE: PRT
<213> ORGANISM: Artificial Sequence
<220> FEATURE:
<223> OTHER INFORMATION: Synthetic construct

<400> SEQUENCE: 640

```
Ser Ser Pro Gly Ser Pro Gly Thr Pro Gly Ser Arg Ser Arg Thr Val
1               5                   10                  15

Arg Thr Pro Pro Lys Ser Pro Ser Cys
            20                  25
```

<210> SEQ ID NO 641
<211> LENGTH: 26
<212> TYPE: PRT
<213> ORGANISM: Artificial Sequence
<220> FEATURE:
<223> OTHER INFORMATION: Synthetic construct

<400> SEQUENCE: 641

```
Ser Ser Pro Gly Ser Pro Gly Thr Pro Gly Ser Arg Ser Arg Thr Val
1               5                   10                  15

Val Arg Thr Pro Pro Lys Ser Pro Ser Cys
            20                  25
```

<210> SEQ ID NO 642
<211> LENGTH: 26
<212> TYPE: PRT
<213> ORGANISM: Artificial Sequence
<220> FEATURE:
<223> OTHER INFORMATION: Synthetic construct

<400> SEQUENCE: 642

```
Ser Ser Pro Gly Ser Pro Gly Thr Pro Gly Ser Arg Ser Arg Thr Val
1               5                   10                  15

Arg Thr Pro Pro Lys Ser Pro Ser Ser Cys
            20                  25
```

<210> SEQ ID NO 643
<211> LENGTH: 27
<212> TYPE: PRT
<213> ORGANISM: Artificial Sequence
<220> FEATURE:
<223> OTHER INFORMATION: Synthetic construct

<400> SEQUENCE: 643

```
Ser Ser Pro Gly Ser Pro Gly Thr Pro Gly Ser Arg Ser Arg Thr Ala
1               5                   10                  15

Val Val Arg Thr Pro Pro Lys Ser Pro Ser Cys
            20                  25
```

<210> SEQ ID NO 644
<211> LENGTH: 27
<212> TYPE: PRT
<213> ORGANISM: Artificial Sequence
<220> FEATURE:
<223> OTHER INFORMATION: Synthetic construct

<400> SEQUENCE: 644

```
Ser Ser Pro Gly Ser Pro Gly Thr Pro Gly Ser Arg Ser Arg Thr Val
1               5                   10                  15

Val Arg Thr Pro Pro Lys Ser Pro Ser Ser Cys
            20                  25
```

<210> SEQ ID NO 645
<211> LENGTH: 27
<212> TYPE: PRT
<213> ORGANISM: Artificial Sequence
<220> FEATURE:
<223> OTHER INFORMATION: Synthetic construct

<400> SEQUENCE: 645

```
Ser Ser Pro Gly Ser Pro Gly Thr Pro Gly Ser Arg Ser Arg Thr Val
1               5                   10                  15

Arg Thr Pro Pro Lys Ser Pro Ser Ser Ala Cys
            20                  25
```

<210> SEQ ID NO 646
<211> LENGTH: 28
<212> TYPE: PRT
<213> ORGANISM: Artificial Sequence
<220> FEATURE:
<223> OTHER INFORMATION: Synthetic construct

<400> SEQUENCE: 646

```
Ser Ser Pro Gly Ser Pro Gly Thr Pro Gly Ser Arg Ser Arg Thr Ala
1               5                   10                  15

Val Val Arg Thr Pro Pro Lys Ser Pro Ser Ser Cys
            20                  25
```

<210> SEQ ID NO 647
<211> LENGTH: 28
<212> TYPE: PRT
<213> ORGANISM: Artificial Sequence
<220> FEATURE:
<223> OTHER INFORMATION: Synthetic construct

<400> SEQUENCE: 647

```
Ser Ser Pro Gly Ser Pro Gly Thr Pro Gly Ser Arg Ser Arg Thr Val
1               5                   10                  15

Val Arg Thr Pro Pro Lys Ser Pro Ser Ser Ala Cys
            20                  25
```

<210> SEQ ID NO 648
<211> LENGTH: 29
<212> TYPE: PRT
<213> ORGANISM: Artificial Sequence
<220> FEATURE:
<223> OTHER INFORMATION: Synthetic construct

<400> SEQUENCE: 648

```
Ser Ser Pro Gly Ser Pro Gly Thr Pro Gly Ser Arg Ser Arg Thr Ala
1               5                   10                  15

Val Val Arg Thr Pro Pro Lys Ser Pro Ser Ser Ala Cys
            20                  25
```

<210> SEQ ID NO 649
<211> LENGTH: 26
<212> TYPE: PRT
<213> ORGANISM: Artificial Sequence
<220> FEATURE:
<223> OTHER INFORMATION: Synthetic construct

<400> SEQUENCE: 649

```
Arg Ser Gly Tyr Ser Ser Pro Gly Ser Pro Gly Thr Pro Gly Ser Arg
1               5                   10                  15

Val Arg Thr Pro Pro Lys Ser Pro Ser Cys
            20                  25
```

<210> SEQ ID NO 650
<211> LENGTH: 27
<212> TYPE: PRT
<213> ORGANISM: Artificial Sequence
<220> FEATURE:
<223> OTHER INFORMATION: Synthetic construct

<400> SEQUENCE: 650

```
Arg Ser Gly Tyr Ser Ser Pro Gly Ser Pro Gly Thr Pro Gly Ser Arg
1               5                   10                  15

Val Val Arg Thr Pro Pro Lys Ser Pro Ser Cys
```

20 25

<210> SEQ ID NO 651
<211> LENGTH: 27
<212> TYPE: PRT
<213> ORGANISM: Artificial Sequence
<220> FEATURE:
<223> OTHER INFORMATION: Synthetic construct

<400> SEQUENCE: 651

Arg Ser Gly Tyr Ser Ser Pro Gly Ser Pro Gly Thr Pro Gly Ser Arg
1 5 10 15

Val Arg Thr Pro Pro Lys Ser Pro Ser Ser Cys
20 25

<210> SEQ ID NO 652
<211> LENGTH: 28
<212> TYPE: PRT
<213> ORGANISM: Artificial Sequence
<220> FEATURE:
<223> OTHER INFORMATION: Synthetic construct

<400> SEQUENCE: 652

Arg Ser Gly Tyr Ser Ser Pro Gly Ser Pro Gly Thr Pro Gly Ser Arg
1 5 10 15

Ala Val Val Arg Thr Pro Pro Lys Ser Pro Ser Cys
20 25

<210> SEQ ID NO 653
<211> LENGTH: 28
<212> TYPE: PRT
<213> ORGANISM: Artificial Sequence
<220> FEATURE:
<223> OTHER INFORMATION: Synthetic construct

<400> SEQUENCE: 653

Arg Ser Gly Tyr Ser Ser Pro Gly Ser Pro Gly Thr Pro Gly Ser Arg
1 5 10 15

Val Val Arg Thr Pro Pro Lys Ser Pro Ser Ser Cys
20 25

<210> SEQ ID NO 654
<211> LENGTH: 28
<212> TYPE: PRT
<213> ORGANISM: Artificial Sequence
<220> FEATURE:
<223> OTHER INFORMATION: Synthetic construct

<400> SEQUENCE: 654

Arg Ser Gly Tyr Ser Ser Pro Gly Ser Pro Gly Thr Pro Gly Ser Arg
1 5 10 15

Val Arg Thr Pro Pro Lys Ser Pro Ser Ser Ala Cys
20 25

<210> SEQ ID NO 655
<211> LENGTH: 29
<212> TYPE: PRT
<213> ORGANISM: Artificial Sequence
<220> FEATURE:
<223> OTHER INFORMATION: Synthetic construct

<400> SEQUENCE: 655

Arg Ser Gly Tyr Ser Ser Pro Gly Ser Pro Gly Thr Pro Gly Ser Arg
1 5 10 15

```
Ala Val Val Arg Thr Pro Pro Lys Ser Pro Ser Ser Cys
            20                  25


<210> SEQ ID NO 656
<211> LENGTH: 29
<212> TYPE: PRT
<213> ORGANISM: Artificial Sequence
<220> FEATURE:
<223> OTHER INFORMATION: Synthetic construct

<400> SEQUENCE: 656

Arg Ser Gly Tyr Ser Ser Pro Gly Ser Pro Gly Thr Pro Gly Ser Arg
1               5                   10                  15

Val Val Arg Thr Pro Pro Lys Ser Pro Ser Ser Ala Cys
            20                  25


<210> SEQ ID NO 657
<211> LENGTH: 30
<212> TYPE: PRT
<213> ORGANISM: Artificial Sequence
<220> FEATURE:
<223> OTHER INFORMATION: Synthetic construct

<400> SEQUENCE: 657

Arg Ser Gly Tyr Ser Ser Pro Gly Ser Pro Gly Thr Pro Gly Ser Arg
1               5                   10                  15

Ala Val Val Arg Thr Pro Pro Lys Ser Pro Ser Ser Ala Cys
            20                  25                  30


<210> SEQ ID NO 658
<211> LENGTH: 26
<212> TYPE: PRT
<213> ORGANISM: Artificial Sequence
<220> FEATURE:
<223> OTHER INFORMATION: Synthetic construct

<400> SEQUENCE: 658

Ser Gly Tyr Ser Ser Pro Gly Ser Pro Gly Thr Pro Gly Ser Arg Ser
1               5                   10                  15

Val Arg Thr Pro Pro Lys Ser Pro Ser Cys
            20                  25


<210> SEQ ID NO 659
<211> LENGTH: 27
<212> TYPE: PRT
<213> ORGANISM: Artificial Sequence
<220> FEATURE:
<223> OTHER INFORMATION: Synthetic construct

<400> SEQUENCE: 659

Ser Gly Tyr Ser Ser Pro Gly Ser Pro Gly Thr Pro Gly Ser Arg Ser
1               5                   10                  15

Val Val Arg Thr Pro Pro Lys Ser Pro Ser Cys
            20                  25


<210> SEQ ID NO 660
<211> LENGTH: 27
<212> TYPE: PRT
<213> ORGANISM: Artificial Sequence
<220> FEATURE:
<223> OTHER INFORMATION: Synthetic construct

<400> SEQUENCE: 660

Ser Gly Tyr Ser Ser Pro Gly Ser Pro Gly Thr Pro Gly Ser Arg Ser
1               5                   10                  15
```

Val Arg Thr Pro Pro Lys Ser Pro Ser Ser Cys
20 25

<210> SEQ ID NO 661
<211> LENGTH: 28
<212> TYPE: PRT
<213> ORGANISM: Artificial Sequence
<220> FEATURE:
<223> OTHER INFORMATION: Synthetic construct

<400> SEQUENCE: 661

Ser Gly Tyr Ser Ser Pro Gly Ser Pro Gly Thr Pro Gly Ser Arg Ser
1 5 10 15

Ala Val Val Arg Thr Pro Pro Lys Ser Pro Ser Cys
20 25

<210> SEQ ID NO 662
<211> LENGTH: 28
<212> TYPE: PRT
<213> ORGANISM: Artificial Sequence
<220> FEATURE:
<223> OTHER INFORMATION: Synthetic construct

<400> SEQUENCE: 662

Ser Gly Tyr Ser Ser Pro Gly Ser Pro Gly Thr Pro Gly Ser Arg Ser
1 5 10 15

Val Val Arg Thr Pro Pro Lys Ser Pro Ser Ser Cys
20 25

<210> SEQ ID NO 663
<211> LENGTH: 28
<212> TYPE: PRT
<213> ORGANISM: Artificial Sequence
<220> FEATURE:
<223> OTHER INFORMATION: Synthetic construct

<400> SEQUENCE: 663

Ser Gly Tyr Ser Ser Pro Gly Ser Pro Gly Thr Pro Gly Ser Arg Ser
1 5 10 15

Val Arg Thr Pro Pro Lys Ser Pro Ser Ser Ala Cys
20 25

<210> SEQ ID NO 664
<211> LENGTH: 29
<212> TYPE: PRT
<213> ORGANISM: Artificial Sequence
<220> FEATURE:
<223> OTHER INFORMATION: Synthetic construct

<400> SEQUENCE: 664

Ser Gly Tyr Ser Ser Pro Gly Ser Pro Gly Thr Pro Gly Ser Arg Ser
1 5 10 15

Ala Val Val Arg Thr Pro Pro Lys Ser Pro Ser Ser Cys
20 25

<210> SEQ ID NO 665
<211> LENGTH: 29
<212> TYPE: PRT
<213> ORGANISM: Artificial Sequence
<220> FEATURE:
<223> OTHER INFORMATION: Synthetic construct

<400> SEQUENCE: 665

Ser Gly Tyr Ser Ser Pro Gly Ser Pro Gly Thr Pro Gly Ser Arg Ser 1               5                   10                  15

Val Val Arg Thr Pro Pro Lys Ser Pro Ser Ser Ala Cys
            20                  25

<210> SEQ ID NO 666
<211> LENGTH: 30
<212> TYPE: PRT
<213> ORGANISM: Artificial Sequence
<220> FEATURE:
<223> OTHER INFORMATION: Synthetic construct

<400> SEQUENCE: 666

Ser Gly Tyr Ser Ser Pro Gly Ser Pro Gly Thr Pro Gly Ser Arg Ser
1               5                   10                  15

Ala Val Val Arg Thr Pro Pro Lys Ser Pro Ser Ser Ala Cys
            20                  25                  30

<210> SEQ ID NO 667
<211> LENGTH: 26
<212> TYPE: PRT
<213> ORGANISM: Artificial Sequence
<220> FEATURE:
<223> OTHER INFORMATION: Synthetic construct

<400> SEQUENCE: 667

Gly Tyr Ser Ser Pro Gly Ser Pro Gly Thr Pro Gly Ser Arg Ser Arg
1               5                   10                  15

Val Arg Thr Pro Pro Lys Ser Pro Ser Cys
            20                  25

<210> SEQ ID NO 668
<211> LENGTH: 27
<212> TYPE: PRT
<213> ORGANISM: Artificial Sequence
<220> FEATURE:
<223> OTHER INFORMATION: Synthetic construct

<400> SEQUENCE: 668

Gly Tyr Ser Ser Pro Gly Ser Pro Gly Thr Pro Gly Ser Arg Ser Arg
1               5                   10                  15

Val Val Arg Thr Pro Pro Lys Ser Pro Ser Cys
            20                  25

<210> SEQ ID NO 669
<211> LENGTH: 27
<212> TYPE: PRT
<213> ORGANISM: Artificial Sequence
<220> FEATURE:
<223> OTHER INFORMATION: Synthetic construct

<400> SEQUENCE: 669

Gly Tyr Ser Ser Pro Gly Ser Pro Gly Thr Pro Gly Ser Arg Ser Arg
1               5                   10                  15

Val Arg Thr Pro Pro Lys Ser Pro Ser Ser Cys
            20                  25

<210> SEQ ID NO 670
<211> LENGTH: 28
<212> TYPE: PRT
<213> ORGANISM: Artificial Sequence
<220> FEATURE:
<223> OTHER INFORMATION: Synthetic construct

<400> SEQUENCE: 670

```
Gly Tyr Ser Ser Pro Gly Ser Pro Gly Thr Pro Gly Ser Arg Ser Arg
1               5                   10                  15

Ala Val Val Arg Thr Pro Pro Lys Ser Pro Ser Cys
            20                  25


<210> SEQ ID NO 671
<211> LENGTH: 28
<212> TYPE: PRT
<213> ORGANISM: Artificial Sequence
<220> FEATURE:
<223> OTHER INFORMATION: Synthetic construct

<400> SEQUENCE: 671

Gly Tyr Ser Ser Pro Gly Ser Pro Gly Thr Pro Gly Ser Arg Ser Arg
1               5                   10                  15

Val Val Arg Thr Pro Pro Lys Ser Pro Ser Ser Cys
            20                  25


<210> SEQ ID NO 672
<211> LENGTH: 28
<212> TYPE: PRT
<213> ORGANISM: Artificial Sequence
<220> FEATURE:
<223> OTHER INFORMATION: Synthetic construct

<400> SEQUENCE: 672

Gly Tyr Ser Ser Pro Gly Ser Pro Gly Thr Pro Gly Ser Arg Ser Arg
1               5                   10                  15

Val Arg Thr Pro Pro Lys Ser Pro Ser Ser Ala Cys
            20                  25


<210> SEQ ID NO 673
<211> LENGTH: 29
<212> TYPE: PRT
<213> ORGANISM: Artificial Sequence
<220> FEATURE:
<223> OTHER INFORMATION: Synthetic construct

<400> SEQUENCE: 673

Gly Tyr Ser Ser Pro Gly Ser Pro Gly Thr Pro Gly Ser Arg Ser Arg
1               5                   10                  15

Ala Val Val Arg Thr Pro Pro Lys Ser Pro Ser Ser Cys
            20                  25


<210> SEQ ID NO 674
<211> LENGTH: 29
<212> TYPE: PRT
<213> ORGANISM: Artificial Sequence
<220> FEATURE:
<223> OTHER INFORMATION: Synthetic construct

<400> SEQUENCE: 674

Gly Tyr Ser Ser Pro Gly Ser Pro Gly Thr Pro Gly Ser Arg Ser Arg
1               5                   10                  15

Val Val Arg Thr Pro Pro Lys Ser Pro Ser Ser Ala Cys
            20                  25


<210> SEQ ID NO 675
<211> LENGTH: 30
<212> TYPE: PRT
<213> ORGANISM: Artificial Sequence
<220> FEATURE:
<223> OTHER INFORMATION: Synthetic construct

<400> SEQUENCE: 675
```

Gly Tyr Ser Ser Pro Gly Ser Pro Gly Thr Pro Gly Ser Arg Ser Arg
1 5 10 15

Ala Val Val Arg Thr Pro Pro Lys Ser Pro Ser Ser Ala Cys
20 25 30

<210> SEQ ID NO 676
<211> LENGTH: 26
<212> TYPE: PRT
<213> ORGANISM: Artificial Sequence
<220> FEATURE:
<223> OTHER INFORMATION: Synthetic construct

<400> SEQUENCE: 676

Tyr Ser Ser Pro Gly Ser Pro Gly Thr Pro Gly Ser Arg Ser Arg Thr
1 5 10 15

Val Arg Thr Pro Pro Lys Ser Pro Ser Cys
20 25

<210> SEQ ID NO 677
<211> LENGTH: 27
<212> TYPE: PRT
<213> ORGANISM: Artificial Sequence
<220> FEATURE:
<223> OTHER INFORMATION: Synthetic construct

<400> SEQUENCE: 677

Tyr Ser Ser Pro Gly Ser Pro Gly Thr Pro Gly Ser Arg Ser Arg Thr
1 5 10 15

Val Val Arg Thr Pro Pro Lys Ser Pro Ser Cys
20 25

<210> SEQ ID NO 678
<211> LENGTH: 27
<212> TYPE: PRT
<213> ORGANISM: Artificial Sequence
<220> FEATURE:
<223> OTHER INFORMATION: Synthetic construct

<400> SEQUENCE: 678

Tyr Ser Ser Pro Gly Ser Pro Gly Thr Pro Gly Ser Arg Ser Arg Thr
1 5 10 15

Val Arg Thr Pro Pro Lys Ser Pro Ser Ser Cys
20 25

<210> SEQ ID NO 679
<211> LENGTH: 28
<212> TYPE: PRT
<213> ORGANISM: Artificial Sequence
<220> FEATURE:
<223> OTHER INFORMATION: Synthetic construct

<400> SEQUENCE: 679

Tyr Ser Ser Pro Gly Ser Pro Gly Thr Pro Gly Ser Arg Ser Arg Thr
1 5 10 15

Ala Val Val Arg Thr Pro Pro Lys Ser Pro Ser Cys
20 25

<210> SEQ ID NO 680
<211> LENGTH: 28
<212> TYPE: PRT
<213> ORGANISM: Artificial Sequence
<220> FEATURE:
<223> OTHER INFORMATION: Synthetic construct

<400> SEQUENCE: 680

Tyr Ser Ser Pro Gly Ser Pro Gly Thr Pro Gly Ser Arg Ser Arg Thr
1               5                   10                  15

Val Val Arg Thr Pro Pro Lys Ser Pro Ser Ser Cys
            20                  25

<210> SEQ ID NO 681
<211> LENGTH: 28
<212> TYPE: PRT
<213> ORGANISM: Artificial Sequence
<220> FEATURE:
<223> OTHER INFORMATION: Synthetic construct

<400> SEQUENCE: 681

Tyr Ser Ser Pro Gly Ser Pro Gly Thr Pro Gly Ser Arg Ser Arg Thr
1               5                   10                  15

Val Arg Thr Pro Pro Lys Ser Pro Ser Ser Ala Cys
            20                  25

<210> SEQ ID NO 682
<211> LENGTH: 29
<212> TYPE: PRT
<213> ORGANISM: Artificial Sequence
<220> FEATURE:
<223> OTHER INFORMATION: Synthetic construct

<400> SEQUENCE: 682

Tyr Ser Ser Pro Gly Ser Pro Gly Thr Pro Gly Ser Arg Ser Arg Thr
1               5                   10                  15

Ala Val Val Arg Thr Pro Pro Lys Ser Pro Ser Ser Cys
            20                  25

<210> SEQ ID NO 683
<211> LENGTH: 29
<212> TYPE: PRT
<213> ORGANISM: Artificial Sequence
<220> FEATURE:
<223> OTHER INFORMATION: Synthetic construct

<400> SEQUENCE: 683

Tyr Ser Ser Pro Gly Ser Pro Gly Thr Pro Gly Ser Arg Ser Arg Thr
1               5                   10                  15

Val Val Arg Thr Pro Pro Lys Ser Pro Ser Ser Ala Cys
            20                  25

<210> SEQ ID NO 684
<211> LENGTH: 30
<212> TYPE: PRT
<213> ORGANISM: Artificial Sequence
<220> FEATURE:
<223> OTHER INFORMATION: Synthetic construct

<400> SEQUENCE: 684

Tyr Ser Ser Pro Gly Ser Pro Gly Thr Pro Gly Ser Arg Ser Arg Thr
1               5                   10                  15

Ala Val Val Arg Thr Pro Pro Lys Ser Pro Ser Ser Ala Cys
            20                  25                  30

<210> SEQ ID NO 685
<211> LENGTH: 26
<212> TYPE: PRT
<213> ORGANISM: Artificial Sequence
<220> FEATURE:
<223> OTHER INFORMATION: Synthetic construct

<400> SEQUENCE: 685

Ser Ser Pro Gly Ser Pro Gly Thr Pro Gly Ser Arg Ser Arg Thr Pro
1 5 10 15

Val Arg Thr Pro Pro Lys Ser Pro Ser Cys
20 25

<210> SEQ ID NO 686
<211> LENGTH: 27
<212> TYPE: PRT
<213> ORGANISM: Artificial Sequence
<220> FEATURE:
<223> OTHER INFORMATION: Synthetic construct

<400> SEQUENCE: 686

Ser Ser Pro Gly Ser Pro Gly Thr Pro Gly Ser Arg Ser Arg Thr Pro
1 5 10 15

Val Val Arg Thr Pro Pro Lys Ser Pro Ser Cys
20 25

<210> SEQ ID NO 687
<211> LENGTH: 27
<212> TYPE: PRT
<213> ORGANISM: Artificial Sequence
<220> FEATURE:
<223> OTHER INFORMATION: Synthetic construct

<400> SEQUENCE: 687

Ser Ser Pro Gly Ser Pro Gly Thr Pro Gly Ser Arg Ser Arg Thr Pro
1 5 10 15

Val Arg Thr Pro Pro Lys Ser Pro Ser Ser Cys
20 25

<210> SEQ ID NO 688
<211> LENGTH: 28
<212> TYPE: PRT
<213> ORGANISM: Artificial Sequence
<220> FEATURE:
<223> OTHER INFORMATION: Synthetic construct

<400> SEQUENCE: 688

Ser Ser Pro Gly Ser Pro Gly Thr Pro Gly Ser Arg Ser Arg Thr Pro
1 5 10 15

Ala Val Val Arg Thr Pro Pro Lys Ser Pro Ser Cys
20 25

<210> SEQ ID NO 689
<211> LENGTH: 28
<212> TYPE: PRT
<213> ORGANISM: Artificial Sequence
<220> FEATURE:
<223> OTHER INFORMATION: Synthetic construct

<400> SEQUENCE: 689

Ser Ser Pro Gly Ser Pro Gly Thr Pro Gly Ser Arg Ser Arg Thr Pro
1 5 10 15

Val Val Arg Thr Pro Pro Lys Ser Pro Ser Ser Cys
20 25

<210> SEQ ID NO 690
<211> LENGTH: 28
<212> TYPE: PRT
<213> ORGANISM: Artificial Sequence
<220> FEATURE:

-continued

<223> OTHER INFORMATION: Synthetic construct

<400> SEQUENCE: 690

Ser Ser Pro Gly Ser Pro Gly Thr Pro Gly Ser Arg Ser Arg Thr Pro
1 5 10 15

Val Arg Thr Pro Pro Lys Ser Pro Ser Ser Ala Cys
20 25

<210> SEQ ID NO 691
<211> LENGTH: 29
<212> TYPE: PRT
<213> ORGANISM: Artificial Sequence
<220> FEATURE:
<223> OTHER INFORMATION: Synthetic construct

<400> SEQUENCE: 691

Ser Ser Pro Gly Ser Pro Gly Thr Pro Gly Ser Arg Ser Arg Thr Pro
1 5 10 15

Ala Val Val Arg Thr Pro Pro Lys Ser Pro Ser Ser Cys
20 25

<210> SEQ ID NO 692
<211> LENGTH: 29
<212> TYPE: PRT
<213> ORGANISM: Artificial Sequence
<220> FEATURE:
<223> OTHER INFORMATION: Synthetic construct

<400> SEQUENCE: 692

Ser Ser Pro Gly Ser Pro Gly Thr Pro Gly Ser Arg Ser Arg Thr Pro
1 5 10 15

Val Val Arg Thr Pro Pro Lys Ser Pro Ser Ser Ala Cys
20 25

<210> SEQ ID NO 693
<211> LENGTH: 30
<212> TYPE: PRT
<213> ORGANISM: Artificial Sequence
<220> FEATURE:
<223> OTHER INFORMATION: Synthetic construct

<400> SEQUENCE: 693

Ser Ser Pro Gly Ser Pro Gly Thr Pro Gly Ser Arg Ser Arg Thr Pro
1 5 10 15

Ala Val Val Arg Thr Pro Pro Lys Ser Pro Ser Ser Ala Cys
20 25 30

<210> SEQ ID NO 694
<211> LENGTH: 27
<212> TYPE: PRT
<213> ORGANISM: Artificial Sequence
<220> FEATURE:
<223> OTHER INFORMATION: Synthetic construct

<400> SEQUENCE: 694

Arg Ser Gly Tyr Ser Ser Pro Gly Ser Pro Gly Thr Pro Gly Ser Arg
1 5 10 15

Ser Val Arg Thr Pro Pro Lys Ser Pro Ser Cys
20 25

<210> SEQ ID NO 695
<211> LENGTH: 28
<212> TYPE: PRT
<213> ORGANISM: Artificial Sequence
<220> FEATURE:
<223> OTHER INFORMATION: Synthetic construct

<400> SEQUENCE: 695

Arg Ser Gly Tyr Ser Ser Pro Gly Ser Pro Gly Thr Pro Gly Ser Arg
1 5 10 15

Ser Val Val Arg Thr Pro Pro Lys Ser Pro Ser Cys
20 25

<210> SEQ ID NO 696
<211> LENGTH: 28
<212> TYPE: PRT
<213> ORGANISM: Artificial Sequence
<220> FEATURE:
<223> OTHER INFORMATION: Synthetic construct

<400> SEQUENCE: 696

Arg Ser Gly Tyr Ser Ser Pro Gly Ser Pro Gly Thr Pro Gly Ser Arg
1 5 10 15

Ser Val Arg Thr Pro Pro Lys Ser Pro Ser Ser Cys
20 25

<210> SEQ ID NO 697
<211> LENGTH: 29
<212> TYPE: PRT
<213> ORGANISM: Artificial Sequence
<220> FEATURE:
<223> OTHER INFORMATION: Synthetic construct

<400> SEQUENCE: 697

Arg Ser Gly Tyr Ser Ser Pro Gly Ser Pro Gly Thr Pro Gly Ser Arg
1 5 10 15

Ser Ala Val Val Arg Thr Pro Pro Lys Ser Pro Ser Cys
20 25

<210> SEQ ID NO 698
<211> LENGTH: 29
<212> TYPE: PRT
<213> ORGANISM: Artificial Sequence
<220> FEATURE:
<223> OTHER INFORMATION: Synthetic construct

<400> SEQUENCE: 698

Arg Ser Gly Tyr Ser Ser Pro Gly Ser Pro Gly Thr Pro Gly Ser Arg
1 5 10 15

Ser Val Val Arg Thr Pro Pro Lys Ser Pro Ser Ser Cys
20 25

<210> SEQ ID NO 699
<211> LENGTH: 29
<212> TYPE: PRT
<213> ORGANISM: Artificial Sequence
<220> FEATURE:
<223> OTHER INFORMATION: Synthetic construct

<400> SEQUENCE: 699

Arg Ser Gly Tyr Ser Ser Pro Gly Ser Pro Gly Thr Pro Gly Ser Arg
1 5 10 15

Ser Val Arg Thr Pro Pro Lys Ser Pro Ser Ser Ala Cys
20 25

<210> SEQ ID NO 700
<211> LENGTH: 30
<212> TYPE: PRT

<213> ORGANISM: Artificial Sequence
<220> FEATURE:
<223> OTHER INFORMATION: Synthetic construct

<400> SEQUENCE: 700

Arg Ser Gly Tyr Ser Ser Pro Gly Ser Pro Gly Thr Pro Gly Ser Arg
1               5                   10                  15

Ser Ala Val Val Arg Thr Pro Pro Lys Ser Pro Ser Ser Cys
            20                  25                  30

<210> SEQ ID NO 701
<211> LENGTH: 30
<212> TYPE: PRT
<213> ORGANISM: Artificial Sequence
<220> FEATURE:
<223> OTHER INFORMATION: Synthetic construct

<400> SEQUENCE: 701

Arg Ser Gly Tyr Ser Ser Pro Gly Ser Pro Gly Thr Pro Gly Ser Arg
1               5                   10                  15

Ser Val Val Arg Thr Pro Pro Lys Ser Pro Ser Ser Ala Cys
            20                  25                  30

<210> SEQ ID NO 702
<211> LENGTH: 31
<212> TYPE: PRT
<213> ORGANISM: Artificial Sequence
<220> FEATURE:
<223> OTHER INFORMATION: Synthetic construct

<400> SEQUENCE: 702

Arg Ser Gly Tyr Ser Ser Pro Gly Ser Pro Gly Thr Pro Gly Ser Arg
1               5                   10                  15

Ser Ala Val Val Arg Thr Pro Pro Lys Ser Pro Ser Ser Ala Cys
            20                  25                  30

<210> SEQ ID NO 703
<211> LENGTH: 27
<212> TYPE: PRT
<213> ORGANISM: Artificial Sequence
<220> FEATURE:
<223> OTHER INFORMATION: Synthetic construct

<400> SEQUENCE: 703

Ser Gly Tyr Ser Ser Pro Gly Ser Pro Gly Thr Pro Gly Ser Arg Ser
1               5                   10                  15

Arg Val Arg Thr Pro Pro Lys Ser Pro Ser Cys
            20                  25

<210> SEQ ID NO 704
<211> LENGTH: 28
<212> TYPE: PRT
<213> ORGANISM: Artificial Sequence
<220> FEATURE:
<223> OTHER INFORMATION: Synthetic construct

<400> SEQUENCE: 704

Ser Gly Tyr Ser Ser Pro Gly Ser Pro Gly Thr Pro Gly Ser Arg Ser
1               5                   10                  15

Arg Val Val Arg Thr Pro Pro Lys Ser Pro Ser Cys
            20                  25

<210> SEQ ID NO 705
<211> LENGTH: 28

<212> TYPE: PRT
<213> ORGANISM: Artificial Sequence
<220> FEATURE:
<223> OTHER INFORMATION: Synthetic construct

<400> SEQUENCE: 705

Ser Gly Tyr Ser Ser Pro Gly Ser Pro Gly Thr Pro Gly Ser Arg Ser
1 5 10 15

Arg Val Arg Thr Pro Pro Lys Ser Pro Ser Ser Cys
20 25

<210> SEQ ID NO 706
<211> LENGTH: 29
<212> TYPE: PRT
<213> ORGANISM: Artificial Sequence
<220> FEATURE:
<223> OTHER INFORMATION: Synthetic construct

<400> SEQUENCE: 706

Ser Gly Tyr Ser Ser Pro Gly Ser Pro Gly Thr Pro Gly Ser Arg Ser
1 5 10 15

Arg Ala Val Val Arg Thr Pro Pro Lys Ser Pro Ser Cys
20 25

<210> SEQ ID NO 707
<211> LENGTH: 29
<212> TYPE: PRT
<213> ORGANISM: Artificial Sequence
<220> FEATURE:
<223> OTHER INFORMATION: Synthetic construct

<400> SEQUENCE: 707

Ser Gly Tyr Ser Ser Pro Gly Ser Pro Gly Thr Pro Gly Ser Arg Ser
1 5 10 15

Arg Val Val Arg Thr Pro Pro Lys Ser Pro Ser Ser Cys
20 25

<210> SEQ ID NO 708
<211> LENGTH: 29
<212> TYPE: PRT
<213> ORGANISM: Artificial Sequence
<220> FEATURE:
<223> OTHER INFORMATION: Synthetic construct

<400> SEQUENCE: 708

Ser Gly Tyr Ser Ser Pro Gly Ser Pro Gly Thr Pro Gly Ser Arg Ser
1 5 10 15

Arg Val Arg Thr Pro Pro Lys Ser Pro Ser Ser Ala Cys
20 25

<210> SEQ ID NO 709
<211> LENGTH: 30
<212> TYPE: PRT
<213> ORGANISM: Artificial Sequence
<220> FEATURE:
<223> OTHER INFORMATION: Synthetic construct

<400> SEQUENCE: 709

Ser Gly Tyr Ser Ser Pro Gly Ser Pro Gly Thr Pro Gly Ser Arg Ser
1 5 10 15

Arg Ala Val Val Arg Thr Pro Pro Lys Ser Pro Ser Ser Cys
20 25 30

<210> SEQ ID NO 710

<211> LENGTH: 30
<212> TYPE: PRT
<213> ORGANISM: Artificial Sequence
<220> FEATURE:
<223> OTHER INFORMATION: Synthetic construct

<400> SEQUENCE: 710

Ser Gly Tyr Ser Ser Pro Gly Ser Pro Gly Thr Pro Gly Ser Arg Ser
1 5 10 15

Arg Val Val Arg Thr Pro Pro Lys Ser Pro Ser Ser Ala Cys
20 25 30

<210> SEQ ID NO 711
<211> LENGTH: 31
<212> TYPE: PRT
<213> ORGANISM: Artificial Sequence
<220> FEATURE:
<223> OTHER INFORMATION: Synthetic construct

<400> SEQUENCE: 711

Ser Gly Tyr Ser Ser Pro Gly Ser Pro Gly Thr Pro Gly Ser Arg Ser
1 5 10 15

Arg Ala Val Val Arg Thr Pro Pro Lys Ser Pro Ser Ser Ala Cys
20 25 30

<210> SEQ ID NO 712
<211> LENGTH: 27
<212> TYPE: PRT
<213> ORGANISM: Artificial Sequence
<220> FEATURE:
<223> OTHER INFORMATION: Synthetic construct

<400> SEQUENCE: 712

Gly Tyr Ser Ser Pro Gly Ser Pro Gly Thr Pro Gly Ser Arg Ser Arg
1 5 10 15

Thr Val Arg Thr Pro Pro Lys Ser Pro Ser Cys
20 25

<210> SEQ ID NO 713
<211> LENGTH: 28
<212> TYPE: PRT
<213> ORGANISM: Artificial Sequence
<220> FEATURE:
<223> OTHER INFORMATION: Synthetic construct

<400> SEQUENCE: 713

Gly Tyr Ser Ser Pro Gly Ser Pro Gly Thr Pro Gly Ser Arg Ser Arg
1 5 10 15

Thr Val Val Arg Thr Pro Pro Lys Ser Pro Ser Cys
20 25

<210> SEQ ID NO 714
<211> LENGTH: 28
<212> TYPE: PRT
<213> ORGANISM: Artificial Sequence
<220> FEATURE:
<223> OTHER INFORMATION: Synthetic construct

<400> SEQUENCE: 714

Gly Tyr Ser Ser Pro Gly Ser Pro Gly Thr Pro Gly Ser Arg Ser Arg
1 5 10 15

Thr Val Arg Thr Pro Pro Lys Ser Pro Ser Ser Cys
20 25

<210> SEQ ID NO 715
<211> LENGTH: 29
<212> TYPE: PRT
<213> ORGANISM: Artificial Sequence
<220> FEATURE:
<223> OTHER INFORMATION: Synthetic construct

<400> SEQUENCE: 715

```
Gly Tyr Ser Ser Pro Gly Ser Pro Gly Thr Pro Gly Ser Arg Ser Arg
1               5                   10                  15

Thr Ala Val Val Arg Thr Pro Pro Lys Ser Pro Ser Cys
            20                  25
```

<210> SEQ ID NO 716
<211> LENGTH: 29
<212> TYPE: PRT
<213> ORGANISM: Artificial Sequence
<220> FEATURE:
<223> OTHER INFORMATION: Synthetic construct

<400> SEQUENCE: 716

```
Gly Tyr Ser Ser Pro Gly Ser Pro Gly Thr Pro Gly Ser Arg Ser Arg
1               5                   10                  15

Thr Val Val Arg Thr Pro Pro Lys Ser Pro Ser Ser Cys
            20                  25
```

<210> SEQ ID NO 717
<211> LENGTH: 29
<212> TYPE: PRT
<213> ORGANISM: Artificial Sequence
<220> FEATURE:
<223> OTHER INFORMATION: Synthetic construct

<400> SEQUENCE: 717

```
Gly Tyr Ser Ser Pro Gly Ser Pro Gly Thr Pro Gly Ser Arg Ser Arg
1               5                   10                  15

Thr Val Arg Thr Pro Pro Lys Ser Pro Ser Ser Ala Cys
            20                  25
```

<210> SEQ ID NO 718
<211> LENGTH: 30
<212> TYPE: PRT
<213> ORGANISM: Artificial Sequence
<220> FEATURE:
<223> OTHER INFORMATION: Synthetic construct

<400> SEQUENCE: 718

```
Gly Tyr Ser Ser Pro Gly Ser Pro Gly Thr Pro Gly Ser Arg Ser Arg
1               5                   10                  15

Thr Ala Val Val Arg Thr Pro Pro Lys Ser Pro Ser Ser Cys
            20                  25                  30
```

<210> SEQ ID NO 719
<211> LENGTH: 30
<212> TYPE: PRT
<213> ORGANISM: Artificial Sequence
<220> FEATURE:
<223> OTHER INFORMATION: Synthetic construct

<400> SEQUENCE: 719

```
Gly Tyr Ser Ser Pro Gly Ser Pro Gly Thr Pro Gly Ser Arg Ser Arg
1               5                   10                  15

Thr Val Val Arg Thr Pro Pro Lys Ser Pro Ser Ser Ala Cys
            20                  25                  30
```

<210> SEQ ID NO 720
<211> LENGTH: 31
<212> TYPE: PRT
<213> ORGANISM: Artificial Sequence
<220> FEATURE:
<223> OTHER INFORMATION: Synthetic construct

<400> SEQUENCE: 720

```
Gly Tyr Ser Ser Pro Gly Ser Pro Gly Thr Pro Gly Ser Arg Ser Arg
1               5                   10                  15

Thr Ala Val Val Arg Thr Pro Pro Lys Ser Pro Ser Ser Ala Cys
            20                  25                  30
```

<210> SEQ ID NO 721
<211> LENGTH: 27
<212> TYPE: PRT
<213> ORGANISM: Artificial Sequence
<220> FEATURE:
<223> OTHER INFORMATION: Synthetic construct

<400> SEQUENCE: 721

```
Tyr Ser Ser Pro Gly Ser Pro Gly Thr Pro Gly Ser Arg Ser Arg Thr
1               5                   10                  15

Pro Val Arg Thr Pro Pro Lys Ser Pro Ser Cys
            20                  25
```

<210> SEQ ID NO 722
<211> LENGTH: 28
<212> TYPE: PRT
<213> ORGANISM: Artificial Sequence
<220> FEATURE:
<223> OTHER INFORMATION: Synthetic construct

<400> SEQUENCE: 722

```
Tyr Ser Ser Pro Gly Ser Pro Gly Thr Pro Gly Ser Arg Ser Arg Thr
1               5                   10                  15

Pro Val Val Arg Thr Pro Pro Lys Ser Pro Ser Cys
            20                  25
```

<210> SEQ ID NO 723
<211> LENGTH: 28
<212> TYPE: PRT
<213> ORGANISM: Artificial Sequence
<220> FEATURE:
<223> OTHER INFORMATION: Synthetic construct

<400> SEQUENCE: 723

```
Tyr Ser Ser Pro Gly Ser Pro Gly Thr Pro Gly Ser Arg Ser Arg Thr
1               5                   10                  15

Pro Val Arg Thr Pro Pro Lys Ser Pro Ser Ser Cys
            20                  25
```

<210> SEQ ID NO 724
<211> LENGTH: 29
<212> TYPE: PRT
<213> ORGANISM: Artificial Sequence
<220> FEATURE:
<223> OTHER INFORMATION: Synthetic construct

<400> SEQUENCE: 724

```
Tyr Ser Ser Pro Gly Ser Pro Gly Thr Pro Gly Ser Arg Ser Arg Thr
1               5                   10                  15

Pro Ala Val Val Arg Thr Pro Pro Lys Ser Pro Ser Cys
            20                  25
```

<210> SEQ ID NO 725
<211> LENGTH: 29
<212> TYPE: PRT
<213> ORGANISM: Artificial Sequence
<220> FEATURE:
<223> OTHER INFORMATION: Synthetic construct

<400> SEQUENCE: 725

Tyr Ser Ser Pro Gly Ser Pro Gly Thr Pro Gly Ser Arg Ser Arg Thr
1 5 10 15

Pro Val Val Arg Thr Pro Pro Lys Ser Pro Ser Ser Cys
20 25

<210> SEQ ID NO 726
<211> LENGTH: 29
<212> TYPE: PRT
<213> ORGANISM: Artificial Sequence
<220> FEATURE:
<223> OTHER INFORMATION: Synthetic construct

<400> SEQUENCE: 726

Tyr Ser Ser Pro Gly Ser Pro Gly Thr Pro Gly Ser Arg Ser Arg Thr
1 5 10 15

Pro Val Arg Thr Pro Pro Lys Ser Pro Ser Ser Ala Cys
20 25

<210> SEQ ID NO 727
<211> LENGTH: 30
<212> TYPE: PRT
<213> ORGANISM: Artificial Sequence
<220> FEATURE:
<223> OTHER INFORMATION: Synthetic construct

<400> SEQUENCE: 727

Tyr Ser Ser Pro Gly Ser Pro Gly Thr Pro Gly Ser Arg Ser Arg Thr
1 5 10 15

Pro Ala Val Val Arg Thr Pro Pro Lys Ser Pro Ser Ser Cys
20 25 30

<210> SEQ ID NO 728
<211> LENGTH: 30
<212> TYPE: PRT
<213> ORGANISM: Artificial Sequence
<220> FEATURE:
<223> OTHER INFORMATION: Synthetic construct

<400> SEQUENCE: 728

Tyr Ser Ser Pro Gly Ser Pro Gly Thr Pro Gly Ser Arg Ser Arg Thr
1 5 10 15

Pro Val Val Arg Thr Pro Pro Lys Ser Pro Ser Ser Ala Cys
20 25 30

<210> SEQ ID NO 729
<211> LENGTH: 31
<212> TYPE: PRT
<213> ORGANISM: Artificial Sequence
<220> FEATURE:
<223> OTHER INFORMATION: Synthetic construct

<400> SEQUENCE: 729

Tyr Ser Ser Pro Gly Ser Pro Gly Thr Pro Gly Ser Arg Ser Arg Thr
1 5 10 15

Pro Ala Val Val Arg Thr Pro Pro Lys Ser Pro Ser Ser Ala Cys 20 25 30

<210> SEQ ID NO 730
<211> LENGTH: 28
<212> TYPE: PRT
<213> ORGANISM: Artificial Sequence
<220> FEATURE:
<223> OTHER INFORMATION: Synthetic construct

<400> SEQUENCE: 730

Arg Ser Gly Tyr Ser Ser Pro Gly Ser Pro Gly Thr Pro Gly Ser Arg
1 5 10 15

Ser Arg Val Arg Thr Pro Pro Lys Ser Pro Ser Cys
20 25

<210> SEQ ID NO 731
<211> LENGTH: 29
<212> TYPE: PRT
<213> ORGANISM: Artificial Sequence
<220> FEATURE:
<223> OTHER INFORMATION: Synthetic construct

<400> SEQUENCE: 731

Arg Ser Gly Tyr Ser Ser Pro Gly Ser Pro Gly Thr Pro Gly Ser Arg
1 5 10 15

Ser Arg Val Val Arg Thr Pro Pro Lys Ser Pro Ser Cys
20 25

<210> SEQ ID NO 732
<211> LENGTH: 29
<212> TYPE: PRT
<213> ORGANISM: Artificial Sequence
<220> FEATURE:
<223> OTHER INFORMATION: Synthetic construct

<400> SEQUENCE: 732

Arg Ser Gly Tyr Ser Ser Pro Gly Ser Pro Gly Thr Pro Gly Ser Arg
1 5 10 15

Ser Arg Val Arg Thr Pro Pro Lys Ser Pro Ser Ser Cys
20 25

<210> SEQ ID NO 733
<211> LENGTH: 30
<212> TYPE: PRT
<213> ORGANISM: Artificial Sequence
<220> FEATURE:
<223> OTHER INFORMATION: Synthetic construct

<400> SEQUENCE: 733

Arg Ser Gly Tyr Ser Ser Pro Gly Ser Pro Gly Thr Pro Gly Ser Arg
1 5 10 15

Ser Arg Ala Val Val Arg Thr Pro Pro Lys Ser Pro Ser Cys
20 25 30

<210> SEQ ID NO 734
<211> LENGTH: 30
<212> TYPE: PRT
<213> ORGANISM: Artificial Sequence
<220> FEATURE:
<223> OTHER INFORMATION: Synthetic construct

<400> SEQUENCE: 734

Arg Ser Gly Tyr Ser Ser Pro Gly Ser Pro Gly Thr Pro Gly Ser Arg
1 5 10 15

Ser Arg Val Val Arg Thr Pro Pro Lys Ser Pro Ser Ser Cys
20 25 30

<210> SEQ ID NO 735
<211> LENGTH: 30
<212> TYPE: PRT
<213> ORGANISM: Artificial Sequence
<220> FEATURE:
<223> OTHER INFORMATION: Synthetic construct

<400> SEQUENCE: 735

Arg Ser Gly Tyr Ser Ser Pro Gly Ser Pro Gly Thr Pro Gly Ser Arg
1 5 10 15

Ser Arg Val Arg Thr Pro Pro Lys Ser Pro Ser Ser Ala Cys
20 25 30

<210> SEQ ID NO 736
<211> LENGTH: 31
<212> TYPE: PRT
<213> ORGANISM: Artificial Sequence
<220> FEATURE:
<223> OTHER INFORMATION: Synthetic construct

<400> SEQUENCE: 736

Arg Ser Gly Tyr Ser Ser Pro Gly Ser Pro Gly Thr Pro Gly Ser Arg
1 5 10 15

Ser Arg Ala Val Val Arg Thr Pro Pro Lys Ser Pro Ser Ser Cys
20 25 30

<210> SEQ ID NO 737
<211> LENGTH: 31
<212> TYPE: PRT
<213> ORGANISM: Artificial Sequence
<220> FEATURE:
<223> OTHER INFORMATION: Synthetic construct

<400> SEQUENCE: 737

Arg Ser Gly Tyr Ser Ser Pro Gly Ser Pro Gly Thr Pro Gly Ser Arg
1 5 10 15

Ser Arg Val Val Arg Thr Pro Pro Lys Ser Pro Ser Ser Ala Cys
20 25 30

<210> SEQ ID NO 738
<211> LENGTH: 28
<212> TYPE: PRT
<213> ORGANISM: Artificial Sequence
<220> FEATURE:
<223> OTHER INFORMATION: Synthetic construct

<400> SEQUENCE: 738

Ser Gly Tyr Ser Ser Pro Gly Ser Pro Gly Thr Pro Gly Ser Arg Ser
1 5 10 15

Arg Thr Val Arg Thr Pro Pro Lys Ser Pro Ser Cys
20 25

<210> SEQ ID NO 739
<211> LENGTH: 29
<212> TYPE: PRT
<213> ORGANISM: Artificial Sequence
<220> FEATURE:
<223> OTHER INFORMATION: Synthetic construct

<400> SEQUENCE: 739

Ser Gly Tyr Ser Ser Pro Gly Ser Pro Gly Thr Pro Gly Ser Arg Ser
1 5 10 15

Arg Thr Val Val Arg Thr Pro Pro Lys Ser Pro Ser Cys
20 25

<210> SEQ ID NO 740
<211> LENGTH: 29
<212> TYPE: PRT
<213> ORGANISM: Artificial Sequence
<220> FEATURE:
<223> OTHER INFORMATION: Synthetic construct

<400> SEQUENCE: 740

Ser Gly Tyr Ser Ser Pro Gly Ser Pro Gly Thr Pro Gly Ser Arg Ser
1 5 10 15

Arg Thr Val Arg Thr Pro Pro Lys Ser Pro Ser Ser Cys
20 25

<210> SEQ ID NO 741
<211> LENGTH: 30
<212> TYPE: PRT
<213> ORGANISM: Artificial Sequence
<220> FEATURE:
<223> OTHER INFORMATION: Synthetic construct

<400> SEQUENCE: 741

Ser Gly Tyr Ser Ser Pro Gly Ser Pro Gly Thr Pro Gly Ser Arg Ser
1 5 10 15

Arg Thr Ala Val Val Arg Thr Pro Pro Lys Ser Pro Ser Cys
20 25 30

<210> SEQ ID NO 742
<211> LENGTH: 30
<212> TYPE: PRT
<213> ORGANISM: Artificial Sequence
<220> FEATURE:
<223> OTHER INFORMATION: Synthetic construct

<400> SEQUENCE: 742

Ser Gly Tyr Ser Ser Pro Gly Ser Pro Gly Thr Pro Gly Ser Arg Ser
1 5 10 15

Arg Thr Val Val Arg Thr Pro Pro Lys Ser Pro Ser Ser Cys
20 25 30

<210> SEQ ID NO 743
<211> LENGTH: 30
<212> TYPE: PRT
<213> ORGANISM: Artificial Sequence
<220> FEATURE:
<223> OTHER INFORMATION: Synthetic construct

<400> SEQUENCE: 743

Ser Gly Tyr Ser Ser Pro Gly Ser Pro Gly Thr Pro Gly Ser Arg Ser
1 5 10 15

Arg Thr Val Arg Thr Pro Pro Lys Ser Pro Ser Ser Ala Cys
20 25 30

<210> SEQ ID NO 744
<211> LENGTH: 31
<212> TYPE: PRT
<213> ORGANISM: Artificial Sequence
<220> FEATURE:
<223> OTHER INFORMATION: Synthetic construct

<400> SEQUENCE: 744

Ser Gly Tyr Ser Ser Pro Gly Ser Pro Gly Thr Pro Gly Ser Arg Ser 1 5 10 15

Arg Thr Ala Val Val Arg Thr Pro Pro Lys Ser Pro Ser Ser Cys
20 25 30

<210> SEQ ID NO 745
<211> LENGTH: 31
<212> TYPE: PRT
<213> ORGANISM: Artificial Sequence
<220> FEATURE:
<223> OTHER INFORMATION: Synthetic construct

<400> SEQUENCE: 745

Ser Gly Tyr Ser Ser Pro Gly Ser Pro Gly Thr Pro Gly Ser Arg Ser
1 5 10 15

Arg Thr Val Val Arg Thr Pro Pro Lys Ser Pro Ser Ser Ala Cys
20 25 30

<210> SEQ ID NO 746
<211> LENGTH: 28
<212> TYPE: PRT
<213> ORGANISM: Artificial Sequence
<220> FEATURE:
<223> OTHER INFORMATION: Synthetic construct

<400> SEQUENCE: 746

Gly Tyr Ser Ser Pro Gly Ser Pro Gly Thr Pro Gly Ser Arg Ser Arg
1 5 10 15

Thr Pro Val Arg Thr Pro Pro Lys Ser Pro Ser Cys
20 25

<210> SEQ ID NO 747
<211> LENGTH: 29
<212> TYPE: PRT
<213> ORGANISM: Artificial Sequence
<220> FEATURE:
<223> OTHER INFORMATION: Synthetic construct

<400> SEQUENCE: 747

Gly Tyr Ser Ser Pro Gly Ser Pro Gly Thr Pro Gly Ser Arg Ser Arg
1 5 10 15

Thr Pro Val Val Arg Thr Pro Pro Lys Ser Pro Ser Cys
20 25

<210> SEQ ID NO 748
<211> LENGTH: 29
<212> TYPE: PRT
<213> ORGANISM: Artificial Sequence
<220> FEATURE:
<223> OTHER INFORMATION: Synthetic construct

<400> SEQUENCE: 748

Gly Tyr Ser Ser Pro Gly Ser Pro Gly Thr Pro Gly Ser Arg Ser Arg
1 5 10 15

Thr Pro Val Arg Thr Pro Pro Lys Ser Pro Ser Ser Cys
20 25

<210> SEQ ID NO 749
<211> LENGTH: 30
<212> TYPE: PRT
<213> ORGANISM: Artificial Sequence
<220> FEATURE:
<223> OTHER INFORMATION: Synthetic construct

<400> SEQUENCE: 749

Gly Tyr Ser Ser Pro Gly Ser Pro Gly Thr Pro Gly Ser Arg Ser Arg
1 5 10 15

Thr Pro Ala Val Val Arg Thr Pro Pro Lys Ser Pro Ser Cys
20 25 30

<210> SEQ ID NO 750
<211> LENGTH: 30
<212> TYPE: PRT
<213> ORGANISM: Artificial Sequence
<220> FEATURE:
<223> OTHER INFORMATION: Synthetic construct

<400> SEQUENCE: 750

Gly Tyr Ser Ser Pro Gly Ser Pro Gly Thr Pro Gly Ser Arg Ser Arg
1 5 10 15

Thr Pro Val Val Arg Thr Pro Pro Lys Ser Pro Ser Ser Cys
20 25 30

<210> SEQ ID NO 751
<211> LENGTH: 30
<212> TYPE: PRT
<213> ORGANISM: Artificial Sequence
<220> FEATURE:
<223> OTHER INFORMATION: Synthetic construct

<400> SEQUENCE: 751

Gly Tyr Ser Ser Pro Gly Ser Pro Gly Thr Pro Gly Ser Arg Ser Arg
1 5 10 15

Thr Pro Val Arg Thr Pro Pro Lys Ser Pro Ser Ser Ala Cys
20 25 30

<210> SEQ ID NO 752
<211> LENGTH: 31
<212> TYPE: PRT
<213> ORGANISM: Artificial Sequence
<220> FEATURE:
<223> OTHER INFORMATION: Synthetic construct

<400> SEQUENCE: 752

Gly Tyr Ser Ser Pro Gly Ser Pro Gly Thr Pro Gly Ser Arg Ser Arg
1 5 10 15

Thr Pro Ala Val Val Arg Thr Pro Pro Lys Ser Pro Ser Ser Cys
20 25 30

<210> SEQ ID NO 753
<211> LENGTH: 31
<212> TYPE: PRT
<213> ORGANISM: Artificial Sequence
<220> FEATURE:
<223> OTHER INFORMATION: Synthetic construct

<400> SEQUENCE: 753

Gly Tyr Ser Ser Pro Gly Ser Pro Gly Thr Pro Gly Ser Arg Ser Arg
1 5 10 15

Thr Pro Val Val Arg Thr Pro Pro Lys Ser Pro Ser Ser Ala Cys
20 25 30

<210> SEQ ID NO 754
<211> LENGTH: 29
<212> TYPE: PRT
<213> ORGANISM: Artificial Sequence
<220> FEATURE:
<223> OTHER INFORMATION: Synthetic construct

<400> SEQUENCE: 754

```
Arg Ser Gly Tyr Ser Ser Pro Gly Ser Pro Gly Thr Pro Gly Ser Arg
1               5                   10                  15

Ser Arg Thr Val Arg Thr Pro Pro Lys Ser Pro Ser Cys
            20                  25


<210> SEQ ID NO 755
<211> LENGTH: 30
<212> TYPE: PRT
<213> ORGANISM: Artificial Sequence
<220> FEATURE:
<223> OTHER INFORMATION: Synthetic construct

<400> SEQUENCE: 755

Arg Ser Gly Tyr Ser Ser Pro Gly Ser Pro Gly Thr Pro Gly Ser Arg
1               5                   10                  15

Ser Arg Thr Val Val Arg Thr Pro Pro Lys Ser Pro Ser Cys
            20                  25                  30


<210> SEQ ID NO 756
<211> LENGTH: 30
<212> TYPE: PRT
<213> ORGANISM: Artificial Sequence
<220> FEATURE:
<223> OTHER INFORMATION: Synthetic construct

<400> SEQUENCE: 756

Arg Ser Gly Tyr Ser Ser Pro Gly Ser Pro Gly Thr Pro Gly Ser Arg
1               5                   10                  15

Ser Arg Thr Val Arg Thr Pro Pro Lys Ser Pro Ser Ser Cys
            20                  25                  30


<210> SEQ ID NO 757
<211> LENGTH: 31
<212> TYPE: PRT
<213> ORGANISM: Artificial Sequence
<220> FEATURE:
<223> OTHER INFORMATION: Synthetic construct

<400> SEQUENCE: 757

Arg Ser Gly Tyr Ser Ser Pro Gly Ser Pro Gly Thr Pro Gly Ser Arg
1               5                   10                  15

Ser Arg Thr Ala Val Val Arg Thr Pro Pro Lys Ser Pro Ser Cys
            20                  25                  30


<210> SEQ ID NO 758
<211> LENGTH: 31
<212> TYPE: PRT
<213> ORGANISM: Artificial Sequence
<220> FEATURE:
<223> OTHER INFORMATION: Synthetic construct

<400> SEQUENCE: 758

Arg Ser Gly Tyr Ser Ser Pro Gly Ser Pro Gly Thr Pro Gly Ser Arg
1               5                   10                  15

Ser Arg Thr Val Val Arg Thr Pro Pro Lys Ser Pro Ser Ser Cys
            20                  25                  30


<210> SEQ ID NO 759
<211> LENGTH: 31
<212> TYPE: PRT
<213> ORGANISM: Artificial Sequence
<220> FEATURE:
<223> OTHER INFORMATION: Synthetic construct
```

<400> SEQUENCE: 759

Arg Ser Gly Tyr Ser Ser Pro Gly Ser Pro Gly Thr Pro Gly Ser Arg
1 5 10 15

Ser Arg Thr Val Arg Thr Pro Pro Lys Ser Pro Ser Ser Ala Cys
20 25 30

<210> SEQ ID NO 760
<211> LENGTH: 32
<212> TYPE: PRT
<213> ORGANISM: Artificial Sequence
<220> FEATURE:
<223> OTHER INFORMATION: Synthetic construct

<400> SEQUENCE: 760

Arg Ser Gly Tyr Ser Ser Pro Gly Ser Pro Gly Thr Pro Gly Ser Arg
1 5 10 15

Ser Arg Thr Ala Val Val Arg Thr Pro Pro Lys Ser Pro Ser Ser Cys
20 25 30

<210> SEQ ID NO 761
<211> LENGTH: 32
<212> TYPE: PRT
<213> ORGANISM: Artificial Sequence
<220> FEATURE:
<223> OTHER INFORMATION: Synthetic construct

<400> SEQUENCE: 761

Arg Ser Gly Tyr Ser Ser Pro Gly Ser Pro Gly Thr Pro Gly Ser Arg
1 5 10 15

Ser Arg Thr Val Val Arg Thr Pro Pro Lys Ser Pro Ser Ser Ala Cys
20 25 30

<210> SEQ ID NO 762
<211> LENGTH: 29
<212> TYPE: PRT
<213> ORGANISM: Artificial Sequence
<220> FEATURE:
<223> OTHER INFORMATION: Synthetic construct

<400> SEQUENCE: 762

Ser Gly Tyr Ser Ser Pro Gly Ser Pro Gly Thr Pro Gly Ser Arg Ser
1 5 10 15

Arg Thr Pro Val Arg Thr Pro Pro Lys Ser Pro Ser Cys
20 25

<210> SEQ ID NO 763
<211> LENGTH: 30
<212> TYPE: PRT
<213> ORGANISM: Artificial Sequence
<220> FEATURE:
<223> OTHER INFORMATION: Synthetic construct

<400> SEQUENCE: 763

Ser Gly Tyr Ser Ser Pro Gly Ser Pro Gly Thr Pro Gly Ser Arg Ser
1 5 10 15

Arg Thr Pro Val Val Arg Thr Pro Pro Lys Ser Pro Ser Cys
20 25 30

<210> SEQ ID NO 764
<211> LENGTH: 30
<212> TYPE: PRT
<213> ORGANISM: Artificial Sequence
<220> FEATURE:
<223> OTHER INFORMATION: Synthetic construct

<400> SEQUENCE: 764

Ser Gly Tyr Ser Ser Pro Gly Ser Pro Gly Thr Pro Gly Ser Arg Ser
1 5 10 15

Arg Thr Pro Val Arg Thr Pro Pro Lys Ser Pro Ser Ser Cys
20 25 30

<210> SEQ ID NO 765
<211> LENGTH: 31
<212> TYPE: PRT
<213> ORGANISM: Artificial Sequence
<220> FEATURE:
<223> OTHER INFORMATION: Synthetic construct

<400> SEQUENCE: 765

Ser Gly Tyr Ser Ser Pro Gly Ser Pro Gly Thr Pro Gly Ser Arg Ser
1 5 10 15

Arg Thr Pro Ala Val Val Arg Thr Pro Pro Lys Ser Pro Ser Cys
20 25 30

<210> SEQ ID NO 766
<211> LENGTH: 31
<212> TYPE: PRT
<213> ORGANISM: Artificial Sequence
<220> FEATURE:
<223> OTHER INFORMATION: Synthetic construct

<400> SEQUENCE: 766

Ser Gly Tyr Ser Ser Pro Gly Ser Pro Gly Thr Pro Gly Ser Arg Ser
1 5 10 15

Arg Thr Pro Val Val Arg Thr Pro Pro Lys Ser Pro Ser Ser Cys
20 25 30

<210> SEQ ID NO 767
<211> LENGTH: 31
<212> TYPE: PRT
<213> ORGANISM: Artificial Sequence
<220> FEATURE:
<223> OTHER INFORMATION: Synthetic construct

<400> SEQUENCE: 767

Ser Gly Tyr Ser Ser Pro Gly Ser Pro Gly Thr Pro Gly Ser Arg Ser
1 5 10 15

Arg Thr Pro Val Arg Thr Pro Pro Lys Ser Pro Ser Ser Ala Cys
20 25 30

<210> SEQ ID NO 768
<211> LENGTH: 32
<212> TYPE: PRT
<213> ORGANISM: Artificial Sequence
<220> FEATURE:
<223> OTHER INFORMATION: Synthetic construct

<400> SEQUENCE: 768

Ser Gly Tyr Ser Ser Pro Gly Ser Pro Gly Thr Pro Gly Ser Arg Ser
1 5 10 15

Arg Thr Pro Ala Val Val Arg Thr Pro Pro Lys Ser Pro Ser Ser Cys
20 25 30

<210> SEQ ID NO 769
<211> LENGTH: 32
<212> TYPE: PRT
<213> ORGANISM: Artificial Sequence
<220> FEATURE:

<223> OTHER INFORMATION: Synthetic construct

<400> SEQUENCE: 769

Ser Gly Tyr Ser Ser Pro Gly Ser Pro Gly Thr Pro Gly Ser Arg Ser
1 5 10 15

Arg Thr Pro Val Val Arg Thr Pro Pro Lys Ser Pro Ser Ser Ala Cys
20 25 30

<210> SEQ ID NO 770
<211> LENGTH: 30
<212> TYPE: PRT
<213> ORGANISM: Artificial Sequence
<220> FEATURE:
<223> OTHER INFORMATION: Synthetic construct

<400> SEQUENCE: 770

Arg Ser Gly Tyr Ser Ser Pro Gly Ser Pro Gly Thr Pro Gly Ser Arg
1 5 10 15

Ser Arg Thr Pro Val Arg Thr Pro Pro Lys Ser Pro Ser Cys
20 25 30

<210> SEQ ID NO 771
<211> LENGTH: 31
<212> TYPE: PRT
<213> ORGANISM: Artificial Sequence
<220> FEATURE:
<223> OTHER INFORMATION: Synthetic construct

<400> SEQUENCE: 771

Arg Ser Gly Tyr Ser Ser Pro Gly Ser Pro Gly Thr Pro Gly Ser Arg
1 5 10 15

Ser Arg Thr Pro Val Val Arg Thr Pro Pro Lys Ser Pro Ser Cys
20 25 30

<210> SEQ ID NO 772
<211> LENGTH: 31
<212> TYPE: PRT
<213> ORGANISM: Artificial Sequence
<220> FEATURE:
<223> OTHER INFORMATION: Synthetic construct

<400> SEQUENCE: 772

Arg Ser Gly Tyr Ser Ser Pro Gly Ser Pro Gly Thr Pro Gly Ser Arg
1 5 10 15

Ser Arg Thr Pro Val Arg Thr Pro Pro Lys Ser Pro Ser Ser Cys
20 25 30

<210> SEQ ID NO 773
<211> LENGTH: 32
<212> TYPE: PRT
<213> ORGANISM: Artificial Sequence
<220> FEATURE:
<223> OTHER INFORMATION: Synthetic construct

<400> SEQUENCE: 773

Arg Ser Gly Tyr Ser Ser Pro Gly Ser Pro Gly Thr Pro Gly Ser Arg
1 5 10 15

Ser Arg Thr Pro Ala Val Val Arg Thr Pro Pro Lys Ser Pro Ser Cys
20 25 30

<210> SEQ ID NO 774
<211> LENGTH: 32
<212> TYPE: PRT
<213> ORGANISM: Artificial Sequence
<220> FEATURE:
<223> OTHER INFORMATION: Synthetic construct

<400> SEQUENCE: 774

Arg Ser Gly Tyr Ser Ser Pro Gly Ser Pro Gly Thr Pro Gly Ser Arg
1               5                   10                  15

Ser Arg Thr Pro Val Val Arg Thr Pro Pro Lys Ser Pro Ser Ser Cys
            20                  25                  30

<210> SEQ ID NO 775
<211> LENGTH: 32
<212> TYPE: PRT
<213> ORGANISM: Artificial Sequence
<220> FEATURE:
<223> OTHER INFORMATION: Synthetic construct

<400> SEQUENCE: 775

Arg Ser Gly Tyr Ser Ser Pro Gly Ser Pro Gly Thr Pro Gly Ser Arg
1               5                   10                  15

Ser Arg Thr Pro Val Arg Thr Pro Pro Lys Ser Pro Ser Ser Ala Cys
            20                  25                  30

<210> SEQ ID NO 776
<211> LENGTH: 27
<212> TYPE: PRT
<213> ORGANISM: Artificial Sequence
<220> FEATURE:
<223> OTHER INFORMATION: Synthetic construct

<400> SEQUENCE: 776

Ser Ser Pro Gly Ser Pro Gly Thr Pro Gly Ser Arg Pro Ser Ser Ala
1               5                   10                  15

Lys Ser Arg Ser Lys Ile Gly Ser Thr Glu Cys
            20                  25

<210> SEQ ID NO 777
<211> LENGTH: 28
<212> TYPE: PRT
<213> ORGANISM: Artificial Sequence
<220> FEATURE:
<223> OTHER INFORMATION: Synthetic construct

<400> SEQUENCE: 777

Ser Ser Pro Gly Ser Pro Gly Thr Pro Gly Ser Arg Ser Pro Ser Ser
1               5                   10                  15

Ala Lys Ser Arg Ser Lys Ile Gly Ser Thr Glu Cys
            20                  25

<210> SEQ ID NO 778
<211> LENGTH: 28
<212> TYPE: PRT
<213> ORGANISM: Artificial Sequence
<220> FEATURE:
<223> OTHER INFORMATION: Synthetic construct

<400> SEQUENCE: 778

Ser Ser Pro Gly Ser Pro Gly Thr Pro Gly Ser Arg Pro Ser Ser Ala
1               5                   10                  15

Lys Ser Arg Ser Lys Ile Gly Ser Thr Glu Asn Cys
            20                  25

<210> SEQ ID NO 779
<211> LENGTH: 29
<212> TYPE: PRT

<213> ORGANISM: Artificial Sequence
<220> FEATURE:
<223> OTHER INFORMATION: Synthetic construct

<400> SEQUENCE: 779

Ser Ser Pro Gly Ser Pro Gly Thr Pro Gly Ser Arg Lys Ser Pro Ser
1 5 10 15

Ser Ala Lys Ser Arg Ser Lys Ile Gly Ser Thr Glu Cys
20 25

<210> SEQ ID NO 780
<211> LENGTH: 29
<212> TYPE: PRT
<213> ORGANISM: Artificial Sequence
<220> FEATURE:
<223> OTHER INFORMATION: Synthetic construct

<400> SEQUENCE: 780

Ser Ser Pro Gly Ser Pro Gly Thr Pro Gly Ser Arg Ser Pro Ser Ser
1 5 10 15

Ala Lys Ser Arg Ser Lys Ile Gly Ser Thr Glu Asn Cys
20 25

<210> SEQ ID NO 781
<211> LENGTH: 29
<212> TYPE: PRT
<213> ORGANISM: Artificial Sequence
<220> FEATURE:
<223> OTHER INFORMATION: Synthetic construct

<400> SEQUENCE: 781

Ser Ser Pro Gly Ser Pro Gly Thr Pro Gly Ser Arg Pro Ser Ser Ala
1 5 10 15

Lys Ser Arg Ser Lys Ile Gly Ser Thr Glu Asn Leu Cys
20 25

<210> SEQ ID NO 782
<211> LENGTH: 30
<212> TYPE: PRT
<213> ORGANISM: Artificial Sequence
<220> FEATURE:
<223> OTHER INFORMATION: Synthetic construct

<400> SEQUENCE: 782

Ser Ser Pro Gly Ser Pro Gly Thr Pro Gly Ser Arg Lys Ser Pro Ser
1 5 10 15

Ser Ala Lys Ser Arg Ser Lys Ile Gly Ser Thr Glu Asn Cys
20 25 30

<210> SEQ ID NO 783
<211> LENGTH: 30
<212> TYPE: PRT
<213> ORGANISM: Artificial Sequence
<220> FEATURE:
<223> OTHER INFORMATION: Synthetic construct

<400> SEQUENCE: 783

Ser Ser Pro Gly Ser Pro Gly Thr Pro Gly Ser Arg Ser Pro Ser Ser
1 5 10 15

Ala Lys Ser Arg Ser Lys Ile Gly Ser Thr Glu Asn Leu Cys
20 25 30

<210> SEQ ID NO 784
<211> LENGTH: 31

<212> TYPE: PRT
<213> ORGANISM: Artificial Sequence
<220> FEATURE:
<223> OTHER INFORMATION: Synthetic construct

<400> SEQUENCE: 784

```
Ser Ser Pro Gly Ser Pro Gly Thr Pro Gly Ser Arg Lys Ser Pro Ser
1               5                   10                  15

Ser Ala Lys Ser Arg Ser Lys Ile Gly Ser Thr Glu Asn Leu Cys
            20                  25                  30
```

<210> SEQ ID NO 785
<211> LENGTH: 28
<212> TYPE: PRT
<213> ORGANISM: Artificial Sequence
<220> FEATURE:
<223> OTHER INFORMATION: Synthetic construct

<400> SEQUENCE: 785

```
Tyr Ser Ser Pro Gly Ser Pro Gly Thr Pro Gly Ser Arg Pro Ser Ser
1               5                   10                  15

Ala Lys Ser Arg Ser Lys Ile Gly Ser Thr Glu Cys
            20                  25
```

<210> SEQ ID NO 786
<211> LENGTH: 29
<212> TYPE: PRT
<213> ORGANISM: Artificial Sequence
<220> FEATURE:
<223> OTHER INFORMATION: Synthetic construct

<400> SEQUENCE: 786

```
Tyr Ser Ser Pro Gly Ser Pro Gly Thr Pro Gly Ser Arg Ser Pro Ser
1               5                   10                  15

Ser Ala Lys Ser Arg Ser Lys Ile Gly Ser Thr Glu Cys
            20                  25
```

<210> SEQ ID NO 787
<211> LENGTH: 29
<212> TYPE: PRT
<213> ORGANISM: Artificial Sequence
<220> FEATURE:
<223> OTHER INFORMATION: Synthetic construct

<400> SEQUENCE: 787

```
Tyr Ser Ser Pro Gly Ser Pro Gly Thr Pro Gly Ser Arg Pro Ser Ser
1               5                   10                  15

Ala Lys Ser Arg Ser Lys Ile Gly Ser Thr Glu Asn Cys
            20                  25
```

<210> SEQ ID NO 788
<211> LENGTH: 30
<212> TYPE: PRT
<213> ORGANISM: Artificial Sequence
<220> FEATURE:
<223> OTHER INFORMATION: Synthetic construct

<400> SEQUENCE: 788

```
Tyr Ser Ser Pro Gly Ser Pro Gly Thr Pro Gly Ser Arg Lys Ser Pro
1               5                   10                  15

Ser Ser Ala Lys Ser Arg Ser Lys Ile Gly Ser Thr Glu Cys
            20                  25                  30
```

<210> SEQ ID NO 789

<211> LENGTH: 30
<212> TYPE: PRT
<213> ORGANISM: Artificial Sequence
<220> FEATURE:
<223> OTHER INFORMATION: Synthetic construct

<400> SEQUENCE: 789

Tyr Ser Ser Pro Gly Ser Pro Gly Thr Pro Gly Ser Arg Ser Pro Ser
1 5 10 15

Ser Ala Lys Ser Arg Ser Lys Ile Gly Ser Thr Glu Asn Cys
20 25 30

<210> SEQ ID NO 790
<211> LENGTH: 30
<212> TYPE: PRT
<213> ORGANISM: Artificial Sequence
<220> FEATURE:
<223> OTHER INFORMATION: Synthetic construct

<400> SEQUENCE: 790

Tyr Ser Ser Pro Gly Ser Pro Gly Thr Pro Gly Ser Arg Pro Ser Ser
1 5 10 15

Ala Lys Ser Arg Ser Lys Ile Gly Ser Thr Glu Asn Leu Cys
20 25 30

<210> SEQ ID NO 791
<211> LENGTH: 31
<212> TYPE: PRT
<213> ORGANISM: Artificial Sequence
<220> FEATURE:
<223> OTHER INFORMATION: Synthetic construct

<400> SEQUENCE: 791

Tyr Ser Ser Pro Gly Ser Pro Gly Thr Pro Gly Ser Arg Lys Ser Pro
1 5 10 15

Ser Ser Ala Lys Ser Arg Ser Lys Ile Gly Ser Thr Glu Asn Cys
20 25 30

<210> SEQ ID NO 792
<211> LENGTH: 31
<212> TYPE: PRT
<213> ORGANISM: Artificial Sequence
<220> FEATURE:
<223> OTHER INFORMATION: Synthetic construct

<400> SEQUENCE: 792

Tyr Ser Ser Pro Gly Ser Pro Gly Thr Pro Gly Ser Arg Ser Pro Ser
1 5 10 15

Ser Ala Lys Ser Arg Ser Lys Ile Gly Ser Thr Glu Asn Leu Cys
20 25 30

<210> SEQ ID NO 793
<211> LENGTH: 32
<212> TYPE: PRT
<213> ORGANISM: Artificial Sequence
<220> FEATURE:
<223> OTHER INFORMATION: Synthetic construct

<400> SEQUENCE: 793

Tyr Ser Ser Pro Gly Ser Pro Gly Thr Pro Gly Ser Arg Lys Ser Pro
1 5 10 15

Ser Ser Ala Lys Ser Arg Ser Lys Ile Gly Ser Thr Glu Asn Leu Cys
20 25 30

<210> SEQ ID NO 794
<211> LENGTH: 28
<212> TYPE: PRT
<213> ORGANISM: Artificial Sequence
<220> FEATURE:
<223> OTHER INFORMATION: Synthetic construct

<400> SEQUENCE: 794

Ser Ser Pro Gly Ser Pro Gly Thr Pro Gly Ser Arg Ser Pro Ser Ser
1 5 10 15

Ala Lys Ser Arg Ser Lys Ile Gly Ser Thr Glu Cys
20 25

<210> SEQ ID NO 795
<211> LENGTH: 29
<212> TYPE: PRT
<213> ORGANISM: Artificial Sequence
<220> FEATURE:
<223> OTHER INFORMATION: Synthetic construct

<400> SEQUENCE: 795

Ser Ser Pro Gly Ser Pro Gly Thr Pro Gly Ser Arg Ser Ser Pro Ser
1 5 10 15

Ser Ala Lys Ser Arg Ser Lys Ile Gly Ser Thr Glu Cys
20 25

<210> SEQ ID NO 796
<211> LENGTH: 29
<212> TYPE: PRT
<213> ORGANISM: Artificial Sequence
<220> FEATURE:
<223> OTHER INFORMATION: Synthetic construct

<400> SEQUENCE: 796

Ser Ser Pro Gly Ser Pro Gly Thr Pro Gly Ser Arg Ser Pro Ser Ser
1 5 10 15

Ala Lys Ser Arg Ser Lys Ile Gly Ser Thr Glu Asn Cys
20 25

<210> SEQ ID NO 797
<211> LENGTH: 30
<212> TYPE: PRT
<213> ORGANISM: Artificial Sequence
<220> FEATURE:
<223> OTHER INFORMATION: Synthetic construct

<400> SEQUENCE: 797

Ser Ser Pro Gly Ser Pro Gly Thr Pro Gly Ser Arg Ser Lys Ser Pro
1 5 10 15

Ser Ser Ala Lys Ser Arg Ser Lys Ile Gly Ser Thr Glu Cys
20 25 30

<210> SEQ ID NO 798
<211> LENGTH: 30
<212> TYPE: PRT
<213> ORGANISM: Artificial Sequence
<220> FEATURE:
<223> OTHER INFORMATION: Synthetic construct

<400> SEQUENCE: 798

Ser Ser Pro Gly Ser Pro Gly Thr Pro Gly Ser Arg Ser Ser Pro Ser
1 5 10 15

Ser Ala Lys Ser Arg Ser Lys Ile Gly Ser Thr Glu Asn Cys
20 25 30

<210> SEQ ID NO 799
<211> LENGTH: 30
<212> TYPE: PRT
<213> ORGANISM: Artificial Sequence
<220> FEATURE:
<223> OTHER INFORMATION: Synthetic construct

<400> SEQUENCE: 799

```
Ser Ser Pro Gly Ser Pro Gly Thr Pro Gly Ser Arg Ser Pro Ser Ser
1               5                   10                  15

Ala Lys Ser Arg Ser Lys Ile Gly Ser Thr Glu Asn Leu Cys
            20                  25                  30
```

<210> SEQ ID NO 800
<211> LENGTH: 31
<212> TYPE: PRT
<213> ORGANISM: Artificial Sequence
<220> FEATURE:
<223> OTHER INFORMATION: Synthetic construct

<400> SEQUENCE: 800

```
Ser Ser Pro Gly Ser Pro Gly Thr Pro Gly Ser Arg Ser Lys Ser Pro
1               5                   10                  15

Ser Ser Ala Lys Ser Arg Ser Lys Ile Gly Ser Thr Glu Asn Cys
            20                  25                  30
```

<210> SEQ ID NO 801
<211> LENGTH: 31
<212> TYPE: PRT
<213> ORGANISM: Artificial Sequence
<220> FEATURE:
<223> OTHER INFORMATION: Synthetic construct

<400> SEQUENCE: 801

```
Ser Ser Pro Gly Ser Pro Gly Thr Pro Gly Ser Arg Ser Ser Pro Ser
1               5                   10                  15

Ser Ala Lys Ser Arg Ser Lys Ile Gly Ser Thr Glu Asn Leu Cys
            20                  25                  30
```

<210> SEQ ID NO 802
<211> LENGTH: 32
<212> TYPE: PRT
<213> ORGANISM: Artificial Sequence
<220> FEATURE:
<223> OTHER INFORMATION: Synthetic construct

<400> SEQUENCE: 802

```
Ser Ser Pro Gly Ser Pro Gly Thr Pro Gly Ser Arg Ser Lys Ser Pro
1               5                   10                  15

Ser Ser Ala Lys Ser Arg Ser Lys Ile Gly Ser Thr Glu Asn Leu Cys
            20                  25                  30
```

<210> SEQ ID NO 803
<211> LENGTH: 29
<212> TYPE: PRT
<213> ORGANISM: Artificial Sequence
<220> FEATURE:
<223> OTHER INFORMATION: Synthetic construct

<400> SEQUENCE: 803

```
Gly Tyr Ser Ser Pro Gly Ser Pro Gly Thr Pro Gly Ser Arg Pro Ser
1               5                   10                  15

Ser Ala Lys Ser Arg Ser Lys Ile Gly Ser Thr Glu Cys
            20                  25
```

<210> SEQ ID NO 804
<211> LENGTH: 30
<212> TYPE: PRT
<213> ORGANISM: Artificial Sequence
<220> FEATURE:
<223> OTHER INFORMATION: Synthetic construct

<400> SEQUENCE: 804

Gly Tyr Ser Ser Pro Gly Ser Pro Gly Thr Pro Gly Ser Arg Ser Pro
1 5 10 15

Ser Ser Ala Lys Ser Arg Ser Lys Ile Gly Ser Thr Glu Cys
20 25 30

<210> SEQ ID NO 805
<211> LENGTH: 30
<212> TYPE: PRT
<213> ORGANISM: Artificial Sequence
<220> FEATURE:
<223> OTHER INFORMATION: Synthetic construct

<400> SEQUENCE: 805

Gly Tyr Ser Ser Pro Gly Ser Pro Gly Thr Pro Gly Ser Arg Pro Ser
1 5 10 15

Ser Ala Lys Ser Arg Ser Lys Ile Gly Ser Thr Glu Asn Cys
20 25 30

<210> SEQ ID NO 806
<211> LENGTH: 31
<212> TYPE: PRT
<213> ORGANISM: Artificial Sequence
<220> FEATURE:
<223> OTHER INFORMATION: Synthetic construct

<400> SEQUENCE: 806

Gly Tyr Ser Ser Pro Gly Ser Pro Gly Thr Pro Gly Ser Arg Lys Ser
1 5 10 15

Pro Ser Ser Ala Lys Ser Arg Ser Lys Ile Gly Ser Thr Glu Cys
20 25 30

<210> SEQ ID NO 807
<211> LENGTH: 31
<212> TYPE: PRT
<213> ORGANISM: Artificial Sequence
<220> FEATURE:
<223> OTHER INFORMATION: Synthetic construct

<400> SEQUENCE: 807

Gly Tyr Ser Ser Pro Gly Ser Pro Gly Thr Pro Gly Ser Arg Ser Pro
1 5 10 15

Ser Ser Ala Lys Ser Arg Ser Lys Ile Gly Ser Thr Glu Asn Cys
20 25 30

<210> SEQ ID NO 808
<211> LENGTH: 31
<212> TYPE: PRT
<213> ORGANISM: Artificial Sequence
<220> FEATURE:
<223> OTHER INFORMATION: Synthetic construct

<400> SEQUENCE: 808

Gly Tyr Ser Ser Pro Gly Ser Pro Gly Thr Pro Gly Ser Arg Pro Ser
1 5 10 15

Ser Ala Lys Ser Arg Ser Lys Ile Gly Ser Thr Glu Asn Leu Cys 20 25 30

<210> SEQ ID NO 809
<211> LENGTH: 32
<212> TYPE: PRT
<213> ORGANISM: Artificial Sequence
<220> FEATURE:
<223> OTHER INFORMATION: Synthetic construct

<400> SEQUENCE: 809

Gly Tyr Ser Ser Pro Gly Ser Pro Gly Thr Pro Gly Ser Arg Lys Ser
1 5 10 15

Pro Ser Ser Ala Lys Ser Arg Ser Lys Ile Gly Ser Thr Glu Asn Cys
20 25 30

<210> SEQ ID NO 810
<211> LENGTH: 32
<212> TYPE: PRT
<213> ORGANISM: Artificial Sequence
<220> FEATURE:
<223> OTHER INFORMATION: Synthetic construct

<400> SEQUENCE: 810

Gly Tyr Ser Ser Pro Gly Ser Pro Gly Thr Pro Gly Ser Arg Ser Pro
1 5 10 15

Ser Ser Ala Lys Ser Arg Ser Lys Ile Gly Ser Thr Glu Asn Leu Cys
20 25 30

<210> SEQ ID NO 811
<211> LENGTH: 29
<212> TYPE: PRT
<213> ORGANISM: Artificial Sequence
<220> FEATURE:
<223> OTHER INFORMATION: Synthetic construct

<400> SEQUENCE: 811

Tyr Ser Ser Pro Gly Ser Pro Gly Thr Pro Gly Ser Arg Ser Pro Ser
1 5 10 15

Ser Ala Lys Ser Arg Ser Lys Ile Gly Ser Thr Glu Cys
20 25

<210> SEQ ID NO 812
<211> LENGTH: 30
<212> TYPE: PRT
<213> ORGANISM: Artificial Sequence
<220> FEATURE:
<223> OTHER INFORMATION: Synthetic construct

<400> SEQUENCE: 812

Tyr Ser Ser Pro Gly Ser Pro Gly Thr Pro Gly Ser Arg Ser Ser Pro
1 5 10 15

Ser Ser Ala Lys Ser Arg Ser Lys Ile Gly Ser Thr Glu Cys
20 25 30

<210> SEQ ID NO 813
<211> LENGTH: 30
<212> TYPE: PRT
<213> ORGANISM: Artificial Sequence
<220> FEATURE:
<223> OTHER INFORMATION: Synthetic construct

<400> SEQUENCE: 813

Tyr Ser Ser Pro Gly Ser Pro Gly Thr Pro Gly Ser Arg Ser Pro Ser
1 5 10 15

Ser Ala Lys Ser Arg Ser Lys Ile Gly Ser Thr Glu Asn Cys
20 25 30

<210> SEQ ID NO 814
<211> LENGTH: 31
<212> TYPE: PRT
<213> ORGANISM: Artificial Sequence
<220> FEATURE:
<223> OTHER INFORMATION: Synthetic construct

<400> SEQUENCE: 814

Tyr Ser Ser Pro Gly Ser Pro Gly Thr Pro Gly Ser Arg Ser Lys Ser
1 5 10 15

Pro Ser Ser Ala Lys Ser Arg Ser Lys Ile Gly Ser Thr Glu Cys
20 25 30

<210> SEQ ID NO 815
<211> LENGTH: 31
<212> TYPE: PRT
<213> ORGANISM: Artificial Sequence
<220> FEATURE:
<223> OTHER INFORMATION: Synthetic construct

<400> SEQUENCE: 815

Tyr Ser Ser Pro Gly Ser Pro Gly Thr Pro Gly Ser Arg Ser Ser Pro
1 5 10 15

Ser Ser Ala Lys Ser Arg Ser Lys Ile Gly Ser Thr Glu Asn Cys
20 25 30

<210> SEQ ID NO 816
<211> LENGTH: 31
<212> TYPE: PRT
<213> ORGANISM: Artificial Sequence
<220> FEATURE:
<223> OTHER INFORMATION: Synthetic construct

<400> SEQUENCE: 816

Tyr Ser Ser Pro Gly Ser Pro Gly Thr Pro Gly Ser Arg Ser Pro Ser
1 5 10 15

Ser Ala Lys Ser Arg Ser Lys Ile Gly Ser Thr Glu Asn Leu Cys
20 25 30

<210> SEQ ID NO 817
<211> LENGTH: 32
<212> TYPE: PRT
<213> ORGANISM: Artificial Sequence
<220> FEATURE:
<223> OTHER INFORMATION: Synthetic construct

<400> SEQUENCE: 817

Tyr Ser Ser Pro Gly Ser Pro Gly Thr Pro Gly Ser Arg Ser Lys Ser
1 5 10 15

Pro Ser Ser Ala Lys Ser Arg Ser Lys Ile Gly Ser Thr Glu Asn Cys
20 25 30

<210> SEQ ID NO 818
<211> LENGTH: 32
<212> TYPE: PRT
<213> ORGANISM: Artificial Sequence
<220> FEATURE:
<223> OTHER INFORMATION: Synthetic construct

<400> SEQUENCE: 818

Tyr Ser Ser Pro Gly Ser Pro Gly Thr Pro Gly Ser Arg Ser Ser Pro
1 5 10 15

Ser Ser Ala Lys Ser Arg Ser Lys Ile Gly Ser Thr Glu Asn Leu Cys
20 25 30

<210> SEQ ID NO 819
<211> LENGTH: 29
<212> TYPE: PRT
<213> ORGANISM: Artificial Sequence
<220> FEATURE:
<223> OTHER INFORMATION: Synthetic construct

<400> SEQUENCE: 819

Ser Ser Pro Gly Ser Pro Gly Thr Pro Gly Ser Arg Ser Arg Pro Ser
1 5 10 15

Ser Ala Lys Ser Arg Ser Lys Ile Gly Ser Thr Glu Cys
20 25

<210> SEQ ID NO 820
<211> LENGTH: 30
<212> TYPE: PRT
<213> ORGANISM: Artificial Sequence
<220> FEATURE:
<223> OTHER INFORMATION: Synthetic construct

<400> SEQUENCE: 820

Ser Ser Pro Gly Ser Pro Gly Thr Pro Gly Ser Arg Ser Arg Ser Pro
1 5 10 15

Ser Ser Ala Lys Ser Arg Ser Lys Ile Gly Ser Thr Glu Cys
20 25 30

<210> SEQ ID NO 821
<211> LENGTH: 30
<212> TYPE: PRT
<213> ORGANISM: Artificial Sequence
<220> FEATURE:
<223> OTHER INFORMATION: Synthetic construct

<400> SEQUENCE: 821

Ser Ser Pro Gly Ser Pro Gly Thr Pro Gly Ser Arg Ser Arg Pro Ser
1 5 10 15

Ser Ala Lys Ser Arg Ser Lys Ile Gly Ser Thr Glu Asn Cys
20 25 30

<210> SEQ ID NO 822
<211> LENGTH: 31
<212> TYPE: PRT
<213> ORGANISM: Artificial Sequence
<220> FEATURE:
<223> OTHER INFORMATION: Synthetic construct

<400> SEQUENCE: 822

Ser Ser Pro Gly Ser Pro Gly Thr Pro Gly Ser Arg Ser Arg Lys Ser
1 5 10 15

Pro Ser Ser Ala Lys Ser Arg Ser Lys Ile Gly Ser Thr Glu Cys
20 25 30

<210> SEQ ID NO 823
<211> LENGTH: 31
<212> TYPE: PRT
<213> ORGANISM: Artificial Sequence
<220> FEATURE:
<223> OTHER INFORMATION: Synthetic construct

<400> SEQUENCE: 823

Ser Ser Pro Gly Ser Pro Gly Thr Pro Gly Ser Arg Ser Arg Ser Pro 1 5 10 15

Ser Ser Ala Lys Ser Arg Ser Lys Ile Gly Ser Thr Glu Asn Cys
20 25 30

<210> SEQ ID NO 824
<211> LENGTH: 31
<212> TYPE: PRT
<213> ORGANISM: Artificial Sequence
<220> FEATURE:
<223> OTHER INFORMATION: Synthetic construct

<400> SEQUENCE: 824

Ser Ser Pro Gly Ser Pro Gly Thr Pro Gly Ser Arg Ser Arg Pro Ser
1 5 10 15

Ser Ala Lys Ser Arg Ser Lys Ile Gly Ser Thr Glu Asn Leu Cys
20 25 30

<210> SEQ ID NO 825
<211> LENGTH: 32
<212> TYPE: PRT
<213> ORGANISM: Artificial Sequence
<220> FEATURE:
<223> OTHER INFORMATION: Synthetic construct

<400> SEQUENCE: 825

Ser Ser Pro Gly Ser Pro Gly Thr Pro Gly Ser Arg Ser Arg Lys Ser
1 5 10 15

Pro Ser Ser Ala Lys Ser Arg Ser Lys Ile Gly Ser Thr Glu Asn Cys
20 25 30

<210> SEQ ID NO 826
<211> LENGTH: 32
<212> TYPE: PRT
<213> ORGANISM: Artificial Sequence
<220> FEATURE:
<223> OTHER INFORMATION: Synthetic construct

<400> SEQUENCE: 826

Ser Ser Pro Gly Ser Pro Gly Thr Pro Gly Ser Arg Ser Arg Ser Pro
1 5 10 15

Ser Ser Ala Lys Ser Arg Ser Lys Ile Gly Ser Thr Glu Asn Leu Cys
20 25 30

<210> SEQ ID NO 827
<211> LENGTH: 30
<212> TYPE: PRT
<213> ORGANISM: Artificial Sequence
<220> FEATURE:
<223> OTHER INFORMATION: Synthetic construct

<400> SEQUENCE: 827

Ser Gly Tyr Ser Ser Pro Gly Ser Pro Gly Thr Pro Gly Ser Arg Pro
1 5 10 15

Ser Ser Ala Lys Ser Arg Ser Lys Ile Gly Ser Thr Glu Cys
20 25 30

<210> SEQ ID NO 828
<211> LENGTH: 31
<212> TYPE: PRT
<213> ORGANISM: Artificial Sequence
<220> FEATURE:
<223> OTHER INFORMATION: Synthetic construct

<400> SEQUENCE: 828

Ser Gly Tyr Ser Ser Pro Gly Ser Pro Gly Thr Pro Gly Ser Arg Ser
1               5                   10                  15

Pro Ser Ser Ala Lys Ser Arg Ser Lys Ile Gly Ser Thr Glu Cys
            20                  25                  30

<210> SEQ ID NO 829
<211> LENGTH: 31
<212> TYPE: PRT
<213> ORGANISM: Artificial Sequence
<220> FEATURE:
<223> OTHER INFORMATION: Synthetic construct

<400> SEQUENCE: 829

Ser Gly Tyr Ser Ser Pro Gly Ser Pro Gly Thr Pro Gly Ser Arg Pro
1               5                   10                  15

Ser Ser Ala Lys Ser Arg Ser Lys Ile Gly Ser Thr Glu Asn Cys
            20                  25                  30

<210> SEQ ID NO 830
<211> LENGTH: 32
<212> TYPE: PRT
<213> ORGANISM: Artificial Sequence
<220> FEATURE:
<223> OTHER INFORMATION: Synthetic construct

<400> SEQUENCE: 830

Ser Gly Tyr Ser Ser Pro Gly Ser Pro Gly Thr Pro Gly Ser Arg Lys
1               5                   10                  15

Ser Pro Ser Ser Ala Lys Ser Arg Ser Lys Ile Gly Ser Thr Glu Cys
            20                  25                  30

<210> SEQ ID NO 831
<211> LENGTH: 32
<212> TYPE: PRT
<213> ORGANISM: Artificial Sequence
<220> FEATURE:
<223> OTHER INFORMATION: Synthetic construct

<400> SEQUENCE: 831

Ser Gly Tyr Ser Ser Pro Gly Ser Pro Gly Thr Pro Gly Ser Arg Ser
1               5                   10                  15

Pro Ser Ser Ala Lys Ser Arg Ser Lys Ile Gly Ser Thr Glu Asn Cys
            20                  25                  30

<210> SEQ ID NO 832
<211> LENGTH: 32
<212> TYPE: PRT
<213> ORGANISM: Artificial Sequence
<220> FEATURE:
<223> OTHER INFORMATION: Synthetic construct

<400> SEQUENCE: 832

Ser Gly Tyr Ser Ser Pro Gly Ser Pro Gly Thr Pro Gly Ser Arg Pro
1               5                   10                  15

Ser Ser Ala Lys Ser Arg Ser Lys Ile Gly Ser Thr Glu Asn Leu Cys
            20                  25                  30

<210> SEQ ID NO 833
<211> LENGTH: 30
<212> TYPE: PRT
<213> ORGANISM: Artificial Sequence
<220> FEATURE:
<223> OTHER INFORMATION: Synthetic construct

<400> SEQUENCE: 833

```
Gly Tyr Ser Ser Pro Gly Ser Pro Gly Thr Pro Gly Ser Arg Ser Pro
1               5                   10                  15

Ser Ser Ala Lys Ser Arg Ser Lys Ile Gly Ser Thr Glu Cys
            20                  25                  30


<210> SEQ ID NO 834
<211> LENGTH: 31
<212> TYPE: PRT
<213> ORGANISM: Artificial Sequence
<220> FEATURE:
<223> OTHER INFORMATION: Synthetic construct

<400> SEQUENCE: 834

Gly Tyr Ser Ser Pro Gly Ser Pro Gly Thr Pro Gly Ser Arg Ser Ser
1               5                   10                  15

Pro Ser Ser Ala Lys Ser Arg Ser Lys Ile Gly Ser Thr Glu Cys
            20                  25                  30


<210> SEQ ID NO 835
<211> LENGTH: 31
<212> TYPE: PRT
<213> ORGANISM: Artificial Sequence
<220> FEATURE:
<223> OTHER INFORMATION: Synthetic construct

<400> SEQUENCE: 835

Gly Tyr Ser Ser Pro Gly Ser Pro Gly Thr Pro Gly Ser Arg Ser Pro
1               5                   10                  15

Ser Ser Ala Lys Ser Arg Ser Lys Ile Gly Ser Thr Glu Asn Cys
            20                  25                  30


<210> SEQ ID NO 836
<211> LENGTH: 32
<212> TYPE: PRT
<213> ORGANISM: Artificial Sequence
<220> FEATURE:
<223> OTHER INFORMATION: Synthetic construct

<400> SEQUENCE: 836

Gly Tyr Ser Ser Pro Gly Ser Pro Gly Thr Pro Gly Ser Arg Ser Lys
1               5                   10                  15

Ser Pro Ser Ser Ala Lys Ser Arg Ser Lys Ile Gly Ser Thr Glu Cys
            20                  25                  30


<210> SEQ ID NO 837
<211> LENGTH: 32
<212> TYPE: PRT
<213> ORGANISM: Artificial Sequence
<220> FEATURE:
<223> OTHER INFORMATION: Synthetic construct

<400> SEQUENCE: 837

Gly Tyr Ser Ser Pro Gly Ser Pro Gly Thr Pro Gly Ser Arg Ser Ser
1               5                   10                  15

Pro Ser Ser Ala Lys Ser Arg Ser Lys Ile Gly Ser Thr Glu Asn Cys
            20                  25                  30


<210> SEQ ID NO 838
<211> LENGTH: 32
<212> TYPE: PRT
<213> ORGANISM: Artificial Sequence
<220> FEATURE:
<223> OTHER INFORMATION: Synthetic construct
```

<400> SEQUENCE: 838

Gly Tyr Ser Ser Pro Gly Ser Pro Gly Thr Pro Gly Ser Arg Ser Pro
1 5 10 15

Ser Ser Ala Lys Ser Arg Ser Lys Ile Gly Ser Thr Glu Asn Leu Cys
20 25 30

<210> SEQ ID NO 839
<211> LENGTH: 30
<212> TYPE: PRT
<213> ORGANISM: Artificial Sequence
<220> FEATURE:
<223> OTHER INFORMATION: Synthetic construct

<400> SEQUENCE: 839

Tyr Ser Ser Pro Gly Ser Pro Gly Thr Pro Gly Ser Arg Ser Arg Pro
1 5 10 15

Ser Ser Ala Lys Ser Arg Ser Lys Ile Gly Ser Thr Glu Cys
20 25 30

<210> SEQ ID NO 840
<211> LENGTH: 31
<212> TYPE: PRT
<213> ORGANISM: Artificial Sequence
<220> FEATURE:
<223> OTHER INFORMATION: Synthetic construct

<400> SEQUENCE: 840

Tyr Ser Ser Pro Gly Ser Pro Gly Thr Pro Gly Ser Arg Ser Arg Ser
1 5 10 15

Pro Ser Ser Ala Lys Ser Arg Ser Lys Ile Gly Ser Thr Glu Cys
20 25 30

<210> SEQ ID NO 841
<211> LENGTH: 31
<212> TYPE: PRT
<213> ORGANISM: Artificial Sequence
<220> FEATURE:
<223> OTHER INFORMATION: Synthetic construct

<400> SEQUENCE: 841

Tyr Ser Ser Pro Gly Ser Pro Gly Thr Pro Gly Ser Arg Ser Arg Pro
1 5 10 15

Ser Ser Ala Lys Ser Arg Ser Lys Ile Gly Ser Thr Glu Asn Cys
20 25 30

<210> SEQ ID NO 842
<211> LENGTH: 32
<212> TYPE: PRT
<213> ORGANISM: Artificial Sequence
<220> FEATURE:
<223> OTHER INFORMATION: Synthetic construct

<400> SEQUENCE: 842

Tyr Ser Ser Pro Gly Ser Pro Gly Thr Pro Gly Ser Arg Ser Arg Lys
1 5 10 15

Ser Pro Ser Ser Ala Lys Ser Arg Ser Lys Ile Gly Ser Thr Glu Cys
20 25 30

<210> SEQ ID NO 843
<211> LENGTH: 32
<212> TYPE: PRT
<213> ORGANISM: Artificial Sequence
<220> FEATURE:
<223> OTHER INFORMATION: Synthetic construct

<400> SEQUENCE: 843

Tyr Ser Ser Pro Gly Ser Pro Gly Thr Pro Gly Ser Arg Ser Arg Ser
1               5                   10                  15

Pro Ser Ser Ala Lys Ser Arg Ser Lys Ile Gly Ser Thr Glu Asn Cys
            20                  25                  30

<210> SEQ ID NO 844
<211> LENGTH: 32
<212> TYPE: PRT
<213> ORGANISM: Artificial Sequence
<220> FEATURE:
<223> OTHER INFORMATION: Synthetic construct

<400> SEQUENCE: 844

Tyr Ser Ser Pro Gly Ser Pro Gly Thr Pro Gly Ser Arg Ser Arg Pro
1               5                   10                  15

Ser Ser Ala Lys Ser Arg Ser Lys Ile Gly Ser Thr Glu Asn Leu Cys
            20                  25                  30

<210> SEQ ID NO 845
<211> LENGTH: 30
<212> TYPE: PRT
<213> ORGANISM: Artificial Sequence
<220> FEATURE:
<223> OTHER INFORMATION: Synthetic construct

<400> SEQUENCE: 845

Ser Ser Pro Gly Ser Pro Gly Thr Pro Gly Ser Arg Ser Arg Thr Pro
1               5                   10                  15

Ser Ser Ala Lys Ser Arg Ser Lys Ile Gly Ser Thr Glu Cys
            20                  25                  30

<210> SEQ ID NO 846
<211> LENGTH: 31
<212> TYPE: PRT
<213> ORGANISM: Artificial Sequence
<220> FEATURE:
<223> OTHER INFORMATION: Synthetic construct

<400> SEQUENCE: 846

Ser Ser Pro Gly Ser Pro Gly Thr Pro Gly Ser Arg Ser Arg Thr Ser
1               5                   10                  15

Pro Ser Ser Ala Lys Ser Arg Ser Lys Ile Gly Ser Thr Glu Cys
            20                  25                  30

<210> SEQ ID NO 847
<211> LENGTH: 31
<212> TYPE: PRT
<213> ORGANISM: Artificial Sequence
<220> FEATURE:
<223> OTHER INFORMATION: Synthetic construct

<400> SEQUENCE: 847

Ser Ser Pro Gly Ser Pro Gly Thr Pro Gly Ser Arg Ser Arg Thr Pro
1               5                   10                  15

Ser Ser Ala Lys Ser Arg Ser Lys Ile Gly Ser Thr Glu Asn Cys
            20                  25                  30

<210> SEQ ID NO 848
<211> LENGTH: 32
<212> TYPE: PRT
<213> ORGANISM: Artificial Sequence
<220> FEATURE:

<223> OTHER INFORMATION: Synthetic construct

<400> SEQUENCE: 848

Ser Ser Pro Gly Ser Pro Gly Thr Pro Gly Ser Arg Ser Arg Thr Lys
1 5 10 15

Ser Pro Ser Ser Ala Lys Ser Arg Ser Lys Ile Gly Ser Thr Glu Cys
20 25 30

<210> SEQ ID NO 849
<211> LENGTH: 32
<212> TYPE: PRT
<213> ORGANISM: Artificial Sequence
<220> FEATURE:
<223> OTHER INFORMATION: Synthetic construct

<400> SEQUENCE: 849

Ser Ser Pro Gly Ser Pro Gly Thr Pro Gly Ser Arg Ser Arg Thr Ser
1 5 10 15

Pro Ser Ser Ala Lys Ser Arg Ser Lys Ile Gly Ser Thr Glu Asn Cys
20 25 30

<210> SEQ ID NO 850
<211> LENGTH: 32
<212> TYPE: PRT
<213> ORGANISM: Artificial Sequence
<220> FEATURE:
<223> OTHER INFORMATION: Synthetic construct

<400> SEQUENCE: 850

Ser Ser Pro Gly Ser Pro Gly Thr Pro Gly Ser Arg Ser Arg Thr Pro
1 5 10 15

Ser Ser Ala Lys Ser Arg Ser Lys Ile Gly Ser Thr Glu Asn Leu Cys
20 25 30

<210> SEQ ID NO 851
<211> LENGTH: 31
<212> TYPE: PRT
<213> ORGANISM: Artificial Sequence
<220> FEATURE:
<223> OTHER INFORMATION: Synthetic construct

<400> SEQUENCE: 851

Arg Ser Gly Tyr Ser Ser Pro Gly Ser Pro Gly Thr Pro Gly Ser Arg
1 5 10 15

Pro Ser Ser Ala Lys Ser Arg Ser Lys Ile Gly Ser Thr Glu Cys
20 25 30

<210> SEQ ID NO 852
<211> LENGTH: 32
<212> TYPE: PRT
<213> ORGANISM: Artificial Sequence
<220> FEATURE:
<223> OTHER INFORMATION: Synthetic construct

<400> SEQUENCE: 852

Arg Ser Gly Tyr Ser Ser Pro Gly Ser Pro Gly Thr Pro Gly Ser Arg
1 5 10 15

Ser Pro Ser Ser Ala Lys Ser Arg Ser Lys Ile Gly Ser Thr Glu Cys
20 25 30

<210> SEQ ID NO 853
<211> LENGTH: 32
<212> TYPE: PRT
<213> ORGANISM: Artificial Sequence
<220> FEATURE:
<223> OTHER INFORMATION: Synthetic construct

<400> SEQUENCE: 853

Arg Ser Gly Tyr Ser Ser Pro Gly Ser Pro Gly Thr Pro Gly Ser Arg
1               5                   10                  15

Pro Ser Ser Ala Lys Ser Arg Ser Lys Ile Gly Ser Thr Glu Asn Cys
            20                  25                  30

<210> SEQ ID NO 854
<211> LENGTH: 31
<212> TYPE: PRT
<213> ORGANISM: Artificial Sequence
<220> FEATURE:
<223> OTHER INFORMATION: Synthetic construct

<400> SEQUENCE: 854

Ser Gly Tyr Ser Ser Pro Gly Ser Pro Gly Thr Pro Gly Ser Arg Ser
1               5                   10                  15

Pro Ser Ser Ala Lys Ser Arg Ser Lys Ile Gly Ser Thr Glu Cys
            20                  25                  30

<210> SEQ ID NO 855
<211> LENGTH: 32
<212> TYPE: PRT
<213> ORGANISM: Artificial Sequence
<220> FEATURE:
<223> OTHER INFORMATION: Synthetic construct

<400> SEQUENCE: 855

Ser Gly Tyr Ser Ser Pro Gly Ser Pro Gly Thr Pro Gly Ser Arg Ser
1               5                   10                  15

Ser Pro Ser Ser Ala Lys Ser Arg Ser Lys Ile Gly Ser Thr Glu Cys
            20                  25                  30

<210> SEQ ID NO 856
<211> LENGTH: 32
<212> TYPE: PRT
<213> ORGANISM: Artificial Sequence
<220> FEATURE:
<223> OTHER INFORMATION: Synthetic construct

<400> SEQUENCE: 856

Ser Gly Tyr Ser Ser Pro Gly Ser Pro Gly Thr Pro Gly Ser Arg Ser
1               5                   10                  15

Pro Ser Ser Ala Lys Ser Arg Ser Lys Ile Gly Ser Thr Glu Asn Cys
            20                  25                  30

<210> SEQ ID NO 857
<211> LENGTH: 31
<212> TYPE: PRT
<213> ORGANISM: Artificial Sequence
<220> FEATURE:
<223> OTHER INFORMATION: Synthetic construct

<400> SEQUENCE: 857

Gly Tyr Ser Ser Pro Gly Ser Pro Gly Thr Pro Gly Ser Arg Ser Arg
1               5                   10                  15

Pro Ser Ser Ala Lys Ser Arg Ser Lys Ile Gly Ser Thr Glu Cys
            20                  25                  30

<210> SEQ ID NO 858
<211> LENGTH: 32
<212> TYPE: PRT

<213> ORGANISM: Artificial Sequence
<220> FEATURE:
<223> OTHER INFORMATION: Synthetic construct

<400> SEQUENCE: 858

Gly Tyr Ser Ser Pro Gly Ser Pro Gly Thr Pro Gly Ser Arg Ser Arg
1 5 10 15

Ser Pro Ser Ser Ala Lys Ser Arg Ser Lys Ile Gly Ser Thr Glu Cys
20 25 30

<210> SEQ ID NO 859
<211> LENGTH: 32
<212> TYPE: PRT
<213> ORGANISM: Artificial Sequence
<220> FEATURE:
<223> OTHER INFORMATION: Synthetic construct

<400> SEQUENCE: 859

Gly Tyr Ser Ser Pro Gly Ser Pro Gly Thr Pro Gly Ser Arg Ser Arg
1 5 10 15

Pro Ser Ser Ala Lys Ser Arg Ser Lys Ile Gly Ser Thr Glu Asn Cys
20 25 30

<210> SEQ ID NO 860
<211> LENGTH: 31
<212> TYPE: PRT
<213> ORGANISM: Artificial Sequence
<220> FEATURE:
<223> OTHER INFORMATION: Synthetic construct

<400> SEQUENCE: 860

Tyr Ser Ser Pro Gly Ser Pro Gly Thr Pro Gly Ser Arg Ser Arg Thr
1 5 10 15

Pro Ser Ser Ala Lys Ser Arg Ser Lys Ile Gly Ser Thr Glu Cys
20 25 30

<210> SEQ ID NO 861
<211> LENGTH: 32
<212> TYPE: PRT
<213> ORGANISM: Artificial Sequence
<220> FEATURE:
<223> OTHER INFORMATION: Synthetic construct

<400> SEQUENCE: 861

Tyr Ser Ser Pro Gly Ser Pro Gly Thr Pro Gly Ser Arg Ser Arg Thr
1 5 10 15

Ser Pro Ser Ser Ala Lys Ser Arg Ser Lys Ile Gly Ser Thr Glu Cys
20 25 30

<210> SEQ ID NO 862
<211> LENGTH: 32
<212> TYPE: PRT
<213> ORGANISM: Artificial Sequence
<220> FEATURE:
<223> OTHER INFORMATION: Synthetic construct

<400> SEQUENCE: 862

Tyr Ser Ser Pro Gly Ser Pro Gly Thr Pro Gly Ser Arg Ser Arg Thr
1 5 10 15

Pro Ser Ser Ala Lys Ser Arg Ser Lys Ile Gly Ser Thr Glu Asn Cys
20 25 30

<210> SEQ ID NO 863
<211> LENGTH: 31

<212> TYPE: PRT
<213> ORGANISM: Artificial Sequence
<220> FEATURE:
<223> OTHER INFORMATION: Synthetic construct

<400> SEQUENCE: 863

Ser Ser Pro Gly Ser Pro Gly Thr Pro Gly Ser Arg Ser Arg Thr Pro
1 5 10 15

Pro Ser Ser Ala Lys Ser Arg Ser Lys Ile Gly Ser Thr Glu Cys
20 25 30

<210> SEQ ID NO 864
<211> LENGTH: 32
<212> TYPE: PRT
<213> ORGANISM: Artificial Sequence
<220> FEATURE:
<223> OTHER INFORMATION: Synthetic construct

<400> SEQUENCE: 864

Ser Ser Pro Gly Ser Pro Gly Thr Pro Gly Ser Arg Ser Arg Thr Pro
1 5 10 15

Ser Pro Ser Ser Ala Lys Ser Arg Ser Lys Ile Gly Ser Thr Glu Cys
20 25 30

<210> SEQ ID NO 865
<211> LENGTH: 32
<212> TYPE: PRT
<213> ORGANISM: Artificial Sequence
<220> FEATURE:
<223> OTHER INFORMATION: Synthetic construct

<400> SEQUENCE: 865

Ser Ser Pro Gly Ser Pro Gly Thr Pro Gly Ser Arg Ser Arg Thr Pro
1 5 10 15

Pro Ser Ser Ala Lys Ser Arg Ser Lys Ile Gly Ser Thr Glu Asn Cys
20 25 30

<210> SEQ ID NO 866
<211> LENGTH: 25
<212> TYPE: PRT
<213> ORGANISM: Artificial Sequence
<220> FEATURE:
<223> OTHER INFORMATION: Synthetic construct

<400> SEQUENCE: 866

Ser Ser Pro Gly Ser Pro Gly Thr Pro Gly Ser Arg Lys Ser Pro Val
1 5 10 15

Val Ser Gly Asp Thr Ser Pro Arg Cys
20 25

<210> SEQ ID NO 867
<211> LENGTH: 26
<212> TYPE: PRT
<213> ORGANISM: Artificial Sequence
<220> FEATURE:
<223> OTHER INFORMATION: Synthetic construct

<400> SEQUENCE: 867

Ser Ser Pro Gly Ser Pro Gly Thr Pro Gly Ser Arg Tyr Lys Ser Pro
1 5 10 15

Val Val Ser Gly Asp Thr Ser Pro Arg Cys
20 25

<210> SEQ ID NO 868

<211> LENGTH: 27
<212> TYPE: PRT
<213> ORGANISM: Artificial Sequence
<220> FEATURE:
<223> OTHER INFORMATION: Synthetic construct

<400> SEQUENCE: 868

Ser Ser Pro Gly Ser Pro Gly Thr Pro Gly Ser Arg Val Tyr Lys Ser
1 5 10 15

Pro Val Val Ser Gly Asp Thr Ser Pro Arg Cys
20 25

<210> SEQ ID NO 869
<211> LENGTH: 27
<212> TYPE: PRT
<213> ORGANISM: Artificial Sequence
<220> FEATURE:
<223> OTHER INFORMATION: Synthetic construct

<400> SEQUENCE: 869

Ser Ser Pro Gly Ser Pro Gly Thr Pro Gly Ser Arg Tyr Lys Ser Pro
1 5 10 15

Val Val Ser Gly Asp Thr Ser Pro Arg His Cys
20 25

<210> SEQ ID NO 870
<211> LENGTH: 28
<212> TYPE: PRT
<213> ORGANISM: Artificial Sequence
<220> FEATURE:
<223> OTHER INFORMATION: Synthetic construct

<400> SEQUENCE: 870

Ser Ser Pro Gly Ser Pro Gly Thr Pro Gly Ser Arg Ile Val Tyr Lys
1 5 10 15

Ser Pro Val Val Ser Gly Asp Thr Ser Pro Arg Cys
20 25

<210> SEQ ID NO 871
<211> LENGTH: 28
<212> TYPE: PRT
<213> ORGANISM: Artificial Sequence
<220> FEATURE:
<223> OTHER INFORMATION: Synthetic construct

<400> SEQUENCE: 871

Ser Ser Pro Gly Ser Pro Gly Thr Pro Gly Ser Arg Val Tyr Lys Ser
1 5 10 15

Pro Val Val Ser Gly Asp Thr Ser Pro Arg His Cys
20 25

<210> SEQ ID NO 872
<211> LENGTH: 28
<212> TYPE: PRT
<213> ORGANISM: Artificial Sequence
<220> FEATURE:
<223> OTHER INFORMATION: Synthetic construct

<400> SEQUENCE: 872

Ser Ser Pro Gly Ser Pro Gly Thr Pro Gly Ser Arg Tyr Lys Ser Pro
1 5 10 15

Val Val Ser Gly Asp Thr Ser Pro Arg His Leu Cys
20 25

<210> SEQ ID NO 873
<211> LENGTH: 29
<212> TYPE: PRT
<213> ORGANISM: Artificial Sequence
<220> FEATURE:
<223> OTHER INFORMATION: Synthetic construct

<400> SEQUENCE: 873

Ser Ser Pro Gly Ser Pro Gly Thr Pro Gly Ser Arg Ile Val Tyr Lys
1 5 10 15

Ser Pro Val Val Ser Gly Asp Thr Ser Pro Arg His Cys
20 25

<210> SEQ ID NO 874
<211> LENGTH: 29
<212> TYPE: PRT
<213> ORGANISM: Artificial Sequence
<220> FEATURE:
<223> OTHER INFORMATION: Synthetic construct

<400> SEQUENCE: 874

Ser Ser Pro Gly Ser Pro Gly Thr Pro Gly Ser Arg Val Tyr Lys Ser
1 5 10 15

Pro Val Val Ser Gly Asp Thr Ser Pro Arg His Leu Cys
20 25

<210> SEQ ID NO 875
<211> LENGTH: 30
<212> TYPE: PRT
<213> ORGANISM: Artificial Sequence
<220> FEATURE:
<223> OTHER INFORMATION: Synthetic construct

<400> SEQUENCE: 875

Ser Ser Pro Gly Ser Pro Gly Thr Pro Gly Ser Arg Ile Val Tyr Lys
1 5 10 15

Ser Pro Val Val Ser Gly Asp Thr Ser Pro Arg His Leu Cys
20 25 30

<210> SEQ ID NO 876
<211> LENGTH: 26
<212> TYPE: PRT
<213> ORGANISM: Artificial Sequence
<220> FEATURE:
<223> OTHER INFORMATION: Synthetic construct

<400> SEQUENCE: 876

Tyr Ser Ser Pro Gly Ser Pro Gly Thr Pro Gly Ser Arg Lys Ser Pro
1 5 10 15

Val Val Ser Gly Asp Thr Ser Pro Arg Cys
20 25

<210> SEQ ID NO 877
<211> LENGTH: 27
<212> TYPE: PRT
<213> ORGANISM: Artificial Sequence
<220> FEATURE:
<223> OTHER INFORMATION: Synthetic construct

<400> SEQUENCE: 877

Tyr Ser Ser Pro Gly Ser Pro Gly Thr Pro Gly Ser Arg Tyr Lys Ser
1 5 10 15

Pro Val Val Ser Gly Asp Thr Ser Pro Arg Cys
20 25

<210> SEQ ID NO 878
<211> LENGTH: 28
<212> TYPE: PRT
<213> ORGANISM: Artificial Sequence
<220> FEATURE:
<223> OTHER INFORMATION: Synthetic construct

<400> SEQUENCE: 878

Tyr Ser Ser Pro Gly Ser Pro Gly Thr Pro Gly Ser Arg Val Tyr Lys
1 5 10 15

Ser Pro Val Val Ser Gly Asp Thr Ser Pro Arg Cys
20 25

<210> SEQ ID NO 879
<211> LENGTH: 28
<212> TYPE: PRT
<213> ORGANISM: Artificial Sequence
<220> FEATURE:
<223> OTHER INFORMATION: Synthetic construct

<400> SEQUENCE: 879

Tyr Ser Ser Pro Gly Ser Pro Gly Thr Pro Gly Ser Arg Tyr Lys Ser
1 5 10 15

Pro Val Val Ser Gly Asp Thr Ser Pro Arg His Cys
20 25

<210> SEQ ID NO 880
<211> LENGTH: 29
<212> TYPE: PRT
<213> ORGANISM: Artificial Sequence
<220> FEATURE:
<223> OTHER INFORMATION: Synthetic construct

<400> SEQUENCE: 880

Tyr Ser Ser Pro Gly Ser Pro Gly Thr Pro Gly Ser Arg Ile Val Tyr
1 5 10 15

Lys Ser Pro Val Val Ser Gly Asp Thr Ser Pro Arg Cys
20 25

<210> SEQ ID NO 881
<211> LENGTH: 29
<212> TYPE: PRT
<213> ORGANISM: Artificial Sequence
<220> FEATURE:
<223> OTHER INFORMATION: Synthetic construct

<400> SEQUENCE: 881

Tyr Ser Ser Pro Gly Ser Pro Gly Thr Pro Gly Ser Arg Val Tyr Lys
1 5 10 15

Ser Pro Val Val Ser Gly Asp Thr Ser Pro Arg His Cys
20 25

<210> SEQ ID NO 882
<211> LENGTH: 29
<212> TYPE: PRT
<213> ORGANISM: Artificial Sequence
<220> FEATURE:
<223> OTHER INFORMATION: Synthetic construct

<400> SEQUENCE: 882

Tyr Ser Ser Pro Gly Ser Pro Gly Thr Pro Gly Ser Arg Tyr Lys Ser
1 5 10 15

Pro Val Val Ser Gly Asp Thr Ser Pro Arg His Leu Cys
20 25

<210> SEQ ID NO 883
<211> LENGTH: 30
<212> TYPE: PRT
<213> ORGANISM: Artificial Sequence
<220> FEATURE:
<223> OTHER INFORMATION: Synthetic construct

<400> SEQUENCE: 883

```
Tyr Ser Ser Pro Gly Ser Pro Gly Thr Pro Gly Ser Arg Ile Val Tyr
1               5                   10                  15

Lys Ser Pro Val Val Ser Gly Asp Thr Ser Pro Arg His Cys
            20                  25                  30
```

<210> SEQ ID NO 884
<211> LENGTH: 30
<212> TYPE: PRT
<213> ORGANISM: Artificial Sequence
<220> FEATURE:
<223> OTHER INFORMATION: Synthetic construct

<400> SEQUENCE: 884

```
Tyr Ser Ser Pro Gly Ser Pro Gly Thr Pro Gly Ser Arg Val Tyr Lys
1               5                   10                  15

Ser Pro Val Val Ser Gly Asp Thr Ser Pro Arg His Leu Cys
            20                  25                  30
```

<210> SEQ ID NO 885
<211> LENGTH: 31
<212> TYPE: PRT
<213> ORGANISM: Artificial Sequence
<220> FEATURE:
<223> OTHER INFORMATION: Synthetic construct

<400> SEQUENCE: 885

```
Tyr Ser Ser Pro Gly Ser Pro Gly Thr Pro Gly Ser Arg Ile Val Tyr
1               5                   10                  15

Lys Ser Pro Val Val Ser Gly Asp Thr Ser Pro Arg His Leu Cys
            20                  25                  30
```

<210> SEQ ID NO 886
<211> LENGTH: 26
<212> TYPE: PRT
<213> ORGANISM: Artificial Sequence
<220> FEATURE:
<223> OTHER INFORMATION: Synthetic construct

<400> SEQUENCE: 886

```
Ser Ser Pro Gly Ser Pro Gly Thr Pro Gly Ser Arg Ser Lys Ser Pro
1               5                   10                  15

Val Val Ser Gly Asp Thr Ser Pro Arg Cys
            20                  25
```

<210> SEQ ID NO 887
<211> LENGTH: 27
<212> TYPE: PRT
<213> ORGANISM: Artificial Sequence
<220> FEATURE:
<223> OTHER INFORMATION: Synthetic construct

<400> SEQUENCE: 887

```
Ser Ser Pro Gly Ser Pro Gly Thr Pro Gly Ser Arg Ser Tyr Lys Ser
1               5                   10                  15

Pro Val Val Ser Gly Asp Thr Ser Pro Arg Cys
```

20 25

<210> SEQ ID NO 888
<211> LENGTH: 28
<212> TYPE: PRT
<213> ORGANISM: Artificial Sequence
<220> FEATURE:
<223> OTHER INFORMATION: Synthetic construct

<400> SEQUENCE: 888

Ser Ser Pro Gly Ser Pro Gly Thr Pro Gly Ser Arg Ser Val Tyr Lys
1 5 10 15

Ser Pro Val Val Ser Gly Asp Thr Ser Pro Arg Cys
20 25

<210> SEQ ID NO 889
<211> LENGTH: 28
<212> TYPE: PRT
<213> ORGANISM: Artificial Sequence
<220> FEATURE:
<223> OTHER INFORMATION: Synthetic construct

<400> SEQUENCE: 889

Ser Ser Pro Gly Ser Pro Gly Thr Pro Gly Ser Arg Ser Tyr Lys Ser
1 5 10 15

Pro Val Val Ser Gly Asp Thr Ser Pro Arg His Cys
20 25

<210> SEQ ID NO 890
<211> LENGTH: 29
<212> TYPE: PRT
<213> ORGANISM: Artificial Sequence
<220> FEATURE:
<223> OTHER INFORMATION: Synthetic construct

<400> SEQUENCE: 890

Ser Ser Pro Gly Ser Pro Gly Thr Pro Gly Ser Arg Ser Ile Val Tyr
1 5 10 15

Lys Ser Pro Val Val Ser Gly Asp Thr Ser Pro Arg Cys
20 25

<210> SEQ ID NO 891
<211> LENGTH: 29
<212> TYPE: PRT
<213> ORGANISM: Artificial Sequence
<220> FEATURE:
<223> OTHER INFORMATION: Synthetic construct

<400> SEQUENCE: 891

Ser Ser Pro Gly Ser Pro Gly Thr Pro Gly Ser Arg Ser Val Tyr Lys
1 5 10 15

Ser Pro Val Val Ser Gly Asp Thr Ser Pro Arg His Cys
20 25

<210> SEQ ID NO 892
<211> LENGTH: 29
<212> TYPE: PRT
<213> ORGANISM: Artificial Sequence
<220> FEATURE:
<223> OTHER INFORMATION: Synthetic construct

<400> SEQUENCE: 892

Ser Ser Pro Gly Ser Pro Gly Thr Pro Gly Ser Arg Ser Tyr Lys Ser
1 5 10 15

```
Pro Val Val Ser Gly Asp Thr Ser Pro Arg His Leu Cys
            20                  25


<210> SEQ ID NO 893
<211> LENGTH: 30
<212> TYPE: PRT
<213> ORGANISM: Artificial Sequence
<220> FEATURE:
<223> OTHER INFORMATION: Synthetic construct

<400> SEQUENCE: 893

Ser Ser Pro Gly Ser Pro Gly Thr Pro Gly Ser Arg Ser Ile Val Tyr
1               5                   10                  15

Lys Ser Pro Val Val Ser Gly Asp Thr Ser Pro Arg His Cys
            20                  25                  30


<210> SEQ ID NO 894
<211> LENGTH: 30
<212> TYPE: PRT
<213> ORGANISM: Artificial Sequence
<220> FEATURE:
<223> OTHER INFORMATION: Synthetic construct

<400> SEQUENCE: 894

Ser Ser Pro Gly Ser Pro Gly Thr Pro Gly Ser Arg Ser Val Tyr Lys
1               5                   10                  15

Ser Pro Val Val Ser Gly Asp Thr Ser Pro Arg His Leu Cys
            20                  25                  30


<210> SEQ ID NO 895
<211> LENGTH: 31
<212> TYPE: PRT
<213> ORGANISM: Artificial Sequence
<220> FEATURE:
<223> OTHER INFORMATION: Synthetic construct

<400> SEQUENCE: 895

Ser Ser Pro Gly Ser Pro Gly Thr Pro Gly Ser Arg Ser Ile Val Tyr
1               5                   10                  15

Lys Ser Pro Val Val Ser Gly Asp Thr Ser Pro Arg His Leu Cys
            20                  25                  30


<210> SEQ ID NO 896
<211> LENGTH: 27
<212> TYPE: PRT
<213> ORGANISM: Artificial Sequence
<220> FEATURE:
<223> OTHER INFORMATION: Synthetic construct

<400> SEQUENCE: 896

Gly Tyr Ser Ser Pro Gly Ser Pro Gly Thr Pro Gly Ser Arg Lys Ser
1               5                   10                  15

Pro Val Val Ser Gly Asp Thr Ser Pro Arg Cys
            20                  25


<210> SEQ ID NO 897
<211> LENGTH: 28
<212> TYPE: PRT
<213> ORGANISM: Artificial Sequence
<220> FEATURE:
<223> OTHER INFORMATION: Synthetic construct

<400> SEQUENCE: 897

Gly Tyr Ser Ser Pro Gly Ser Pro Gly Thr Pro Gly Ser Arg Tyr Lys
1               5                   10                  15
```

Ser Pro Val Val Ser Gly Asp Thr Ser Pro Arg Cys
20 25

<210> SEQ ID NO 898
<211> LENGTH: 29
<212> TYPE: PRT
<213> ORGANISM: Artificial Sequence
<220> FEATURE:
<223> OTHER INFORMATION: Synthetic construct

<400> SEQUENCE: 898

Gly Tyr Ser Ser Pro Gly Ser Pro Gly Thr Pro Gly Ser Arg Val Tyr
1 5 10 15

Lys Ser Pro Val Val Ser Gly Asp Thr Ser Pro Arg Cys
20 25

<210> SEQ ID NO 899
<211> LENGTH: 29
<212> TYPE: PRT
<213> ORGANISM: Artificial Sequence
<220> FEATURE:
<223> OTHER INFORMATION: Synthetic construct

<400> SEQUENCE: 899

Gly Tyr Ser Ser Pro Gly Ser Pro Gly Thr Pro Gly Ser Arg Tyr Lys
1 5 10 15

Ser Pro Val Val Ser Gly Asp Thr Ser Pro Arg His Cys
20 25

<210> SEQ ID NO 900
<211> LENGTH: 30
<212> TYPE: PRT
<213> ORGANISM: Artificial Sequence
<220> FEATURE:
<223> OTHER INFORMATION: Synthetic construct

<400> SEQUENCE: 900

Gly Tyr Ser Ser Pro Gly Ser Pro Gly Thr Pro Gly Ser Arg Ile Val
1 5 10 15

Tyr Lys Ser Pro Val Val Ser Gly Asp Thr Ser Pro Arg Cys
20 25 30

<210> SEQ ID NO 901
<211> LENGTH: 30
<212> TYPE: PRT
<213> ORGANISM: Artificial Sequence
<220> FEATURE:
<223> OTHER INFORMATION: Synthetic construct

<400> SEQUENCE: 901

Gly Tyr Ser Ser Pro Gly Ser Pro Gly Thr Pro Gly Ser Arg Val Tyr
1 5 10 15

Lys Ser Pro Val Val Ser Gly Asp Thr Ser Pro Arg His Cys
20 25 30

<210> SEQ ID NO 902
<211> LENGTH: 30
<212> TYPE: PRT
<213> ORGANISM: Artificial Sequence
<220> FEATURE:
<223> OTHER INFORMATION: Synthetic construct

<400> SEQUENCE: 902

Gly Tyr Ser Ser Pro Gly Ser Pro Gly Thr Pro Gly Ser Arg Tyr Lys

```
1               5                   10                  15

Ser Pro Val Val Ser Gly Asp Thr Ser Pro Arg His Leu Cys
            20                  25                  30


<210> SEQ ID NO 903
<211> LENGTH: 31
<212> TYPE: PRT
<213> ORGANISM: Artificial Sequence
<220> FEATURE:
<223> OTHER INFORMATION: Synthetic construct

<400> SEQUENCE: 903

Gly Tyr Ser Ser Pro Gly Ser Pro Gly Thr Pro Gly Ser Arg Ile Val
1               5                   10                  15

Tyr Lys Ser Pro Val Val Ser Gly Asp Thr Ser Pro Arg His Cys
            20                  25                  30


<210> SEQ ID NO 904
<211> LENGTH: 31
<212> TYPE: PRT
<213> ORGANISM: Artificial Sequence
<220> FEATURE:
<223> OTHER INFORMATION: Synthetic construct

<400> SEQUENCE: 904

Gly Tyr Ser Ser Pro Gly Ser Pro Gly Thr Pro Gly Ser Arg Val Tyr
1               5                   10                  15

Lys Ser Pro Val Val Ser Gly Asp Thr Ser Pro Arg His Leu Cys
            20                  25                  30


<210> SEQ ID NO 905
<211> LENGTH: 32
<212> TYPE: PRT
<213> ORGANISM: Artificial Sequence
<220> FEATURE:
<223> OTHER INFORMATION: Synthetic construct

<400> SEQUENCE: 905

Gly Tyr Ser Ser Pro Gly Ser Pro Gly Thr Pro Gly Ser Arg Ile Val
1               5                   10                  15

Tyr Lys Ser Pro Val Val Ser Gly Asp Thr Ser Pro Arg His Leu Cys
            20                  25                  30


<210> SEQ ID NO 906
<211> LENGTH: 27
<212> TYPE: PRT
<213> ORGANISM: Artificial Sequence
<220> FEATURE:
<223> OTHER INFORMATION: Synthetic construct

<400> SEQUENCE: 906

Tyr Ser Ser Pro Gly Ser Pro Gly Thr Pro Gly Ser Arg Ser Lys Ser
1               5                   10                  15

Pro Val Val Ser Gly Asp Thr Ser Pro Arg Cys
            20                  25


<210> SEQ ID NO 907
<211> LENGTH: 28
<212> TYPE: PRT
<213> ORGANISM: Artificial Sequence
<220> FEATURE:
<223> OTHER INFORMATION: Synthetic construct

<400> SEQUENCE: 907
```

```
Tyr Ser Ser Pro Gly Ser Pro Gly Thr Pro Gly Ser Arg Ser Tyr Lys
1               5                   10                  15

Ser Pro Val Val Ser Gly Asp Thr Ser Pro Arg Cys
            20                  25


<210> SEQ ID NO 908
<211> LENGTH: 29
<212> TYPE: PRT
<213> ORGANISM: Artificial Sequence
<220> FEATURE:
<223> OTHER INFORMATION: Synthetic construct

<400> SEQUENCE: 908

Tyr Ser Ser Pro Gly Ser Pro Gly Thr Pro Gly Ser Arg Ser Val Tyr
1               5                   10                  15

Lys Ser Pro Val Val Ser Gly Asp Thr Ser Pro Arg Cys
            20                  25


<210> SEQ ID NO 909
<211> LENGTH: 29
<212> TYPE: PRT
<213> ORGANISM: Artificial Sequence
<220> FEATURE:
<223> OTHER INFORMATION: Synthetic construct

<400> SEQUENCE: 909

Tyr Ser Ser Pro Gly Ser Pro Gly Thr Pro Gly Ser Arg Ser Tyr Lys
1               5                   10                  15

Ser Pro Val Val Ser Gly Asp Thr Ser Pro Arg His Cys
            20                  25


<210> SEQ ID NO 910
<211> LENGTH: 30
<212> TYPE: PRT
<213> ORGANISM: Artificial Sequence
<220> FEATURE:
<223> OTHER INFORMATION: Synthetic construct

<400> SEQUENCE: 910

Tyr Ser Ser Pro Gly Ser Pro Gly Thr Pro Gly Ser Arg Ser Ile Val
1               5                   10                  15

Tyr Lys Ser Pro Val Val Ser Gly Asp Thr Ser Pro Arg Cys
            20                  25                  30


<210> SEQ ID NO 911
<211> LENGTH: 30
<212> TYPE: PRT
<213> ORGANISM: Artificial Sequence
<220> FEATURE:
<223> OTHER INFORMATION: Synthetic construct

<400> SEQUENCE: 911

Tyr Ser Ser Pro Gly Ser Pro Gly Thr Pro Gly Ser Arg Ser Val Tyr
1               5                   10                  15

Lys Ser Pro Val Val Ser Gly Asp Thr Ser Pro Arg His Cys
            20                  25                  30


<210> SEQ ID NO 912
<211> LENGTH: 30
<212> TYPE: PRT
<213> ORGANISM: Artificial Sequence
<220> FEATURE:
<223> OTHER INFORMATION: Synthetic construct

<400> SEQUENCE: 912
```

Tyr Ser Ser Pro Gly Ser Pro Gly Thr Pro Gly Ser Arg Ser Tyr Lys
1               5                   10                  15

Ser Pro Val Val Ser Gly Asp Thr Ser Pro Arg His Leu Cys
            20                  25                  30

<210> SEQ ID NO 913
<211> LENGTH: 31
<212> TYPE: PRT
<213> ORGANISM: Artificial Sequence
<220> FEATURE:
<223> OTHER INFORMATION: Synthetic construct

<400> SEQUENCE: 913

Tyr Ser Ser Pro Gly Ser Pro Gly Thr Pro Gly Ser Arg Ser Ile Val
1               5                   10                  15

Tyr Lys Ser Pro Val Val Ser Gly Asp Thr Ser Pro Arg His Cys
            20                  25                  30

<210> SEQ ID NO 914
<211> LENGTH: 31
<212> TYPE: PRT
<213> ORGANISM: Artificial Sequence
<220> FEATURE:
<223> OTHER INFORMATION: Synthetic construct

<400> SEQUENCE: 914

Tyr Ser Ser Pro Gly Ser Pro Gly Thr Pro Gly Ser Arg Ser Val Tyr
1               5                   10                  15

Lys Ser Pro Val Val Ser Gly Asp Thr Ser Pro Arg His Leu Cys
            20                  25                  30

<210> SEQ ID NO 915
<211> LENGTH: 32
<212> TYPE: PRT
<213> ORGANISM: Artificial Sequence
<220> FEATURE:
<223> OTHER INFORMATION: Synthetic construct

<400> SEQUENCE: 915

Tyr Ser Ser Pro Gly Ser Pro Gly Thr Pro Gly Ser Arg Ser Ile Val
1               5                   10                  15

Tyr Lys Ser Pro Val Val Ser Gly Asp Thr Ser Pro Arg His Leu Cys
            20                  25                  30

<210> SEQ ID NO 916
<211> LENGTH: 27
<212> TYPE: PRT
<213> ORGANISM: Artificial Sequence
<220> FEATURE:
<223> OTHER INFORMATION: Synthetic construct

<400> SEQUENCE: 916

Ser Ser Pro Gly Ser Pro Gly Thr Pro Gly Ser Arg Ser Arg Lys Ser
1               5                   10                  15

Pro Val Val Ser Gly Asp Thr Ser Pro Arg Cys
            20                  25

<210> SEQ ID NO 917
<211> LENGTH: 28
<212> TYPE: PRT
<213> ORGANISM: Artificial Sequence
<220> FEATURE:
<223> OTHER INFORMATION: Synthetic construct

<400> SEQUENCE: 917

Ser Ser Pro Gly Ser Pro Gly Thr Pro Gly Ser Arg Ser Arg Tyr Lys
1 5 10 15

Ser Pro Val Val Ser Gly Asp Thr Ser Pro Arg Cys
20 25

<210> SEQ ID NO 918
<211> LENGTH: 29
<212> TYPE: PRT
<213> ORGANISM: Artificial Sequence
<220> FEATURE:
<223> OTHER INFORMATION: Synthetic construct

<400> SEQUENCE: 918

Ser Ser Pro Gly Ser Pro Gly Thr Pro Gly Ser Arg Ser Arg Val Tyr
1 5 10 15

Lys Ser Pro Val Val Ser Gly Asp Thr Ser Pro Arg Cys
20 25

<210> SEQ ID NO 919
<211> LENGTH: 29
<212> TYPE: PRT
<213> ORGANISM: Artificial Sequence
<220> FEATURE:
<223> OTHER INFORMATION: Synthetic construct

<400> SEQUENCE: 919

Ser Ser Pro Gly Ser Pro Gly Thr Pro Gly Ser Arg Ser Arg Tyr Lys
1 5 10 15

Ser Pro Val Val Ser Gly Asp Thr Ser Pro Arg His Cys
20 25

<210> SEQ ID NO 920
<211> LENGTH: 30
<212> TYPE: PRT
<213> ORGANISM: Artificial Sequence
<220> FEATURE:
<223> OTHER INFORMATION: Synthetic construct

<400> SEQUENCE: 920

Ser Ser Pro Gly Ser Pro Gly Thr Pro Gly Ser Arg Ser Arg Ile Val
1 5 10 15

Tyr Lys Ser Pro Val Val Ser Gly Asp Thr Ser Pro Arg Cys
20 25 30

<210> SEQ ID NO 921
<211> LENGTH: 30
<212> TYPE: PRT
<213> ORGANISM: Artificial Sequence
<220> FEATURE:
<223> OTHER INFORMATION: Synthetic construct

<400> SEQUENCE: 921

Ser Ser Pro Gly Ser Pro Gly Thr Pro Gly Ser Arg Ser Arg Val Tyr
1 5 10 15

Lys Ser Pro Val Val Ser Gly Asp Thr Ser Pro Arg His Cys
20 25 30

<210> SEQ ID NO 922
<211> LENGTH: 30
<212> TYPE: PRT
<213> ORGANISM: Artificial Sequence
<220> FEATURE:
<223> OTHER INFORMATION: Synthetic construct

<400> SEQUENCE: 922

Ser Ser Pro Gly Ser Pro Gly Thr Pro Gly Ser Arg Ser Arg Tyr Lys
1 5 10 15

Ser Pro Val Val Ser Gly Asp Thr Ser Pro Arg His Leu Cys
20 25 30

<210> SEQ ID NO 923
<211> LENGTH: 31
<212> TYPE: PRT
<213> ORGANISM: Artificial Sequence
<220> FEATURE:
<223> OTHER INFORMATION: Synthetic construct

<400> SEQUENCE: 923

Ser Ser Pro Gly Ser Pro Gly Thr Pro Gly Ser Arg Ser Arg Ile Val
1 5 10 15

Tyr Lys Ser Pro Val Val Ser Gly Asp Thr Ser Pro Arg His Cys
20 25 30

<210> SEQ ID NO 924
<211> LENGTH: 31
<212> TYPE: PRT
<213> ORGANISM: Artificial Sequence
<220> FEATURE:
<223> OTHER INFORMATION: Synthetic construct

<400> SEQUENCE: 924

Ser Ser Pro Gly Ser Pro Gly Thr Pro Gly Ser Arg Ser Arg Val Tyr
1 5 10 15

Lys Ser Pro Val Val Ser Gly Asp Thr Ser Pro Arg His Leu Cys
20 25 30

<210> SEQ ID NO 925
<211> LENGTH: 32
<212> TYPE: PRT
<213> ORGANISM: Artificial Sequence
<220> FEATURE:
<223> OTHER INFORMATION: Synthetic construct

<400> SEQUENCE: 925

Ser Ser Pro Gly Ser Pro Gly Thr Pro Gly Ser Arg Ser Arg Ile Val
1 5 10 15

Tyr Lys Ser Pro Val Val Ser Gly Asp Thr Ser Pro Arg His Leu Cys
20 25 30

<210> SEQ ID NO 926
<211> LENGTH: 28
<212> TYPE: PRT
<213> ORGANISM: Artificial Sequence
<220> FEATURE:
<223> OTHER INFORMATION: Synthetic construct

<400> SEQUENCE: 926

Ser Gly Tyr Ser Ser Pro Gly Ser Pro Gly Thr Pro Gly Ser Arg Lys
1 5 10 15

Ser Pro Val Val Ser Gly Asp Thr Ser Pro Arg Cys
20 25

<210> SEQ ID NO 927
<211> LENGTH: 29
<212> TYPE: PRT
<213> ORGANISM: Artificial Sequence
<220> FEATURE:

<223> OTHER INFORMATION: Synthetic construct

<400> SEQUENCE: 927

Ser Gly Tyr Ser Ser Pro Gly Ser Pro Gly Thr Pro Gly Ser Arg Tyr
1 5 10 15

Lys Ser Pro Val Val Ser Gly Asp Thr Ser Pro Arg Cys
20 25

<210> SEQ ID NO 928
<211> LENGTH: 30
<212> TYPE: PRT
<213> ORGANISM: Artificial Sequence
<220> FEATURE:
<223> OTHER INFORMATION: Synthetic construct

<400> SEQUENCE: 928

Ser Gly Tyr Ser Ser Pro Gly Ser Pro Gly Thr Pro Gly Ser Arg Val
1 5 10 15

Tyr Lys Ser Pro Val Val Ser Gly Asp Thr Ser Pro Arg Cys
20 25 30

<210> SEQ ID NO 929
<211> LENGTH: 30
<212> TYPE: PRT
<213> ORGANISM: Artificial Sequence
<220> FEATURE:
<223> OTHER INFORMATION: Synthetic construct

<400> SEQUENCE: 929

Ser Gly Tyr Ser Ser Pro Gly Ser Pro Gly Thr Pro Gly Ser Arg Tyr
1 5 10 15

Lys Ser Pro Val Val Ser Gly Asp Thr Ser Pro Arg His Cys
20 25 30

<210> SEQ ID NO 930
<211> LENGTH: 31
<212> TYPE: PRT
<213> ORGANISM: Artificial Sequence
<220> FEATURE:
<223> OTHER INFORMATION: Synthetic construct

<400> SEQUENCE: 930

Ser Gly Tyr Ser Ser Pro Gly Ser Pro Gly Thr Pro Gly Ser Arg Ile
1 5 10 15

Val Tyr Lys Ser Pro Val Val Ser Gly Asp Thr Ser Pro Arg Cys
20 25 30

<210> SEQ ID NO 931
<211> LENGTH: 31
<212> TYPE: PRT
<213> ORGANISM: Artificial Sequence
<220> FEATURE:
<223> OTHER INFORMATION: Synthetic construct

<400> SEQUENCE: 931

Ser Gly Tyr Ser Ser Pro Gly Ser Pro Gly Thr Pro Gly Ser Arg Val
1 5 10 15

Tyr Lys Ser Pro Val Val Ser Gly Asp Thr Ser Pro Arg His Cys
20 25 30

<210> SEQ ID NO 932
<211> LENGTH: 31
<212> TYPE: PRT
<213> ORGANISM: Artificial Sequence
<220> FEATURE:
<223> OTHER INFORMATION: Synthetic construct

<400> SEQUENCE: 932

Ser Gly Tyr Ser Ser Pro Gly Ser Pro Gly Thr Pro Gly Ser Arg Tyr
1 5 10 15

Lys Ser Pro Val Val Ser Gly Asp Thr Ser Pro Arg His Leu Cys
20 25 30

<210> SEQ ID NO 933
<211> LENGTH: 32
<212> TYPE: PRT
<213> ORGANISM: Artificial Sequence
<220> FEATURE:
<223> OTHER INFORMATION: Synthetic construct

<400> SEQUENCE: 933

Ser Gly Tyr Ser Ser Pro Gly Ser Pro Gly Thr Pro Gly Ser Arg Ile
1 5 10 15

Val Tyr Lys Ser Pro Val Val Ser Gly Asp Thr Ser Pro Arg His Cys
20 25 30

<210> SEQ ID NO 934
<211> LENGTH: 32
<212> TYPE: PRT
<213> ORGANISM: Artificial Sequence
<220> FEATURE:
<223> OTHER INFORMATION: Synthetic construct

<400> SEQUENCE: 934

Ser Gly Tyr Ser Ser Pro Gly Ser Pro Gly Thr Pro Gly Ser Arg Val
1 5 10 15

Tyr Lys Ser Pro Val Val Ser Gly Asp Thr Ser Pro Arg His Leu Cys
20 25 30

<210> SEQ ID NO 935
<211> LENGTH: 28
<212> TYPE: PRT
<213> ORGANISM: Artificial Sequence
<220> FEATURE:
<223> OTHER INFORMATION: Synthetic construct

<400> SEQUENCE: 935

Gly Tyr Ser Ser Pro Gly Ser Pro Gly Thr Pro Gly Ser Arg Ser Lys
1 5 10 15

Ser Pro Val Val Ser Gly Asp Thr Ser Pro Arg Cys
20 25

<210> SEQ ID NO 936
<211> LENGTH: 29
<212> TYPE: PRT
<213> ORGANISM: Artificial Sequence
<220> FEATURE:
<223> OTHER INFORMATION: Synthetic construct

<400> SEQUENCE: 936

Gly Tyr Ser Ser Pro Gly Ser Pro Gly Thr Pro Gly Ser Arg Ser Tyr
1 5 10 15

Lys Ser Pro Val Val Ser Gly Asp Thr Ser Pro Arg Cys
20 25

<210> SEQ ID NO 937
<211> LENGTH: 30
<212> TYPE: PRT

<213> ORGANISM: Artificial Sequence
<220> FEATURE:
<223> OTHER INFORMATION: Synthetic construct

<400> SEQUENCE: 937

Gly Tyr Ser Ser Pro Gly Ser Pro Gly Thr Pro Gly Ser Arg Ser Val
1 5 10 15

Tyr Lys Ser Pro Val Val Ser Gly Asp Thr Ser Pro Arg Cys
20 25 30

<210> SEQ ID NO 938
<211> LENGTH: 30
<212> TYPE: PRT
<213> ORGANISM: Artificial Sequence
<220> FEATURE:
<223> OTHER INFORMATION: Synthetic construct

<400> SEQUENCE: 938

Gly Tyr Ser Ser Pro Gly Ser Pro Gly Thr Pro Gly Ser Arg Ser Tyr
1 5 10 15

Lys Ser Pro Val Val Ser Gly Asp Thr Ser Pro Arg His Cys
20 25 30

<210> SEQ ID NO 939
<211> LENGTH: 31
<212> TYPE: PRT
<213> ORGANISM: Artificial Sequence
<220> FEATURE:
<223> OTHER INFORMATION: Synthetic construct

<400> SEQUENCE: 939

Gly Tyr Ser Ser Pro Gly Ser Pro Gly Thr Pro Gly Ser Arg Ser Ile
1 5 10 15

Val Tyr Lys Ser Pro Val Val Ser Gly Asp Thr Ser Pro Arg Cys
20 25 30

<210> SEQ ID NO 940
<211> LENGTH: 31
<212> TYPE: PRT
<213> ORGANISM: Artificial Sequence
<220> FEATURE:
<223> OTHER INFORMATION: Synthetic construct

<400> SEQUENCE: 940

Gly Tyr Ser Ser Pro Gly Ser Pro Gly Thr Pro Gly Ser Arg Ser Val
1 5 10 15

Tyr Lys Ser Pro Val Val Ser Gly Asp Thr Ser Pro Arg His Cys
20 25 30

<210> SEQ ID NO 941
<211> LENGTH: 31
<212> TYPE: PRT
<213> ORGANISM: Artificial Sequence
<220> FEATURE:
<223> OTHER INFORMATION: Synthetic construct

<400> SEQUENCE: 941

Gly Tyr Ser Ser Pro Gly Ser Pro Gly Thr Pro Gly Ser Arg Ser Tyr
1 5 10 15

Lys Ser Pro Val Val Ser Gly Asp Thr Ser Pro Arg His Leu Cys
20 25 30

<210> SEQ ID NO 942
<211> LENGTH: 32

<212> TYPE: PRT
<213> ORGANISM: Artificial Sequence
<220> FEATURE:
<223> OTHER INFORMATION: Synthetic construct

<400> SEQUENCE: 942

Gly Tyr Ser Ser Pro Gly Ser Pro Gly Thr Pro Gly Ser Arg Ser Ile
1 5 10 15

Val Tyr Lys Ser Pro Val Val Ser Gly Asp Thr Ser Pro Arg His Cys
20 25 30

<210> SEQ ID NO 943
<211> LENGTH: 32
<212> TYPE: PRT
<213> ORGANISM: Artificial Sequence
<220> FEATURE:
<223> OTHER INFORMATION: Synthetic construct

<400> SEQUENCE: 943

Gly Tyr Ser Ser Pro Gly Ser Pro Gly Thr Pro Gly Ser Arg Ser Val
1 5 10 15

Tyr Lys Ser Pro Val Val Ser Gly Asp Thr Ser Pro Arg His Leu Cys
20 25 30

<210> SEQ ID NO 944
<211> LENGTH: 28
<212> TYPE: PRT
<213> ORGANISM: Artificial Sequence
<220> FEATURE:
<223> OTHER INFORMATION: Synthetic construct

<400> SEQUENCE: 944

Tyr Ser Ser Pro Gly Ser Pro Gly Thr Pro Gly Ser Arg Ser Arg Lys
1 5 10 15

Ser Pro Val Val Ser Gly Asp Thr Ser Pro Arg Cys
20 25

<210> SEQ ID NO 945
<211> LENGTH: 29
<212> TYPE: PRT
<213> ORGANISM: Artificial Sequence
<220> FEATURE:
<223> OTHER INFORMATION: Synthetic construct

<400> SEQUENCE: 945

Tyr Ser Ser Pro Gly Ser Pro Gly Thr Pro Gly Ser Arg Ser Arg Tyr
1 5 10 15

Lys Ser Pro Val Val Ser Gly Asp Thr Ser Pro Arg Cys
20 25

<210> SEQ ID NO 946
<211> LENGTH: 30
<212> TYPE: PRT
<213> ORGANISM: Artificial Sequence
<220> FEATURE:
<223> OTHER INFORMATION: Synthetic construct

<400> SEQUENCE: 946

Tyr Ser Ser Pro Gly Ser Pro Gly Thr Pro Gly Ser Arg Ser Arg Val
1 5 10 15

Tyr Lys Ser Pro Val Val Ser Gly Asp Thr Ser Pro Arg Cys
20 25 30

<210> SEQ ID NO 947

<211> LENGTH: 30
<212> TYPE: PRT
<213> ORGANISM: Artificial Sequence
<220> FEATURE:
<223> OTHER INFORMATION: Synthetic construct

<400> SEQUENCE: 947

Tyr Ser Ser Pro Gly Ser Pro Gly Thr Pro Gly Ser Arg Ser Arg Tyr
1 5 10 15

Lys Ser Pro Val Val Ser Gly Asp Thr Ser Pro Arg His Cys
20 25 30

<210> SEQ ID NO 948
<211> LENGTH: 31
<212> TYPE: PRT
<213> ORGANISM: Artificial Sequence
<220> FEATURE:
<223> OTHER INFORMATION: Synthetic construct

<400> SEQUENCE: 948

Tyr Ser Ser Pro Gly Ser Pro Gly Thr Pro Gly Ser Arg Ser Arg Ile
1 5 10 15

Val Tyr Lys Ser Pro Val Val Ser Gly Asp Thr Ser Pro Arg Cys
20 25 30

<210> SEQ ID NO 949
<211> LENGTH: 31
<212> TYPE: PRT
<213> ORGANISM: Artificial Sequence
<220> FEATURE:
<223> OTHER INFORMATION: Synthetic construct

<400> SEQUENCE: 949

Tyr Ser Ser Pro Gly Ser Pro Gly Thr Pro Gly Ser Arg Ser Arg Val
1 5 10 15

Tyr Lys Ser Pro Val Val Ser Gly Asp Thr Ser Pro Arg His Cys
20 25 30

<210> SEQ ID NO 950
<211> LENGTH: 31
<212> TYPE: PRT
<213> ORGANISM: Artificial Sequence
<220> FEATURE:
<223> OTHER INFORMATION: Synthetic construct

<400> SEQUENCE: 950

Tyr Ser Ser Pro Gly Ser Pro Gly Thr Pro Gly Ser Arg Ser Arg Tyr
1 5 10 15

Lys Ser Pro Val Val Ser Gly Asp Thr Ser Pro Arg His Leu Cys
20 25 30

<210> SEQ ID NO 951
<211> LENGTH: 32
<212> TYPE: PRT
<213> ORGANISM: Artificial Sequence
<220> FEATURE:
<223> OTHER INFORMATION: Synthetic construct

<400> SEQUENCE: 951

Tyr Ser Ser Pro Gly Ser Pro Gly Thr Pro Gly Ser Arg Ser Arg Ile
1 5 10 15

Val Tyr Lys Ser Pro Val Val Ser Gly Asp Thr Ser Pro Arg His Cys
20 25 30

<210> SEQ ID NO 952
<211> LENGTH: 32
<212> TYPE: PRT
<213> ORGANISM: Artificial Sequence
<220> FEATURE:
<223> OTHER INFORMATION: Synthetic construct

<400> SEQUENCE: 952

Tyr Ser Ser Pro Gly Ser Pro Gly Thr Pro Gly Ser Arg Ser Arg Val
1 5 10 15

Tyr Lys Ser Pro Val Val Ser Gly Asp Thr Ser Pro Arg His Leu Cys
20 25 30

<210> SEQ ID NO 953
<211> LENGTH: 28
<212> TYPE: PRT
<213> ORGANISM: Artificial Sequence
<220> FEATURE:
<223> OTHER INFORMATION: Synthetic construct

<400> SEQUENCE: 953

Ser Ser Pro Gly Ser Pro Gly Thr Pro Gly Ser Arg Ser Arg Thr Lys
1 5 10 15

Ser Pro Val Val Ser Gly Asp Thr Ser Pro Arg Cys
20 25

<210> SEQ ID NO 954
<211> LENGTH: 29
<212> TYPE: PRT
<213> ORGANISM: Artificial Sequence
<220> FEATURE:
<223> OTHER INFORMATION: Synthetic construct

<400> SEQUENCE: 954

Ser Ser Pro Gly Ser Pro Gly Thr Pro Gly Ser Arg Ser Arg Thr Tyr
1 5 10 15

Lys Ser Pro Val Val Ser Gly Asp Thr Ser Pro Arg Cys
20 25

<210> SEQ ID NO 955
<211> LENGTH: 30
<212> TYPE: PRT
<213> ORGANISM: Artificial Sequence
<220> FEATURE:
<223> OTHER INFORMATION: Synthetic construct

<400> SEQUENCE: 955

Ser Ser Pro Gly Ser Pro Gly Thr Pro Gly Ser Arg Ser Arg Thr Val
1 5 10 15

Tyr Lys Ser Pro Val Val Ser Gly Asp Thr Ser Pro Arg Cys
20 25 30

<210> SEQ ID NO 956
<211> LENGTH: 30
<212> TYPE: PRT
<213> ORGANISM: Artificial Sequence
<220> FEATURE:
<223> OTHER INFORMATION: Synthetic construct

<400> SEQUENCE: 956

Ser Ser Pro Gly Ser Pro Gly Thr Pro Gly Ser Arg Ser Arg Thr Tyr
1 5 10 15

Lys Ser Pro Val Val Ser Gly Asp Thr Ser Pro Arg His Cys
20 25 30

<210> SEQ ID NO 957
<211> LENGTH: 31
<212> TYPE: PRT
<213> ORGANISM: Artificial Sequence
<220> FEATURE:
<223> OTHER INFORMATION: Synthetic construct

<400> SEQUENCE: 957

Ser Ser Pro Gly Ser Pro Gly Thr Pro Gly Ser Arg Ser Arg Thr Ile
1 5 10 15

Val Tyr Lys Ser Pro Val Val Ser Gly Asp Thr Ser Pro Arg Cys
20 25 30

<210> SEQ ID NO 958
<211> LENGTH: 31
<212> TYPE: PRT
<213> ORGANISM: Artificial Sequence
<220> FEATURE:
<223> OTHER INFORMATION: Synthetic construct

<400> SEQUENCE: 958

Ser Ser Pro Gly Ser Pro Gly Thr Pro Gly Ser Arg Ser Arg Thr Val
1 5 10 15

Tyr Lys Ser Pro Val Val Ser Gly Asp Thr Ser Pro Arg His Cys
20 25 30

<210> SEQ ID NO 959
<211> LENGTH: 31
<212> TYPE: PRT
<213> ORGANISM: Artificial Sequence
<220> FEATURE:
<223> OTHER INFORMATION: Synthetic construct

<400> SEQUENCE: 959

Ser Ser Pro Gly Ser Pro Gly Thr Pro Gly Ser Arg Ser Arg Thr Tyr
1 5 10 15

Lys Ser Pro Val Val Ser Gly Asp Thr Ser Pro Arg His Leu Cys
20 25 30

<210> SEQ ID NO 960
<211> LENGTH: 32
<212> TYPE: PRT
<213> ORGANISM: Artificial Sequence
<220> FEATURE:
<223> OTHER INFORMATION: Synthetic construct

<400> SEQUENCE: 960

Ser Ser Pro Gly Ser Pro Gly Thr Pro Gly Ser Arg Ser Arg Thr Ile
1 5 10 15

Val Tyr Lys Ser Pro Val Val Ser Gly Asp Thr Ser Pro Arg His Cys
20 25 30

<210> SEQ ID NO 961
<211> LENGTH: 32
<212> TYPE: PRT
<213> ORGANISM: Artificial Sequence
<220> FEATURE:
<223> OTHER INFORMATION: Synthetic construct

<400> SEQUENCE: 961

Ser Ser Pro Gly Ser Pro Gly Thr Pro Gly Ser Arg Ser Arg Thr Val
1 5 10 15

Tyr Lys Ser Pro Val Val Ser Gly Asp Thr Ser Pro Arg His Leu Cys
20 25 30

<210> SEQ ID NO 962
<211> LENGTH: 29
<212> TYPE: PRT
<213> ORGANISM: Artificial Sequence
<220> FEATURE:
<223> OTHER INFORMATION: Synthetic construct

<400> SEQUENCE: 962

Arg Ser Gly Tyr Ser Ser Pro Gly Ser Pro Gly Thr Pro Gly Ser Arg
1 5 10 15

Lys Ser Pro Val Val Ser Gly Asp Thr Ser Pro Arg Cys
20 25

<210> SEQ ID NO 963
<211> LENGTH: 30
<212> TYPE: PRT
<213> ORGANISM: Artificial Sequence
<220> FEATURE:
<223> OTHER INFORMATION: Synthetic construct

<400> SEQUENCE: 963

Arg Ser Gly Tyr Ser Ser Pro Gly Ser Pro Gly Thr Pro Gly Ser Arg
1 5 10 15

Tyr Lys Ser Pro Val Val Ser Gly Asp Thr Ser Pro Arg Cys
20 25 30

<210> SEQ ID NO 964
<211> LENGTH: 31
<212> TYPE: PRT
<213> ORGANISM: Artificial Sequence
<220> FEATURE:
<223> OTHER INFORMATION: Synthetic construct

<400> SEQUENCE: 964

Arg Ser Gly Tyr Ser Ser Pro Gly Ser Pro Gly Thr Pro Gly Ser Arg
1 5 10 15

Val Tyr Lys Ser Pro Val Val Ser Gly Asp Thr Ser Pro Arg Cys
20 25 30

<210> SEQ ID NO 965
<211> LENGTH: 31
<212> TYPE: PRT
<213> ORGANISM: Artificial Sequence
<220> FEATURE:
<223> OTHER INFORMATION: Synthetic construct

<400> SEQUENCE: 965

Arg Ser Gly Tyr Ser Ser Pro Gly Ser Pro Gly Thr Pro Gly Ser Arg
1 5 10 15

Tyr Lys Ser Pro Val Val Ser Gly Asp Thr Ser Pro Arg His Cys
20 25 30

<210> SEQ ID NO 966
<211> LENGTH: 32
<212> TYPE: PRT
<213> ORGANISM: Artificial Sequence
<220> FEATURE:
<223> OTHER INFORMATION: Synthetic construct

<400> SEQUENCE: 966

Arg Ser Gly Tyr Ser Ser Pro Gly Ser Pro Gly Thr Pro Gly Ser Arg
1 5 10 15

Ile Val Tyr Lys Ser Pro Val Val Ser Gly Asp Thr Ser Pro Arg Cys 20 25 30

<210> SEQ ID NO 967
<211> LENGTH: 32
<212> TYPE: PRT
<213> ORGANISM: Artificial Sequence
<220> FEATURE:
<223> OTHER INFORMATION: Synthetic construct

<400> SEQUENCE: 967

Arg Ser Gly Tyr Ser Ser Pro Gly Ser Pro Gly Thr Pro Gly Ser Arg
1 5 10 15

Val Tyr Lys Ser Pro Val Val Ser Gly Asp Thr Ser Pro Arg His Cys
20 25 30

<210> SEQ ID NO 968
<211> LENGTH: 32
<212> TYPE: PRT
<213> ORGANISM: Artificial Sequence
<220> FEATURE:
<223> OTHER INFORMATION: Synthetic construct

<400> SEQUENCE: 968

Arg Ser Gly Tyr Ser Ser Pro Gly Ser Pro Gly Thr Pro Gly Ser Arg
1 5 10 15

Tyr Lys Ser Pro Val Val Ser Gly Asp Thr Ser Pro Arg His Leu Cys
20 25 30

<210> SEQ ID NO 969
<211> LENGTH: 29
<212> TYPE: PRT
<213> ORGANISM: Artificial Sequence
<220> FEATURE:
<223> OTHER INFORMATION: Synthetic construct

<400> SEQUENCE: 969

Ser Gly Tyr Ser Ser Pro Gly Ser Pro Gly Thr Pro Gly Ser Arg Ser
1 5 10 15

Lys Ser Pro Val Val Ser Gly Asp Thr Ser Pro Arg Cys
20 25

<210> SEQ ID NO 970
<211> LENGTH: 30
<212> TYPE: PRT
<213> ORGANISM: Artificial Sequence
<220> FEATURE:
<223> OTHER INFORMATION: Synthetic construct

<400> SEQUENCE: 970

Ser Gly Tyr Ser Ser Pro Gly Ser Pro Gly Thr Pro Gly Ser Arg Ser
1 5 10 15

Tyr Lys Ser Pro Val Val Ser Gly Asp Thr Ser Pro Arg Cys
20 25 30

<210> SEQ ID NO 971
<211> LENGTH: 31
<212> TYPE: PRT
<213> ORGANISM: Artificial Sequence
<220> FEATURE:
<223> OTHER INFORMATION: Synthetic construct

<400> SEQUENCE: 971

Ser Gly Tyr Ser Ser Pro Gly Ser Pro Gly Thr Pro Gly Ser Arg Ser
1 5 10 15

Val Tyr Lys Ser Pro Val Val Ser Gly Asp Thr Ser Pro Arg Cys
20 25 30

<210> SEQ ID NO 972
<211> LENGTH: 31
<212> TYPE: PRT
<213> ORGANISM: Artificial Sequence
<220> FEATURE:
<223> OTHER INFORMATION: Synthetic construct

<400> SEQUENCE: 972

Ser Gly Tyr Ser Ser Pro Gly Ser Pro Gly Thr Pro Gly Ser Arg Ser
1 5 10 15

Tyr Lys Ser Pro Val Val Ser Gly Asp Thr Ser Pro Arg His Cys
20 25 30

<210> SEQ ID NO 973
<211> LENGTH: 32
<212> TYPE: PRT
<213> ORGANISM: Artificial Sequence
<220> FEATURE:
<223> OTHER INFORMATION: Synthetic construct

<400> SEQUENCE: 973

Ser Gly Tyr Ser Ser Pro Gly Ser Pro Gly Thr Pro Gly Ser Arg Ser
1 5 10 15

Ile Val Tyr Lys Ser Pro Val Val Ser Gly Asp Thr Ser Pro Arg Cys
20 25 30

<210> SEQ ID NO 974
<211> LENGTH: 32
<212> TYPE: PRT
<213> ORGANISM: Artificial Sequence
<220> FEATURE:
<223> OTHER INFORMATION: Synthetic construct

<400> SEQUENCE: 974

Ser Gly Tyr Ser Ser Pro Gly Ser Pro Gly Thr Pro Gly Ser Arg Ser
1 5 10 15

Val Tyr Lys Ser Pro Val Val Ser Gly Asp Thr Ser Pro Arg His Cys
20 25 30

<210> SEQ ID NO 975
<211> LENGTH: 32
<212> TYPE: PRT
<213> ORGANISM: Artificial Sequence
<220> FEATURE:
<223> OTHER INFORMATION: Synthetic construct

<400> SEQUENCE: 975

Ser Gly Tyr Ser Ser Pro Gly Ser Pro Gly Thr Pro Gly Ser Arg Ser
1 5 10 15

Tyr Lys Ser Pro Val Val Ser Gly Asp Thr Ser Pro Arg His Leu Cys
20 25 30

<210> SEQ ID NO 976
<211> LENGTH: 29
<212> TYPE: PRT
<213> ORGANISM: Artificial Sequence
<220> FEATURE:
<223> OTHER INFORMATION: Synthetic construct

<400> SEQUENCE: 976

Gly Tyr Ser Ser Pro Gly Ser Pro Gly Thr Pro Gly Ser Arg Ser Arg
1 5 10 15

```
Lys Ser Pro Val Val Ser Gly Asp Thr Ser Pro Arg Cys
            20                  25


<210> SEQ ID NO 977
<211> LENGTH: 30
<212> TYPE: PRT
<213> ORGANISM: Artificial Sequence
<220> FEATURE:
<223> OTHER INFORMATION: Synthetic construct

<400> SEQUENCE: 977

Gly Tyr Ser Ser Pro Gly Ser Pro Gly Thr Pro Gly Ser Arg Ser Arg
1               5                   10                  15

Tyr Lys Ser Pro Val Val Ser Gly Asp Thr Ser Pro Arg Cys
            20                  25                  30


<210> SEQ ID NO 978
<211> LENGTH: 31
<212> TYPE: PRT
<213> ORGANISM: Artificial Sequence
<220> FEATURE:
<223> OTHER INFORMATION: Synthetic construct

<400> SEQUENCE: 978

Gly Tyr Ser Ser Pro Gly Ser Pro Gly Thr Pro Gly Ser Arg Ser Arg
1               5                   10                  15

Val Tyr Lys Ser Pro Val Val Ser Gly Asp Thr Ser Pro Arg Cys
            20                  25                  30


<210> SEQ ID NO 979
<211> LENGTH: 31
<212> TYPE: PRT
<213> ORGANISM: Artificial Sequence
<220> FEATURE:
<223> OTHER INFORMATION: Synthetic construct

<400> SEQUENCE: 979

Gly Tyr Ser Ser Pro Gly Ser Pro Gly Thr Pro Gly Ser Arg Ser Arg
1               5                   10                  15

Tyr Lys Ser Pro Val Val Ser Gly Asp Thr Ser Pro Arg His Cys
            20                  25                  30


<210> SEQ ID NO 980
<211> LENGTH: 32
<212> TYPE: PRT
<213> ORGANISM: Artificial Sequence
<220> FEATURE:
<223> OTHER INFORMATION: Synthetic construct

<400> SEQUENCE: 980

Gly Tyr Ser Ser Pro Gly Ser Pro Gly Thr Pro Gly Ser Arg Ser Arg
1               5                   10                  15

Ile Val Tyr Lys Ser Pro Val Val Ser Gly Asp Thr Ser Pro Arg Cys
            20                  25                  30


<210> SEQ ID NO 981
<211> LENGTH: 32
<212> TYPE: PRT
<213> ORGANISM: Artificial Sequence
<220> FEATURE:
<223> OTHER INFORMATION: Synthetic construct

<400> SEQUENCE: 981

Gly Tyr Ser Ser Pro Gly Ser Pro Gly Thr Pro Gly Ser Arg Ser Arg
```

1 5 10 15

Val Tyr Lys Ser Pro Val Val Ser Gly Asp Thr Ser Pro Arg His Cys
20 25 30

<210> SEQ ID NO 982
<211> LENGTH: 32
<212> TYPE: PRT
<213> ORGANISM: Artificial Sequence
<220> FEATURE:
<223> OTHER INFORMATION: Synthetic construct

<400> SEQUENCE: 982

Gly Tyr Ser Ser Pro Gly Ser Pro Gly Thr Pro Gly Ser Arg Ser Arg
1 5 10 15

Tyr Lys Ser Pro Val Val Ser Gly Asp Thr Ser Pro Arg His Leu Cys
20 25 30

<210> SEQ ID NO 983
<211> LENGTH: 29
<212> TYPE: PRT
<213> ORGANISM: Artificial Sequence
<220> FEATURE:
<223> OTHER INFORMATION: Synthetic construct

<400> SEQUENCE: 983

Tyr Ser Ser Pro Gly Ser Pro Gly Thr Pro Gly Ser Arg Ser Arg Thr
1 5 10 15

Lys Ser Pro Val Val Ser Gly Asp Thr Ser Pro Arg Cys
20 25

<210> SEQ ID NO 984
<211> LENGTH: 30
<212> TYPE: PRT
<213> ORGANISM: Artificial Sequence
<220> FEATURE:
<223> OTHER INFORMATION: Synthetic construct

<400> SEQUENCE: 984

Tyr Ser Ser Pro Gly Ser Pro Gly Thr Pro Gly Ser Arg Ser Arg Thr
1 5 10 15

Tyr Lys Ser Pro Val Val Ser Gly Asp Thr Ser Pro Arg Cys
20 25 30

<210> SEQ ID NO 985
<211> LENGTH: 31
<212> TYPE: PRT
<213> ORGANISM: Artificial Sequence
<220> FEATURE:
<223> OTHER INFORMATION: Synthetic construct

<400> SEQUENCE: 985

Tyr Ser Ser Pro Gly Ser Pro Gly Thr Pro Gly Ser Arg Ser Arg Thr
1 5 10 15

Val Tyr Lys Ser Pro Val Val Ser Gly Asp Thr Ser Pro Arg Cys
20 25 30

<210> SEQ ID NO 986
<211> LENGTH: 31
<212> TYPE: PRT
<213> ORGANISM: Artificial Sequence
<220> FEATURE:
<223> OTHER INFORMATION: Synthetic construct

<400> SEQUENCE: 986

```
Tyr Ser Ser Pro Gly Ser Pro Gly Thr Pro Gly Ser Arg Ser Arg Thr
1               5                   10                  15

Tyr Lys Ser Pro Val Val Ser Gly Asp Thr Ser Pro Arg His Cys
            20                  25                  30


<210> SEQ ID NO 987
<211> LENGTH: 32
<212> TYPE: PRT
<213> ORGANISM: Artificial Sequence
<220> FEATURE:
<223> OTHER INFORMATION: Synthetic construct

<400> SEQUENCE: 987

Tyr Ser Ser Pro Gly Ser Pro Gly Thr Pro Gly Ser Arg Ser Arg Thr
1               5                   10                  15

Ile Val Tyr Lys Ser Pro Val Val Ser Gly Asp Thr Ser Pro Arg Cys
            20                  25                  30


<210> SEQ ID NO 988
<211> LENGTH: 32
<212> TYPE: PRT
<213> ORGANISM: Artificial Sequence
<220> FEATURE:
<223> OTHER INFORMATION: Synthetic construct

<400> SEQUENCE: 988

Tyr Ser Ser Pro Gly Ser Pro Gly Thr Pro Gly Ser Arg Ser Arg Thr
1               5                   10                  15

Val Tyr Lys Ser Pro Val Val Ser Gly Asp Thr Ser Pro Arg His Cys
            20                  25                  30


<210> SEQ ID NO 989
<211> LENGTH: 32
<212> TYPE: PRT
<213> ORGANISM: Artificial Sequence
<220> FEATURE:
<223> OTHER INFORMATION: Synthetic construct

<400> SEQUENCE: 989

Tyr Ser Ser Pro Gly Ser Pro Gly Thr Pro Gly Ser Arg Ser Arg Thr
1               5                   10                  15

Tyr Lys Ser Pro Val Val Ser Gly Asp Thr Ser Pro Arg His Leu Cys
            20                  25                  30


<210> SEQ ID NO 990
<211> LENGTH: 29
<212> TYPE: PRT
<213> ORGANISM: Artificial Sequence
<220> FEATURE:
<223> OTHER INFORMATION: Synthetic construct

<400> SEQUENCE: 990

Ser Ser Pro Gly Ser Pro Gly Thr Pro Gly Ser Arg Ser Arg Thr Pro
1               5                   10                  15

Lys Ser Pro Val Val Ser Gly Asp Thr Ser Pro Arg Cys
            20                  25


<210> SEQ ID NO 991
<211> LENGTH: 30
<212> TYPE: PRT
<213> ORGANISM: Artificial Sequence
<220> FEATURE:
<223> OTHER INFORMATION: Synthetic construct

<400> SEQUENCE: 991
```

```
Ser Ser Pro Gly Ser Pro Gly Thr Pro Gly Ser Arg Ser Arg Thr Pro
1               5                   10                  15

Tyr Lys Ser Pro Val Val Ser Gly Asp Thr Ser Pro Arg Cys
            20                  25                  30


<210> SEQ ID NO 992
<211> LENGTH: 31
<212> TYPE: PRT
<213> ORGANISM: Artificial Sequence
<220> FEATURE:
<223> OTHER INFORMATION: Synthetic construct

<400> SEQUENCE: 992

Ser Ser Pro Gly Ser Pro Gly Thr Pro Gly Ser Arg Ser Arg Thr Pro
1               5                   10                  15

Val Tyr Lys Ser Pro Val Val Ser Gly Asp Thr Ser Pro Arg Cys
            20                  25                  30


<210> SEQ ID NO 993
<211> LENGTH: 31
<212> TYPE: PRT
<213> ORGANISM: Artificial Sequence
<220> FEATURE:
<223> OTHER INFORMATION: Synthetic construct

<400> SEQUENCE: 993

Ser Ser Pro Gly Ser Pro Gly Thr Pro Gly Ser Arg Ser Arg Thr Pro
1               5                   10                  15

Tyr Lys Ser Pro Val Val Ser Gly Asp Thr Ser Pro Arg His Cys
            20                  25                  30


<210> SEQ ID NO 994
<211> LENGTH: 32
<212> TYPE: PRT
<213> ORGANISM: Artificial Sequence
<220> FEATURE:
<223> OTHER INFORMATION: Synthetic construct

<400> SEQUENCE: 994

Ser Ser Pro Gly Ser Pro Gly Thr Pro Gly Ser Arg Ser Arg Thr Pro
1               5                   10                  15

Ile Val Tyr Lys Ser Pro Val Val Ser Gly Asp Thr Ser Pro Arg Cys
            20                  25                  30


<210> SEQ ID NO 995
<211> LENGTH: 32
<212> TYPE: PRT
<213> ORGANISM: Artificial Sequence
<220> FEATURE:
<223> OTHER INFORMATION: Synthetic construct

<400> SEQUENCE: 995

Ser Ser Pro Gly Ser Pro Gly Thr Pro Gly Ser Arg Ser Arg Thr Pro
1               5                   10                  15

Val Tyr Lys Ser Pro Val Val Ser Gly Asp Thr Ser Pro Arg His Cys
            20                  25                  30


<210> SEQ ID NO 996
<211> LENGTH: 32
<212> TYPE: PRT
<213> ORGANISM: Artificial Sequence
<220> FEATURE:
<223> OTHER INFORMATION: Synthetic construct
```

<400> SEQUENCE: 996

Ser Ser Pro Gly Ser Pro Gly Thr Pro Gly Ser Arg Ser Arg Thr Pro
1 5 10 15

Tyr Lys Ser Pro Val Val Ser Gly Asp Thr Ser Pro Arg His Leu Cys
20 25 30

<210> SEQ ID NO 997
<211> LENGTH: 30
<212> TYPE: PRT
<213> ORGANISM: Artificial Sequence
<220> FEATURE:
<223> OTHER INFORMATION: Synthetic construct

<400> SEQUENCE: 997

Arg Ser Gly Tyr Ser Ser Pro Gly Ser Pro Gly Thr Pro Gly Ser Arg
1 5 10 15

Ser Lys Ser Pro Val Val Ser Gly Asp Thr Ser Pro Arg Cys
20 25 30

<210> SEQ ID NO 998
<211> LENGTH: 31
<212> TYPE: PRT
<213> ORGANISM: Artificial Sequence
<220> FEATURE:
<223> OTHER INFORMATION: Synthetic construct

<400> SEQUENCE: 998

Arg Ser Gly Tyr Ser Ser Pro Gly Ser Pro Gly Thr Pro Gly Ser Arg
1 5 10 15

Ser Tyr Lys Ser Pro Val Val Ser Gly Asp Thr Ser Pro Arg Cys
20 25 30

<210> SEQ ID NO 999
<211> LENGTH: 32
<212> TYPE: PRT
<213> ORGANISM: Artificial Sequence
<220> FEATURE:
<223> OTHER INFORMATION: Synthetic construct

<400> SEQUENCE: 999

Arg Ser Gly Tyr Ser Ser Pro Gly Ser Pro Gly Thr Pro Gly Ser Arg
1 5 10 15

Ser Val Tyr Lys Ser Pro Val Val Ser Gly Asp Thr Ser Pro Arg Cys
20 25 30

<210> SEQ ID NO 1000
<211> LENGTH: 32
<212> TYPE: PRT
<213> ORGANISM: Artificial Sequence
<220> FEATURE:
<223> OTHER INFORMATION: Synthetic construct

<400> SEQUENCE: 1000

Arg Ser Gly Tyr Ser Ser Pro Gly Ser Pro Gly Thr Pro Gly Ser Arg
1 5 10 15

Ser Tyr Lys Ser Pro Val Val Ser Gly Asp Thr Ser Pro Arg His Cys
20 25 30

<210> SEQ ID NO 1001
<211> LENGTH: 30
<212> TYPE: PRT
<213> ORGANISM: Artificial Sequence
<220> FEATURE:
<223> OTHER INFORMATION: Synthetic construct

<400> SEQUENCE: 1001

Ser Gly Tyr Ser Ser Pro Gly Ser Pro Gly Thr Pro Gly Ser Arg Ser
1 5 10 15

Arg Lys Ser Pro Val Val Ser Gly Asp Thr Ser Pro Arg Cys
20 25 30

<210> SEQ ID NO 1002
<211> LENGTH: 31
<212> TYPE: PRT
<213> ORGANISM: Artificial Sequence
<220> FEATURE:
<223> OTHER INFORMATION: Synthetic construct

<400> SEQUENCE: 1002

Ser Gly Tyr Ser Ser Pro Gly Ser Pro Gly Thr Pro Gly Ser Arg Ser
1 5 10 15

Arg Tyr Lys Ser Pro Val Val Ser Gly Asp Thr Ser Pro Arg Cys
20 25 30

<210> SEQ ID NO 1003
<211> LENGTH: 32
<212> TYPE: PRT
<213> ORGANISM: Artificial Sequence
<220> FEATURE:
<223> OTHER INFORMATION: Synthetic construct

<400> SEQUENCE: 1003

Ser Gly Tyr Ser Ser Pro Gly Ser Pro Gly Thr Pro Gly Ser Arg Ser
1 5 10 15

Arg Val Tyr Lys Ser Pro Val Val Ser Gly Asp Thr Ser Pro Arg Cys
20 25 30

<210> SEQ ID NO 1004
<211> LENGTH: 32
<212> TYPE: PRT
<213> ORGANISM: Artificial Sequence
<220> FEATURE:
<223> OTHER INFORMATION: Synthetic construct

<400> SEQUENCE: 1004

Ser Gly Tyr Ser Ser Pro Gly Ser Pro Gly Thr Pro Gly Ser Arg Ser
1 5 10 15

Arg Tyr Lys Ser Pro Val Val Ser Gly Asp Thr Ser Pro Arg His Cys
20 25 30

<210> SEQ ID NO 1005
<211> LENGTH: 30
<212> TYPE: PRT
<213> ORGANISM: Artificial Sequence
<220> FEATURE:
<223> OTHER INFORMATION: Synthetic construct

<400> SEQUENCE: 1005

Gly Tyr Ser Ser Pro Gly Ser Pro Gly Thr Pro Gly Ser Arg Ser Arg
1 5 10 15

Thr Lys Ser Pro Val Val Ser Gly Asp Thr Ser Pro Arg Cys
20 25 30

<210> SEQ ID NO 1006
<211> LENGTH: 31
<212> TYPE: PRT
<213> ORGANISM: Artificial Sequence
<220> FEATURE:

<223> OTHER INFORMATION: Synthetic construct

<400> SEQUENCE: 1006

Gly Tyr Ser Ser Pro Gly Ser Pro Gly Thr Pro Gly Ser Arg Ser Arg
1 5 10 15

Thr Tyr Lys Ser Pro Val Val Ser Gly Asp Thr Ser Pro Arg Cys
20 25 30

<210> SEQ ID NO 1007
<211> LENGTH: 32
<212> TYPE: PRT
<213> ORGANISM: Artificial Sequence
<220> FEATURE:
<223> OTHER INFORMATION: Synthetic construct

<400> SEQUENCE: 1007

Gly Tyr Ser Ser Pro Gly Ser Pro Gly Thr Pro Gly Ser Arg Ser Arg
1 5 10 15

Thr Val Tyr Lys Ser Pro Val Val Ser Gly Asp Thr Ser Pro Arg Cys
20 25 30

<210> SEQ ID NO 1008
<211> LENGTH: 32
<212> TYPE: PRT
<213> ORGANISM: Artificial Sequence
<220> FEATURE:
<223> OTHER INFORMATION: Synthetic construct

<400> SEQUENCE: 1008

Gly Tyr Ser Ser Pro Gly Ser Pro Gly Thr Pro Gly Ser Arg Ser Arg
1 5 10 15

Thr Tyr Lys Ser Pro Val Val Ser Gly Asp Thr Ser Pro Arg His Cys
20 25 30

<210> SEQ ID NO 1009
<211> LENGTH: 30
<212> TYPE: PRT
<213> ORGANISM: Artificial Sequence
<220> FEATURE:
<223> OTHER INFORMATION: Synthetic construct

<400> SEQUENCE: 1009

Tyr Ser Ser Pro Gly Ser Pro Gly Thr Pro Gly Ser Arg Ser Arg Thr
1 5 10 15

Pro Lys Ser Pro Val Val Ser Gly Asp Thr Ser Pro Arg Cys
20 25 30

<210> SEQ ID NO 1010
<211> LENGTH: 31
<212> TYPE: PRT
<213> ORGANISM: Artificial Sequence
<220> FEATURE:
<223> OTHER INFORMATION: Synthetic construct

<400> SEQUENCE: 1010

Tyr Ser Ser Pro Gly Ser Pro Gly Thr Pro Gly Ser Arg Ser Arg Thr
1 5 10 15

Pro Tyr Lys Ser Pro Val Val Ser Gly Asp Thr Ser Pro Arg Cys
20 25 30

<210> SEQ ID NO 1011
<211> LENGTH: 32
<212> TYPE: PRT
<213> ORGANISM: Artificial Sequence
<220> FEATURE:
<223> OTHER INFORMATION: Synthetic construct

<400> SEQUENCE: 1011

Tyr Ser Ser Pro Gly Ser Pro Gly Thr Pro Gly Ser Arg Ser Arg Thr
1               5                   10                  15

Pro Val Tyr Lys Ser Pro Val Val Ser Gly Asp Thr Ser Pro Arg Cys
            20                  25                  30

<210> SEQ ID NO 1012
<211> LENGTH: 32
<212> TYPE: PRT
<213> ORGANISM: Artificial Sequence
<220> FEATURE:
<223> OTHER INFORMATION: Synthetic construct

<400> SEQUENCE: 1012

Tyr Ser Ser Pro Gly Ser Pro Gly Thr Pro Gly Ser Arg Ser Arg Thr
1               5                   10                  15

Pro Tyr Lys Ser Pro Val Val Ser Gly Asp Thr Ser Pro Arg His Cys
            20                  25                  30

<210> SEQ ID NO 1013
<211> LENGTH: 31
<212> TYPE: PRT
<213> ORGANISM: Artificial Sequence
<220> FEATURE:
<223> OTHER INFORMATION: Synthetic construct

<400> SEQUENCE: 1013

Arg Ser Gly Tyr Ser Ser Pro Gly Ser Pro Gly Thr Pro Gly Ser Arg
1               5                   10                  15

Ser Arg Lys Ser Pro Val Val Ser Gly Asp Thr Ser Pro Arg Cys
            20                  25                  30

<210> SEQ ID NO 1014
<211> LENGTH: 32
<212> TYPE: PRT
<213> ORGANISM: Artificial Sequence
<220> FEATURE:
<223> OTHER INFORMATION: Synthetic construct

<400> SEQUENCE: 1014

Arg Ser Gly Tyr Ser Ser Pro Gly Ser Pro Gly Thr Pro Gly Ser Arg
1               5                   10                  15

Ser Arg Tyr Lys Ser Pro Val Val Ser Gly Asp Thr Ser Pro Arg Cys
            20                  25                  30

<210> SEQ ID NO 1015
<211> LENGTH: 31
<212> TYPE: PRT
<213> ORGANISM: Artificial Sequence
<220> FEATURE:
<223> OTHER INFORMATION: Synthetic construct

<400> SEQUENCE: 1015

Ser Gly Tyr Ser Ser Pro Gly Ser Pro Gly Thr Pro Gly Ser Arg Ser
1               5                   10                  15

Arg Thr Lys Ser Pro Val Val Ser Gly Asp Thr Ser Pro Arg Cys
            20                  25                  30

<210> SEQ ID NO 1016
<211> LENGTH: 32
<212> TYPE: PRT

<213> ORGANISM: Artificial Sequence
<220> FEATURE:
<223> OTHER INFORMATION: Synthetic construct

<400> SEQUENCE: 1016

Ser Gly Tyr Ser Ser Pro Gly Ser Pro Gly Thr Pro Gly Ser Arg Ser
1 5 10 15

Arg Thr Tyr Lys Ser Pro Val Val Ser Gly Asp Thr Ser Pro Arg Cys
20 25 30

<210> SEQ ID NO 1017
<211> LENGTH: 31
<212> TYPE: PRT
<213> ORGANISM: Artificial Sequence
<220> FEATURE:
<223> OTHER INFORMATION: Synthetic construct

<400> SEQUENCE: 1017

Gly Tyr Ser Ser Pro Gly Ser Pro Gly Thr Pro Gly Ser Arg Ser Arg
1 5 10 15

Thr Pro Lys Ser Pro Val Val Ser Gly Asp Thr Ser Pro Arg Cys
20 25 30

<210> SEQ ID NO 1018
<211> LENGTH: 32
<212> TYPE: PRT
<213> ORGANISM: Artificial Sequence
<220> FEATURE:
<223> OTHER INFORMATION: Synthetic construct

<400> SEQUENCE: 1018

Gly Tyr Ser Ser Pro Gly Ser Pro Gly Thr Pro Gly Ser Arg Ser Arg
1 5 10 15

Thr Pro Tyr Lys Ser Pro Val Val Ser Gly Asp Thr Ser Pro Arg Cys
20 25 30

<210> SEQ ID NO 1019
<211> LENGTH: 32
<212> TYPE: PRT
<213> ORGANISM: Artificial Sequence
<220> FEATURE:
<223> OTHER INFORMATION: Synthetic construct

<400> SEQUENCE: 1019

Arg Ser Gly Tyr Ser Ser Pro Gly Ser Pro Gly Thr Pro Gly Ser Arg
1 5 10 15

Ser Arg Thr Lys Ser Pro Val Val Ser Gly Asp Thr Ser Pro Arg Cys
20 25 30

<210> SEQ ID NO 1020
<211> LENGTH: 32
<212> TYPE: PRT
<213> ORGANISM: Artificial Sequence
<220> FEATURE:
<223> OTHER INFORMATION: Synthetic construct

<400> SEQUENCE: 1020

Ser Gly Tyr Ser Ser Pro Gly Ser Pro Gly Thr Pro Gly Ser Arg Ser
1 5 10 15

Arg Thr Pro Lys Ser Pro Val Val Ser Gly Asp Thr Ser Pro Arg Cys
20 25 30

<210> SEQ ID NO 1021
<211> LENGTH: 17

<212> TYPE: PRT
<213> ORGANISM: Artificial Sequence
<220> FEATURE:
<223> OTHER INFORMATION: Synthetic construct

<400> SEQUENCE: 1021

Ser Arg Thr Pro Ser Leu Pro Val Arg Thr Pro Pro Lys Ser Pro Ser
1 5 10 15

Cys

<210> SEQ ID NO 1022
<211> LENGTH: 18
<212> TYPE: PRT
<213> ORGANISM: Artificial Sequence
<220> FEATURE:
<223> OTHER INFORMATION: Synthetic construct

<400> SEQUENCE: 1022

Ser Arg Thr Pro Ser Leu Pro Val Val Arg Thr Pro Pro Lys Ser Pro
1 5 10 15

Ser Cys

<210> SEQ ID NO 1023
<211> LENGTH: 18
<212> TYPE: PRT
<213> ORGANISM: Artificial Sequence
<220> FEATURE:
<223> OTHER INFORMATION: Synthetic construct

<400> SEQUENCE: 1023

Ser Arg Thr Pro Ser Leu Pro Val Arg Thr Pro Pro Lys Ser Pro Ser
1 5 10 15

Ser Cys

<210> SEQ ID NO 1024
<211> LENGTH: 19
<212> TYPE: PRT
<213> ORGANISM: Artificial Sequence
<220> FEATURE:
<223> OTHER INFORMATION: Synthetic construct

<400> SEQUENCE: 1024

Ser Arg Thr Pro Ser Leu Pro Ala Val Val Arg Thr Pro Pro Lys Ser
1 5 10 15

Pro Ser Cys

<210> SEQ ID NO 1025
<211> LENGTH: 19
<212> TYPE: PRT
<213> ORGANISM: Artificial Sequence
<220> FEATURE:
<223> OTHER INFORMATION: Synthetic construct

<400> SEQUENCE: 1025

Ser Arg Thr Pro Ser Leu Pro Val Val Arg Thr Pro Pro Lys Ser Pro
1 5 10 15

Ser Ser Cys

<210> SEQ ID NO 1026
<211> LENGTH: 19
<212> TYPE: PRT
<213> ORGANISM: Artificial Sequence
<220> FEATURE:
<223> OTHER INFORMATION: Synthetic construct

<400> SEQUENCE: 1026

Ser Arg Thr Pro Ser Leu Pro Val Arg Thr Pro Pro Lys Ser Pro Ser
1 5 10 15

Ser Ala Cys

<210> SEQ ID NO 1027
<211> LENGTH: 20
<212> TYPE: PRT
<213> ORGANISM: Artificial Sequence
<220> FEATURE:
<223> OTHER INFORMATION: Synthetic construct

<400> SEQUENCE: 1027

Ser Arg Thr Pro Ser Leu Pro Ala Val Val Arg Thr Pro Pro Lys Ser
1 5 10 15

Pro Ser Ser Cys
20

<210> SEQ ID NO 1028
<211> LENGTH: 20
<212> TYPE: PRT
<213> ORGANISM: Artificial Sequence
<220> FEATURE:
<223> OTHER INFORMATION: Synthetic construct

<400> SEQUENCE: 1028

Ser Arg Thr Pro Ser Leu Pro Val Val Arg Thr Pro Pro Lys Ser Pro
1 5 10 15

Ser Ser Ala Cys
20

<210> SEQ ID NO 1029
<211> LENGTH: 21
<212> TYPE: PRT
<213> ORGANISM: Artificial Sequence
<220> FEATURE:
<223> OTHER INFORMATION: Synthetic construct

<400> SEQUENCE: 1029

Ser Arg Thr Pro Ser Leu Pro Ala Val Val Arg Thr Pro Pro Lys Ser
1 5 10 15

Pro Ser Ser Ala Cys
20

<210> SEQ ID NO 1030
<211> LENGTH: 18
<212> TYPE: PRT
<213> ORGANISM: Artificial Sequence
<220> FEATURE:
<223> OTHER INFORMATION: Synthetic construct

<400> SEQUENCE: 1030

Arg Ser Arg Thr Pro Ser Leu Pro Val Arg Thr Pro Pro Lys Ser Pro
1 5 10 15

Ser Cys

<210> SEQ ID NO 1031
<211> LENGTH: 19
<212> TYPE: PRT
<213> ORGANISM: Artificial Sequence
<220> FEATURE:
<223> OTHER INFORMATION: Synthetic construct

<400> SEQUENCE: 1031

Arg Ser Arg Thr Pro Ser Leu Pro Val Val Arg Thr Pro Pro Lys Ser
1               5                   10                  15

Pro Ser Cys

<210> SEQ ID NO 1032
<211> LENGTH: 19
<212> TYPE: PRT
<213> ORGANISM: Artificial Sequence
<220> FEATURE:
<223> OTHER INFORMATION: Synthetic construct

<400> SEQUENCE: 1032

Arg Ser Arg Thr Pro Ser Leu Pro Val Arg Thr Pro Pro Lys Ser Pro
1               5                   10                  15

Ser Ser Cys

<210> SEQ ID NO 1033
<211> LENGTH: 20
<212> TYPE: PRT
<213> ORGANISM: Artificial Sequence
<220> FEATURE:
<223> OTHER INFORMATION: Synthetic construct

<400> SEQUENCE: 1033

Arg Ser Arg Thr Pro Ser Leu Pro Ala Val Val Arg Thr Pro Pro Lys
1               5                   10                  15

Ser Pro Ser Cys
            20

<210> SEQ ID NO 1034
<211> LENGTH: 20
<212> TYPE: PRT
<213> ORGANISM: Artificial Sequence
<220> FEATURE:
<223> OTHER INFORMATION: Synthetic construct

<400> SEQUENCE: 1034

Arg Ser Arg Thr Pro Ser Leu Pro Val Val Arg Thr Pro Pro Lys Ser
1               5                   10                  15

Pro Ser Ser Cys
            20

<210> SEQ ID NO 1035
<211> LENGTH: 20
<212> TYPE: PRT
<213> ORGANISM: Artificial Sequence
<220> FEATURE:
<223> OTHER INFORMATION: Synthetic construct

<400> SEQUENCE: 1035

Arg Ser Arg Thr Pro Ser Leu Pro Val Arg Thr Pro Pro Lys Ser Pro
1               5                   10                  15

Ser Ser Ala Cys
            20

<210> SEQ ID NO 1036
<211> LENGTH: 21
<212> TYPE: PRT
<213> ORGANISM: Artificial Sequence
<220> FEATURE:
<223> OTHER INFORMATION: Synthetic construct

<400> SEQUENCE: 1036

Arg Ser Arg Thr Pro Ser Leu Pro Ala Val Val Arg Thr Pro Pro Lys
1 5 10 15

Ser Pro Ser Ser Cys
20

<210> SEQ ID NO 1037
<211> LENGTH: 21
<212> TYPE: PRT
<213> ORGANISM: Artificial Sequence
<220> FEATURE:
<223> OTHER INFORMATION: Synthetic construct

<400> SEQUENCE: 1037

Arg Ser Arg Thr Pro Ser Leu Pro Val Val Arg Thr Pro Pro Lys Ser
1 5 10 15

Pro Ser Ser Ala Cys
20

<210> SEQ ID NO 1038
<211> LENGTH: 22
<212> TYPE: PRT
<213> ORGANISM: Artificial Sequence
<220> FEATURE:
<223> OTHER INFORMATION: Synthetic construct

<400> SEQUENCE: 1038

Arg Ser Arg Thr Pro Ser Leu Pro Ala Val Val Arg Thr Pro Pro Lys
1 5 10 15

Ser Pro Ser Ser Ala Cys
20

<210> SEQ ID NO 1039
<211> LENGTH: 18
<212> TYPE: PRT
<213> ORGANISM: Artificial Sequence
<220> FEATURE:
<223> OTHER INFORMATION: Synthetic construct

<400> SEQUENCE: 1039

Ser Arg Thr Pro Ser Leu Pro Thr Val Arg Thr Pro Pro Lys Ser Pro
1 5 10 15

Ser Cys

<210> SEQ ID NO 1040
<211> LENGTH: 19
<212> TYPE: PRT
<213> ORGANISM: Artificial Sequence
<220> FEATURE:
<223> OTHER INFORMATION: Synthetic construct

<400> SEQUENCE: 1040

Ser Arg Thr Pro Ser Leu Pro Thr Val Val Arg Thr Pro Pro Lys Ser
1 5 10 15

Pro Ser Cys

<210> SEQ ID NO 1041
<211> LENGTH: 19
<212> TYPE: PRT
<213> ORGANISM: Artificial Sequence
<220> FEATURE:
<223> OTHER INFORMATION: Synthetic construct

<400> SEQUENCE: 1041

Ser Arg Thr Pro Ser Leu Pro Thr Val Arg Thr Pro Pro Lys Ser Pro
1               5                   10                  15

Ser Ser Cys

<210> SEQ ID NO 1042
<211> LENGTH: 20
<212> TYPE: PRT
<213> ORGANISM: Artificial Sequence
<220> FEATURE:
<223> OTHER INFORMATION: Synthetic construct

<400> SEQUENCE: 1042

Ser Arg Thr Pro Ser Leu Pro Thr Ala Val Val Arg Thr Pro Pro Lys
1               5                   10                  15

Ser Pro Ser Cys
            20

<210> SEQ ID NO 1043
<211> LENGTH: 20
<212> TYPE: PRT
<213> ORGANISM: Artificial Sequence
<220> FEATURE:
<223> OTHER INFORMATION: Synthetic construct

<400> SEQUENCE: 1043

Ser Arg Thr Pro Ser Leu Pro Thr Val Val Arg Thr Pro Pro Lys Ser
1               5                   10                  15

Pro Ser Ser Cys
            20

<210> SEQ ID NO 1044
<211> LENGTH: 20
<212> TYPE: PRT
<213> ORGANISM: Artificial Sequence
<220> FEATURE:
<223> OTHER INFORMATION: Synthetic construct

<400> SEQUENCE: 1044

Ser Arg Thr Pro Ser Leu Pro Thr Val Arg Thr Pro Pro Lys Ser Pro
1               5                   10                  15

Ser Ser Ala Cys
            20

<210> SEQ ID NO 1045
<211> LENGTH: 21
<212> TYPE: PRT
<213> ORGANISM: Artificial Sequence
<220> FEATURE:
<223> OTHER INFORMATION: Synthetic construct

<400> SEQUENCE: 1045

Ser Arg Thr Pro Ser Leu Pro Thr Ala Val Val Arg Thr Pro Pro Lys
1               5                   10                  15

Ser Pro Ser Ser Cys
            20

<210> SEQ ID NO 1046
<211> LENGTH: 21
<212> TYPE: PRT
<213> ORGANISM: Artificial Sequence
<220> FEATURE:
<223> OTHER INFORMATION: Synthetic construct

<400> SEQUENCE: 1046

Ser Arg Thr Pro Ser Leu Pro Thr Val Val Arg Thr Pro Pro Lys Ser
1               5                   10                  15

Pro Ser Ser Ala Cys
            20

<210> SEQ ID NO 1047
<211> LENGTH: 22
<212> TYPE: PRT
<213> ORGANISM: Artificial Sequence
<220> FEATURE:
<223> OTHER INFORMATION: Synthetic construct

<400> SEQUENCE: 1047

Ser Arg Thr Pro Ser Leu Pro Thr Ala Val Val Arg Thr Pro Pro Lys
1               5                   10                  15

Ser Pro Ser Ser Ala Cys
            20

<210> SEQ ID NO 1048
<211> LENGTH: 19
<212> TYPE: PRT
<213> ORGANISM: Artificial Sequence
<220> FEATURE:
<223> OTHER INFORMATION: Synthetic construct

<400> SEQUENCE: 1048

Ser Arg Ser Arg Thr Pro Ser Leu Pro Val Arg Thr Pro Pro Lys Ser
1               5                   10                  15

Pro Ser Cys

<210> SEQ ID NO 1049
<211> LENGTH: 20
<212> TYPE: PRT
<213> ORGANISM: Artificial Sequence
<220> FEATURE:
<223> OTHER INFORMATION: Synthetic construct

<400> SEQUENCE: 1049

Ser Arg Ser Arg Thr Pro Ser Leu Pro Val Val Arg Thr Pro Pro Lys
1               5                   10                  15

Ser Pro Ser Cys
            20

<210> SEQ ID NO 1050
<211> LENGTH: 20
<212> TYPE: PRT
<213> ORGANISM: Artificial Sequence
<220> FEATURE:
<223> OTHER INFORMATION: Synthetic construct

<400> SEQUENCE: 1050

Ser Arg Ser Arg Thr Pro Ser Leu Pro Val Arg Thr Pro Pro Lys Ser
1               5                   10                  15

Pro Ser Ser Cys
            20

<210> SEQ ID NO 1051
<211> LENGTH: 21
<212> TYPE: PRT
<213> ORGANISM: Artificial Sequence
<220> FEATURE:
<223> OTHER INFORMATION: Synthetic construct

<400> SEQUENCE: 1051

Ser Arg Ser Arg Thr Pro Ser Leu Pro Ala Val Val Arg Thr Pro Pro
1 5 10 15

Lys Ser Pro Ser Cys
20

<210> SEQ ID NO 1052
<211> LENGTH: 21
<212> TYPE: PRT
<213> ORGANISM: Artificial Sequence
<220> FEATURE:
<223> OTHER INFORMATION: Synthetic construct

<400> SEQUENCE: 1052

Ser Arg Ser Arg Thr Pro Ser Leu Pro Val Val Arg Thr Pro Pro Lys
1 5 10 15

Ser Pro Ser Ser Cys
20

<210> SEQ ID NO 1053
<211> LENGTH: 21
<212> TYPE: PRT
<213> ORGANISM: Artificial Sequence
<220> FEATURE:
<223> OTHER INFORMATION: Synthetic construct

<400> SEQUENCE: 1053

Ser Arg Ser Arg Thr Pro Ser Leu Pro Val Arg Thr Pro Pro Lys Ser
1 5 10 15

Pro Ser Ser Ala Cys
20

<210> SEQ ID NO 1054
<211> LENGTH: 22
<212> TYPE: PRT
<213> ORGANISM: Artificial Sequence
<220> FEATURE:
<223> OTHER INFORMATION: Synthetic construct

<400> SEQUENCE: 1054

Ser Arg Ser Arg Thr Pro Ser Leu Pro Ala Val Val Arg Thr Pro Pro
1 5 10 15

Lys Ser Pro Ser Ser Cys
20

<210> SEQ ID NO 1055
<211> LENGTH: 22
<212> TYPE: PRT
<213> ORGANISM: Artificial Sequence
<220> FEATURE:
<223> OTHER INFORMATION: Synthetic construct

<400> SEQUENCE: 1055

Ser Arg Ser Arg Thr Pro Ser Leu Pro Val Val Arg Thr Pro Pro Lys
1 5 10 15

Ser Pro Ser Ser Ala Cys
20

<210> SEQ ID NO 1056
<211> LENGTH: 23
<212> TYPE: PRT
<213> ORGANISM: Artificial Sequence
<220> FEATURE:
<223> OTHER INFORMATION: Synthetic construct

<400> SEQUENCE: 1056

Ser Arg Ser Arg Thr Pro Ser Leu Pro Ala Val Val Arg Thr Pro Pro
1 5 10 15

Lys Ser Pro Ser Ser Ala Cys
20

<210> SEQ ID NO 1057
<211> LENGTH: 19
<212> TYPE: PRT
<213> ORGANISM: Artificial Sequence
<220> FEATURE:
<223> OTHER INFORMATION: Synthetic construct

<400> SEQUENCE: 1057

Arg Ser Arg Thr Pro Ser Leu Pro Thr Val Arg Thr Pro Pro Lys Ser
1 5 10 15

Pro Ser Cys

<210> SEQ ID NO 1058
<211> LENGTH: 20
<212> TYPE: PRT
<213> ORGANISM: Artificial Sequence
<220> FEATURE:
<223> OTHER INFORMATION: Synthetic construct

<400> SEQUENCE: 1058

Arg Ser Arg Thr Pro Ser Leu Pro Thr Val Val Arg Thr Pro Pro Lys
1 5 10 15

Ser Pro Ser Cys
20

<210> SEQ ID NO 1059
<211> LENGTH: 20
<212> TYPE: PRT
<213> ORGANISM: Artificial Sequence
<220> FEATURE:
<223> OTHER INFORMATION: Synthetic construct

<400> SEQUENCE: 1059

Arg Ser Arg Thr Pro Ser Leu Pro Thr Val Arg Thr Pro Pro Lys Ser
1 5 10 15

Pro Ser Ser Cys
20

<210> SEQ ID NO 1060
<211> LENGTH: 21
<212> TYPE: PRT
<213> ORGANISM: Artificial Sequence
<220> FEATURE:
<223> OTHER INFORMATION: Synthetic construct

<400> SEQUENCE: 1060

Arg Ser Arg Thr Pro Ser Leu Pro Thr Ala Val Val Arg Thr Pro Pro
1 5 10 15

Lys Ser Pro Ser Cys
20

<210> SEQ ID NO 1061
<211> LENGTH: 21
<212> TYPE: PRT
<213> ORGANISM: Artificial Sequence
<220> FEATURE:
<223> OTHER INFORMATION: Synthetic construct

<400> SEQUENCE: 1061

Arg Ser Arg Thr Pro Ser Leu Pro Thr Val Val Arg Thr Pro Pro Lys
1 5 10 15

Ser Pro Ser Ser Cys
20

<210> SEQ ID NO 1062
<211> LENGTH: 21
<212> TYPE: PRT
<213> ORGANISM: Artificial Sequence
<220> FEATURE:
<223> OTHER INFORMATION: Synthetic construct

<400> SEQUENCE: 1062

Arg Ser Arg Thr Pro Ser Leu Pro Thr Val Arg Thr Pro Pro Lys Ser
1 5 10 15

Pro Ser Ser Ala Cys
20

<210> SEQ ID NO 1063
<211> LENGTH: 22
<212> TYPE: PRT
<213> ORGANISM: Artificial Sequence
<220> FEATURE:
<223> OTHER INFORMATION: Synthetic construct

<400> SEQUENCE: 1063

Arg Ser Arg Thr Pro Ser Leu Pro Thr Ala Val Val Arg Thr Pro Pro
1 5 10 15

Lys Ser Pro Ser Ser Cys
20

<210> SEQ ID NO 1064
<211> LENGTH: 22
<212> TYPE: PRT
<213> ORGANISM: Artificial Sequence
<220> FEATURE:
<223> OTHER INFORMATION: Synthetic construct

<400> SEQUENCE: 1064

Arg Ser Arg Thr Pro Ser Leu Pro Thr Val Val Arg Thr Pro Pro Lys
1 5 10 15

Ser Pro Ser Ser Ala Cys
20

<210> SEQ ID NO 1065
<211> LENGTH: 23
<212> TYPE: PRT
<213> ORGANISM: Artificial Sequence
<220> FEATURE:
<223> OTHER INFORMATION: Synthetic construct

<400> SEQUENCE: 1065

Arg Ser Arg Thr Pro Ser Leu Pro Thr Ala Val Val Arg Thr Pro Pro
1 5 10 15

Lys Ser Pro Ser Ser Ala Cys
20

<210> SEQ ID NO 1066
<211> LENGTH: 19
<212> TYPE: PRT
<213> ORGANISM: Artificial Sequence
<220> FEATURE:
<223> OTHER INFORMATION: Synthetic construct

<400> SEQUENCE: 1066

Ser Arg Thr Pro Ser Leu Pro Thr Pro Val Arg Thr Pro Pro Lys Ser
1 5 10 15

Pro Ser Cys

<210> SEQ ID NO 1067
<211> LENGTH: 20
<212> TYPE: PRT
<213> ORGANISM: Artificial Sequence
<220> FEATURE:
<223> OTHER INFORMATION: Synthetic construct

<400> SEQUENCE: 1067

Ser Arg Thr Pro Ser Leu Pro Thr Pro Val Val Arg Thr Pro Pro Lys
1 5 10 15

Ser Pro Ser Cys
20

<210> SEQ ID NO 1068
<211> LENGTH: 20
<212> TYPE: PRT
<213> ORGANISM: Artificial Sequence
<220> FEATURE:
<223> OTHER INFORMATION: Synthetic construct

<400> SEQUENCE: 1068

Ser Arg Thr Pro Ser Leu Pro Thr Pro Val Arg Thr Pro Pro Lys Ser
1 5 10 15

Pro Ser Ser Cys
20

<210> SEQ ID NO 1069
<211> LENGTH: 21
<212> TYPE: PRT
<213> ORGANISM: Artificial Sequence
<220> FEATURE:
<223> OTHER INFORMATION: Synthetic construct

<400> SEQUENCE: 1069

Ser Arg Thr Pro Ser Leu Pro Thr Pro Ala Val Val Arg Thr Pro Pro
1 5 10 15

Lys Ser Pro Ser Cys
20

<210> SEQ ID NO 1070
<211> LENGTH: 21
<212> TYPE: PRT
<213> ORGANISM: Artificial Sequence
<220> FEATURE:
<223> OTHER INFORMATION: Synthetic construct

<400> SEQUENCE: 1070

Ser Arg Thr Pro Ser Leu Pro Thr Pro Val Val Arg Thr Pro Pro Lys
1 5 10 15

Ser Pro Ser Ser Cys
20

<210> SEQ ID NO 1071
<211> LENGTH: 21
<212> TYPE: PRT
<213> ORGANISM: Artificial Sequence
<220> FEATURE:
<223> OTHER INFORMATION: Synthetic construct

<400> SEQUENCE: 1071

Ser Arg Thr Pro Ser Leu Pro Thr Pro Val Arg Thr Pro Pro Lys Ser
1 5 10 15

Pro Ser Ser Ala Cys
20

<210> SEQ ID NO 1072
<211> LENGTH: 22
<212> TYPE: PRT
<213> ORGANISM: Artificial Sequence
<220> FEATURE:
<223> OTHER INFORMATION: Synthetic construct

<400> SEQUENCE: 1072

Ser Arg Thr Pro Ser Leu Pro Thr Pro Ala Val Val Arg Thr Pro Pro
1 5 10 15

Lys Ser Pro Ser Ser Cys
20

<210> SEQ ID NO 1073
<211> LENGTH: 22
<212> TYPE: PRT
<213> ORGANISM: Artificial Sequence
<220> FEATURE:
<223> OTHER INFORMATION: Synthetic construct

<400> SEQUENCE: 1073

Ser Arg Thr Pro Ser Leu Pro Thr Pro Val Val Arg Thr Pro Pro Lys
1 5 10 15

Ser Pro Ser Ser Ala Cys
20

<210> SEQ ID NO 1074
<211> LENGTH: 23
<212> TYPE: PRT
<213> ORGANISM: Artificial Sequence
<220> FEATURE:
<223> OTHER INFORMATION: Synthetic construct

<400> SEQUENCE: 1074

Ser Arg Thr Pro Ser Leu Pro Thr Pro Ala Val Val Arg Thr Pro Pro
1 5 10 15

Lys Ser Pro Ser Ser Ala Cys
20

<210> SEQ ID NO 1075
<211> LENGTH: 20
<212> TYPE: PRT
<213> ORGANISM: Artificial Sequence
<220> FEATURE:
<223> OTHER INFORMATION: Synthetic construct

<400> SEQUENCE: 1075

Ser Arg Ser Arg Thr Pro Ser Leu Pro Thr Val Arg Thr Pro Pro Lys
1 5 10 15

Ser Pro Ser Cys
20

<210> SEQ ID NO 1076
<211> LENGTH: 21
<212> TYPE: PRT
<213> ORGANISM: Artificial Sequence
<220> FEATURE:
<223> OTHER INFORMATION: Synthetic construct

<400> SEQUENCE: 1076

Ser Arg Ser Arg Thr Pro Ser Leu Pro Thr Val Val Arg Thr Pro Pro
1 5 10 15

Lys Ser Pro Ser Cys
20

<210> SEQ ID NO 1077
<211> LENGTH: 21
<212> TYPE: PRT
<213> ORGANISM: Artificial Sequence
<220> FEATURE:
<223> OTHER INFORMATION: Synthetic construct

<400> SEQUENCE: 1077

Ser Arg Ser Arg Thr Pro Ser Leu Pro Thr Val Arg Thr Pro Pro Lys
1 5 10 15

Ser Pro Ser Ser Cys
20

<210> SEQ ID NO 1078
<211> LENGTH: 22
<212> TYPE: PRT
<213> ORGANISM: Artificial Sequence
<220> FEATURE:
<223> OTHER INFORMATION: Synthetic construct

<400> SEQUENCE: 1078

Ser Arg Ser Arg Thr Pro Ser Leu Pro Thr Ala Val Val Arg Thr Pro
1 5 10 15

Pro Lys Ser Pro Ser Cys
20

<210> SEQ ID NO 1079
<211> LENGTH: 22
<212> TYPE: PRT
<213> ORGANISM: Artificial Sequence
<220> FEATURE:
<223> OTHER INFORMATION: Synthetic construct

<400> SEQUENCE: 1079

Ser Arg Ser Arg Thr Pro Ser Leu Pro Thr Val Val Arg Thr Pro Pro
1 5 10 15

Lys Ser Pro Ser Ser Cys
20

<210> SEQ ID NO 1080
<211> LENGTH: 22
<212> TYPE: PRT
<213> ORGANISM: Artificial Sequence
<220> FEATURE:
<223> OTHER INFORMATION: Synthetic construct

<400> SEQUENCE: 1080

Ser Arg Ser Arg Thr Pro Ser Leu Pro Thr Val Arg Thr Pro Pro Lys
1 5 10 15

Ser Pro Ser Ser Ala Cys
20

<210> SEQ ID NO 1081
<211> LENGTH: 23
<212> TYPE: PRT
<213> ORGANISM: Artificial Sequence
<220> FEATURE:

<223> OTHER INFORMATION: Synthetic construct

<400> SEQUENCE: 1081

Ser Arg Ser Arg Thr Pro Ser Leu Pro Thr Ala Val Val Arg Thr Pro
1 5 10 15

Pro Lys Ser Pro Ser Ser Cys
20

<210> SEQ ID NO 1082
<211> LENGTH: 23
<212> TYPE: PRT
<213> ORGANISM: Artificial Sequence
<220> FEATURE:
<223> OTHER INFORMATION: Synthetic construct

<400> SEQUENCE: 1082

Ser Arg Ser Arg Thr Pro Ser Leu Pro Thr Val Val Arg Thr Pro Pro
1 5 10 15

Lys Ser Pro Ser Ser Ala Cys
20

<210> SEQ ID NO 1083
<211> LENGTH: 24
<212> TYPE: PRT
<213> ORGANISM: Artificial Sequence
<220> FEATURE:
<223> OTHER INFORMATION: Synthetic construct

<400> SEQUENCE: 1083

Ser Arg Ser Arg Thr Pro Ser Leu Pro Thr Ala Val Val Arg Thr Pro
1 5 10 15

Pro Lys Ser Pro Ser Ser Ala Cys
20

<210> SEQ ID NO 1084
<211> LENGTH: 20
<212> TYPE: PRT
<213> ORGANISM: Artificial Sequence
<220> FEATURE:
<223> OTHER INFORMATION: Synthetic construct

<400> SEQUENCE: 1084

Arg Ser Arg Thr Pro Ser Leu Pro Thr Pro Val Arg Thr Pro Pro Lys
1 5 10 15

Ser Pro Ser Cys
20

<210> SEQ ID NO 1085
<211> LENGTH: 21
<212> TYPE: PRT
<213> ORGANISM: Artificial Sequence
<220> FEATURE:
<223> OTHER INFORMATION: Synthetic construct

<400> SEQUENCE: 1085

Arg Ser Arg Thr Pro Ser Leu Pro Thr Pro Val Val Arg Thr Pro Pro
1 5 10 15

Lys Ser Pro Ser Cys
20

<210> SEQ ID NO 1086
<211> LENGTH: 21
<212> TYPE: PRT
<213> ORGANISM: Artificial Sequence
<220> FEATURE:
<223> OTHER INFORMATION: Synthetic construct

<400> SEQUENCE: 1086

Arg Ser Arg Thr Pro Ser Leu Pro Thr Pro Val Arg Thr Pro Pro Lys
1 5 10 15

Ser Pro Ser Ser Cys
20

<210> SEQ ID NO 1087
<211> LENGTH: 22
<212> TYPE: PRT
<213> ORGANISM: Artificial Sequence
<220> FEATURE:
<223> OTHER INFORMATION: Synthetic construct

<400> SEQUENCE: 1087

Arg Ser Arg Thr Pro Ser Leu Pro Thr Pro Ala Val Val Arg Thr Pro
1 5 10 15

Pro Lys Ser Pro Ser Cys
20

<210> SEQ ID NO 1088
<211> LENGTH: 22
<212> TYPE: PRT
<213> ORGANISM: Artificial Sequence
<220> FEATURE:
<223> OTHER INFORMATION: Synthetic construct

<400> SEQUENCE: 1088

Arg Ser Arg Thr Pro Ser Leu Pro Thr Pro Val Val Arg Thr Pro Pro
1 5 10 15

Lys Ser Pro Ser Ser Cys
20

<210> SEQ ID NO 1089
<211> LENGTH: 22
<212> TYPE: PRT
<213> ORGANISM: Artificial Sequence
<220> FEATURE:
<223> OTHER INFORMATION: Synthetic construct

<400> SEQUENCE: 1089

Arg Ser Arg Thr Pro Ser Leu Pro Thr Pro Val Arg Thr Pro Pro Lys
1 5 10 15

Ser Pro Ser Ser Ala Cys
20

<210> SEQ ID NO 1090
<211> LENGTH: 23
<212> TYPE: PRT
<213> ORGANISM: Artificial Sequence
<220> FEATURE:
<223> OTHER INFORMATION: Synthetic construct

<400> SEQUENCE: 1090

Arg Ser Arg Thr Pro Ser Leu Pro Thr Pro Ala Val Val Arg Thr Pro
1 5 10 15

Pro Lys Ser Pro Ser Ser Cys
20

<210> SEQ ID NO 1091
<211> LENGTH: 23
<212> TYPE: PRT

<213> ORGANISM: Artificial Sequence
<220> FEATURE:
<223> OTHER INFORMATION: Synthetic construct

<400> SEQUENCE: 1091

Arg Ser Arg Thr Pro Ser Leu Pro Thr Pro Val Val Arg Thr Pro Pro
1               5                   10                  15

Lys Ser Pro Ser Ser Ala Cys
            20

<210> SEQ ID NO 1092
<211> LENGTH: 24
<212> TYPE: PRT
<213> ORGANISM: Artificial Sequence
<220> FEATURE:
<223> OTHER INFORMATION: Synthetic construct

<400> SEQUENCE: 1092

Arg Ser Arg Thr Pro Ser Leu Pro Thr Pro Ala Val Val Arg Thr Pro
1               5                   10                  15

Pro Lys Ser Pro Ser Ser Ala Cys
            20

<210> SEQ ID NO 1093
<211> LENGTH: 21
<212> TYPE: PRT
<213> ORGANISM: Artificial Sequence
<220> FEATURE:
<223> OTHER INFORMATION: Synthetic construct

<400> SEQUENCE: 1093

Ser Arg Ser Arg Thr Pro Ser Leu Pro Thr Pro Val Arg Thr Pro Pro
1               5                   10                  15

Lys Ser Pro Ser Cys
            20

<210> SEQ ID NO 1094
<211> LENGTH: 22
<212> TYPE: PRT
<213> ORGANISM: Artificial Sequence
<220> FEATURE:
<223> OTHER INFORMATION: Synthetic construct

<400> SEQUENCE: 1094

Ser Arg Ser Arg Thr Pro Ser Leu Pro Thr Pro Val Val Arg Thr Pro
1               5                   10                  15

Pro Lys Ser Pro Ser Cys
            20

<210> SEQ ID NO 1095
<211> LENGTH: 22
<212> TYPE: PRT
<213> ORGANISM: Artificial Sequence
<220> FEATURE:
<223> OTHER INFORMATION: Synthetic construct

<400> SEQUENCE: 1095

Ser Arg Ser Arg Thr Pro Ser Leu Pro Thr Pro Val Arg Thr Pro Pro
1               5                   10                  15

Lys Ser Pro Ser Ser Cys
            20

<210> SEQ ID NO 1096
<211> LENGTH: 23

<212> TYPE: PRT
<213> ORGANISM: Artificial Sequence
<220> FEATURE:
<223> OTHER INFORMATION: Synthetic construct

<400> SEQUENCE: 1096

Ser Arg Ser Arg Thr Pro Ser Leu Pro Thr Pro Ala Val Val Arg Thr
1 5 10 15

Pro Pro Lys Ser Pro Ser Cys
20

<210> SEQ ID NO 1097
<211> LENGTH: 23
<212> TYPE: PRT
<213> ORGANISM: Artificial Sequence
<220> FEATURE:
<223> OTHER INFORMATION: Synthetic construct

<400> SEQUENCE: 1097

Ser Arg Ser Arg Thr Pro Ser Leu Pro Thr Pro Val Val Arg Thr Pro
1 5 10 15

Pro Lys Ser Pro Ser Ser Cys
20

<210> SEQ ID NO 1098
<211> LENGTH: 23
<212> TYPE: PRT
<213> ORGANISM: Artificial Sequence
<220> FEATURE:
<223> OTHER INFORMATION: Synthetic construct

<400> SEQUENCE: 1098

Ser Arg Ser Arg Thr Pro Ser Leu Pro Thr Pro Val Arg Thr Pro Pro
1 5 10 15

Lys Ser Pro Ser Ser Ala Cys
20

<210> SEQ ID NO 1099
<211> LENGTH: 24
<212> TYPE: PRT
<213> ORGANISM: Artificial Sequence
<220> FEATURE:
<223> OTHER INFORMATION: Synthetic construct

<400> SEQUENCE: 1099

Ser Arg Ser Arg Thr Pro Ser Leu Pro Thr Pro Ala Val Val Arg Thr
1 5 10 15

Pro Pro Lys Ser Pro Ser Ser Cys
20

<210> SEQ ID NO 1100
<211> LENGTH: 24
<212> TYPE: PRT
<213> ORGANISM: Artificial Sequence
<220> FEATURE:
<223> OTHER INFORMATION: Synthetic construct

<400> SEQUENCE: 1100

Ser Arg Ser Arg Thr Pro Ser Leu Pro Thr Pro Val Val Arg Thr Pro
1 5 10 15

Pro Lys Ser Pro Ser Ser Ala Cys
20

<210> SEQ ID NO 1101

<211> LENGTH: 25
<212> TYPE: PRT
<213> ORGANISM: Artificial Sequence
<220> FEATURE:
<223> OTHER INFORMATION: Synthetic construct

<400> SEQUENCE: 1101

Ser Arg Ser Arg Thr Pro Ser Leu Pro Thr Pro Ala Val Val Arg Thr
1               5                   10                  15

Pro Pro Lys Ser Pro Ser Ser Ala Cys
            20                  25

<210> SEQ ID NO 1102
<211> LENGTH: 22
<212> TYPE: PRT
<213> ORGANISM: Artificial Sequence
<220> FEATURE:
<223> OTHER INFORMATION: Synthetic construct

<400> SEQUENCE: 1102

Ser Arg Thr Pro Ser Leu Pro Pro Ser Ser Ala Lys Ser Arg Ser Lys
1               5                   10                  15

Ile Gly Ser Thr Glu Cys
            20

<210> SEQ ID NO 1103
<211> LENGTH: 23
<212> TYPE: PRT
<213> ORGANISM: Artificial Sequence
<220> FEATURE:
<223> OTHER INFORMATION: Synthetic construct

<400> SEQUENCE: 1103

Ser Arg Thr Pro Ser Leu Pro Ser Pro Ser Ser Ala Lys Ser Arg Ser
1               5                   10                  15

Lys Ile Gly Ser Thr Glu Cys
            20

<210> SEQ ID NO 1104
<211> LENGTH: 23
<212> TYPE: PRT
<213> ORGANISM: Artificial Sequence
<220> FEATURE:
<223> OTHER INFORMATION: Synthetic construct

<400> SEQUENCE: 1104

Ser Arg Thr Pro Ser Leu Pro Pro Ser Ser Ala Lys Ser Arg Ser Lys
1               5                   10                  15

Ile Gly Ser Thr Glu Asn Cys
            20

<210> SEQ ID NO 1105
<211> LENGTH: 24
<212> TYPE: PRT
<213> ORGANISM: Artificial Sequence
<220> FEATURE:
<223> OTHER INFORMATION: Synthetic construct

<400> SEQUENCE: 1105

Ser Arg Thr Pro Ser Leu Pro Lys Ser Pro Ser Ser Ala Lys Ser Arg
1               5                   10                  15

Ser Lys Ile Gly Ser Thr Glu Cys
            20

<210> SEQ ID NO 1106
<211> LENGTH: 24
<212> TYPE: PRT
<213> ORGANISM: Artificial Sequence
<220> FEATURE:
<223> OTHER INFORMATION: Synthetic construct

<400> SEQUENCE: 1106

Ser Arg Thr Pro Ser Leu Pro Ser Pro Ser Ser Ala Lys Ser Arg Ser
1 5 10 15

Lys Ile Gly Ser Thr Glu Asn Cys
20

<210> SEQ ID NO 1107
<211> LENGTH: 24
<212> TYPE: PRT
<213> ORGANISM: Artificial Sequence
<220> FEATURE:
<223> OTHER INFORMATION: Synthetic construct

<400> SEQUENCE: 1107

Ser Arg Thr Pro Ser Leu Pro Pro Ser Ser Ala Lys Ser Arg Ser Lys
1 5 10 15

Ile Gly Ser Thr Glu Asn Leu Cys
20

<210> SEQ ID NO 1108
<211> LENGTH: 25
<212> TYPE: PRT
<213> ORGANISM: Artificial Sequence
<220> FEATURE:
<223> OTHER INFORMATION: Synthetic construct

<400> SEQUENCE: 1108

Ser Arg Thr Pro Ser Leu Pro Lys Ser Pro Ser Ser Ala Lys Ser Arg
1 5 10 15

Ser Lys Ile Gly Ser Thr Glu Asn Cys
20 25

<210> SEQ ID NO 1109
<211> LENGTH: 25
<212> TYPE: PRT
<213> ORGANISM: Artificial Sequence
<220> FEATURE:
<223> OTHER INFORMATION: Synthetic construct

<400> SEQUENCE: 1109

Ser Arg Thr Pro Ser Leu Pro Ser Pro Ser Ser Ala Lys Ser Arg Ser
1 5 10 15

Lys Ile Gly Ser Thr Glu Asn Leu Cys
20 25

<210> SEQ ID NO 1110
<211> LENGTH: 26
<212> TYPE: PRT
<213> ORGANISM: Artificial Sequence
<220> FEATURE:
<223> OTHER INFORMATION: Synthetic construct

<400> SEQUENCE: 1110

Ser Arg Thr Pro Ser Leu Pro Lys Ser Pro Ser Ser Ala Lys Ser Arg
1 5 10 15

Ser Lys Ile Gly Ser Thr Glu Asn Leu Cys
20 25

<210> SEQ ID NO 1111
<211> LENGTH: 23
<212> TYPE: PRT
<213> ORGANISM: Artificial Sequence
<220> FEATURE:
<223> OTHER INFORMATION: Synthetic construct

<400> SEQUENCE: 1111

```
Arg Ser Arg Thr Pro Ser Leu Pro Pro Ser Ser Ala Lys Ser Arg Ser
1               5                   10                  15

Lys Ile Gly Ser Thr Glu Cys
            20
```

<210> SEQ ID NO 1112
<211> LENGTH: 24
<212> TYPE: PRT
<213> ORGANISM: Artificial Sequence
<220> FEATURE:
<223> OTHER INFORMATION: Synthetic construct

<400> SEQUENCE: 1112

```
Arg Ser Arg Thr Pro Ser Leu Pro Ser Pro Ser Ser Ala Lys Ser Arg
1               5                   10                  15

Ser Lys Ile Gly Ser Thr Glu Cys
            20
```

<210> SEQ ID NO 1113
<211> LENGTH: 24
<212> TYPE: PRT
<213> ORGANISM: Artificial Sequence
<220> FEATURE:
<223> OTHER INFORMATION: Synthetic construct

<400> SEQUENCE: 1113

```
Arg Ser Arg Thr Pro Ser Leu Pro Pro Ser Ser Ala Lys Ser Arg Ser
1               5                   10                  15

Lys Ile Gly Ser Thr Glu Asn Cys
            20
```

<210> SEQ ID NO 1114
<211> LENGTH: 25
<212> TYPE: PRT
<213> ORGANISM: Artificial Sequence
<220> FEATURE:
<223> OTHER INFORMATION: Synthetic construct

<400> SEQUENCE: 1114

```
Arg Ser Arg Thr Pro Ser Leu Pro Lys Ser Pro Ser Ser Ala Lys Ser
1               5                   10                  15

Arg Ser Lys Ile Gly Ser Thr Glu Cys
            20                  25
```

<210> SEQ ID NO 1115
<211> LENGTH: 25
<212> TYPE: PRT
<213> ORGANISM: Artificial Sequence
<220> FEATURE:
<223> OTHER INFORMATION: Synthetic construct

<400> SEQUENCE: 1115

```
Arg Ser Arg Thr Pro Ser Leu Pro Ser Pro Ser Ser Ala Lys Ser Arg
1               5                   10                  15

Ser Lys Ile Gly Ser Thr Glu Asn Cys
            20                  25
```

<210> SEQ ID NO 1116
<211> LENGTH: 25
<212> TYPE: PRT
<213> ORGANISM: Artificial Sequence
<220> FEATURE:
<223> OTHER INFORMATION: Synthetic construct

<400> SEQUENCE: 1116

Arg Ser Arg Thr Pro Ser Leu Pro Pro Ser Ser Ala Lys Ser Arg Ser
1 5 10 15

Lys Ile Gly Ser Thr Glu Asn Leu Cys
20 25

<210> SEQ ID NO 1117
<211> LENGTH: 26
<212> TYPE: PRT
<213> ORGANISM: Artificial Sequence
<220> FEATURE:
<223> OTHER INFORMATION: Synthetic construct

<400> SEQUENCE: 1117

Arg Ser Arg Thr Pro Ser Leu Pro Lys Ser Pro Ser Ser Ala Lys Ser
1 5 10 15

Arg Ser Lys Ile Gly Ser Thr Glu Asn Cys
20 25

<210> SEQ ID NO 1118
<211> LENGTH: 26
<212> TYPE: PRT
<213> ORGANISM: Artificial Sequence
<220> FEATURE:
<223> OTHER INFORMATION: Synthetic construct

<400> SEQUENCE: 1118

Arg Ser Arg Thr Pro Ser Leu Pro Ser Pro Ser Ser Ala Lys Ser Arg
1 5 10 15

Ser Lys Ile Gly Ser Thr Glu Asn Leu Cys
20 25

<210> SEQ ID NO 1119
<211> LENGTH: 27
<212> TYPE: PRT
<213> ORGANISM: Artificial Sequence
<220> FEATURE:
<223> OTHER INFORMATION: Synthetic construct

<400> SEQUENCE: 1119

Arg Ser Arg Thr Pro Ser Leu Pro Lys Ser Pro Ser Ser Ala Lys Ser
1 5 10 15

Arg Ser Lys Ile Gly Ser Thr Glu Asn Leu Cys
20 25

<210> SEQ ID NO 1120
<211> LENGTH: 23
<212> TYPE: PRT
<213> ORGANISM: Artificial Sequence
<220> FEATURE:
<223> OTHER INFORMATION: Synthetic construct

<400> SEQUENCE: 1120

Ser Arg Thr Pro Ser Leu Pro Thr Pro Ser Ser Ala Lys Ser Arg Ser
1 5 10 15

Lys Ile Gly Ser Thr Glu Cys

20

<210> SEQ ID NO 1121
<211> LENGTH: 24
<212> TYPE: PRT
<213> ORGANISM: Artificial Sequence
<220> FEATURE:
<223> OTHER INFORMATION: Synthetic construct

<400> SEQUENCE: 1121

Ser Arg Thr Pro Ser Leu Pro Thr Ser Pro Ser Ser Ala Lys Ser Arg
1 5 10 15

Ser Lys Ile Gly Ser Thr Glu Cys
20

<210> SEQ ID NO 1122
<211> LENGTH: 24
<212> TYPE: PRT
<213> ORGANISM: Artificial Sequence
<220> FEATURE:
<223> OTHER INFORMATION: Synthetic construct

<400> SEQUENCE: 1122

Ser Arg Thr Pro Ser Leu Pro Thr Pro Ser Ser Ala Lys Ser Arg Ser
1 5 10 15

Lys Ile Gly Ser Thr Glu Asn Cys
20

<210> SEQ ID NO 1123
<211> LENGTH: 25
<212> TYPE: PRT
<213> ORGANISM: Artificial Sequence
<220> FEATURE:
<223> OTHER INFORMATION: Synthetic construct

<400> SEQUENCE: 1123

Ser Arg Thr Pro Ser Leu Pro Thr Lys Ser Pro Ser Ser Ala Lys Ser
1 5 10 15

Arg Ser Lys Ile Gly Ser Thr Glu Cys
20 25

<210> SEQ ID NO 1124
<211> LENGTH: 25
<212> TYPE: PRT
<213> ORGANISM: Artificial Sequence
<220> FEATURE:
<223> OTHER INFORMATION: Synthetic construct

<400> SEQUENCE: 1124

Ser Arg Thr Pro Ser Leu Pro Thr Ser Pro Ser Ser Ala Lys Ser Arg
1 5 10 15

Ser Lys Ile Gly Ser Thr Glu Asn Cys
20 25

<210> SEQ ID NO 1125
<211> LENGTH: 25
<212> TYPE: PRT
<213> ORGANISM: Artificial Sequence
<220> FEATURE:
<223> OTHER INFORMATION: Synthetic construct

<400> SEQUENCE: 1125

Ser Arg Thr Pro Ser Leu Pro Thr Pro Ser Ser Ala Lys Ser Arg Ser
1 5 10 15

Lys Ile Gly Ser Thr Glu Asn Leu Cys
            20                  25

<210> SEQ ID NO 1126
<211> LENGTH: 26
<212> TYPE: PRT
<213> ORGANISM: Artificial Sequence
<220> FEATURE:
<223> OTHER INFORMATION: Synthetic construct

<400> SEQUENCE: 1126

Ser Arg Thr Pro Ser Leu Pro Thr Lys Ser Pro Ser Ser Ala Lys Ser
1               5                   10                  15

Arg Ser Lys Ile Gly Ser Thr Glu Asn Cys
            20                  25

<210> SEQ ID NO 1127
<211> LENGTH: 26
<212> TYPE: PRT
<213> ORGANISM: Artificial Sequence
<220> FEATURE:
<223> OTHER INFORMATION: Synthetic construct

<400> SEQUENCE: 1127

Ser Arg Thr Pro Ser Leu Pro Thr Ser Pro Ser Ser Ala Lys Ser Arg
1               5                   10                  15

Ser Lys Ile Gly Ser Thr Glu Asn Leu Cys
            20                  25

<210> SEQ ID NO 1128
<211> LENGTH: 27
<212> TYPE: PRT
<213> ORGANISM: Artificial Sequence
<220> FEATURE:
<223> OTHER INFORMATION: Synthetic construct

<400> SEQUENCE: 1128

Ser Arg Thr Pro Ser Leu Pro Thr Lys Ser Pro Ser Ser Ala Lys Ser
1               5                   10                  15

Arg Ser Lys Ile Gly Ser Thr Glu Asn Leu Cys
            20                  25

<210> SEQ ID NO 1129
<211> LENGTH: 24
<212> TYPE: PRT
<213> ORGANISM: Artificial Sequence
<220> FEATURE:
<223> OTHER INFORMATION: Synthetic construct

<400> SEQUENCE: 1129

Ser Arg Ser Arg Thr Pro Ser Leu Pro Pro Ser Ser Ala Lys Ser Arg
1               5                   10                  15

Ser Lys Ile Gly Ser Thr Glu Cys
            20

<210> SEQ ID NO 1130
<211> LENGTH: 25
<212> TYPE: PRT
<213> ORGANISM: Artificial Sequence
<220> FEATURE:
<223> OTHER INFORMATION: Synthetic construct

<400> SEQUENCE: 1130

Ser Arg Ser Arg Thr Pro Ser Leu Pro Ser Pro Ser Ser Ala Lys Ser
1               5                   10                  15

-continued

Arg Ser Lys Ile Gly Ser Thr Glu Cys
20 25

<210> SEQ ID NO 1131
<211> LENGTH: 25
<212> TYPE: PRT
<213> ORGANISM: Artificial Sequence
<220> FEATURE:
<223> OTHER INFORMATION: Synthetic construct

<400> SEQUENCE: 1131

Ser Arg Ser Arg Thr Pro Ser Leu Pro Pro Ser Ser Ala Lys Ser Arg
1 5 10 15

Ser Lys Ile Gly Ser Thr Glu Asn Cys
20 25

<210> SEQ ID NO 1132
<211> LENGTH: 26
<212> TYPE: PRT
<213> ORGANISM: Artificial Sequence
<220> FEATURE:
<223> OTHER INFORMATION: Synthetic construct

<400> SEQUENCE: 1132

Ser Arg Ser Arg Thr Pro Ser Leu Pro Lys Ser Pro Ser Ser Ala Lys
1 5 10 15

Ser Arg Ser Lys Ile Gly Ser Thr Glu Cys
20 25

<210> SEQ ID NO 1133
<211> LENGTH: 26
<212> TYPE: PRT
<213> ORGANISM: Artificial Sequence
<220> FEATURE:
<223> OTHER INFORMATION: Synthetic construct

<400> SEQUENCE: 1133

Ser Arg Ser Arg Thr Pro Ser Leu Pro Ser Pro Ser Ser Ala Lys Ser
1 5 10 15

Arg Ser Lys Ile Gly Ser Thr Glu Asn Cys
20 25

<210> SEQ ID NO 1134
<211> LENGTH: 26
<212> TYPE: PRT
<213> ORGANISM: Artificial Sequence
<220> FEATURE:
<223> OTHER INFORMATION: Synthetic construct

<400> SEQUENCE: 1134

Ser Arg Ser Arg Thr Pro Ser Leu Pro Pro Ser Ser Ala Lys Ser Arg
1 5 10 15

Ser Lys Ile Gly Ser Thr Glu Asn Leu Cys
20 25

<210> SEQ ID NO 1135
<211> LENGTH: 27
<212> TYPE: PRT
<213> ORGANISM: Artificial Sequence
<220> FEATURE:
<223> OTHER INFORMATION: Synthetic construct

<400> SEQUENCE: 1135

Ser Arg Ser Arg Thr Pro Ser Leu Pro Lys Ser Pro Ser Ser Ala Lys

```
1               5                   10                  15

Ser Arg Ser Lys Ile Gly Ser Thr Glu Asn Cys
            20                  25


<210> SEQ ID NO 1136
<211> LENGTH: 27
<212> TYPE: PRT
<213> ORGANISM: Artificial Sequence
<220> FEATURE:
<223> OTHER INFORMATION: Synthetic construct

<400> SEQUENCE: 1136

Ser Arg Ser Arg Thr Pro Ser Leu Pro Ser Pro Ser Ser Ala Lys Ser
1               5                   10                  15

Arg Ser Lys Ile Gly Ser Thr Glu Asn Leu Cys
            20                  25


<210> SEQ ID NO 1137
<211> LENGTH: 28
<212> TYPE: PRT
<213> ORGANISM: Artificial Sequence
<220> FEATURE:
<223> OTHER INFORMATION: Synthetic construct

<400> SEQUENCE: 1137

Ser Arg Ser Arg Thr Pro Ser Leu Pro Lys Ser Pro Ser Ser Ala Lys
1               5                   10                  15

Ser Arg Ser Lys Ile Gly Ser Thr Glu Asn Leu Cys
            20                  25


<210> SEQ ID NO 1138
<211> LENGTH: 24
<212> TYPE: PRT
<213> ORGANISM: Artificial Sequence
<220> FEATURE:
<223> OTHER INFORMATION: Synthetic construct

<400> SEQUENCE: 1138

Arg Ser Arg Thr Pro Ser Leu Pro Thr Pro Ser Ser Ala Lys Ser Arg
1               5                   10                  15

Ser Lys Ile Gly Ser Thr Glu Cys
            20


<210> SEQ ID NO 1139
<211> LENGTH: 25
<212> TYPE: PRT
<213> ORGANISM: Artificial Sequence
<220> FEATURE:
<223> OTHER INFORMATION: Synthetic construct

<400> SEQUENCE: 1139

Arg Ser Arg Thr Pro Ser Leu Pro Thr Ser Pro Ser Ser Ala Lys Ser
1               5                   10                  15

Arg Ser Lys Ile Gly Ser Thr Glu Cys
            20                  25


<210> SEQ ID NO 1140
<211> LENGTH: 25
<212> TYPE: PRT
<213> ORGANISM: Artificial Sequence
<220> FEATURE:
<223> OTHER INFORMATION: Synthetic construct

<400> SEQUENCE: 1140
```

Arg Ser Arg Thr Pro Ser Leu Pro Thr Pro Ser Ser Ala Lys Ser Arg
1 5 10 15

Ser Lys Ile Gly Ser Thr Glu Asn Cys
20 25

<210> SEQ ID NO 1141
<211> LENGTH: 26
<212> TYPE: PRT
<213> ORGANISM: Artificial Sequence
<220> FEATURE:
<223> OTHER INFORMATION: Synthetic construct

<400> SEQUENCE: 1141

Arg Ser Arg Thr Pro Ser Leu Pro Thr Lys Ser Pro Ser Ser Ala Lys
1 5 10 15

Ser Arg Ser Lys Ile Gly Ser Thr Glu Cys
20 25

<210> SEQ ID NO 1142
<211> LENGTH: 26
<212> TYPE: PRT
<213> ORGANISM: Artificial Sequence
<220> FEATURE:
<223> OTHER INFORMATION: Synthetic construct

<400> SEQUENCE: 1142

Arg Ser Arg Thr Pro Ser Leu Pro Thr Ser Pro Ser Ser Ala Lys Ser
1 5 10 15

Arg Ser Lys Ile Gly Ser Thr Glu Asn Cys
20 25

<210> SEQ ID NO 1143
<211> LENGTH: 26
<212> TYPE: PRT
<213> ORGANISM: Artificial Sequence
<220> FEATURE:
<223> OTHER INFORMATION: Synthetic construct

<400> SEQUENCE: 1143

Arg Ser Arg Thr Pro Ser Leu Pro Thr Pro Ser Ser Ala Lys Ser Arg
1 5 10 15

Ser Lys Ile Gly Ser Thr Glu Asn Leu Cys
20 25

<210> SEQ ID NO 1144
<211> LENGTH: 27
<212> TYPE: PRT
<213> ORGANISM: Artificial Sequence
<220> FEATURE:
<223> OTHER INFORMATION: Synthetic construct

<400> SEQUENCE: 1144

Arg Ser Arg Thr Pro Ser Leu Pro Thr Lys Ser Pro Ser Ser Ala Lys
1 5 10 15

Ser Arg Ser Lys Ile Gly Ser Thr Glu Asn Cys
20 25

<210> SEQ ID NO 1145
<211> LENGTH: 27
<212> TYPE: PRT
<213> ORGANISM: Artificial Sequence
<220> FEATURE:
<223> OTHER INFORMATION: Synthetic construct

<400> SEQUENCE: 1145

Arg Ser Arg Thr Pro Ser Leu Pro Thr Ser Pro Ser Ser Ala Lys Ser
1 5 10 15

Arg Ser Lys Ile Gly Ser Thr Glu Asn Leu Cys
20 25

<210> SEQ ID NO 1146
<211> LENGTH: 28
<212> TYPE: PRT
<213> ORGANISM: Artificial Sequence
<220> FEATURE:
<223> OTHER INFORMATION: Synthetic construct

<400> SEQUENCE: 1146

Arg Ser Arg Thr Pro Ser Leu Pro Thr Lys Ser Pro Ser Ser Ala Lys
1 5 10 15

Ser Arg Ser Lys Ile Gly Ser Thr Glu Asn Leu Cys
20 25

<210> SEQ ID NO 1147
<211> LENGTH: 24
<212> TYPE: PRT
<213> ORGANISM: Artificial Sequence
<220> FEATURE:
<223> OTHER INFORMATION: Synthetic construct

<400> SEQUENCE: 1147

Ser Arg Thr Pro Ser Leu Pro Thr Pro Pro Ser Ser Ala Lys Ser Arg
1 5 10 15

Ser Lys Ile Gly Ser Thr Glu Cys
20

<210> SEQ ID NO 1148
<211> LENGTH: 25
<212> TYPE: PRT
<213> ORGANISM: Artificial Sequence
<220> FEATURE:
<223> OTHER INFORMATION: Synthetic construct

<400> SEQUENCE: 1148

Ser Arg Thr Pro Ser Leu Pro Thr Pro Ser Pro Ser Ser Ala Lys Ser
1 5 10 15

Arg Ser Lys Ile Gly Ser Thr Glu Cys
20 25

<210> SEQ ID NO 1149
<211> LENGTH: 25
<212> TYPE: PRT
<213> ORGANISM: Artificial Sequence
<220> FEATURE:
<223> OTHER INFORMATION: Synthetic construct

<400> SEQUENCE: 1149

Ser Arg Thr Pro Ser Leu Pro Thr Pro Pro Ser Ser Ala Lys Ser Arg
1 5 10 15

Ser Lys Ile Gly Ser Thr Glu Asn Cys
20 25

<210> SEQ ID NO 1150
<211> LENGTH: 26
<212> TYPE: PRT
<213> ORGANISM: Artificial Sequence
<220> FEATURE:
<223> OTHER INFORMATION: Synthetic construct

<400> SEQUENCE: 1150

Ser Arg Thr Pro Ser Leu Pro Thr Pro Lys Ser Pro Ser Ser Ala Lys
1 5 10 15

Ser Arg Ser Lys Ile Gly Ser Thr Glu Cys
20 25

<210> SEQ ID NO 1151
<211> LENGTH: 26
<212> TYPE: PRT
<213> ORGANISM: Artificial Sequence
<220> FEATURE:
<223> OTHER INFORMATION: Synthetic construct

<400> SEQUENCE: 1151

Ser Arg Thr Pro Ser Leu Pro Thr Pro Ser Pro Ser Ser Ala Lys Ser
1 5 10 15

Arg Ser Lys Ile Gly Ser Thr Glu Asn Cys
20 25

<210> SEQ ID NO 1152
<211> LENGTH: 26
<212> TYPE: PRT
<213> ORGANISM: Artificial Sequence
<220> FEATURE:
<223> OTHER INFORMATION: Synthetic construct

<400> SEQUENCE: 1152

Ser Arg Thr Pro Ser Leu Pro Thr Pro Pro Ser Ser Ala Lys Ser Arg
1 5 10 15

Ser Lys Ile Gly Ser Thr Glu Asn Leu Cys
20 25

<210> SEQ ID NO 1153
<211> LENGTH: 27
<212> TYPE: PRT
<213> ORGANISM: Artificial Sequence
<220> FEATURE:
<223> OTHER INFORMATION: Synthetic construct

<400> SEQUENCE: 1153

Ser Arg Thr Pro Ser Leu Pro Thr Pro Lys Ser Pro Ser Ser Ala Lys
1 5 10 15

Ser Arg Ser Lys Ile Gly Ser Thr Glu Asn Cys
20 25

<210> SEQ ID NO 1154
<211> LENGTH: 27
<212> TYPE: PRT
<213> ORGANISM: Artificial Sequence
<220> FEATURE:
<223> OTHER INFORMATION: Synthetic construct

<400> SEQUENCE: 1154

Ser Arg Thr Pro Ser Leu Pro Thr Pro Ser Pro Ser Ser Ala Lys Ser
1 5 10 15

Arg Ser Lys Ile Gly Ser Thr Glu Asn Leu Cys
20 25

<210> SEQ ID NO 1155
<211> LENGTH: 28
<212> TYPE: PRT
<213> ORGANISM: Artificial Sequence
<220> FEATURE:
<223> OTHER INFORMATION: Synthetic construct

<400> SEQUENCE: 1155

Ser Arg Thr Pro Ser Leu Pro Thr Pro Lys Ser Pro Ser Ser Ala Lys
1 5 10 15

Ser Arg Ser Lys Ile Gly Ser Thr Glu Asn Leu Cys
20 25

<210> SEQ ID NO 1156
<211> LENGTH: 25
<212> TYPE: PRT
<213> ORGANISM: Artificial Sequence
<220> FEATURE:
<223> OTHER INFORMATION: Synthetic construct

<400> SEQUENCE: 1156

Ser Arg Ser Arg Thr Pro Ser Leu Pro Thr Pro Ser Ser Ala Lys Ser
1 5 10 15

Arg Ser Lys Ile Gly Ser Thr Glu Cys
20 25

<210> SEQ ID NO 1157
<211> LENGTH: 26
<212> TYPE: PRT
<213> ORGANISM: Artificial Sequence
<220> FEATURE:
<223> OTHER INFORMATION: Synthetic construct

<400> SEQUENCE: 1157

Ser Arg Ser Arg Thr Pro Ser Leu Pro Thr Ser Pro Ser Ser Ala Lys
1 5 10 15

Ser Arg Ser Lys Ile Gly Ser Thr Glu Cys
20 25

<210> SEQ ID NO 1158
<211> LENGTH: 26
<212> TYPE: PRT
<213> ORGANISM: Artificial Sequence
<220> FEATURE:
<223> OTHER INFORMATION: Synthetic construct

<400> SEQUENCE: 1158

Ser Arg Ser Arg Thr Pro Ser Leu Pro Thr Pro Ser Ser Ala Lys Ser
1 5 10 15

Arg Ser Lys Ile Gly Ser Thr Glu Asn Cys
20 25

<210> SEQ ID NO 1159
<211> LENGTH: 27
<212> TYPE: PRT
<213> ORGANISM: Artificial Sequence
<220> FEATURE:
<223> OTHER INFORMATION: Synthetic construct

<400> SEQUENCE: 1159

Ser Arg Ser Arg Thr Pro Ser Leu Pro Thr Lys Ser Pro Ser Ser Ala
1 5 10 15

Lys Ser Arg Ser Lys Ile Gly Ser Thr Glu Cys
20 25

<210> SEQ ID NO 1160
<211> LENGTH: 27
<212> TYPE: PRT
<213> ORGANISM: Artificial Sequence
<220> FEATURE:

<223> OTHER INFORMATION: Synthetic construct

<400> SEQUENCE: 1160

Ser Arg Ser Arg Thr Pro Ser Leu Pro Thr Ser Pro Ser Ser Ala Lys
1 5 10 15

Ser Arg Ser Lys Ile Gly Ser Thr Glu Asn Cys
20 25

<210> SEQ ID NO 1161
<211> LENGTH: 27
<212> TYPE: PRT
<213> ORGANISM: Artificial Sequence
<220> FEATURE:
<223> OTHER INFORMATION: Synthetic construct

<400> SEQUENCE: 1161

Ser Arg Ser Arg Thr Pro Ser Leu Pro Thr Pro Ser Ser Ala Lys Ser
1 5 10 15

Arg Ser Lys Ile Gly Ser Thr Glu Asn Leu Cys
20 25

<210> SEQ ID NO 1162
<211> LENGTH: 28
<212> TYPE: PRT
<213> ORGANISM: Artificial Sequence
<220> FEATURE:
<223> OTHER INFORMATION: Synthetic construct

<400> SEQUENCE: 1162

Ser Arg Ser Arg Thr Pro Ser Leu Pro Thr Lys Ser Pro Ser Ser Ala
1 5 10 15

Lys Ser Arg Ser Lys Ile Gly Ser Thr Glu Asn Cys
20 25

<210> SEQ ID NO 1163
<211> LENGTH: 28
<212> TYPE: PRT
<213> ORGANISM: Artificial Sequence
<220> FEATURE:
<223> OTHER INFORMATION: Synthetic construct

<400> SEQUENCE: 1163

Ser Arg Ser Arg Thr Pro Ser Leu Pro Thr Ser Pro Ser Ser Ala Lys
1 5 10 15

Ser Arg Ser Lys Ile Gly Ser Thr Glu Asn Leu Cys
20 25

<210> SEQ ID NO 1164
<211> LENGTH: 29
<212> TYPE: PRT
<213> ORGANISM: Artificial Sequence
<220> FEATURE:
<223> OTHER INFORMATION: Synthetic construct

<400> SEQUENCE: 1164

Ser Arg Ser Arg Thr Pro Ser Leu Pro Thr Lys Ser Pro Ser Ser Ala
1 5 10 15

Lys Ser Arg Ser Lys Ile Gly Ser Thr Glu Asn Leu Cys
20 25

<210> SEQ ID NO 1165
<211> LENGTH: 25
<212> TYPE: PRT
<213> ORGANISM: Artificial Sequence
<220> FEATURE:
<223> OTHER INFORMATION: Synthetic construct

<400> SEQUENCE: 1165

```
Arg Ser Arg Thr Pro Ser Leu Pro Thr Pro Pro Ser Ser Ala Lys Ser
1               5                   10                  15

Arg Ser Lys Ile Gly Ser Thr Glu Cys
            20                  25
```

<210> SEQ ID NO 1166
<211> LENGTH: 26
<212> TYPE: PRT
<213> ORGANISM: Artificial Sequence
<220> FEATURE:
<223> OTHER INFORMATION: Synthetic construct

<400> SEQUENCE: 1166

```
Arg Ser Arg Thr Pro Ser Leu Pro Thr Pro Ser Pro Ser Ser Ala Lys
1               5                   10                  15

Ser Arg Ser Lys Ile Gly Ser Thr Glu Cys
            20                  25
```

<210> SEQ ID NO 1167
<211> LENGTH: 26
<212> TYPE: PRT
<213> ORGANISM: Artificial Sequence
<220> FEATURE:
<223> OTHER INFORMATION: Synthetic construct

<400> SEQUENCE: 1167

```
Arg Ser Arg Thr Pro Ser Leu Pro Thr Pro Pro Ser Ser Ala Lys Ser
1               5                   10                  15

Arg Ser Lys Ile Gly Ser Thr Glu Asn Cys
            20                  25
```

<210> SEQ ID NO 1168
<211> LENGTH: 27
<212> TYPE: PRT
<213> ORGANISM: Artificial Sequence
<220> FEATURE:
<223> OTHER INFORMATION: Synthetic construct

<400> SEQUENCE: 1168

```
Arg Ser Arg Thr Pro Ser Leu Pro Thr Pro Lys Ser Pro Ser Ser Ala
1               5                   10                  15

Lys Ser Arg Ser Lys Ile Gly Ser Thr Glu Cys
            20                  25
```

<210> SEQ ID NO 1169
<211> LENGTH: 27
<212> TYPE: PRT
<213> ORGANISM: Artificial Sequence
<220> FEATURE:
<223> OTHER INFORMATION: Synthetic construct

<400> SEQUENCE: 1169

```
Arg Ser Arg Thr Pro Ser Leu Pro Thr Pro Ser Pro Ser Ser Ala Lys
1               5                   10                  15

Ser Arg Ser Lys Ile Gly Ser Thr Glu Asn Cys
            20                  25
```

<210> SEQ ID NO 1170
<211> LENGTH: 27
<212> TYPE: PRT

<213> ORGANISM: Artificial Sequence
<220> FEATURE:
<223> OTHER INFORMATION: Synthetic construct

<400> SEQUENCE: 1170

Arg Ser Arg Thr Pro Ser Leu Pro Thr Pro Pro Ser Ser Ala Lys Ser
1 5 10 15

Arg Ser Lys Ile Gly Ser Thr Glu Asn Leu Cys
20 25

<210> SEQ ID NO 1171
<211> LENGTH: 28
<212> TYPE: PRT
<213> ORGANISM: Artificial Sequence
<220> FEATURE:
<223> OTHER INFORMATION: Synthetic construct

<400> SEQUENCE: 1171

Arg Ser Arg Thr Pro Ser Leu Pro Thr Pro Lys Ser Pro Ser Ser Ala
1 5 10 15

Lys Ser Arg Ser Lys Ile Gly Ser Thr Glu Asn Cys
20 25

<210> SEQ ID NO 1172
<211> LENGTH: 28
<212> TYPE: PRT
<213> ORGANISM: Artificial Sequence
<220> FEATURE:
<223> OTHER INFORMATION: Synthetic construct

<400> SEQUENCE: 1172

Arg Ser Arg Thr Pro Ser Leu Pro Thr Pro Ser Pro Ser Ser Ala Lys
1 5 10 15

Ser Arg Ser Lys Ile Gly Ser Thr Glu Asn Leu Cys
20 25

<210> SEQ ID NO 1173
<211> LENGTH: 29
<212> TYPE: PRT
<213> ORGANISM: Artificial Sequence
<220> FEATURE:
<223> OTHER INFORMATION: Synthetic construct

<400> SEQUENCE: 1173

Arg Ser Arg Thr Pro Ser Leu Pro Thr Pro Lys Ser Pro Ser Ser Ala
1 5 10 15

Lys Ser Arg Ser Lys Ile Gly Ser Thr Glu Asn Leu Cys
20 25

<210> SEQ ID NO 1174
<211> LENGTH: 26
<212> TYPE: PRT
<213> ORGANISM: Artificial Sequence
<220> FEATURE:
<223> OTHER INFORMATION: Synthetic construct

<400> SEQUENCE: 1174

Ser Arg Ser Arg Thr Pro Ser Leu Pro Thr Pro Pro Ser Ser Ala Lys
1 5 10 15

Ser Arg Ser Lys Ile Gly Ser Thr Glu Cys
20 25

<210> SEQ ID NO 1175
<211> LENGTH: 27

<212> TYPE: PRT
<213> ORGANISM: Artificial Sequence
<220> FEATURE:
<223> OTHER INFORMATION: Synthetic construct

<400> SEQUENCE: 1175

Ser Arg Ser Arg Thr Pro Ser Leu Pro Thr Pro Ser Pro Ser Ser Ala
1               5                   10                  15

Lys Ser Arg Ser Lys Ile Gly Ser Thr Glu Cys
            20                  25

<210> SEQ ID NO 1176
<211> LENGTH: 27
<212> TYPE: PRT
<213> ORGANISM: Artificial Sequence
<220> FEATURE:
<223> OTHER INFORMATION: Synthetic construct

<400> SEQUENCE: 1176

Ser Arg Ser Arg Thr Pro Ser Leu Pro Thr Pro Pro Ser Ser Ala Lys
1               5                   10                  15

Ser Arg Ser Lys Ile Gly Ser Thr Glu Asn Cys
            20                  25

<210> SEQ ID NO 1177
<211> LENGTH: 28
<212> TYPE: PRT
<213> ORGANISM: Artificial Sequence
<220> FEATURE:
<223> OTHER INFORMATION: Synthetic construct

<400> SEQUENCE: 1177

Ser Arg Ser Arg Thr Pro Ser Leu Pro Thr Pro Lys Ser Pro Ser Ser
1               5                   10                  15

Ala Lys Ser Arg Ser Lys Ile Gly Ser Thr Glu Cys
            20                  25

<210> SEQ ID NO 1178
<211> LENGTH: 28
<212> TYPE: PRT
<213> ORGANISM: Artificial Sequence
<220> FEATURE:
<223> OTHER INFORMATION: Synthetic construct

<400> SEQUENCE: 1178

Ser Arg Ser Arg Thr Pro Ser Leu Pro Thr Pro Ser Pro Ser Ser Ala
1               5                   10                  15

Lys Ser Arg Ser Lys Ile Gly Ser Thr Glu Asn Cys
            20                  25

<210> SEQ ID NO 1179
<211> LENGTH: 28
<212> TYPE: PRT
<213> ORGANISM: Artificial Sequence
<220> FEATURE:
<223> OTHER INFORMATION: Synthetic construct

<400> SEQUENCE: 1179

Ser Arg Ser Arg Thr Pro Ser Leu Pro Thr Pro Pro Ser Ser Ala Lys
1               5                   10                  15

Ser Arg Ser Lys Ile Gly Ser Thr Glu Asn Leu Cys
            20                  25

<210> SEQ ID NO 1180

<211> LENGTH: 29
<212> TYPE: PRT
<213> ORGANISM: Artificial Sequence
<220> FEATURE:
<223> OTHER INFORMATION: Synthetic construct

<400> SEQUENCE: 1180

Ser Arg Ser Arg Thr Pro Ser Leu Pro Thr Pro Lys Ser Pro Ser Ser
1               5                   10                  15

Ala Lys Ser Arg Ser Lys Ile Gly Ser Thr Glu Asn Cys
            20                  25

<210> SEQ ID NO 1181
<211> LENGTH: 29
<212> TYPE: PRT
<213> ORGANISM: Artificial Sequence
<220> FEATURE:
<223> OTHER INFORMATION: Synthetic construct

<400> SEQUENCE: 1181

Ser Arg Ser Arg Thr Pro Ser Leu Pro Thr Pro Ser Pro Ser Ser Ala
1               5                   10                  15

Lys Ser Arg Ser Lys Ile Gly Ser Thr Glu Asn Leu Cys
            20                  25

<210> SEQ ID NO 1182
<211> LENGTH: 30
<212> TYPE: PRT
<213> ORGANISM: Artificial Sequence
<220> FEATURE:
<223> OTHER INFORMATION: Synthetic construct

<400> SEQUENCE: 1182

Ser Arg Ser Arg Thr Pro Ser Leu Pro Thr Pro Lys Ser Pro Ser Ser
1               5                   10                  15

Ala Lys Ser Arg Ser Lys Ile Gly Ser Thr Glu Asn Leu Cys
            20                  25                  30

<210> SEQ ID NO 1183
<211> LENGTH: 20
<212> TYPE: PRT
<213> ORGANISM: Artificial Sequence
<220> FEATURE:
<223> OTHER INFORMATION: Synthetic construct

<400> SEQUENCE: 1183

Ser Arg Thr Pro Ser Leu Pro Lys Ser Pro Val Val Ser Gly Asp Thr
1               5                   10                  15

Ser Pro Arg Cys
            20

<210> SEQ ID NO 1184
<211> LENGTH: 21
<212> TYPE: PRT
<213> ORGANISM: Artificial Sequence
<220> FEATURE:
<223> OTHER INFORMATION: Synthetic construct

<400> SEQUENCE: 1184

Ser Arg Thr Pro Ser Leu Pro Tyr Lys Ser Pro Val Val Ser Gly Asp
1               5                   10                  15

Thr Ser Pro Arg Cys
            20

-continued

<210> SEQ ID NO 1185
<211> LENGTH: 22
<212> TYPE: PRT
<213> ORGANISM: Artificial Sequence
<220> FEATURE:
<223> OTHER INFORMATION: Synthetic construct

<400> SEQUENCE: 1185

```
Ser Arg Thr Pro Ser Leu Pro Val Tyr Lys Ser Pro Val Val Ser Gly
1               5                   10                  15

Asp Thr Ser Pro Arg Cys
            20
```

<210> SEQ ID NO 1186
<211> LENGTH: 22
<212> TYPE: PRT
<213> ORGANISM: Artificial Sequence
<220> FEATURE:
<223> OTHER INFORMATION: Synthetic construct

<400> SEQUENCE: 1186

```
Ser Arg Thr Pro Ser Leu Pro Tyr Lys Ser Pro Val Val Ser Gly Asp
1               5                   10                  15

Thr Ser Pro Arg His Cys
            20
```

<210> SEQ ID NO 1187
<211> LENGTH: 23
<212> TYPE: PRT
<213> ORGANISM: Artificial Sequence
<220> FEATURE:
<223> OTHER INFORMATION: Synthetic construct

<400> SEQUENCE: 1187

```
Ser Arg Thr Pro Ser Leu Pro Ile Val Tyr Lys Ser Pro Val Val Ser
1               5                   10                  15

Gly Asp Thr Ser Pro Arg Cys
            20
```

<210> SEQ ID NO 1188
<211> LENGTH: 23
<212> TYPE: PRT
<213> ORGANISM: Artificial Sequence
<220> FEATURE:
<223> OTHER INFORMATION: Synthetic construct

<400> SEQUENCE: 1188

```
Ser Arg Thr Pro Ser Leu Pro Val Tyr Lys Ser Pro Val Val Ser Gly
1               5                   10                  15

Asp Thr Ser Pro Arg His Cys
            20
```

<210> SEQ ID NO 1189
<211> LENGTH: 23
<212> TYPE: PRT
<213> ORGANISM: Artificial Sequence
<220> FEATURE:
<223> OTHER INFORMATION: Synthetic construct

<400> SEQUENCE: 1189

```
Ser Arg Thr Pro Ser Leu Pro Tyr Lys Ser Pro Val Val Ser Gly Asp
1               5                   10                  15

Thr Ser Pro Arg His Leu Cys
            20
```

<210> SEQ ID NO 1190
<211> LENGTH: 24
<212> TYPE: PRT
<213> ORGANISM: Artificial Sequence
<220> FEATURE:
<223> OTHER INFORMATION: Synthetic construct

<400> SEQUENCE: 1190

Ser Arg Thr Pro Ser Leu Pro Ile Val Tyr Lys Ser Pro Val Val Ser
1 5 10 15

Gly Asp Thr Ser Pro Arg His Cys
20

<210> SEQ ID NO 1191
<211> LENGTH: 24
<212> TYPE: PRT
<213> ORGANISM: Artificial Sequence
<220> FEATURE:
<223> OTHER INFORMATION: Synthetic construct

<400> SEQUENCE: 1191

Ser Arg Thr Pro Ser Leu Pro Val Tyr Lys Ser Pro Val Val Ser Gly
1 5 10 15

Asp Thr Ser Pro Arg His Leu Cys
20

<210> SEQ ID NO 1192
<211> LENGTH: 25
<212> TYPE: PRT
<213> ORGANISM: Artificial Sequence
<220> FEATURE:
<223> OTHER INFORMATION: Synthetic construct

<400> SEQUENCE: 1192

Ser Arg Thr Pro Ser Leu Pro Ile Val Tyr Lys Ser Pro Val Val Ser
1 5 10 15

Gly Asp Thr Ser Pro Arg His Leu Cys
20 25

<210> SEQ ID NO 1193
<211> LENGTH: 21
<212> TYPE: PRT
<213> ORGANISM: Artificial Sequence
<220> FEATURE:
<223> OTHER INFORMATION: Synthetic construct

<400> SEQUENCE: 1193

Arg Ser Arg Thr Pro Ser Leu Pro Lys Ser Pro Val Val Ser Gly Asp
1 5 10 15

Thr Ser Pro Arg Cys
20

<210> SEQ ID NO 1194
<211> LENGTH: 22
<212> TYPE: PRT
<213> ORGANISM: Artificial Sequence
<220> FEATURE:
<223> OTHER INFORMATION: Synthetic construct

<400> SEQUENCE: 1194

Arg Ser Arg Thr Pro Ser Leu Pro Tyr Lys Ser Pro Val Val Ser Gly
1 5 10 15

Asp Thr Ser Pro Arg Cys
20

<210> SEQ ID NO 1195
<211> LENGTH: 23
<212> TYPE: PRT
<213> ORGANISM: Artificial Sequence
<220> FEATURE:
<223> OTHER INFORMATION: Synthetic construct

<400> SEQUENCE: 1195

Arg Ser Arg Thr Pro Ser Leu Pro Val Tyr Lys Ser Pro Val Val Ser
1               5                   10                  15

Gly Asp Thr Ser Pro Arg Cys
            20

<210> SEQ ID NO 1196
<211> LENGTH: 23
<212> TYPE: PRT
<213> ORGANISM: Artificial Sequence
<220> FEATURE:
<223> OTHER INFORMATION: Synthetic construct

<400> SEQUENCE: 1196

Arg Ser Arg Thr Pro Ser Leu Pro Tyr Lys Ser Pro Val Val Ser Gly
1               5                   10                  15

Asp Thr Ser Pro Arg His Cys
            20

<210> SEQ ID NO 1197
<211> LENGTH: 24
<212> TYPE: PRT
<213> ORGANISM: Artificial Sequence
<220> FEATURE:
<223> OTHER INFORMATION: Synthetic construct

<400> SEQUENCE: 1197

Arg Ser Arg Thr Pro Ser Leu Pro Ile Val Tyr Lys Ser Pro Val Val
1               5                   10                  15

Ser Gly Asp Thr Ser Pro Arg Cys
            20

<210> SEQ ID NO 1198
<211> LENGTH: 24
<212> TYPE: PRT
<213> ORGANISM: Artificial Sequence
<220> FEATURE:
<223> OTHER INFORMATION: Synthetic construct

<400> SEQUENCE: 1198

Arg Ser Arg Thr Pro Ser Leu Pro Val Tyr Lys Ser Pro Val Val Ser
1               5                   10                  15

Gly Asp Thr Ser Pro Arg His Cys
            20

<210> SEQ ID NO 1199
<211> LENGTH: 24
<212> TYPE: PRT
<213> ORGANISM: Artificial Sequence
<220> FEATURE:
<223> OTHER INFORMATION: Synthetic construct

<400> SEQUENCE: 1199

Arg Ser Arg Thr Pro Ser Leu Pro Tyr Lys Ser Pro Val Val Ser Gly
1               5                   10                  15

Asp Thr Ser Pro Arg His Leu Cys

20

<210> SEQ ID NO 1200
<211> LENGTH: 25
<212> TYPE: PRT
<213> ORGANISM: Artificial Sequence
<220> FEATURE:
<223> OTHER INFORMATION: Synthetic construct

<400> SEQUENCE: 1200

Arg Ser Arg Thr Pro Ser Leu Pro Ile Val Tyr Lys Ser Pro Val Val
1 5 10 15

Ser Gly Asp Thr Ser Pro Arg His Cys
20 25

<210> SEQ ID NO 1201
<211> LENGTH: 25
<212> TYPE: PRT
<213> ORGANISM: Artificial Sequence
<220> FEATURE:
<223> OTHER INFORMATION: Synthetic construct

<400> SEQUENCE: 1201

Arg Ser Arg Thr Pro Ser Leu Pro Val Tyr Lys Ser Pro Val Val Ser
1 5 10 15

Gly Asp Thr Ser Pro Arg His Leu Cys
20 25

<210> SEQ ID NO 1202
<211> LENGTH: 26
<212> TYPE: PRT
<213> ORGANISM: Artificial Sequence
<220> FEATURE:
<223> OTHER INFORMATION: Synthetic construct

<400> SEQUENCE: 1202

Arg Ser Arg Thr Pro Ser Leu Pro Ile Val Tyr Lys Ser Pro Val Val
1 5 10 15

Ser Gly Asp Thr Ser Pro Arg His Leu Cys
20 25

<210> SEQ ID NO 1203
<211> LENGTH: 21
<212> TYPE: PRT
<213> ORGANISM: Artificial Sequence
<220> FEATURE:
<223> OTHER INFORMATION: Synthetic construct

<400> SEQUENCE: 1203

Ser Arg Thr Pro Ser Leu Pro Thr Lys Ser Pro Val Val Ser Gly Asp
1 5 10 15

Thr Ser Pro Arg Cys
20

<210> SEQ ID NO 1204
<211> LENGTH: 22
<212> TYPE: PRT
<213> ORGANISM: Artificial Sequence
<220> FEATURE:
<223> OTHER INFORMATION: Synthetic construct

<400> SEQUENCE: 1204

Ser Arg Thr Pro Ser Leu Pro Thr Tyr Lys Ser Pro Val Val Ser Gly
1 5 10 15

Asp Thr Ser Pro Arg Cys
20

<210> SEQ ID NO 1205
<211> LENGTH: 23
<212> TYPE: PRT
<213> ORGANISM: Artificial Sequence
<220> FEATURE:
<223> OTHER INFORMATION: Synthetic construct

<400> SEQUENCE: 1205

Ser Arg Thr Pro Ser Leu Pro Thr Val Tyr Lys Ser Pro Val Val Ser
1 5 10 15

Gly Asp Thr Ser Pro Arg Cys
20

<210> SEQ ID NO 1206
<211> LENGTH: 23
<212> TYPE: PRT
<213> ORGANISM: Artificial Sequence
<220> FEATURE:
<223> OTHER INFORMATION: Synthetic construct

<400> SEQUENCE: 1206

Ser Arg Thr Pro Ser Leu Pro Thr Tyr Lys Ser Pro Val Val Ser Gly
1 5 10 15

Asp Thr Ser Pro Arg His Cys
20

<210> SEQ ID NO 1207
<211> LENGTH: 24
<212> TYPE: PRT
<213> ORGANISM: Artificial Sequence
<220> FEATURE:
<223> OTHER INFORMATION: Synthetic construct

<400> SEQUENCE: 1207

Ser Arg Thr Pro Ser Leu Pro Thr Ile Val Tyr Lys Ser Pro Val Val
1 5 10 15

Ser Gly Asp Thr Ser Pro Arg Cys
20

<210> SEQ ID NO 1208
<211> LENGTH: 24
<212> TYPE: PRT
<213> ORGANISM: Artificial Sequence
<220> FEATURE:
<223> OTHER INFORMATION: Synthetic construct

<400> SEQUENCE: 1208

Ser Arg Thr Pro Ser Leu Pro Thr Val Tyr Lys Ser Pro Val Val Ser
1 5 10 15

Gly Asp Thr Ser Pro Arg His Cys
20

<210> SEQ ID NO 1209
<211> LENGTH: 24
<212> TYPE: PRT
<213> ORGANISM: Artificial Sequence
<220> FEATURE:
<223> OTHER INFORMATION: Synthetic construct

<400> SEQUENCE: 1209

Ser Arg Thr Pro Ser Leu Pro Thr Tyr Lys Ser Pro Val Val Ser Gly
1 5 10 15

Asp Thr Ser Pro Arg His Leu Cys
20

<210> SEQ ID NO 1210
<211> LENGTH: 25
<212> TYPE: PRT
<213> ORGANISM: Artificial Sequence
<220> FEATURE:
<223> OTHER INFORMATION: Synthetic construct

<400> SEQUENCE: 1210

Ser Arg Thr Pro Ser Leu Pro Thr Ile Val Tyr Lys Ser Pro Val Val
1 5 10 15

Ser Gly Asp Thr Ser Pro Arg His Cys
20 25

<210> SEQ ID NO 1211
<211> LENGTH: 25
<212> TYPE: PRT
<213> ORGANISM: Artificial Sequence
<220> FEATURE:
<223> OTHER INFORMATION: Synthetic construct

<400> SEQUENCE: 1211

Ser Arg Thr Pro Ser Leu Pro Thr Val Tyr Lys Ser Pro Val Val Ser
1 5 10 15

Gly Asp Thr Ser Pro Arg His Leu Cys
20 25

<210> SEQ ID NO 1212
<211> LENGTH: 26
<212> TYPE: PRT
<213> ORGANISM: Artificial Sequence
<220> FEATURE:
<223> OTHER INFORMATION: Synthetic construct

<400> SEQUENCE: 1212

Ser Arg Thr Pro Ser Leu Pro Thr Ile Val Tyr Lys Ser Pro Val Val
1 5 10 15

Ser Gly Asp Thr Ser Pro Arg His Leu Cys
20 25

<210> SEQ ID NO 1213
<211> LENGTH: 22
<212> TYPE: PRT
<213> ORGANISM: Artificial Sequence
<220> FEATURE:
<223> OTHER INFORMATION: Synthetic construct

<400> SEQUENCE: 1213

Ser Arg Ser Arg Thr Pro Ser Leu Pro Lys Ser Pro Val Val Ser Gly
1 5 10 15

Asp Thr Ser Pro Arg Cys
20

<210> SEQ ID NO 1214
<211> LENGTH: 23
<212> TYPE: PRT
<213> ORGANISM: Artificial Sequence
<220> FEATURE:
<223> OTHER INFORMATION: Synthetic construct

<400> SEQUENCE: 1214

Ser Arg Ser Arg Thr Pro Ser Leu Pro Tyr Lys Ser Pro Val Val Ser 1 5 10 15

Gly Asp Thr Ser Pro Arg Cys
20

<210> SEQ ID NO 1215
<211> LENGTH: 24
<212> TYPE: PRT
<213> ORGANISM: Artificial Sequence
<220> FEATURE:
<223> OTHER INFORMATION: Synthetic construct

<400> SEQUENCE: 1215

Ser Arg Ser Arg Thr Pro Ser Leu Pro Val Tyr Lys Ser Pro Val Val
1 5 10 15

Ser Gly Asp Thr Ser Pro Arg Cys
20

<210> SEQ ID NO 1216
<211> LENGTH: 24
<212> TYPE: PRT
<213> ORGANISM: Artificial Sequence
<220> FEATURE:
<223> OTHER INFORMATION: Synthetic construct

<400> SEQUENCE: 1216

Ser Arg Ser Arg Thr Pro Ser Leu Pro Tyr Lys Ser Pro Val Val Ser
1 5 10 15

Gly Asp Thr Ser Pro Arg His Cys
20

<210> SEQ ID NO 1217
<211> LENGTH: 25
<212> TYPE: PRT
<213> ORGANISM: Artificial Sequence
<220> FEATURE:
<223> OTHER INFORMATION: Synthetic construct

<400> SEQUENCE: 1217

Ser Arg Ser Arg Thr Pro Ser Leu Pro Ile Val Tyr Lys Ser Pro Val
1 5 10 15

Val Ser Gly Asp Thr Ser Pro Arg Cys
20 25

<210> SEQ ID NO 1218
<211> LENGTH: 25
<212> TYPE: PRT
<213> ORGANISM: Artificial Sequence
<220> FEATURE:
<223> OTHER INFORMATION: Synthetic construct

<400> SEQUENCE: 1218

Ser Arg Ser Arg Thr Pro Ser Leu Pro Val Tyr Lys Ser Pro Val Val
1 5 10 15

Ser Gly Asp Thr Ser Pro Arg His Cys
20 25

<210> SEQ ID NO 1219
<211> LENGTH: 25
<212> TYPE: PRT
<213> ORGANISM: Artificial Sequence
<220> FEATURE:
<223> OTHER INFORMATION: Synthetic construct

<400> SEQUENCE: 1219

```
Ser Arg Ser Arg Thr Pro Ser Leu Pro Tyr Lys Ser Pro Val Val Ser
1               5                   10                  15

Gly Asp Thr Ser Pro Arg His Leu Cys
            20                  25


<210> SEQ ID NO 1220
<211> LENGTH: 26
<212> TYPE: PRT
<213> ORGANISM: Artificial Sequence
<220> FEATURE:
<223> OTHER INFORMATION: Synthetic construct

<400> SEQUENCE: 1220

Ser Arg Ser Arg Thr Pro Ser Leu Pro Ile Val Tyr Lys Ser Pro Val
1               5                   10                  15

Val Ser Gly Asp Thr Ser Pro Arg His Cys
            20                  25


<210> SEQ ID NO 1221
<211> LENGTH: 26
<212> TYPE: PRT
<213> ORGANISM: Artificial Sequence
<220> FEATURE:
<223> OTHER INFORMATION: Synthetic construct

<400> SEQUENCE: 1221

Ser Arg Ser Arg Thr Pro Ser Leu Pro Val Tyr Lys Ser Pro Val Val
1               5                   10                  15

Ser Gly Asp Thr Ser Pro Arg His Leu Cys
            20                  25


<210> SEQ ID NO 1222
<211> LENGTH: 27
<212> TYPE: PRT
<213> ORGANISM: Artificial Sequence
<220> FEATURE:
<223> OTHER INFORMATION: Synthetic construct

<400> SEQUENCE: 1222

Ser Arg Ser Arg Thr Pro Ser Leu Pro Ile Val Tyr Lys Ser Pro Val
1               5                   10                  15

Val Ser Gly Asp Thr Ser Pro Arg His Leu Cys
            20                  25


<210> SEQ ID NO 1223
<211> LENGTH: 22
<212> TYPE: PRT
<213> ORGANISM: Artificial Sequence
<220> FEATURE:
<223> OTHER INFORMATION: Synthetic construct

<400> SEQUENCE: 1223

Arg Ser Arg Thr Pro Ser Leu Pro Thr Lys Ser Pro Val Val Ser Gly
1               5                   10                  15

Asp Thr Ser Pro Arg Cys
            20


<210> SEQ ID NO 1224
<211> LENGTH: 23
<212> TYPE: PRT
<213> ORGANISM: Artificial Sequence
<220> FEATURE:
<223> OTHER INFORMATION: Synthetic construct

<400> SEQUENCE: 1224
```

```
Arg Ser Arg Thr Pro Ser Leu Pro Thr Tyr Lys Ser Pro Val Val Ser
1               5                   10                  15

Gly Asp Thr Ser Pro Arg Cys
            20


<210> SEQ ID NO 1225
<211> LENGTH: 24
<212> TYPE: PRT
<213> ORGANISM: Artificial Sequence
<220> FEATURE:
<223> OTHER INFORMATION: Synthetic construct

<400> SEQUENCE: 1225

Arg Ser Arg Thr Pro Ser Leu Pro Thr Val Tyr Lys Ser Pro Val Val
1               5                   10                  15

Ser Gly Asp Thr Ser Pro Arg Cys
            20


<210> SEQ ID NO 1226
<211> LENGTH: 24
<212> TYPE: PRT
<213> ORGANISM: Artificial Sequence
<220> FEATURE:
<223> OTHER INFORMATION: Synthetic construct

<400> SEQUENCE: 1226

Arg Ser Arg Thr Pro Ser Leu Pro Thr Tyr Lys Ser Pro Val Val Ser
1               5                   10                  15

Gly Asp Thr Ser Pro Arg His Cys
            20


<210> SEQ ID NO 1227
<211> LENGTH: 25
<212> TYPE: PRT
<213> ORGANISM: Artificial Sequence
<220> FEATURE:
<223> OTHER INFORMATION: Synthetic construct

<400> SEQUENCE: 1227

Arg Ser Arg Thr Pro Ser Leu Pro Thr Ile Val Tyr Lys Ser Pro Val
1               5                   10                  15

Val Ser Gly Asp Thr Ser Pro Arg Cys
            20                  25


<210> SEQ ID NO 1228
<211> LENGTH: 25
<212> TYPE: PRT
<213> ORGANISM: Artificial Sequence
<220> FEATURE:
<223> OTHER INFORMATION: Synthetic construct

<400> SEQUENCE: 1228

Arg Ser Arg Thr Pro Ser Leu Pro Thr Val Tyr Lys Ser Pro Val Val
1               5                   10                  15

Ser Gly Asp Thr Ser Pro Arg His Cys
            20                  25


<210> SEQ ID NO 1229
<211> LENGTH: 25
<212> TYPE: PRT
<213> ORGANISM: Artificial Sequence
<220> FEATURE:
<223> OTHER INFORMATION: Synthetic construct
```

<400> SEQUENCE: 1229

Arg Ser Arg Thr Pro Ser Leu Pro Thr Tyr Lys Ser Pro Val Val Ser
1               5                   10                  15

Gly Asp Thr Ser Pro Arg His Leu Cys
            20                  25

<210> SEQ ID NO 1230
<211> LENGTH: 26
<212> TYPE: PRT
<213> ORGANISM: Artificial Sequence
<220> FEATURE:
<223> OTHER INFORMATION: Synthetic construct

<400> SEQUENCE: 1230

Arg Ser Arg Thr Pro Ser Leu Pro Thr Ile Val Tyr Lys Ser Pro Val
1               5                   10                  15

Val Ser Gly Asp Thr Ser Pro Arg His Cys
            20                  25

<210> SEQ ID NO 1231
<211> LENGTH: 26
<212> TYPE: PRT
<213> ORGANISM: Artificial Sequence
<220> FEATURE:
<223> OTHER INFORMATION: Synthetic construct

<400> SEQUENCE: 1231

Arg Ser Arg Thr Pro Ser Leu Pro Thr Val Tyr Lys Ser Pro Val Val
1               5                   10                  15

Ser Gly Asp Thr Ser Pro Arg His Leu Cys
            20                  25

<210> SEQ ID NO 1232
<211> LENGTH: 27
<212> TYPE: PRT
<213> ORGANISM: Artificial Sequence
<220> FEATURE:
<223> OTHER INFORMATION: Synthetic construct

<400> SEQUENCE: 1232

Arg Ser Arg Thr Pro Ser Leu Pro Thr Ile Val Tyr Lys Ser Pro Val
1               5                   10                  15

Val Ser Gly Asp Thr Ser Pro Arg His Leu Cys
            20                  25

<210> SEQ ID NO 1233
<211> LENGTH: 22
<212> TYPE: PRT
<213> ORGANISM: Artificial Sequence
<220> FEATURE:
<223> OTHER INFORMATION: Synthetic construct

<400> SEQUENCE: 1233

Ser Arg Thr Pro Ser Leu Pro Thr Pro Lys Ser Pro Val Val Ser Gly
1               5                   10                  15

Asp Thr Ser Pro Arg Cys
            20

<210> SEQ ID NO 1234
<211> LENGTH: 23
<212> TYPE: PRT
<213> ORGANISM: Artificial Sequence
<220> FEATURE:
<223> OTHER INFORMATION: Synthetic construct

<400> SEQUENCE: 1234

Ser Arg Thr Pro Ser Leu Pro Thr Pro Tyr Lys Ser Pro Val Val Ser
1 5 10 15

Gly Asp Thr Ser Pro Arg Cys
20

<210> SEQ ID NO 1235
<211> LENGTH: 24
<212> TYPE: PRT
<213> ORGANISM: Artificial Sequence
<220> FEATURE:
<223> OTHER INFORMATION: Synthetic construct

<400> SEQUENCE: 1235

Ser Arg Thr Pro Ser Leu Pro Thr Pro Val Tyr Lys Ser Pro Val Val
1 5 10 15

Ser Gly Asp Thr Ser Pro Arg Cys
20

<210> SEQ ID NO 1236
<211> LENGTH: 24
<212> TYPE: PRT
<213> ORGANISM: Artificial Sequence
<220> FEATURE:
<223> OTHER INFORMATION: Synthetic construct

<400> SEQUENCE: 1236

Ser Arg Thr Pro Ser Leu Pro Thr Pro Tyr Lys Ser Pro Val Val Ser
1 5 10 15

Gly Asp Thr Ser Pro Arg His Cys
20

<210> SEQ ID NO 1237
<211> LENGTH: 25
<212> TYPE: PRT
<213> ORGANISM: Artificial Sequence
<220> FEATURE:
<223> OTHER INFORMATION: Synthetic construct

<400> SEQUENCE: 1237

Ser Arg Thr Pro Ser Leu Pro Thr Pro Ile Val Tyr Lys Ser Pro Val
1 5 10 15

Val Ser Gly Asp Thr Ser Pro Arg Cys
20 25

<210> SEQ ID NO 1238
<211> LENGTH: 25
<212> TYPE: PRT
<213> ORGANISM: Artificial Sequence
<220> FEATURE:
<223> OTHER INFORMATION: Synthetic construct

<400> SEQUENCE: 1238

Ser Arg Thr Pro Ser Leu Pro Thr Pro Val Tyr Lys Ser Pro Val Val
1 5 10 15

Ser Gly Asp Thr Ser Pro Arg His Cys
20 25

<210> SEQ ID NO 1239
<211> LENGTH: 25
<212> TYPE: PRT
<213> ORGANISM: Artificial Sequence
<220> FEATURE:

<223> OTHER INFORMATION: Synthetic construct

<400> SEQUENCE: 1239

Ser Arg Thr Pro Ser Leu Pro Thr Pro Tyr Lys Ser Pro Val Val Ser
1 5 10 15

Gly Asp Thr Ser Pro Arg His Leu Cys
20 25

<210> SEQ ID NO 1240
<211> LENGTH: 26
<212> TYPE: PRT
<213> ORGANISM: Artificial Sequence
<220> FEATURE:
<223> OTHER INFORMATION: Synthetic construct

<400> SEQUENCE: 1240

Ser Arg Thr Pro Ser Leu Pro Thr Pro Ile Val Tyr Lys Ser Pro Val
1 5 10 15

Val Ser Gly Asp Thr Ser Pro Arg His Cys
20 25

<210> SEQ ID NO 1241
<211> LENGTH: 26
<212> TYPE: PRT
<213> ORGANISM: Artificial Sequence
<220> FEATURE:
<223> OTHER INFORMATION: Synthetic construct

<400> SEQUENCE: 1241

Ser Arg Thr Pro Ser Leu Pro Thr Pro Val Tyr Lys Ser Pro Val Val
1 5 10 15

Ser Gly Asp Thr Ser Pro Arg His Leu Cys
20 25

<210> SEQ ID NO 1242
<211> LENGTH: 27
<212> TYPE: PRT
<213> ORGANISM: Artificial Sequence
<220> FEATURE:
<223> OTHER INFORMATION: Synthetic construct

<400> SEQUENCE: 1242

Ser Arg Thr Pro Ser Leu Pro Thr Pro Ile Val Tyr Lys Ser Pro Val
1 5 10 15

Val Ser Gly Asp Thr Ser Pro Arg His Leu Cys
20 25

<210> SEQ ID NO 1243
<211> LENGTH: 23
<212> TYPE: PRT
<213> ORGANISM: Artificial Sequence
<220> FEATURE:
<223> OTHER INFORMATION: Synthetic construct

<400> SEQUENCE: 1243

Ser Arg Ser Arg Thr Pro Ser Leu Pro Thr Lys Ser Pro Val Val Ser
1 5 10 15

Gly Asp Thr Ser Pro Arg Cys
20

<210> SEQ ID NO 1244
<211> LENGTH: 24
<212> TYPE: PRT
<213> ORGANISM: Artificial Sequence
<220> FEATURE:
<223> OTHER INFORMATION: Synthetic construct

<400> SEQUENCE: 1244

Ser Arg Ser Arg Thr Pro Ser Leu Pro Thr Tyr Lys Ser Pro Val Val
1 5 10 15

Ser Gly Asp Thr Ser Pro Arg Cys
20

<210> SEQ ID NO 1245
<211> LENGTH: 25
<212> TYPE: PRT
<213> ORGANISM: Artificial Sequence
<220> FEATURE:
<223> OTHER INFORMATION: Synthetic construct

<400> SEQUENCE: 1245

Ser Arg Ser Arg Thr Pro Ser Leu Pro Thr Val Tyr Lys Ser Pro Val
1 5 10 15

Val Ser Gly Asp Thr Ser Pro Arg Cys
20 25

<210> SEQ ID NO 1246
<211> LENGTH: 25
<212> TYPE: PRT
<213> ORGANISM: Artificial Sequence
<220> FEATURE:
<223> OTHER INFORMATION: Synthetic construct

<400> SEQUENCE: 1246

Ser Arg Ser Arg Thr Pro Ser Leu Pro Thr Tyr Lys Ser Pro Val Val
1 5 10 15

Ser Gly Asp Thr Ser Pro Arg His Cys
20 25

<210> SEQ ID NO 1247
<211> LENGTH: 26
<212> TYPE: PRT
<213> ORGANISM: Artificial Sequence
<220> FEATURE:
<223> OTHER INFORMATION: Synthetic construct

<400> SEQUENCE: 1247

Ser Arg Ser Arg Thr Pro Ser Leu Pro Thr Ile Val Tyr Lys Ser Pro
1 5 10 15

Val Val Ser Gly Asp Thr Ser Pro Arg Cys
20 25

<210> SEQ ID NO 1248
<211> LENGTH: 26
<212> TYPE: PRT
<213> ORGANISM: Artificial Sequence
<220> FEATURE:
<223> OTHER INFORMATION: Synthetic construct

<400> SEQUENCE: 1248

Ser Arg Ser Arg Thr Pro Ser Leu Pro Thr Val Tyr Lys Ser Pro Val
1 5 10 15

Val Ser Gly Asp Thr Ser Pro Arg His Cys
20 25

<210> SEQ ID NO 1249
<211> LENGTH: 26
<212> TYPE: PRT

<213> ORGANISM: Artificial Sequence
<220> FEATURE:
<223> OTHER INFORMATION: Synthetic construct

<400> SEQUENCE: 1249

Ser Arg Ser Arg Thr Pro Ser Leu Pro Thr Tyr Lys Ser Pro Val Val
1               5                   10                  15

Ser Gly Asp Thr Ser Pro Arg His Leu Cys
            20                  25

<210> SEQ ID NO 1250
<211> LENGTH: 27
<212> TYPE: PRT
<213> ORGANISM: Artificial Sequence
<220> FEATURE:
<223> OTHER INFORMATION: Synthetic construct

<400> SEQUENCE: 1250

Ser Arg Ser Arg Thr Pro Ser Leu Pro Thr Ile Val Tyr Lys Ser Pro
1               5                   10                  15

Val Val Ser Gly Asp Thr Ser Pro Arg His Cys
            20                  25

<210> SEQ ID NO 1251
<211> LENGTH: 27
<212> TYPE: PRT
<213> ORGANISM: Artificial Sequence
<220> FEATURE:
<223> OTHER INFORMATION: Synthetic construct

<400> SEQUENCE: 1251

Ser Arg Ser Arg Thr Pro Ser Leu Pro Thr Val Tyr Lys Ser Pro Val
1               5                   10                  15

Val Ser Gly Asp Thr Ser Pro Arg His Leu Cys
            20                  25

<210> SEQ ID NO 1252
<211> LENGTH: 28
<212> TYPE: PRT
<213> ORGANISM: Artificial Sequence
<220> FEATURE:
<223> OTHER INFORMATION: Synthetic construct

<400> SEQUENCE: 1252

Ser Arg Ser Arg Thr Pro Ser Leu Pro Thr Ile Val Tyr Lys Ser Pro
1               5                   10                  15

Val Val Ser Gly Asp Thr Ser Pro Arg His Leu Cys
            20                  25

<210> SEQ ID NO 1253
<211> LENGTH: 23
<212> TYPE: PRT
<213> ORGANISM: Artificial Sequence
<220> FEATURE:
<223> OTHER INFORMATION: Synthetic construct

<400> SEQUENCE: 1253

Arg Ser Arg Thr Pro Ser Leu Pro Thr Pro Lys Ser Pro Val Val Ser
1               5                   10                  15

Gly Asp Thr Ser Pro Arg Cys
            20

<210> SEQ ID NO 1254
<211> LENGTH: 24

<212> TYPE: PRT
<213> ORGANISM: Artificial Sequence
<220> FEATURE:
<223> OTHER INFORMATION: Synthetic construct

<400> SEQUENCE: 1254

Arg Ser Arg Thr Pro Ser Leu Pro Thr Pro Tyr Lys Ser Pro Val Val
1               5                   10                  15

Ser Gly Asp Thr Ser Pro Arg Cys
            20

<210> SEQ ID NO 1255
<211> LENGTH: 25
<212> TYPE: PRT
<213> ORGANISM: Artificial Sequence
<220> FEATURE:
<223> OTHER INFORMATION: Synthetic construct

<400> SEQUENCE: 1255

Arg Ser Arg Thr Pro Ser Leu Pro Thr Pro Val Tyr Lys Ser Pro Val
1               5                   10                  15

Val Ser Gly Asp Thr Ser Pro Arg Cys
            20                  25

<210> SEQ ID NO 1256
<211> LENGTH: 25
<212> TYPE: PRT
<213> ORGANISM: Artificial Sequence
<220> FEATURE:
<223> OTHER INFORMATION: Synthetic construct

<400> SEQUENCE: 1256

Arg Ser Arg Thr Pro Ser Leu Pro Thr Pro Tyr Lys Ser Pro Val Val
1               5                   10                  15

Ser Gly Asp Thr Ser Pro Arg His Cys
            20                  25

<210> SEQ ID NO 1257
<211> LENGTH: 26
<212> TYPE: PRT
<213> ORGANISM: Artificial Sequence
<220> FEATURE:
<223> OTHER INFORMATION: Synthetic construct

<400> SEQUENCE: 1257

Arg Ser Arg Thr Pro Ser Leu Pro Thr Pro Ile Val Tyr Lys Ser Pro
1               5                   10                  15

Val Val Ser Gly Asp Thr Ser Pro Arg Cys
            20                  25

<210> SEQ ID NO 1258
<211> LENGTH: 26
<212> TYPE: PRT
<213> ORGANISM: Artificial Sequence
<220> FEATURE:
<223> OTHER INFORMATION: Synthetic construct

<400> SEQUENCE: 1258

Arg Ser Arg Thr Pro Ser Leu Pro Thr Pro Val Tyr Lys Ser Pro Val
1               5                   10                  15

Val Ser Gly Asp Thr Ser Pro Arg His Cys
            20                  25

<210> SEQ ID NO 1259

<211> LENGTH: 26
<212> TYPE: PRT
<213> ORGANISM: Artificial Sequence
<220> FEATURE:
<223> OTHER INFORMATION: Synthetic construct

<400> SEQUENCE: 1259

Arg Ser Arg Thr Pro Ser Leu Pro Thr Pro Tyr Lys Ser Pro Val Val
1 5 10 15

Ser Gly Asp Thr Ser Pro Arg His Leu Cys
20 25

<210> SEQ ID NO 1260
<211> LENGTH: 27
<212> TYPE: PRT
<213> ORGANISM: Artificial Sequence
<220> FEATURE:
<223> OTHER INFORMATION: Synthetic construct

<400> SEQUENCE: 1260

Arg Ser Arg Thr Pro Ser Leu Pro Thr Pro Ile Val Tyr Lys Ser Pro
1 5 10 15

Val Val Ser Gly Asp Thr Ser Pro Arg His Cys
20 25

<210> SEQ ID NO 1261
<211> LENGTH: 27
<212> TYPE: PRT
<213> ORGANISM: Artificial Sequence
<220> FEATURE:
<223> OTHER INFORMATION: Synthetic construct

<400> SEQUENCE: 1261

Arg Ser Arg Thr Pro Ser Leu Pro Thr Pro Val Tyr Lys Ser Pro Val
1 5 10 15

Val Ser Gly Asp Thr Ser Pro Arg His Leu Cys
20 25

<210> SEQ ID NO 1262
<211> LENGTH: 28
<212> TYPE: PRT
<213> ORGANISM: Artificial Sequence
<220> FEATURE:
<223> OTHER INFORMATION: Synthetic construct

<400> SEQUENCE: 1262

Arg Ser Arg Thr Pro Ser Leu Pro Thr Pro Ile Val Tyr Lys Ser Pro
1 5 10 15

Val Val Ser Gly Asp Thr Ser Pro Arg His Leu Cys
20 25

<210> SEQ ID NO 1263
<211> LENGTH: 24
<212> TYPE: PRT
<213> ORGANISM: Artificial Sequence
<220> FEATURE:
<223> OTHER INFORMATION: Synthetic construct

<400> SEQUENCE: 1263

Ser Arg Ser Arg Thr Pro Ser Leu Pro Thr Pro Lys Ser Pro Val Val
1 5 10 15

Ser Gly Asp Thr Ser Pro Arg Cys
20

<210> SEQ ID NO 1264
<211> LENGTH: 25
<212> TYPE: PRT
<213> ORGANISM: Artificial Sequence
<220> FEATURE:
<223> OTHER INFORMATION: Synthetic construct

<400> SEQUENCE: 1264

Ser Arg Ser Arg Thr Pro Ser Leu Pro Thr Pro Tyr Lys Ser Pro Val
1 5 10 15

Val Ser Gly Asp Thr Ser Pro Arg Cys
20 25

<210> SEQ ID NO 1265
<211> LENGTH: 26
<212> TYPE: PRT
<213> ORGANISM: Artificial Sequence
<220> FEATURE:
<223> OTHER INFORMATION: Synthetic construct

<400> SEQUENCE: 1265

Ser Arg Ser Arg Thr Pro Ser Leu Pro Thr Pro Val Tyr Lys Ser Pro
1 5 10 15

Val Val Ser Gly Asp Thr Ser Pro Arg Cys
20 25

<210> SEQ ID NO 1266
<211> LENGTH: 26
<212> TYPE: PRT
<213> ORGANISM: Artificial Sequence
<220> FEATURE:
<223> OTHER INFORMATION: Synthetic construct

<400> SEQUENCE: 1266

Ser Arg Ser Arg Thr Pro Ser Leu Pro Thr Pro Tyr Lys Ser Pro Val
1 5 10 15

Val Ser Gly Asp Thr Ser Pro Arg His Cys
20 25

<210> SEQ ID NO 1267
<211> LENGTH: 27
<212> TYPE: PRT
<213> ORGANISM: Artificial Sequence
<220> FEATURE:
<223> OTHER INFORMATION: Synthetic construct

<400> SEQUENCE: 1267

Ser Arg Ser Arg Thr Pro Ser Leu Pro Thr Pro Ile Val Tyr Lys Ser
1 5 10 15

Pro Val Val Ser Gly Asp Thr Ser Pro Arg Cys
20 25

<210> SEQ ID NO 1268
<211> LENGTH: 27
<212> TYPE: PRT
<213> ORGANISM: Artificial Sequence
<220> FEATURE:
<223> OTHER INFORMATION: Synthetic construct

<400> SEQUENCE: 1268

Ser Arg Ser Arg Thr Pro Ser Leu Pro Thr Pro Val Tyr Lys Ser Pro
1 5 10 15

Val Val Ser Gly Asp Thr Ser Pro Arg His Cys
20 25

<210> SEQ ID NO 1269
<211> LENGTH: 27
<212> TYPE: PRT
<213> ORGANISM: Artificial Sequence
<220> FEATURE:
<223> OTHER INFORMATION: Synthetic construct

<400> SEQUENCE: 1269

Ser Arg Ser Arg Thr Pro Ser Leu Pro Thr Pro Tyr Lys Ser Pro Val
1 5 10 15

Val Ser Gly Asp Thr Ser Pro Arg His Leu Cys
20 25

<210> SEQ ID NO 1270
<211> LENGTH: 28
<212> TYPE: PRT
<213> ORGANISM: Artificial Sequence
<220> FEATURE:
<223> OTHER INFORMATION: Synthetic construct

<400> SEQUENCE: 1270

Ser Arg Ser Arg Thr Pro Ser Leu Pro Thr Pro Ile Val Tyr Lys Ser
1 5 10 15

Pro Val Val Ser Gly Asp Thr Ser Pro Arg His Cys
20 25

<210> SEQ ID NO 1271
<211> LENGTH: 28
<212> TYPE: PRT
<213> ORGANISM: Artificial Sequence
<220> FEATURE:
<223> OTHER INFORMATION: Synthetic construct

<400> SEQUENCE: 1271

Ser Arg Ser Arg Thr Pro Ser Leu Pro Thr Pro Val Tyr Lys Ser Pro
1 5 10 15

Val Val Ser Gly Asp Thr Ser Pro Arg His Leu Cys
20 25

<210> SEQ ID NO 1272
<211> LENGTH: 29
<212> TYPE: PRT
<213> ORGANISM: Artificial Sequence
<220> FEATURE:
<223> OTHER INFORMATION: Synthetic construct

<400> SEQUENCE: 1272

Ser Arg Ser Arg Thr Pro Ser Leu Pro Thr Pro Ile Val Tyr Lys Ser
1 5 10 15

Pro Val Val Ser Gly Asp Thr Ser Pro Arg His Leu Cys
20 25

<210> SEQ ID NO 1273
<211> LENGTH: 27
<212> TYPE: PRT
<213> ORGANISM: Artificial Sequence
<220> FEATURE:
<223> OTHER INFORMATION: Synthetic construct

<400> SEQUENCE: 1273

Pro Ser Ser Ala Lys Ser Arg Ser Lys Ile Gly Ser Thr Glu Lys Ser
1 5 10 15

Pro Val Val Ser Gly Asp Thr Ser Pro Arg Cys
20 25

<210> SEQ ID NO 1274
<211> LENGTH: 28
<212> TYPE: PRT
<213> ORGANISM: Artificial Sequence
<220> FEATURE:
<223> OTHER INFORMATION: Synthetic construct

<400> SEQUENCE: 1274

Pro Ser Ser Ala Lys Ser Arg Ser Lys Ile Gly Ser Thr Glu Tyr Lys
1 5 10 15

Ser Pro Val Val Ser Gly Asp Thr Ser Pro Arg Cys
20 25

<210> SEQ ID NO 1275
<211> LENGTH: 29
<212> TYPE: PRT
<213> ORGANISM: Artificial Sequence
<220> FEATURE:
<223> OTHER INFORMATION: Synthetic construct

<400> SEQUENCE: 1275

Pro Ser Ser Ala Lys Ser Arg Ser Lys Ile Gly Ser Thr Glu Val Tyr
1 5 10 15

Lys Ser Pro Val Val Ser Gly Asp Thr Ser Pro Arg Cys
20 25

<210> SEQ ID NO 1276
<211> LENGTH: 29
<212> TYPE: PRT
<213> ORGANISM: Artificial Sequence
<220> FEATURE:
<223> OTHER INFORMATION: Synthetic construct

<400> SEQUENCE: 1276

Pro Ser Ser Ala Lys Ser Arg Ser Lys Ile Gly Ser Thr Glu Tyr Lys
1 5 10 15

Ser Pro Val Val Ser Gly Asp Thr Ser Pro Arg His Cys
20 25

<210> SEQ ID NO 1277
<211> LENGTH: 30
<212> TYPE: PRT
<213> ORGANISM: Artificial Sequence
<220> FEATURE:
<223> OTHER INFORMATION: Synthetic construct

<400> SEQUENCE: 1277

Pro Ser Ser Ala Lys Ser Arg Ser Lys Ile Gly Ser Thr Glu Ile Val
1 5 10 15

Tyr Lys Ser Pro Val Val Ser Gly Asp Thr Ser Pro Arg Cys
20 25 30

<210> SEQ ID NO 1278
<211> LENGTH: 30
<212> TYPE: PRT
<213> ORGANISM: Artificial Sequence
<220> FEATURE:
<223> OTHER INFORMATION: Synthetic construct

<400> SEQUENCE: 1278

Pro Ser Ser Ala Lys Ser Arg Ser Lys Ile Gly Ser Thr Glu Val Tyr
1 5 10 15

Lys Ser Pro Val Val Ser Gly Asp Thr Ser Pro Arg His Cys 20 25 30

<210> SEQ ID NO 1279
<211> LENGTH: 30
<212> TYPE: PRT
<213> ORGANISM: Artificial Sequence
<220> FEATURE:
<223> OTHER INFORMATION: Synthetic construct

<400> SEQUENCE: 1279

Pro Ser Ser Ala Lys Ser Arg Ser Lys Ile Gly Ser Thr Glu Tyr Lys
1 5 10 15

Ser Pro Val Val Ser Gly Asp Thr Ser Pro Arg His Leu Cys
20 25 30

<210> SEQ ID NO 1280
<211> LENGTH: 31
<212> TYPE: PRT
<213> ORGANISM: Artificial Sequence
<220> FEATURE:
<223> OTHER INFORMATION: Synthetic construct

<400> SEQUENCE: 1280

Pro Ser Ser Ala Lys Ser Arg Ser Lys Ile Gly Ser Thr Glu Ile Val
1 5 10 15

Tyr Lys Ser Pro Val Val Ser Gly Asp Thr Ser Pro Arg His Cys
20 25 30

<210> SEQ ID NO 1281
<211> LENGTH: 31
<212> TYPE: PRT
<213> ORGANISM: Artificial Sequence
<220> FEATURE:
<223> OTHER INFORMATION: Synthetic construct

<400> SEQUENCE: 1281

Pro Ser Ser Ala Lys Ser Arg Ser Lys Ile Gly Ser Thr Glu Val Tyr
1 5 10 15

Lys Ser Pro Val Val Ser Gly Asp Thr Ser Pro Arg His Leu Cys
20 25 30

<210> SEQ ID NO 1282
<211> LENGTH: 32
<212> TYPE: PRT
<213> ORGANISM: Artificial Sequence
<220> FEATURE:
<223> OTHER INFORMATION: Synthetic construct

<400> SEQUENCE: 1282

Pro Ser Ser Ala Lys Ser Arg Ser Lys Ile Gly Ser Thr Glu Ile Val
1 5 10 15

Tyr Lys Ser Pro Val Val Ser Gly Asp Thr Ser Pro Arg His Leu Cys
20 25 30

<210> SEQ ID NO 1283
<211> LENGTH: 28
<212> TYPE: PRT
<213> ORGANISM: Artificial Sequence
<220> FEATURE:
<223> OTHER INFORMATION: Synthetic construct

<400> SEQUENCE: 1283

Ser Pro Ser Ser Ala Lys Ser Arg Ser Lys Ile Gly Ser Thr Glu Lys
1 5 10 15

```
Ser Pro Val Val Ser Gly Asp Thr Ser Pro Arg Cys
            20                  25


<210> SEQ ID NO 1284
<211> LENGTH: 29
<212> TYPE: PRT
<213> ORGANISM: Artificial Sequence
<220> FEATURE:
<223> OTHER INFORMATION: Synthetic construct

<400> SEQUENCE: 1284

Ser Pro Ser Ser Ala Lys Ser Arg Ser Lys Ile Gly Ser Thr Glu Tyr
1               5                   10                  15

Lys Ser Pro Val Val Ser Gly Asp Thr Ser Pro Arg Cys
            20                  25


<210> SEQ ID NO 1285
<211> LENGTH: 30
<212> TYPE: PRT
<213> ORGANISM: Artificial Sequence
<220> FEATURE:
<223> OTHER INFORMATION: Synthetic construct

<400> SEQUENCE: 1285

Ser Pro Ser Ser Ala Lys Ser Arg Ser Lys Ile Gly Ser Thr Glu Val
1               5                   10                  15

Tyr Lys Ser Pro Val Val Ser Gly Asp Thr Ser Pro Arg Cys
            20                  25                  30


<210> SEQ ID NO 1286
<211> LENGTH: 30
<212> TYPE: PRT
<213> ORGANISM: Artificial Sequence
<220> FEATURE:
<223> OTHER INFORMATION: Synthetic construct

<400> SEQUENCE: 1286

Ser Pro Ser Ser Ala Lys Ser Arg Ser Lys Ile Gly Ser Thr Glu Tyr
1               5                   10                  15

Lys Ser Pro Val Val Ser Gly Asp Thr Ser Pro Arg His Cys
            20                  25                  30


<210> SEQ ID NO 1287
<211> LENGTH: 31
<212> TYPE: PRT
<213> ORGANISM: Artificial Sequence
<220> FEATURE:
<223> OTHER INFORMATION: Synthetic construct

<400> SEQUENCE: 1287

Ser Pro Ser Ser Ala Lys Ser Arg Ser Lys Ile Gly Ser Thr Glu Ile
1               5                   10                  15

Val Tyr Lys Ser Pro Val Val Ser Gly Asp Thr Ser Pro Arg Cys
            20                  25                  30


<210> SEQ ID NO 1288
<211> LENGTH: 31
<212> TYPE: PRT
<213> ORGANISM: Artificial Sequence
<220> FEATURE:
<223> OTHER INFORMATION: Synthetic construct

<400> SEQUENCE: 1288

Ser Pro Ser Ser Ala Lys Ser Arg Ser Lys Ile Gly Ser Thr Glu Val
1               5                   10                  15
```

Tyr Lys Ser Pro Val Val Ser Gly Asp Thr Ser Pro Arg His Cys
20 25 30

<210> SEQ ID NO 1289
<211> LENGTH: 31
<212> TYPE: PRT
<213> ORGANISM: Artificial Sequence
<220> FEATURE:
<223> OTHER INFORMATION: Synthetic construct

<400> SEQUENCE: 1289

Ser Pro Ser Ser Ala Lys Ser Arg Ser Lys Ile Gly Ser Thr Glu Tyr
1 5 10 15

Lys Ser Pro Val Val Ser Gly Asp Thr Ser Pro Arg His Leu Cys
20 25 30

<210> SEQ ID NO 1290
<211> LENGTH: 32
<212> TYPE: PRT
<213> ORGANISM: Artificial Sequence
<220> FEATURE:
<223> OTHER INFORMATION: Synthetic construct

<400> SEQUENCE: 1290

Ser Pro Ser Ser Ala Lys Ser Arg Ser Lys Ile Gly Ser Thr Glu Ile
1 5 10 15

Val Tyr Lys Ser Pro Val Val Ser Gly Asp Thr Ser Pro Arg His Cys
20 25 30

<210> SEQ ID NO 1291
<211> LENGTH: 32
<212> TYPE: PRT
<213> ORGANISM: Artificial Sequence
<220> FEATURE:
<223> OTHER INFORMATION: Synthetic construct

<400> SEQUENCE: 1291

Ser Pro Ser Ser Ala Lys Ser Arg Ser Lys Ile Gly Ser Thr Glu Val
1 5 10 15

Tyr Lys Ser Pro Val Val Ser Gly Asp Thr Ser Pro Arg His Leu Cys
20 25 30

<210> SEQ ID NO 1292
<211> LENGTH: 28
<212> TYPE: PRT
<213> ORGANISM: Artificial Sequence
<220> FEATURE:
<223> OTHER INFORMATION: Synthetic construct

<400> SEQUENCE: 1292

Pro Ser Ser Ala Lys Ser Arg Ser Lys Ile Gly Ser Thr Glu Asn Lys
1 5 10 15

Ser Pro Val Val Ser Gly Asp Thr Ser Pro Arg Cys
20 25

<210> SEQ ID NO 1293
<211> LENGTH: 29
<212> TYPE: PRT
<213> ORGANISM: Artificial Sequence
<220> FEATURE:
<223> OTHER INFORMATION: Synthetic construct

<400> SEQUENCE: 1293

Pro Ser Ser Ala Lys Ser Arg Ser Lys Ile Gly Ser Thr Glu Asn Tyr

```
1               5                   10                  15

Lys Ser Pro Val Val Ser Gly Asp Thr Ser Pro Arg Cys
            20                  25


<210> SEQ ID NO 1294
<211> LENGTH: 30
<212> TYPE: PRT
<213> ORGANISM: Artificial Sequence
<220> FEATURE:
<223> OTHER INFORMATION: Synthetic construct

<400> SEQUENCE: 1294

Pro Ser Ser Ala Lys Ser Arg Ser Lys Ile Gly Ser Thr Glu Asn Val
1               5                   10                  15

Tyr Lys Ser Pro Val Val Ser Gly Asp Thr Ser Pro Arg Cys
            20                  25                  30


<210> SEQ ID NO 1295
<211> LENGTH: 30
<212> TYPE: PRT
<213> ORGANISM: Artificial Sequence
<220> FEATURE:
<223> OTHER INFORMATION: Synthetic construct

<400> SEQUENCE: 1295

Pro Ser Ser Ala Lys Ser Arg Ser Lys Ile Gly Ser Thr Glu Asn Tyr
1               5                   10                  15

Lys Ser Pro Val Val Ser Gly Asp Thr Ser Pro Arg His Cys
            20                  25                  30


<210> SEQ ID NO 1296
<211> LENGTH: 31
<212> TYPE: PRT
<213> ORGANISM: Artificial Sequence
<220> FEATURE:
<223> OTHER INFORMATION: Synthetic construct

<400> SEQUENCE: 1296

Pro Ser Ser Ala Lys Ser Arg Ser Lys Ile Gly Ser Thr Glu Asn Ile
1               5                   10                  15

Val Tyr Lys Ser Pro Val Val Ser Gly Asp Thr Ser Pro Arg Cys
            20                  25                  30


<210> SEQ ID NO 1297
<211> LENGTH: 31
<212> TYPE: PRT
<213> ORGANISM: Artificial Sequence
<220> FEATURE:
<223> OTHER INFORMATION: Synthetic construct

<400> SEQUENCE: 1297

Pro Ser Ser Ala Lys Ser Arg Ser Lys Ile Gly Ser Thr Glu Asn Val
1               5                   10                  15

Tyr Lys Ser Pro Val Val Ser Gly Asp Thr Ser Pro Arg His Cys
            20                  25                  30


<210> SEQ ID NO 1298
<211> LENGTH: 31
<212> TYPE: PRT
<213> ORGANISM: Artificial Sequence
<220> FEATURE:
<223> OTHER INFORMATION: Synthetic construct

<400> SEQUENCE: 1298
```

```
Pro Ser Ser Ala Lys Ser Arg Ser Lys Ile Gly Ser Thr Glu Asn Tyr
1               5                   10                  15

Lys Ser Pro Val Val Ser Gly Asp Thr Ser Pro Arg His Leu Cys
            20                  25                  30


<210> SEQ ID NO 1299
<211> LENGTH: 32
<212> TYPE: PRT
<213> ORGANISM: Artificial Sequence
<220> FEATURE:
<223> OTHER INFORMATION: Synthetic construct

<400> SEQUENCE: 1299

Pro Ser Ser Ala Lys Ser Arg Ser Lys Ile Gly Ser Thr Glu Asn Ile
1               5                   10                  15

Val Tyr Lys Ser Pro Val Val Ser Gly Asp Thr Ser Pro Arg His Cys
            20                  25                  30


<210> SEQ ID NO 1300
<211> LENGTH: 32
<212> TYPE: PRT
<213> ORGANISM: Artificial Sequence
<220> FEATURE:
<223> OTHER INFORMATION: Synthetic construct

<400> SEQUENCE: 1300

Pro Ser Ser Ala Lys Ser Arg Ser Lys Ile Gly Ser Thr Glu Asn Val
1               5                   10                  15

Tyr Lys Ser Pro Val Val Ser Gly Asp Thr Ser Pro Arg His Leu Cys
            20                  25                  30


<210> SEQ ID NO 1301
<211> LENGTH: 29
<212> TYPE: PRT
<213> ORGANISM: Artificial Sequence
<220> FEATURE:
<223> OTHER INFORMATION: Synthetic construct

<400> SEQUENCE: 1301

Lys Ser Pro Ser Ser Ala Lys Ser Arg Ser Lys Ile Gly Ser Thr Glu
1               5                   10                  15

Lys Ser Pro Val Val Ser Gly Asp Thr Ser Pro Arg Cys
            20                  25


<210> SEQ ID NO 1302
<211> LENGTH: 30
<212> TYPE: PRT
<213> ORGANISM: Artificial Sequence
<220> FEATURE:
<223> OTHER INFORMATION: Synthetic construct

<400> SEQUENCE: 1302

Lys Ser Pro Ser Ser Ala Lys Ser Arg Ser Lys Ile Gly Ser Thr Glu
1               5                   10                  15

Tyr Lys Ser Pro Val Val Ser Gly Asp Thr Ser Pro Arg Cys
            20                  25                  30


<210> SEQ ID NO 1303
<211> LENGTH: 31
<212> TYPE: PRT
<213> ORGANISM: Artificial Sequence
<220> FEATURE:
<223> OTHER INFORMATION: Synthetic construct

<400> SEQUENCE: 1303
```

```
Lys Ser Pro Ser Ser Ala Lys Ser Arg Ser Lys Ile Gly Ser Thr Glu
1               5                   10                  15

Val Tyr Lys Ser Pro Val Val Ser Gly Asp Thr Ser Pro Arg Cys
            20                  25                  30


<210> SEQ ID NO 1304
<211> LENGTH: 31
<212> TYPE: PRT
<213> ORGANISM: Artificial Sequence
<220> FEATURE:
<223> OTHER INFORMATION: Synthetic construct

<400> SEQUENCE: 1304

Lys Ser Pro Ser Ser Ala Lys Ser Arg Ser Lys Ile Gly Ser Thr Glu
1               5                   10                  15

Tyr Lys Ser Pro Val Val Ser Gly Asp Thr Ser Pro Arg His Cys
            20                  25                  30


<210> SEQ ID NO 1305
<211> LENGTH: 32
<212> TYPE: PRT
<213> ORGANISM: Artificial Sequence
<220> FEATURE:
<223> OTHER INFORMATION: Synthetic construct

<400> SEQUENCE: 1305

Lys Ser Pro Ser Ser Ala Lys Ser Arg Ser Lys Ile Gly Ser Thr Glu
1               5                   10                  15

Ile Val Tyr Lys Ser Pro Val Val Ser Gly Asp Thr Ser Pro Arg Cys
            20                  25                  30


<210> SEQ ID NO 1306
<211> LENGTH: 32
<212> TYPE: PRT
<213> ORGANISM: Artificial Sequence
<220> FEATURE:
<223> OTHER INFORMATION: Synthetic construct

<400> SEQUENCE: 1306

Lys Ser Pro Ser Ser Ala Lys Ser Arg Ser Lys Ile Gly Ser Thr Glu
1               5                   10                  15

Val Tyr Lys Ser Pro Val Val Ser Gly Asp Thr Ser Pro Arg His Cys
            20                  25                  30


<210> SEQ ID NO 1307
<211> LENGTH: 32
<212> TYPE: PRT
<213> ORGANISM: Artificial Sequence
<220> FEATURE:
<223> OTHER INFORMATION: Synthetic construct

<400> SEQUENCE: 1307

Lys Ser Pro Ser Ser Ala Lys Ser Arg Ser Lys Ile Gly Ser Thr Glu
1               5                   10                  15

Tyr Lys Ser Pro Val Val Ser Gly Asp Thr Ser Pro Arg His Leu Cys
            20                  25                  30


<210> SEQ ID NO 1308
<211> LENGTH: 29
<212> TYPE: PRT
<213> ORGANISM: Artificial Sequence
<220> FEATURE:
<223> OTHER INFORMATION: Synthetic construct
```

<400> SEQUENCE: 1308

Ser Pro Ser Ser Ala Lys Ser Arg Ser Lys Ile Gly Ser Thr Glu Asn
1 5 10 15

Lys Ser Pro Val Val Ser Gly Asp Thr Ser Pro Arg Cys
20 25

<210> SEQ ID NO 1309
<211> LENGTH: 30
<212> TYPE: PRT
<213> ORGANISM: Artificial Sequence
<220> FEATURE:
<223> OTHER INFORMATION: Synthetic construct

<400> SEQUENCE: 1309

Ser Pro Ser Ser Ala Lys Ser Arg Ser Lys Ile Gly Ser Thr Glu Asn
1 5 10 15

Tyr Lys Ser Pro Val Val Ser Gly Asp Thr Ser Pro Arg Cys
20 25 30

<210> SEQ ID NO 1310
<211> LENGTH: 31
<212> TYPE: PRT
<213> ORGANISM: Artificial Sequence
<220> FEATURE:
<223> OTHER INFORMATION: Synthetic construct

<400> SEQUENCE: 1310

Ser Pro Ser Ser Ala Lys Ser Arg Ser Lys Ile Gly Ser Thr Glu Asn
1 5 10 15

Val Tyr Lys Ser Pro Val Val Ser Gly Asp Thr Ser Pro Arg Cys
20 25 30

<210> SEQ ID NO 1311
<211> LENGTH: 31
<212> TYPE: PRT
<213> ORGANISM: Artificial Sequence
<220> FEATURE:
<223> OTHER INFORMATION: Synthetic construct

<400> SEQUENCE: 1311

Ser Pro Ser Ser Ala Lys Ser Arg Ser Lys Ile Gly Ser Thr Glu Asn
1 5 10 15

Tyr Lys Ser Pro Val Val Ser Gly Asp Thr Ser Pro Arg His Cys
20 25 30

<210> SEQ ID NO 1312
<211> LENGTH: 32
<212> TYPE: PRT
<213> ORGANISM: Artificial Sequence
<220> FEATURE:
<223> OTHER INFORMATION: Synthetic construct

<400> SEQUENCE: 1312

Ser Pro Ser Ser Ala Lys Ser Arg Ser Lys Ile Gly Ser Thr Glu Asn
1 5 10 15

Ile Val Tyr Lys Ser Pro Val Val Ser Gly Asp Thr Ser Pro Arg Cys
20 25 30

<210> SEQ ID NO 1313
<211> LENGTH: 32
<212> TYPE: PRT
<213> ORGANISM: Artificial Sequence
<220> FEATURE:
<223> OTHER INFORMATION: Synthetic construct

<400> SEQUENCE: 1313

Ser Pro Ser Ser Ala Lys Ser Arg Ser Lys Ile Gly Ser Thr Glu Asn
1 5 10 15

Val Tyr Lys Ser Pro Val Val Ser Gly Asp Thr Ser Pro Arg His Cys
20 25 30

<210> SEQ ID NO 1314
<211> LENGTH: 32
<212> TYPE: PRT
<213> ORGANISM: Artificial Sequence
<220> FEATURE:
<223> OTHER INFORMATION: Synthetic construct

<400> SEQUENCE: 1314

Ser Pro Ser Ser Ala Lys Ser Arg Ser Lys Ile Gly Ser Thr Glu Asn
1 5 10 15

Tyr Lys Ser Pro Val Val Ser Gly Asp Thr Ser Pro Arg His Leu Cys
20 25 30

<210> SEQ ID NO 1315
<211> LENGTH: 29
<212> TYPE: PRT
<213> ORGANISM: Artificial Sequence
<220> FEATURE:
<223> OTHER INFORMATION: Synthetic construct

<400> SEQUENCE: 1315

Pro Ser Ser Ala Lys Ser Arg Ser Lys Ile Gly Ser Thr Glu Asn Leu
1 5 10 15

Lys Ser Pro Val Val Ser Gly Asp Thr Ser Pro Arg Cys
20 25

<210> SEQ ID NO 1316
<211> LENGTH: 30
<212> TYPE: PRT
<213> ORGANISM: Artificial Sequence
<220> FEATURE:
<223> OTHER INFORMATION: Synthetic construct

<400> SEQUENCE: 1316

Pro Ser Ser Ala Lys Ser Arg Ser Lys Ile Gly Ser Thr Glu Asn Leu
1 5 10 15

Tyr Lys Ser Pro Val Val Ser Gly Asp Thr Ser Pro Arg Cys
20 25 30

<210> SEQ ID NO 1317
<211> LENGTH: 31
<212> TYPE: PRT
<213> ORGANISM: Artificial Sequence
<220> FEATURE:
<223> OTHER INFORMATION: Synthetic construct

<400> SEQUENCE: 1317

Pro Ser Ser Ala Lys Ser Arg Ser Lys Ile Gly Ser Thr Glu Asn Leu
1 5 10 15

Val Tyr Lys Ser Pro Val Val Ser Gly Asp Thr Ser Pro Arg Cys
20 25 30

<210> SEQ ID NO 1318
<211> LENGTH: 31
<212> TYPE: PRT
<213> ORGANISM: Artificial Sequence
<220> FEATURE:

<223> OTHER INFORMATION: Synthetic construct

<400> SEQUENCE: 1318

Pro Ser Ser Ala Lys Ser Arg Ser Lys Ile Gly Ser Thr Glu Asn Leu
1 5 10 15

Tyr Lys Ser Pro Val Val Ser Gly Asp Thr Ser Pro Arg His Cys
20 25 30

<210> SEQ ID NO 1319
<211> LENGTH: 32
<212> TYPE: PRT
<213> ORGANISM: Artificial Sequence
<220> FEATURE:
<223> OTHER INFORMATION: Synthetic construct

<400> SEQUENCE: 1319

Pro Ser Ser Ala Lys Ser Arg Ser Lys Ile Gly Ser Thr Glu Asn Leu
1 5 10 15

Ile Val Tyr Lys Ser Pro Val Val Ser Gly Asp Thr Ser Pro Arg Cys
20 25 30

<210> SEQ ID NO 1320
<211> LENGTH: 32
<212> TYPE: PRT
<213> ORGANISM: Artificial Sequence
<220> FEATURE:
<223> OTHER INFORMATION: Synthetic construct

<400> SEQUENCE: 1320

Pro Ser Ser Ala Lys Ser Arg Ser Lys Ile Gly Ser Thr Glu Asn Leu
1 5 10 15

Val Tyr Lys Ser Pro Val Val Ser Gly Asp Thr Ser Pro Arg His Cys
20 25 30

<210> SEQ ID NO 1321
<211> LENGTH: 32
<212> TYPE: PRT
<213> ORGANISM: Artificial Sequence
<220> FEATURE:
<223> OTHER INFORMATION: Synthetic construct

<400> SEQUENCE: 1321

Pro Ser Ser Ala Lys Ser Arg Ser Lys Ile Gly Ser Thr Glu Asn Leu
1 5 10 15

Tyr Lys Ser Pro Val Val Ser Gly Asp Thr Ser Pro Arg His Leu Cys
20 25 30

<210> SEQ ID NO 1322
<211> LENGTH: 30
<212> TYPE: PRT
<213> ORGANISM: Artificial Sequence
<220> FEATURE:
<223> OTHER INFORMATION: Synthetic construct

<400> SEQUENCE: 1322

Lys Ser Pro Ser Ser Ala Lys Ser Arg Ser Lys Ile Gly Ser Thr Glu
1 5 10 15

Asn Lys Ser Pro Val Val Ser Gly Asp Thr Ser Pro Arg Cys
20 25 30

<210> SEQ ID NO 1323
<211> LENGTH: 31
<212> TYPE: PRT
<213> ORGANISM: Artificial Sequence
<220> FEATURE:
<223> OTHER INFORMATION: Synthetic construct

<400> SEQUENCE: 1323

Lys Ser Pro Ser Ser Ala Lys Ser Arg Ser Lys Ile Gly Ser Thr Glu
1 5 10 15

Asn Tyr Lys Ser Pro Val Val Ser Gly Asp Thr Ser Pro Arg Cys
20 25 30

<210> SEQ ID NO 1324
<211> LENGTH: 32
<212> TYPE: PRT
<213> ORGANISM: Artificial Sequence
<220> FEATURE:
<223> OTHER INFORMATION: Synthetic construct

<400> SEQUENCE: 1324

Lys Ser Pro Ser Ser Ala Lys Ser Arg Ser Lys Ile Gly Ser Thr Glu
1 5 10 15

Asn Val Tyr Lys Ser Pro Val Val Ser Gly Asp Thr Ser Pro Arg Cys
20 25 30

<210> SEQ ID NO 1325
<211> LENGTH: 32
<212> TYPE: PRT
<213> ORGANISM: Artificial Sequence
<220> FEATURE:
<223> OTHER INFORMATION: Synthetic construct

<400> SEQUENCE: 1325

Lys Ser Pro Ser Ser Ala Lys Ser Arg Ser Lys Ile Gly Ser Thr Glu
1 5 10 15

Asn Tyr Lys Ser Pro Val Val Ser Gly Asp Thr Ser Pro Arg His Cys
20 25 30

<210> SEQ ID NO 1326
<211> LENGTH: 30
<212> TYPE: PRT
<213> ORGANISM: Artificial Sequence
<220> FEATURE:
<223> OTHER INFORMATION: Synthetic construct

<400> SEQUENCE: 1326

Ser Pro Ser Ser Ala Lys Ser Arg Ser Lys Ile Gly Ser Thr Glu Asn
1 5 10 15

Leu Lys Ser Pro Val Val Ser Gly Asp Thr Ser Pro Arg Cys
20 25 30

<210> SEQ ID NO 1327
<211> LENGTH: 31
<212> TYPE: PRT
<213> ORGANISM: Artificial Sequence
<220> FEATURE:
<223> OTHER INFORMATION: Synthetic construct

<400> SEQUENCE: 1327

Ser Pro Ser Ser Ala Lys Ser Arg Ser Lys Ile Gly Ser Thr Glu Asn
1 5 10 15

Leu Tyr Lys Ser Pro Val Val Ser Gly Asp Thr Ser Pro Arg Cys
20 25 30

<210> SEQ ID NO 1328
<211> LENGTH: 32
<212> TYPE: PRT

<213> ORGANISM: Artificial Sequence
<220> FEATURE:
<223> OTHER INFORMATION: Synthetic construct

<400> SEQUENCE: 1328

Ser Pro Ser Ser Ala Lys Ser Arg Ser Lys Ile Gly Ser Thr Glu Asn
1               5                   10                  15

Leu Val Tyr Lys Ser Pro Val Val Ser Gly Asp Thr Ser Pro Arg Cys
            20                  25                  30

<210> SEQ ID NO 1329
<211> LENGTH: 32
<212> TYPE: PRT
<213> ORGANISM: Artificial Sequence
<220> FEATURE:
<223> OTHER INFORMATION: Synthetic construct

<400> SEQUENCE: 1329

Ser Pro Ser Ser Ala Lys Ser Arg Ser Lys Ile Gly Ser Thr Glu Asn
1               5                   10                  15

Leu Tyr Lys Ser Pro Val Val Ser Gly Asp Thr Ser Pro Arg His Cys
            20                  25                  30

<210> SEQ ID NO 1330
<211> LENGTH: 31
<212> TYPE: PRT
<213> ORGANISM: Artificial Sequence
<220> FEATURE:
<223> OTHER INFORMATION: Synthetic construct

<400> SEQUENCE: 1330

Lys Ser Pro Ser Ser Ala Lys Ser Arg Ser Lys Ile Gly Ser Thr Glu
1               5                   10                  15

Asn Leu Lys Ser Pro Val Val Ser Gly Asp Thr Ser Pro Arg Cys
            20                  25                  30

<210> SEQ ID NO 1331
<211> LENGTH: 32
<212> TYPE: PRT
<213> ORGANISM: Artificial Sequence
<220> FEATURE:
<223> OTHER INFORMATION: Synthetic construct

<400> SEQUENCE: 1331

Lys Ser Pro Ser Ser Ala Lys Ser Arg Ser Lys Ile Gly Ser Thr Glu
1               5                   10                  15

Asn Leu Tyr Lys Ser Pro Val Val Ser Gly Asp Thr Ser Pro Arg Cys
            20                  25                  30

<210> SEQ ID NO 1332
<211> LENGTH: 441
<212> TYPE: PRT
<213> ORGANISM: Homo sapiens

<400> SEQUENCE: 1332

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

```
Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440
```

<210> SEQ ID NO 1333
<211> LENGTH: 317
<212> TYPE: PRT
<213> ORGANISM: Artificial Sequence
<220> FEATURE:

<223> OTHER INFORMATION: Synthetic construct

<400> SEQUENCE: 1333

```
Met Lys Pro Phe Ser Val Pro Ile Leu Thr Val Glu Glu Met Thr Asn
1               5                   10                  15

Ser Arg Phe Pro Ile Pro Leu Glu Lys Leu Phe Thr Gly Pro Ser Ser
            20                  25                  30

Ala Phe Val Val Gln Pro Gln Asn Gly Arg Cys Thr Thr Asp Gly Val
        35                  40                  45

Leu Leu Gly Thr Thr Gln Leu Ser Pro Val Asn Ile Cys Thr Phe Arg
    50                  55                  60

Gly Asp Val Thr His Ile Ala Gly Thr Gln Asn Tyr Thr Met Asn Leu
65                  70                  75                  80

Ala Ser Gln Asn Trp Asn Asn Tyr Asp Pro Thr Glu Glu Ile Pro Ala
                85                  90                  95

Pro Leu Gly Thr Pro Asp Phe Val Gly Arg Ile Gln Gly Val Leu Thr
            100                 105                 110

Gln Thr Thr Arg Arg Asp Gly Ser Thr Arg Gly His Lys Ala Thr Val
        115                 120                 125

Ser Thr Gly Ser Val His Phe Thr Pro Lys Leu Gly Ser Val Gln Phe
    130                 135                 140

Ser Thr Asp Thr Ser Asn Asp Phe Glu Thr Gly Gln Asn Thr Arg Phe
145                 150                 155                 160

Thr Pro Val Gly Val Val Gln Asp Gly Ser Thr Thr His Gln Asn Glu
                165                 170                 175

Pro Gln Gln Trp Val Leu Pro Asp Tyr Ser Gly Arg Asp Ser His Asn
            180                 185                 190

Val His Leu Ala Pro Ala Val Ala Pro Thr Phe Pro Gly Glu Gln Leu
        195                 200                 205

Leu Phe Phe Arg Ser Thr Met Pro Gly Cys Ser Gly Tyr Pro Asn Met
    210                 215                 220

Asn Leu Asp Cys Leu Leu Pro Gln Glu Trp Val Gln His Phe Tyr Gln
225                 230                 235                 240

Glu Ser Ala Pro Ala Gln Ser Asp Val Ala Leu Leu Arg Phe Val Asn
                245                 250                 255

Pro Asp Thr Gly Arg Val Leu Phe Glu Cys Lys Leu His Lys Ser Gly
            260                 265                 270

Tyr Val Thr Val Ala His Thr Gly Gln His Asp Leu Val Ile Pro Pro
        275                 280                 285

Asn Gly Tyr Phe Arg Phe Asp Ser Trp Val Asn Gln Phe Tyr Thr Leu
    290                 295                 300

Ala Pro Met Gly Asn Gly Ala Gly Arg Arg Arg Ala Leu
305                 310                 315
```

<210> SEQ ID NO 1334
<211> LENGTH: 59
<212> TYPE: DNA
<213> ORGANISM: Artificial Sequence
<220> FEATURE:
<223> OTHER INFORMATION: Synthetic construct

<400> SEQUENCE: 1334

```
ctgtgaacat cgctactttc cgcggcgacg tcacacacat cgcttgcaca caaaactac      59
```

<210> SEQ ID NO 1335
<211> LENGTH: 59

<212> TYPE: DNA
<213> ORGANISM: Artificial Sequence
<220> FEATURE:
<223> OTHER INFORMATION: Synthetic construct

<400> SEQUENCE: 1335
gtagttttgt gtgcaagcga tgtgtgtgac gtcgccgcgg aaagtagcga tgttcacag 59

<210> SEQ ID NO 1336
<211> LENGTH: 41
<212> TYPE: DNA
<213> ORGANISM: Artificial Sequence
<220> FEATURE:
<223> OTHER INFORMATION: Synthetic construct

<400> SEQUENCE: 1336
gcaattcagc acagacacct gcaacgattt cgagactggc c 41

<210> SEQ ID NO 1337
<211> LENGTH: 41
<212> TYPE: DNA
<213> ORGANISM: Artificial Sequence
<220> FEATURE:
<223> OTHER INFORMATION: Synthetic construct

<400> SEQUENCE: 1337
ggccagtctc gaaatcgttg caggtgtctg tgctgaattg c 41

<210> SEQ ID NO 1338
<211> LENGTH: 42
<212> TYPE: DNA
<213> ORGANISM: Artificial Sequence
<220> FEATURE:
<223> OTHER INFORMATION: Synthetic construct

<400> SEQUENCE: 1338
ccgtgggtgt cgttcaagac tgcagcacca ctcaccagaa cg 42

<210> SEQ ID NO 1339
<211> LENGTH: 42
<212> TYPE: DNA
<213> ORGANISM: Artificial Sequence
<220> FEATURE:
<223> OTHER INFORMATION: Synthetic construct

<400> SEQUENCE: 1339
cgttctggtg agtggtgctg cagtcttgaa cgacacccac gg 42

<210> SEQ ID NO 1340
<211> LENGTH: 45
<212> TYPE: DNA
<213> ORGANISM: Artificial Sequence
<220> FEATURE:
<223> OTHER INFORMATION: Synthetic construct

<400> SEQUENCE: 1340
gacgtcacac acatcgctgg aaagacacaa aactacacca tgaac 45

<210> SEQ ID NO 1341
<211> LENGTH: 45
<212> TYPE: DNA
<213> ORGANISM: Artificial Sequence
<220> FEATURE:
<223> OTHER INFORMATION: Synthetic construct

<400> SEQUENCE: 1341

-continued gttcatggtg tagttttgtg tctttccagc gatgtgtgtg acgtc 45

<210> SEQ ID NO 1342
<211> LENGTH: 45
<212> TYPE: DNA
<213> ORGANISM: Artificial Sequence
<220> FEATURE:
<223> OTHER INFORMATION: Synthetic construct

<400> SEQUENCE: 1342
caattcagca cagacacctc aaagaacgat ttcgagactg gccag 45

<210> SEQ ID NO 1343
<211> LENGTH: 45
<212> TYPE: DNA
<213> ORGANISM: Artificial Sequence
<220> FEATURE:
<223> OTHER INFORMATION: Synthetic construct

<400> SEQUENCE: 1343
ctggccagtc tcgaaatcgt tctttgaggt gtctgtgctg aattg 45

<210> SEQ ID NO 1344
<211> LENGTH: 45
<212> TYPE: DNA
<213> ORGANISM: Artificial Sequence
<220> FEATURE:
<223> OTHER INFORMATION: Synthetic construct

<400> SEQUENCE: 1344
gtgggtgtcg ttcaagacgg caagagcacc actcaccaga acgaa 45

<210> SEQ ID NO 1345
<211> LENGTH: 45
<212> TYPE: DNA
<213> ORGANISM: Artificial Sequence
<220> FEATURE:
<223> OTHER INFORMATION: Synthetic construct

<400> SEQUENCE: 1345
ttcgttctgg tgagtggtgc tcttgccgtc ttgaacgaca cccac 45

<210> SEQ ID NO 1346
<211> LENGTH: 9
<212> TYPE: PRT
<213> ORGANISM: Artificial Sequence
<220> FEATURE:
<223> OTHER INFORMATION: Synthetic construct

<400> SEQUENCE: 1346

His Ala Gly Thr Tyr Gly Leu Gly Asp
1 5

<210> SEQ ID NO 1347
<211> LENGTH: 12
<212> TYPE: PRT
<213> ORGANISM: Artificial Sequence
<220> FEATURE:
<223> OTHER INFORMATION: Synthetic construct

<400> SEQUENCE: 1347

Ser Ser Pro Gly Ser Pro Gly Thr Pro Gly Ser Arg
1 5 10

<210> SEQ ID NO 1348
<211> LENGTH: 11

<212> TYPE: PRT
<213> ORGANISM: Artificial Sequence
<220> FEATURE:
<223> OTHER INFORMATION: Synthetic construct

<400> SEQUENCE: 1348

Ser Arg Ser Arg Thr Pro Ser Leu Thr Thr Pro
1 5 10

<210> SEQ ID NO 1349
<211> LENGTH: 13
<212> TYPE: PRT
<213> ORGANISM: Artificial Sequence
<220> FEATURE:
<223> OTHER INFORMATION: Synthetic construct

<400> SEQUENCE: 1349

Ala Val Val Arg Thr Pro Pro Lys Ser Pro Ser Ser Ala
1 5 10

<210> SEQ ID NO 1350
<211> LENGTH: 9
<212> TYPE: PRT
<213> ORGANISM: Artificial Sequence
<220> FEATURE:
<223> OTHER INFORMATION: Synthetic construct

<400> SEQUENCE: 1350

Lys Ser Pro Ser Ser Ala Lys Ser Arg
1 5

<210> SEQ ID NO 1351
<211> LENGTH: 9
<212> TYPE: PRT
<213> ORGANISM: Artificial Sequence
<220> FEATURE:
<223> OTHER INFORMATION: Synthetic construct

<400> SEQUENCE: 1351

Ser Lys Ile Gly Ser Thr Glu Asn Leu
1 5

<210> SEQ ID NO 1352
<211> LENGTH: 9
<212> TYPE: PRT
<213> ORGANISM: Artificial Sequence
<220> FEATURE:
<223> OTHER INFORMATION: Synthetic construct

<400> SEQUENCE: 1352

Ile Val Tyr Lys Ser Pro Val Val Ser
1 5

<210> SEQ ID NO 1353
<211> LENGTH: 9
<212> TYPE: PRT
<213> ORGANISM: Artificial Sequence
<220> FEATURE:
<223> OTHER INFORMATION: Synthetic construct

<400> SEQUENCE: 1353

Ser Gly Asp Thr Ser Pro Arg His Leu
1 5

<210> SEQ ID NO 1354
<211> LENGTH: 31
<212> TYPE: PRT

<213> ORGANISM: Artificial Sequence
<220> FEATURE:
<223> OTHER INFORMATION: Synthetic construct

<400> SEQUENCE: 1354

```
Ser Gly Tyr Ser Ser Pro Gly Ser Pro Gly Thr Pro Gly Ser Arg Ser
1               5                   10                  15

Arg Thr Pro Lys Ser Pro Val Val Ser Gly Asp Thr Ser Pro Arg
            20                  25                  30
```

<210> SEQ ID NO 1355
<211> LENGTH: 27
<212> TYPE: PRT
<213> ORGANISM: Artificial Sequence
<220> FEATURE:
<223> OTHER INFORMATION: Synthetic construct

<400> SEQUENCE: 1355

```
His Ala Gly Thr Tyr Gly Leu Gly Asp Lys Ser Pro Ser Ser Ala Lys
1               5                   10                  15

Ser Arg Ser Lys Ile Gly Ser Thr Glu Asn Leu
            20                  25
```

<210> SEQ ID NO 1356
<211> LENGTH: 24
<212> TYPE: PRT
<213> ORGANISM: Artificial Sequence
<220> FEATURE:
<223> OTHER INFORMATION: Synthetic construct

<400> SEQUENCE: 1356

```
Ser Arg Ser Arg Thr Pro Ser Leu Pro Thr Pro Ala Val Val Arg Thr
1               5                   10                  15

Pro Pro Lys Ser Pro Ser Ser Ala
            20
```

<210> SEQ ID NO 1357
<211> LENGTH: 318
<212> TYPE: PRT
<213> ORGANISM: Artificial Sequence
<220> FEATURE:
<223> OTHER INFORMATION: Synthetic construct

<400> SEQUENCE: 1357

```
Met Gly Lys Pro Phe Ser Val Pro Ile Leu Thr Val Glu Glu Met Thr
1               5                   10                  15

Asn Ser Arg Phe Pro Ile Pro Leu Glu Lys Leu Phe Thr Gly Pro Ser
            20                  25                  30

Ser Ala Phe Val Val Gln Pro Gln Asn Gly Arg Cys Thr Thr Asp Gly
        35                  40                  45

Val Leu Leu Gly Thr Thr Gln Leu Ser Pro Val Asn Ile Cys Thr Phe
    50                  55                  60

Arg Gly Asp Val Thr His Ile Ala Gly Cys Gln Asn Tyr Thr Met Asn
65                  70                  75                  80

Leu Ala Ser Gln Asn Trp Asn Asn Tyr Asp Pro Thr Glu Glu Ile Pro
                85                  90                  95

Ala Pro Leu Gly Thr Pro Asp Phe Val Gly Arg Ile Gln Gly Val Leu
            100                 105                 110

Thr Gln Thr Thr Arg Arg Asp Gly Ser Thr Arg Gly His Lys Ala Thr
        115                 120                 125

Val Ser Thr Gly Ser Val His Phe Thr Pro Lys Leu Gly Ser Val Gln
```

```
    130                 135                 140

Phe Ser Thr Asp Thr Cys Asn Asp Phe Glu Thr Gly Gln Asn Thr Arg
145                 150                 155                 160

Phe Thr Pro Val Gly Val Val Gln Asp Cys Ser Thr Thr His Gln Asn
                165                 170                 175

Glu Pro Gln Gln Trp Val Leu Pro Asp Tyr Ser Gly Arg Asp Ser His
            180                 185                 190

Asn Val His Leu Ala Pro Ala Val Ala Pro Thr Phe Pro Gly Glu Gln
        195                 200                 205

Leu Leu Phe Phe Arg Ser Thr Met Pro Gly Cys Ser Gly Tyr Pro Asn
    210                 215                 220

Met Asn Leu Asp Cys Leu Leu Pro Gln Glu Trp Val Gln His Phe Tyr
225                 230                 235                 240

Gln Glu Ser Ala Pro Ala Gln Ser Asp Val Ala Leu Leu Arg Phe Val
                245                 250                 255

Asn Pro Asp Thr Gly Arg Val Leu Phe Glu Cys Lys Leu His Lys Ser
            260                 265                 270

Gly Tyr Val Thr Val Ala His Thr Gly Gln His Asp Leu Val Ile Pro
        275                 280                 285

Pro Asn Gly Tyr Phe Arg Phe Asp Ser Trp Val Asn Gln Phe Tyr Thr
    290                 295                 300

Leu Ala Pro Met Gly Asn Gly Ala Gly Arg Arg Arg Ala Leu
305                 310                 315


<210> SEQ ID NO 1358
<211> LENGTH: 957
<212> TYPE: DNA
<213> ORGANISM: Artificial Sequence
<220> FEATURE:
<223> OTHER INFORMATION: Synthetic construct

<400> SEQUENCE: 1358

atgggcaagc ccttctcggt ccctatcctg acagttgagg aaatgaccaa ctctagattc      60

ccaatcccgc tggaaaagct cttcaccgga ccctcctctg ctttcgttgt gcagcctcaa     120

aacggtcgtt gcaccactga tggtgtcctg ctcggcacaa cccagctctc acctgtgaac     180

atctgtactt tccgcggcga cgtcacacac atcgctggat gccaaaacta caccatgaac     240

ttggcctcgc agaactggaa caactacgat ccaaccgagg aaatccccgc tcctttggga     300

actcccgact tcgtgggacg tatccaaggt gtcctgacac agactacacg tcgcgacggc     360

tctactcgcg gacacaaggc cactgtgtcg acaggttccg tccacttcac ccctaagctg     420

ggctctgtgc aattcagcac agacacctgc aacgatttcg agactggcca gaacaccagg     480

ttcactcccg tgggtgtcgt tcaagactgc agcaccactc accagaacga accccagcaa     540

tgggtcctcc ctgactactc gggcagggat tcccacaacg ttcacttggc tcccgccgtg     600

gctccaacct tccctggaga gcagttgctg ttcttcagat ccactatgcc aggctgctct     660

ggatacccga acatgaacct cgactgtctc ttgcctcagg agtgggtgca acacttctac     720

caggaatctg ccccagctca aagcgacgtc gctctgctcc gtttcgttaa ccccgatacc     780

ggtcgcgtgc tcttcgagtg taagttgcac aagtctggtt acgtcactgt tgcccacaca     840

ggccagcacg acctggtcat ccctcccaac ggctacttcc gcttcgatag ctgggtcaac     900

cagttctaca cactcgcccc gatgggaaac ggagccggtc gtcgcagagc cttgtaa        957


<210> SEQ ID NO 1359
```

<211> LENGTH: 321
<212> TYPE: PRT
<213> ORGANISM: Artificial Sequence
<220> FEATURE:
<223> OTHER INFORMATION: Synthetic construct

<400> SEQUENCE: 1359

Met Gly Lys Pro Phe Ser Val Pro Ile Leu Thr Val Glu Glu Met Thr
1               5                   10                  15

Asn Ser Arg Phe Pro Ile Pro Leu Glu Lys Leu Phe Thr Gly Pro Ser
            20                  25                  30

Ser Ala Phe Val Val Gln Pro Gln Asn Gly Arg Cys Thr Thr Asp Gly
        35                  40                  45

Val Leu Leu Gly Thr Thr Gln Leu Ser Pro Val Asn Ile Cys Thr Phe
    50                  55                  60

Arg Gly Asp Val Thr His Ile Ala Gly Lys Thr Gln Asn Tyr Thr Met
65                  70                  75                  80

Asn Leu Ala Ser Gln Asn Trp Asn Asn Tyr Asp Pro Thr Glu Glu Ile
                85                  90                  95

Pro Ala Pro Leu Gly Thr Pro Asp Phe Val Gly Arg Ile Gln Gly Val
            100                 105                 110

Leu Thr Gln Thr Thr Arg Arg Asp Gly Ser Thr Arg Gly His Lys Ala
        115                 120                 125

Thr Val Ser Thr Gly Ser Val His Phe Thr Pro Lys Leu Gly Ser Val
    130                 135                 140

Gln Phe Ser Thr Asp Thr Ser Lys Asn Asp Phe Glu Thr Gly Gln Asn
145                 150                 155                 160

Thr Arg Phe Thr Pro Val Gly Val Val Gln Asp Gly Lys Ser Thr Thr
                165                 170                 175

His Gln Asn Glu Pro Gln Gln Trp Val Leu Pro Asp Tyr Ser Gly Arg
            180                 185                 190

Asp Ser His Asn Val His Leu Ala Pro Ala Val Ala Pro Thr Phe Pro
        195                 200                 205

Gly Glu Gln Leu Leu Phe Phe Arg Ser Thr Met Pro Gly Cys Ser Gly
    210                 215                 220

Tyr Pro Asn Met Asn Leu Asp Cys Leu Leu Pro Gln Glu Trp Val Gln
225                 230                 235                 240

His Phe Tyr Gln Glu Ser Ala Pro Ala Gln Ser Asp Val Ala Leu Leu
                245                 250                 255

Arg Phe Val Asn Pro Asp Thr Gly Arg Val Leu Phe Glu Cys Lys Leu
            260                 265                 270

His Lys Ser Gly Tyr Val Thr Val Ala His Thr Gly Gln His Asp Leu
        275                 280                 285

Val Ile Pro Pro Asn Gly Tyr Phe Arg Phe Asp Ser Trp Val Asn Gln
    290                 295                 300

Phe Tyr Thr Leu Ala Pro Met Gly Asn Gly Ala Gly Arg Arg Arg Ala
305                 310                 315                 320

Leu

<210> SEQ ID NO 1360
<211> LENGTH: 966
<212> TYPE: DNA
<213> ORGANISM: Artificial Sequence
<220> FEATURE:
<223> OTHER INFORMATION: Synthetic construct

<400> SEQUENCE: 1360
atgggcaagc ccttctcggt ccctatcctg acagttgagg aaatgaccaa ctctagattc 60
ccaatcccgc tggaaaagct cttcaccgga ccctcctctg ctttcgttgt gcagcctcaa 120
aacggtcgtt gcaccactga tggtgtcctg ctcggcacaa cccagctctc acctgtgaac 180
atctgtactt tccgcggcga cgtcacacac atcgctggaa agacacaaaa ctacaccatg 240
aacttggcct cgcagaactg gaacaactac gatccaaccg aggaaatccc cgctcctttg 300
ggaactcccg acttcgtggg acgtatccaa ggtgtcctga cacagactac acgtcgcgac 360
ggctctactc gcggacacaa ggccactgtg tcgacaggtt ccgtccactt caccccctaag 420 ctgggctctg tgcaattcag cacagacacc tcaaagaacg atttcgagac tggccagaac 480
accaggttca ctcccgtggg tgtcgttcaa gacggcaaga gcaccactca ccagaacgaa 540
ccccagcaat gggtcctccc tgactactcg ggcagggatt cccacaacgt tcacttggct 600
cccgccgtgg ctccaacctt ccctggagag cagttgctgt tcttcagatc cactatgcca 660
ggctgctctg gatacccgaa catgaacctc gactgtctct tgcctcagga gtgggtgcaa 720
cacttctacc aggaatctgc cccagctcaa agcgacgtcg ctctgctccg tttcgttaac 780
cccgataccg gtcgcgtgct cttcgagtgt aagttgcaca agtctggtta cgtcactgtt 840
gcccacacag gccagcacga cctggtcatc cctcccaacg gctacttccg cttcgatagc 900
tgggtcaacc agttctacac actcgccccg atgggaaacg gagccggtcg tcgcagagcc 960
ttgtaa 966

<210> SEQ ID NO 1361
<211> LENGTH: 47
<212> TYPE: DNA
<213> ORGANISM: Artificial Sequence
<220> FEATURE:
<223> OTHER INFORMATION: Synthetic construct

<400> SEQUENCE: 1361
aactttaaga aggagatata ccatgggcaa gcccttctcg gtcccta 47

<210> SEQ ID NO 1362
<211> LENGTH: 57
<212> TYPE: DNA
<213> ORGANISM: Artificial Sequence
<220> FEATURE:
<223> OTHER INFORMATION: Synthetic construct

<400> SEQUENCE: 1362
cggatctcag tggtggtggt ggtggtgctc gagttacaag gctctgcgac gaccggc 57

<210> SEQ ID NO 1363
<211> LENGTH: 696
<212> TYPE: DNA
<213> ORGANISM: Artificial Sequence
<220> FEATURE:
<223> OTHER INFORMATION: Synthetic construct

<400> SEQUENCE: 1363
atgggtggtg gtggttcttg cggcggcggc ggctctgcgg gcaatacgaa ctcgggcggc 60
tccacgacga ccatcaccaa caacaactcg ggcaccaact catccagcac gacctacacg 120
gttaaaagcg gcgataccct gtggggtatt tcacagcgtt atggcatttc ggttgctcag 180
atccaaagcg cgaacaatct gaaatctacc attatctaca tcggccaaaa actggtcctg 240
accggtagcg cgagctctac gaactcaggc ggttcgaaca atagcgcttc taccacgccg 300

```
accacgtcgg tgaccccggc caaaccgacg agccagacca ccgtcaaagt gaaatctggc    360

gataccctgt gggccctgag tgttaaatat aaaacgtcca ttgcacaact gaaatcatgg    420

aaccatctga gttccgacac catttacatc ggtcagaacc tgatcgtcag tcaatccgcg    480

gccgcaagca atccgtctac cggctcaggt tcgaccgcca cgaacaatag caattctacg    540

tcatcgaaca gtaatgcatc cattcacaaa gtggttaaag gcgacaccct gtggggtctg    600

agtcagaaaa gtggttcccc gattgcgtct atcaaagcat ggaaccacct gagcagcgac    660

acgattctga ttggccagta tctgcgtatt aaataa                              696
```

```
<210> SEQ ID NO 1364
<211> LENGTH: 230
<212> TYPE: PRT
<213> ORGANISM: Artificial Sequence
<220> FEATURE:
<223> OTHER INFORMATION: Synthetic construct

<400> SEQUENCE: 1364

Gly Gly Gly Gly Ser Cys Gly Gly Gly Gly Ser Ala Gly Asn Thr Asn
1               5                   10                  15

Ser Gly Gly Ser Thr Thr Thr Ile Thr Asn Asn Asn Ser Gly Thr Asn
            20                  25                  30

Ser Ser Ser Thr Thr Tyr Thr Val Lys Ser Gly Asp Thr Leu Trp Gly
        35                  40                  45

Ile Ser Gln Arg Tyr Gly Ile Ser Val Ala Gln Ile Gln Ser Ala Asn
    50                  55                  60

Asn Leu Lys Ser Thr Ile Ile Tyr Ile Gly Gln Lys Leu Val Leu Thr
65                  70                  75                  80

Gly Ser Ala Ser Ser Thr Asn Ser Gly Gly Ser Asn Asn Ser Ala Ser
                85                  90                  95

Thr Thr Pro Thr Thr Ser Val Thr Pro Ala Lys Pro Thr Ser Gln Thr
            100                 105                 110

Thr Val Lys Val Lys Ser Gly Asp Thr Leu Trp Ala Leu Ser Val Lys
        115                 120                 125

Tyr Lys Thr Ser Ile Ala Gln Leu Lys Ser Trp Asn His Leu Ser Ser
    130                 135                 140

Asp Thr Ile Tyr Ile Gly Gln Asn Leu Ile Val Ser Gln Ser Ala Ala
145                 150                 155                 160

Ala Ser Asn Pro Ser Thr Gly Ser Gly Ser Thr Ala Thr Asn Asn Ser
                165                 170                 175

Asn Ser Thr Ser Ser Asn Ser Asn Ala Ser Ile His Lys Val Val Lys
            180                 185                 190

Gly Asp Thr Leu Trp Gly Leu Ser Gln Lys Ser Gly Ser Pro Ile Ala
        195                 200                 205

Ser Ile Lys Ala Trp Asn His Leu Ser Ser Asp Thr Ile Leu Ile Gly
    210                 215                 220

Gln Tyr Leu Arg Ile Lys
225                 230


<210> SEQ ID NO 1365
<211> LENGTH: 54
<212> TYPE: DNA
<213> ORGANISM: Artificial Sequence
<220> FEATURE:
<223> OTHER INFORMATION: Synthetic construct

<400> SEQUENCE: 1365
```

-continued

```
tttaactttaagaaggagatatacatatgggtggtggtggttcttgcggcggcg              54


<210> SEQ ID NO 1366
<211> LENGTH: 53
<212> TYPE: DNA
<213> ORGANISM: Artificial Sequence
<220> FEATURE:
<223> OTHER INFORMATION: Synthetic construct

<400> SEQUENCE: 1366

gtggtggtggtggtggtgctcgagttatttaatacgcagatactggccaatca               53
```